US012570666B2

(12) United States Patent
Panknin et al.

(10) Patent No.: US 12,570,666 B2
(45) Date of Patent: Mar. 10, 2026

(54) FUROINDAZOLE DERIVATIVES

(71) Applicant: Bayer Aktiengesellschaft, Leverkusen (DE)

(72) Inventors: Olaf Panknin, Berlin (DE); Frank Sacher, Berlin (DE); Nicole Schmidt, Berlin (DE); Gernot Langer, Falkensee (DE); Katrin Nowak-Reppel, Berlin (DE); Reinhard Nubbemeyer, Berlin (DE); Sabine Pilari, Berlin (DE); Antje Rottmann, Berlin (DE); Hideki Miyatake Ondozabal, Berlin (DE); Holger Siebeneicher, Berlin (DE); Antonius Ter Laak, Berlin (DE); Hana Cernecka, Wuppertal (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 847 days.

(21) Appl. No.: 17/786,268

(22) PCT Filed: Dec. 14, 2020

(86) PCT No.: PCT/EP2020/085905
§ 371 (c)(1),
(2) Date: Jun. 16, 2022

(87) PCT Pub. No.: WO2021/122415
PCT Pub. Date: Jun. 24, 2021

(65) Prior Publication Data

US 2023/0112499 A1 Apr. 13, 2023

(30) Foreign Application Priority Data

Dec. 19, 2019 (EP) .................................... 19217856

(51) Int. Cl.
*C07D 491/048* (2006.01)
*C07D 519/00* (2006.01)

(52) U.S. Cl.
CPC ....... *C07D 491/048* (2013.01); *C07D 519/00* (2013.01); *C07B 2200/05* (2013.01)

(58) Field of Classification Search
CPC ............................ C07D 491/08; C07D 519/00
See application file for complete search history.

(56) References Cited

FOREIGN PATENT DOCUMENTS

| | | | |
|---|---|---|---|
| WO | 0183487 | A1 | 11/2001 |
| WO | 2009023773 | A2 | 2/2009 |
| WO | 2013092791 | A1 | 6/2013 |
| WO | 2014095798 | A1 | 6/2014 |
| WO | 2015197550 | A1 | 12/2015 |
| WO | 2016085990 | A1 | 6/2016 |
| WO | 2016169911 | A1 | 10/2016 |
| WO | 2019084271 | A1 | 5/2019 |
| WO | 2019201939 | A1 | 10/2019 |

OTHER PUBLICATIONS

International Search Report mailed Feb. 1, 2021 for PCT Application No. PCT/EP2020/085905, filed Dec. 14, 2020, 3 pages.
Zobaer et al. (Dec. 1, 2017). "Three classes of ligands each bind to distinct sites on the orphan G protein-coupled receptor GPR84", Scientific Reports, 7:17953, XP055766532, DOI: 10.1038/s41598-017-18159-3.

*Primary Examiner* — Rebecca L Anderson
(74) *Attorney, Agent, or Firm* — Morrison & Foerster LLP

(57) ABSTRACT

Furindazole compounds of general formula (I):

(I)

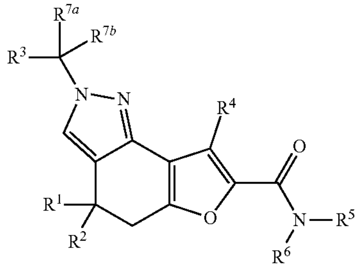

pharmaceutical compositions and combinations comprising compounds of formula (I) and the use of compounds of formula (I) for manufacturing pharmaceutical compositions for the treatment or prophylaxis of diseases.

12 Claims, No Drawings

FUROINDAZOLE DERIVATIVES

CROSS REFERENCE TO RELATED APPLICATIONS

This application is a national stage application under 35 U.S.C. § 371 of International Application No. PCT/EP2020/085905, filed internationally on Dec. 14, 2020, which claims the benefit of priority to European Application No. 19217856.4, filed Dec. 19, 2019.

The present invention covers furoindazole compounds of general formula (I) as described and defined herein, methods of preparing said compounds, intermediate compounds useful for preparing said compounds, pharmaceutical compositions comprising said compounds, and the use of said compounds for manufacturing pharmaceutical compositions for the treatment or prophylaxis of diseases, in particular of autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders.

BACKGROUND

The present invention covers furoindazole compounds of general formula (I) which are antagonists of the G-protein coupled receptor 84 (also known as GPR84). The relevance of GPR84 for human disease has been described and studied in several publications.

Medium-chain free fatty acids (MCFFAs) are fatty acids with tails of 6 to 12 carbons and can activate GPR84 (Wang J et al., J. Biol. Chem. 2006 Nov. 10, 281(45): 34457-64). There are two sources of FAs for animal metabolism, exogenously-derived (dietary) FAs and endogenously-synthesized FAs. The biosynthesis of the latter is catalysed by FASN. MCFFAs stimulate release of IL6 from fibroblasts (Smith and Tasi, Nat. Prod. Rep. 2007 Oct., 24(5): 1041-72) and myristic acid increases IL6 and IL8 levels in human coronary arterial smooth muscle (HCASM) and endothelial (HCEC) cells (Soto-Vaca A. et al., J. Agric. Food Chem. 2013 Oct. 23, 61(42): 10074-9).

GPR84 belongs to the group of Free Fatty Acid (FFA) receptors (Wang J. et al., J. Biol. Chem. 2006 Nov. 10, 281(45): 34457-64). The group of FFA receptors consists of 4 GPCRs (FFA1-FFA2) and the new members GPR42 and GPR84. FFA receptors are involved in biological processes such as metabolic and immune function receptors (Wang J. et al., J. Biol. Chem. 2006 Nov. 10, 281(45): 34457-64).

In contrast to all other FFA receptors which have a broader expression pattern, GPR84 has been described to be expressed primarily in various leukocyte populations and adipocytes (Wang J. et al., J. Biol. Chem. 2006 Nov. 10, 281(45): 34457-64; Lattin J. E. et al., Immunome Res. 2008 Apr. 29, 4: 5; Nagasaki H. et al., FEBS Lett. 2012 Feb. 17, 586(4): 368-72).

Activation of GPR84 promotes a comprehensive fibrotic and inflammatory cellular response, exerted by enhanced migration of macrophages and neutrophils, promoted pro-inflammatory M1 macrophage polarization and response and secretion of key inflammatory cytokines such as IL1beta and TNFalpha (Gagnon L. et al., Am. J. Pathol. 2018 May, 188(5): 1132-1148; Muredda L. et al., Arch. Physiol. Biochem. 2018 May, 124(2): 97-108; Huang Q. et al., Dev. Comp. Immunol. 2014, 45(2): 252-258). Based on the involvement of GPR84 in fibrotic and inflammatory cellular response several diseases have been suggested to be GPR84 dependent.

GPR84 as microglia-associated protein is expressed in neuroinflammatory conditions and is described as a potential target for the treatment of multiple sclerosis (Bouchard C. et al., Glia 2007 June, 55(8): 790-800) and for endometriosis associated and inflammatory pain (Sacher F. et al. 2018, Conference Abstract SRI 2018). Furthermore, inhibition of activity and/or the knockout of GPR84 are also effective in the treatment of neuropathic pain in several preclinical models (Roman et al. 2010, 7th Forum of European Neuroscience (FENS)).

The relevance of GPR84 for inflammatory kidney diseases has been shown in experiments using Gpr84-knockout mice or GPR84 antagonist in models of kidney fibrosis and models for inflammatory liver diseases like non-alcoholic, alcoholic- and toxic fatty liver diseases (Puengel et al. 2018, 2018 International Liver Congress (ILC) of the European Association for the Study of the Liver (EASL); Thibodeau J. F. et al. 2018, 51st Annual Meeting and Exposition of the American Society of Nephrology (ASN): Kidney Week 2018).

As described previously for macrophages and monocytes, inflammatory changes in adipose tissue enhance expression of GPR84 in adipocytes and modulation of GPR84 regulates adipocyte immune response capabilities (Muredda et al., Archives of Physiology and Biochemistry 2017 August, 124(2): 1-12) indicating the relevance of GPR84 in metabolic and metabolic-endocrine disorders like metabolic syndrome, insulin resistance, diabetes mellitus type I and type II, and polycystic ovary syndrome (PCOS) through normalization of adipose tissue inflammation.

Regulation of neutrophil activity and general inflammation by GPR84 was also described to be relevant for lung diseases like asthma, idiopathic pulmonary fibrosis and chronic obstructive pulmonary disease (Nguyen et al. 2018; Annual Congress Scientific Sessions of the American Heart Association (AHA 2018); Saniere L. et al. 2019; 2019 International Conference of the American Thoracic Society (ATS)).

Few compounds are known as GPR84 antagonists, for example the patent applications WO2013092791 and WO2014095798 disclose dihydropyrimidinoisoquinolinones having activity as GPR84 antagonists. Such compounds find utility in several therapeutic applications including inflammatory conditions.

The patent applications WO2015197550 and WO2016169911 disclose related dihydropyridoisoquinolinones as GPR84 antagonists.

The patent application WO2018161831 discloses dibenzoannulen hydrogen phosphates as GPR84 antagonists.

The patent application WO2009023773 discloses galactokinase inhibitors that were identified by a high throughput screening approach. Among the identified hits were two furoindazole compounds.

The patent application US20090163545 discloses compounds for altering the lifespan of eukaryotic organisms that were identified by a cell-based phenotypic high throughput screening approach. Among the identified hits were two furoindazole compounds.

The patent applications U.S. Pat. No. 6,245,796B1, WO2001083487 and WO2011071136 disclose aromatic tricyclic pyrrole or pyrazole derivatives as 5-HT2c ligands.

The patent application WO2016085990 discloses compounds inhibiting serine hydroxy-methyltransferase 2 activity that were identified by a high throughput screening approach. Among the identified hits were nine furoindazole compounds.

The patent application WO2019084271 discloses compounds inhibiting the non-canonical poly(A) RNA polymerase associated domain containing protein 5 (PAPD5) originating from diverse compound classes that were identified by a high throughput screening approach. Among the identified hits were eight furoindazole compounds.

However, the state of the art does not describe the furoindazole compounds of general formula (I) of the present invention as described and defined herein.

It has now been found, and this constitutes the basis of the present invention, that the compounds of the present invention have surprising and advantageous properties.

In particular, the compounds of the present invention have surprisingly been found to be effective antagonists of human GPR84 and may be used for the treatment or prophylaxis of diseases, in particular of autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders.

DESCRIPTION

In accordance with a first aspect, the present invention covers compounds of general formula (I):

(I)

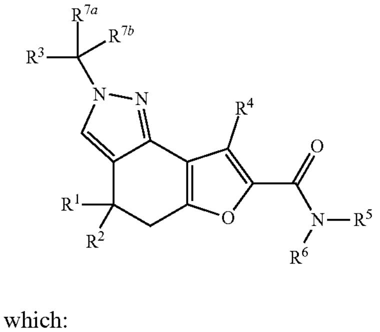

in which:

$R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl; or $R^1$ and $R^2$ together with the carbon atom to which they are attached form a 3- to 6-membered cycloalkyl or heterocycloalkyl ring;

$R^3$ represents $C_3$-$C_6$-cycloalkyl, 3- to 6-membered heterocycloalkyl, heterocycloalkyl fused with phenyl or heteroaryl, or heteroaryl, wherein said groups are optionally substituted, one or more times, independently of each other, with $R^8$, or $R^3$ represents phenyl, which is optionally substituted, one or more times, independently of each other, with $R^8$, and additionally $R^{7a}$ and $R^{7b}$ represent deuterium;

$R^4$ represents hydrogen, $C_1$-$C_4$-alkyl, $C_1$-$C_4$-haloalkyl or $C_3$-$C_6$-cycloalkyl;

$R^5$, $R^6$ represent, independently of each other, hydrogen, $C_1$-$C_4$-alkyl, $C_2$-$C_4$-hydroxyalkyl, ($C_1$-$C_4$-alkoxy)-($C_2$-$C_4$-alkyl)-, $C_3$-$C_6$-cycloalkyl, $C_1$-$C_4$-haloalkyl, $C_3$-$C_6$-halocycloalkyl, 3- to 6-membered heterocycloalkyl, heterospirocycloalkyl, phenyl, heteroaryl, heterocycloalkyl fused with phenyl or heteroaryl, 3- to 6-membered heterocycloalkyl-($C_1$-$C_3$-alkyl)-, heterospirocycloalkyl-($C_1$-$C_3$-alkyl)-, (heterocycloalkyl fused with phenyl or heteroaryl)-($C_1$-$C_3$-alkyl)-, phenyl-($C_1$-$C_3$-alkyl)- or heteroaryl-($C_1$-$C_3$-alkyl)-, wherein said 3- to 6-membered heterocycloalkyl, heterospirocycloalkyl, heterocycloalkyl fused with phenyl or heteroaryl, phenyl or heteroaryl groups are optionally substituted, one or more times, independently of each other, with $R^9$, or $R^5$ and $R^6$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^9$;

$R^{7a}$ represents hydrogen, deuterium, or $C_1$-$C_4$-alkyl;

$R^{7b}$ represents hydrogen, deuterium, or $C_1$-$C_4$-alkyl;

$R^8$ represents halogen, cyano, $C_1$-$C_4$-alkyl, $C_1$-$C_4$-haloalkyl, $C_1$-$C_3$-alkoxy, $C_1$-$C_3$-haloalkoxy, $C_3$-$C_6$-cycloalkyl, $C_3$-$C_6$-cycloalkyl-($C_1$-$C_3$-alkyl)-, $R^{13}$—(C═O)—, $R^{10}$—O—(C═O)—, $R^{11}$—NH—(C═O)—, or $R^{12}$—($SO_2$)—;

$R^9$ represents halogen, cyano, $C_1$-$C_4$-alkyl, $C_1$-$C_4$-haloalkyl, $H_2N$—$C_1$-$C_4$-alkyl, $C_1$-$C_3$-alkoxy, $C_1$-$C_3$-haloalkoxy, $C_3$-$C_6$-cycloalkyl, $R^{10}$—O—(C═O)—, oxo, 5- to 6-membered heterocycloalkyl-, 5- to 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

$R^{10}$ represents hydrogen, $C_1$-$C_4$-alkyl, or phenyl-$CH_2$—;

$R^{11}$ represents hydrogen, $C_1$-$C_4$-alkyl, or 5- to 6-membered heterocycloalkyl-($C_1$-$C_3$-alkyl)-;

$R^{12}$ represents $C_1$-$C_4$-alkyl or phenyl;

$R^{13}$ represents $C_1$-$C_4$-alkyl, $C_1$-$C_4$-haloalkyl, ($C_1$-$C_4$-alkoxy)-($C_1$-$C_4$-alkyl)-, $C_1$-$C_4$-alkyl-(C═O)—, $C_3$-$C_6$-cycloalkyl, or phenyl, wherein said $C_3$-$C_6$-cycloalkyl group is optionally substituted with $C_1$-$C_4$-alkyl or hydroxy and said phenyl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

and stereoisomers, tautomers, N-oxides, hydrates, solvates, and salts thereof, and mixtures of same.

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means 1, 2, 3, 4 or 5, particularly 1, 2, 3 or 4, more particularly 1, 2 or 3, even more particularly 1 or 2.

As used herein, an oxo substituent represents an oxygen atom, which is bound to a carbon atom via a double bond.

Should a composite substituent be composed of more than one parts, e.g. ($C_1$-$C_4$-alkoxy)-($C_1$-$C_4$-alkyl)-, it is possible for the position of a given part to be at any suitable position of said composite substituent, i.e. the $C_1$-$C_4$-alkoxy part can be attached to any carbon atom of the $C_1$-$C_4$-alkyl part of said ($C_1$-$C_4$-alkoxy)-($C_1$-$C_4$-alkyl)-group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulphur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_4$-alkyl" means a linear or branched, saturated, monovalent hydrocarbon group having 1, 2, 3, or 4 carbon atoms, e.g. a methyl, ethyl, propyl, isopropyl, butyl, sec-butyl, isobutyl, tert-butyl. Particularly, said group has 1, 2, or 3 carbon atoms ("$C_1$-$C_3$-alkyl"), e.g. a methyl, ethyl, propyl, or isopropyl group, more particularly 1 or 2 carbon atoms ("$C_1$-$C_2$-alkyl"), e.g. a methyl or ethyl group.

The term "$C_2$-$C_4$-hydroxyalkyl" means a linear or branched, saturated, monovalent hydrocarbon group in which the term "$C_2$-$C_4$-alkyl" is defined supra, and in which one hydrogen atom is replaced with a hydroxy group, e.g. a 1-hydroxyethyl, 2-hydroxyethyl, 3-hydroxypropyl, 2-hydroxypropyl, 1-hydroxypropyl, 1-hydroxypropan-2-yl, 2-hydroxypropan-2-yl, 3-hydroxy-2-methyl-propyl, 2-hydroxy-2-methyl-propyl, 1-hydroxy-2-methyl-propyl group.

The term "$C_1$-$C_4$-haloalkyl" means a linear or branched, saturated, monovalent hydrocarbon group in which the term "$C_1$-$C_4$-alkyl" is as defined supra, and in which one or more of the hydrogen atoms are replaced, identically or differently, with a halogen atom. Particularly, said halogen atom is a fluorine atom. Said $C_1$-$C_4$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

The term "$C_1$-$C_4$-alkoxy" means a linear or branched, saturated, monovalent group of formula ($C_1$-$C_4$-alkyl)-O—, in which the term "$C_1$-$C_4$-alkyl" is as defined supra, e.g. a methoxy, ethoxy, n-propoxy, isopropoxy, n-butoxy, sec-butoxy, isobutoxy, or tert-butoxy group.

The term "$C_1$-$C_4$-haloalkoxy" means a linear or branched, saturated, monovalent $C_1$-$C_4$-alkoxy group, as defined supra, in which one or more of the hydrogen atoms is replaced, identically or differently, with a halogen atom. Particularly, said halogen atom is a fluorine atom. Said $C_1$-$C_4$-haloalkoxy group is, for example, fluoromethoxy, difluoromethoxy, trifluoromethoxy, 2,2,2-trifluoroethoxy or pentafluoroethoxy.

The term "$C_3$-$C_6$-cycloalkyl" means a saturated, monovalent, monocyclic hydrocarbon ring which contains 3, 4, 5, or 6 carbon atoms ("$C_3$-$C_6$-cycloalkyl"). Said $C_3$-$C_6$-cycloalkyl group is for example, e.g. a cyclopropyl, cyclobutyl, cyclopentyl, or cyclohexyl group.

The term "$C_3$-$C_6$-halocycloalkyl" means a saturated, monovalent, monocyclic hydrocarbon ring in which the term "$C_3$-$C_6$-halocycloalkyl" is as defined supra, and in which one or more of the hydrogen atoms are replaced, identically or differently, with a halogen atom. Particularly, said halogen atom is a fluorine atom.

The term "4- to 6-membered heterocycloalkyl" means a monocyclic, saturated heterocycle with 4, 5 or 6 ring atoms in total, which contains one or two identical or different ring heteroatoms from the series N, O and S, it being possible for said heterocycloalkyl group to be attached to the rest of the molecule via any one of the carbon atoms or, if present, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example.

Particularly, "4- to 6-membered heterocycloalkyl" means a 4- to 6-membered heterocycloalkyl as defined supra containing one ring nitrogen or oxygen atom and optionally one further ring heteroatom from the series: N, O, S. More particularly, "5- or 6-membered heterocycloalkyl" means a monocyclic, saturated heterocycle with 5 or 6 ring atoms in total, containing one ring nitrogen or oxygen atom and optionally one further ring heteroatom from the series: N, O.

The term "heterocycloalkyl fused with phenyl or heteroaryl" means a bicyclic heterocycle with 8, 9 or 10 ring atoms in total, in which the two rings share two adjacent ring atoms, and in which the "heterocycloalkyl" part contains one or two identical or different ring heteroatoms from the series: N, O and/or S, and the term "heteroaryl" means a monocyclic aromatic ring having 5 or 6 ring atoms (a "5- to 6-membered heteroaryl" group), which contains at least one ring heteroatom and optionally one, two or three further ring heteroatoms from the series N, O and/or S; it being possible for said fused heterocycloalkyl group to be attached to the rest of the molecule via any one of the carbon atoms or, if present, a nitrogen atom.

The term "heterospirocycloalkyl" means a bicyclic, saturated heterocycle with 6, 7, 8, 9, or 11 ring atoms in total, in which the two rings share one common ring carbon atom, which "heterospirocycloalkyl" contains one or two identical or different ring heteroatoms from the series: N, O, S; it being possible for said heterospirocycloalkyl group to be attached to the rest of the molecule via any one of the carbon atoms, except the spiro carbon atom, or, if present, a nitrogen atom.

Said heterospirocycloalkyl group is, for example, azaspiro[2.3]hexyl, azaspiro[3.3]heptyl, oxaazaspiro[3.3]heptyl, thiaazaspiro[3.3]heptyl, oxaspiro[3.3]heptyl, oxazaspiro[5.3]nonyl, oxazaspiro[4.3]octyl, azaspiro[4,5]decyl, oxazaspiro [5.5]undecyl, diazaspiro[3.3]heptyl, thiazaspiro[3.3]heptyl, thiazaspiro[4.3]octyl, azaspiro[5.5]undecyl, or one of the further homologous scaffolds such as spiro[3.4]-, spiro[4.4]-, spiro[2.4]-, spiro[2.5]-, spiro[2.6]-, spiro[3.5]-, spiro[3.6]-, spiro[4.5]- and spiro[4.6]-.

The term "heteroaryl" means a monovalent, monocyclic, bicyclic or tricyclic aromatic ring having 5, 6, 8, 9, or 10 ring atoms (a "5- to 10-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a tricyclic heteroaryl group, such as, for example, carbazolyl, acridinyl or phenazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

Particularly, the heteroaryl group is a pyridinyl group.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_{10}$" encompasses $C_3$, $C_4$, $C_5$, $C_6$, $C_7$, $C_8$, $C_9$, $C_{10}$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butylphenyl)sulfonyl]oxy and [(4-methoxyphenyl)sulfonyl]oxy.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulphur, fluorine, chlorine, bromine and iodine, such as 2H (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$ containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases, deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases, the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an indazole moiety can exist as a 1H tautomer, or a 2H tautomer, or even a mixture in any amount of the two tautomers, namely:

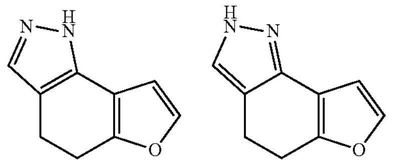

1H tautomer 2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also covers useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quaternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as “hydrochloride”, “trifluoroacetate”, “sodium salt”, or “x HCl”, “x $CF_3COOH$”, “x Na*”, for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term “prodrugs” here designates compounds which themselves can be biologically active or inactive but are converted (for example metabolically or hydrolytically) into compounds according to the invention during their residence time in the body.

In accordance with a second embodiment of the first aspect, the present invention covers compounds of general formula (I), supra, in which:

$R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl; or $R^1$ and $R^2$ together with the carbon atom to which they are attached form a 3- to 6-membered cycloalkyl or heterocycloalkyl ring;

$R^3$ represents $C_3$-$C_6$-cycloalkyl, 3- to 6-membered heterocycloalkyl, heterocycloalkyl fused with phenyl or heteroaryl, or heteroaryl, wherein said groups are optionally substituted, one or more times, independently of each other, with $R^8$, or $R^3$ represents phenyl, which is optionally substituted, one or more times, independently of each other, with $R^8$, and additionally $R^{7a}$ and $R^{7b}$ represent deuterium;

$R^4$ represents hydrogen, $C_1$-$C_4$-alkyl, $C_1$-$C_4$-haloalkyl or $C_3$-$C_6$-cycloalkyl;

$R^5$, $R^6$ represent, independently of each other, hydrogen, $C_1$-$C_4$-alkyl, $C_2$-$C_4$-hydroxyalkyl, ($C_1$-$C_4$-alkoxy)-($C_2$-$C_4$-alkyl)-, $C_3$-$C_6$-cycloalkyl, $C_1$-$C_4$-haloalkyl, $C_3$-$C_6$-halocycloalkyl, 3- to 6-membered heterocycloalkyl, phenyl, heteroaryl, heterocycloalkyl fused with phenyl or heteroaryl, 3- to 6-membered heterocycloalkyl-($C_1$-$C_3$-alkyl)-, (heterocycloalkyl fused with phenyl or heteroaryl)-($C_1$-$C_3$-alkyl)-, phenyl-($C_1$-$C_3$-alkyl)- or heteroaryl-($C_1$-$C_3$-alkyl)-, wherein said 3- to 6-membered heterocycloalkyl, phenyl or heteroaryl group is optionally substituted, one or more times, independently of each other, with $R^9$, or $R^5$ and $R^6$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^9$;

$R^{7a}$ represents hydrogen, deuterium, or $C_1$-$C_4$-alkyl;

$R^{7b}$ represents hydrogen, deuterium, or $C_1$-$C_4$-alkyl;

$R^8$ represents halogen, cyano, $C_1$-$C_4$-alkyl, $C_1$-$C_4$-haloalkyl, $C_1$-$C_3$-alkoxy, $C_1$-$C_3$-haloalkoxy, $C_3$-$C_6$-cycloalkyl, $C_1$-$C_4$-alkyl-(C═O)—, $R^{10}$—O—(C═O)—, $R^{11}$—NH—(C═O)—, or $R^{12}$—($SO_2$)—;

$R^9$ represents halogen, cyano, $C_1$-$C_4$-alkyl, $C_1$-$C_4$-haloalkyl, $H_2N$—$C_1$-$C_4$-alkyl, $C_1$-$C_3$-alkoxy, $C_1$-$C_3$-haloalkoxy, $C_3$-$C_6$-cycloalkyl, $R^{10}$—O—(C═O)—, oxo, 5- to 6-membered heterocycloalkyl-, 5- to 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

$R^{10}$ represents hydrogen, $C_1$-$C_4$-alkyl, or phenyl-$CH_2$—;

$R^{11}$ represents hydrogen, $C_1$-$C_4$-alkyl, or 5- to 6-membered heterocycloalkyl-($C_1$-$C_3$-alkyl)-;

$R^{12}$ represents $C_1$-$C_4$-alkyl or phenyl;

and stereoisomers, tautomers, N-oxides, hydrates, solvates, and salts thereof, and mixtures of same.

In accordance with a third embodiment of the first aspect, the present invention covers compounds of general formula (I), supra, in which:

$R^1$ represents hydrogen, $C_1$-$C_4$-alkyl or $C_1$-$C_4$-haloalkyl;

$R^2$ represents hydrogen or $C_1$-$C_4$-alkyl; or $R^1$ and $R^2$ together with the carbon atom to which they are attached form a 3- to 4-membered cycloalkyl or heterocycloalkyl ring;

$R^3$ represents $C_3$-$C_6$-cycloalkyl, 4- to 6-membered heterocycloalkyl, heterocycloalkyl fused with heteroaryl, or heteroaryl, wherein said groups are optionally substituted, one or more times, independently of each other, with $R^8$, or $R^3$ represents phenyl, which is optionally substituted, one or more times, independently of each other, with $R^8$, and additionally $R^{7a}$ and $R^{7b}$ represent deuterium;

$R^4$ represents hydrogen, $C_1$-$C_4$-alkyl, $C_1$-$C_4$-haloalkyl or $C_3$-$C_6$-cycloalkyl;

$R^5$, $R^6$ represent, independently of each other, hydrogen, $C_2$-$C_4$-hydroxyalkyl, ($C_1$-$C_4$-alkoxy)-($C_2$-$C_4$-alkyl)-, 3- to 6-membered heterocycloalkyl, heterospirocycloalkyl, phenyl, heteroaryl, 4- to 6-membered heterocycloalkyl-($C_1$-$C_3$-alkyl)-, heterospirocycloalkyl-($C_1$-$C_3$-alkyl)-, (heterocycloalkyl fused with heteroaryl)-($C_1$-$C_3$-alkyl)-, or heteroaryl-($C_1$-$C_3$-alkyl)-, wherein said 3- to 6-membered heterocycloalkyl, phenyl or heteroaryl groups are optionally substituted, one or more times, independently of each other, with $R^9$, or $R^5$ and $R^6$ together with the nitrogen atom to which they are attached form a 5-membered nitrogen containing heterocyclic ring, which may be optionally substituted, once with $R^9$;

$R^{7a}$ represents hydrogen, deuterium, or methyl;

$R^{7b}$ represents hydrogen, deuterium, or methyl;

$R^8$ represents halogen, cyano, $C_1$-$C_4$-alkyl, $C_1$-$C_4$-haloalkyl, $C_1$-$C_3$-alkoxy, $C_3$-$C_6$-cycloalkyl, $C_3$-$C_6$-cycloalkyl-($C_1$-$C_3$-alkyl)-, $R^{13}$—(C═O)—, $R^{10}$—O—(C═O)—, $R^{11}$—NH—(C═O)—, or $R^{12}$—($SO_2$)—;

$R^9$ represents halogen, cyano, $C_1$-$C_4$-alkyl, $C_1$-$C_4$-haloalkyl, $H_2N$—$C_1$-$C_4$-alkyl, $C_3$-$C_6$-cycloalkyl, $R^{10}$—O—(C═O)—, oxo, 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-haloalkyl, or $C_1$-$C_3$-alkoxy;

$R^{10}$ represents hydrogen, $C_1$-$C_4$-alkyl, or phenyl-$CH_2$—;

$R^{11}$ represents 5- to 6-membered heterocycloalkyl-($C_1$-$C_3$-alkyl)-;

$R^{12}$ represents $C_1$-$C_4$-alkyl;

$R^{13}$ represents $C_1$-$C_4$-alkyl, ($C_1$-$C_4$-alkoxy)-($C_1$-$C_4$-alkyl)-, $C_1$-$C_4$-alkyl-(C═O)—, $C_3$-$C_6$-cycloalkyl, or phenyl, wherein said $C_3$-$C_6$-cycloalkyl group is optionally substituted with methyl or hydroxy;

and stereoisomers, tautomers, N-oxides, hydrates, solvates, and salts thereof, and mixtures of same.

In accordance with a fourth embodiment of the first aspect, the present invention covers compounds of general formula (I), supra, in which:

$R^1$ represents hydrogen, methyl or trifluoromethyl;

$R^2$ represents hydrogen or methyl; or $R^1$ and $R^2$ together with the carbon atom to which they are attached form a 3- to 4-membered cycloalkyl ring;

$R^3$ represents cyclopropyl, 4- to 6-membered heterocycloalkyl, 2,3-dihydro[1,4]dioxino[2,3-b]pyridin-2-yl, or heteroaryl, wherein said groups are optionally substituted, one or more times, independently of each other, with $R^8$, or $R^3$ represents phenyl, which is optionally substituted, one or more times, independently of each other, with $R^8$, and additionally $R^{7a}$ and $R^{7b}$ represent deuterium;

$R^4$ represents hydrogen, methyl, $C_1$-haloalkyl or cyclopropyl;

$R^5$ represents hydrogen;

$R^6$ represents methoxy-ethyl, 5-membered heteroaryl, 4- to 6-membered heterocycloalkyl-($C_1$-$C_2$-alkyl)-, heterospirocycloalkyl-methyl, 2,3-dihydro[1,4]dioxino[2,3-b]pyridin-2-ylmethyl, or 5- to 6-membered heteroaryl-($C_1$-$C_2$-alkyl)-, wherein said 4- to 6-membered heterocycloalkyl or heteroaryl groups are optionally substituted, one or more times, independently of each other, with $R^9$;

$R^{7a}$ represents hydrogen, deuterium, or methyl;

$R^{7b}$ represents hydrogen, deuterium, or methyl;

$R^8$ represents fluoro, chloro, $C_1$-$C_2$-alkyl, trifluoromethyl, $C_1$-$C_3$-alkoxy, cyclopropyl, cyclopropylmethyl, $R^{13}$—(C═O)—, $R^{10}$—O—(C═O)—, $R^{11}$—NH—(C═O)—, or $R^{12}$—($SO_2$)—;

$R^9$ represents fluoro, chloro, $C_1$-$C_3$-alkyl, trifluoromethyl, cyclopropyl, or oxo;

$R^{10}$ represents $C_1$-$C_4$-alkyl, or phenyl-$CH_2$—;

$R^{11}$ represents 5- to 6-membered heterocycloalkyl-methyl;

$R^{12}$ represents methyl;

$R^{13}$ represents methyl, methoxymethyl, ethyl-(C═O)—, cyclopropyl, or phenyl, wherein said cyclopropyl group is optionally substituted with methyl or hydroxy;

and stereoisomers, tautomers, N-oxides, hydrates, solvates, and salts thereof, and mixtures of same.

In accordance with a fifth embodiment of the first aspect, the present invention covers compounds of general formula (I), supra, in which:

$R^1$ represents hydrogen or methyl;

$R^2$ represents hydrogen or methyl; or $R^1$ and $R^2$ together with the carbon atom to which they are attached form a 3- to 4-membered cycloalkyl ring;

$R^3$ represents cyclopropyl, 2,3-dihydro[1,4]dioxino[2,3-b]pyridin-2-yl, oxetan-3-yl, oxolan-3-yl, oxolan-2-yl, 3-methyloxetan-3-yl, 3-fluorooxetan-3-yl, pyridin-4-yl, pyridin-3-yl, pyridin-2-yl, oxan-4-yl, 1,4-dioxan-2-yl, 6-methylpyridin-3-yl, 5-methylpyridin-2-yl, 3-methylpyridin-2-yl, 2-methylpyridin-4-yl, 6-methylpyridin-2-yl, 3-chloropyridin-2-yl, 6-ethylpyridin-3-yl, 1-acetylpiperidin-4-yl, 3-chloro-5-ethoxypyridin-2-yl, 1-benzoylpiperidin-4-yl, or a group selected from:

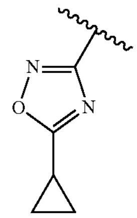
,
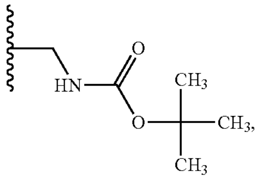
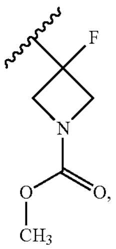

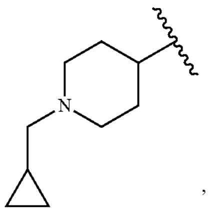
,
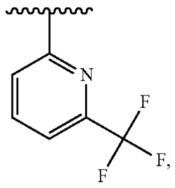

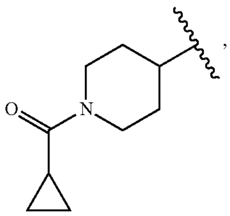
,
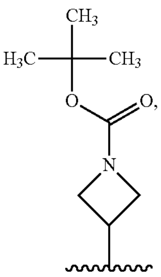

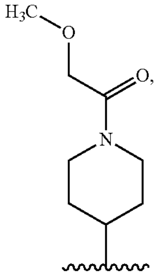
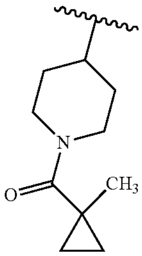
,
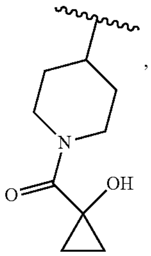
,

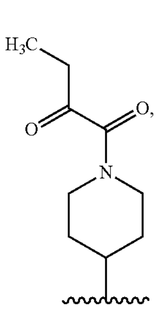
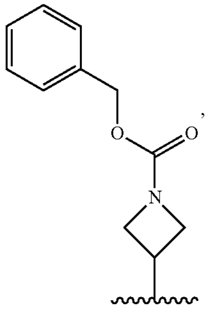
,

-continued

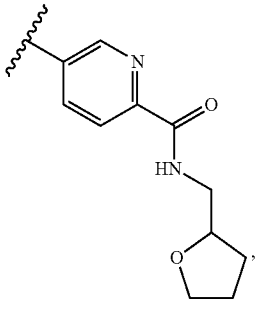

, or

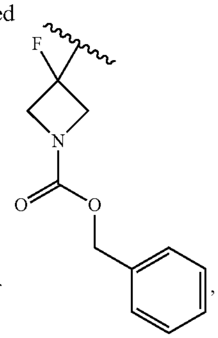

, or $R^3$ represents phenyl, and additionally $R^{7a}$ and $R^{7b}$ represent deuterium;

$R^4$ represents methyl, difluoromethyl, trifluoromethyl, or cyclopropyl;

$R^5$ represents hydrogen;

$R^6$ represents (oxolan-2-yl)methyl, (1,3-oxazol-4-yl)methyl, (1,2-oxazol-3-yl)methyl, (4-methyloxolan-2-yl)methyl, (pyrimidin-2-yl)methyl, (pyrazin-2-yl)methyl, (5-methyloxolan-2-yl)methyl, (5-methyloxolan-2-yl)methyl, (1,4-dioxan-2-yl)methyl, (4-methylphenyl)methyl, (5-methylpyrimidin-2-yl)methyl, (5-methylpyrazin-2-yl)methyl, (5-chloropyrazin-2-yl)methyl, (5-cyclopropyl-pyrazin-2-yl)methyl, 2,3-dihydro[1,4]dioxino[2,3-b]pyridin-2-ylmethyl, 1,3-oxazol-2-ylmethyl, 1,3-thiazol-2-ylmethyl, (1-methyl-1H-pyrazol-3-yl)methyl, (1-methyl-1H-imidazol-4-yl)methyl, (5-isopropyl-1,2-oxazol-3-yl)methyl, (5-cyclopropyl-1,2-oxazol-3-yl)methyl, (5,5-dimethyltetrahydrofuran-2-yl)methyl, (4,4-difluorotetrahydrofuran-2-yl)methyl, (6,6-dimethyl-1,4-dioxan-2-yl)methyl, 5-oxaspiro[2.4]heptan-6-ylmethyl, or 2,6-dioxaspiro[3.4]octan-7-ylmethyl;

$R^{7a}$ represents hydrogen;

$R^{7b}$ represents hydrogen;

and stereoisomers, tautomers, N-oxides, hydrates, solvates, and salts thereof, and mixtures of same.

Further embodiments of the first aspect of the present invention:

In a further embodiment of the first aspect, the present invention covers compounds of formula (I), supra, in which:

$R^1$ represents hydrogen, $C_1$-$C_4$-alkyl or $C_1$-$C_4$-haloalkyl;

and stereoisomers, tautomers, N-oxides, hydrates, solvates, and salts thereof, and mixtures of same.

In a further embodiment of the first aspect, the present invention covers compounds of formula (I), supra, in which:

$R^1$ represents hydrogen, methyl or trifluoromethyl;

and stereoisomers, tautomers, N-oxides, hydrates, solvates, and salts thereof, and mixtures of same.

In a further embodiment of the first aspect, the present invention covers compounds of formula (I), supra, in which:

$R^1$ represents hydrogen or $C_1$-$C_4$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^1$ represents hydrogen or $C_1$-$C_3$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^1$ represents hydrogen or methyl;

and stereoisomers, tautomers, N-oxides, hydrates, solvates, and salts thereof, and mixtures of same.

In a further embodiment of the first aspect, the present invention covers compounds of formula (I), supra, in which:

$R^2$ represents hydrogen, $C_1$-$C_4$-alkyl or $C_1$-$C_4$-haloalkyl;

and stereoisomers, tautomers, N-oxides, hydrates, solvates, and salts thereof, and mixtures of same.

In a further embodiment of the first aspect, the present invention covers compounds of formula (I), supra, in which:

$R^2$ represents hydrogen or $C_1$-$C_4$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^2$ represents hydrogen or $C_1$-$C_3$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^2$ represents hydrogen or methyl;

and stereoisomers, tautomers, N-oxides, hydrates, solvates, and salts thereof, and mixtures of same.

In a further embodiment of the first aspect, the present invention covers compounds of formula (I), supra, in which:

$R^1$ and $R^2$ together with the carbon atom to which they are attached form a 3- to 6-membered cycloalkyl or heterocycloalkyl ring;

and stereoisomers, tautomers, N-oxides, hydrates, solvates, and salts thereof, and mixtures of same.

In a further embodiment of the first aspect, the present invention covers compounds of formula (I), supra, in which:

$R^1$ and $R^2$ together with the carbon atom to which they are attached form a 3- to 6-membered cycloalkyl ring;

and stereoisomers, tautomers, N-oxides, hydrates, solvates, and salts thereof, and mixtures of same.

In a further embodiment of the first aspect, the present invention covers compounds of formula (I), supra, in which:

$R^1$ and $R^2$ together with the carbon atom to which they are attached form a 3- to 5-membered cycloalkyl ring;

and stereoisomers, tautomers, N-oxides, hydrates, solvates, and salts thereof, and mixtures of same.

In a further embodiment of the first aspect, the present invention covers compounds of formula (I), supra, in which:

$R^1$ and $R^2$ together with the carbon atom to which they are attached form a 3- to 4-membered cycloalkyl ring;

and stereoisomers, tautomers, N-oxides, hydrates, solvates, and salts thereof, and mixtures of same.

In a further embodiment of the first aspect, the present invention covers compounds of formula (I), supra, in which:

$R^3$ represents $C_3$-$C_6$-cycloalkyl, 3- to 6-membered heterocycloalkyl, heterocycloalkyl fused with phenyl or heteroaryl, or heteroaryl, wherein said groups are optionally substituted, one or more times, independently of each other, with $R^8$; and stereoisomers, tautomers, N-oxides, hydrates, solvates, and salts thereof, and mixtures of same.

In a further embodiment of the first aspect, the present invention covers compounds of formula (I), supra, in which:

$R^3$ represents $C_3$-$C_6$-cycloalkyl, 4- to 6-membered heterocycloalkyl, heterocycloalkyl fused with phenyl or heteroaryl, or 5- to 6-membered heteroaryl, wherein said groups are optionally substituted, one or more times, independently of each other, with $R^8$; and stereoisomers, tautomers, N-oxides, hydrates, solvates, and salts thereof, and mixtures of same.

In a further embodiment of the first aspect, the present invention covers compounds of formula (I), supra, in which:

$R^3$ represents $C_3$-$C_6$-cycloalkyl, 4- to 6-membered heterocycloalkyl, heterocycloalkyl fused with heteroaryl, or 5- to 6-membered heteroaryl, wherein said groups are optionally substituted, one or more times, independently of each other, with $R^8$; and stereoisomers, tautomers, N-oxides, hydrates, solvates, and salts thereof, and mixtures of same.

In a further embodiment of the first aspect, the present invention covers compounds of formula (I), supra, in which:

$R^3$ represents cyclopropyl, 4- to 6-membered heterocycloalkyl, 2,3-dihydro[1,4]dioxino[2,3-b]pyridin-2-yl, or 5- to 6-membered heteroaryl, wherein said groups are optionally substituted, one or more times, independently of each other, with $R^8$;

and stereoisomers, tautomers, N-oxides, hydrates, solvates, and salts thereof, and mixtures of same.

In a further embodiment of the first aspect, the present invention covers compounds of formula (I), supra, in which:

$R^3$ represents $C_3$-$C_6$-cycloalkyl, 4- to 6-membered heterocycloalkyl, heterocycloalkyl fused with heteroaryl, or heteroaryl, wherein said groups are optionally substituted, one or more times, independently of each other, with $R^8$;

and stereoisomers, tautomers, N-oxides, hydrates, solvates, and salts thereof, and mixtures of same.

In a further embodiment of the first aspect, the present invention covers compounds of formula (I), supra, in which:

$R^3$ represents cyclopropyl, 4- to 6-membered heterocycloalkyl, 2,3-dihydro[1,4]dioxino[2,3-b]pyridin-2-yl, or heteroaryl, wherein said groups are optionally substituted, one or more times, independently of each other, with $R^8$; and stereoisomers, tautomers, N-oxides, hydrates, solvates, and salts thereof, and mixtures of same.

In a further embodiment of the first aspect, the present invention covers compounds of formula (I), supra, in which:

$R^3$ represents cyclopropyl, 2,3-dihydro[1,4]dioxino[2,3-b]pyridin-2-yl, oxetan-3-yl, oxolan-3-yl, oxolan-2-yl, 3-methyloxetan-3-yl, 3-fluorooxetan-3-yl, pyridin-4-yl, pyridin-3-yl, pyridin-2-yl, oxan-4-yl, 1,4-dioxan-2-yl, 6-methylpyridin-3-yl, 5-methylpyridin-2-yl, 3-methylpyridin-2-yl, 2-methylpyridin-4-yl, 6-methylpyridin-2-yl, 3-chloropyridin-2-yl, 6-ethylpyridin-3-yl, 1-acetylpiperidin-4-yl, 3-chloro-5-ethoxypyridin-2-yl, 1-benzoylpiperidin-4-yl, or a group selected from:

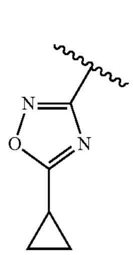
,
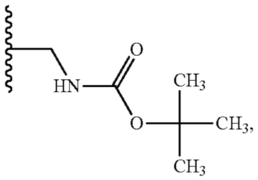
,
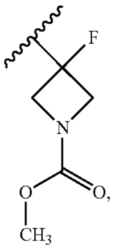
,
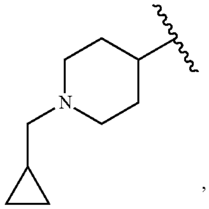
,
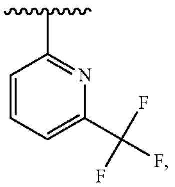
,

-continued

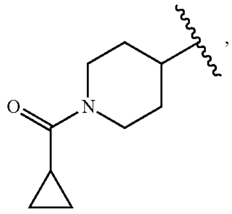
,
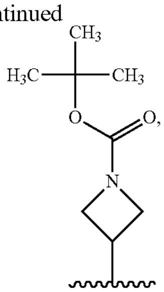
,
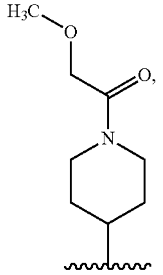
,
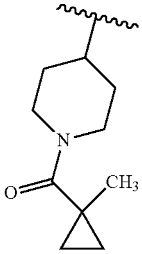
,
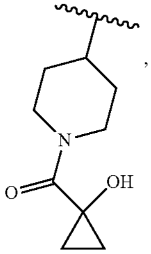
,
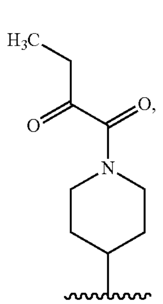
,
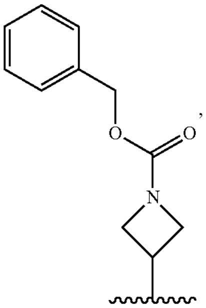
,
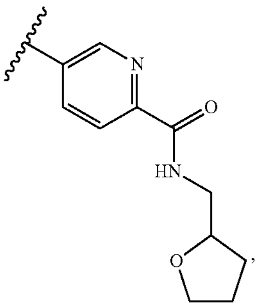
, or
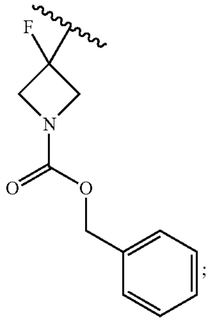
;

and stereoisomers, tautomers, N-oxides, hydrates, solvates, and salts thereof, and mixtures of same.

In a further embodiment of the first aspect, the present invention covers compounds of formula (I), supra, in which:

$R^3$ represents phenyl, which is optionally substituted, one or more times, independently of each other, with $R^8$, and additionally $R^{7a}$ and $R^{7b}$ represent deuterium; and stereoisomers, tautomers, N-oxides, hydrates, solvates, and salts thereof, and mixtures of same.

In a further embodiment of the first aspect, the present invention covers compounds of formula (I), supra, in which:

$R^3$ represents phenyl, which is optionally substituted, one or two times, independently of each other, with $R^8$, and additionally $R^{7a}$ and $R^{7b}$ represent deuterium; and stereoisomers, tautomers, N-oxides, hydrates, solvates, and salts thereof, and mixtures of same.

In a further embodiment of the first aspect, the present invention covers compounds of formula (I), supra, in which:

$R^3$ represents phenyl, and additionally $R^{7a}$ and $R^{7b}$ represent deuterium; and stereoisomers, tautomers, N-oxides, hydrates, solvates, and salts thereof, and mixtures of same.

In a further embodiment of the first aspect, the present invention covers compounds of formula (I), supra, in which:

$R^4$ represents hydrogen, $C_1$-$C_4$-alkyl, $C_1$-$C_4$-haloalkyl or $C_3$-$C_8$-cycloalkyl;

and stereoisomers, tautomers, N-oxides, hydrates, solvates, and salts thereof, and mixtures of same.

In a further embodiment of the first aspect, the present invention covers compounds of formula (I), supra, in which:

$R^4$ represents hydrogen, $C_1$-$C_3$-alkyl, $C_1$-$C_3$-haloalkyl or $C_3$-$C_6$-cycloalkyl; and stereoisomers, tautomers, N-oxides, hydrates, solvates, and salts thereof, and mixtures of same.

In a further embodiment of the first aspect, the present invention covers compounds of formula (I), supra, in which:

$R^4$ represents hydrogen, $C_1$-$C_3$-alkyl, $C_1$-$C_3$-haloalkyl or $C_3$-$C_5$-cycloalkyl and stereoisomers, tautomers, N-oxides, hydrates, solvates, and salts thereof, and mixtures of same.

In a further embodiment of the first aspect, the present invention covers compounds of formula (I), supra, in which:

$R^4$ represents hydrogen, methyl, $C_1$-haloalkyl or cyclopropyl; and stereoisomers, tautomers, N-oxides, hydrates, solvates, and salts thereof, and mixtures of same.

In a further embodiment of the first aspect, the present invention covers compounds of formula (I), supra, in which:

$R^4$ represents hydrogen, methyl, trifluoromethyl, or cyclopropyl; and stereoisomers, tautomers, N-oxides, hydrates, solvates, and salts thereof, and mixtures of same.

In a further embodiment of the first aspect, the present invention covers compounds of formula (I), supra, in which:

$R^5$, $R^6$ represent, independently of each other, hydrogen, $C_1$-$C_4$-alkyl, $C_2$-$C_4$-hydroxyalkyl, ($C_1$-$C_4$-alkoxy)-($C_2$-$C_4$-alkyl)-, $C_3$-$C_6$-cycloalkyl, $C_1$-$C_4$-haloalkyl, $C_3$-$C_6$-halocycloalkyl, 3- to 6-membered heterocycloalkyl, heterospirocycloalkyl, phenyl, heteroaryl, heterocycloalkyl fused with phenyl or heteroaryl, 3- to 6-membered heterocycloalkyl-($C_1$-$C_3$-alkyl)-, heterospirocycloalkyl-($C_1$-$C_3$-alkyl)-, (heterocycloalkyl fused with phenyl or heteroaryl)-($C_1$-$C_3$-alkyl)-, phenyl-($C_1$-$C_3$-alkyl)- or heteroaryl-($C_1$-$C_3$-alkyl)-, wherein said 3- to 6-membered heterocycloalkyl, heterospirocycloalkyl, heterocycloalkyl fused with phenyl or heteroaryl, phenyl or heteroaryl groups are optionally substituted, one or more times, independently of each other, with $R^9$; and stereoisomers, tautomers, N-oxides, hydrates, solvates, and salts thereof, and mixtures of same.

In a further embodiment of the first aspect, the present invention covers compounds of formula (I), supra, in which:

$R^5$, $R^6$ represent, independently of each other, hydrogen, $C_2$-$C_4$-hydroxyalkyl, ($C_1$-$C_4$-alkoxy)-($C_2$-$C_4$-alkyl)-, 3- to 6-membered heterocycloalkyl, heterospirocycloalkyl, phenyl, heteroaryl, 4- to 6-membered heterocycloalkyl-($C_1$-$C_3$-alkyl)-, heterospirocycloalkyl-($C_1$-$C_3$-alkyl)-, (heterocycloalkyl fused with heteroaryl)-($C_1$-$C_3$-alkyl)-, or heteroaryl-($C_1$-$C_3$-alkyl)-, wherein said 3- to 6-membered heterocycloalkyl, phenyl or heteroaryl groups are optionally substituted, one or more times, independently of each other, with $R^9$;

and stereoisomers, tautomers, N-oxides, hydrates, solvates, and salts thereof, and mixtures of same.

In a further embodiment of the first aspect, the present invention covers compounds of formula (I), supra, in which:

$R^5$, $R^6$ represent, independently of each other, hydrogen, $C_1$-$C_4$-alkyl, $C_2$-$C_4$-hydroxyalkyl, ($C_1$-$C_4$-alkoxy)-($C_2$-$C_4$-alkyl)-, $C_3$-$C_6$-cycloalkyl, $C_1$-$C_4$-haloalkyl, $C_3$-$C_6$-halocycloalkyl, 3- to 6-membered heterocycloalkyl, phenyl, heteroaryl, heterocycloalkyl fused with phenyl or heteroaryl, 3- to 6-membered heterocycloalkyl-($C_1$-$C_3$-alkyl)-, (heterocycloalkyl fused with phenyl or heteroaryl)-($C_1$-$C_3$-alkyl)-, phenyl-($C_1$-$C_3$-alkyl)- or heteroaryl-($C_1$-$C_3$-alkyl)-, wherein said 3- to 6-membered heterocycloalkyl, phenyl or heteroaryl group is optionally substituted, one or more times, independently of each other, with $R^9$;

and stereoisomers, tautomers, N-oxides, hydrates, solvates, and salts thereof, and mixtures of same.

In a further embodiment of the first aspect, the present invention covers compounds of formula (I), supra, in which:

$R^5$ and $R^6$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^9$; and stereoisomers, tautomers, N-oxides, hydrates, solvates, and salts thereof, and mixtures of same.

In a further embodiment of the first aspect, the present invention covers compounds of formula (I), supra, in which:

$R^5$ and $R^6$ together with the nitrogen atom to which they are attached form a 5- to 6-membered nitrogen containing heterocyclic ring, optionally containing one additional heteroatom or heteroatom containing group selected from O, NH and S, and which may be optionally substituted, one or more times, independently of each other, with $R^9$; and stereoisomers, tautomers, N-oxides, hydrates, solvates, and salts thereof, and mixtures of same.

In a further embodiment of the first aspect, the present invention covers compounds of formula (I), supra, in which:

$R^5$ and $R^6$ together with the nitrogen atom to which they are attached form a 5- to 6-membered nitrogen containing heterocyclic ring, which may be optionally substituted, one or more times, independently of each other, with $R^9$;

and stereoisomers, tautomers, N-oxides, hydrates, solvates, and salts thereof, and mixtures of same.

In a further embodiment of the first aspect, the present invention covers compounds of formula (I), supra, in which:

$R^5$ and $R^6$ together with the nitrogen atom to which they are attached form a 5-membered nitrogen containing heterocyclic ring, which is substituted with aminomethyl; and stereoisomers, tautomers, N-oxides, hydrates, solvates, and salts thereof, and mixtures of same.

In a further embodiment of the first aspect, the present invention covers compounds of formula (I), supra, in which:

$R^5$ represents hydrogen;

and stereoisomers, tautomers, N-oxides, hydrates, solvates, and salts thereof, and mixtures of same.

In a further embodiment of the first aspect, the present invention covers compounds of formula (I), supra, in which:

$R^6$ represents methoxy-ethyl, 5-membered heteroaryl, 4- to 5-membered heterocycloalkyl-($C_1$-$C_2$-alkyl)-, heterospirocycloalkyl-methyl, 2,3-dihydro[1,4]dioxino[2,3-b]pyridin-2-ylmethyl, or 5- to 6-membered heteroaryl-($C_1$-$C_2$-alkyl)-, wherein said 4- to 5-membered heterocycloalkyl or heteroaryl groups are optionally substituted, one or more times, independently of each other, with $R^9$; and stereoisomers, tautomers, N-oxides, hydrates, solvates, and salts thereof, and mixtures of same.

In a further embodiment of the first aspect, the present invention covers compounds of formula (I), supra, in which:

$R^6$ represents (oxolan-2-yl)methyl, (1,3-oxazol-4-yl)methyl, (1,2-oxazol-3-yl)methyl, (4-methyloxolan-2-yl)methyl, (pyrimidin-2-yl)methyl, (pyrazin-2-yl)methyl, (5-methyloxolan-2-yl)methyl, (5-methyloxolan-2-yl)methyl, (1,4-dioxan-2-yl)methyl, (4-methylphenyl)methyl, (5-methylpyrimidin-2-yl)methyl, (5-methylpyrazin-2-yl)methyl, (5-chloropyrazin-2-yl)methyl, (5-cyclopropyl-pyrazin-2-yl)methyl, 2,3-dihydro[1,4]dioxino[2,3-b]pyridin-2-ylmethyl, 1,3-oxazol-2-ylmethyl, 1,3-thiazol-2-ylmethyl, (1-methyl-1H-pyrazol-3-yl)methyl, (1-methyl-1H-imidazol-4-yl)methyl, (5-isopropyl-1,2-oxazol-3-yl)methyl, (5-cyclopropyl-1,2-oxazol-3-yl)methyl, (5,5-dimethyltetrahydrofuran-2-yl)methyl, (4,4-difluoroetrahydrofuran-2-yl)methyl, (6,6-dimethyl-1,4-dioxan-2-yl)methyl, 5-oxaspiro[2.4]heptan-6-ylmethyl, or 2,6-dioxaspiro[3.4]octan-7-ylmethyl;

and stereoisomers, tautomers, N-oxides, hydrates, solvates, and salts thereof, and mixtures of same.

In a further embodiment of the first aspect, the present invention covers compounds of formula (I), supra, in which:

$R^6$ represents $C_1$-$C_4$-alkyl, $C_2$-$C_4$-hydroxyalkyl, ($C_1$-$C_4$-alkoxy)-($C_2$-$C_4$-alkyl)-, $C_3$-$C_6$-cycloalkyl, $C_1$-$C_4$-haloalkyl, $C_3$-$C_6$-halocycloalkyl, 3- to 6-membered heterocycloalkyl, phenyl, heteroaryl, heterocycloalkyl fused with phenyl or heteroaryl, 3- to 6-membered heterocycloalkyl-($C_1$-$C_3$-alkyl)-, (heterocycloalkyl fused with phenyl or heteroaryl)-($C_1$-$C_3$-alkyl)-, phenyl-($C_1$-$C_3$-alkyl)- or heteroaryl-($C_1$-$C_3$-alkyl)-, wherein said 3- to 6-membered heterocycloalkyl, phenyl or heteroaryl group is optionally substituted, one or more times, independently of each other, with $R^9$;

and stereoisomers, tautomers, N-oxides, hydrates, solvates, and salts thereof, and mixtures of same.

In a further embodiment of the first aspect, the present invention covers compounds of formula (I), supra, in which:

$R^6$ represents $C_1$-$C_3$-alkyl, $C_2$-$C_4$-hydroxyalkyl, ($C_1$-$C_3$-alkoxy)-($C_2$-$C_4$-alkyl)-, $C_3$-$C_5$-cycloalkyl, $C_1$-$C_3$-haloalkyl, 4- to 6-membered heterocycloalkyl, phenyl, 5- to 6-membered heteroaryl, heterocycloalkyl fused with heteroaryl, 4- to 6-membered heterocycloalkyl-($C_1$-$C_3$-alkyl)-, (heterocycloalkyl fused with heteroaryl)-($C_1$-$C_3$-alkyl)-, phenyl-($C_1$-$C_3$-alkyl)- or 5- to 6-membered heteroaryl-($C_1$-$C_3$-alkyl)-, wherein said 4- to 6-membered heterocycloalkyl, phenyl or heteroaryl group is optionally substituted, one or more times, independently of each other, with $R^9$;

and stereoisomers, tautomers, N-oxides, hydrates, solvates, and salts thereof, and mixtures of same.

In a further embodiment of the first aspect, the present invention covers compounds of formula (I), supra, in which:

$R^6$ represents $C_2$-$C_4$-hydroxyalkyl, methoxy-($C_2$-$C_4$-alkyl)-, phenyl, 5- to 6-membered heteroaryl, 4- to 6-membered heterocycloalkyl-($C_1$-$C_2$-alkyl)-, (2,3-dihydro[1,4]dioxino[2,3-b]pyridin-2-yl)-methyl, phenyl-($C_1$-$C_2$-alkyl)- or 5- to 6-membered heteroaryl-methyl, wherein said 4- to 6-membered heterocycloalkyl, phenyl or heteroaryl group is optionally substituted, one or more times, independently of each other, with $R^9$; and stereoisomers, tautomers, N-oxides, hydrates, solvates, and salts thereof, and mixtures of same.

In a further embodiment of the first aspect, the present invention covers compounds of formula (I), supra, in which:

$R^{7a}$ represents hydrogen, deuterium, or $C_1$-$C_4$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^{7b}$ represents hydrogen, deuterium, or $C_1$-$C_4$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^{7a}$ represents hydrogen, deuterium, or methyl;

and stereoisomers, tautomers, N-oxides, hydrates, solvates, and salts thereof, and mixtures of same.

In a further embodiment of the first aspect, the present invention covers compounds of formula (I), supra, in which:

$R^{7b}$ represents hydrogen, deuterium, or methyl;

and stereoisomers, tautomers, N-oxides, hydrates, solvates, and salts thereof, and mixtures of same.

In a further embodiment of the first aspect, the present invention covers compounds of formula (I), supra, in which:

$R^{7a}$ represents hydrogen or deuterium;

and stereoisomers, tautomers, N-oxides, hydrates, solvates, and salts thereof, and mixtures of same.

In a further embodiment of the first aspect, the present invention covers compounds of formula (I), supra, in which:

$R^{7b}$ represents hydrogen or deuterium;

and stereoisomers, tautomers, N-oxides, hydrates, solvates, and salts thereof, and mixtures of same.

In a further embodiment of the first aspect, the present invention covers compounds of formula (I), supra, in which:

$R^{7a}$ represents hydrogen;

and stereoisomers, tautomers, N-oxides, hydrates, solvates, and salts thereof, and mixtures of same.

In a further embodiment of the first aspect, the present invention covers compounds of formula (I), supra, in which:

$R^{7b}$ represents hydrogen;

and stereoisomers, tautomers, N-oxides, hydrates, solvates, and salts thereof, and mixtures of same.

In a further embodiment of the first aspect, the present invention covers compounds of formula (I), supra, in which:

$R^8$ represents halogen, cyano, $C_1$-$C_4$-alkyl, $C_1$-$C_4$-haloalkyl, $C_1$-$C_3$-alkoxy, $C_1$-$C_3$-haloalkoxy, $C_3$-$C_6$-cycloalkyl, $C_3$-$C_6$-cycloalkyl-($C_1$-$C_3$-alkyl)-, $R^{13}$—(C═O)—, $R^{10}$—O—(C═O)—, $R^{11}$—NH—(C═O)—, or $R^2$—($SO_2$)—;

and stereoisomers, tautomers, N-oxides, hydrates, solvates, and salts thereof, and mixtures of same.

In a further embodiment of the first aspect, the present invention covers compounds of formula (I), supra, in which:

$R^8$ represents halogen, cyano, $C_1$-$C_4$-alkyl, $C_1$-$C_4$-haloalkyl, $C_1$-$C_3$-alkoxy, $C_3$-$C_6$-cycloalkyl, $C_3$-$C_6$-cycloalkyl-($C_1$-$C_3$-alkyl)-, $R^{13}$—(C═O)—, $R^{10}$—O—(C═O)—, $R^{11}$—NH—(C═O)—, or $R^{12}$—($SO_2$)—;

and stereoisomers, tautomers, N-oxides, hydrates, solvates, and salts thereof, and mixtures of same.

In a further embodiment of the first aspect, the present invention covers compounds of formula (I), supra, in which:

$R^8$ represents fluoro, chloro, $C_1$-$C_2$-alkyl, trifluoromethyl, $C_1$-$C_3$-alkoxy, cyclopropyl, cyclopropylmethyl, $R^{13}$—(C═O)—, $R^{10}$—O—(C═O)—, $R^{11}$—NH—(C═O)—, or $R^{12}$—($SO_2$)—;

and stereoisomers, tautomers, N-oxides, hydrates, solvates, and salts thereof, and mixtures of same.

In a further embodiment of the first aspect, the present invention covers compounds of formula (I), supra, in which:

$R^8$ represents halogen, cyano, $C_1$-$C_4$-alkyl, $C_1$-$C_4$-haloalkyl, $C_1$-$C_3$-alkoxy, $C_1$-$C_3$-haloalkoxy, $C_3$-$C_6$-cycloalkyl, $C_1$-$C_4$-alkyl-(C═O)—, $R^{10}$—O—(C═O)—, $R^{11}$—NH—(C═O)—, or $R^{12}$—($SO_2$)—;

and stereoisomers, tautomers, N-oxides, hydrates, solvates, and salts thereof, and mixtures of same.

In a further embodiment of the first aspect, the present invention covers compounds of formula (I), supra, in which:

$R^8$ represents halogen, $C_1$-$C_3$-alkyl, $C_1$-$C_3$-haloalkyl, $C_1$-$C_3$-alkoxy, $C_3$-$C_6$-cycloalkyl, $C_1$-$C_3$-alkyl-(C═O)—, $R^{10}$—O—(C═O)—, $R^{11}$—NH—(C═O)—, or $R^{12}$—($SO_2$)—;

and stereoisomers, tautomers, N-oxides, hydrates, solvates, and salts thereof, and mixtures of same.

In a further embodiment of the first aspect, the present invention covers compounds of formula (I), supra, in which:

$R^8$ represents fluoro, chloro, methyl, trifluoromethyl, ethoxy, cyclopropyl, methyl-(C═O)—, $R^{10}$—O—(C═O)—, $R^{11}$—NH—(C═O)—, or $R^{12}$—($SO_2$)—;

and stereoisomers, tautomers, N-oxides, hydrates, solvates, and salts thereof, and mixtures of same.

In a further embodiment of the first aspect, the present invention covers compounds of formula (I), supra, in which:

$R^9$ represents halogen, cyano, $C_1$-$C_4$-alkyl, $C_1$-$C_4$-haloalkyl, $H_2N$—$C_1$-$C_4$-alkyl, $C_1$-$C_3$-alkoxy, $C_1$-$C_3$-haloalkoxy, $C_3$-$C_6$-cycloalkyl, $R^{10}$—O—(C═O)—, oxo, 5- to 6-membered heterocycloalkyl-, 5- to 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

and stereoisomers, tautomers, N-oxides, hydrates, solvates, and salts thereof, and mixtures of same.

In a further embodiment of the first aspect, the present invention covers compounds of formula (I), supra, in which:

$R^9$ represents halogen, cyano, $C_1$-$C_4$-alkyl, $C_1$-$C_4$-haloalkyl, $H_2N$—$C_1$-$C_4$-alkyl, $C_3$-$C_6$-cycloalkyl, $R^{10}$—O—(C═O)—, oxo, 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-haloalkyl, or $C_1$-$C_3$-alkoxy;

and stereoisomers, tautomers, N-oxides, hydrates, solvates, and salts thereof, and mixtures of same.

In a further embodiment of the first aspect, the present invention covers compounds of formula (I), supra, in which:

$R^9$ represents halogen, cyano, $C_1$-$C_5$-alkyl, $C_1$-$C_3$-haloalkyl, $H_2N$—$C_1$-$C_3$-alkyl, $C_1$-$C_3$-alkoxy, $C_3$-$C_6$-cycloalkyl, $R^{10}$—O(C═O)—, oxo, 5- to 6-membered heterocycloalkyl-, 5- to 6-membered heterocycloalkyl-($C_1$-$C_2$-alkyl)-, phenyl, or 5- to 6-membered heteroaryl, wherein said phenyl or heteroaryl group is optionally substituted, one or more times, independently of each other, with halogen, $C_1$-$C_5$-alkyl, $C_1$-$C_3$-haloalkyl, or $C_1$-$C_3$-alkoxy and stereoisomers, tautomers, N-oxides, hydrates, solvates, and salts thereof, and mixtures of same.

In a further embodiment of the first aspect, the present invention covers compounds of formula (I), supra, in which:

$R^9$ represents fluoro, cyano, $C_1$-$C_3$-alkyl, trifluoromethyl, aminomethyl, ethoxy, cyclopropyl, $R^{10}$—O—(C═O)—, oxo, 6-membered heterocycloalkyl-methyl, phenyl, or 5- to 6-membered heteroaryl, wherein said phenyl or heteroaryl group is optionally substituted with chloro, trifluoromethyl, or methoxy;

and stereoisomers, tautomers, N-oxides, hydrates, solvates, and salts thereof, and mixtures of same.

In a further embodiment of the first aspect, the present invention covers compounds of formula (I), supra, in which:

$R^9$ represents fluoro, chloro, $C_1$-$C_3$-alkyl, trifluoromethyl, cyclopropyl, or oxo; and stereoisomers, tautomers, N-oxides, hydrates, solvates, and salts thereof, and mixtures of same.

In a further embodiment of the first aspect, the present invention covers compounds of formula (I), supra, in which:

$R^{10}$ represents hydrogen, $C_1$-$C_4$-alkyl, or phenyl-$CH_2$—;

and stereoisomers, tautomers, N-oxides, hydrates, solvates, and salts thereof, and mixtures of same.

In a further embodiment of the first aspect, the present invention covers compounds of formula (I), supra, in which:

$R^{10}$ represents $C_1$-$C_4$-alkyl, or phenyl-$CH_2$—;

and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents hydrogen, $C_1$-$C_4$-alkyl, or 5- to 6-membered heterocycloalkyl-($C_1$-$C_3$-alkyl)-;

and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents $C_1$-$C_4$-alkyl, or 5- to 6-membered heterocycloalkyl-($C_1$-$C_3$-alkyl)-; and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents $C_1$-$C_3$-alkyl, or 5- to 6-membered heterocycloalkyl-($C_1$-$C_2$-alkyl); and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents $C_1$-$C_3$-alkyl, or 5- to 6-membered heterocycloalkyl-methyl and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents 5- to 6-membered heterocycloalkyl-($C_1$-$C_3$-alkyl)-; and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents 5- to 6-membered heterocycloalkyl-methyl; and stereoisomers, tautomers, N-oxides, hydrates, solvates, and salts thereof, and mixtures of same.

In a further embodiment of the first aspect, the present invention covers compounds of formula (I), supra, in which:

$R^{11}$ represents tetrahydrofuran-2-yl-methyl, or 1,4-dioxan-2-yl-methyl; and stereoisomers, tautomers, N-oxides, hydrates, solvates, and salts thereof, and mixtures of same.

In a further embodiment of the first aspect, the present invention covers compounds of formula (I), supra, in which:

$R^{12}$ represents $C_1$-$C_4$-alkyl or phenyl;

and stereoisomers, tautomers, N-oxides, hydrates, solvates, and salts thereof, and mixtures of same.

In a further embodiment of the first aspect, the present invention covers compounds of formula (I), supra, in which:

$R^{12}$ represents $C_1$-$C_3$-alkyl or phenyl;

and stereoisomers, tautomers, N-oxides, hydrates, solvates, and salts thereof, and mixtures of same.

In a further embodiment of the first aspect, the present invention covers compounds of formula (I), supra, in which:

$R^{12}$ represents $C_1$-$C_4$-alkyl;

and stereoisomers, tautomers, N-oxides, hydrates, solvates, and salts thereof, and mixtures of same.

In a further embodiment of the first aspect, the present invention covers compounds of formula (I), supra, in which:

$R^{12}$ represents methyl;

and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents $C_1$-$C_4$-alkyl, $C_1$-$C_4$-haloalkyl, ($C_1$-$C_4$-alkoxy)-($C_1$-$C_4$-alkyl)-, $C_1$-$C_4$-alkyl-(C═O)—, $C_3$-$C_6$-cycloalkyl, or phenyl, wherein said $C_3$-$C_6$-cycloalkyl group is optionally substituted with $C_1$-$C_4$-alkyl or hydroxy and said phenyl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents $C_1$-$C_4$-alkyl, ($C_1$-$C_4$-alkoxy)-($C_1$-$C_4$-alkyl)-, $C_1$-$C_4$-alkyl-(C═O)—, $C_3$-$C_6$-cycloalkyl, or phenyl, wherein said $C_3$-$C_6$-cycloalkyl group is optionally substituted with methyl or hydroxy;

and stereoisomers, tautomers, N-oxides, hydrates, solvates, and salts thereof, and mixtures of same.

In a further embodiment of the first aspect, the present invention covers compounds of formula (I), supra, in which:

$R^{13}$ represents methyl, methoxymethyl, ethyl-(C═O)—, cyclopropyl, or phenyl, wherein said cyclopropyl group is optionally substituted with methyl or hydroxy;

and stereoisomers, tautomers, N-oxides, hydrates, solvates, and salts thereof, and mixtures of same.

In a particular further embodiment of the first aspect, the present invention covers combinations of two or more of the above-mentioned embodiments under the heading "further embodiments of the first aspect of the present invention".

The present invention covers any sub-combination within any embodiment or aspect of the present invention of compounds of general formula (I), supra.

The present invention covers any sub-combination within any embodiment or aspect of the present invention of intermediate compounds of general formula (II).

The present invention covers the compounds of general formula (I) which are disclosed in the Example Section of this text, infra.

The compounds according to the invention of general formula (I) can be prepared according to the following schemes 1, 2, 3 and 4. The schemes and procedures described below illustrate synthetic routes to the compounds of general formula (I) of the invention and are not intended to be limiting. It is clear to the person skilled in the art that the order of transformations as exemplified in schemes 1, 2, 3 and 4 can be modified in various ways. The order of transformations exemplified in these schemes is therefore not intended to be limiting. In addition, interconversion of any of the substituents $R^1$, $R^2$, $R^3$, $R^4$, $R^5$, $R^6$, $R^{7a}$ or $R^{7b}$ can be achieved before and/or after the exemplified transformations. These modifications can be such as the introduction of protecting groups, cleavage of protecting groups, reduction or oxidation of functional groups, halogenation, metalation, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

Routes for the preparation of compounds of general formula (I) and corresponding intermediates are described in schemes 1, 2, 3 and 4.

Scheme 1: Route for the preparation of compounds of general formula (I) in which X is a leaving group, R is methyl, ethyl or tert-butyl and $R^1$, $R^2$, $R^3$, $R^4$, $R^5$, $R^6$, $R^{7a}$ and $R^{7b}$ have the meaning as given for the general formula (I), spura.

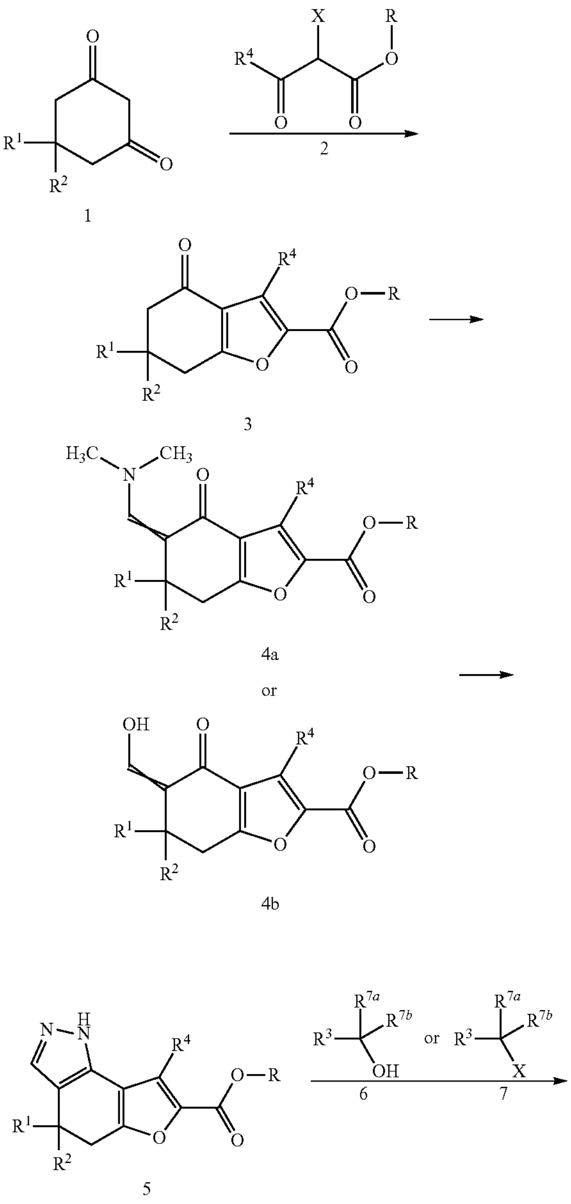
1
2
3
4a
or
4b
5
6
or
7

-continued

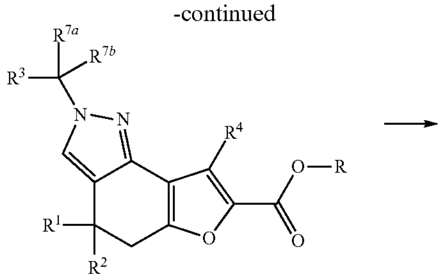

8

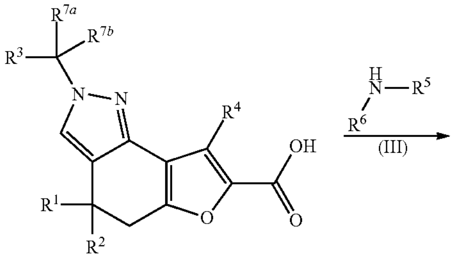

9

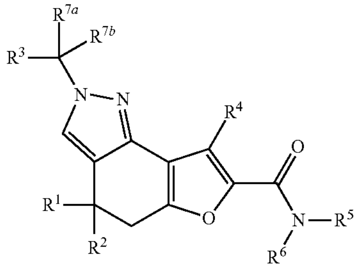

(I)

Tetrahydrobenzofuranes of general formula (3) can be obtained via aldol condensation of (1) and (2) followed by intramolecular cyclisation according to the procedures described by Stetter at al. (Chem. Ber. 1960, 93, 603-607) as depicted in Scheme 1. Compounds (1) and (2) are either commercially available or can be prepared according to procedures available from the public domain, as understandable to the person skilled in the art. Depending on the reactivity of the involved centers the regioisomer of (3) can be obtained [i.e. in cases where nucleophilic displacement of the leaving group of (2) by the acidic methylene unit of (1) is taking place prior to intramolecular condensation with the ketone moiety of (2)].

In general, 1,3-diketones of formula (I) can be reacted with alpha-carbonylesters of general formula (2) in the presence of inorganic bases like sodium hydroxide or potassium hydroxide, preferably potassium hydroxide, in protic solvents such as for example methanol, ethanol or water or mixtures thereof, preferably a mixture of the alcohol incorporated in ester (2) and water, at temperatures between 0° C. and the boiling point of the solvent (mixture), preferably between room temperature and 50° C. The reaction times vary between 15 hours and several days. It is usually necessary to isomerize the primary formed cyclisation products to the tetrahydrobenzofuranes of general formula (3) by treatment with acids such as aqueous hydrochloric acid at pH 1-4 at temperatures between 0° C. and the boiling point of the solvent (mixture), preferably at room temperature, for 1-6 hours.

Alternatively, (1) and (2) may be reacted in the presence of organic bases like triethylamine in aprotic solvents like dichloromethane, dichloroethane or tetrahydrofuran, preferably dichloromethane or dichloroethane, at temperatures between room temperature and the boiling point of the solvent, preferably at 40-60° C. (pressure tube), for 12-72 h followed by treatment with acids such as aqueous hydrochloric acid at pH 1-4 at temperatures between 0° C. and the boiling point of the solvent (mixture), preferably at room temperature, for 3-24 hours.

Alternatively, (1) and (2) may be reacted without further additives in toluene at temperatures between room temperature and 120° C., preferably at 80-120° C. for 12-hours.

Enamines of general formula (4a) can be synthesized from tetrahydrobenzofuranes of general formula (3) by alpha-methylation with electrophiles like 1-tert-butoxy-N,N,N',N' tetramethylmethanediamine (Bredereck's reagent) or 1,1-dimethoxy-N,N-dimethylmethanamine, preferably 1-tert-butoxy-N,N,N',N'-tetramethylmethanediamine, in aprotic solvents like benzene, toluene or dioxane, preferably toluene, at temperatures between room temperature and the boiling point of the solvent, preferably at 100-110° C., for 15 hours or up to several days.

Alternatively, tetrahydrobenzofuranes of general formula (3) can be transferred to alpha-hydroxymethyleneketones of general formula (4b) by formylation with formic acid derivatives such as ethyl formate or methyl formate in the presence of bases such as sodium methylate, sodium ethylate, potassium tert-butoxide or sodium hydride in solvents such as methanol, ethanol, toluene or tetrahydrofuran or mixtures thereof at temperatures between 0° C. and the boiling point of the solvent (mixture), preferably between room temperature and 50° C., for 1-18 hours.

Furoindazoles of general formula (5) can be obtained starting from either enamines of general formula (4a) or alpha-hydroxymethyleneketones of general formula (4b) by reacting (4a) or (4b) with hydrazine or hydrazine derivatives such as hydrazine hydrates or hydrazine salts, preferably hydrazine hydrate or hydrazine dihydrochloride, in polar protic solvents like ethanol or water or mixtures thereof, preferably ethanol/water mixtures, at temperatures between room temperature and the boiling point of the solvent (mixture), preferably at 70-80° C., for 4-18 hours.

2-Substituted furoindazole esters of general formula (8) can be synthesized from furoindazoles of general formula (5) either by Mitsunobu reaction with alcohols of general formula (6) in the presence of activating reagents such as diisopropyl azodicarboxylate (DIAD) or N,N,N',N'-tetramethylazodicarboxamide (TMAD) and a tertiary posphine such as triphenylphosphine or tri-n-butylphosphine, preferably a combination of TMAD and tri-n-butylphosphine, in aprotic solvents such as tetrahydrofuran or toluene, preferably toluene, at temperatures between room temperature and the boiling point of the solvent, preferably at room temperature, for 12-48 hours. Alternatively, 2-substituted furoindazoles of general formula (8) can be synthesized from furoindazoles of general formula (5) by reaction with electrophiles of general formula (7) such as alkyl halides or alkyl tosylates or alkyl mesylates, preferably alkyl bromides, in the presence of an inorganic base such as potassium carbonate or in the presence of an organic base such as triethylamine or N,N-diisopropylethylamine, preferably potassium carbonate, in a polar, aprotic solvent such as acetonitrile or ethyl acetate, preferably acetonitrile, at temperatures between room temperature and the boiling point of the solvent, preferably at 60-75° C. It can be beneficial to add a catalyst like 4-dimethylaminopyridine (DMAP) to the mixture. Generally, depending on the reactivity of the involved centers the 1-substituted regioisomer of (8) can be obtained in certain cases as well.

Carboxylic acids of general formula (9) may be obtained from carboxylic esters of formula (8) by saponification with inorganic bases such as lithium hydroxide, potassium hydroxide or sodium hydroxide, preferably lithium hydroxide, in a suitable solvent such as methanol, ethanol, tetrahydrofuran, water or mixtures thereof, preferably a mixture of the alcohol incorporated in ester (8), THF and water, at temperatures between 0° C. and the boiling point of the solvent (mixture), typically at 70° C., for 4-48 hours.

Furoindazoles of general formula (I) may be synthesized from suitably functionalized carboxylic acids of general formula (9) by reaction with appropriate amines $HN(R^5)(R^6)$ (III). For amide formation, however, all processes that are known from peptide chemistry to the person skilled in the art may be applied. The acids of general formula (9) can be reacted with an appropriate amine in aprotic polar solvents, such as for example DMF, acetonitrile or N-methylpyrrolid-2-one via an activated acid derivative, which is obtainable for example with hydroxybenzotriazole and a carbodiimide such as for example diisopropylcarbodiimide, or else with preformed reagents, such as for example O-(7-azabenzotriazol-1-yl)-1,1,3,3-tetramethyluronium hexafluorophosphate (see for example *Chem. Comm.* 1994, 201-203), or else with activating agents such as dicyclohexylcarbodiimide/N,N-dimethylaminopyridine or N-ethyl-N'N'-dimethylaminopropylcarbodiimide/N,N-dimethylaminopyridine. The addition of a suitable base such as for example N-methylmorpholine, triethylamine or DIPEA may be necessary. In certain cases, the activated acid derivative might be isolated prior to reaction with the appropriate amine. Amide formation may also be accomplished via the acid halide (which can be formed from a carboxylic acid by reaction with e.g. oxalyl chloride, thionyl chloride or sulfuryl chloride), mixed acid anhydride (which can be formed from a carboxylic acid by reaction with e.g. isobutylchloroformate), imidazolide (which can be formed from a carboxylic acid by reaction with e.g. carbonyldiimidazole) or azide (which can be formed from a carboxylic acid by reaction with e.g. diphenylphosphorylazide).

Scheme 2: Alternative route for the preparation of intermediates of general formula (3) in which Hal is a halogen atom, R is methyl, ethyl or tert-butyl and $R^1$, $R^2$, and $R^4$ have the meaning as given for general formula (I), supra.

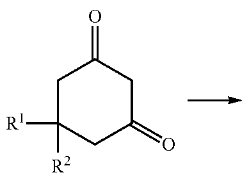

1

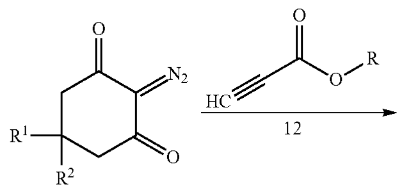

12

11

-continued

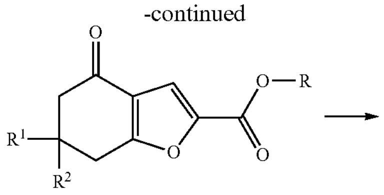

13

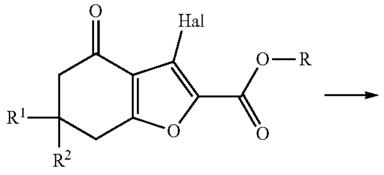

14

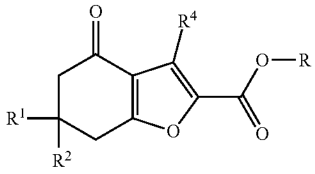

3

An alternative route for the preparation of tetrahydrobenzofurane intermediates of general formula (3) is depicted in Scheme 2. 1,3-Diketones of general formula (I) may be converted to diazodicarbonyl compounds of general formula (11) by diazo transfer as described in Synthesis 2011, 16, 2549-2552 or Synlett 2009, 18, 2943-2944.

Bicyclic furane esters of general formula (13) can be synthesized in a [3+2] cycloaddition from diazodicarbonyl compounds of general formula (11) and terminal alkynes of general formula (12) in the presence of a metal catalyst such as $Ru(PPh_3)_3Cl_2$ according to the procedures described by Lee at al. (Eur. J. Org. Chem. 2014, 3430-3442).

Halogenated furanes of general formula (14) may be obtained from furanes of general formula (13) by any aromatic halogenation reaction known to the person skilled in the art. For example, compounds of formula (13) may be reacted with halogen electrophiles such as N-bromosuccinimide (NBS) or N-iodosuccinimide (NIS), preferably NBS, in polar solvents such as pyridine or N,N-dimethylformamide, preferably pyridine, at temperatures between 0° C. and the boiling point of the solvent, preferably at room temperature. The reaction times vary between 2 hours and several days.

Tetrahydrobenzofurane intermediates of general formula (3) in turn may be obtained from halogenated furanes of general formula (14) by Suzuki reaction or radical processes like light-induced reactions applying photocatalysts.

An alternative route for the preparation of 8-methyl-furoindazoles of general formula (Ia) is depicted in Scheme 3. 3-Methyl-tetrahydrobenzofuranes of general formula (16) can be synthesized from 1,3-dicarbonyls of general formula (I) by a two-step procedure involving reaction of the enolate of (1) with allenic sulfonium salt (15) [prepared in situ by reaction of propargyl bromide with dimethyl sulfide] and subsequent acid catalysed isomerization to (16) according to the procedures described by Kanematsu et al. (J. Org. Chem. 1993, 58, 3960-3968 and Heterocycles 1990, 31, 6, 1003-1006).

Brominated furanes of general formula (17) may be obtained from furanes of general formula (16) by any aromatic bromination reaction known to the person skilled in the art. For example, compounds of formula (16) may be reacted with bromo electrophiles such as N-bromosuccinimide (NBS) in polar solvents such as pyridine or N,N-dimethylformamide, preferably pyridine, at temperatures between 0° C. and the boiling point of the solvent, preferably at room temperature. The reaction times vary between 2 hours and several days.

Enamines of general formula (18a) and alpha-hydroxymethyleneketones of general formula (18b) can be synthesized starting from compounds of general formula (17) according to the procedures described for (4a) and (4b) in Scheme 1.

8-Methyl-furoindazoles of general formula (19) can be obtained from either (18a) or (18b) by reaction with hydrazine derivatives as described for the synthesis of (5) in Scheme 1.

Scheme 3: Alternative route for the preparation of compounds of general formula (Ia) in which $R^4 = CH_3$ and $R^1$, $R^2$, $R^3$, $R^5$, $R^6$, $R^{7a}$ and $R^{7b}$ have the meaning as given for general formula (I), spura.

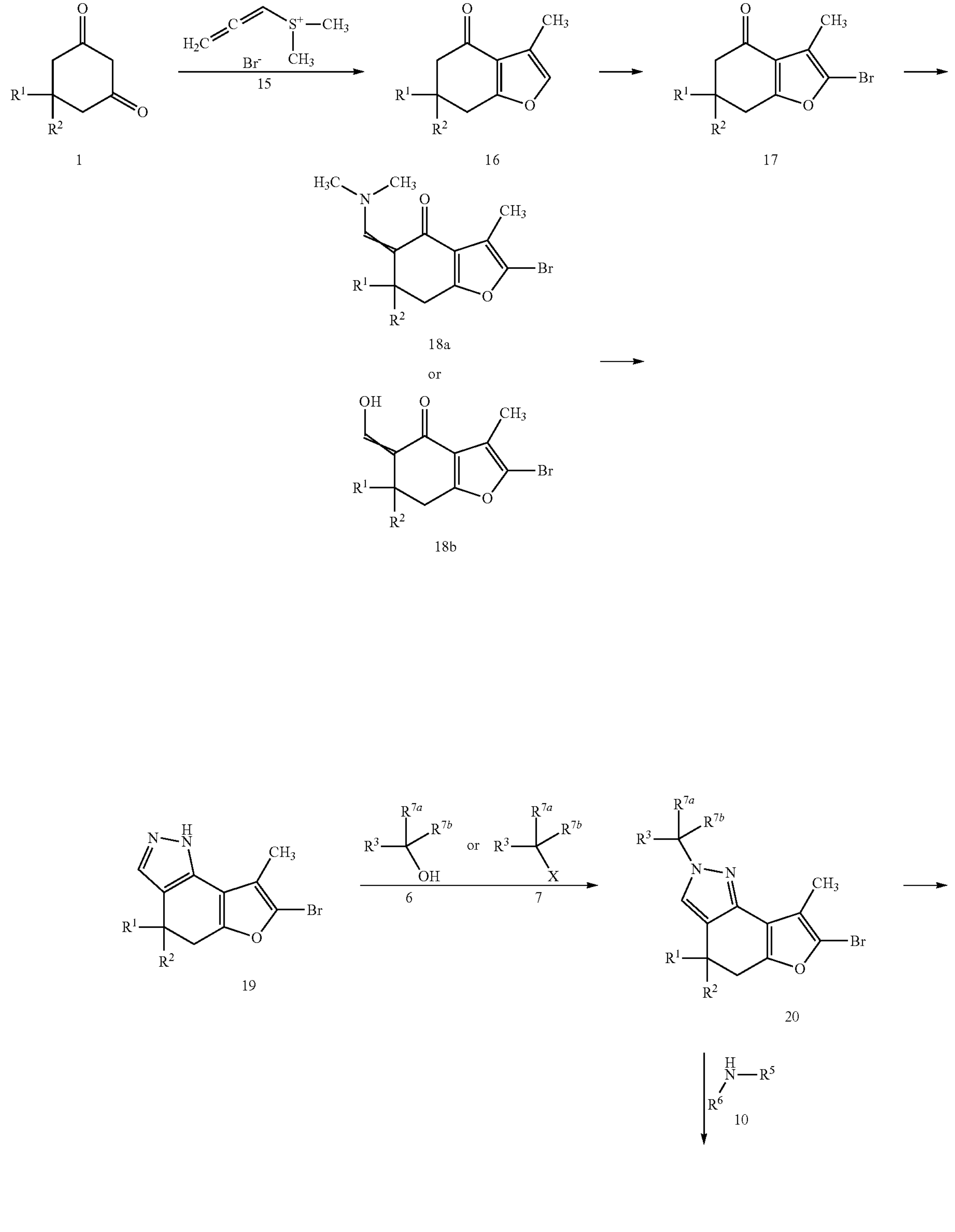

1

15

16

17

18a or

18b

19

6 or

7

20

10

-continued

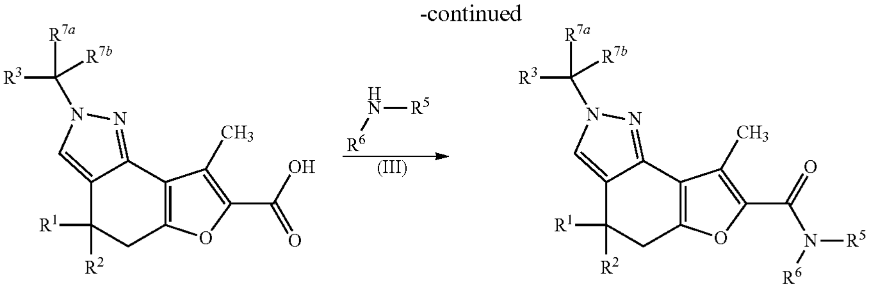

21

(Ia)

2-Substituted furoindazoles of general formula (20) can be synthesized from compounds of general formula (19) and alcohols (6) or electrophiles (7) as described for the synthesis of (8) from (5) in Scheme 1.

Carboxylic acids of general formula (21) may be obtained from bromo-furoindazoles (20) by carbonylation reactions. Bromides of general formula (20) can be reacted in the presence of a carbon monoxide source such as for example molybdenum hexacarbonyl or under a carbon monoxide atmosphere at pressures between 1 and 20 bar (autoclave), preferably under a carbon monoxide atmosphere at 15 bar (autoclave), and in the presence of a suitable palladium catalyst such as palladium actetate or bis(triphenylphosphine) palladium(II) dichloride, preferably palladium acetate, and in the presence of a ligand such as 1,1'-bis (diphenylphosphino)ferrocene and a suitable base such as potassium acetate in a polar solvent such as dimethylsulfoxide at temperatures between room temperature and 180° C., preferably at 100° C., for 12-24 h.

8-Methyl-furoindazoles of general formula (Ia) can be synthesized from suitably functionalized carboxylic acids of general formula (21) by amide coupling reactions with appropriate amines $HN(R^5)(R^6)$ (Ill) as described for the synthesis of furoindazoles of general formula (I) from (9) in Scheme 1.

Alternatively, 8-methyl-furoindazoles of general formula (Ia) may be directly synthesized from aryl bromides of general formula (20) by reaction with appropriate amines $HN(R^5)(R^6)$ (Ill) under palladium catalyzed carbonylation conditions. For this carbonylation all processes that are known to the person skilled in the art may be applied. Bromides of formula (20) can be reacted with an appropriate amine (Ill) in the presence of a carbon monoxide source such as for example molybdenum hexacarbonyl or under a carbon monoxide atmosphere at pressures between 1 and 20 bar (autoclave) and in the presence of a palladium catalyst such as for example palladium(II) acetate and a base such as sodium carbonate in a polar aprotic solvent such as for example dioxane at temperatures between room temperature and the boiling point of the solvent, preferably at 110-140° C. (pressure tube). It might be necessary to add a ligand such as tri-tert-butylphosphonium tetrafluoroborate to the mixture.

An alternative approach to 8-methyl-furoindazoles of general formula (Ia) is depicted in Scheme 4. 8-Methyl-furoindazoles of general formula (24) can be obtained starting from 1,3-dicarbonyl compounds of general formula (I) in four steps via (16) and (22a) or (22b) and (23) according to the corresponding procedures described in Scheme 1 and Scheme 3.

Compounds of general formula (24) in turn can be formylated to give aldehydes of general formula (25) by all formylation processes that are known to the person skilled in the art. Furanes of general formula (24) can be reacted under Vilsmeier-Haack conditions with mixtures of N,N-dimethylformamide and phosphoryl chloride at temperatures between 0° C. and room temperature for 1-18 hours.

Carboxamides of general formula (Ia) can be directly obtained from aldehydes of general formula (24) similar to the procedures described in Synthesis 2003, 7, 1055-1064. Aldehydes of general formula (24) can be reacted with an appropriate amine (Ill) in the presence of cyanide salts like sodium cyanide or potassium cyanide and in the presence of oxidizing agents like manganese(IV) dioxide in solvents like tetrahydrofuran, dichloromethane or dimethylsulfoxide, preferably tetrahydrofuran, at temperatures between 0° C. and the boiling point of the solvent, preferably at room temperature for 24-96 hours.

Scheme 4: Alternative route for the preparation of compounds of general formula (Ia) in which $R^4 = CH_3$ and $R^1$, $R^2$, $R^3$, $R^5$, $R^6$, $R^{7a}$ and $R^{7b}$ have the meaning as given for general formula (I), spura.

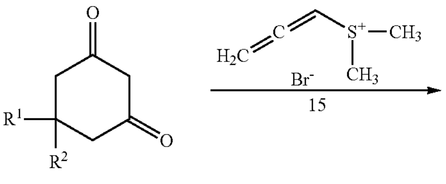

1

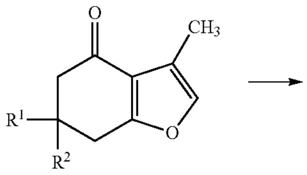

16

-continued

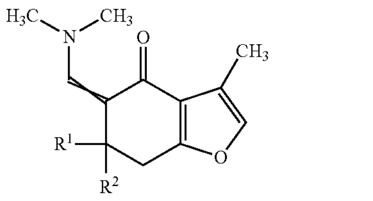

22a or

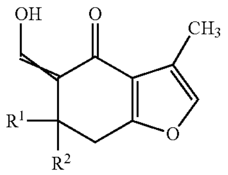

22b

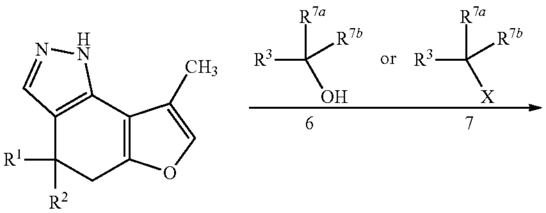

23

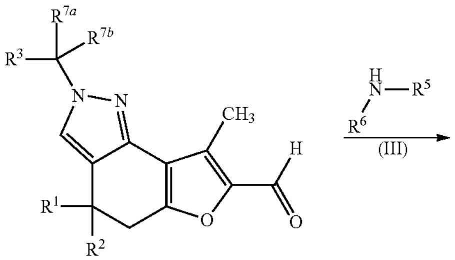

25

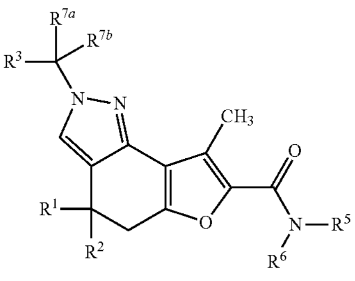

(Ia)

Specific examples are described in the Experimental Section.

In accordance with a second aspect, the present invention covers methods of preparing compounds of general formula (I) as defined supra, said methods comprising the step of allowing an intermediate compound of general formula (II):

(II)

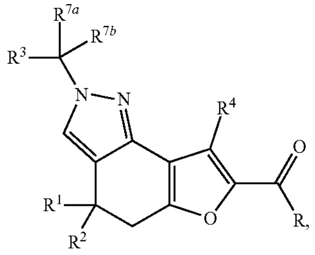

in which R is H or OH or OMe or OEt and $R^1$, $R^2$, $R^3$, $R^4$, $R^{7a}$ and $R^{7b}$ are as defined for the compound of general formula (I) as defined supra, to react with a compound of general formula (III):

(III)

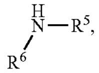

in which $R^5$ and $R^6$ are as defined for the compound of general formula (I) as defined supra, thereby giving a compound of general formula (I):

(I)

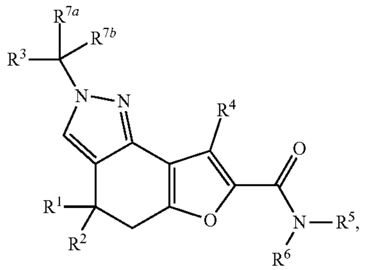

in which $R^1$, $R^2$, $R^3$, $R^5$, $R^6$, $R^{7a}$ and $R^{7b}$ are as defined supra.

In accordance with a third aspect, the present invention covers methods of preparing compounds of general formula (I) as defined supra, said methods comprising the step of allowing an intermediate compound of general formula (II):

(II)

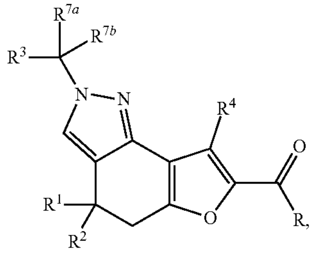

in which R is H, OH, OMe, or OEt and $R^1$, $R^2$, $R^3$, $R^4$, $R^{7a}$ and $R^{7b}$ are as defined for the compound of general formula (I) as defined supra, to react with a compound of general formula (III):

(III)

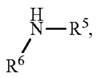

in which $R^5$ and $R^6$ are as defined for the compound of general formula (I) as defined supra, thereby giving a compound of general formula (I):

(I)

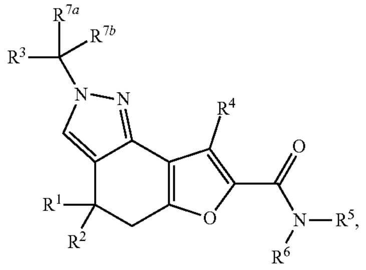

in which $R^1$, $R^2$, $R^3$, $R^5$, $R^6$, $R^{7a}$ and $R^{7b}$ are as defined supra, then optionally converting said compound into solvates, salts and/or solvates of such salts using the corresponding (i) solvents and/or (ii) bases or acids.

The present invention covers methods of preparing compounds of the present invention of general formula (I), said methods comprising the steps as described in the Experimental Section herein.

In accordance with a fourth aspect, the present invention covers intermediate compounds which are useful for the preparation of the compounds of general formula (I), supra.

Particularly, the invention covers the intermediate compounds of general formula (II):

(II)

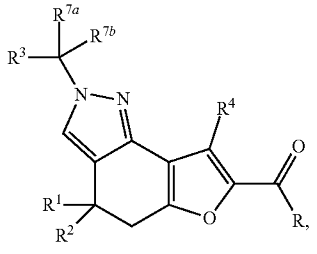

in which R is H or OH or OMe or OEt and $R^1$, $R^2$, $R^3$, $R^4$, $R^{7a}$ and $R^{7b}$ are as defined for the compound of general formula (I) supra.

In accordance with a fifth aspect, the present invention covers the use of said intermediate compounds for the preparation of a compound of general formula (I) as defined supra.

Particularly, the invention covers the use of intermediate compounds of general formula (II):

(II)

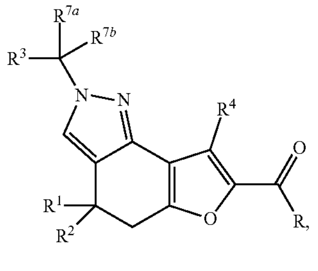

in which R is H or OH or OMe or OEt and $R^1$, $R^2$, $R^3$, $R^4$, $R^{7a}$ and $R^{7b}$ are as defined for the compound of general formula (I) supra, for the preparation of a compound of general formula (I) as defined supra.

The present invention covers the intermediate compounds which are disclosed in the Example Section of this text, infra.

The present invention covers any sub-combination within any embodiment or aspect of the present invention of intermediate compounds of general formula (II), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action which could not have been predicted. Compounds of the present invention have surprisingly been found to be effective antagonists of GPR84 and it is possible therefore that said compounds be used for the treatment or prophylaxis of diseases, in particular of autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

Compounds of the present invention can be utilized to inhibit, antagonize, block, reduce, decrease GPR84 signal transduction, activity and cellular function. This method comprises administering to a mammal in need thereof, including a human, an amount of a compound of this invention, or a pharmaceutically acceptable salt, isomer, polymorph, metabolite, hydrate, solvate or ester thereof; which is effective to treat the disorder.

In particular of autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

The Present Invention Also Provides Methods of Treating PCOS and Symptoms

These disorders have been well characterized in humans, but also exist with a similar aetiology in other mammals and can be treated by administering pharmaceutical compositions of the present invention.

The term "treating", or "treatment" as used in the present text is used conventionally, e.g., the management or care of a subject for the purpose of combating, alleviating, reducing, relieving, improving the condition of a disease or disorder, such as PCOS or IPF.

The compounds of the present invention can be used in particular in therapy and prevention, i.e. prophylaxis and treatment of autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

In accordance with a further aspect, the present invention covers compounds of general formula (I), as described supra, or stereoisomers, tautomers, N-oxides, hydrates, solvates, and salts thereof, particularly pharmaceutically acceptable salts thereof, or mixtures of same, for use in the treatment or prophylaxis of diseases, in particular autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

The pharmaceutical activity of the compounds according to the invention can be explained by their activity as GPR84 antagonists.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, for the treatment or prophylaxis of diseases, in particular autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

In accordance with a further aspect, the present invention covers the use of a compound of formula (I), described supra, or a stereoisomer, a tautomer, an N-oxide, a hydrate, a solvate, or a salt thereof, particularly a pharmaceutically acceptable salt thereof, or a mixture of same, for the prophylaxis or treatment of diseases, in particular autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

In accordance with a further aspect, the present invention covers the use of compounds of general formula (I), as described supra, or stereoisomers, tautomers, N-oxides, hydrates, solvates, and salts thereof, particularly pharmaceutically acceptable salts thereof, or mixtures of same, in a method of treatment or prophylaxis of diseases, in particular autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

In accordance with a further aspect, the present invention covers use of a compound of general formula (I), as described supra, or stereoisomers, tautomers, N-oxides, hydrates, solvates, and salts thereof, particularly pharmaceutically acceptable salts thereof, or mixtures of same, for the preparation of a pharmaceutical composition, preferably a medicament, for the prophylaxis or treatment of diseases, in particular autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals.

In accordance with a further aspect, the present invention covers a method of treatment or prophylaxis of diseases, in particular autoimmune diseases such as multiple sclerosis, psoriasis, psoriatic arthritis, rheumatoid arthritis, ankylosing spondylitis, systemic lupus erythematosus, primary and secondary autoimmune uveitis, inflammatory disorders like endometriosis, inflammatory eye diseases, inflammatory kidney diseases, inflammatory liver diseases like non-alcoholic, alcoholic- and toxic fatty liver diseases, lung diseases like asthma, idiopathic pulmonary fibrosis, chronic obstructive pulmonary disease and metabolic and metabolic-endocrine disorders like metabolic syndrome, insulin resistance, diabetes mellitus type I and type II, and polycystic ovary syndrome (PCOS) disorders, neuropathic and inflammatory pain disorders in humans and animals, using an effective amount of a compound of general formula (I), as described supra, or stereoisomers, tautomers, N-oxides, hydrates, solvates, and salts thereof, particularly pharmaceutically acceptable salts thereof, or mixtures of same.

In accordance with a further aspect, the present invention covers pharmaceutical compositions, in particular a medicament, comprising a compound of general formula (I), as described supra, or a stereoisomer, a tautomer, an N-oxide, a hydrate, a solvate, a salt thereof, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore covers pharmaceutical compositions, in particular medicaments, which comprise at least one compound according to the invention, conventionally together with one or more pharmaceutically suitable excipients, and to their use for the above-mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophilizates, capsules (for example hard or soft gelatine capsules), sugar-coated tablets, granules, pellets, powders, emulsions, suspensions, aerosols or solutions. It is possible to incorporate the compounds according to the invention in crystalline and/or amorphized and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophilizates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example gelatine, hydroxypropylmethylcellulose),
- synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

EXPERIMENTAL SECTION

NMR peak forms are stated as they appear in the spectra, possible higher order effects have not been considered.

The $^1$H-NMR data of selected compounds are listed in the form of $^1$H-NMR peaklists. Therein, for each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\gamma_2$ (intensity$_2$), . . . , $\gamma_i$ (intensity$_i$), . . . , $\gamma_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Chemical names were generated using the ACD/Name software from ACD/Labs. In some cases, generally accepted names of commercially available reagents were used in place of ACD/Name generated names.

The following Table 1 lists the abbreviations used in this paragraph and in the Examples section as far as they are not explained within the text body. Other abbreviations have their meanings customary per se to the skilled person.

The following table lists the abbreviations used herein.

TABLE 1

| Abbreviations | |
|---|---|
| Abbreviation | Meaning |
| br. | broad signal in NMR |
| br. s. | broad singlet |
| CDI | di-1H-imidazol-1-ylmethanone |
| conc. | concentrated |
| CPME | cyclopentyl methyl ether |
| d | doublet |
| dd | doublet of doublets |
| ddd | doublet of doublet of doublets |
| dt | doublet of triplets |
| DCM | dichloromethane |
| DEA | diethylamine |
| DIPEA | N,N-diisopropylethyl amine |
| DMAP | N,N-dimethylpyridin-4-amine |
| DMF | N,N-dimethylformamide |
| DMSO | dimethyl sulfoxide |
| EDC | N-(3-dimethylaminopropyl)-N'-ethylcarbodiimide hydrochloride |
| ESI | electrospray ionization |
| ESIpos | Positive electrospray ionization |
| ESIneg | Negative electrospray ionization |
| EtOAc | ethyl acetate |
| EtOH | ethanol |
| eq. | equivalent |
| GP | General procedure |
| h | hour(s) |
| HATU | O-(7-azabenzotriazol-1-yl)-1,1,3,3-tetramethyluronium hexafluorophosphate |
| HCl | hydrochloric acid |
| HCOOH | formic acid |
| HPLC, LC | high performance liquid chromatography |
| LC-MS/LCMS | Liquid chromatography mass spectrometry |
| m | multiplet |
| min | minute(s) |
| MS | mass spectroscopy |
| MeCN | acetonitrile |
| MeOH | methanol |
| NMR | nuclear magnetic resonance |
| q | quartet |
| quint | quintet |
| $R_t$ | retention time |
| rt | room temperature |
| s | singlet |
| sept | septet |
| t | triplet |
| TFA | trifluoroacetic acid |
| THF | tetrahydrofuran |
| TMAD | N,N,N',N'-tetramethylazodicarboxamide |
| UPLC | ultra performance liquid chromatography |
| UPLC-MS | ultra performance liquid chromatography mass spectrometry |

The various aspects of the invention described in this application are illustrated by the following examples which are not meant to limit the invention in any way.

The example testing experiments described herein serve to illustrate the present invention and the invention is not limited to the examples given.

EXPERIMENTAL SECTION—GENERAL PART

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartridges KP-Sil® or KP—NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−). In most of the cases method 1 is used. If not, it is indicated.

Method 1:

Instrument: Waters Acquity UPLC-MS SQD 3001; Column: Acquity UPLC BEH C18 1.7 μm, 50×2.1 mm; Eluent A: water+0.2 vol % ammonia, Eluent B: acetonitrile; Gradient: 0-1.6 min 1-99% B, 1.6-2.0 min 99% B; Flow rate: 0.8 mL/min; Temperature: 60° C.; Injection: 2 μL; DAD scan: 210-400 nm; ELSD.

Method 2:

Instrument: Waters Acquity UPLC-MS SQD 3001; Column: Acquity UPLC BEH C18 1.7 μm, 50×2.1 mm; Eluent A: water+0.1 vol % formic acid, Eluent B: acetonitrile; Gradient: 0-1.6 min 1-99% B, 1.6-2.0 min 99% B; Flow rate: 0.8 mL/min; Temperature: 60° C.; Injection: 2 μL; DAD scan: 210-400 nm.

LC-MS Standard Procedures

Method A:

Instrument: Waters Acquity UPLCMS SingleQuad; Colum: Acquity UPLC BEH C18 1.7 μm, 50×2.1 mm; Eluent A: water+0.2 vol % aqueous ammonia (32%), Eluent B: acetonitrile; Gradient: 0-1.6 min 1-99% B, 1.6-2.0 min 99% B; Flow: 0.8 mL/min; Temperature: 60° C.; DAD scan: 210-400 nm.

Method B: 5-95AB, Shimadzu

Instrument: SHIMADZU LCMS-2020 SingleQuad; Column: Chromolith@Flash RP-18E 25-2 MM; Eluent A: water+0.0375 vol % trifluoroacetic acid, Eluent B: acetonitrile+0.01875 vol % trifluoroacetic acid; Gradient: 0-0.8 min, 5-95% B, 0.8-1.2 min 95% B; Flow: 1.5 mL/min; Temperature: 50° C.; PDA: 220 nm & 254 nm.

Method C: 5-95AB, Agilent

Instrument: Agilent 1100\G1956A SingleQuad; Column: Kinetex@ 5 μm EVO C18 30*2.1 mm; Eluent A: water+0.0375 vol % trifluoroacetic acid, Eluent B: acetonitrile+0.01875 vol % trifluoroacetic acid; Gradient: 0-0.8 min 5-95% B, 0.8-1.2 min 95% B; Flow: 1.5 mL/min; Temperature: 50° C.; PDA: 220 nm & 254 nm.

Method D: 5-95CD, Shimadzu

Instrument: SHIMADZU LCMS-2020 SingleQuad; Column: Kinetex EVO C18 2.1*30 mm, μm; Eluent A: water+0.025 vol % ammonium hydroxide, Eluent B: acetonitrile; gradient: 0-0.8 min, 5-95% B, 0.8-1.2 min 95% B; Flow: 1.5 mL/min; Temperature: 40° C.; PDA: 220 nm & 254 nm.

Method E: 5-95CD, Shimadzu

Instrument: SHIMADZU LCMS-2020 SingleQuad; Column: Kinetex EVO C18 2.1*30 mm, um; eluent A: water+0.025 vol % ammonium hydroxide, eluent B: acetonitrile; gradient: 0-0.8 min, 5-95% B, 0.8-1.2 min, 95% B; flow 1.5 ml/min; temperature: 40° C.; PDA: 220 nm & 254 nm.

Analytical characterization of enantiomers was performed by analytical chiral HPLC. In the description of the individual examples is referred to the applied HPLC procedure.

Purification Methods:

Biotage Isolera™ chromatography system (http://www.biotage.com/product-area/flash-purification) using pre-packed silica and pre-packed modified silica cartridges.

Preparative HPLC, Method A: Instrument: pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; eluent A: water+0.2 vol-% ammonia (32%), eluent B: acetonitrile;

gradient A: 0-15 min 1-25% B; flow: 60 ml/min;
gradient B: 0-15 min 10-50% B; flow: 60 ml/min;
gradient C: 0-15 min 15-55% B; flow: 60 ml/min;
gradient D: 0-15 min 30-70% B; flow: 60 ml/min;
gradient E: 0-15 min 40-80% B; flow: 60 ml/min;
gradient F: 0-15 min 65-100% B; flow: 60 ml/min;
temperature: 25° C.; solution: max. 250 mg/2 ml dimethyl sulfoxide; injection: 1×2 ml; Detection: UV 254 nm; Software: SCPA PrepCon5.

Preparative HPLC, Method B: Instrument: pump: Labomatic HD-5000 or HD-3000, head HDK 280, lowpressure gradient module ND-B1000; manual injection valve: Rheodyne 3725i038; detector: Knauer Azura UVD 2.15; collector: Labomatic Labocol Vario-4000; column: Chromatorex RP C-18 10 μm, 125×30 mm; eluent A: water+0.1 vol % formic acid (99%), eluent B: acetonitrile;

gradient A: 0-15 min 1-25% B; flow: 60 ml/min;
gradient B: 0-15 min 10-50% B; flow: 60 ml/min;
gradient C: 0-15 min 15-55% B; flow: 60 ml/min;

gradient D: 0-15 min 30-70% B; flow: 60 ml/min;
gradient E: 0-15 min 40-80% B; flow: 60 ml/min;
gradient F: 0-15 min 65-100% B; flow: 60 ml/min;
temperature: 25° C.; solution: max. 250 mg/2 ml dimethyl sulfoxide; injection: 1×2 ml; Detection: UV 254 nm; Software: SCPA PrepCon5.

EXPERIMENTAL SECTION—GENERAL PROCEDURES

General Procedure a (GP A):

Alpha-formylation reaction (3→4a/b, Scheme 1 or 17→18a/b, Scheme 3 or 16→22a/b, Scheme 4)

(conditions A: enamine formation); similar to H. Bredereck et al., Liebigs Ann. Chem. 1980, 3, 344-357 and WO2010/078427, p. 222.

To a solution of the respective ketone (1 eq.) in toluene at r.t. is added 1-tert-butoxy-N,N,N',N'-tetramethylmethanediamine (Bredereck's reagent, CAS No. [5815-08-7]; 1.2-5 eq.) or 1,1-dimethoxy-N,N-dimethylmethanamine (1.2-5 eq.) and the reaction mixture is stirred at 100-120° C. until TLC and/or LCMS indicate complete consumption of the starting material (overnight or up to 6 days). The reaction mixture is concentrated under reduced pressure and used in the subsequent reaction without further purification steps.

Alpha-formylation reaction (3→4a/b, Scheme 1 or 17→18a/b, Scheme 3 or 16→22a/b, Scheme 4)

(conditions B: enol formation); similar to M. L. Hammond et al., J. Med. Chem. 1989, 32, 1006-1020 and D. J. Goldsmith et al., J. Org. Chem. 1980, 45, 3989-3993 and G. Grandolini et al., Gazzetta Chimica Italiana 1976, 106, 1083-1094.

To a solution of ethyl formate (CAS No. [109-94-4]; 2.0-6.0 eq.) in toluene is added sodium hydride (3.0 eq., 60% purity) at 0° C. After stirring for 0.5 hours, a solution of the respective ketone (1.0 eq.) in toluene is added to the above mixture. The reaction mixture is stirred at room temperature or 45° C. until TLC and/or LCMS indicate complete consumption of the starting material (typically 2 h or up to overnight). The reaction mixture is quenched with 2 N aqueous hydrochloric acid and the phases separated. The aqueous phase is extracted with ethyl acetate and the combined organic phases are washed with brine, dried with anhydrous sodium sulfate, filtrated and concentrated under reduced pressure. The obtained crude desired product is used in the subsequent reaction without further purification steps.

General Procedure B (GP B):

Furoindazole formation (4a/b→5, Scheme 1 or 18a/b→19, Scheme 3 or 22a/b→23, Scheme 4); similar to G. Grandolini et al., Gazzetta Chimica Italiana 1976, 106, 1083-1094 and W. A. Remers et al., J. Heterocycl. Chem. 1975, 12, 421-422.

To a solution of the respective enamine or enol (1.0 eq.) in ethanol is added a solution of hydrazine hydrate 1:1 (CAS No. [7803-57-8]; 5.0 eq.) or hydrazine dihydrochloride (CAS No. [5341-61-7]; 2.0 eq.) in water or ethanol at room temperature. The reaction mixture is stirred at 60-70° C. until TLC and/or LCMS indicate complete consumption of the starting material (typically 2 h or up to overnight). After quenching with sodium hypochlorite at 0° C., the biphasic mixture is concentrated under reduced pressure. The residue is either directly submitted to column chromatography ($SiO_2$) or partitioned between water and ethyl acetate. The aqueous layer is extracted with ethyl acetate and the combined organic layers are washed brine, filtrated and concentrated under reduced pressure to give the crude title compound which is purified via column chromatography ($SiO_2$) where appropriate.

General Procedure C (GP C):

Furoindazole alkylation (5→8, Scheme 1 or 19→20, Scheme 3 or 23→24, Scheme 4)

(conditions A: Mitsunobu reaction; in analogy to D. L. Selwood et al., J. Med. Chem. 2009, 52, 2694-2707)

To a solution of the respective furoindazole (1.0 eq.) and alcohol (1-2 eq.) in toluene at rt is added tri-n-butylphosphine (CAS No. [998-40-3]; 1.5-3 eq.) and N,N,N',N' tetramethylazodicarboxamide (TMAD, CAS No. [10465-78-8]; 1.5-3 eq.) and the reaction mixture is stirred at rt until TLC and/or LCMS indicate complete consumption of the starting material (typically overnight). The reaction mixture is diluted with water and the phases separated. The aqueous phase is extracted with dichloromethane (two to three times), the combined organic phases dried with $MgSO_4$ or $Na_2SO_4$, filtrated and concentrated. The obtained crude material is subjected to column chromatography ($SiO_2$) to give the desired alkylation product. Usually, the 2-substituted indazoles are obtained as major products.

Furoindazole alkylation (5→8, Scheme 1 or 19→20, Scheme 3 or 23→24, Scheme 4)

(conditions B: reaction with alkyl (pseudo)halides)

A solution of the respective furoindazole (1.0 eq.) and alkyl (pseudo)halide (1.5-3 eq.) in acetonitrile or ethyl acetate at rt is treated with potassium carbonate (5-15 eq.) and N,N-dimethylpyridin-4-amine (DMAP, CAS No. [1122-58-3]; 2.5 mol %). The reaction mixture is stirred at 60-70° C. until TLC and/or LCMS indicate complete consumption of the starting material (typically overnight or up to several days). The reaction mixture is cooled to rt and filtrated. The filtrate is concentrated under reduced pressure and the residue subjected to column chromatography ($SiO_2$) to give the desired alkylation product.

General Procedure D (GP D):

Saponification of furoindazole ester (8→9, Scheme 1)

A solution of the respective furoindazole ester (1.0 eq.) in a mixture of tetrahydrofuran and ethanol (1:1) at rt is treated with aqueous lithium hydroxide (2 M, 15 eq.). In some cases, aqueous sodium hydroxide (30 eq.) in THF is used instead. The reaction mixture is stirred at 60-70° C. until TLC and/or LCMS indicate complete consumption of the starting material (typically overnight). The reaction mixture is cooled to rt, acidified with aqueous hydrochloric acid to pH 3-5 and extracted with ethyl acetate. The desired carboxylic acid either precipitates in the aqueous phase (potentially as HCl salt) and can be isolated by filtration and drying and is used in the subsequent reaction without further purification steps. Alternatively, the phases are separated, the organic phase washed with brine, dried over $Na_2SO_2$, filtrated and concentrated under reduced pressure to give the desired carboxylic acid which is used in the subsequent reaction without further purification steps.

General Procedure E (GP E):

Carboxylation of furoindazole bromide (20→21, Scheme 3)

The furoindazole bromide (1.0 eq.) is placed into a steel autoclave under argon atmosphere and dissolved in dimethyl sulfoxide (ca. 15 mL/mmol). Palladium(II) acetate (5.0 mol %), 1,1'-bis(diphenylphosphino)ferrocene (CAS No. [12150-46-8]; 0.20 eq.) and potassium acetate (4.0 eq.) are added and the mixture is purged 3 times with carbon monoxide. The mixture is stirred for 30 min at 20° C. under a carbon monoxide pressure of ca. 11 bar. The autoclave is set under vacuum again, then a carbon monoxide pressure of ca. 15 bar is applied, and the mixture heated to 100° C. until TLC and/or LCMS indicate complete consumption of the starting material (usually 23 h), yielding a maximum pressure of ca. 18 bar. The reaction is cooled to rt, the pressure released, and the reaction mixture added to ice-water. The mixture is acidified with aqueous 1 M HCl (pH ca 2.5), stirred for 20 min and diluted with dichloromethane or ethyl acetate. The phases are separated, and the aqueous phase extracted with dichloromethane or ethyl acetate.

The combined organic phases are dried, filtrated and concentrated under reduced pressure. The obtained crude carboxylic acid is taken to the next step without further purification.

General Procedure F (GP F):

Vilsmeier-Haack formylation of furoindazoles (24→25, Scheme 4)

Phosphorylchloride (10 eq.) is dropwise added under ice cooling to N,N-dimethylformamide (10 eq.) and stirred for 15 minutes. A solution of the furoindazole (1.0 eq.) in N,N-dimethylformamide is dropwise added, the mixture warmed to rt and stirred until TLC and/or LCMS indicate complete consumption of the starting material (usually 1-2 hours). The reaction mixture is added to ice-water and the pH adjusted to ca 9 by addition of aqueous sodium hydroxide (4 M). The mixture is extracted with dichloromethane, the phases separated, and the combined organic phases are dried, filtrated and concentrated under reduced pressure. The obtained crude aldehyde is purified via column chromatography ($SiO_2$) where appropriate.

General Procedure G (GP G):

Amide formation (9→(I), Scheme 1 or 21→(Ia), Scheme 3)

(conditions A: amide coupling)

A solution of the carboxylic acid or corresponding salt (1.0 eq.) in DMF is treated with HATU (1.5 eq.) and DIPEA (3.0 eq.) and stirred for a couple of minutes at rt upon which the amine component (1-1.5 eq.) is added and stirring at rt continued until TLC and/or LCMS indicate complete consumption of the starting material (usually overnight). In most cases the reaction mixture is filtrated and purified by preparative HPLC to give the desired amide. In some cases, the reaction mixture is diluted with water and extracted with ethyl acetate. The organic phase is dried, filtered and purified by column chromatography ($SiO_2$) to give the desired amide.

Alternatively, a solution of the carboxylic acid or corresponding salt (1.0 eq.) in DMF is treated with 2,4,6-tripropyl-1,3,5,2,4,6-trioxatriphosphinane 2,4,6-trioxide (T3P, 50 wt % solution in DMF, 1.5-3 eq.), DIPEA (3-5 eq.) and the amine component (1-1.5 eq.) and the reaction mixture stirred at rt until TLC and/or LCMS indicate complete consumption of the starting material (usually overnight). The reaction mixture is filtrated and purified by preparative HPLC to give the desired amide.

Amide formation (20→(Ia), Scheme 3)

(conditions B: carbonylation of bromides to yield amides directly)

A solution of the furoindazole bromide (1.0 eq.) in 1,4-dioxane (containing ca. 1% water) is treated with the corresponding amine (3-5 eq.), molybdenum hexacarbonyl (CAS No. [13939-06-5]; 2.0 eq.), sodium carbonate (CAS No. [497-19-8]; 3.0 eq.), tri-tert-butylphosphonium tetrafluoroborate (CAS No. [131274-22-1]; 0.10 eq.) and palladium(II) acetate (CAS No. [3375-31-3]; 0.20 eq.) The reaction mixture is vigorously stirred at 120-140° C. until TLC and/or LCMS indicate complete consumption of the starting material (usually 18 h). The mixture is cooled to rt, solids are filtered off over Celite and rinsed with ethyl acetate. The filtrate is concentrated under reduced pressure and the obtained crude product purified by preparative HPLC.

Amide formation (25→(Ia), Scheme 4)

(conditions C: conversion of aldehydes to amides); similar to J. K. Taylor et al., Synthesis 2003, 7, 1055-1064.

A solution of the furoindazole aldehyde (1.0 eq.) in DMSO or THF is treated with the corresponding amine (5.0 eq.), sodium cyanide (1.0 eq.) and manganese(IV) dioxide (15 eq.) and stirred at rt for 30 minutes. Another amount of manganese(IV) dioxide (15 eq.) is added and stirring at rt continued until TLC and/or LCMS indicate complete consumption of the starting material (24 hours or up to several days). The reaction mixture is filtered over Celite, the filtrate concentrated under reduced pressure and the obtained crude product purified by preparative HPLC to give the desired amide.

General Procedure H (GP H):

Amide formation (9→(I), Scheme 1 or 21→(Ia), Scheme 3)

(Conditions A: Amide Coupling)

A solution of the carboxylic acid or corresponding salt (1.0 eq.) in DMF is treated with HATU (1.5 eq.) and DIPEA (3-6 eq.) and stirred for a couple of minutes at rt upon which the amine component (1-1.5 eq.) is added and stirring at rt continued until TLC and/or LCMS indicate complete consumption of the starting material (usually overnight). In most cases the reaction mixture is diluted with saturated ammonium chloride and extracted with ethyl acetate. The combined organic phase is washed with water, dried by hydrophobic filtration and purified by preparative HPLC to give the desired amide. In some cases the reaction mixture is filtrated and purified by preparative HPLC to give the desired amide.

Amide formation (9→(I), Scheme 1 or 21→(Ia), Scheme 3)

(Conditions B: Amide Coupling)

A solution of the carboxylic acid or corresponding salt (1.0 eq.) in DMF is treated with HATU (1.5 eq.) and DIPEA (3-6 eq.) and stirred for a couple of minutes at rt upon which the amine component (1-2 eq.) is added and stirring at rt continued until TLC and/or LCMS indicate complete consumption of the starting material (usually overnight). In most cases the reaction mixture is diluted with ethyl acetate and water. The water phase is extracted with ethyl acetate. The combined organic phase is washed with brine, dried over $Na_2SO_4$, and filtrated or hydrophobic filtration and purified by preparative HPLC to give the desired amide. In some cases the reaction mixture is filtrated and purified by preparative HPLC to give the desired amide.

(Conditions C: Amide Coupling)

A solution of the carboxylic acid or corresponding salt (1.0 eq.) in THF (and sometimes DMF to dissolve) is treated with HATU (1.5 eq.) and DIPEA (3-6 eq.) and stirred for a couple of minutes at rt upon which the amine component (1-2 eq.) is added and stirring at rt continued until TLC and/or LCMS indicate complete consumption of the starting material (usually 72 hours). In most cases the reaction mixture is diluted with sat. $NaHCO_3$/water (1:5) and ethyl acetate and stirred for 30 minutes. The phases were separated and the ethyl acetate phase is extracted with water. The combined organic phase was dried over $Na_2SO_4$, and filtrated or hydrophobic filtration and purified by preparative HPLC to give the desired amide. In some cases the reaction mixture is filtrated and purified by preparative HPLC to give the desired amide.

(Conditions D: Amide Coupling)

A solution of the carboxylic acid or corresponding salt (1.0 eq.) in DMF or THF is treated with HATU (1.5 eq.) and DIPEA (3-6 eq.) and stirred for a couple of minutes at rt upon which the amine component (1-1.5 eq.) is added and stirring at rt continued until TLC and/or LCMS indicate complete consumption of the starting material (usually overnight). In most cases the reaction mixture is diluted with saturated sodium bicarbonate/water and extracted with ethyl acetate. The combined organic phase is washed with brine, dried by hydrophobic filtration or over sodium sulfate and purified by preparative HPLC to give the desired amide. In some cases the reaction mixture is filtrated and purified by preparative HPLC to give the desired amide.

EXPERIMENTAL SECTION—INTERMEDIATES

Intermediate 1

Step 1

(5E/Z)-5-[(dimethylamino)methylidene]-6,7-dihydro-1-benzofuran-4(5H)-one

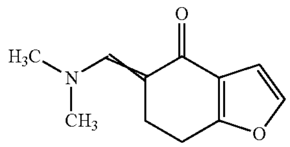

According to GP A (conditions A) 6,7-dihydro-1-benzofuran-4(5H)-one (commercially available, CAS No. [16806-93-2]; 5.00 g, 36.7 mmol) was reacted with 1-tert-butoxy-N,N,N',N'-tetramethylmethanediamine (Bredereck's reagent, CAS No. [5815-08-7]; 1.20 eq., 7.68 g, 44.1 mmol) in toluene (100 mL) at 100° C. for 2 h. Another amount of 1-tert-butoxy-N,N,N',N'-tetramethylmethanediamine (1.20 eq., 7.68 g, 44.1 mmol) was added and stirring at 100° C. continued for another 6 h. The reaction mixture was concentrated under reduced pressure and the obtained crude title compound used in the subsequent reaction without further purification steps.

UPLC-MS (Method 1): $R_t$=0.83 min; MS (ESIpos): m/z=192 $[M+H]^+$.

Step 2

4,5-dihydro-1H-furo[2,3-g]indazole

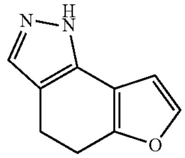 [SMILES: c1cc2c(o1)CCc1cn[nH]c1-2]

According to GP B crude (5E/Z)-5-[(dimethylamino)methylidene]-6,7-dihydro-1-benzofuran-4(5H)-one (1.0 eq., 7.0 g, 37 mmol) from step 1 was reacted with hydrazine hydrate 1:1 (5.0 eq., 8.9 mL, 180 mmol) in ethanol (100 mL) at 70° C. for 3 h to give upon column chromatography ($SiO_2$, DCM/MeOH) the title compound (5.6 g, 35% over two steps).

UPLC-MS (Method 1): $R_t$=0.80 min; MS (ESIpos): m/z=161 $[M+H]^+$.

Step 3

2-[(pyridin-2-yl)methyl]-4,5-dihydro-2H-furo[2,3-g]indazole

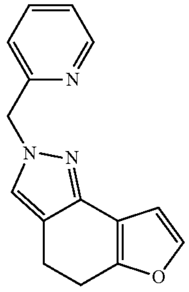 [SMILES: c1ccc(Cn2cc3c(n2)-c2ccoc2CC3)nc1]

According to GP C (conditions B) 4,5-dihydro-1H-furo[2,3-g]indazole (1.0 eq., 5.6 g, mmol) from step 2 was reacted with 2-(bromomethyl)pyridine (1.2 eq., 7.2 g, 42 mmol), potassium carbonate (15 eq., 73 g, 530 mmol) and DMAP (2.5 mol %, 110 mg, 880 μmol) in EtOAc (150 mL) at 75° C. for 3 days to give upon column chromatography ($SiO_2$, DCM/MeOH) the title compound (6.0 g, 52%).

$^1H$ NMR (400 MHz, DMSO-d6) δ[ppm]: 2.86 (s, 4H), 5.34 (s, 2H), 6.62 (d, 1H), 7.03-7.05 (m, 1H), 7.27-7.31 (m, 1H), 7.57-7.60 (m, 2H), 7.76 (dt, 1H), 8.52-8.53 (m, 1H).

UPLC-MS (Method 1): $R_t$=0.96 min; MS (ESIpos): m/z=252 $[M+H]^+$.

Step 4

2-[(pyridin-2-yl)methyl]-4,5-dihydro-2H-furo[2,3-g]indazole-7-carbaldehyde

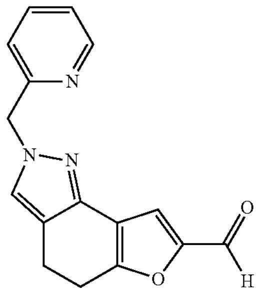 [SMILES: O=Cc1cc2c(o1)CCc1cn(Cc3ccccn3)nc1-2]

According to GP F 2-[(pyridin-2-yl)methyl]-4,5-dihydro-2H-furo[2,3-g]indazole (1.00 eq., 1.00 g, 3.98 mmol) from step 3 was reacted with phosphoric trichloride (CAS No. [10025-87-3]; 5.0 eq., 1.9 mL, 20 mmol) and DMF (5.0 eq., 1.5 mL, 20 mmol) at rt for 1 h to give upon column chromatography ($SiO_2$, DCM/MeOH) and subsequent preparative HPLC the title compound (63 mg, 5%).

$^1H$ NMR (400 MHz, DMSO-d6) δ[ppm]: 2.91-2.95 (m, 2H), 3.00-3.04 (m, 2H), 5.39 (s, 2H), 7.09 (d, 1H), 7.31 (ddd, 1H), 7.67 (s, 1H), 7.70 (s, 1H), 7.77 (dt, 1H), 8.52-8.54 (m, 1H), 9.52 (s, 1H).

UPLC-MS (Method 1): $R_t$=0.83 min; MS (ESIpos): m/z=280 $[M+H]^+$.

Intermediate 2

Step 1 ethyl 8-methyl-2-[(pyridin-2-yl)methyl]-4,5-dihydro-2H-furo[2,3-g]indazole-7-carboxylate

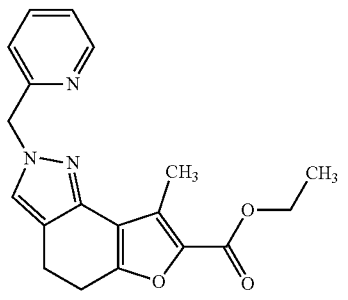 [SMILES: CCOC(=O)c1oc2c(c1C)-c1nn(Cc3ccccn3)cc1CC2]

According to GP C (conditions B) ethyl 8-methyl-4,5-dihydro-1H-furo[2,3-g]indazole-7-carboxylate (commercially available; 1.0 eq., 3.0 g, 12 mmol) was reacted with 2-(bromomethyl)pyridine (1.6 eq., 3.4 g, 20 mmol), potassium carbonate (15.0 eq., 25.3 g, 183 mmol) and DMAP (2.5 mol %, 37 mg, 300 μmol) in EtOAc (200 mL) at 75° C. for 44 h. Another amount of 2-(bromomethyl)pyridine (1.3 eq., 2.7 g, 16 mmol) and DMAP (2.5 mol %, 37 mg, 300 μmol) was added and stirring at 75° C. continued for another 3 days to give upon column chromatography ($SiO_2$, hexane/DCM) the title compound (3.7 g, 71%).

$^1$H NMR (400 MHz, DMSO-d6) δ[ppm]: 1.29 (t, 3H), 2.46 (s, 3H), 2.85-2.95 (m, 4H), 4.26 (q, 2H), 5.39 (s, 2H), 7.07 (d, 1H), 7.31 (ddd, 1H), 7.65 (s, 1H), 7.77 (dt, 1H), 8.53-8.55 (m, 1H).

UPLC-MS (Method 1): $R_t$=1.15 min; MS (ESIpos): m/z=338 $[M+H]^+$.

Step 2

8-methyl-2-[(pyridin-2-yl)methyl]-4,5-dihydro-2H-furo[2,3-g]indazole-7-carboxylic acid

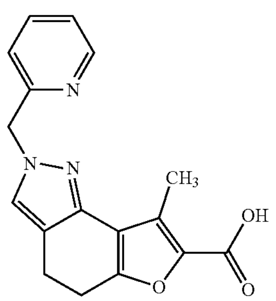 [SMILES: Cc1c(C(=O)O)oc2c1-c1nn(Cc3ccccn3)cc1CC2]

According to GP D ethyl 8-methyl-2-[(pyridin-2-yl)methyl]-4,5-dihydro-2H-furo[2,3-g]indazole-7-carboxylate (3.68 g, 10.9 mmol) from step 1 was reacted with aqueous lithium hydroxide (2 M; 15 eq., 82 mL, 160 mmol) in a 1:1 mixture of ethanol and THF (40 mL) at 70° C. overnight. Upon acidification (pH 2-3) with 6 N aqueous hydrochloric acid and dilution with EtOAc a precipitate was formed which was isolated by filtration. The precipitate was taken up with EtOAc, dried with $Na_2SO_2$, filtrated and concentrated under reduced pressure to give the desired carboxylic acid (1.9 g, 54%).

$^1$H NMR (400 MHz, DMSO-d6) δ[ppm]: 2.44 (s, 3H), 2.84-2.93 (m, 4H), 5.39 (s, 2H), 7.07 (d, 1H), 7.32 (dd, 1H), 7.65 (s, 1H), 7.78 (dt, 1H), 8.53-8.55 (m, 1H), 12.80 (br. s., 1H).

UPLC-MS (Method 1): $R_t$=0.50 min; MS (ESIpos): m/z=310 $[M+H]^+$.

Intermediate 3

Step 1 ethyl 8-methyl-2-[(pyridin-3-yl)methyl]-4,5-dihydro-2H-furo[2,3-g]indazole-7-carboxylate

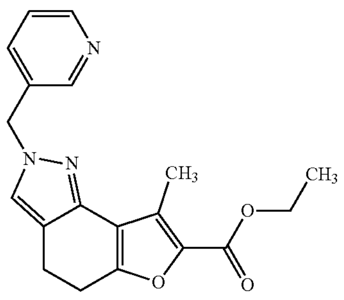

According to GP C (conditions A) ethyl 8-methyl-4,5-dihydro-1H-furo[2,3-g]indazole-7-carboxylate (commercially available; 1.0 eq., 1.0 g, 4.1 mmol) was reacted with (pyridin-3-yl)methanol (1.10 eq., 487 mg, 4.47 mmol), tri-n-butylphosphine (CAS No. [998-40-3]; 1.6 eq., 1.6 mL, 6.5 mmol) and TMAD (CAS No. [10465-78-8]; 1.6 eq., 1.1 g, 6.5 mmol) in toluene (30 mL) at rt overnight to give upon column chromatography (Si—NH $SiO_2$, DCM/MeOH) and trituration with hexane the title compound (1.6 g, 75% purity, 70%).

$^1$H NMR (400 MHz, DMSO-d6) δ[ppm]: 1.29 (t, 3H), 2.48 (s, 3H), 2.83-2.93 (m, 4H), 4.26 (q, 2H), 5.35 (s, 2H), 7.36-7.39 (m, 1H), 7.64 (t, 1H), 7.66 (s, 1H), 8.50 (dd, 1H), 8.52 (d, 1H).

UPLC-MS (Method 1): $R_t$=1.10 min; MS (ESIpos): m/z=338 $[M+H]^+$.

Step 2

8-methyl-2-[(pyridin-3-yl)methyl]-4,5-dihydro-2H-furo[2,3-g]indazole-7-carboxylic acid

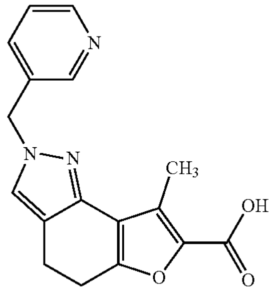 [SMILES: Cc1c(C(=O)O)oc2c1-c1nn(Cc3cccnc3)cc1CC2]

According to GP D ethyl 8-methyl-2-[(pyridin-3-yl)methyl]-4,5-dihydro-2H-furo[2,3-g]indazole-7-carboxylate (1.50 g, 75% purity, 3.33 mmol) from step 1 was reacted with aqueous lithium hydroxide (2 M; 15 eq., 82 mL, 160 mmol) in a 1:1 mixture of ethanol and THF (20 mL) at 70° C. overnight. Upon acidification (pH 4) with 4 N aqueous hydrochloric acid a precipitate was formed which was isolated by filtration and dried to give the desired carboxylic acid (331 mg, 77% purity, 25%).

$^1$H NMR (400 MHz, DMSO-d6) δ[ppm]: 2.46 (s, 3H), 2.82-2.91 (m, 4H), 5.34 (s, 2H), 7.38 (ddd, 1H), 7.64-7.67 (m, 2H), 8.50 (dd, 1H), 8.52 (d, 1H), 12.83 (br. s., 1H).

UPLC-MS (Method 1): $R_t$=0.47 min; MS (ESIpos): m/z=310 $[M+H]^+$.

Intermediate 4

Step 1 ethyl 8-methyl-2-[(pyridin-4-yl)methyl]-4,5-dihydro-2H-furo[2,3-g]indazole-7-carboxylate

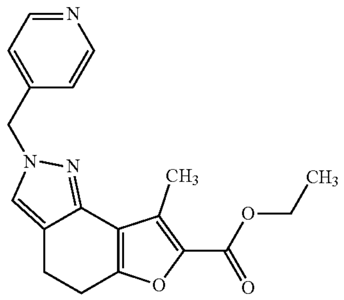 [SMILES: CCOC(=O)c1oc2c(c1C)-c1nn(Cc3ccncc3)cc1CC2]

According to GP C (conditions A) ethyl 8-methyl-4,5-dihydro-1H-furo[2,3-g]indazole-7-carboxylate (commercially available; 1.0 eq., 1.0 g, 4.1 mmol) was reacted with (pyridin-4-yl)methanol (1.10 eq., 487 mg, 4.47 mmol), tri-n-butylphosphine (CAS No. [998-40-3]; 1.6 eq., 1.6 mL, 6.5 mmol) and TMAD (CAS No. [10465-78-8]; 1.6 eq., 1.1 g, 6.5 mmol) in toluene (30 mL) at rt overnight. Another amount of (pyridin-4-yl)methanol (0.40 eq., 175 mg, 1.6 mmol), tri-n-butylphosphine (0.4 eq., 0.4 mL, 1.6 mmol) and TMAD (0.4 eq., 0.3 g, 1.6 mmol) were added and stirring continued for 2 days to give upon column chromatography (Si—NH $SiO_2$, DCM/MeOH) the title compound (3 g, 20% purity, 44%).

$^1$H NMR (400 MHz, DMSO-d6) δ[ppm]: 1.29 (t, 3H), 2.47 (s, 3H), 2.87-2.97 (m, 4H), 4.26 (q, 2H), 5.37 (s, 2H), 7.13-7.15 (m, 2H), 7.68 (s, 1H), 8.52-8.53 (m, 2H).

UPLC-MS (Method 1): $R_t$=1.09 min; MS (ESIpos): m/z=338 $[M+H]^+$.

Step 2

8-methyl-2-[(pyridin-4-yl)methyl]-4,5-dihydro-2H-furo[2,3-g]indazole-7-carboxylic acid

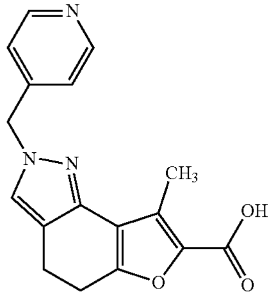 [SMILES: Cc1c(C(=O)O)oc2c1-c1nn(Cc3ccncc3)cc1CC2]

According to GP D ethyl 8-methyl-2-[(pyridin-4-yl)methyl]-4,5-dihydro-2H-furo[2,3-g]indazole-7-carboxylate (3 g, 20% purity, 4 mmol) from step 1 was reacted with aqueous lithium hydroxide (2 M; 15 eq., 31 mL, 61 mmol) in a 1:1 mixture of ethanol and THF (22 mL) at 70° C. overnight. Upon acidification with 4 N aqueous hydrochloric acid (pH 4) a precipitate was formed which was isolated by filtration and dried to give the desired carboxylic acid (467 mg, 35%).

$^1$H NMR (400 MHz, DMSO-d6) δ[ppm]: 2.45 (s, 3H), 2.85-2.94 (m, 4H), 5.37 (s, 2H), 7.13-7.15 (m, 2H), 7.67 (s, 1H), 8.52-8.53 (m, 2H), 12.81 (br. s., 1H).

UPLC-MS (Method 1): $R_t$=0.50 min; MS (ESIpos): m/z=310 $[M+H]^+$.

Intermediate 5

Step 1 ethyl 2-(cyclopropylmethyl)-8-methyl-4,5-dihydro-2H-furo[2,3-g]indazole-7-carboxylate

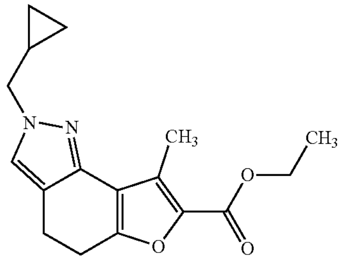 [SMILES: CCOC(=O)c1oc2c(c1C)-c1nn(CC3CC3)cc1CC2]

According to GP C (conditions A) ethyl 8-methyl-4,5-dihydro-1H-furo[2,3-g]indazole-7-carboxylate (commercially available; 1.0 eq., 1.0 g, 4.1 mmol) was reacted with cyclopropylmethanol (1.5 eq., 490 μL, 6.1 mmol), tri-n-butylphosphine (CAS No. [998-40-3]; 1.6 eq., 1.6 mL, 6.5 mmol) and TMAD (CAS No. [10465-78-8]; 1.6 eq., 1.1 g, 6.5 mmol) in toluene (20 mL) at rt overnight to give upon column chromatography (Si—HP $SiO_2$, hexane/EtOAc) the title compound (957 mg, 75%) along with the corresponding N1-isomer (155 mg, 12%).

$^1H$ NMR (400 MHz, DMSO-d6) δ[ppm]: 0.33-0.37 (m, 2H), 0.49-0.54 (m, 2H), 1.18-1.26 (m, 1H), 1.30 (t, 3H), 2.83-2.93 (m, 4H), 3.92 (d, 2H), 4.27 (q, 2H), 7.56 (s, 1H).

UPLC-MS (Method 1): $R_t$=1.31 min; MS (ESIpos): m/z=301 $[M+H]^+$.

Step 2

2-(cyclopropylmethyl)-8-methyl-4,5-dihydro-2H-furo[2,3-g]indazole-7-carboxylic acid

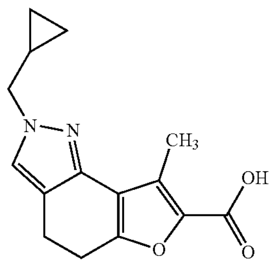 [SMILES: Cc1c(C(=O)O)oc2c1-c1nn(CC3CC3)cc1CC2]

According to GP D ethyl 2-(cyclopropylmethyl)-8-methyl-4,5-dihydro-2H-furo[2,3-g]indazole-7-carboxylate (1.00 eq., 955 mg, 3.18 mmol) from step 1 was reacted with aqueous lithium hydroxide (2 M; 15 eq., 24 mL, 48 mmol) in a 1:1 mixture of ethanol and THF (22 mL) at 70° C. overnight. Upon acidification with 6 N aqueous hydrochloric acid (pH 4) a precipitate was formed which was isolated by filtration, washed with water and dried to give the desired carboxylic acid (945 mg, 100%).

$^1H$ NMR (400 MHz, DMSO-d6) δ[ppm]: 0.33-0.37 (m, 2H), 0.49-0.54 (m, 2H), 1.17-1.27 (m, 1H), 2.48 (s, 3H), 2.82-2.91 (m, 4H), 3.91 (d, 2H), 7.54 (s, 1H), 12.81 (br. s., 1H).

UPLC-MS (Method 1): $R_t$=0.55 min; MS (ESIpos): m/z=273 $[M+H]^+$.

Intermediate 6

Step 1 ethyl 2-{[(2R/S)-2,3-dihydro[1,4]dioxino[2,3-b]pyridin-2-yl]methyl}-8-methyl-4,5-dihydro-2H-furo[2,3-g]indazole-7-carboxylate

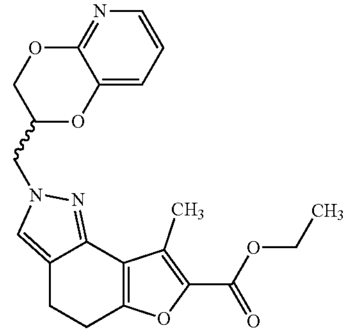 [SMILES: CCOC(=O)c1oc2c(c1C)-c1nn(CC3COc4ncccc4O3)cc1CC2]

According to GP C (conditions B) ethyl 8-methyl-4,5-dihydro-1H-furo[2,3-g]indazole-7-carboxylate (commercially available; 1.0 eq., 930 mg, 3.78 mmol) was reacted with [(2R/S)-2,3-dihydro[1,4]dioxino[2,3-b]pyridin-2-yl]methyl 4-methylbenzene-1-sulfonate (preparation described in: G. Guillaumet et al., Tetrahedron 2004, 60, 6461-6473, cpd. 16B; 1.5 eq., 1.8 g, 5.7 mmol), potassium carbonate (15 eq., 7.8 g, 57 mmol) and DMAP (0.30 eq., 140 mg, 1.1 mmol) in MeCN (50 mL) at 60° C. for 9 days to give upon 2-fold column chromatography (Si—HP $SiO_2$, hexane/EtOAc) the title compound (443 mg, 28%).

$^1H$ NMR (400 MHz, DMSO-d6) δ[ppm]: 1.29 (t, 3H), 2.84-2.94 (m, 4H), 4.18-4.29 (m, 3H), 4.36-4.48 (m, 2H), 4.53 (dd, 1H), 4.62-4.66 (m, 1H), 6.96 (dd, 1H), 7.31 (dd, 1H), 7.56 (s, 1H), 7.77 (dd, 1H).

UPLC-MS (Method 1): $R_t$=1.17 min; MS (ESIpos): m/z=396 $[M+H]^+$.

Step 2

2-{[(2R/S)-2,3-dihydro[1,4]dioxino[2,3-b]pyridin-2-yl]methyl}-8-methyl-4,5-dihydro-2H-furo[2,3-g]indazole-7-carboxylic acid

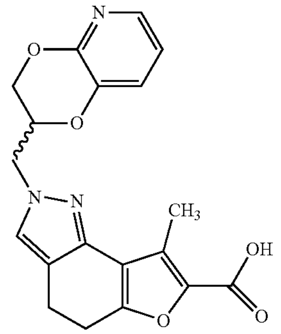 [SMILES: Cc1c(C(=O)O)oc2c1-c1nn(CC3COc4ncccc4O3)cc1CC2]

In a modification of GP D ethyl 2-{[(2R/S)-2,3-dihydro[1,4]dioxino[2,3-b]pyridin-2-yl]methyl}-8-methyl-4,5-dihydro-2H-furo[2,3-g]indazole-7-carboxylate (1.00 eq., 418 mg, 1.06 mmol) from step 1 was reacted with aqueous sodium hydroxide (4 M; 30 eq., 7.9 mL, 32 mmol) in THF (6 mL) at 70° C. overnight. Upon acidification with 6 N aqueous hydrochloric acid (pH 2) and dilution with EtOAc a precipitate was formed which was isolated by filtration. The filtrate was kept. The precipitate was taken up with EtOAc, dried with $Na_2SO_2$, filtrated and concentrated under reduced pressure to give a first crop of the desired carboxylic acid (190 mg, 47%). The above obtained filtrate was separated, and the aqueous phase extracted with EtOAc. The combined organic phases were washed with brine, dried with $Na_2SO_4$, filtrated and concentrated under reduced pressure to give a second crop of the desired carboxylic acid (160 mg, 39%).

$^1$H NMR (400 MHz, DMSO-d6) δ[ppm]: 2.48 (s, 3H), 2.83-2.92 (m, 4H), 4.20 (dd, 1H), 4.36-4.47 (m, 2H), 4.52 (dd, 1H), 4.62-4.67 (m, 1H), 6.96 (dd, 1H), 7.31 (dd, 1H), 7.55 (s, 1H), 7.76 (dd, 1H), 12.83 (br. s., 1H).

UPLC-MS (Method 1): $R_t$=0.51 min; MS (ESIpos): m/z=368 $[M+H]^+$

Intermediate 7

Step 1 ethyl 8-methyl-2-{[6-(trifluoromethyl)pyridin-2-yl]methyl}-4,5-dihydro-2H-furo[2,3-g]indazole-7-carboxylate

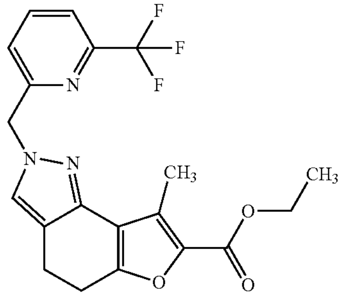 [SMILES: CCOC(=O)c1oc2c(c1C)-c1nn(Cc3cccc(C(F)(F)F)n3)cc1CC2]

According to GP C (conditions B) ethyl 8-methyl-4,5-dihydro-1H-furo[2,3-g]indazole-7-carboxylate (commercially available; 1.00 eq., 500 mg, 2.03 mmol) was reacted with 2-(chloromethyl)-6-(trifluoromethyl)pyridine (1.5 eq., 596 mg, 3.05 mmol), potassium carbonate (15.0 eq., 4.21 g, 30.5 mmol) in MeCN (10 mL) at 60° C. for 3 days to give upon column chromatography ($SiO_2$, hexane/EtOAc) the title compound (493 mg, 57%).

$^1$H NMR (400 MHz, DMSO-d6) δ[ppm]: 1.29 (t, 3H), 2.46 (s, 3H), 2.87-2.96 (m, 4H), 4.26 (q, 2H), 5.52 (s, 2H), 7.27 (d, 1H), 7.72 (s, 1H), 7.84 (d, 1H), 8.08 (t, 1H).

UPLC-MS (Method 1): $R_t$=1.36 min; MS (ESIpos): m/z=406 $[M+H]^+$.

Step 2

8-methyl-2-{[6-(trifluoromethyl)pyridin-2-yl]methyl}-4,5-dihydro-2H-furo[2,3-g]indazole-7-carboxylic acid

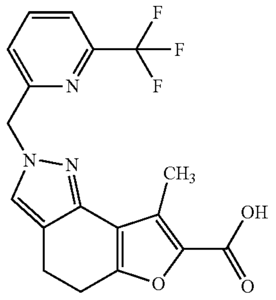 [SMILES: Cc1c(C(=O)O)oc2c1-c1nn(Cc3cccc(C(F)(F)F)n3)cc1CC2]

According to GP D ethyl 8-methyl-2-{[6-(trifluoromethyl)pyridin-2-yl]methyl}-4,5-dihydro-2H-furo[2,3-g]indazole-7-carboxylate (438 mg, 1.19 mmol) from step 1 was reacted with aqueous lithium hydroxide (1 M; 15 eq., 18 mL, 18 mmol) in a 1:1 mixture of ethanol and THF (35 mL) at 70° C. overnight. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to the desired carboxylic acid (405 mg, 87%).

$^1$H NMR (400 MHz, DMSO-d6) δ[ppm]: 2.44 (s, 3H), 2.86-2.94 (m, 4H), 5.51 (s, 2H), 7.26 (d, 1H), 7.71 (s, 1H), 7.84 (d, 1H), 8.08 (t, 1H), 12.84 (br. s., 1H).

UPLC-MS (Method 1): $R_t$=0.66 min; MS (ESIpos): m/z=378 $[M+H]^+$.

Intermediate 8

Step 1 ethyl 8-methyl-2-{[5-(trifluoromethyl)pyridin-2-yl]methyl}-4,5-dihydro-2H-furo[2,3-g]indazole-7-carboxylate

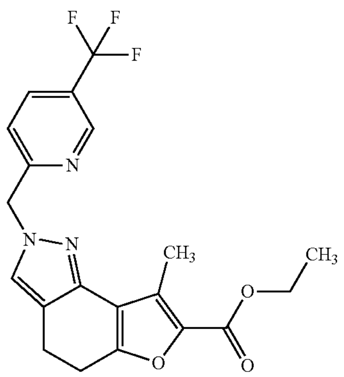 [SMILES: CCOC(=O)c1oc2c(c1C)-c1nn(Cc3ccc(C(F)(F)F)cn3)cc1CC2]

In a modification of GP C (conditions B) an ice-cooled solution of ethyl 8-methyl-4,5-dihydro-1H-furo[2,3-g]indazole-7-carboxylate (commercially available; 1.00 eq., 171 mg, 694 μmol) in DMF (6 mL) was treated with sodium hydride (CAS No. [7646-69-7]; 55% purity, 1.2 eq., 36 mg, 830 μmol) for 30 minutes upon which 2-(bromomethyl)-5-(trifluoromethyl)pyridine (1.20 eq., 200 mg, 833 μmol) was added, the reaction mixture warmed to rt and stirring continued for 45 minutes. The reaction mixture was diluted with sat. aqueous ammonium chloride and EtOAc, the phases were separated, and the aqueous phase extracted with EtOAc. The combined organic phases were dried with $Na_2SO_4$, filtrated, concentrated under reduced pressure and the obtained material subjected to column chromatography (Si—NH $SiO_2$, DCM/MeOH) to give the title compound (81 mg, 24%).

$^1$H NMR (400 MHz, DMSO-d6) δ[ppm]: 1.29 (t, 3H), 2.46 (s, 3H), 2.87-2.96 (m, 4H), 4.26 (q, 2H), 5.54 (s, 2H), 7.25 (d, 1H), 7.71 (s, 1H), 8.21 (dd, 1H), 8.95 (d, 1H).

UPLC-MS (Method 1): $R_t$=1.34 min; MS (ESIpos): m/z=406 $[M+H]^+$.

Step 2

8-methyl-2-{[5-(trifluoromethyl)pyridin-2-yl]methyl}-4,5-dihydro-2H-furo[2,3-g]indazole-7-carboxylic acid

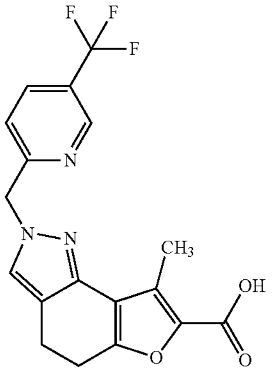 [SMILES: Cc1c(C(=O)O)oc2c1-c1nn(Cc3ccc(C(F)(F)F)cn3)cc1CC2]

According to GP D ethyl 8-methyl-2-{[5-(trifluoromethyl)pyridin-2-yl]methyl}-4,5-dihydro-2H-furo[2,3-g]indazole-7-carboxylate (76.0 mg, 187 μmol) from step 1 was reacted with aqueous lithium hydroxide (1 M; 30 eq., 5.6 mL, 5.6 mmol) in a 1:1 mixture of ethanol and THF (20 mL) at 70° C. overnight. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to the desired carboxylic acid (71 mg, 84%).

$^1$H NMR (400 MHz, DMSO-d6) δ[ppm]: 2.44 (s, 3H), 2.86-2.94 (m, 4H), 5.53 (s, 2H), 7.25 (d, 1H), 7.70 (s, 1H), 8.21 (d, 1H), 8.95 (d, 1H), 12.80 (br. s., 1H).

UPLC-MS (Method 1): $R_t$=0.62 min; MS (ESIpos): m/z=378 $[M+H]^+$.

Intermediates 9-1 and 9-2

Step 1 ethyl 2-[(3-chloro-5-fluoropyridin-2-yl)methyl]-8-methyl-4,5-dihydro-2H-furo[2,3-g]indazole-7-carboxylate

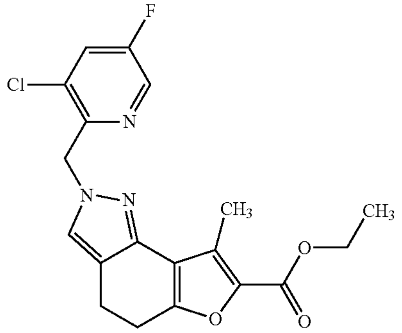 [SMILES: CCOC(=O)c1oc2c(c1C)-c1nn(Cc3ncc(F)cc3Cl)cc1CC2]

According to GP C (conditions B) ethyl 8-methyl-4,5-dihydro-1H-furo[2,3-g]indazole-7-carboxylate (commercially available; 1.00 eq., 500 mg, 2.03 mmol) was reacted with 2-(bromomethyl)-3-chloro-5-fluoropyridine (1.5 eq., 684 mg, 3.05 mmol), potassium carbonate (15.0 eq., 4.21 g, 30.5 mmol) in MeCN (10 mL) at 60° C. for 3 days to give upon column chromatography ($SiO_2$, hexane/EtOAc) the title compound (364 mg, 44%).

$^1$H NMR (400 MHz, DMSO-d6) δ[ppm]: 1.29 (t, 3H), 2.44 (s, 3H), 2.83-2.93 (m, 4H), 4.26 (q, 2H), 5.51 (s, 2H), 7.56 (s, 1H), 8.16 (dd, 1H), 8.58 (d, 1H).

UPLC-MS (Method 1): $R_t$=1.33 min; MS (ESIpos): m/z=390/392 $[M+H]^+$ (Cl isotope pattern).

Step 2

2-[(3-chloro-5-fluoropyridin-2-yl)methyl]-8-methyl-4,5-dihydro-2H-furo[2,3-g]indazole-7-carboxylic acid (Intermediate 9-1) and 2-[(3-chloro-5-ethoxypyridin-2-yl)methyl]-8-methyl-4,5-dihydro-2H-furo[2,3-g]indazole-7-carboxylic acid (Intermediate 9-2)

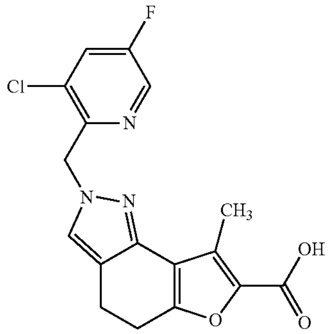

-continued

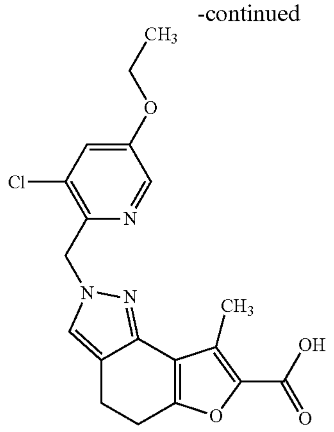

According to GP D ethyl 2-[(3-chloro-5-fluoropyridin-2-yl)methyl]-8-methyl-4,5-dihydro-2H-furo[2,3-g]indazole-7-carboxylate (1.00 eq, 355 mg, 911 μmol) from step 1 was reacted with aqueous lithium hydroxide (1 M; 15 eq., 14 mL, 14 mmol) in a 1:1 mixture of ethanol and THF (27 mL) at 70° C. overnight. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give a 1:1 mixture of the title compounds (405 mg).

9-1: UPLC-MS (Method 1): $R_t$=0.60 min; MS (ESIpos): m/z=362/364 $[M+H]^+$ (Cl isotope pattern).

9-2: UPLC-MS (Method 1): $R_t$=0.67 min; MS (ESIpos): m/z=388/390 $[M+H]^+$ (Cl isotope pattern).

Intermediate 10

Step 1 ethyl 2-[(3-chloropyridin-2-yl)methyl]-8-methyl-4,5-dihydro-2H-furo[2,3-g]indazole-7-carboxylate

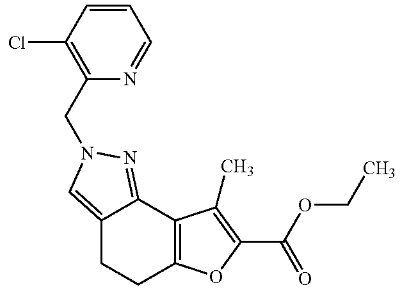 [SMILES: CCOC(=O)c1oc2c(c1C)-c1nn(Cc3ncccc3Cl)cc1CC2]

According to GP C (conditions B) ethyl 8-methyl-4,5-dihydro-1H-furo[2,3-g]indazole-7-carboxylate (commercially available; 1.00 eq., 250 mg, 1.02 mmol) was reacted with 3-chloro-2-(chloromethyl)pyridine (1.50 eq., 247 mg, 1.52 mmol), potassium carbonate (15 eq., 2.1 g, 15 mmol) in MeCN (5 mL) at 60° C. overnight to give after filtration the crude title compound (388 mg, 95%) which was not further purified.

$^1$H NMR (400 MHz, DMSO-d6) δ[ppm]: 1.29 (t, 3H), 2.44 (s, 3H), 2.84-2.94 (m, 4H), 4.26 (q, 2H), 5.53 (s, 2H), 7.42 (dd, 1H), 7.56 (s, 1H), 7.98 (dd, 1H), 8.50 (dd, 1H).

UPLC-MS (Method 1): $R_t$=1.29 min; MS (ESIpos): m/z=372/374 $[M+H]^+$ (Cl isotope pattern).

Step 2

2-[(3-chloropyridin-2-yl)methyl]-8-methyl-4,5-dihydro-2H-furo[2,3-g]indazole-7-carboxylic acid

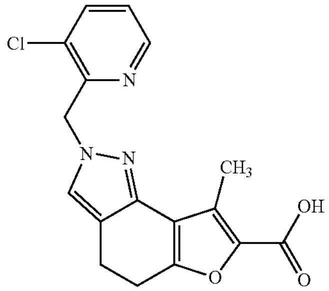 [SMILES: Cc1c(C(=O)O)oc2c1-c1nn(Cc3ncccc3Cl)cc1CC2]

According to GP D ethyl 2-[(3-chloropyridin-2-yl)methyl]-8-methyl-4,5-dihydro-2H-furo[2,3-g]indazole-7-carboxylate (1.00 eq., 382 mg, 1.03 mmol) from step 1 was reacted with aqueous lithium hydroxide (1 M; 15 eq., 7.7 mL, 15 mmol) in a 1:1 mixture of ethanol and THF (10 mL) at 70° C. for 3 days. Upon acidification with 4 N aqueous hydrochloric acid (pH 4) and dilution with EtOAc a precipitate was formed which was isolated by filtration, washed with water and dried to give a first crop of the desired carboxylic acid (204 mg, 57%). The filtrate was separated, and the aqueous phase extracted with EtOAc.

The combined organic phases were dried with $Na_2SO_4$, filtrated and concentrated under reduced pressure to give a second crop of the desired carboxylic acid (123 mg, 31%).

$^1$H NMR (400 MHz, DMSO-d6) δ[ppm]: 2.42 (s, 3H), 2.83-2.91 (m, 4H), 5.52 (s, 2H), 7.42 (dd, 1H), 7.55 (s, 1H), 7.98 (dd, 1H), 8.50 (dd, 1H), 12.81 (br. s., 1H).

UPLC-MS (Method 1): $R_t$=0.56 min; MS (ESIpos): m/z=344/346 $[M+H]^+$ (Cl isotope pattern).

Intermediate 11

Step 1 ethyl 8-methyl-2-[(3-methylpyridin-2-yl)methyl]-4,5-dihydro-2H-furo[2,3-g]indazole-7-carboxylate

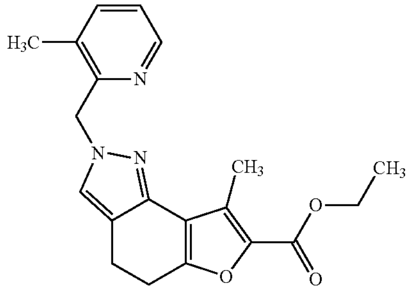 [SMILES: CCOC(=O)c1oc2c(c1C)-c1nn(Cc3ncccc3C)cc1CC2]

According to GP C (conditions B) ethyl 8-methyl-4,5-dihydro-1H-furo[2,3-g]indazole-7-carboxylate (commercially available; 1.00 eq., 264 mg, 1.07 mmol) was reacted with 2-(chloromethyl)-3-methylpyridine hydrogen chloride (1/1) (1.50 eq., 286 mg, 1.61 mmol), potassium carbonate (15 eq., 2.2 g, 16 mmol) in MeCN (5 mL) at 60° C. for two days to give after filtration the crude title compound (413 mg, 100%) which was not further purified.

$^1$H NMR (400 MHz, DMSO-d6) δ[ppm]: 1.29 (t, 3H), 2.39 (s, 3H), 2.46 (s, 3H), 2.82-2.92 (m, 4H), 4.26 (q, 2H), 5.39 (s, 2H), 7.25 (dd, 1H), 7.47 (s, 1H), 7.62 (dd, 1H), 8.35 (dd, 1H).

UPLC-MS (Method 1): $R_t$=1.23 min; MS (ESIpos): m/z=352 $[M+H]^+$.

Step 2

8-methyl-2-[(3-methylpyridin-2-yl)methyl]-4,5-dihydro-2H-furo[2,3-g]indazole-7-carboxylic acid

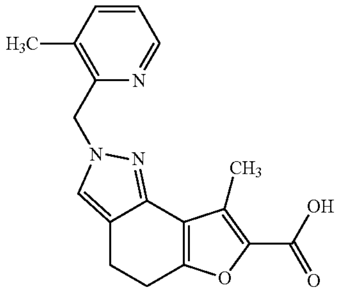 [SMILES: Cc1cccnc1Cn1cc2c(n1)-c1c(oc(C(=O)O)c1C)CC2]

According to GP D ethyl 8-methyl-2-[(3-methylpyridin-2-yl)methyl]-4,5-dihydro-2H-furo[2,3-g]indazole-7-carboxylate (1.00 eq., 400 mg, 1.14 mmol) from step 1 was reacted with aqueous lithium hydroxide (1 M; 15 eq., 17 mL, 17 mmol) in a 1:1 mixture of ethanol and THF (10 mL) at 70° C. overnight. Upon acidification with 4 N aqueous hydrochloric acid (pH 4) and dilution with EtOAc a precipitate was formed which was isolated by filtration, washed with water and dried to give a first crop of the desired carboxylic acid (209 mg, 56%). The filtrate was separated, and the aqueous phase extracted with EtOAc.

The combined organic phases were washed with brine, dried with $Na_2SO_4$, filtrated and concentrated under reduced pressure to give a second crop of the desired carboxylic acid (54 mg, 12%).

$^1$H NMR (400 MHz, DMSO-d6) δ[ppm]: 2.39 (s, 3H), 2.44 (s, 3H), 2.81-2.90 (m, 4H), 5.38 (s, 2H), 7.25 (dd, 1H), 7.46 (s, 1H), 7.62 (dd, 1H), 8.35 (dd, 1H), 12.79 (br. s., 1H).

UPLC-MS (Method 1): $R_t$=0.50 min; MS (ESIpos): m/z=324 $[M+H]^+$.

Intermediate 12

Step 1 ethyl 8-methyl-2-[(5-methylpyridin-2-yl)methyl]-4,5-dihydro-2H-furo[2,3-g]indazole-7-carboxylate

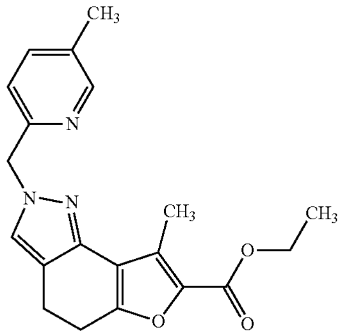 [SMILES: CCOC(=O)c1oc2c(c1C)-c1nn(Cc3ccc(C)cn3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (5-methylpyridin-2-yl)methanol (1.50 eq., 225 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography ($SiO_2$, hexane/EtOAc) the title compound (395 mg, 88%).

$^1$H NMR (400 MHz, DMSO-d6) δ[ppm]: 1.29 (t, 3H), 2.27 (s, 3H), 2.46 (s, 3H), 2.84-2.94 (m, 4H), 4.26 (q, 2H), 5.34 (s, 2H), 7.01 (dd, 1H), 7.58 (dd, 1H), 7.62 (s, 1H), 8.37 (dd, 1H).

UPLC-MS (Method 1): $R_t$=1.18 min; MS (ESIpos): m/z=352 $[M+H]^+$.

Step 2

8-methyl-2-[(5-methylpyridin-2-yl)methyl]-4,5-dihydro-2H-furo[2,3-g]indazole-7-carboxylic acid

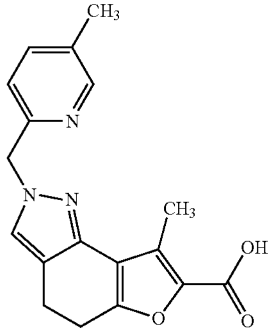 [SMILES: Cc1ccc(Cn2cc3c(n2)-c2c(oc(C(=O)O)c2C)CC3)nc1]

According to GP D ethyl 8-methyl-2-[(5-methylpyridin-2-yl)methyl]-4,5-dihydro-2H-furo[2,3-g]indazole-7-carboxylate (1.00 eq., 388 mg, 1.10 mmol) from step 1 was reacted with aqueous lithium hydroxide (2 M; 15 eq., 8.3 mL, 17 mmol) in a 1:1 mixture of ethanol and THF (16 mL) at 70° C. overnight. The reaction mixture was acidified with aqueous 6 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (328 mg, 85%).

$^1$H NMR (400 MHz, DMSO-d6) δ[ppm]: 2.27 (s, 3H), 2.44 (s, 3H), 2.83-2.92 (m, 4H), 5.33 (s, 2H), 7.01 (dd, 1H), 7.59 (dd, 1H), 7.61 (s, 1H), 8.37 (dd, 1H), 12.78 (br. s., 1H).

UPLC-MS (Method 1): $R_t$=0.54 min; MS (ESIpos): m/z=324 [M+H]$^+$.

Intermediate 13

Step 1 methyl (5E/Z)-5-[(dimethylamino)methylidene]-3-methyl-4-oxo-4,5,6,7-tetrahydro-1-benzofuran-2-carboxylate

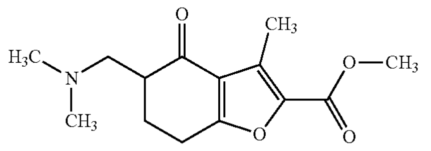

According to GP A (conditions A) methyl 3-methyl-4-oxo-4,5,6,7-tetrahydro-1-benzofuran-2-carboxylate (commercially available, CAS No. [40200-70-2]; 10.0 g, 48.0 mmol) was reacted with 1-tert-butoxy-N,N,N',N'-tetramethylmethanediamine (Bredereck's reagent, CAS No. [5815-08-7]; 1.2 eq., 12 mL, 58 mmol) in toluene (100 mL) at 100° C. overnight. Another amount of 1-tert-butoxy-N,N,N',N'-tetramethylmethanediamine (0.50 eq., 5.0 mL, 24 mmol) was added and stirring at 100° C. continued for another 5 days. The reaction mixture was concentrated under reduced pressure and the obtained crude title compound used in the subsequent reaction without further purification steps.

UPLC-MS (Method 1): $R_t$=0.95/1.01 min; MS (ESIpos): m/z=264 [M+H]$^+$.

Step 2 methyl 8-methyl-4,5-dihydro-1H-furo[2,3-g]indazole-7-carboxylate

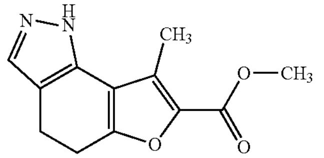 [SMILES: COC(=O)c1oc2c(c1C)-c1[nH]ncc1CC2]

According to GP B crude methyl (5E/Z)-5-[(dimethylamino)methylidene]-3-methyl-4-oxo-4,5,6,7-tetrahydro-1-benzofuran-2-carboxylate (1.0 eq., 13 g, 48 mmol) from step 1 was reacted with hydrazine hydrate 1:1 (4.0 eq., 9.5 mL, 195 mmol) in ethanol (150 mL) at 70° C. for 4 h and at rt overnight to give upon column chromatography ($SiO_2$, hexane/EtOAc) the title compound (771 mg, 7% over 2 steps).

$^1$H NMR (400 MHz, DMSO-d6) δ[ppm]: 2.51 (s, 3H; partially covered by solvent peak), 2.84-2.93 (m, 4H), 3.80 (s, 3H), 7.52 (s, 1H), 12.49 (s, 1H).

UPLC-MS (Method 1): $R_t$=0.88 min; MS (ESIpos): m/z=233 [M+H]$^+$.

Step 3 methyl 8-methyl-2-[(6-methylpyridin-2-yl)methyl]-4,5-dihydro-2H-furo[2,3-g]indazole-7-carboxylate

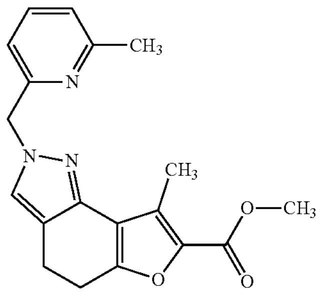 [SMILES: COC(=O)c1oc2c(c1C)-c1nn(Cc3cccc(C)n3)cc1CC2]

According to GP C (conditions B) methyl 8-methyl-4,5-dihydro-1H-furo[2,3-g]indazole-7-carboxylate (1.0 eq., 770 mg, 3.3 mmol) from step 2 was reacted with 2-(bromomethyl)-6-methylpyridine (1.50 eq., 926 mg, 4.98 mmol), potassium carbonate (10 eq., 4.6 g, 33 mmol) in MeCN (10 mL) at 60° C. overnight to give after filtration the crude title compound (1.27 g, 100%) which was not further purified.

$^1$H NMR (400 MHz, DMSO-d6) δ[ppm]: 2.46-2.46 (m, 6H), 2.85-2.94 (m, 4H), 3.79 (s, 3H), 5.33 (s, 2H), 6.79 (d, 1H), 7.16 (d, 1H), 7.62-7.66 (m, 2H).

UPLC-MS (Method 1): $R_t$=1.14 min; MS (ESIpos): m/z=338 [M+H]$^+$.

Step 4

8-methyl-2-[(6-methylpyridin-2-yl)methyl]-4,5-dihydro-2H-furo[2,3-g]indazole-7-carboxylic acid

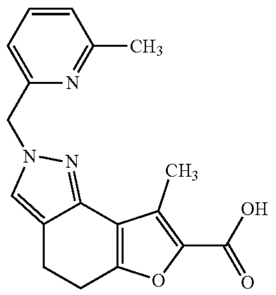 [SMILES: Cc1cccc(Cn2cc3c(n2)-c2c(oc(C(=O)O)c2C)CC3)n1]

In a modification of GP D methyl 8-methyl-2-[(6-methylpyridin-2-yl)methyl]-4,5-dihydro-2H-furo[2,3-g]indazole-7-carboxylate (1.0 eq., 1.2 g, 2.2 mmol) from step 3 was reacted with aqueous sodium hydroxide (4 M; 30 eq., 17 mL, 66 mmol) in THF (14 mL) at 70° C. for two days. The reaction mixture was acidified with aqueous 2 N HCl (pH 4-5) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (980 mg, 85% purity, 100%).

$^1$H NMR (400 MHz, DMSO-d6) δ[ppm]: 2.45-2.46 (m, 6H), 2.84-2.92 (m, 4H), 5.33 (s, 2H), 6.79 (d, 1H), 7.16 (d, 1H), 7.62-7.66 (m, 2H), 12.52 (br. s., 1H).

UPLC-MS (Method 1): $R_t$=0.55 min; MS (ESIpos): m/z=324 $[M+H]^+$.

Intermediates 14-1 and 14-2

Step 1 ethyl 8-methyl-2-[(2-methylpyridin-3-yl)methyl]-4,5-dihydro-2H-furo[2,3-g]indazole-7-carboxylate

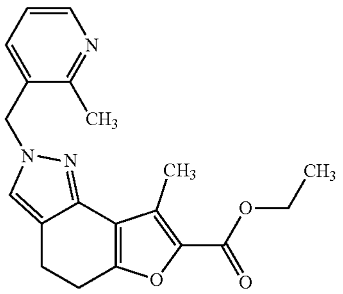 [SMILES: CCOC(=O)c1oc2c(c1C)-c1nn(Cc3cccnc3C)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (2-methylpyridin-3-yl)methanol (1.50 eq., 225 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography ($SiO_2$, hexane/EtOAc) the title compound (315 mg, 71%).

$^1$H NMR (400 MHz, DMSO-d6) δ[ppm]: 1.29 (t, 3H), 2.47 (s, 3H), 2.54 (s, 3H), 2.84-2.94 (m, 4H), 4.26 (q, 2H), 5.35 (s, 2H), 7.17-7.25 (m, 2H), 7.59 (s, 1H), 8.36 (dd, 1H).

UPLC-MS (Method 1): $R_t$=1.12 min; MS (ESIpos): m/z=352 $[M+H]^+$.

Step 2

8-methyl-2-[(2-methylpyridin-3-yl)methyl]-4,5-dihydro-2H-furo[2,3-g]indazole-7-carboxylic acid hydrogen chloride (1/1) and 8-methyl-2-[(2-methylpyridin-3-yl)methyl]-4,5-dihydro-2H-furo[2,3-g]indazole-7-carboxylic acid

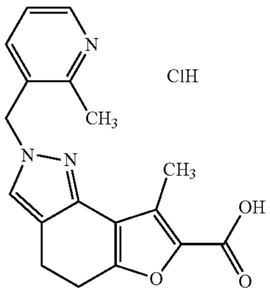

-continued

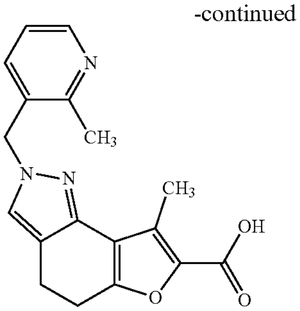

According to GP D ethyl 8-methyl-2-[(2-methylpyridin-3-yl)methyl]-4,5-dihydro-2H-furo[2,3-g]indazole-7-carboxylate (1.00 eq., 313 mg, 891 μmol) from step 1 was reacted with aqueous lithium hydroxide (2 M; 15 eq., 6.7 mL, 13 mmol) in a 1:1 mixture of ethanol and THF (14 mL) at 70° C. overnight. Upon acidification with 6 N aqueous hydrochloric acid (pH 4) and dilution with EtOAc a precipitate was formed which was isolated by filtration and dried to give the hydrochloride salt of the desired carboxylic acid (Intermediate 14-1, 225 mg, 67%). The filtrate was separated, and the aqueous phase extracted with EtOAc. The combined organic phases were washed with brine, dried with $Na_2SO_4$, filtrated and concentrated under reduced pressure to give the desired carboxylic acid (Intermediate 14-2, 47 mg, 15%).

14-1: $^1$H NMR (400 MHz, DMSO-d6) δ[ppm]: 2.44 (s, 3H), 2.79 (s, 3H), 2.86-2.94 (m, 4H), 5.52 (s, 2H), 7.68 (s, 1H), 7.73-7.77 (m, 1H), 7.83-7.85 (m, 1H), 8.65 (dd, 1H), 12.84 (br. s., 1H).

14-1: UPLC-MS (Method 1): $R_t$=0.50 min; MS (ESIpos): m/z=324 $[M-Cl^-]^+$.

Intermediates 15-1 and 15-2

Step 1 ethyl 8-methyl-2-[(6-methylpyridin-3-yl)methyl]-4,5-dihydro-2H-furo[2,3-g]indazole-7-carboxylate

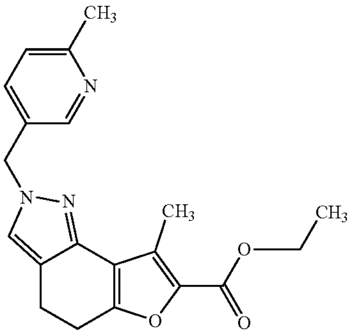 [SMILES: CCOC(=O)c1oc2c(c1C)-c1nn(Cc3ccc(C)nc3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (6-methylpyridin-3-yl)methanol (1.50 eq., 225 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography ($SiO_2$, hexane/EtOAc) the title compound (299 mg, 66%).

$^1H$ NMR (400 MHz, DMSO-d6) δ[ppm]: 1.29 (t, 3H), 2.43 (s, 3H), 2.48 (s, 3H), 2.83-2.92 (m, 4H), 4.26 (q, 2H), 5.28 (s, 2H), 7.22 (d, 1H), 7.56 (dd, 1H), 7.63 (s, 1H), 8.40 (d, 1H).

UPLC-MS (Method 1): $R_t$=1.17 min; MS (ESIpos): m/z=352 $[M+H]^+$.

Step 2

8-methyl-2-[(6-methylpyridin-3-yl)methyl]-4,5-dihydro-2H-furo[2,3-g]indazole-7-carboxylic acid hydrogen chloride (1/1) and 8-methyl-2-[(6-methylpyridin-3-yl)methyl]-4,5-dihydro-2H-furo[2,3-g]indazole-7-carboxylic acid

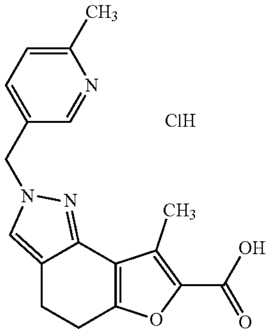

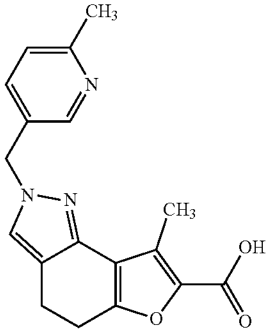

According to GP D ethyl 8-methyl-2-[(6-methylpyridin-3-yl)methyl]-4,5-dihydro-2H-furo[2,3-g]indazole-7-carboxylate (1.00 eq., 291 mg, 828 μmol) from step 1 was reacted with aqueous lithium hydroxide (2 M; 15 eq., 6.2 mL, 12 mmol) in a 1:1 mixture of ethanol and THF (12 mL) at 70° C. overnight. Upon acidification with 6 N aqueous hydrochloric acid (pH 3) and dilution with EtOAc a precipitate was formed which was isolated by filtration and dried to give the hydrochloride salt of the desired carboxylic acid (Intermediate 15-1, 195 mg, 63%). The filtrate was separated, and the aqueous phase extracted with EtOAc. The combined organic phases were washed with brine, dried with $Na_2SO_4$, filtrated and concentrated under reduced pressure to give the desired carboxylic acid (Intermediate 15-2, 44 mg, 15%).

15-1: $^1H$ NMR (400 MHz, DMSO-d6) δ[ppm]: 2.46 (s, 3H), 2.57 (s, 3H), 2.82-2.91 (m, 4H), 5.39 (s, 2H), 7.57 (d, 1H), 7.67 (s, 1H), 7.94 (d, 1H), 8.59 (d, 1H), 12.84 (br. s., 1H).

15-1: UPLC-MS (Method 1): $R_t$=0.51 min; MS (ESIpos): m/z=324 $[M-Cl^-]^+$.

Intermediates 16-1 and 16-2

Step 1 ethyl 2-[(2,6-dimethylpyridin-3-yl)methyl]-8-methyl-4,5-dihydro-2H-furo[2,3-g]indazole-7-carboxylate

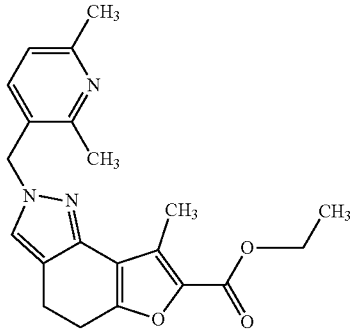 [SMILES: CCOC(=O)c1oc2c(c1C)-c1nn(Cc3ccc(C)nc3C)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (2,6-dimethylpyridin-3-yl)methanol (1.50 eq., 251 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography ($SiO_2$, hexane/EtOAc) the title compound (312 mg, 63%).

$^1H$ NMR (400 MHz, DMSO-d6) δ[ppm]: 1.29 (t, 3H), 2.39 (s, 3H), 2.47 (s, 3H), 2.83-2.93 (m, 4H), 4.26 (q, 2H), 5.29 (s, 2H), 7.04 (d, 1H), 7.20 (d, 1H), 7.55 (s, 1H).

UPLC-MS (Method 1): $R_t$=1.23 min; MS (ESIpos): m/z=366 $[M+H]^+$.

Step 2

2-[(2,6-dimethylpyridin-3-yl)methyl]-8-methyl-4,5-dihydro-2H-furo[2,3-g]indazole-7-carboxylic acid hydrogen chloride (1/1) and 2-[(2,6-dimethylpyridin-3-yl)methyl]-8-methyl-4,5-dihydro-2H-furo[2,3-g]indazole-7-carboxylic acid

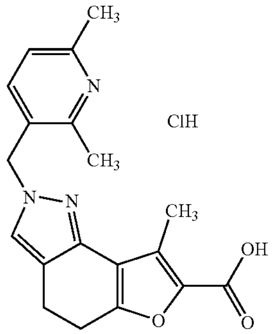

-continued

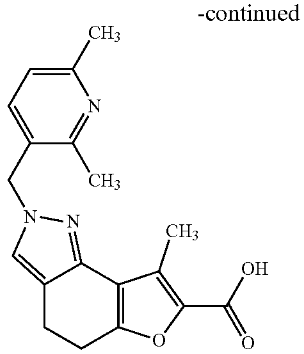

According to GP D ethyl 2-[(2,6-dimethylpyridin-3-yl)methyl]-8-methyl-4,5-dihydro-2H-furo[2,3-g]indazole-7-carboxylate (1.00 eq., 305 mg, 835 μmol) from step 1 was reacted with aqueous lithium hydroxide (2 M; 15 eq., 6.3 mL, 13 mmol) in a 1:1 mixture of ethanol and THF (12 mL) at 70° C. overnight. Upon acidification with 6 N aqueous hydrochloric acid (pH 3) and dilution with EtOAc a precipitate was formed which was isolated by filtration and dried to give the hydrochloride salt of the desired carboxylic acid (Intermediate 16-1, 86 mg, 27%). The filtrate was separated, and the aqueous phase extracted with EtOAc. The combined organic phases were washed with brine, dried with $Na_2SO_4$, filtrated and concentrated under reduced pressure to give the desired carboxylic acid (Intermediate 16-2, 91 mg, 24%).

16-1: $^1$H NMR (400 MHz, DMSO-d6) δ[ppm]: 2.44 (s, 3H), 2.62 (br. s., 3H), 2.74 (br. s., 3H), 2.84-2.93 (m, 4H), 5.45 (s, 2H), 7.57 (br. s., 2H), 7.65 (s, 1H), 7.81 (br. s., 1H), 12.83 (br. s., 1H).

16-1: UPLC-MS (Method 1): $R_t$=0.58 min; MS (ESIpos): m/z=338 $[M-Cl^-]^+$.

Intermediates 17-1 and 17-2

Step 1 ethyl 8-methyl-2-[(2-methylpyridin-4-yl)methyl]-4,5-dihydro-2H-furo[2,3-g]indazole-7-carboxylate

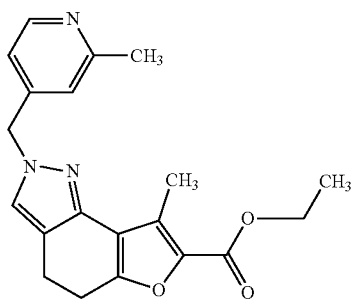 [SMILES: CCOC(=O)c1oc2c(c1C)-c1nn(Cc3ccnc(C)c3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (2-methylpyridin-4-yl)methanol (1.10 eq., 165 mg, 1.34 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (12 mL) at rt overnight to give upon column chromatography ($SiO_2$, $CH_2Cl_2$/hexane) the title compound (524 mg, 44% purity, 54%).

$^1$H NMR (400 MHz, DMSO-d6) δ[ppm]: 1.29 (t, 3H), 2.43 (s, 3H), 2.47 (s, 3H), 2.85-2.95 (m, 4H), 4.26 (q, 2H), 5.31 (s, 2H), 6.94 (d, 1H), 7.05 (s, 1H), 7.66 (s, 1H), 8.38 (d, 1H).

UPLC-MS (Method 1): $R_t$=1.15 min; MS (ESIpos): m/z=352 $[M+H]^+$.

Step 2

8-methyl-2-[(2-methylpyridin-4-yl)methyl]-4,5-dihydro-2H-furo[2,3-g]indazole-7-carboxylic acid hydrogen chloride (1/1) and 8-methyl-2-[(2-methylpyridin-4-yl)methyl]-4,5-dihydro-2H-furo[2,3-g]indazole-7-carboxylic acid and

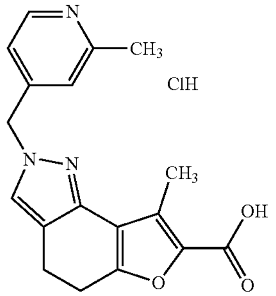

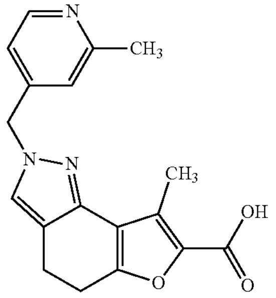

According to GP D ethyl 8-methyl-2-[(2-methylpyridin-4-yl)methyl]-4,5-dihydro-2H-furo[2,3-g]indazole-7-carboxylate (1.00 eq., 522 mg, 1.22 mmol) from step 1 was reacted with aqueous lithium hydroxide (2 M; 17 eq., 10 mL, 21 mmol) in a 1:1 mixture of ethanol and THF (12 mL) at 70° C. overnight and at rt for two days. Upon acidification with 4 N aqueous hydrochloric acid (pH 3.5) and dilution with EtOAc a precipitate was formed which was isolated by filtration and dried to give the hydrochloride salt of the desired carboxylic acid (Intermediate 17-1, 168 mg, 61%). The filtrate was separated, and the aqueous phase extracted with EtOAc. The combined organic phases were washed with brine, dried with $Na_2SO_4$, filtrated and concentrated under reduced pressure to give the desired carboxylic acid (Intermediate 17-2, 285 mg, 50% purity, 36%).

17-1: $^1$H NMR (400 MHz, DMSO-d6) δ[ppm]: 2.44 (s, 3H), 2.66 (s, 3H), 2.87-2.95 (m, 4H), 5.57 (s, 2H), 7.39 (d, 1H), 7.53 (s, 1H), 7.73 (s, 1H), 8.65 (d, 1H), 12.84 (br. s., 1H).

17-1: UPLC-MS (Method 1): $R_t$=0.51 min; MS (ESIpos): m/z=324 $[M-Cl^-]^+$.

Intermediates 18-1 and 18-2

Step 1 ethyl 2-[(2,6-dimethylpyridin-4-yl)methyl]-8-methyl-4,5-dihydro-2H-furo[2,3-g]indazole-7-carboxylate

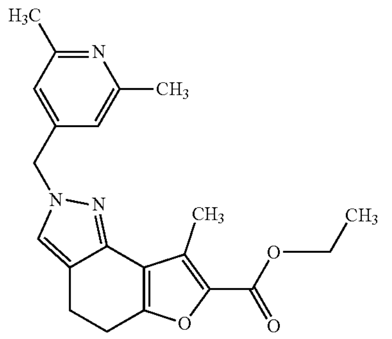 [SMILES: CCOC(=O)c1oc2c(c1C)-c1nn(Cc3cc(C)nc(C)c3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (2,6-dimethylpyridin-4-yl)methanol (1.50 eq., 251 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography ($SiO_2$, hexane/EtOAc) the title compound (419 mg, 83%).

$^1$H NMR (400 MHz, DMSO-d6) δ[ppm]: 1.29 (t, 3H), 2.22 (s, 3H), 2.41 (s, 3H), 2.47 (s, 3H), 2.85-2.95 (m, 4H), 4.26 (q, 2H), 5.28 (s, 2H), 6.71 (s, 1H), 7.00 (s, 1H), 7.62 (s, 1H).

UPLC-MS (Method 1): $R_t$=1.29 min; MS (ESIpos): m/z=366 $[M+H]^+$.

Step 2

2-[(2,6-dimethylpyridin-4-yl)methyl]-8-methyl-4,5-dihydro-2H-furo[2,3-g]indazole-7-carboxylic acid hydrogen chloride (1/1) and 2-[(2,6-dimethylpyridin-4-yl)methyl]-8-methyl-4,5-dihydro-2H-furo[2,3-g]indazole-7-carboxylic acid

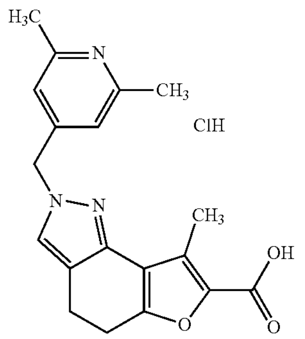

-continued

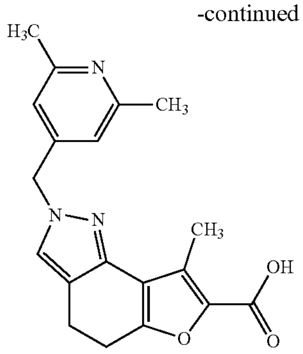

According to GP D ethyl 2-[(2,6-dimethylpyridin-4-yl)methyl]-8-methyl-4,5-dihydro-2H-furo[2,3-g]indazole-7-carboxylate (1.00 eq., 408 mg, 1.12 mmol) from step 1 was reacted with aqueous lithium hydroxide (2 M; 15 eq., 8.4 mL, 17 mmol) in a 1:1 mixture of ethanol and THF (16 mL) at 70° C. overnight. Upon acidification with 6 N aqueous hydrochloric acid (pH 3) and dilution with EtOAc a precipitate was formed which was isolated by filtration and dried to give the hydrochloride salt of the desired carboxylic acid (Intermediate 18-1, 94 mg, 22%). The filtrate was separated, and the aqueous phase extracted with EtOAc. The combined organic phases were washed with brine, dried with $Na_2SO_4$, filtrated and concentrated under reduced pressure to give the desired carboxylic acid (Intermediate 18-2, 161 mg, 32%).

18-1: $^1$H NMR (400 MHz, DMSO-d6) δ[ppm]: 2.35 (br. s., 3H), 2.45 (s, 3H), 2.55 (br. s., 3H), 2.85-2.94 (m, 4H), 5.46 (s, 2H), 6.97 (br. s., 1H), 7.33 (br. s., 1H), 7.69 (s, 1H), 12.83 (br. s., 1H).

18-1: UPLC-MS (Method 1): $R_t$=0.58 min; MS (ESIpos): m/z=338 $[M-Cl^-]^+$.

Intermediate 19

Step 1 ethyl 8-methyl-2-[(pyrimidin-2-yl)methyl]-4,5-dihydro-2H-furo[2,3-g]indazole-7-carboxylate

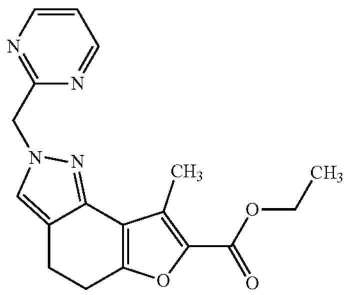 [SMILES: CCOC(=O)c1oc2c(c1C)-c1nn(Cc3ncccn3)cc1CC2]

According to GP C (conditions B) ethyl 8-methyl-4,5-dihydro-1H-furo[2,3-g]indazole-7-carboxylate (commercially available; 1.00 eq., 260 mg, 1.06 mmol) was reacted with 2-(chloromethyl)pyrimidine (1.50 eq., 204 mg, 1.58 mmol) and potassium carbonate (15 eq., 2.2 g, 16 mmol) in MeCN (5 mL) at 60° C. overnight. DMAP (5 mol %, 6.5 mg, 53 μmol) was added and stirring at 60° C. continued for 4 days to give after filtration the crude title compound (332 mg, 79%) which was not further purified.

$^1H$ NMR (400 MHz, DMSO-d6) δ[ppm]: 1.29 (t, 3H), 2.44 (s, 3H), 2.86-2.95 (m, 4H), 4.26 (q, 2H), 5.51 (s, 2H), 7.45 (t, 1H), 7.63 (s, 1H), 8.79-8.80 (m, 2H).

UPLC-MS (Method 1): $R_t$=1.03 min; MS (ESIpos): m/z=339 $[M+H]^+$.

Step 2

8-methyl-2-[(pyrimidin-2-yl)methyl]-4,5-dihydro-2H-furo[2,3-g]indazole-7-carboxylic acid

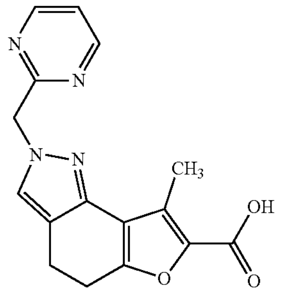 [SMILES: Cc1c(C(=O)O)oc2c1-c1nn(Cc3ncccn3)cc1CC2]

According to GP D ethyl 8-methyl-2-[(pyrimidin-2-yl)methyl]-4,5-dihydro-2H-furo[2,3-g]indazole-7-carboxylate (1.00 eq., 332 mg, 834 μmol) from step 1 was reacted with aqueous lithium hydroxide (2 M; 15 eq., 6.3 mL, 13 mmol) in a 1:1 mixture of ethanol and THF (8 mL) at 70° C. overnight. The reaction mixture was acidified with aqueous 4 N HCl (pH 4) and concentrated under reduced pressure to give the crude title compound along with salts (1.8 g) which was not further purified.

UPLC-MS (Method 1): $R_t$=0.44 min; MS (ESIpos): m/z=311 $[M+H]^+$.

Intermediate 20

Step 1 ethyl 8-methyl-2-[(pyrimidin-5-yl)methyl]-4,5-dihydro-2H-furo[2,3-g]indazole-7-carboxylate

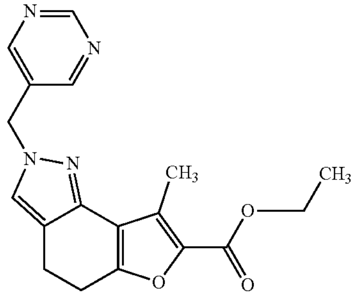 [SMILES: CCOC(=O)c1oc2c(c1C)-c1nn(Cc3cncnc3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (pyrimidin-5-yl)methanol (1.50 eq., 201 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography (Si—NH $SiO_2$, hexane/$CH_2Cl_2$/MeOH) the title compound (483 mg, 52% purity, 61%).

$^1H$ NMR (400 MHz, DMSO-d6) δ[ppm]: 1.29 (t, 3H), 2.47 (s, 3H), 2.83-2.93 (m, 4H), 4.26 (q, 2H), 5.39 (s, 2H), 7.70 (s, 1H), 8.74 (s, 2H), 9.13 (s, 1H).

UPLC-MS (Method 1): $R_t$=1.02 min; MS (ESIpos): m/z=339 $[M+H]^+$.

Step 2

8-methyl-2-[(pyrimidin-5-yl)methyl]-4,5-dihydro-2H-furo[2,3-g]indazole-7-carboxylic acid

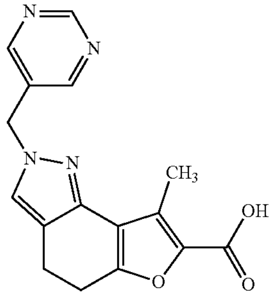 [SMILES: Cc1c(C(=O)O)oc2c1-c1nn(Cc3cncnc3)cc1CC2]

According to GP D ethyl ethyl 8-methyl-2-[(pyrimidin-5-yl)methyl]-4,5-dihydro-2H-furo[2,3-g]indazole-7-carboxylate (1.00 eq., 480 mg, 52% purity, 738 μmol) from step 1 was reacted with aqueous lithium hydroxide (2 M; 15 eq., 5.5 mL, 11 mmol) in a 1:1 mixture of ethanol and THF (5.2 mL) at 70° C. overnight. The reaction mixture was acidified with aqueous 6 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (439 mg, 37% purity, 71%).

$^1H$ NMR (400 MHz, DMSO-d6) δ[ppm]: 2.46 (s, 3H), 2.83-2.92 (m, 4H), 5.38 (s, 2H), 7.70 (s, 1H), 8.74 (s, 2H), 9.13 (s, 1H), 12.73 (br. s., 1H).

UPLC-MS (Method 1): $R_t$=0.44 min; MS (ESIpos): m/z=311 $[M+H]^+$.

Intermediate 21

Step 1 ethyl 2-{[(2R)-1,4-dioxan-2-yl]methyl}-8-methyl-4,5-dihydro-2H-furo[2,3-g]indazole-7-carboxylate

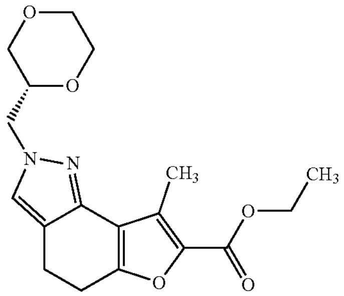 [SMILES: CCOC(=O)c1oc2c(c1C)-c1nn(C[C@@H]3COCCO3)cc1CC2]

According to GP C (conditions A) ethyl 8-methyl-4,5-dihydro-1H-furo[2,3-g]indazole-7-carboxylate (commercially available; 1.00 eq., 250 mg, 1.02 mmol) was reacted with [(2R)-1,4-dioxan-2-yl]methanol (1.50 eq., 180 mg, 1.52 mmol), tri-n-butylphosphine (CAS No. [998-40-3]; 1.6 eq., 410 μL, 1.6 mmol) and TMAD (CAS No. [10465-78-8]; 1.60 eq., 280 mg, 1.62 mmol) in toluene (8 mL) at rt overnight. Another amount of tri-n-butylphosphine (0.30 eq., 76 μL, 300 μmol) and TMAD (0.30 eq., 52 mg, 0.31 mmol) was added and stirring at rt continued for four days to give upon two consecutive column chromatographies ($SiO_2$, $CH_2Cl_2$/MeOH) the title compound (739 mg, 35-40% purity, 74%).

UPLC-MS (Method 1): $R_t$=1.12 min; MS (ESIpos): m/z=347 $[M+H]^+$.

Step 2

2-{[(2R)-1,4-dioxan-2-yl]methyl}-8-methyl-4,5-dihydro-2H-furo[2,3-g]indazole-7-carboxylic acid

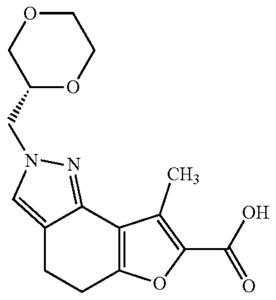 [SMILES: Cc1c(C(=O)O)oc2c1-c1nn(C[C@@H]3COCCO3)cc1CC2]

According to GP D ethyl 2-{[(2R)-1,4-dioxan-2-yl]methyl}-8-methyl-4,5-dihydro-2H-furo[2,3-g]indazole-7-carboxylate (1.00 eq., 739 mg, 40% purity, 850 μmol) from step 1 was reacted with aqueous lithium hydroxide (2 M; 15 eq., 6.4 mL, 13 mmol) in a 1:1 mixture of ethanol and THF (6 mL) at 70° C. overnight. The reaction mixture was acidified with aqueous 4 N HCl (pH 3) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (712 mg, 41% purity, 100%).

UPLC-MS (Method 1): $R_t$=0.49 min; MS (ESIpos): m/z=319 $[M+H]^+$.

Intermediate 22

Step 1 ethyl 2-{[(2S)-1,4-dioxan-2-yl]methyl}-8-methyl-4,5-dihydro-2H-furo[2,3-g]indazole-7-carboxylate

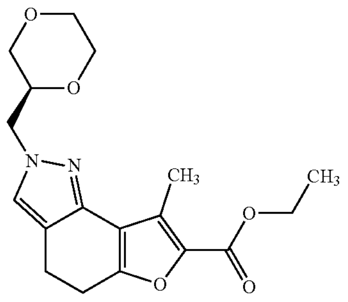 [SMILES: CCOC(=O)c1oc2c(c1C)-c1nn(C[C@H]3COCCO3)cc1CC2]

According to GP C (conditions A) ethyl 8-methyl-4,5-dihydro-1H-furo[2,3-g]indazole-7-carboxylate (commercially available; 1.00 eq., 347 mg, 1.41 mmol) was reacted with [(2S)-1,4-dioxan-2-yl]methanol (CAS No. [406913-93-7]; 1.50 eq., 250 mg, 2.12 mmol), tri-n-butylphosphine (CAS No. [998-40-3]; 1.6 eq., 560 μL, 2.3 mmol) and TMAD (CAS No. [10465-78-8]; 1.60 eq., 389 mg, 2.26 mmol) in toluene (8 mL) at rt for 4 days to give upon column chromatography (Si—NH $SiO_2$, hexane/$CH_2Cl_2$) the title compound (483 mg, 65% purity, 64%).

$^1H$ NMR (400 MHz, DMSO-d6) δ[ppm]: 1.30 (t, 3H), 2.82-2.93 (m, 4H), 3.26 (dd, 1H), 3.45 (dt, 1H), 3.54 (dt, 1H), 3.62-3.64 (m, 1H), 3.72-3.76 (m, 2H), 3.80-3.87 (m, 1H), 4.05-4.14 (m, 2H), 4.27 (q, 2H), 7.48 (s, 1H).

UPLC-MS (Method 1): $R_t$=1.13 min; MS (ESIpos): m/z=347 $[M+H]^+$.

Step 2

2-{[(2S)-1,4-dioxan-2-yl]methyl}-8-methyl-4,5-dihydro-2H-furo[2,3-g]indazole-7-carboxylic acid

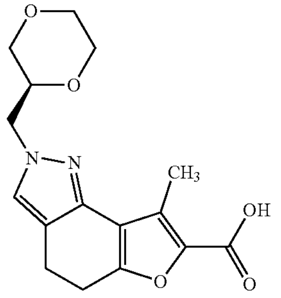 [SMILES: Cc1c(C(=O)O)oc2c1-c1nn(C[C@H]3COCCO3)cc1CC2]

According to GP D ethyl 2-{[(2S)-1,4-dioxan-2-yl]methyl}-8-methyl-4,5-dihydro-2H-furo[2,3-g]indazole-7-carboxylate (1.00 eq., 480 mg, 65% purity, 900 μmol) from step 1 was reacted with aqueous lithium hydroxide (2 M; 23 eq., 10 mL, 21 mmol) in a 1:1 mixture of ethanol and THF (10 mL) at 70° C. overnight. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (422 mg, 64% purity, 61%).

$^1H$ NMR (400 MHz, DMSO-d6) δ[ppm]: 2.47 (s, 3H), 2.81-2.91 (m, 4H), 3.26 (dd, 1H), 3.44 (dt, 1H), 3.54 (dt, 1H), 3.62-3.64 (m, 1H), 3.72-3.75 (m, 2H), 3.82-3.87 (m, 1H), 4.05-4.14 (m, 2H), 7.47 (s, 1H), 12.73 (br. s., 1H).

UPLC-MS (Method 1): $R_t$=0.48 min; MS (ESIpos): m/z=319 $[M+H]^+$.

Intermediate 23

Step 1 ethyl 8-methyl-2-[(oxetan-3-yl)methyl]-4,5-dihydro-2H-furo[2,3-g]indazole-7-carboxylate

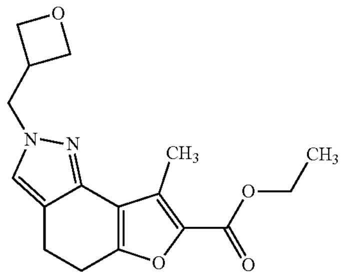 [SMILES: CCOC(=O)c1oc2c(c1C)-c1nn(CC3COC3)cc1CC2]

According to GP C (conditions B) ethyl 8-methyl-4,5-dihydro-1H-furo[2,3-g]indazole-7-carboxylate (commercially available; 1.00 eq., 270 mg, 1.10 mmol) was reacted with 3-(bromomethyl)oxetane (1.50 eq., 248 mg, 1.64 mmol) and potassium carbonate (15 eq., 2.3 g, 16 mmol) in MeCN (8 mL) at 60° C. overnight. DMAP (5 mol %, 6.7 mg, 55 µmol) was added and stirring at 60° C. continued for 4 days to give after filtration the crude title compound (509 mg, 68% purity, 100%) which was not further purified.

$^1H$ NMR (400 MHz, DMSO-d6) δ[ppm]: 1.29 (t, 3H), 2.48 (s, 3H), 2.81-2.85 (m, 2H), 2.88-2.92 (m, 2H), 3.36-3.40 (m, 1H), 4.26 (q, 2H), 4.35-4.43 (m, 3H), 4.49 (d, 1H), 4.64 (dd, 2H), 7.55 (s, 1H).

UPLC-MS (Method 1): $R_t$=1.07 min; MS (ESIpos): m/z=317 $[M+H]^+$.

Step 2

8-methyl-2-[(oxetan-3-yl)methyl]-4,5-dihydro-2H-furo[2,3-g]indazole-7-carboxylic acid

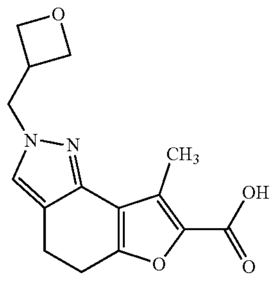 [SMILES: Cc1c(C(=O)O)oc2c1-c1nn(CC3COC3)cc1CC2]

According to GP D ethyl 8-methyl-2-[(oxetan-3-yl)methyl]-4,5-dihydro-2H-furo[2,3-g]indazole-7-carboxylate (1.00 eq., 510 mg, 68% purity, 1.1 mmol) from step 1 was reacted with aqueous lithium hydroxide (2 M; 15 eq., 8.2 mL, 16 mmol) in a 1:1 mixture of ethanol and THF (10 mL) at 70° C. overnight. The reaction mixture was neutralized with aqueous 4 N HCl (pH 6) and concentrated under reduced pressure to give the crude title compound along with salts (1.9 g) which was not further purified.

UPLC-MS (Method 1): $R_t$=0.44 min; MS (ESIpos): m/z=289 $[M+H]^+$.

Intermediate 24

Step 1 ethyl 8-methyl-2-[(3-methyloxetan-3-yl)methyl]-4,5-dihydro-2H-furo[2,3-g]indazole-7-carboxylate

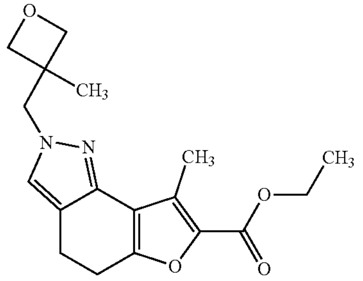 [SMILES: CCOC(=O)c1oc2c(c1C)-c1nn(CC3(C)COC3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (3-methyloxetan-3-yl)methanol (1.5 eq., 190 µL, 1.8 mmol), tri-n-butylphosphine (CAS No. [998-40-3]; 1.6 eq., 490 µL, 1.9 mmol) and TMAD (CAS No. [10465-78-8]; 1.60 eq., 336 mg, 1.95 mmol) in toluene (8 mL) at rt overnight to give upon column chromatography (Si—NH $SiO_2$, hexane/$CH_2Cl_2$) the title compound (529 mg, 52% purity, 68%).

$^1H$ NMR (400 MHz, DMSO-d6) δ[ppm]: 1.17 (s, 3H), 1.29 (t, 3H), 2.48 (s, 3H), 2.83-2.93 (m, 4H), 4.21-4.29 (m, 6H), 4.60 (d, 2H), 7.55 (s, 1H).

UPLC-MS (Method 1): $R_t$=1.17 min; MS (ESIpos): m/z=331 $[M+H]^+$.

Step 2

8-methyl-2-[(3-methyloxetan-3-yl)methyl]-4,5-dihydro-2H-furo[2,3-g]indazole-7-carboxylic acid

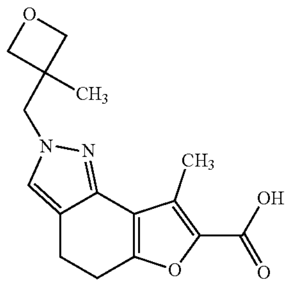 [SMILES: Cc1c(C(=O)O)oc2c1-c1nn(CC3(C)COC3)cc1CC2]

According to GP D ethyl 8-methyl-2-[(3-methyloxetan-3-yl)methyl]-4,5-dihydro-2H-furo[2,3-g]indazole-7-carboxylate (1.00 eq., 527 mg, 52% purity, 829 μmol) from step 1 was reacted with aqueous lithium hydroxide (2 M; 15 eq., 6.2 mL, 12 mmol) in a 1:1 mixture of ethanol and THF (6 mL) at 70° C. overnight. The reaction mixture was acidified with aqueous 4 N HCl (pH 3) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (500 mg, 42% purity, 84%).

$^1$H NMR (400 MHz, DMSO-d6) δ[ppm]: 1.16 (s, 3H), 2.45 (s, 3H), 2.81-2.89 (m, 4H), 4.22 (d, 2H), 4.26 (s, 2H), 4.60 (d, 2H), 7.52 (s, 1H), 12.75 (br. s., 1H).

UPLC-MS (Method 1): $R_t$=0.49 min; MS (ESIpos): m/z=303 [M+H]$^+$.

Intermediate 25

Step 1 ethyl 2-[(3-fluorooxetan-3-yl)methyl]-8-methyl-4,5-dihydro-2H-furo[2,3-g]indazole-7-carboxylate

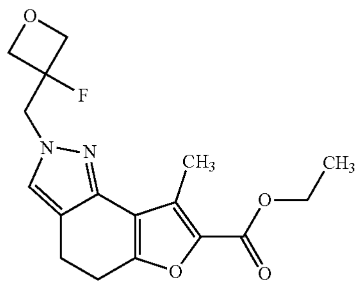 [SMILES: CCOC(=O)c1oc2c(c1C)-c1nn(CC3(F)COC3)cc1CC2]

According to GP C (conditions B) ethyl 8-methyl-4,5-dihydro-1H-furo[2,3-g]indazole-7-carboxylate (commercially available; 1.00 eq., 270 mg, 1.10 mmol) was reacted with 3-(bromomethyl)-3-fluorooxetane (1.50 eq., 278 mg, 1.64 mmol) and potassium carbonate (15 eq., 2.3 g, 16 mmol) in MeCN (8 mL) at 60° C. overnight. DMAP (5 mol %, 6.7 mg, 55 μmol) was added and stirring at 60° C. continued for 4 days to give after filtration the crude title compound (433 mg, 85% purity, 100%) which was not further purified.

$^1$H NMR (400 MHz, DMSO-d6) δ[ppm]: 1.29 (t, 3H), 2.83-2.94 (m, 4H), 4.27 (q, 2H), 4.59-4.68 (m, 4H), 4.75-4.85 (m, 2H), 7.55 (s, 1H).

UPLC-MS (Method 1): $R_t$=1.13 min; MS (ESIpos): m/z=335 [M+H]$^+$.

Step 2

2-[(3-fluorooxetan-3-yl)methyl]-8-methyl-4,5-dihydro-2H-furo[2,3-g]indazole-7-carboxylic acid

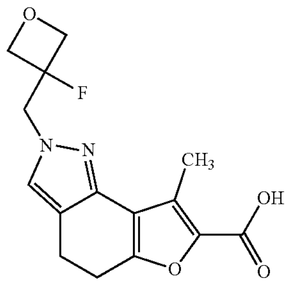 [SMILES: Cc1c(C(=O)O)oc2c1-c1nn(CC3(F)COC3)cc1CC2]

According to GP D ethyl 2-[(3-fluorooxetan-3-yl)methyl]-8-methyl-4,5-dihydro-2H-furo[2,3-g]indazole-7-carboxylate (1.00 eq., 433 mg, 85% purity, 1.1 mmol) from step 1 was reacted with aqueous lithium hydroxide (2 M; 15 eq., 8.3 mL, 17 mmol) in a 1:1 mixture of ethanol and THF (10 mL) at 70° C. overnight. The reaction mixture was neutralized with aqueous 4 N HCl (pH 6) and concentrated under reduced pressure to give the crude title compound along with salts (1.8 g) which was not further purified.

UPLC-MS (Method 1): $R_t$=0.46 min; MS (ESIpos): m/z=307 [M+H]$^+$.

Intermediate 26

Step 1 ethyl 8-methyl-2-{[(2R)-oxetan-2-yl]methyl}-4,5-dihydro-2H-furo[2,3-g]indazole-7-carboxylate

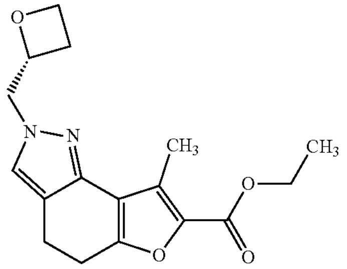 [SMILES: CCOC(=O)c1oc2c(c1C)-c1nn(C[C@H]3CCO3)cc1CC2]

According to GP C (conditions A) ethyl 8-methyl-4,5-dihydro-1H-furo[2,3-g]indazole-7-carboxylate (commercially available; 1.00 eq., 330 mg, 1.34 mmol) was reacted with [(2R)-oxetan-2-yl]methanol (1.50 eq., 177 mg, 2.01 mmol), tri-n-butylphosphine (CAS No. [998-40-3]; 1.6 eq., 540 μL, 2.1 mmol) and TMAD (CAS No. [10465-78-8]; 1.60 eq., 369 mg, 2.14 mmol) in toluene (5 mL) at rt overnight to give upon column chromatography ($SiO_2$, hexane/EtOAc) the title compound (197 mg, 46%).

$^1$H NMR (400 MHz, DMSO-d6) δ[ppm]: 1.29 (t, 3H), 2.37-2.46 (m, 1H), 2.60-2.68 (m, 1H), 2.83-2.93 (m, 4H), 4.24-4.37 (m, 5H), 4.46-4.51 (m, 1H), 4.94-5.00 (m, 1H), 7.52 (s, 1H).

UPLC-MS (Method 1): $R_t$=1.00 min; MS (ESIpos): m/z=317 [M+H]$^+$.

Step 2

8-methyl-2-{[(2R)-oxetan-2-yl]methyl}-4,5-dihydro-2H-furo[2,3-g]indazole-7-carboxylic acid

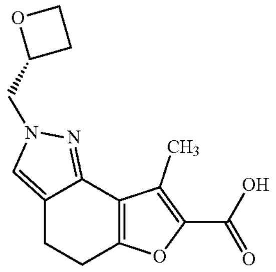 [SMILES: Cc1c(C(=O)O)oc2c1-c1nn(C[C@H]3CCO3)cc1CC2]

According to GP D ethyl 8-methyl-2-{[(2R)-oxetan-2-yl]methyl}-4,5-dihydro-2H-furo[2,3-g]indazole-7-carboxylate (1.00 eq., 190 mg, 601 μmol) from step 1 was reacted with aqueous lithium hydroxide (2 M; 15 eq., 4.5 mL, 9.0 mmol) in a 1:1 mixture of ethanol and THF (8 mL) at 70° C. for three days. The reaction mixture was acidified with aqueous 6 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (198 mg, 91%).

UPLC-MS (Method 1): $R_t$=0.50 min; MS (ESIpos): m/z=289 $[M+H]^+$.

Intermediate 27

Step 1 ethyl 8-methyl-2-{[(2S)-oxetan-2-yl]methyl}-4,5-dihydro-2H-furo[2,3-g]indazole-7-carboxylate

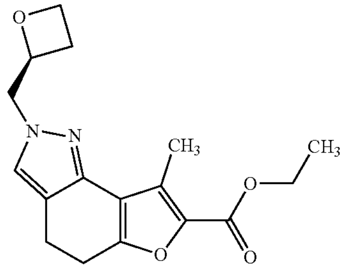 [SMILES: CCOC(=O)c1oc2c(c1C)-c1nn(C[C@@H]3CCO3)cc1CC2]

According to GP C (conditions A) ethyl 8-methyl-4,5-dihydro-1H-furo[2,3-g]indazole-7-carboxylate (commercially available; 1.00 eq., 330 mg, 1.34 mmol) was reacted with [(2S)-oxetan-2-yl]methanol (1.50 eq., 177 mg, 2.01 mmol), tri-n-butylphosphine (CAS No. [998-40-3]; 1.6 eq., 540 μL, 2.1 mmol) and TMAD (CAS No. [10465-78-8]; 1.60 eq., 369 mg, 2.14 mmol) in toluene (5 mL) at rt overnight to give upon column chromatography ($SiO_2$, hexane/EtOAc) the title compound (233 mg, 53%).

$^1$H NMR (400 MHz, DMSO-d6) δ[ppm]: 1.29 (t, 3H), 2.37-2.46 (m, 1H), 2.60-2.68 (m, 1H), 2.83-2.94 (m, 4H), 4.24-4.37 (m, 5H), 4.47-4.51 (m, 1H), 4.94-5.00 (m, 1H), 7.52 (s, 1H).

UPLC-MS (Method 1): $R_t$=1.11 min; MS (ESIpos): m/z=317 $[M+H]^+$.

Step 2

8-methyl-2-{[(2S)-oxetan-2-yl]methyl}-4,5-dihydro-2H-furo[2,3-g]indazole-7-carboxylic acid

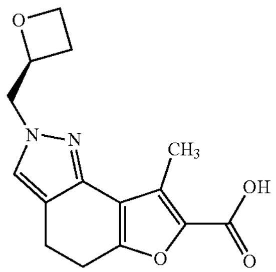 [SMILES: Cc1c(C(=O)O)oc2c1-c1nn(C[C@@H]3CCO3)cc1CC2]

According to GP D ethyl 8-methyl-2-{[(2S)-oxetan-2-yl]methyl}-4,5-dihydro-2H-furo[2,3-g]indazole-7-carboxylate (1.00 eq., 228 mg, 721 μmol) from step 1 was reacted with aqueous lithium hydroxide (2 M; 15 eq., 5.4 mL, 11 mmol) in a 1:1 mixture of ethanol and THF (10 mL) at 70° C. for three days. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (198 mg, 86%).

$^1$H NMR (400 MHz, DMSO-d6) δ[ppm]: 2.38-2.45 (m, 1H), 2.47 (s, 3H), 2.60-2.68 (m, 1H), 2.82-2.91 (m, 4H), 4.24-4.36 (m, 3H), 4.46-4.51 (m, 1H), 4.94-5.00 (m, 1H), 7.50 (s, 1H), 12.80 (br. s., 1H).

UPLC-MS (Method 1): $R_t$=0.50 min; MS (ESIpos): m/z=289 $[M+H]^+$.

Intermediate 28

Step 1 ethyl 8-methyl-2-{[(2R)-4-methylmorpholin-2-yl]methyl}-4,5-dihydro-2H-furo[2,3-g]indazole-7-carboxylate

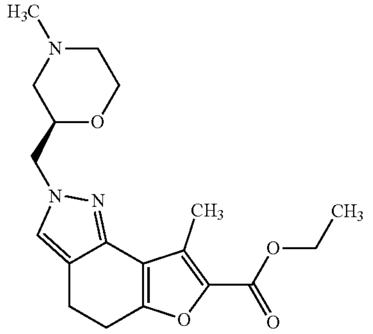 [SMILES: CCOC(=O)c1oc2c(c1C)-c1nn(C[C@H]3CN(C)CCO3)cc1CC2]

According to GP C (conditions A) ethyl 8-methyl-4,5-dihydro-1H-furo[2,3-g]indazole-7-carboxylate (commercially available; 1.00 eq., 313 mg, 1.27 mmol) was reacted with [(2R)-4-methylmorpholin-2-yl]methanol (CAS No.

[1159598-35-2]; 1.50 eq., 250 mg, 1.91 mmol), tri-n-butylphosphine (CAS No. [998-40-3]; 1.6 eq., 510 μL, 2.0 mmol) and TMAD (CAS No. [10465-78-8]; 1.60 eq., 350 mg, 2.03 mmol) in toluene (8 mL) at rt overnight. Another amount of tri-n-butylphosphine (0.30 eq., 95 μL, 0.38 mmol) and TMAD (0.30 eq., 66 mg, 0.38 mmol) was added and stirring at rt continued for three days to give upon column chromatography (Si—NH $SiO_2$, $CH_2Cl_2$/MeOH) the title compound (921 mg, 44% purity, 88%).

$^1$H NMR (400 MHz, DMSO-d6) δ[ppm]: 1.30 (t, 3H), 1.72-1.78 (m, 1H), 1.96 (dt, 1H), 2.16 (s, 3H), 2.54-2.57 (m, 1H), 2.63-2.66 (m, 1H), 2.82-2.86 (m, 3H), 2.89-2.93 (m, 2H), 3.45 (dt, 1H), 3.74-3.80 (m, 2H), 4.10 (d, 2H), 4.27 (q, 2H), 7.48 (s, 1H). UPLC-MS (Method 1): $R_t$=1.10 min; MS (ESIpos): m/z=360 $[M+H]^+$.

Specific rotation: $[\alpha]_D^{20}$=−7.2°+/−0.49° (C=10.0 mg/mL, methanol).

Step 2

8-methyl-2-{[(2R)-4-methylmorpholin-2-yl]methyl}-4,5-dihydro-2H-furo[2,3-g]indazole-7-carboxylic acid

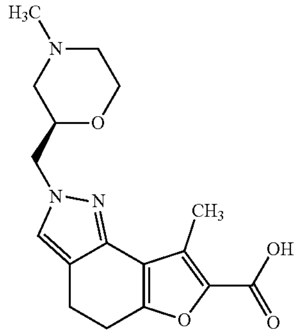 [SMILES: Cc1c(C(=O)O)oc2c1-c1nn(C[C@H]3CN(C)CCO3)cc1CC2]

According to GP D ethyl 8-methyl-2-{[(2R)-4-methylmorpholin-2-yl]methyl}-4,5-dihydro-2H-furo[2,3-g]indazole-7-carboxylate (1.00 eq., 912 mg, 44% purity, 1.12 mmol) from step 1 was reacted with aqueous lithium hydroxide (2 M; 15 eq., 8.4 mL, 17 mmol) in a 1:1 mixture of ethanol and THF (12 mL) at 70° C. overnight. The reaction mixture was acidified with aqueous 4 N HCl (pH 4) and concentrated under reduced pressure to give the crude title compound along with salts (1.15 g) which was not further purified.

UPLC-MS (Method 1): $R_t$=0.50 min; MS (ESIpos): m/z=332 $[M+H]^+$.

Intermediate 29

Step 1 ethyl 8-methyl-2-{[(2S)-4-methylmorpholin-2-yl]methyl}-4,5-dihydro-2H-furo[2,3-g]indazole-7-carboxylate

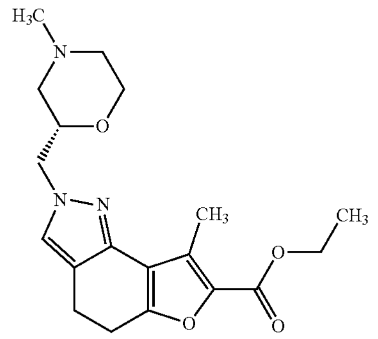 [SMILES: CCOC(=O)c1oc2c(c1C)-c1nn(C[C@@H]3CN(C)CCO3)cc1CC2]

According to GP C (conditions A) ethyl 8-methyl-4,5-dihydro-1H-furo[2,3-g]indazole-7-carboxylate (commercially available; 1.00 eq., 313 mg, 1.27 mmol) was reacted with [(2S)-4-methylmorpholin-2-yl]methanol (CAS No. [1159598-33-0]; 1.50 eq., 250 mg, 1.91 mmol), tri-n-butylphosphine (CAS No. [998-40-3]; 1.6 eq., 510 μL, 2.0 mmol) and TMAD (CAS No. [10465-78-8]; 1.60 eq., 350 mg, 2.03 mmol) in toluene (8 mL) at rt overnight. Another amount of tri-n-butylphosphine (0.30 eq., 95 μL, 0.38 mmol) and TMAD (0.30 eq., 66 mg, 0.38 mmol) was added and stirring at rt continued for three days to give upon column chromatography (Si—NH $SiO_2$, $CH_2Cl_2$/MeOH) the title compound (192 mg, 85% purity, 36%).

$^1$H NMR (400 MHz, DMSO-d6) δ[ppm]: 1.30 (t, 3H), 1.72-1.77 (m, 1H), 1.96 (dt, 1H), 2.16 (s, 3H), 2.54-2.57 (m, 1H), 2.63-2.67 (m, 1H), 2.82-2.86 (m, 3H), 2.89-2.93 (m, 2H), 3.45 (dt, 1H), 3.75-3.80 (m, 2H), 4.10 (d, 2H), 4.27 (q, 2H), 7.48 (s, 1H).

UPLC-MS (Method 1): $R_t$=1.10 min; MS (ESIpos): m/z=360 $[M+H]^+$.

Step 2

8-methyl-2-{[(2S)-4-methylmorpholin-2-yl]methyl}-4,5-dihydro-2H-furo[2,3-g]indazole-7-carboxylic acid

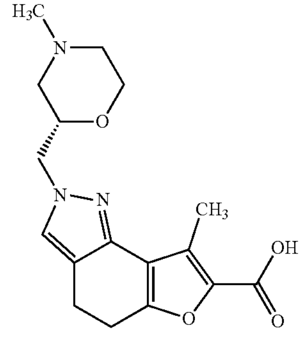 [SMILES: Cc1c(C(=O)O)oc2c1-c1nn(C[C@@H]3CN(C)CCO3)cc1CC2]

According to GP D ethyl 8-methyl-2-{[(2S)-4-methylmorpholin-2-yl]methyl}-4,5-dihydro-2H-furo[2,3-g]indazole-7-carboxylate (1.00 eq., 192 mg, 85% purity, 534 μmol) from step 1 was reacted with aqueous lithium hydroxide (2 M; 15 eq., 4.0 mL, 8.0 mmol) in a 1:1 mixture of ethanol and THF (6 mL) at 70° C. overnight. The reaction mixture was acidified with aqueous 4 N HCl (pH 4) and concentrated under reduced pressure to give the crude title compound along with salts (691 mg) which was not further purified.

UPLC-MS (Method 1): $R_t$=0.50 min; MS (ESIpos): m/z=332 $[M+H]^+$.

Intermediate 30

Step 1 ethyl 8-methyl-2-[(2R)-tetrahydrofuran-2-ylmethyl]-4,5-dihydro-2H-furo[2,3-g]indazole-7-carboxylate

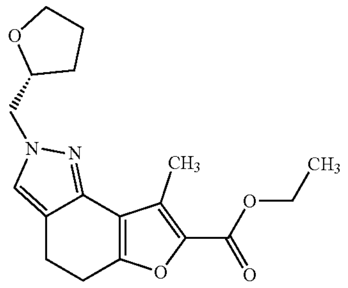 [SMILES: CCOC(=O)c1oc2c(c1C)-c1nn(C[C@H]3CCCO3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (2R)-tetrahydrofuran-2-ylmethanol (CAS No. [22415-59-4]; 1.1 eq., 130 μL, 1.3 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography (Si—NH $SiO_2$, $CH_2Cl_2$/MeOH) the title compound (470 mg, 68% purity, 79%).

$^1$H NMR (400 MHz, DMSO-d6) δ[ppm]: 1.29 (t, 3H), 1.54-1.57 (m, 1H), 1.75-1.82 (m, 2H), 1.90-1.97 (m, 1H), 2.82-2.93 (m, 4H), 3.60-3.65 (m, 1H), 3.72-3.78 (m, 1H), 4.03-4.17 (m, 3H), 4.27 (q, 2H), 7.49 (s, 1H).

UPLC-MS (Method 1): $R_t$=1.22 min; MS (ESIpos): m/z=331 $[M+H]^+$.

Step 2

8-methyl-2-[(2R)-tetrahydrofuran-2-ylmethyl]-4,5-dihydro-2H-furo[2,3-g]indazole-7-carboxylic acid

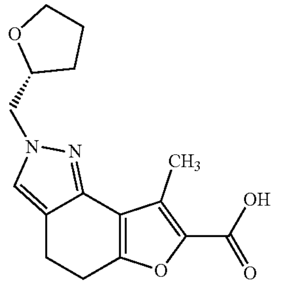 [SMILES: Cc1c(C(=O)O)oc2c1-c1nn(C[C@H]3CCCO3)cc1CC2]

According to GP D ethyl 8-methyl-2-[(2R)-tetrahydrofuran-2-ylmethyl]-4,5-dihydro-2H-furo[2,3-g]indazole-7-carboxylate (1.00 eq., 470 mg, 68% purity, 967 μmol) from step 1 was reacted with aqueous lithium hydroxide (2 M; 18 eq., 8.5 mL, 17 mmol) in a 1:1 mixture of ethanol and THF (8 mL) at 70° C. for 24 h and subsequently at rt for two days. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (380 mg, 69% purity, 76%).

$^1$H NMR (400 MHz, DMSO-d6) δ[ppm]: 1.54-1.57 (m, 1H), 1.75-1.82 (m, 2H), 1.88-1.97 (m, 1H), 2.47 (s, 3H), 2.81-2.90 (m, 4H), 3.60-3.65 (m, 1H), 3.72-3.78 (m, 1H), 4.02-4.17 (m, 3H), 7.47 (s, 1H), 12.73 (br. s., 1H).

UPLC-MS (Method 1): $R_t$=0.52 min; MS (ESIpos): m/z=303 $[M+H]^+$.

Intermediate 31

Step 1 ethyl 8-methyl-2-[(2S)-tetrahydrofuran-2-ylmethyl]-4,5-dihydro-2H-furo[2,3-g]indazole-7-carboxylate

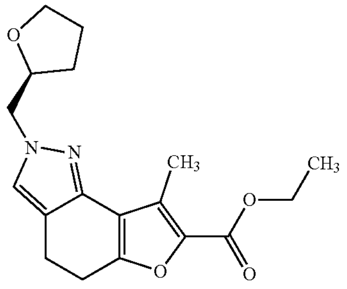 [SMILES: CCOC(=O)c1oc2c(c1C)-c1nn(C[C@@H]3CCCO3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (2S)-tetrahydrofuran-2-ylmethanol (CAS No. [57203-01-7]; 1.1 eq., 130 μL, 1.3 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography (Si—NH $SiO_2$, $CH_2Cl_2$/MeOH) the title compound (437 mg, 72% purity, 78%).

$^1$H NMR (400 MHz, DMSO-d6) δ[ppm]: 1.29 (t, 3H), 1.54-1.57 (m, 1H), 1.75-1.82 (m, 2H), 1.90-1.97 (m, 1H), 2.82-2.93 (m, 4H), 3.60-3.65 (m, 1H), 3.72-3.78 (m, 1H), 4.03-4.16 (m, 3H), 4.27 (q, 2H), 7.48 (s, 1H).

UPLC-MS (Method 1): $R_t$=1.22 min; MS (ESIpos): m/z=331 $[M+H]^+$.

Step 2

8-methyl-2-[(2S)-tetrahydrofuran-2-ylmethyl]-4,5-dihydro-2H-furo[2,3-g]indazole-7-carboxylic acid

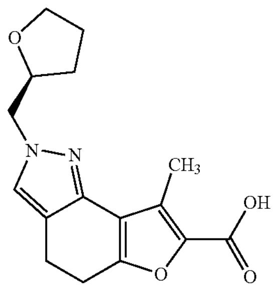 [SMILES: Cc1c(C(=O)O)oc2c1-c1nn(C[C@@H]3CCCO3)cc1CC2]

According to GP D ethyl 8-methyl-2-[(2S)-tetrahydrofuran-2-ylmethyl]-4,5-dihydro-2H-furo[2,3-g]indazole-7-carboxylate (1.00 eq., 435 mg, 72% purity, 948 μmol) from step 1 was reacted with aqueous lithium hydroxide (2 M; 21 eq., 9.9 mL, 20 mmol) in a 1:1 mixture of ethanol and THF (10 mL) at 70° C. for 24 h and subsequently at rt for two days. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (373 mg, 78% purity, 73%).

$^1H$ NMR (400 MHz, DMSO-d6) δ[ppm]: 1.54-1.57 (m, 1H), 1.75-1.82 (m, 2H), 1.88-1.96 (m, 1H), 2.47 (s, 3H), 2.81-2.90 (m, 4H), 3.60-3.65 (m, 1H), 3.72-3.78 (m, 1H), 4.02-4.16 (m, 3H), 7.47 (s, 1H), 12.72 (br. s., 1H).

UPLC-MS (Method 1): $R_t$=0.51 min; MS (ESIpos): m/z=303 $[M+H]^+$.

Intermediate 32

Step 1 ethyl 2-{[1-(tert-butoxycarbonyl)azetidin-3-yl]methyl}-8-methyl-4,5-dihydro-2H-furo[2,3-g]indazole-7-carboxylate

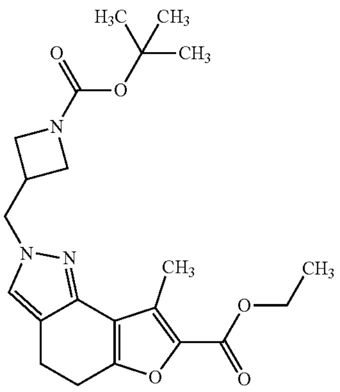 [SMILES: CCOC(=O)c1oc2c(c1C)-c1nn(CC3CN(C(=O)OC(C)(C)C)C3)cc1CC2]

According to GP C (conditions A) ethyl 8-methyl-4,5-dihydro-1H-furo[2,3-g]indazole-7-carboxylate (commercially available; 1.00 eq., 330 mg, 1.34 mmol) was reacted with tert-butyl 3-(hydroxymethyl)azetidine-1-carboxylate (CAS No. [142253-56-3]; 1.50 eq., 376 mg, 2.01 mmol), tri-n-butylphosphine (CAS No. [998-40-3]; 1.6 eq., 540 μL, 2.1 mmol) and TMAD (CAS No. [10465-78-8]; 1.60 eq., 369 mg, 2.14 mmol) in toluene (9 mL) at rt overnight to give upon column chromatography ($SiO_2$, hexane/EtOAc) the title compound (420 mg, 69%).

$^1H$ NMR (400 MHz, DMSO-d6) δ[ppm]: 1.29 (t, 3H), 1.35 (s, 9H), 2.81-2.98 (m, 5H), 3.66-3.69 (m, 2H), 3.88 (br. s., 2H), 4.24-4.29 (m, 4H), 7.58 (s, 1H).

UPLC-MS (Method 1): $R_t$=1.34 min; MS (ESIpos): m/z=416 $[M+H]^+$.

Step 2

2-{[1-(tert-butoxycarbonyl)azetidin-3-yl]methyl}-8-methyl-4,5-dihydro-2H-furo[2,3-g]indazole-7-carboxylic acid

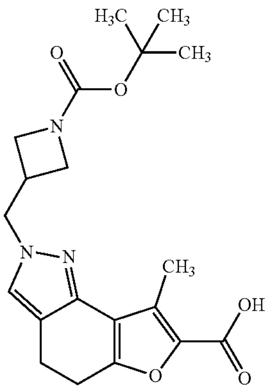 [SMILES: Cc1c(C(=O)O)oc2c1-c1nn(CC3CN(C(=O)OC(C)(C)C)C3)cc1CC2]

According to GP D ethyl 2-{[1-(tert-butoxycarbonyl)azetidin-3-yl]methyl}-8-methyl-4,5-dihydro-2H-furo[2,3-g]indazole-7-carboxylate (1.00 eq., 417 mg, 1.00 mmol) from step 1 was reacted with aqueous lithium hydroxide (2 M; 15 eq., 7.5 mL, 15 mmol) in a 1:1 mixture of ethanol and THF (8 mL) at 70° C. for 24 h and subsequently at rt for two days. The reaction mixture was acidified with aqueous 4 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (327 mg, 76%).

$^1H$ NMR (400 MHz, DMSO-d6) δ[ppm]: 1.35 (s, 9H), 2.47 (s, 3H), 2.80-2.96 (m, 5H), 3.66-3.69 (m, 2H), 3.85-3.94 (m, 2H), 4.26 (d, 2H), 7.56 (s, 1H), 12.85 (br. s., 1H).

UPLC-MS (Method 1): $R_t$=0.65 min; MS (ESIpos): m/z=388 $[M+H]^+$.

Intermediate 33

Step 1 ethyl 8-methyl-2-[(3R)-tetrahydrofuran-3-ylmethyl]-4,5-dihydro-2H-furo[2,3-g]indazole-7-carboxylate

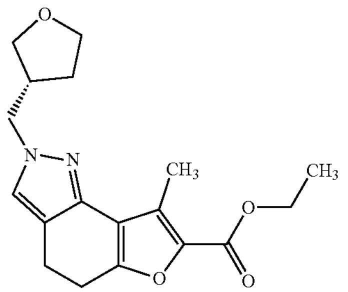 [SMILES: CCOC(=O)c1oc2c(c1C)-c1nn(C[C@H]3CCOC3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (3R)-tetrahydrofuran-3-ylmethanol (CAS No. [124506-31-6]; 1.5 eq., 187 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt overnight to give upon column chromatography ($SiO_2$, hexane/EtOAc) the title compound (465 mg, 100%).

$^1H$ NMR (400 MHz, DMSO-d6) δ[ppm]: 1.29 (t, 3H), 1.56-1.65 (m, 1H), 1.88-1.96 (m, 1H), 2.65-2.74 (m, 1H), 2.81-2.94 (m, 4H), 3.49 (dd, 1H), 3.59-3.68 (m, 2H), 3.73-3.80 (m, 1H), 4.00-4.09 (m, 2H), 4.27 (q, 2H), 7.56 (s, 1H).

UPLC-MS (Method 1): $R_t$=1.17 min; MS (ESIpos): m/z=331 $[M+H]^+$.

Step 2

8-methyl-2-[(3R)-tetrahydrofuran-3-ylmethyl]-4,5-dihydro-2H-furo[2,3-g]indazole-7-carboxylic acid

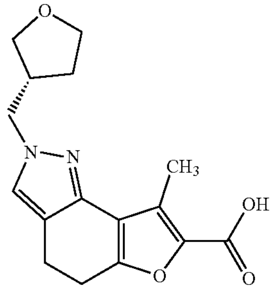 [SMILES: Cc1c(C(=O)O)oc2c1-c1nn(C[C@H]3CCOC3)cc1CC2]

According to GP D ethyl 8-methyl-2-[(3R)-tetrahydrofuran-3-ylmethyl]-4,5-dihydro-2H-furo[2,3-g]indazole-7-carboxylate (1.00 eq., 458 mg, 1.39 mmol) from step 1 was reacted with aqueous lithium hydroxide (2 M; 15 eq., 10 mL, 21 mmol) in a 1:1 mixture of ethanol and THF (20 mL) at 70° C. overnight and for two days at rt. The reaction mixture was acidified with aqueous 6 N HCl (pH 3) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (166 mg, 38%).

$^1H$ NMR (400 MHz, DMSO-d6) δ[ppm]: 1.56-1.65 (m, 1H), 1.88-1.96 (m, 1H), 2.47 (s, 3H), 2.63-2.72 (m, 1H), 2.81-2.91 (m, 4H), 3.49 (dd, 1H), 3.59-3.68 (m, 2H), 3.74-3.78 (m, 1H), 3.99-4.08 (m, 2H), 7.54 (s, 1H), 12.78 (br. s., 1H).

UPLC-MS (Method 1): $R_t$=0.48 min; MS (ESIpos): m/z=303 $[M+H]^+$.

Intermediate 34

Step 1 ethyl 8-methyl-2-[(3S)-tetrahydrofuran-3-ylmethyl]-4,5-dihydro-2H-furo[2,3-g]indazole-7-carboxylate

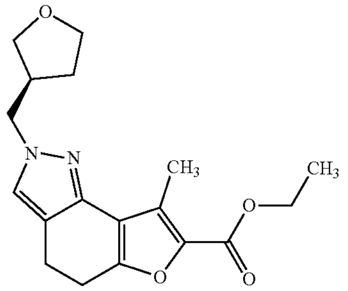 [SMILES: CCOC(=O)c1oc2c(c1C)-c1nn(C[C@@H]3CCOC3)cc1CC2]

According to GP C (conditions A) ethyl 8-methyl-4,5-dihydro-1H-furo[2,3-g]indazole-7-carboxylate (commercially available; 1.00 eq., 402 mg, 1.63 mmol) was reacted with (3S)-tetrahydrofuran-3-ylmethanol (CAS No. [124391-75-9]; 1.5 eq., 250 mg, 2.45 mmol), tri-n-butylphosphine (CAS No. [998-40-3]; 1.6 eq., 650 μL, 2.6 mmol) and TMAD (CAS No. [10465-78-8]; 1.60 eq., 450 mg, 2.61 mmol) in toluene (8 mL) at rt overnight to give upon column chromatography ($SiO_2$, hexane/EtOAc) the title compound (365 mg, 67%).

$^1H$ NMR (400 MHz, DMSO-d6) δ[ppm]: 1.29 (t, 3H), 1.56-1.65 (m, 1H), 1.88-1.96 (m, 1H), 2.65-2.74 (m, 1H), 2.82-2.93 (m, 4H), 3.49 (dd, 1H), 3.59-3.68 (m, 2H), 3.73-3.79 (m, 1H), 4.00-4.09 (m, 2H), 4.26 (q, 2H), 7.56 (s, 1H).

UPLC-MS (Method 1): $R_t$=1.11 min; MS (ESIpos): m/z=331 $[M+H]^+$.

Step 2

8-methyl-2-[(3S)-tetrahydrofuran-3-ylmethyl]-4,5-dihydro-2H-furo[2,3-g]indazole-7-carboxylic acid

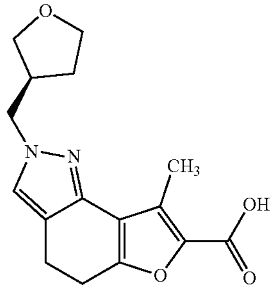 [SMILES: Cc1c(C(=O)O)oc2c1-c1nn(C[C@@H]3CCOC3)cc1CC2]

According to GP D ethyl 8-methyl-2-[(3S)-tetrahydrofuran-3-ylmethyl]-4,5-dihydro-2H-furo[2,3-g]indazole-7-carboxylate (1.00 eq., 357 mg, 1.08 mmol) from step 1 was reacted with aqueous lithium hydroxide (2 M; 15 eq., 8.1 mL, 16 mmol) in a 1:1 mixture of ethanol and THF (16 mL) at 70° C. overnight. The reaction mixture was acidified with aqueous 6 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (311 mg, 86%).

$^1$H NMR (400 MHz, DMSO-d6) δ[ppm]: 1.56-1.65 (m, 1H), 1.88-1.96 (m, 1H), 2.48 (s, 3H), 2.63-2.72 (m, 1H), 2.81-2.92 (m, 4H), 3.49 (dd, 1H), 3.59-3.68 (m, 2H), 3.74-3.78 (m, 1H), 4.00-4.09 (m, 2H), 7.55 (s, 1H), 12.78 (br. s., 1H).

UPLC-MS (Method 1): $R_t$=0.47 min; MS (ESIpos): m/z=303 $[M+H]^+$.

Intermediate 35

Step 1 ethyl 2-chloro-4,4,4-trifluoro-3-oxobutanoate

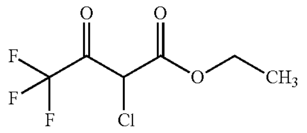

To a solution of ethyl 4,4,4-trifluoro-3-oxobutanoate (1.00 eq., 500 mmol, 92.0 g) in dichloromethane (100 mL) was added a solution of sulfuryl chloride (CAS No. [7791-25-5]; 1.10 eq., 550 mmol, 44 mL) in dichloromethane (50 mL) at −5 to 0° C. The reaction mixture was warmed to room temperature and stirred at this temperature for 12 hours. The mixture was poured into water and extracted with ethyl acetate. The organic layer was washed with brine and concentrated under reduced pressure. The obtained material was purified by column chromatography (100-200 mesh, petroleum ether: ethyl acetate=50:1, then 5:1) to give ethyl 2-chloro-4,4,4-trifluoro-3-oxobutanoate (66.0 g, 60%) as yellow oil.

$^1$H NMR (400 MHz, $CDCl_3$) 5 [ppm]: 1.34 (t, 3H), 4.33 (q, 2H), 4.48 (s, 1H).

Step 2 ethyl 4-oxo-3-(trifluoromethyl)-4,5,6,7-tetrahydro-1-benzofuran-2-carboxylate

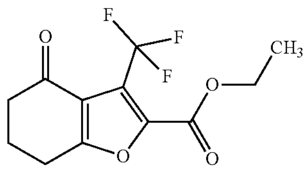 [SMILES: CCOC(=O)c1oc2c(c1C(F)(F)F)C(=O)CCC2]

To a solution of cyclohexane-1,3-dione (1.00 eq., 44.6 mmol, 5.00 g) in toluene (15 mL) was added ethyl 2-chloro-4,4,4-trifluoro-3-oxobutanoate (2.20 eq, 98.1 mmol, 21.4 g) from step 1 at 20° C. and the reaction mixture subsequently stirred at 100° C. for 36 hours. The mixture was poured into water and extracted with ethyl acetate. The organic layer was washed with brine and concentrated under reduced pressure. The obtained material was purified by column chromatography (100-200 mesh, petroleum ether: ethyl acetate=50:1, then 20:1) to give ethyl 4-oxo-3-(trifluoromethyl)-4,5,6,7-tetrahydro-1-benzofuran-2-carboxylate (7.2 g, 57%) as a yellow oil.

$^1$H NMR (400 MHz, $CDCl_3$) 5 [ppm]: 1.40 (t, 3H), 2.23 (quint, 2H), 2.59-2.62 (m, 2H), 2.99 (t, 2H), 4.43 (q, 2H), 4.48 (s, 1H).

LC-MS (Method B): $R_t$=0.89 min; MS (ESIpos): m/z=277 $[M+H]^+$.

Step 3

(5E/Z)-ethyl 5-(hydroxymethylene)-4-oxo-3-(trifluoromethyl)-4,5,6,7-tetrahydro-1-benzofuran-2-carboxylate

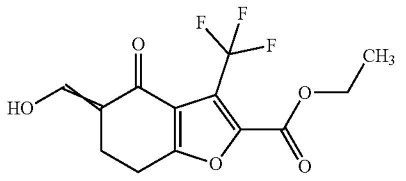 [SMILES: CCOC(=O)c1oc2c(c1C(F)(F)F)C(=O)C(=CO)CC2]

According to GP A (conditions B) a solution of ethyl formate (CAS No. [109-94-4]; 6.0 eq., 87 mmol, 7.0 mL) in toluene (40 mL) was treated with sodium hydride (CAS No. [7646-69-7]; 3.00 eq., 43.4 mmol, 1.74 g, 60% purity) at 0° C. After stirring for 0.5 hours, a solution of ethyl 4-oxo-3-(trifluoromethyl)-4,5,6,7-tetrahydro-1-benzofuran-2-carboxylate (1.00 eq., 14.5 mmol, 4.00 g) from step 2 in toluene (10 mL) was added to the mixture. The reaction mixture was stirred at room temperature for 2 hours and quenched with aqueous 2N HCl (pH-3). The phases were separated, and the aqueous phase extracted with ethyl acetate. The combined organic phases were washed with brine, dried over anhydrous sodium sulfate, filtrated and concentrated to give crude (5E/Z)-ethyl 5-(hydroxymethylene)-4-oxo-3-(trifluoromethyl)-4,5,6,7-tetrahydro-1-benzofuran-2-carboxylate (4.4 g, 100%) as brown oil which was not further purified.

$^1$H NMR (400 MHz, $CDCl_3$) δ [ppm]: 1.41 (t, 3H), 2.70 (t, 2H), 2.97 (t, 2H), 4.44 (q, 2H), 4.48 (s, 1H), 7.37-7.40 (m, 1H), 13.48-13.50 (m, 1H).

LC-MS (Method B): $R_t$=0.73 min; MS (ESIpos): m/z=305 $[M+H]^+$.

Step 4 ethyl 8-(trifluoromethyl)-4,5-dihydro-1H-furo[2,3-g]indazole-7-carboxylate

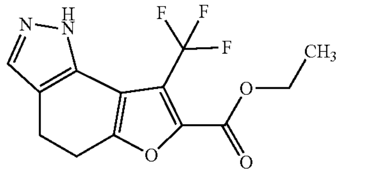 [SMILES: CCOC(=O)c1oc2c(c1C(F)(F)F)-c1[nH]ncc1CC2]

According to GP B a solution of crude (5E/Z)-ethyl 5-(hydroxymethylene)-4-oxo-3-(trifluoromethyl)-4,5,6,7-tetrahydro-1-benzofuran-2-carboxylate (1.0 eq., 15 mmol, 4.4 g) from step 3 in ethanol (60 mL) was treated with a solution of hydrazine dihydrochloride (CAS No. [5341-61-7]; 2.0 eq., 29 mmol, 3.0 g) in water (20 mL) at room temperature. The reaction mixture was stirred at 60° C. for 2 hours, quenched with saturated aqueous sodium carbonate solution (pH ~9) and extracted with ethyl acetate. The organic phase was washed with brine, dried over anhydrous sodium sulfate, filtrated and concentrated. The obtained material was purified by column chromatography (100-200 mesh, petroleum ether: ethyl acetate=20:1 then 2:1) and dissolved in methanol. The mixture was concentrated again to give ethyl 8-(trifluoromethyl)-4,5-dihydro-1H-furo[2,3-g]indazole-7-carboxylate (2.2 g, 51%) as a yellow solid.

$^1$H NMR (400 MHz, DMSO-d6) δ[ppm]: 1.31 (t, 3H), 2.86-2.90 (m, 2H), 2.97-3.01 (m, 2H), 4.34 (q, 2H), 7.58 (s, 1H), 12.64 (br s, 1H).

LC-MS (Method B): $R_t$=0.70 min; MS (ESIpos): m/z=301 $[M+H]^+$.

Step 5 ethyl 2-[(pyridin-2-yl)methyl]-8-(trifluoromethyl)-4,5-dihydro-2H-furo[2,3-g]indazole-7-carboxylate

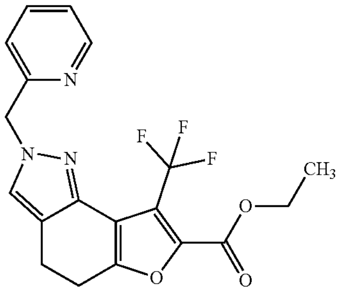 [SMILES: CCOC(=O)c1oc2c(c1C(F)(F)F)-c1nn(Cc3ccccn3)cc1CC2]

According to GP C (conditions A) ethyl 8-(trifluoromethyl)-4,5-dihydro-1H-furo[2,3-g]indazole-7-carboxylate (1.00 eq., 500 mg, 1.67 mmol) from step 4 was reacted with (pyridin-2-yl)methanol (1.1 eq., 200 mg, 1.83 mmol), tri-n-butylphosphine (CAS No. [998-40-3]; 1.6 eq., 660 μL, 2.7 mmol) and TMAD (CAS No. [10465-78-8]; 1.60 eq., 459 mg, 2.66 mmol) in toluene (21 mL) at rt overnight to give upon column chromatography ($SiO_2$, hexane/EtOAc) the title compound (322 mg, 48%; along with another product fraction of 264 mg which contained ca 15% of the corresponding N1-regioisomer).

$^1$H NMR (400 MHz, DMSO-d6) δ[ppm]: 1.30 (t, 3H), 2.87-2.91 (m, 2H), 2.98-3.02 (m, 2H), 4.34 (q, 2H), 5.40 (s, 2H), 7.09 (d, 1H), 7.31 (ddd, 1H), 7.71 (s, 1H), 7.78 (dt, 1H), 8.54 (ddd, 1H).

UPLC-MS (Method 1): $R_t$=1.34 min; MS (ESIpos): m/z=392 $[M+H]^+$.

Step 6

2-[(pyridin-2-yl)methyl]-8-(trifluoromethyl)-4,5-dihydro-2H-furo[2,3-g]indazole-7-carboxylic acid

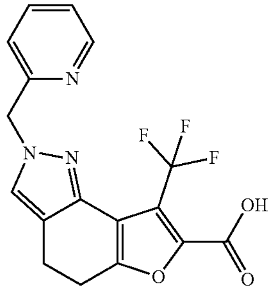 [SMILES: O=C(O)c1oc2c(c1C(F)(F)F)-c1nn(Cc3ccccn3)cc1CC2]

According to GP D ethyl 2-[(pyridin-2-yl)methyl]-8-(trifluoromethyl)-4,5-dihydro-2H-furo[2,3-g]indazole-7-carboxylate (1.00 eq., 320 mg, 818 μmol) from step 5 was reacted with aqueous lithium hydroxide (2 M; 15 eq., 6.1 mL, 12 mmol) in a 1:1 mixture of ethanol and THF (12 mL) at 70° C. for 2.5 hours. The reaction mixture was acidified with aqueous 2 N HCl (pH 4) and the formed precipitate filtered off. The solid was washed with water and EtOAc and dried to give the desired carboxylic acid (255 mg, 83%).

$^1$H NMR (400 MHz, DMSO-d6) δ[ppm]: 2.86-2.90 (m, 2H), 2.95-2.99 (m, 2H), 5.39 (s, 2H), 7.08 (d, 1H), 7.31 (dd, 1H), 7.69 (s, 1H), 7.78 (dt, 1H), 8.54 (ddd, 1H), 13.89 (br. s., 1H).

$^{19}$F NMR (377 MHz, DMSO-d6) δ[ppm]: −54.73 (s, 3F).

UPLC-MS (Method 1): $R_t$=0.52 min; MS (ESIpos): m/z=364 $[M+H]^+$.

Intermediate 36

Step 1 methyl 2-chloro-3-cyclopropyl-3-oxopropanoate

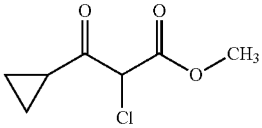

To a solution of methyl 3-cyclopropyl-3-oxopropanoate (1.00 eq., 20.0 g, 141 mmol) in dichloromethane (150 mL) was added sulfuryl chloride (0.99 eq., 12 mL, 140 mmol) at 0° C. The reaction mixture was stirred at 25° C. for 2 hours. Water (200 mL) was added to the mixture and the organic layer was separated. The organic layer was washed with saturated sodium bicarbonate, brine and concentrated under reduced pressure to give a residue. The residue was purified by column chromatography (petroleum ether:ethyl acetate=50:1, then 20:1) to give methyl 2-chloro-3-cyclopropyl-3-oxopropanoate (27.0 g, 98%) as yellow oil.

$^1$H NMR (400 MHz, $CDCl_3$): δ [ppm]=1.07-1.11 (m, 2H), 1.17-1.21 (m, 2H), 2.27-2.33 (m, 1H), 3.86 (s, 3H), 4.95 (s, 1H).

LC-MS (Method C): $R_t$=0.55 min; MS (ESIpos): m/z=177 $[M+H]^+$.

Step 2 methyl 3-cyclopropyl-4-oxo-4,5,6,7-tetrahydro-1-benzofuran-2-carboxylate

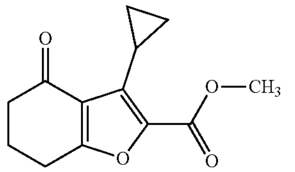 [SMILES: COC(=O)c1oc2c(c1C1CC1)C(=O)CCC2]

To a mixture of methyl 2-chloro-3-cyclopropyl-3-oxopropanoate (1.00 eq., 17.0 g, 96.3 mmol) from step 1 in 1,2-dichloroethane (100 mL) were added cyclohexane-1,3-dione (1.00 eq., 10.8 g, 96.3 mmol) and triethylamine (1.2 eq., 16 mL, 120 mmol) at room temperature. The mixture was stirred at 50° C. for 60 hours under nitrogen protection. The pH was adjusted to ~1 by aqueous hydrochloride (12 M) and the mixture was stirred for another 16 hours. Water was added to the mixture and the organic layer was separated. The aqueous phase was extracted with ethyl acetate. The combined organic layers were washed with saturated sodium carbonate solution, dried over anhydrous sodium sulfate, filtered and concentrated under reduced pressure to give a residue. The residue was purified by flash column chromatography (petroleum ether:ethyl acetate=1:0 to 5:1) to give methyl 3-cyclopropyl-4-oxo-4,5,6,7-tetrahydro-1-benzofuran-2-carboxylate (8.0 g, 35%) as a light yellow solid.

$^1$H NMR (400 MHz, DMSO-d6): 5 [ppm]=0.86-0.91 (m, 2H), 1.20-1.23 (m, 2H), 2.01-2.07 (m, 2H), 2.41-2.44 (m, 2H), 2.65-2.72 (m, 1H), 2.90 (t, 2H), 3.81 (s, 3H).

LC-MS (Method C): $R_t$=0.80 min; MS (ESIpos): m/z=235 $[M+H]^+$.

Step 3

(5E/Z)-methyl 3-cyclopropyl-5-(hydroxymethylene)-4-oxo-4,5,6,7-tetrahydro-1-benzofuran-2-carboxylate

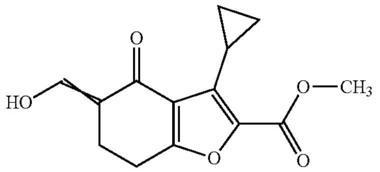 [SMILES: COC(=O)c1oc2c(c1C1CC1)C(=O)C(=CO)CC2]

According to GP A (conditions B) a mixture of sodium hydride (2.00 eq., 1.02 g, 60% purity, 25.6 mmol) in toluene (60 mL) was treated with methyl formate (3.0 eq., 2.4 mL, 38 mmol) and methyl 3-cyclopropyl-4-oxo-4,5,6,7-tetrahydro-1-benzofuran-2-carboxylate (1.00 eq., 3.00 g, 12.8 mmol) from step 2 at 0° C. The mixture was stirred at 40° C. for 12 hours and subsequently quenched with saturated aqueous ammonium chloride and diluted with water. The mixture was extracted with ethyl acetate, the organic phase was washed with brine, dried over anhydrous sodium sulfate, filtered and concentrated to give (5E/Z)-methyl 3-cyclopropyl-5-(hydroxymethylene)-4-oxo-4,5,6,7-tetrahydro-1-benzofuran-2-carboxylate (3.50 g) which was used directly without further purification.

LC-MS (Method C): $R_t$=0.84 min; MS (ESIpos): m/z=263 $[M+H]^+$.

Step 4 methyl 8-cyclopropyl-4,5-dihydro-1H-furo[2,3-g]indazole-7-carboxylate

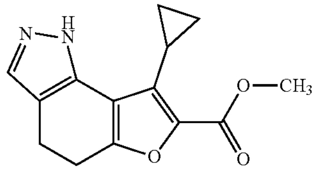 [SMILES: COC(=O)c1oc2c(c1C1CC1)-c1[nH]ncc1CC2]

According to GP B a solution of crude (5E/Z)-methyl 3-cyclopropyl-5-(hydroxymethylene)-4-oxo-4,5,6,7-tetrahydro-1-benzofuran-2-carboxylate (3.50 g, 13.3 mmol) from step 3 in methanol (50 mL) and water (5.0 mL) was added hydrazine dihydrochloride (3.00 eq., 4.20 g, 40.0 mmol) at 25° C. The mixture was stirred at 50° C. for 1 hour. The mixture was added slowly to saturated aqueous sodium carbonate at 0° C. The precipitate was collected and purified by flash column chromatography (petroleum ether:ethyl acetate=1:0 to 1:1) to give methyl 8-cyclopropyl-4,5-dihydro-1H-furo[2,3-g]indazole-7-carboxylate (1.50 g, 42% over two steps) as a yellow solid.

$^1$H NMR (400 MHz, DMSO-d6): δ [ppm]=0.88-0.93 (m, 2H), 1.52-1.54 (m, 2H), 2.74-2.87 (m, 5H), 3.80 (s, 3H), 7.51 (s, 1H), 12.46 (br s, 1H).

LC-MS (Method D): $R_t$=0.89 min; MS (ESIpos): m/z=259 $[M+H]^+$.

Step 5 methyl 8-cyclopropyl-2-[(pyridin-2-yl)methyl]-4,5-dihydro-2H-furo[2,3-g]indazole-7-carboxylate

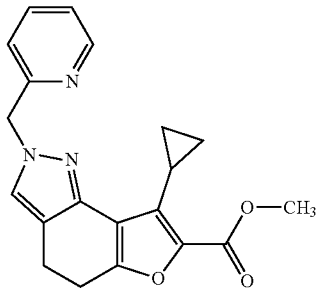 [SMILES: COC(=O)c1oc2c(c1C1CC1)-c1nn(Cc3ccccn3)cc1CC2]

According to GP C (conditions A) methyl 8-cyclopropyl-4,5-dihydro-1H-furo[2,3-g]indazole-7-carboxylate (1.00 eq., 400 mg, 1.55 mmol) from step 4 was reacted with (pyridin-2-yl)methanol (1.1 eq., 186 mg, 1.70 mmol), tri-n-butylphosphine (CAS No. [998-40-3]; 1.6 eq., 620 μL, 2.5 mmol) and TMAD (CAS No. [10465-78-8]; 1.60 eq., 427 mg, 2.48 mmol) in toluene (20 mL) at rt overnight to give upon column chromatography ($SiO_2$, hexane/EtOAc) the title compound (391 mg, 69%).

$^1$H NMR (400 MHz, DMSO-d6) δ[ppm]: 0.83-0.88 (m, 2H), 1.43-1.47 (m, 2H), 2.68-2.75 (m, 1H), 2.78-2.89 (m, 4H), 3.79 (s, 3H), 5.36 (s, 2H), 7.04 (d, 1H), 7.31 (ddd, 1H), 7.64 (s, 1H), 7.78 (dt, 1H), 8.54 (ddd, 1H).

UPLC-MS (Method 1): $R_t$=1.18 min; MS (ESIpos): m/z=350 $[M+H]^+$.

Step 6

8-cyclopropyl-2-[(pyridin-2-yl)methyl]-4,5-dihydro-2H-furo[2,3-g]indazole-7-carboxylic acid

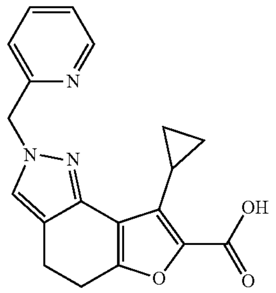 [SMILES: O=C(O)c1oc2c(c1C1CC1)-c1nn(Cc3ccccn3)cc1CC2]

According to GP D methyl 8-cyclopropyl-2-[(pyridin-2-yl)methyl]-4,5-dihydro-2H-furo[2,3-g]indazole-7-carboxylate (1.00 eq., 385 mg, 1.10 mmol) from step 5 was reacted with aqueous lithium hydroxide (2 M; 15 eq., 8.3 mL, 17 mmol) in a 1:1 mixture of ethanol and THF (18 mL) at 70° C. for 4 hours. The reaction mixture was concentrated under reduced pressure, the concentrate acidified with aqueous 2 N HCl (pH 3) and the formed precipitate filtered off. The solid was washed with water and EtOAc and dried to give the desired carboxylic acid (360 mg, 93%).

$^1H$ NMR (400 MHz, DMSO-d6) δ[ppm]: 0.79-0.84 (m, 2H), 1.41-1.45 (m, 2H), 2.73-2.87 (m, 5H), 5.37 (s, 2H), 7.06 (d, 1H), 7.33 (dd, 1H), 7.64 (s, 1H), 7.80 (dt, 1H), 8.54-8.56 (m, 1H), 12.83 (br. s., 1H).

UPLC-MS (Method 1): $R_t$=0.55 min; MS (ESIpos): m/z=336 $[M+H]^+$.

Intermediate 37

Step 1

3,6,6-trimethyl-6,7-dihydro-1-benzofuran-4(5H)-one

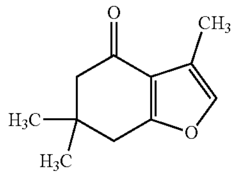

In analogy to K. Kanematsu et al., Heterocycles 1990, 31, 6, 1003-1006 and J. Org. Chem. 1993, 58, 3960-3968:

To a solution of 3-bromoprop-1-yne (CAS No. [106-96-7]; 2.00 eq., 25 mL, 290 mmol) in anhydrous acetonitrile (20 mL) was added dimethyl sulfide (CAS No.:[75-18-3]; 0.57 eq., 6.0 mL, 82 mmol) and the reaction mixture stirred in a light-protected flask at rt overnight. A solution of sodium ethoxide (1.1 eq., 37 mL of a 21% solution in ethanol, 160 mmol) and 5,5-dimethylcyclohexane-1,3-dione (CAS No. [126-81-8]; 1.00 eq., 20.0 g, 143 mmol) in ethanol (365 mL) was added and the mixture heated to reflux for 1.5 hours. The reaction mixture was diluted with water, concentrated under reduced pressure and the obtained residue extracted with dichloromethane. The combined organic layers were concentrated under reduced pressure, the residue taken up with toluene (150 mL) and treated with 4-methylbenzenesulfonic acid (CAS No. [104-15-4]; 1.11 eq., 27.3 g, 159 mmol) at room temperature overnight. The reaction mixture was quenched with saturated aqueous $NaHCO_3$, the layers separated, and the aqueous layer extracted with dichloromethane. The combined organic layers were filtered with a hydrophobic filter, concentrated under reduced pressure and the obtained crude product subjected to column chromatography ($SiO_2$, hexane/EtOAc) to give the title compound (9.4 g, 34%).

$^1H$ NMR (400 MHz, DMSO-d6) δ[ppm]: 1.04 (s, 6H), 2.09 (d, 3H), 2.30 (s, 2H), 2.74 (s, 2H), 7.43-7.44 (m, 1H).

UPLC-MS (Method 1): $R_t$=1.11 min; MS (ESIpos): m/z=179 $[M+H]^+$.

Step 2

2-bromo-3,6,6-trimethyl-6,7-dihydro-1-benzofuran-4(5H)-one

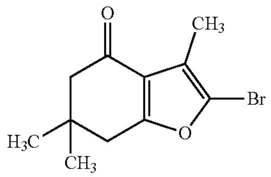

In analogy to U.S. Pat. No. 6,048,880; example 2, step 2 (page 20):

A solution of 3,6,6-trimethyl-6,7-dihydro-1-benzofuran-4(5H)-one (1.00 eq., 7.64 g, 42.9 mmol) from step 1 in pyridine (60 mL) was treated with 1-bromopyrrolidine-2,5-dione (NBS, CAS No. [128-08-5]; 1.01 eq., 7.71 g, 43.3 mmol) and stirred at rt for two days. Another amount of 1-bromopyrrolidine-2,5-dione (1.00 eq., 7.63 g, 42.9 mmol) was added and stirring at rt continued overnight. The reaction mixture acidified with aqueous 2 N HCl (pH 4) and extracted with dichloromethane. The combined organic layers were dried with $Na_2SO_4$, filtered, concentrated under reduced pressure and the crude product subjected to column chromatography ($SiO_2$, hexane/EtOAc) to give the title compound (5.7 g, 52%).

$^1H$ NMR (400 MHz, DMSO-d6) δ[ppm]: 1.05 (s, 6H), 2.05 (s, 3H), 2.32 (s, 2H), 2.76 (s, 2H).

UPLC-MS (Method 1): $R_t$=1.32 min; MS (ESIpos): m/z=257/259 $[M+H]^+$ (Br isotope pattern).

Step 3

(5E/Z)-2-bromo-5-[(dimethylamino)methylidene]-3,6,6-trimethyl-6,7-dihydro-1-benzofuran-4(5H)-one

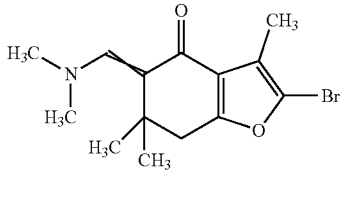 [SMILES: Cc1c(Br)oc2c1C(=O)C(=CN(C)C)C(C)(C)C2]

According to GP A (conditions A) 2-bromo-3,6,6-trimethyl-6,7-dihydro-1-benzofuran-4(5H)-one (1.00 eq., 3.50 g, 13.6 mmol) from step 2 was reacted with 1-tert-butoxy-N,N,N',N'-tetramethylmethanediamine (Bredereck's reagent, CAS No. [5815-08-7]; 1.20 eq., 3.37 mL, 16.3 mmol) in toluene (35 mL) at 100° C. for 3 h. Another amount of 1-tert-butoxy-N,N,N',N'-tetramethylmethanediamine (1.20 eq., 3.37 mL, 16.3 mmol) was added and stirring at 100° C. continued for another 24 h. Another amount of 1-tert-butoxy-N,N,N',N'-tetramethylmethanediamine (1.20 eq., 3.37 mL, 16.3 mmol) was added and stirring at 100° C. continued for 10 h and subsequently at rt for three days. The reaction mixture was concentrated under reduced pressure and the obtained crude title compound used in the subsequent reaction without further purification steps.

UPLC-MS (Method 1): $R_t$=1.33/1.37 min; MS (ESIpos): m/z=312/314 $[M+H]^+$ (Br isotope pattern).

Step 4

7-bromo-4,4,8-trimethyl-4,5-dihydro-1H-furo[2,3-g]indazole

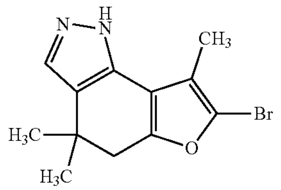

According to GP B crude (5E/Z)-2-bromo-5-[(dimethylamino)methylidene]-3,6,6-trimethyl-6,7-dihydro-1-benzofuran-4(5H)-one (1.0 eq., 4.3 g, 14 mmol) from step 3 was reacted with hydrazine hydrate 1:1 (5.0 eq., 3.3 mL, 68 mmol) in ethanol (50 mL) at 70° C. overnight to give upon column chromatography ($SiO_2$, hexane/EtOAc) the title compound (1.38 g, 35% over two steps).

$^1$H NMR (400 MHz, DMSO-d6) δ[ppm]: 1.22 (s, 6H), 2.13 (s, 3H), 2.66 (s, 2H), 7.53 (s, 1H), 12.39 (s, 1H).

UPLC-MS (Method 1): $R_t$=1.25 min; MS (ESIpos): m/z=281/283 $[M+H]^+$ (Br isotope pattern).

Step 5

7-bromo-4,4,8-trimethyl-2-[(pyridin-2-yl)methyl]-4,5-dihydro-2H-furo[2,3-g]indazole

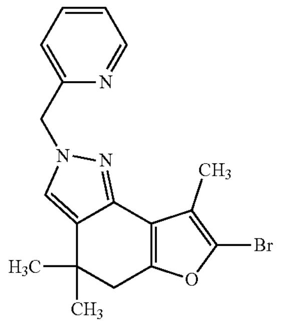 [SMILES: Cc1c(Br)oc2c1-c1nn(Cc3ccccn3)cc1C(C)(C)C2]

According to GP C (conditions B) 7-bromo-4,4,8-trimethyl-4,5-dihydro-1H-furo[2,3-g]indazole (1.0 eq., 5.6 g, 35 mmol) from step 4 was reacted with 2-(bromomethyl)pyridine (1.5 eq., 1.2 g, 6.9 mmol), potassium carbonate (15 eq., 9.6 g, 69 mmol) and DMAP (14 mg, 120 μmol, 2.5 mol %) in EtOAc (75 mL) at 75° C. overnight. Another amount of 2-(bromomethyl)pyridine (0.75 eq., 600 mg, 3.5 mmol) was added and stirring at 75° C. continued for another 3 days to give upon column chromatography ($SiO_2$, hexane/EtOAc) the title compound (200 mg, 7%).

$^1$H NMR (400 MHz, DMSO-d6) δ[ppm]: 1.26 (s, 6H), 2.08 (s, 3H), 2.69 (s, 2H), 5.36 (s, 2H), 7.04 (d, 1H), 7.31 (ddd, 1H), 7.69 (s, 1H), 7.78 (dt, 1H), 8.53-8.55 (m, 1H).

UPLC-MS (Method 1): $R_t$=1.39 min; MS (ESIpos): m/z=371/373 $[M+H]^+$ (Br isotope pattern).

Intermediate 38

Step 1

3-methyl-5H-spiro[[1]benzofuran-6,1'-cyclopropan]-4(7H)-one

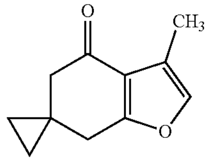

In analogy to K. Kanematsu et al., Heterocycles 1990, 31, 6, 1003-1006 and J. Org. Chem. 1993, 58, 3960-3968:

To a solution of 3-bromoprop-1-yne (CAS No. [106-96-7]; 2.00 eq., 12 mL, 145 mmol) in anhydrous acetonitrile (10 mL) was added dimethyl sulfide (CAS No.:[75-18-3]; 0.57 eq., 3.0 mL, 41 mmol) and the reaction mixture stirred in a light-protected flask at rt overnight. A solution of sodium ethoxide (1.1 eq., 19 mL of a 21% solution in ethanol, 81 mmol) and spiro[2.5]octane-5,7-dione (CAS No. [893411-52-4]; 1.00 eq., 10.0 g, 72.4 mmol) in ethanol (190 mL) was added and the mixture heated to reflux for 1.5 hours. The reaction mixture was diluted with water, concentrated under reduced pressure and the obtained residue extracted with dichloromethane. The combined organic layers were concentrated under reduced pressure, the residue taken up with toluene (75 mL) and treated with 4-methylbenzenesulfonic acid (CAS No. [104-15-4]; 4 mol %, 0.50 g, 2.9 mmol) at room temperature overnight. The reaction mixture was quenched with saturated aqueous $NaHCO_3$, the layers separated, and the aqueous layer extracted with dichloromethane.

The combined organic layers were filtered with a hydrophobic filter, concentrated under reduced pressure and the obtained crude product subjected to column chromatography ($SiO_2$, hexane/EtOAc) to give the title compound (3.8 g, 29%).

$^1$H NMR (400 MHz, DMSO-d6) δ[ppm]: 0.42-0.44 (m, 2H), 0.47-0.50 (m, 2H), 2.11 (d, 3H), 2.28 (s, 2H), 2.75 (s, 2H), 7.44 (m, 1H).

UPLC-MS (Method 1): $R_t$=1.07 min; MS (ESIpos): m/z=177 $[M+H]^+$.

Step 2

2-bromo-3-methyl-5H-spiro[[1]benzofuran-6,1'-cyclopropan]-4(7H)-one

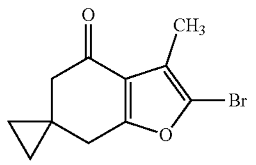

A solution of 3-methyl-5H-spiro[[1]benzofuran-6,1'-cyclopropan]-4(7H)-one (1.00 eq., 3.80 g, 21.6 mmol) from step 1 in pyridine (30 mL) was treated with 1-bromopyrrolidine-2,5-dione (NBS, CAS No. [128-08-5]; 1.01 eq., 3.88 g, 21.8 mmol) and stirred at rt overnight. Another amount of 1-bromopyrrolidine-2,5-dione (1.00 eq., 3.84 g, 21.6 mmol) was added and stirring at rt continued overnight. The reaction mixture acidified with aqueous 2 N HCl (pH 4) and extracted with dichloromethane. The combined organic layers were dried with $Na_2SO_4$, filtered, concentrated under reduced pressure and the crude product subjected to column chromatography ($SiO_2$, hexane/EtOAc) to give the title compound (2.68 g, 46%).

$^1H$ NMR (400 MHz, DMSO-d6) δ[ppm]: 0.42-0.46 (m, 2H), 0.48-0.52 (m, 2H), 2.07 (s, 3H), 2.31 (s, 2H), 2.78 (s, 2H).

UPLC-MS (Method 1): $R_t$=1.28 min; MS (ESIpos): m/z=255/257 $[M+H]^+$ (Br isotope pattern).

Step 3

(5E/Z)-2-bromo-5-[(dimethylamino)methylidene]-3-methyl-5H-spiro[[1]benzofuran-6,1'-cyclopropan]-4(7H)-one

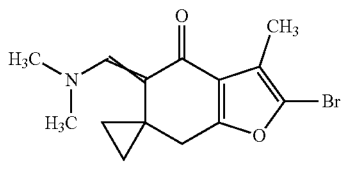 [SMILES: Cc1c(Br)oc2c1C(=O)C(=CN(C)C)C1(CC1)C2]

According to GP A (conditions A) 2-bromo-3-methyl-5H-spiro[[1]benzofuran-6,1'-cyclopropan]-4(7H)-one (1.00 eq., 2.00 g, 7.84 mmol) from step 2 was reacted with 1-tert-butoxy-N,N,N',N'-tetramethylmethanediamine (Bredereck's reagent, CAS No. [5815-08-7]; 1.2 eq., 1.9 mL, 9.4 mmol) in toluene (20 mL) at 100° C. overnight. The reaction mixture was concentrated under reduced pressure and the obtained crude title compound used in the subsequent reaction without further purification steps.

UPLC-MS (Method 1): $R_t$=1.33 min; MS (ESIpos): m/z=310/312 $[M+H]^+$ (Br isotope pattern).

Step 4

7'-bromo-8'-methyl-1',5'-dihydrospiro[cyclopropane-1,4'-furo[2,3-g]indazole]

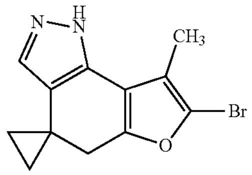 [SMILES: Cc1c(Br)oc2c1-c1[nH]ncc1C1(CC1)C2]

According to GP B crude (5E/Z)-2-bromo-5-[(dimethylamino)methylidene]-3-methyl-5H-spiro[[1]benzofuran-6,1'-cyclopropan]-4(7H)-one (1.0 eq., 2.5 g, 8.1 mmol) from step 3 was reacted with hydrazine hydrate 1:1 (5.0 eq., 2.0 mL, 40 mmol) in ethanol (35 mL) at 70° C. for 5 hours to give upon column chromatography ($SiO_2$, hexane/EtOAc) the title compound (1.3 g, 59% over two steps).

$^1H$ NMR (400 MHz, DMSO-d6) δ[ppm]: 0.78-0.80 (m, 2H), 0.82-0.85 (m, 2H), 2.14 (s, 3H), 2.78 (s, 2H), 7.29 (s, 1H), 12.33 (s, 1H).

UPLC-MS (Method 1): $R_t$=1.20 min; MS (ESIpos): m/z=279/281 $[M+H]^+$ (Br isotope pattern).

Step 5

7'-bromo-8'-methyl-2'-[(pyridin-2-yl)methyl]-2',5'-dihydrospiro[cyclopropane-1,4'-furo[2,3-g]indazole]

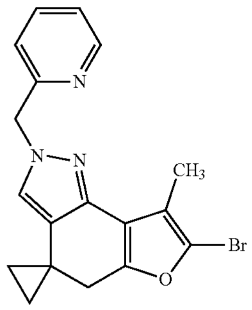 [SMILES: Cc1c(Br)oc2c1-c1nn(Cc3ccccn3)cc1C1(CC1)C2]

According to GP C (conditions A) 7'-bromo-8'-methyl-1',5'-dihydrospiro[cyclopropane-1,4'-furo[2,3-g]indazole] (1.00 eq., 300 mg, 1.22 mmol) from step 4 was reacted with (pyridin-2-yl)methanol (1.1 eq., 376 mg, 3.45 mmol), tri-n-butylphosphine (CAS No. [998-40-3]; 1.6 eq., 1.2 mL, 5.0 mmol) and TMAD (CAS No. [10465-78-8]; 1.60 eq., 864 mg, 5.02 mmol) in toluene (40 mL) at rt for two days to give upon column chromatography ($SiO_2$, hexane/EtOAc) the title compound (933 mg, 72%).

$^1H$ NMR (400 MHz, DMSO-d6) δ[ppm]: 0.78-0.82 (m, 2H), 0.84-0.88 (m, 2H), 2.09 (s, 3H), 2.80 (s, 2H), 5.34 (s, 2H), 7.03 (d, 1H), 7.33 (ddd, 1H), 7.44 (s, 1H), 7.80 (dt, 1H), 8.54 (ddd, 1H).

UPLC-MS (Method 1): $R_t$=1.33 min; MS (ESIpos): m/z=370/372 $[M+H]^+$ (Br isotope pattern).

Step 6

8'-methyl-2'-[(pyridin-2-yl)methyl]-2',5'-dihydrospiro[cyclopropane-1,4'-furo[2,3-g]indazole]-7'-carboxylic acid

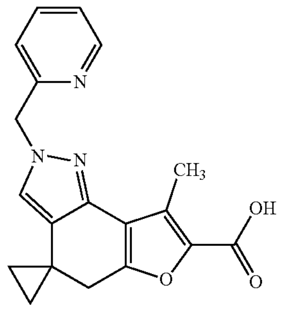 [SMILES: Cc1c(C(=O)O)oc2c1-c1nn(Cc3ccccn3)cc1C1(CC1)C2]

According to GP E 7'-bromo-8'-methyl-2'-[(pyridin-2-yl)methyl]-2',5'-dihydrospiro[cyclopropane-1,4'-furo[2,3-g]indazole] (1.00 eq., 500 mg, 1.35 mmol) from step 5 was carbonylated in a steel autoclave (50 mL) in the presence of bis(diphenylphosphino)ferrocene (CAS No. [12150-46-8]; 0.200 eq., 155 mg, 271 μmol), palladium(II) acetate (5.0 mol %, 15 mg, 68 μmol) and potassium acetate (4.0 eq., 530 mg, 5.40 mmol) in DMSO (20 mL) under a carbon monoxide pressure of ca. 15 bar at 100° C. for 23 hours to give upon work-up the crude title compound (0.9 g, 32% purity, 65%) which was used in the subsequent reactions without further purification steps.

UPLC-MS (Method 1): $R_t$=0.64 min; MS (ESIpos): m/z=336 $[M+H]^+$.

Intermediate 39

7'-bromo-8'-methyl-2'-[(pyridin-3-yl)methyl]-2',5'-dihydrospiro[cyclopropane-1,4'-furo[2,3-g]indazole]

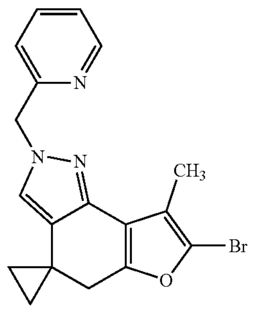 [SMILES: Cc1c(Br)oc2c1-c1nn(Cc3ccccn3)cc1C1(CC1)C2]

According to GP C (conditions A) 7'-bromo-8'-methyl-1',5'-dihydrospiro[cyclopropane-1,4'-furo[2,3-g]indazole] (1.00 eq., 200 mg, 716 μmol) from Intermediate 38, step 4 was reacted with (pyridin-3-yl)methanol (1.10 eq., 86.0 mg, 788 μmol), tri-n-butylphosphine (CAS No. [998-40-3]; 1.60 eq., 286 μL, 1.15 mmol) and TMAD (CAS No. [10465-78-8]; 1.60 eq., 197 mg, 1.15 mmol) in toluene (10 mL) at rt overnight to give upon column chromatography ($SiO_2$, $CH_2Cl_2$/MeOH) the title compound (430 mg, 38% purity, 62%).

$^1$H NMR (400 MHz, DMSO-d6) δ[ppm]: 0.77-0.81 (m, 2H), 0.83-0.87 (m, 2H), 2.11 (s, 3H), 2.79 (s, 2H), 5.28 (s, 2H), 7.38 (dd, 1H), 7.44 (s, 1H), 7.60-7.62 (m, 1H), 8.48-8.50 (m, 2H).

UPLC-MS (Method 1): $R_t$=1.31 min; MS (ESIpos): m/z=370/372 $[M+H]^+$ (Br isotope pattern).

Intermediate 40-1

Step 1

7'-bromo-2'-{[(2S)-1,4-dioxan-2-yl]methyl}-8'-methyl-2',5'-dihydrospiro[cyclopropane-1,4'-furo[2,3-g]indazole]

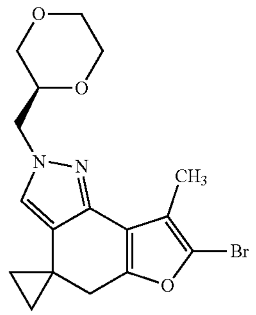 [SMILES: Cc1c(Br)oc2c1-c1nn(C[C@H]3COCCO3)cc1C1(CC1)C2]

According to GP C (conditions A) 7'-bromo-8'-methyl-1',5'-dihydrospiro[cyclopropane-1,4'-furo[2,3-g]indazole] (1.00 eq., 700 mg, 2.51 mmol) from Intermediate 38, step 4 was reacted with [(2S)-1,4-dioxan-2-yl]methanol (CAS No. [406913-93-7]; 1.10 eq., 326 mg, 2.76 mol), tri-n-butylphosphine (CAS No. [998-40-3]; 1.6 eq., 1.0 mL, 4.0 mmol) and TMAD (CAS No. [10465-78-8]; 1.60 eq., 691 mg, 4.01 mmol) in toluene (32 mL) at rt for two days to give upon column chromatography ($SiO_2$, hexane/EtOAc) the title compound (595 mg, 65% purity, 41%).

$^1$H NMR (400 MHz, DMSO-d6) δ[ppm]: 0.76-0.80 (m, 2H), 0.82-0.85 (m, 2H), 2.12 (s, 3H), 2.77-2.78 (m, 2H), 3.24 (dd, 1H), 3.43 (dt, 1H), 3.53 (dt, 1H), 3.61-3.64 (m, 1H), 3.69-3.73 (m, 2H), 3.78-3.84 (m, 1H), 3.97-4.07 (m, 2H), 7.25 (s, 1H).

UPLC-MS (Method 1): $R_t$=1.31 min; MS (ESIpos): m/z=379/381 $[M+H]^+$ (Br isotope pattern).

Step 2

2'-{[(2S)-1,4-dioxan-2-yl]methyl}-8'-methyl-2',5'-dihydrospiro[cyclopropane-1,4'-furo[2,3-g]indazole]-7'-carboxylic acid

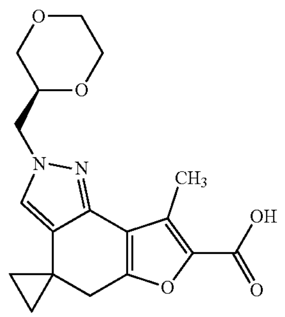 [SMILES: Cc1c(C(=O)O)oc2c1-c1nn(C[C@H]3COCCO3)cc1C1(CC1)C2]

According to GP E 7'-bromo-2'-{[(2S)-1,4-dioxan-2-yl]methyl}-8'-methyl-2',5'-dihydrospiro[cyclopropane-1,4'-furo[2,3-g]indazole] (1.00 eq., 989 mg, 2.61 mmol) from step 1 was carbonylated in a steel autoclave (90 mL) in the presence of bis(diphenylphosphino)ferrocene (CAS No. [12150-46-8]; 0.201 eq., 300 mg, 524 μmol), palladium(II) acetate (5.0 mol %, 29 mg, 130 μmol) and potassium acetate (4.00 eq., 1.02 g, 10.4 mmol) in DMSO (40 mL) under a carbon monoxide pressure of ca. 16 bar at 100° C. for 23 hours to give upon work-up the crude title compound (0.67 g, 60% purity, 45%) which was used in the subsequent reactions without further purification steps.

$^1$H NMR (400 MHz, DMSO-d6) δ[ppm]: 0.78-0.87 (m, 4H), 2.85-2.86 (m, 2H), 3.25 (dd, 1H), 3.44 (dt, 1H), 3.54 (dt, 1H), 3.61-3.64 (m, 1H), 3.70-3.74 (m, 2H), 3.80-3.86 (m, 1H), 4.00-4.06 (m, 2H), 7.29 (s, 1H), 12.86 (br. s., 1H).

UPLC-MS (Method 1): $R_t$=0.51 min; MS (ESIpos): m/z=345 [M+H]$^+$.

Intermediate 40-2

7'-bromo-N,N,8'-trimethylspiro[cyclopropane-1,4'-furo[2,3-g]indazole]-2'(5'H)-carboxamide

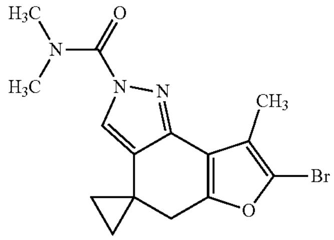 [SMILES: Cc1c(Br)oc2c1-c1nn(C(=O)N(C)C)cc1C1(CC1)C2]

Isolated from the reaction mixture of Intermediate 40-1, step 1 (166 mg, 18%).

Intermediate 41

Step 1 ethyl 3-methyl-4-oxo-4,7-dihydro-5H-spiro[[1]benzofuran-6,1'-cyclopropane]-2-carboxylate

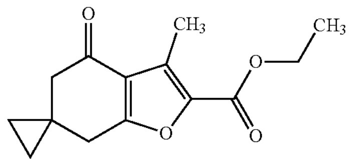 [SMILES: CCOC(=O)c1oc2c(c1C)C(=O)CC1(CC1)C2]

To a mixture of spiro[2.5]octane-5,7-dione (CAS No. [893411-52-4]; 1.00 eq., 5.00 g, 36.2 mmol) in 1,2-dichloroethane (80 mL) were added ethyl 2-chloro-3-oxobutanoate (CAS No. [609-15-4]; 1.0 eq., 5.0 mL, 36 mmol) and triethylamine (1.2 eq, 6.1 mL, 43 mmol) at room temperature and the mixture was stirred at 50° C. for 15 hours. The pH was adjusted to ~2 by aqueous 2 N HCl and then stirring at room temperature continued for another 7 hours. Water was added to the mixture and the organic layer was separated. The organic layer was washed with water, filtered with a hydrophobic filter, concentrated under reduced pressure and the obtained crude product subjected to column chromatography ($SiO_2$, hexane/EtOAc) to give the title compound (3.5 g, 36%).

$^1$H NMR (400 MHz, DMSO-d6) δ[ppm]: 0.44-0.48 (m, 2H), 0.50-0.54 (m, 2H), 1.29 (t, 3H), 2.35 (s, 2H), 2.47 (s, 3H), 2.86 (s, 2H), 4.29 (q, 2H).

UPLC-MS (Method 1): $R_t$=1.14 min; MS (ESIpos): m/z=249 [M+H]$^+$.

Step 2 ethyl (5E/Z)-5-[(dimethylamino)methylidene]-3-methyl-4-oxo-4,7-dihydro-5H-spiro[[1]benzofuran-6,1'-cyclopropane]-2-carboxylate

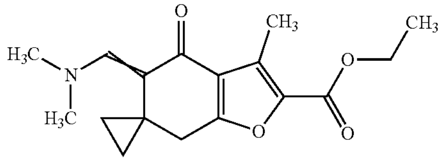 [SMILES: CCOC(=O)c1oc2c(c1C)C(=O)C(=CN(C)C)C1(CC1)C2]

According to GP A (conditions A) ethyl 3-methyl-4-oxo-4,7-dihydro-5H-spiro[[1]benzofuran-6,1'-cyclopropane]-2-carboxylate (1.00 eq., 3.40 g, 13.7 mmol) from step 1 was reacted with 1-tert-butoxy-N,N,N',N'-tetramethylmethanediamine (Bredereck's reagent, CAS No. [5815-08-7]; 1.2 eq., 3.4 mL, 16 mmol) in toluene (35 mL) at 100° C. for 5 days. The reaction mixture was concentrated under reduced pressure and the obtained crude title compound used in the subsequent reaction without further purification steps.

UPLC-MS (Method 1): $R_t$=1.16/1.23 min; MS (ESIpos): m/z=304 [M+H]$^+$.

Step 3 ethyl 8'-methyl-1',5'-dihydrospiro[cyclopropane-1,4'-furo[2,3-g]indazole]-7'-carboxylate

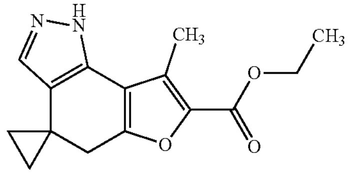 [SMILES: CCOC(=O)c1oc2c(c1C)-c1[nH]ncc1C1(CC1)C2]

According to GP B crude ethyl (5E/Z)-5-[(dimethylamino)methylidene]-3-methyl-4-oxo-4,7-dihydro-5H-spiro[[1]benzofuran-6,1'-cyclopropane]-2-carboxylate (1.0 eq., 4.2 g, 14 mmol) from step 2 was reacted with hydrazine hydrate 1:1 (5.0 eq., 3.3 mL, 68 mmol) in ethanol (35 mL) at 70° C. for 5 hours to give upon column chromatography ($SiO_2$, hexane/EtOAc) the title compound (1.49 g, 84% purity, 34% over two steps).

$^1$H NMR (400 MHz, DMSO-d6) δ[ppm]: 0.80-0.82 (m, 2H), 0.85-0.88 (m, 2H), 1.30 (t, 3H), 2.53 (s, 3H), 2.87 (s, 2H), 4.27 (q, 2H), 7.34 (s, 1H), 12.44 (s, 1H).

UPLC-MS (Method 1): $R_t$=1.03 min; MS (ESIpos): m/z=273 [M+H]$^+$.

Step 4 ethyl 2'-(cyclopropylmethyl)-8'-methyl-2',5'-dihydrospiro[cyclopropane-1,4'-furo[2,3-g]indazole]-7'-carboxylate

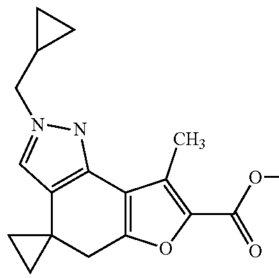

According to GP C (conditions A) ethyl 8'-methyl-1',5'-dihydrospiro[cyclopropane-1,4'-furo[2,3-g]indazole]-7'-carboxylate (1.00 eq., 400 mg, 1.47 mmol) from step 3 was reacted with cyclopropylmethanol (1.5 eq., 180 μL, 2.2 mmol), tri-n-butylphosphine (CAS No. [998-40-3]; 1.6 eq., 590 μL, 2.4 mmol) and TMAD (CAS No. [10465-78-8]; 1.60 eq., 405 mg, 2.35 mmol) in toluene (7 mL) at rt overnight to give upon column chromatography ($SiO_2$, hexane/EtOAc) the title compound (263 mg, 49%).

$^1H$ NMR (400 MHz, DMSO-d6) δ[ppm]: 0.31-0.35 (m, 2H), 0.48-0.53 (m, 2H), 0.79-0.83 (m, 2H), 0.85-0.89 (m, 2H), 1.16-1.24 (m, 1H), 1.29 (t, 3H), 2.52 (s, 3H), 2.87 (s, 2H), 3.88 (d, 2H), 4.27 (q, 2H), 7.37 (s, 1H).

UPLC-MS (Method 1): $R_t$=1.40 min; MS (ESIpos): m/z=327 $[M+H]^+$.

Step 5

2'-(cyclopropylmethyl)-8'-methyl-2',5'-dihydrospiro[cyclopropane-1,4'-furo[2,3-g]indazole]-7'-carboxylic acid

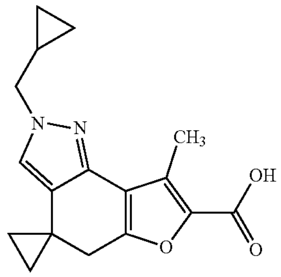 [SMILES: Cc1c(C(=O)O)oc2c1-c1nn(CC3CC3)cc1C1(CC1)C2]

According to GP D ethyl 2'-(cyclopropylmethyl)-8'-methyl-2',5'-dihydrospiro[cyclopropane-1,4'-furo[2,3-g]indazole]-7'-carboxylate (1.00 eq., 260 mg, 797 μmol) from step 4 was reacted with aqueous lithium hydroxide (2 M; 15 eq., 6.0 mL, 12 mmol) in a 1:1 mixture of ethanol and THF (12 mL) at 70° C. for 4 hours and at room temperature for 4 days. The reaction mixture was concentrated under reduced pressure, the concentrate acidified with aqueous 2 N HCl (pH 3) and the formed precipitate filtered off. The solid was washed with water and EtOAc and dried to give the desired carboxylic acid (146 mg, 55%).

$^1H$ NMR (400 MHz, DMSO-d6) δ[ppm]: 0.33-0.34 (m, 2H), 0.50-0.52 (m, 2H), 0.80-0.86 (m, 4H), 1.17-1.23 (m, 1H), 2.83 (s, 2H), 3.87 (d, 2H), 7.34 (s, 1H).

UPLC-MS (Method 1): $R_t$=0.59 min; MS (ESIpos): m/z=299 $[M+H]^+$.

Intermediate 42

Step 1 ethyl 3-methyl-4-oxo-4,7-dihydro-5H-spiro[[1]benzofuran-6,1'-cyclobutane]-2-carboxylate

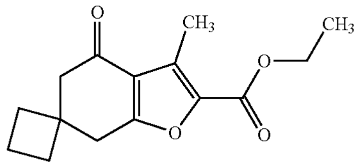 [SMILES: CCOC(=O)c1oc2c(c1C)C(=O)CC1(CCC1)C2]

To a mixture of spiro[3.5]nonane-6,8-dione (CAS No. [221342-48-9]; 1.00 eq., 2.00 g, 13.1 mmol) in 1,2-dichloroethane (30 mL) were added ethyl 2-chloro-3-oxobutanoate (CAS No. [609-15-4]; 1.0 eq., 1.8 mL, 13 mmol) and triethylamine (1.2 eq, 2.2 mL, 16 mmol) at room temperature and the mixture was stirred at 50° C. for three days and then left standing at room temperature for another three days. The pH was adjusted to ~2 by aqueous 2 N HCl and then stirring at room temperature continued for another two hours. Water was added to the mixture and the organic layer was separated. The organic layer was washed with water, filtered with a hydrophobic filter, concentrated under reduced pressure and the obtained crude product subjected to column chromatography ($SiO_2$, hexane/EtOAc) to give the title compound (955 mg, 26%).

$^1H$ NMR (400 MHz, DMSO-d6) δ[ppm]: 1.29 (t, 3H), 1.77-1.94 (m, 6H), 2.44 (s, 3H), 2.62 (s, 2H), 3.09 (s, 2H), 4.28 (q, 2H).

UPLC-MS (Method 1): $R_t$=1.23 min; MS (ESIpos): m/z=263 $[M+H]^+$.

Step 2 ethyl (5E/Z)-5-[(dimethylamino)methylidene]-3-methyl-4-oxo-4,7-dihydro-5H-spiro[[1]benzofuran-6,1'-cyclobutane]-2-carboxylate

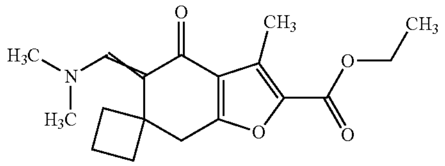 [SMILES: CCOC(=O)c1oc2c(c1C)C(=O)C(=CN(C)C)C1(CCC1)C2]

According to GP A (conditions A) ethyl 3-methyl-4-oxo-4,7-dihydro-5H-spiro[[1]benzofuran-6,1'-cyclobutane]-2-carboxylate (1.00 eq., 500 mg, 1.91 mmol) from step 1 was reacted with 1-tert-butoxy-N,N,N',N'-tetramethylmethanediamine (Bredereck's reagent, CAS No. [5815-08-7]; 1.2 eq., 470 μL, 2.3 mmol) in toluene (5 mL) at 100° C. for three days. The reaction mixture was concentrated under reduced pressure and the obtained crude title compound used in the subsequent reaction without further purification steps.

UPLC-MS (Method 1): $R_t$=1.23/1.25 min; MS (ESIpos): m/z=318 $[M+H]^+$.

Step 3 ethyl 8'-methyl-1',5'-dihydrospiro[cyclobutane-1,4'-furo[2,3-g]indazole]-7'-carboxylate

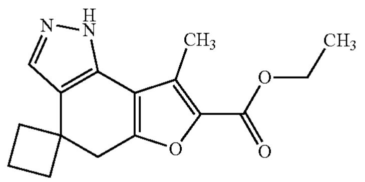 [SMILES: CCOC(=O)c1oc2c(c1C)-c1[nH]ncc1C1(CCC1)C2]

According to GP B crude ethyl (5E/Z)-5-[(dimethylamino)methylidene]-3-methyl-4-oxo-4,7-dihydro-5H-spiro[[1]benzofuran-6,1'-cyclobutane]-2-carboxylate (1.0 eq., 600 mg, 1.9 mmol) from step 2 was reacted with hydrazine hydrate 1:1 (5.0 eq., 460 μL, 9.5 mmol) in ethanol (5 mL) at 70° C. for 13 hours to give upon column chromatography ($SiO_2$, hexane/EtOAc) the title compound (134 mg, 25% over two steps).

$^1$H NMR (400 MHz, DMSO-d6) δ[ppm]: 1.30 (t, 3H), 1.93-2.13 (m, 6H), 3.05 (s, 2H), 4.27 (q, 2H), 7.79 (s, 1H), 12.54 (s, 1H).

UPLC-MS (Method 1): $R_t$=1.12 min; MS (ESIpos): m/z=287 $[M+H]^+$.

Step 4 ethyl 8'-methyl-2'-[(pyridin-2-yl)methyl]-2',5'-dihydrospiro[cyclobutane-1,4'-furo[2,3-g]indazole]-7'-carboxylate

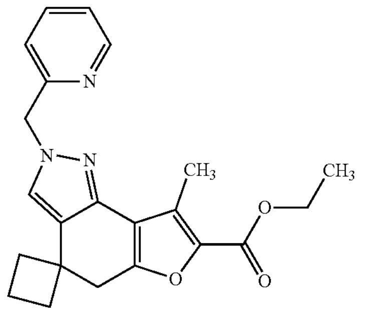 [SMILES: CCOC(=O)c1oc2c(c1C)-c1nn(Cc3ccccn3)cc1C1(CCC1)C2]

According to GP C (conditions A) ethyl 8'-methyl-1',5'-dihydrospiro[cyclobutane-1,4'-furo[2,3-g]indazole]-7'-carboxylate (1.00 eq., 130 mg, 454 μmol) from step 3 was reacted with (pyridin-2-yl)methanol (1.1 eq., 55 mg, 500 μmol), tri-n-butylphosphine (CAS No. [998-40-3]; 1.6 eq., 180 μL, 730 μmol) and TMAD (CAS No. [10465-78-8]; 1.60 eq., 125 mg, 726 μmol) in toluene (7.5 mL) at rt for two days to give upon column chromatography ($SiO_2$, hexane/EtOAc) the title compound (111 mg, 58%).

$^1$H NMR (400 MHz, DMSO-d6) δ[ppm]: 1.29 (t, 3H), 1.89-2.13 (m, 6H), 2.45 (s, 3H), 3.08 (s, 2H), 4.26 (q, 2H), 5.41 (s, 2H), 7.06 (d, 1H), 7.31 (ddd, 1H), 7.78 (dt, 1H), 7.94 (s, 1H), 8.55 (ddd, 1H).

UPLC-MS (Method 1): $R_t$=1.27 min; MS (ESIpos): m/z=378 $[M+H]^+$.

Step 5

8'-methyl-2'-[(pyridin-2-yl)methyl]-2',5'-dihydrospiro[cyclobutane-1,4'-furo[2,3-g]indazole]-7'-carboxylic acid

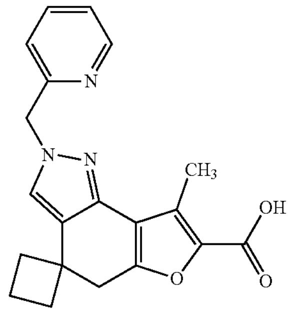 [SMILES: Cc1c(C(=O)O)oc2c1-c1nn(Cc3ccccn3)cc1C1(CCC1)C2]

According to GP D ethyl 8'-methyl-2'-[(pyridin-2-yl)methyl]-2',5'-dihydrospiro[cyclobutane-1,4'-furo[2,3-g]indazole]-7'-carboxylate (1.00 eq., 100 mg, 265 μmol) from step 4 was reacted with aqueous lithium hydroxide (2 M; 15 eq., 2.0 mL, 4.0 mmol) in a 1:1 mixture of ethanol and THF (4 mL) at 70° C. for 4 hours and at room temperature overnight. The reaction mixture was concentrated under reduced pressure, the concentrate acidified with aqueous 2 N HCl (pH 3) and the formed precipitate filtered off. The solid was washed with water and EtOAc and dried to give the desired carboxylic acid (70 mg, 64%).

$^1$H NMR (400 MHz, DMSO-d6) δ[ppm]: 1.91-2.05 (m, 2H), 2.06-2.13 (m, 4H), 2.42 (s, 3H), 3.03 (s, 2H), 5.40 (s, 2H), 7.05 (d, 1H), 7.31 (ddd, 1H), 7.78 (dt, 1H), 7.92 (s, 1H), 8.54 (ddd, 1H).

UPLC-MS (Method 1): $R_t$=0.63 min; MS (ESIpos): m/z=350 $[M+H]^+$.

Intermediate 43

8-methyl-N-[(2S)-tetrahydrofuran-2-ylmethyl]-4,5-dihydro-1H-furo[2,3-g]indazole-7-carboxamide

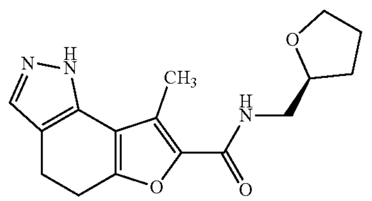 [SMILES: Cc1c(C(=O)NC[C@@H]2CCCO2)oc2c1-c1[nH]ncc1CC2]

To an ice-cooled solution of 1-[(2S)-tetrahydrofuran-2-yl]methanamine (CAS No. [7175-81-7]; 3.0 eq., 1.3 mL, 12 mmol) in dichloromethane (20 mL) under argon atmosphere was dropwise added trimethylaluminum (CAS No. [75-24-1]; 3.0 eq., 2.0 M solution in toluene, 6.1 mL, 12 mmol) and stirring continued for 5 minutes. To this mixture was added dropwise a suspension of ethyl 8-methyl-4,5-dihydro-1H-furo[2,3-g]indazole-7-carboxylate (commercially available; 1.00 eq., 1.00 g, 4.06 mmol) in dichloromethane (10 mL).

The reaction mixture was warmed to rt and stirred for one hour upon which it was warmed to 40° C. and stirring at 40° C. continued for four days. The reaction mixture was quenched with a saturated aqueous solution of potassium sodium tartrate, the phases separated, and the aqueous phase extracted with dichloromethane twice. The combined organic phases were washed with brine, dried with $MgSO_4$, filtered and concentrated under reduced pressure. The obtained crude material was subjected to column chromatography (Si—NH $SiO_2$, EtOAc/MeOH) and subsequent trituration with acetonitrile to give the title compound (453 mg, 35%).

$^1$H NMR (400 MHz, DMSO-d6) δ[ppm]: 1.54-1.62 (m, 1H), 1.73-1.92 (m, 3H), 2.83-2.92 (m, 4H), 3.18-3.28 (m, 2H), 3.58-3.64 (m, 1H), 3.74-3.79 (m, 1H), 3.91-3.98 (m, 1H), 7.50 (s, 1H), 7.97 (t, 1H), 12.41 (s, 1H).

UPLC-MS (Method 1): $R_t$=0.82 min; MS (ESIpos): m/z=302 $[M+H]^+$.

Intermediate 44

Step 1 ethyl 8-methyl-2-[phenyl($^2H_2$)methyl]-4,5-dihydro-2H-furo[2,3-g]indazole-7-carboxylate

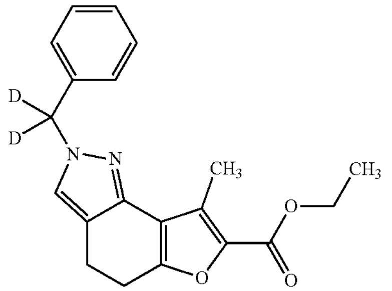 [SMILES: [2H]C([2H])(c1ccccc1)n1cc2c(n1)-c1c(oc(C(=O)OCC)c1C)CC2]

According to GP C (conditions A) ethyl 8-methyl-4,5-dihydro-1H-furo[2,3-g]indazole-7-carboxylate (commercially available; 1.00 eq., 304 mg, 1.23 mmol) was reacted with phenyl($^2H_2$)methanol (CAS No. [21175-64-4]; 1.5 eq., 190 μL, 1.9 mmol), tri-n-butylphosphine (CAS No. [998-40-3]; 1.6 eq., 490 μL, 2.0 mmol) and TMAD (CAS No. [10465-78-8]; 1.60 eq., 340 mg, 1.98 mmol) in toluene (8 mL) at rt for three days to give upon column chromatography ($SiO_2$, hexane/EtOAc) the title compound (364 mg, 83%).

$^1$H NMR (400 MHz, DMSO-d6) δ[ppm]: 1.29 (t, 3H), 2.48 (s, 3H), 2.83-2.93 (m, 4H), 4.26 (q, 2H), 7.22-7.36 (m, 5H), 7.61 (s, 1H).

UPLC-MS (Method 1): $R_t$=1.33 min; MS (ESIpos): m/z=339 $[M+H]^+$.

Step 2

8-methyl-2-[phenyl($^2H_2$)methyl]-4,5-dihydro-2H-furo[2,3-g]indazole-7-carboxylic acid

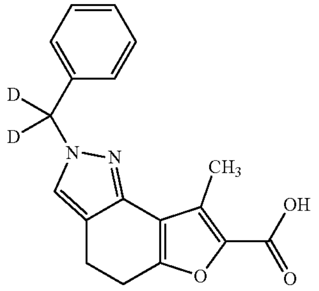 [SMILES: [2H]C([2H])(c1ccccc1)n1cc2c(n1)-c1c(oc(C(=O)O)c1C)CC2]

According to GP D ethyl 8-methyl-2-[phenyl($^2H_2$)methyl]-4,5-dihydro-2H-furo[2,3-g]indazole-7-carboxylate (1.00 eq., 355 mg, 1.05 mmol) from step 1 was reacted with aqueous lithium hydroxide (2 M; 15 eq., 7.9 mL, 16 mmol) in a 1:1 mixture of ethanol and THF (14 mL) at 70° C. overnight and for two days at rt. The reaction mixture was acidified with aqueous 6 N HCl (pH 3-4) upon which a precipitate was formed. The precipitate was isolated by filtration, washed with water and dried under reduced pressure to give the desired carboxylic acid (214 mg, 64%).

$^1$H NMR (400 MHz, DMSO-d6) δ[ppm]: 2.46 (s, 3H), 2.82-2.91 (m, 4H), 7.23-7.30 (m, 3H), 7.33-7.37 (m, 2H), 7.59 (s, 1H), 12.80 (br. s., 1H).

UPLC-MS (Method 1): $R_t$=0.58 min; MS (ESIpos): m/z=311 $[M+H]^+$.

Intermediate 45

Step 1 ethyl 2-[(5-cyclopropyl-1,2,4-oxadiazol-3-yl)methyl]-8-methyl-4,5-dihydro-2H-furo[2,3-g]indazole-7-carboxylate

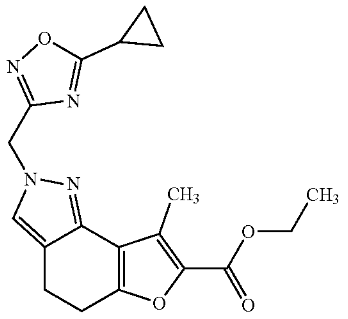 [SMILES: CCOC(=O)c1oc2c(c1C)-c1nn(Cc3noc(C4CC4)n3)cc1CC2]

According to GP C (conditions A) ethyl 8-methyl-4,5-dihydro-1H-furo[2,3-g]indazole-7-carboxylate (commercially available; 1.00 eq., 300 mg, 1.22 mmol) was reacted with (5-cyclopropyl-1,2,4-oxadiazol-3-yl)methanol (CAS No. [915920-06-8]; 1.5 eq., 256 mg, 1.83 mmol), tri-n-butylphosphine (CAS No. [998-40-3]; 1.6 eq., 490 μL, 1.9 mmol) and TMAD (CAS No. [10465-78-8]; 1.60 eq., 336 mg, 1.95 mmol) in toluene (8 mL) at rt for three days to give upon column chromatography ($SiO_2$, hexane/EtOAc) the title compound (363 mg, 73%).

$^1H$ NMR (400 MHz, DMSO-d6) δ[ppm]: 1.06-1.10 (m, 2H), 1.21-1.25 (m, 2H), 1.29 (t, 3H), 2.29-2.36 (m, 1H), 2.46 (s, 3H), 2.84-2.94 (m, 4H), 4.26 (q, 2H), 5.41 (s, 2H), 7.62 (s, 1H).

UPLC-MS (Method 1): $R_t$=1.19 min; MS (ESIpos): m/z=369 $[M+H]^+$.

Step 2

2-[(5-cyclopropyl-1,2,4-oxadiazol-3-yl)methyl]-8-methyl-4,5-dihydro-2H-furo[2,3-g]indazole-7-carboxylic acid

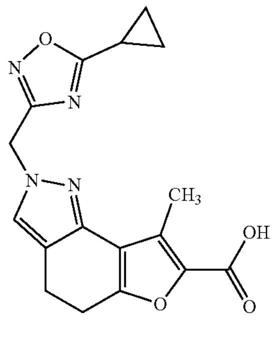 [SMILES: Cc1c(C(=O)O)oc2c1-c1nn(Cc3noc(C4CC4)n3)cc1CC2]

According to GP D ethyl 2-[(5-cyclopropyl-1,2,4-oxadiazol-3-yl)methyl]-8-methyl-4,5-dihydro-2H-furo[2,3-g]indazole-7-carboxylate (1.00 eq., 354 mg, 961 μmol) from step 1 was reacted with aqueous lithium hydroxide (2 M; 15 eq., 7.2 mL, 14 mmol) in a 1:1 mixture of ethanol and THF (14 mL) at 70° C. overnight. The reaction mixture was acidified with aqueous 6 N HCl (pH 3-4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (275 mg, 76%).

$^1H$ NMR (400 MHz, DMSO-d6) δ[ppm]: 1.06-1.10 (m, 2H), 1.20-1.25 (m, 2H), 2.29-2.36 (m, 1H), 2.44 (s, 3H), 2.82-2.92 (m, 4H), 5.41 (s, 2H), 7.61 (s, 1H), 12.81 (br. s., 1H).

UPLC-MS (Method 1): $R_t$=0.51 min; MS (ESIpos): m/z=341 $[M+H]^+$.

Intermediate 46

Step 1 ethyl 2-{2-[(tert-butoxycarbonyl)amino]ethyl}-8-methyl-4,5-dihydro-2H-furo[2,3-g]indazole-7-carboxylate

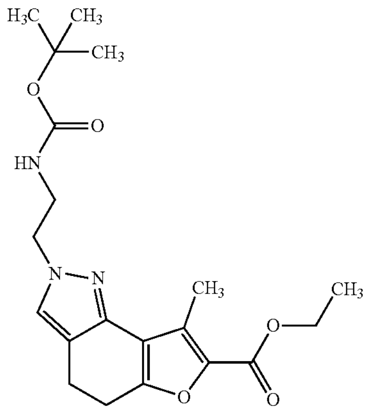 [SMILES: CCOC(=O)c1oc2c(c1C)-c1nn(CCNC(=O)OC(C)(C)C)cc1CC2]

According to GP C (conditions A) ethyl 8-methyl-4,5-dihydro-1H-furo[2,3-g]indazole-7-carboxylate (commercially available; 1.00 eq., 350 mg, 1.42 mmol) was reacted with tert-butyl (2-hydroxyethyl)carbamate (CAS No. [26690-80-2]; 1.50 eq., 344 mg, 2.13 mmol), tri-n-butylphosphine (CAS No. [998-40-3]; 1.6 eq., 570 μL, 2.3 mmol) and TMAD (CAS No. [10465-78-8]; 1.60 eq., 392 mg, 2.27 mmol) in toluene (8 mL) at rt overnight to give upon column chromatography ($SiO_2$, hexane/EtOAc) and subsequent trituration with acetonitrile the title compound (285 mg, 46%).

$^1H$ NMR (400 MHz, DMSO-d6) δ[ppm]: 1.29 (t, 3H), 1.36 (s, 9H), 2.81-2.92 (m, 4H), 3.25-3.30 (m, 2H), 4.08 (t, 2H), 4.27 (q, 2H), 6.95 (t, 1H), 7.47 (s, 1H).

UPLC-MS (Method 1): $R_t$=1.21 min; MS (ESIpos): m/z=390 $[M+H]^+$.

Step 2

2-{2-[(tert-butoxycarbonyl)amino]ethyl}-8-methyl-4,5-dihydro-2H-furo[2,3-g]indazole-7-carboxylic acid

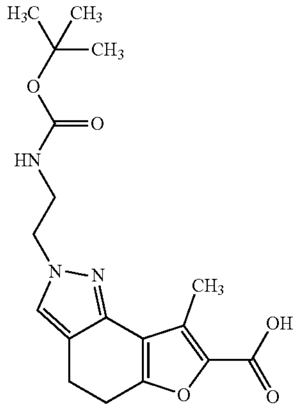 [SMILES: Cc1c(C(=O)O)oc2c1-c1nn(CCNC(=O)OC(C)(C)C)cc1CC2]

According to GP D ethyl 2-{2-[(tert-butoxycarbonyl)amino]ethyl}-8-methyl-4,5-dihydro-2H-furo[2,3-g]indazole-7-carboxylate (1.00 eq., 280 mg, 719 μmol) from step 1 was reacted with aqueous lithium hydroxide (2 M; 15 eq., 5.4 mL, 11 mmol) in a 1:1 mixture of ethanol and THF (9 mL) at 70° C. overnight. The reaction mixture was acidified with aqueous 6 N HCl (pH 4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid (301 mg, 100%).

$^1H$ NMR (400 MHz, DMSO-d6) δ[ppm]: 1.36 (s, 9H), 2.47 (s, 3H), 2.80-2.89 (m, 4H), 3.25-3.30 (m, 2H), 4.08 (t, 2H), 6.94 (t, 1H), 7.45 (s, 1H), 12.68 (br. s., 1H).

UPLC-MS (Method 1): $R_t$=0.54 min; MS (ESIpos): m/z=362 $[M+H]^+$.

Intermediate 47

Step 1 ethyl 2-{2-[4-(tert-butoxycarbonyl)piperazin-1-yl]ethyl}-8-methyl-4,5-dihydro-2H-furo[2,3-g]indazole-7-carboxylate

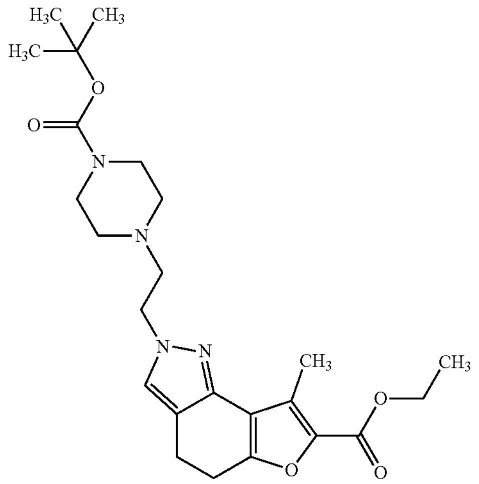 [SMILES: CCOC(=O)c1oc2c(c1C)-c1nn(CCN3CCN(C(=O)OC(C)(C)C)CC3)cc1CC2]

According to GP C (conditions A) ethyl 8-methyl-4,5-dihydro-1H-furo[2,3-g]indazole-7-carboxylate (commercially available; 1.00 eq., 350 mg, 1.42 mmol) was reacted with tert-butyl 4-(2-hydroxyethyl)piperazine-1-carboxylate (CAS No. [77279-24-4]; 1.50 eq., 491 mg, 2.13 mmol), tri-n-butylphosphine (CAS No. [998-40-3]; 1.6 eq., 570 μL, 2.3 mmol) and TMAD (CAS No. [10465-78-8]; 1.60 eq., 392 mg, 2.27 mmol) in toluene (8 mL) at rt overnight to give upon column chromatography ($SiO_2$, hexane/EtOAc) and subsequent trituration with acetonitrile the title compound (567 mg, 83%).

$^1H$ NMR (400 MHz, DMSO-d6) δ[ppm]: 1.29 (t, 3H), 1.39 (s, 9H), 2.37-2.39 (m, 4H), 2.49 (s, 3H), 2.70 (t, 2H), 2.82-2.92 (m, 4H), 3.27-3.30 (m, 4H), 4.18 (t, 2H), 4.26 (q, 2H), 7.54 (s, 1H).

UPLC-MS (Method 1): $R_t$=1.32 min; MS (ESIpos): m/z=459 $[M+H]^+$.

Step 2

2-{2-[4-(tert-butoxycarbonyl)piperazin-1-yl]ethyl}-8-methyl-4,5-dihydro-2H-furo[2,3-g]indazole-7-carboxylic acid hydrogen chloride (1/1)

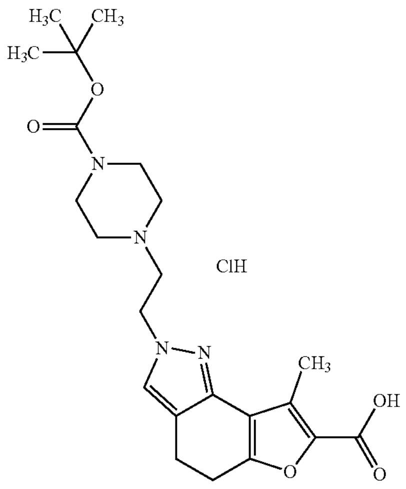 [SMILES: Cc1c(C(=O)O)oc2c1-c1nn(CCN3CCN(C(=O)OC(C)(C)C)CC3)cc1CC2 ; Cl]

According to GP D ethyl 2-{2-[4-(tert-butoxycarbonyl)piperazin-1-yl]ethyl}-8-methyl-4,5-dihydro-2H-furo[2,3-g]indazole-7-carboxylate (1.00 eq., 560 mg, 1.22 mmol) from step 1 was reacted with aqueous lithium hydroxide (2 M; 15 eq., 9.2 mL, 18 mmol) in a 1:1 mixture of ethanol and THF (18 mL) at 70° C. overnight. The reaction mixture was acidified with aqueous 6 N HCl (pH 3-4) and diluted with EtOAc. The phases were separated, and the aqueous phase extracted with EtOAc. The combined organic phases were washed with brine, dried with $Na_2SO_4$, filtrated and concentrated under reduced pressure to give the desired carboxylic acid as HCl salt (518 mg, 86%).

$^1H$ NMR (400 MHz, DMSO-d6) δ[ppm]: 1.41 (s, 9H), 2.84-2.93 (m, 4H), 3.05-3.20 (m, 4H), 3.50-3.57 (m, 4H), 4.01 (br. s., 2H), 4.53 (br. s., 2H), 7.61 (s, 1H), 10.35 (br. s., 1H), 12.85 (br. s., 1H).

UPLC-MS (Method 1): $R_t$=0.62 min; MS (ESIpos): m/z=431 $[M-Cl^-]^+$.

Intermediate 48

Step 1 ethyl 2'-{[(2S)-1,4-dioxan-2-yl]methyl}-8'-methyl-2',5'-dihydrospiro[cyclobutane-1,4'-furo[2,3-g]indazole]-7'-carboxylate

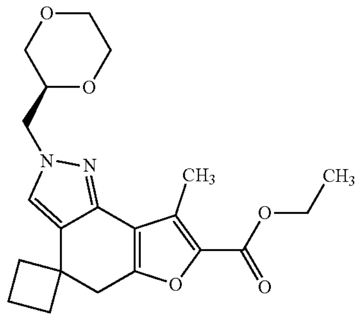 [SMILES: CCOC(=O)c1oc2c(c1C)-c1nn(C[C@H]3COCCO3)cc1C1(CCC1)C2]

According to GP C (conditions A) ethyl 8'-methyl-1',5'-dihydrospiro[cyclobutane-1,4'-furo[2,3-g]indazole]-7'-carboxylate (prepared according to Intermediate 42, step 3; 1.00 eq., 500 mg, 1.75 mmol) was reacted with [(2S)-1,4-dioxan-2-yl]methanol (CAS No. [406913-93-7]; 1.10 eq., 227 mg, 1.92 mmol), tri-n-butylphosphine (CAS No. [998-40-3]; 1.6 eq., 700 μL, 2.8 mmol) and TMAD (CAS No. [10465-78-8]; 1.60 eq., 481 mg, 2.79 mmol) in toluene (30 mL) at rt for 2 days to give upon column chromatography ($SiO_2$, hexane/ethyl acetate) the title compound (291 mg, 86% purity, 34%).

$^1$H NMR (400 MHz, DMSO-d6) δ[ppm]: 1.30 (t, 3H), 2.06-2.13 (m, 6H), 2.49 (s, 3H), 3.05-3.06 (m, 2H), 3.28 (dd, 1H), 3.46 (dt, 1H), 3.56 (dt, 1H), 3.62-3.65 (m, 1H), 3.73-3.76 (m, 2H), 3.85-3.91 (m, 1H), 4.10-4.12 (m, 2H), 4.27 (q, 2H), 7.76 (s, 1H).

UPLC-MS (Method 1): $R_t$=1.26 min; MS (ESIpos): m/z=387 $[M+H]^+$.

Step 2

2'-{[(2S)-1,4-dioxan-2-yl]methyl}-8'-methyl-2',5'-dihydrospiro[cyclobutane-1,4'-furo[2,3-g]indazole]-7'-carboxylic acid

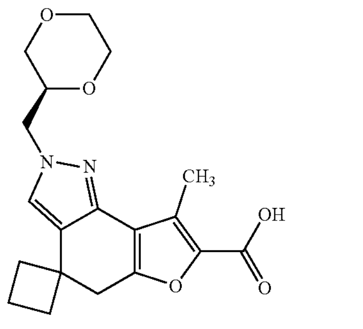 [SMILES: Cc1c(C(=O)O)oc2c1-c1nn(C[C@H]3COCCO3)cc1C1(CCC1)C2]

According to GP D ethyl 2'-{[(2S)-1,4-dioxan-2-yl]methyl}-8'-methyl-2',5'-dihydrospiro[cyclobutane-1,4'-furo[2,3-g]indazole]-7'-carboxylate (1.00 eq., 240 mg, 621 μmol) from step 1 was reacted with aqueous lithium hydroxide (2 M; 15 eq., 4.7 mL, 9.3 mmol) in a 1:1 mixture of ethanol and THF (10 mL) at 70° C. for 4 hours and at room temperature for 3 days. The reaction mixture was concentrated under reduced pressure, the concentrate acidified with aqueous 2 N HCl (pH 3) and the formed precipitate filtered off. The solid was washed with water and EtOAc and dried to give the desired carboxylic acid (209 mg, 60% purity, 56%).

UPLC-MS (Method 1): $R_t$=0.56 min; MS (ESIpos): m/z=359 $[M+H]^+$.

Intermediate 49

Step 1 ethyl 2-[(6-cyanopyridin-3-yl)methyl]-8-methyl-4,5-dihydro-2H-furo[2,3-g]indazole-7-carboxylate

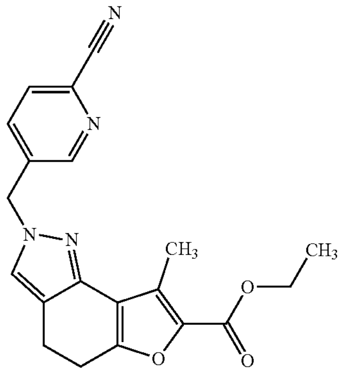 [SMILES: CCOC(=O)c1oc2c(c1C)-c1nn(Cc3ccc(C#N)nc3)cc1CC2]

According to GP C (conditions A) ethyl 8-methyl-4,5-dihydro-1H-furo[2,3-g]indazole-7-carboxylate (commercially available; 1.00 eq., 245 mg, 994 μmol) was reacted with 5-(hydroxymethyl)pyridine-2-carbonitrile (CAS No. [58553-48-3]; 1.50 eq., 200 mg, 1.49 mmol), tri-n-butylphosphine (CAS No. [998-40-3]; 1.6 eq., 400 μL, 1.6 mmol) and TMAD (CAS No. [10465-78-8]; 1.60 eq., 274 mg, 1.59 mmol) in toluene (8 mL) at rt overnight and at 40° C. for one day. Another amount of tri-n-butylphosphine (1.0 eq., 250 μL, 1.0 mmol) and TMAD (1.0 eq., 170 mg, 1.0 mmol) were added and stirring at 40° C. continued for 10 days to give upon column chromatography ($SiO_2$, hexane/EtOAc) the title compound (72 mg, 18%).

$^1$H NMR (400 MHz, DMSO-d6) δ[ppm]: 1.29 (t, 3H), 2.47 (s, 3H), 2.86-2.94 (m, 4H), 4.26 (q, 2H), 5.48 (s, 2H), 7.71 (s, 1H), 7.82 (dd, 1H), 8.03 (dd, 1H), 8.86-8.87 (m, 1H).

UPLC-MS (Method 1): $R_t$=1.20 min; MS (ESIpos): m/z=363 $[M+H]^+$.

Step 2

2-[(6-carboxypyridin-3-yl)methyl]-8-methyl-4,5-dihydro-2H-furo[2,3-g]indazole-7-carboxylic acid

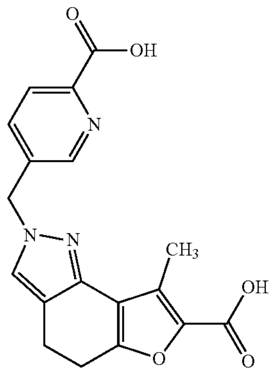 [SMILES: Cc1c(C(=O)O)oc2c1-c1nn(Cc3ccc(C(=O)O)nc3)cc1CC2]

According to GP D ethyl 2-[(6-cyanopyridin-3-yl)methyl]-8-methyl-4,5-dihydro-2H-furo[2,3-g]indazole-7-carboxylate (1.00 eq., 72.0 mg, 199 μmol) from step 1 was reacted with aqueous lithium hydroxide (2 M; 15 eq., 1.5 mL, 3.0 mmol) in a 1:1 mixture of ethanol and THF (2 mL) at 70° C. overnight and at room temperature for 2 days. The reaction mixture was acidified with aqueous 6 N HCl (pH 3) and concentrated under reduced pressure and the obtained crude dicarboxylic acid (268 mg) used without further purification.

UPLC-MS (Method 1): $R_t$=0.18 min; MS (ESIpos): m/z=354 $[M+H]^+$.

Intermediate 50

Step 1 ethyl 4-oxo-3-(trifluoromethyl)-4,7-dihydro-5H-spiro[[1]benzofuran-6,1'-cyclopropane]-2-carboxylate

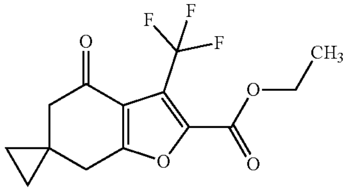 [SMILES: CCOC(=O)c1oc2c(c1C(F)(F)F)C(=O)CC1(CC1)C2]

To a solution of spiro[2.5]octane-5,7-dione (CAS No. [893411-52-4]; 1.00 eq., 67.5 mmol, 9.33 g) in toluene (30 mL) was added ethyl 2-chloro-4,4,4-trifluoro-3-oxobutanoate (see Intermediate 35, step 1; 2.2 eq, 150 mmol, 23 mL) and the reaction mixture subsequently stirred at 100° C. for 43 hours. The mixture was poured into water and extracted twice with ethyl acetate. The combined organic layer was washed with brine, dried with $Na_2SO_4$, filtrated and concentrated under reduced pressure. The obtained material was purified by column chromatography (Si—NH $SiO_2$, hexane/EtOAc) to give the title compound (3.2 g, 15%).

$^1$H NMR (400 MHz, DMSO-d6) δ[ppm]: 0.48-0.51 (m, 2H), 0.54-0.57 (m, 2H), 1.30 (t, 3H), 2.45 (s, 2H), 2.96 (s, 2H), 4.36 (q, 2H).

UPLC-MS (Method 1): $R_t$=1.22 min; MS (ESIpos): m/z=303 $[M+H]^+$.

Step 2 ethyl (5E/Z)-5-[(dimethylamino)methylidene]-4-oxo-3-(trifluoromethyl)-4,7-dihydro-5H-spiro[[1]benzofuran-6,1'-cyclopropane]-2-carboxylate

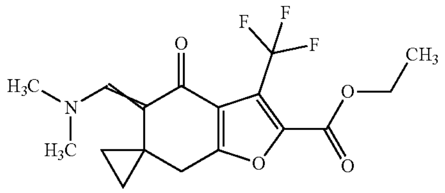 [SMILES: CCOC(=O)c1oc2c(c1C(F)(F)F)C(=O)C(=CN(C)C)C1(CC1)C2]

According to GP A (conditions A) ethyl 4-oxo-3-(trifluoromethyl)-4,7-dihydro-5H-spiro[[1]benzofuran-6,1'-cyclopropane]-2-carboxylate (1.00 eq., 1.53 g, 5.06 mmol) from step 1 was reacted with 1-tert-butoxy-N,N,N',N'-tetramethylmethanediamine (Bredereck's reagent, CAS No. [5815-08-7]; 1.2 eq., 1.1 mL, 6.1 mmol) in toluene (30 mL) at 100° C. for 29 h. Another amount of 1-tert-butoxy-N,N,N',N' tetramethylmethanediamine (1.5 eq., 1.4 mL, 7.6 mmol) was added and stirring at 100° C. continued for another 19 h. The reaction mixture was concentrated under reduced pressure and the obtained crude title compound used in the subsequent reaction without further purification steps.

UPLC-MS (Method 1): $R_t$=1.23/1.29 min; MS (ESIpos): m/z=358 $[M+H]^+$.

Step 3 ethyl 8'-(trifluoromethyl)-1',5'-dihydrospiro[cyclopropane-1,4'-furo[2,3-g]indazole]-7'-carboxylate

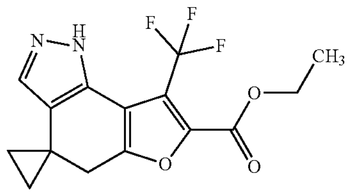 [SMILES: CCOC(=O)c1oc2c(c1C(F)(F)F)-c1[nH]ncc1C1(CC1)C2]

According to GP B crude ethyl (5E/Z)-5-[(dimethylamino)methylidene]-4-oxo-3-(trifluoromethyl)-4,7-dihydro-5H-spiro[[1]benzofuran-6,1'-cyclopropane]-2-carboxylate (1.00 eq., 1.81 g, 5.06 mmol) from step 2 was reacted with hydrazine dihydrochloride (CAS No. [5341-61-7]; 2.0 eq., 1.1 g, 10 mmol) in a mixture of ethanol (13 mL) and water (2 mL) at 70° C. for 1 hour to give upon column chromatography ($SiO_2$, hexane/EtOAc) the title compound (192 mg, 11% over two steps).

$^1$H NMR (500 MHz, DMSO-d6) δ[ppm]: 0.83-0.86 (m, 2H), 0.88-0.91 (m, 2H), 1.31 (t, 3H), 2.97 (s, 2H), 4.35 (q, 2H), 7.42 (s, 1H), 12.62 (s, 1H).

$^{19}$F NMR (470 MHz, DMSO-d6) δ[ppm]: −55.0 (s).

UPLC-MS (Method 1): $R_t$=1.15 min; MS (ESIpos): m/z=327 $[M+H]^+$.

Step 4 ethyl 2'-{[(2S)-1,4-dioxan-2-yl]methyl}-8'-(trifluoromethyl)-2',5'-dihydrospiro[cyclopropane-1,4'-furo[2,3-g]indazole]-7'-carboxylate

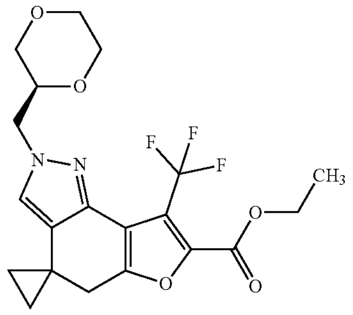 [SMILES: CCOC(=O)c1oc2c(c1C(F)(F)F)-c1nn(C[C@H]3COCCO3)cc1C1(CC1)C2]

According to GP C (conditions A) ethyl 8'-(trifluoromethyl)-1',5'-dihydrospiro[cyclopropane-1,4'-furo[2,3-g]indazole]-7'-carboxylate (1.00 eq., 142 mg, 435 μmol) from step 3 was reacted with [(2S)-1,4-dioxan-2-yl]methanol (CAS No. [406913-93-7]; 1.1 eq., 77 mg, 650 μmol), tri-n-butylphosphine (CAS No. [998-40-3]; 1.6 eq., 170 μL, 700 μmol) and TMAD (CAS No. [10465-78-8]; 1.60 eq., 120 mg, 696 μmol) in toluene (5 mL) at rt for 5 days to give upon column chromatography ($SiO_2$, hexane/ethyl acetate) the title compound (97 mg, 52%).

$^1$H NMR (400 MHz, DMSO-d6) δ[ppm]: 0.79-0.91 (m, 4H), 1.31 (t, 3H), 2.92-3.02 (m, 2H), 3.25 (dd, 1H), 3.43 (dt, 1H), 3.53 (dt, 1H), 3.61-3.64 (m, 1H), 3.71-3.75 (m, 2H), 3.79-3.85 (m, 1H), 4.10-4.11 (m, 2H), 4.35 (q, 2H), 7.38 (s, 1H).

UPLC-MS (Method 1): $R_t$=1.29 min; MS (ESIpos): m/z=427 $[M+H]^+$.

Step 5

2'-{[(2S)-1,4-dioxan-2-yl]methyl}-8'-(trifluoromethyl)-2',5'-dihydrospiro[cyclopropane-1,4'-furo[2,3-g]indazole]-7'-carboxylic acid

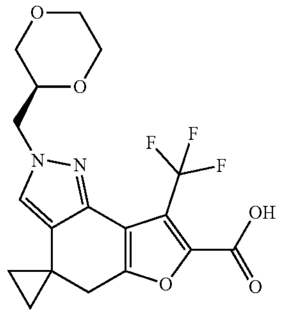 [SMILES: O=C(O)c1oc2c(c1C(F)(F)F)-c1nn(C[C@H]3COCCO3)cc1C1(CC1)C2]

According to GP D ethyl 2'-{[(2S)-1,4-dioxan-2-yl]methyl}-8'-(trifluoromethyl)-2',5'-dihydrospiro[cyclopropane-1,4'-furo[2,3-g]indazole]-7'-carboxylate (1.0 eq., 97 mg, 230 μmol) from step 4 was reacted with aqueous lithium hydroxide (2 M; 15 eq., 1.7 mL, 3.4 mmol) in a 1:1 mixture of ethanol and THF (4 mL) at 70° C. for 4 hours. The reaction mixture was acidified with aqueous 2 N HCl (pH 2) and the formed precipitate filtered off. The solid was washed with water and EtOAc and dried to give a first crop of the desired carboxylic acid (57 mg, 60%). The combined filtrates and washing solutions were re-extracted with ethyl acetate (twice), the combined organic phases dried with $Na_2SO_4$, filtrated and concentrated under reduced pressure to give a second crop of the desired carboxylic acid (34 mg, 87% purity, 33%).

$^1$H NMR (400 MHz, DMSO-d6) δ[ppm]: 0.79-0.92 (m, 4H), 2.90-2.99 (m, 2H), 3.25 (dd, 1H), 3.43 (dt, 1H), 3.53 (dt, 1H), 3.61-3.64 (m, 1H), 3.70-3.75 (m, 2H), 3.80-3.85 (m, 1H), 4.00-4.11 (m, 2H), 7.37 (s, 1H), 13.94 (br. s., 1H).

UPLC-MS (Method 1): $R_t$=0.55 min; MS (ESIpos): m/z=399 $[M+H]^+$.

Intermediate 51

Step 1 ethyl 2-[(4-fluoropyridin-2-yl)methyl]-8-methyl-4,5-dihydro-2H-furo[2,3-g]indazole-7-carboxylate

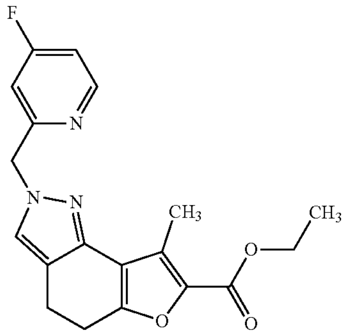 [SMILES: CCOC(=O)c1oc2c(c1C)-c1nn(Cc3cc(F)ccn3)cc1CC2]

Ethyl 8-methyl-4,5-dihydro-1H-furo[2,3-g]indazole-7-carboxylate (commercially available; 1.0 eq, 100 mg, 406 μmol), 2-(chloromethyl)-4-fluoropyridine (1.5 eq, 88.7 mg, 609 μmol) and caesium carbonate (CAS No [534-17-8], 3.0 eq, 397 mg, 1.22 mmol) were added to DMF (3.0 ml) and stirred 24 h at rt overnight under nitrogen. 2, 2-(chloromethyl)-4-fluoropyridine (1.5 eq, 88.7 mg, 609 μmol) and caesium carbonate (CAS No [534-17-8], 3.0 eq, 397 mg, 1.22 mmol) were added again and stirred at rt overnight under nitrogen. The reaction mixture was filtered and washed with ethyl acetate. The filtrate was evaporated and purified by column chromatography ($SiO_2$, hexane/ethyl acetate) to give the product (53.1 mg, 37% yield).

$^1$H NMR (400 MHz, DMSO-d6) δ[ppm]: 1.27-1.31 (m, 3H) 2.46 (s, 3H) 2.85-2.94 (m, 4H) 4.23-4.29 (m, 2H) 5.40 (s, 2H) 7.19-7.22 (m, 1H) 7.65 (s, 1H) 7.71 (td, 1H) 8.55 (d, 1H)

LC-MS (Method 1): $R_t$=1.22 min; MS (ESIpos): m/z=356 $[M+H]^+$

Step 2

2-[(4-fluoropyridin-2-yl)methyl]-8-methyl-4,5-dihydro-2H-furo[2,3-g]indazole-7-carboxylic acid

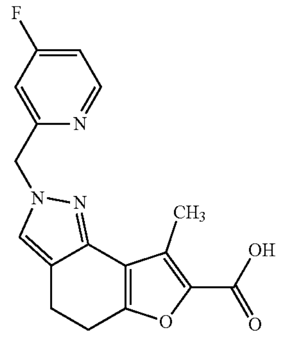 [SMILES: Cc1c(C(=O)O)oc2c1-c1nn(Cc3cc(F)ccn3)cc1CC2]

According to GP D ethyl 2-[(4-fluoropyridin-2-yl)methyl]-8-methyl-4,5-dihydro-2H-furo[2,3-g]indazole-7-carboxylate (1.0 eq, 53.0 mg, 149 μmol) from step 1 was reacted with aqueous lithium hydroxide (2 M; 5 eq, 370 μL, 750 μmol) in a 1:1 mixture of ethanol and THF (2.0 mL) at 70° C. overnight. Upon acidification (pH 2) with 6 N aqueous hydrochloric acid and evaporated. To the residue were added DCM (20 ml) and i-PrOH (1 ml) and stirred at rt. The DCM phase was decanted and evaporated. And then THF (20 ml) was added and co-evaporated. The crude (75 mg) was used in the subsequent reaction without further purification steps.

LC-MS (Method 1): $R_t$=0.52 min; MS (ESIpos): m/z=328 $[M+H]^+$

Intermediate 52

Step 1 ethyl 8-methyl-2-[(pyridazin-3-yl)methyl]-4,5-dihydro-2H-furo[2,3-g]indazole-7-carboxylate

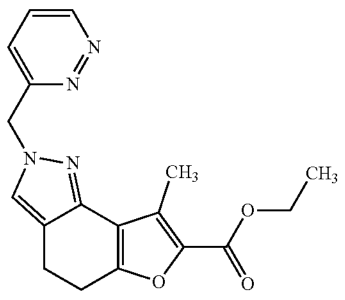 [SMILES: CCOC(=O)c1oc2c(c1C)-c1nn(Cc3cccnn3)cc1CC2]

A solution of ethyl 8-methyl-4,5-dihydro-1H-furo[2,3-g]indazole-7-carboxylate (commercially available; 1.0 eq, 180 mg, 731 μmol) and 3-(chloromethyl)pyridazine chloride (CAS No [27349-66-2], 1.5 eq, 180 mg, 1096 μmol) in DMF (24.0 ml) under nitrogen is treated with caesium carbonate (CAS No [534-17-8], 20.0 eq., 4.76 g, 14.6 mmol) and stirred at 80° C. overnight. The solid was filtered and washed with ethyl acetate and was evaporated. The residue was purified by column chromatography ($SiO_2$, hexane/ethyl acetate) to give the product (87 mg, 35% yield).

$^1H$ NMR (400 MHz, DMSO-d6) δ[ppm]: 1.27-1.31 (m, 3H) 2.46 (s, 3H) 2.85-2.95 (m, 4H) 4.21-4.30 (m, 2H) 5.63 (s, 2H) 7.38-7.43 (m, 1H), 7.67-7.71 (m, 1H) 7.72 (s, 1H) 9.13-9.22 (m, 1H)

LC-MS (Method 1): $R_t$=1.02 min; MS (ESIpos): m/z=339 $[M+H]^+$

Step 2

8-methyl-2-[(pyridazin-3-yl)methyl]-4,5-dihydro-2H-furo[2,3-g]indazole-7-carboxylic acid

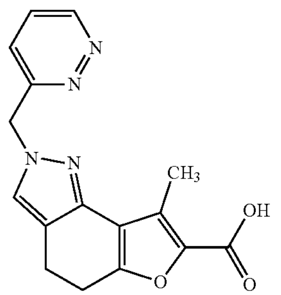

According to GP D ethyl 8-methyl-2-[(pyridazin-3-yl)methyl]-4,5-dihydro-2H-furo[2,3-g]indazole-7-carboxylate (1.0 eq, 87.0 mg, 257 μmol) from step 1 was reacted with aqueous lithium hydroxide (2 M; 5 eq, 640 μL, 1.3 mmol) in a 1:1 mixture of ethanol and THF (5.0 mL) at 70° C. overnight. Upon acidification (pH 2) with 6 N aqueous hydrochloric acid, the resulting mixture was evaporated. To the residue were added DCM (50 ml) and i-PrOH (4×5 ml) and stirred 30 min at rt. Hexane was added until precipitation, filtered, washed with hexane/DCM (1:1) and evaporated. To the residue, was added DCM and brine (2 ml) and stirred. The phases were separated, and the DCM phase was evaporated to give the product (35.0 mg, 44% yield).

LC-MS (Method 2): $R_t$=0.72 min; MS (ESIpos): m/z=311 $[M+H]^+$

Intermediate 53

Step 1 ethyl 2-[(6-chloropyridin-3-yl)methyl]-8-methyl-4,5-dihydro-2H-furo[2,3-g]indazole-7-carboxylate

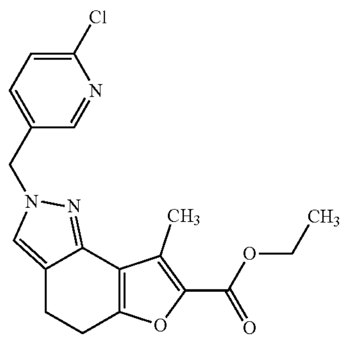 [SMILES: CCOC(=O)c1oc2c(c1C)-c1nn(Cc3ccc(Cl)nc3)cc1CC2]

According to GP C (conditions A) Ethyl 8-methyl-4,5-dihydro-1H-furo[2,3-g]indazole-7-carboxylate (commercially available; 1.00 eq., 250 mg, 1.05 mmol) was reacted with (6-chloropyridin-3-yl)methanol (1.5 eq., 218 mg, 1.52 mmol), tri-n-butylphosphine (CAS No. [998-40-3]; 1.6 eq., 0.4 mL, 1.6 mmol) and TMAD (CAS No. [10465-81-3]; 1.6 eq., 279 mg, 1.6 mmol) in toluene (5.8 ml) at rt overnight. The reaction mixture was filtered and extracted with water. The water phase was extracted twice with DCM. The combined organic layers (DCM and toluene phases) were dried over a hydrophobic filter paper and evaporated to give a crude material. It was then purified by column chromatography ($SiO_2$, hexane/EtOAc) to give the title compound (140 mg, 36% yield).

LC-MS (Method 1): $R_t$=1.28 min; MS (ESIpos): m/z=372 $[M+H]^+$

Step 2 ethyl 2-[(6-ethylpyridin-3-yl)methyl]-8-methyl-4,5-dihydro-2H-furo[2,3-g]indazole-7-carboxylate

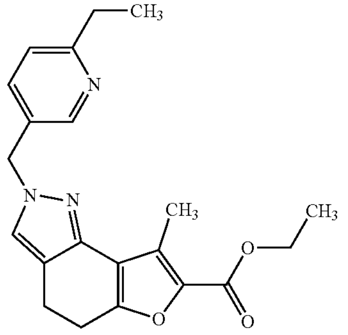 [SMILES: CCOC(=O)c1oc2c(c1C)-c1nn(Cc3ccc(CC)nc3)cc1CC2]

Ethyl 2-[(6-chloropyridin-3-yl)methyl]-8-methyl-4,5-dihydro-2H-furo[2,3-g]indazole-7-carboxylate (1.0 eq, 350 mg, 941 μmol) from step 1 was dissolved in dioxane (22 ml) and flushed with nitrogen. 1,1'-Bis(diphenylphosphino)ferrocenedichloropalladium(II) (76.8 mg, 94.1 μmol; CAS-RN: [72287-26-4]) was firstly added and diethylzinc in hexane (CAS No [557-20-0], 4.5 eq, 4.2 ml, 1.0 M, 4.2 mmol) was then added dropwise. The resulting reaction mixture was stirred for 4 h at 100° C. To the reaction mixture were added water and DCM. The layers were separated, and the water layer was extracted with DCM and with ethyl acetate. The organic layers were dried by hydrophobic filtration and evaporated. The crude material was purified by silica gel column chromatography (hexane/DCM) to give the title compound (187 mg, 55% yield).

LC-MS (Method 1): $R_t$=1.26 min; MS (ESIpos): m/z=366 $[M+H]^+$

Step 3

2-[(6-ethylpyridin-3-yl)methyl]-8-methyl-4,5-dihydro-2H-furo[2,3-g]indazole-7-carboxylic acid

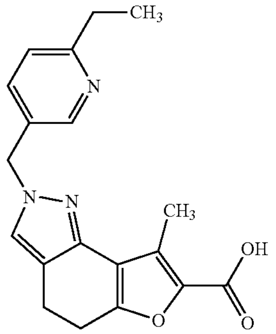 [SMILES: CCc1ccc(Cn2cc3c(n2)-c2c(oc(C(=O)O)c2C)CC3)cn1]

According to GP D ethyl 2-[(6-ethylpyridin-3-yl)methyl]-8-methyl-4,5-dihydro-2H-furo[2,3-g]indazole-7-carboxylate (1.0 eq, 94.0 mg, 257 μmol) from step 2 was reacted with aqueous lithium hydroxide (2 M; 5 eq, 640 μL, 1.3 mmol) in a 1:1 mixture of ethanol and THF (3.0 mL) at 70° C. overnight. Upon acidification (pH 2) with 6 N aqueous hydrochloric acid, the resulting mixture was evaporated. To the residue was added DCM (30 ml), water (20 ml) and i-PrOH (2 ml). The water phase was extracted with DCM/i-PrOH (9:1). The combined organic phase was dried over a hydrophobic filter paper and evaporated to give the product (55 mg, 63% yield) as a crude material, which was used in the next step without further purification.

LC-MS (Method 1): $R_t$=0.56 min; MS (ESIpos): m/z=338 $[M+H]^+$

Intermediate 54

Step 1 ethyl 8-methyl-2-[(1,3-oxazol-2-yl)methyl]-4,5-dihydro-2H-furo[2,3-g]indazole-7-carboxylate

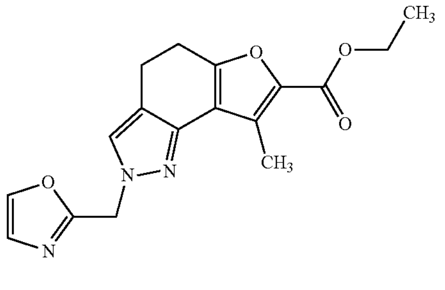 [SMILES: CCOC(=O)c1oc2c(c1C)-c1nn(Cc3ncco3)cc1CC2]

Ethyl 8-methyl-4,5-dihydro-1H-furo[2,3-g]indazole-7-carboxylate (commercially available; 1.00 eq., 100 mg, 406 μmol) was reacted with (1,3-oxazol-2-yl)methanol (CAS No [14774-37-9], 1.5 eq., 60.4 mg, 609 μmol), tri-n-butylphosphine (CAS No. [998-40-3]; 1.6 eq., 160 μL, 650 μmol) and 1,1'-(azodicarbonyl)dipiperidine (CAS No. [10465-81-3]; 1.6 eq., 112 mg, 650 μmol) in toluene (3.0 ml) at rt overnight. The same amounts of reagents were added and stirred again at rt overnight. The reaction mixture was filtered and extracted with water. The water phase was re-extracted with DCM. The organic layers were combined and dried over a hydrophobic filter paper and evaporated to give a crude material. It was then purified by column chromatography (NH, $SiO_2$, hexane/DCM) to give the title compound (60 mg), which was used in the next step without further purification.

LC-MS (Method 1): $R_t$=1.10 min; MS (ESIpos): m/z=328 $[M+H]^+$

Step 2

8-methyl-2-[(1,3-oxazol-2-yl)methyl]-4,5-dihydro-2H-furo[2,3-g]indazole-7-carboxylic acid

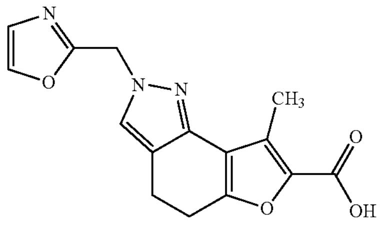 [SMILES: Cc1c(C(=O)O)oc2c1-c1nn(Cc3ncco3)cc1CC2]

According to GP D ethyl 8-methyl-2-[(1,3-oxazol-2-yl)methyl]-4,5-dihydro-2H-furo[2,3-g]indazole-7-carboxylate (1.0 eq, 60 mg, 183 μmol) from step 1 was reacted with aqueous lithium hydroxide (2 M; 15 eq, 1.4 mL, 2.7 mmol) in a 1:1 mixture of ethanol and THF (1.3 mL) at 70° C. overnight. Upon acidification (pH 2) with 6 N aqueous hydrochloric acid, the resulting mixture was evaporated. The resulting crude material was used in the subsequent reaction without further purification steps (90 mg).

LC-MS (Method 1): $R_t$=0.47 min; MS (ESIpos): m/z=300 $[M+H]^+$

Intermediate 55

Step 1 ethyl 8-methyl-2-[(oxan-4-yl)methyl]-4,5-dihydro-2H-furo[2,3-g]indazole-7-carboxylate

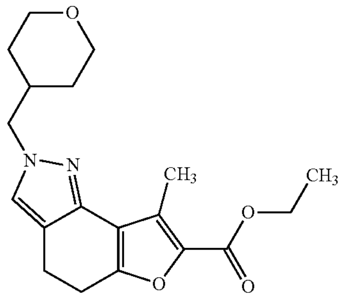

Ethyl 8-methyl-4,5-dihydro-1H-furo[2,3-g]indazole-7-carboxylate (commercially available; 1.00 eq., 100 mg, 406 μmol) was reacted with (oxan-4-yl)methanol (CAS No [14774-37-9], 1.5 eq., 70.8 mg, 609 μmol), tri-n-butylphosphine (CAS No. [998-40-3]; 1.6 eq., 160 μL, 650 μmol) and 1,1'-(azodicarbonyl)dipiperidine (CAS No. [10465-81-3]; 1.6 eq., 112 mg, 650 μmol) in toluene (3.0 ml) at rt overnight. The same amounts of reagents were added and stirred again at rt overnight. The reaction mixture was filtered and extracted with water. The water phase was extracted with DCM. The combined organic layers were dried over a hydrophobic filter paper and evaporated to give a crude material. It was then purified by column chromatography (NH, $SiO_2$, hexane/DCM) to give the title compound (314 mg), which was used in the next step without further purification.

LC-MS (Method 1): $R_t$=1.21 min; MS (ESIpos): m/z=345 $[M+H]^+$

Step 2

8-methyl-2-[(oxan-4-yl)methyl]-4,5-dihydro-2H-furo[2,3-g]indazole-7-carboxylic acid

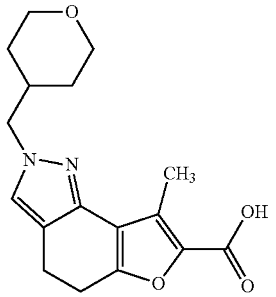 [SMILES: Cc1c(C(=O)O)oc2c1-c1nn(CC3CCOCC3)cc1CC2]

According to GP D ethyl 8-methyl-2-[(oxan-4-yl)methyl]-4,5-dihydro-2H-furo[2,3-g]indazole-7-carboxylate (1.0 eq, 210 mg, 610 μmol) from step 1 was reacted with aqueous lithium hydroxide (2 M; 15 eq, 4.6 mL, 9.1 mmol) in a 1:1 mixture of ethanol and THF (4.3 mL) at 70° C. overnight. Upon acidification (pH 2) with 6 N aqueous hydrochloric acid, the resulting mixture was evaporated, and the crude material was used in the subsequent reaction without further purification steps (350 mg).

LC-MS (Method 1): $R_t$=0.53 min; MS (ESIpos): m/z=317 $[M+H]^+$

Intermediate 56

Step 1 ethyl 8-methyl-2-{[(2R and 2S)-oxan-2-yl]methyl}-4,5-dihydro-2H-furo[2,3-g]indazole-7-carboxylate (Racemate

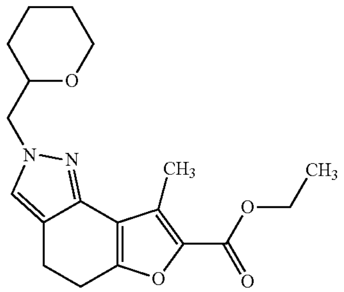 [SMILES: CCOC(=O)c1oc2c(c1C)-c1nn(CC3CCCCO3)cc1CC2]

According to GP C (conditions A) ethyl 8-methyl-4,5-dihydro-1H-furo[2,3-g]indazole-7-carboxylate (commercially available; 100 mg, 406 μmol) and [(2R and 2S)-oxan-2-yl]methanol (racemate, 70.8 mg, 609 μmol, CAS-RN: [100-72-1]) were suspended in toluene (3 mL) together with TMAD (112 mg, 650 μmol, CAS No. [10465-78-8]). Carefully tri-n-butylphosphine (160 μl, 650 μmol, CAS No. [998-40-3]) was added and the reaction mixture stirred for 18 h at rt. Further TMAD (112 mg, 650 μmol) and tri-n-butylphosphine (160 μl, 650 μmol) were then added and stirring continued for 18 h at rt and 4 h at 45° C. After additional tri-n-butylphosphine (160 μl, 650 μmol), stirring was prolonged for 3 days at rt. After filtration, water was added to the filtrate, and the aqueous phase was extracted with dichloromethane. After evaporation of the organic layer, the crude material was purified by Biotage Isolera™ chromatography (SNAP KP—NH—28 g), eluting with hexane-dichloromethane, 1:0 to 3:2) to afford the title compound (100 mg, 72% yield).

LC-MS (Method 1): $R_t$=1.33 min; MS (ESIpos): m/z=345 $[M+H]^+$

Step 2

8-methyl-2-{[(2R and 2S)-oxan-2-yl]methyl}-4,5-dihydro-2H-furo[2,3-g]indazole-7-carboxylic acid (Racemate)

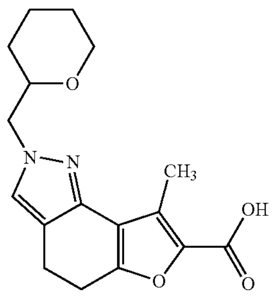 [SMILES: Cc1c(C(=O)O)oc2c1-c1nn(CC3CCCCO3)cc1CC2]

According to GP D ethyl 8-methyl-2-{[(2R and 2S)-oxan-2-yl]methyl}-4,5-dihydro-2H-furo[2,3-g]indazole-7-carboxylate (racemate, 100 mg, 290 μmol) from step 1 was reacted with aqueous lithium hydroxide (15 eq, 2.2 ml, 2.0 M, 4.4 mmol) in a 1:1 mixture of ethanol and THF (4.1 mL) at 70° C. overnight. The reaction mixture was acidified with aqueous 6 N HCl (pH 4) and concentrated in vacuo. The resulting crude product (140 mg) was used in the next step without further purification.

LC-MS (Method 1): $R_t$=0.59 min; MS (ESIpos): m/z=317 $[M+H]^+$

Intermediate 57

Step 1 ethyl 2-[(6-methylpyridin-3-yl)methyl]-8-(trifluoromethyl)-4,5-dihydro-2H-furo[2,3-g]indazole-7-carboxylate

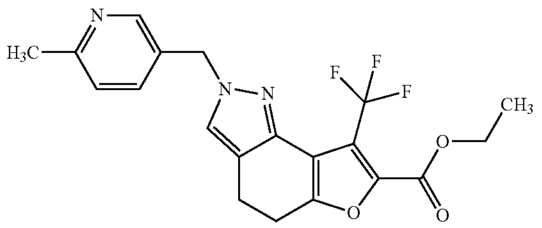 [SMILES: CCOC(=O)c1oc2c(c1C(F)(F)F)-c1nn(Cc3ccc(C)nc3)cc1CC2]

According to GP C (conditions A) ethyl 8-(trifluoromethyl)-4,5-dihydro-1H-furo[2,3-g]indazole-7-carboxylate (1.0 eq., 325 mg, 1.08 mmol) from Intermediate 35 step 4 was reacted with (6-methylpyridin-3-yl)methanol (CAS No [34107-46-5], 1.7 eq., 227 mg, 1.84 mmol), tri-n-butylphosphine (CAS No. [998-40-3]; 1.6 eq., 430 μL, 1.7 mmol) and TMAD (CAS No. [10465-78-8]; 1.6 eq., 298 mg, 1.73 mmol) in toluene (10 ml) at rt overnight. The reaction mixture was filtered and extracted with water. The water phase was re-extracted with DCM. The organic phases were dried over $Na_2SO_4$, filtered and evaporated under reduced pressure to give a crude material. The crude was then purified by column chromatography (NH, $SiO_2$, hexane/DCM) to give the title product (460.5 mg), which was used in the next step without further purification.

LC-MS (Method 1): $R_t$=1.24 min; MS (ESIpos): m/z=406 $[M+H]^+$

Step 2

2-[(6-methylpyridin-3-yl)methyl]-8-(trifluoromethyl)-4,5-dihydro-2H-furo[2,3-g]indazole-7-carboxylic acid

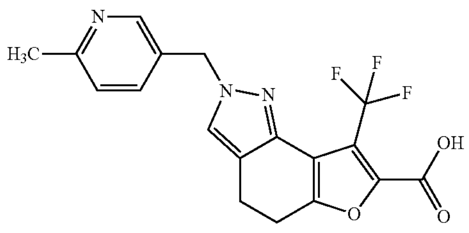 [SMILES: Cc1ccc(Cn2cc3c(n2)-c2c(oc(C(=O)O)c2C(F)(F)F)CC3)cn1]

According to GP D ethyl 2-[(6-methylpyridin-3-yl)methyl]-8-(trifluoromethyl)-4,5-dihydro-2H-furo[2,3-g]indazole-7-carboxylate (1.0 eq, 460 mg, 1.13 mmol) from step 1 was reacted with aqueous lithium hydroxide (2 M; 5 eq, 2.8 mL, 5.7 mmol) in a 1:1 mixture of ethanol and THF (9.2 mL) at 70° C. overnight. Upon acidification (pH 2) with 6 N aqueous hydrochloric acid and the resulting mixture was evaporated. To the crude was added DCM (75 ml) and i-PrOH (2×0.5 ml) and stirred at rt. The DCM phase was decanted and the remaining solid was dissolved in DCM (75 ml) and i-PrOH (5 ml) and stirred at rt and the resulting DCM phase was decanted and the solution was evaporated to yield the product as a solid (226 mg, 53% yield).

LC-MS (Method 1): $R_t$=0.56 min; MS (ESIpos): m/z=378 $[M+H]^+$

Intermediate 58

Step 1 methyl 8-cyclopropyl-2-{[(2S)-1,4-dioxan-2-yl]methyl}-4,5-dihydro-2H-furo[2,3-g]indazole-7-carboxylate

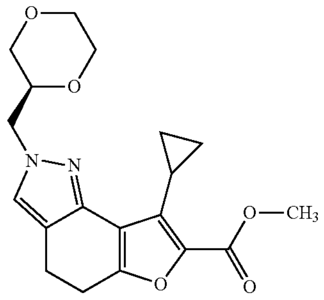 [SMILES: COC(=O)c1oc2c(c1C1CC1)-c1nn(C[C@H]3COCCO3)cc1CC2]

According to GP C (conditions A) methyl 8-cyclopropyl-4,5-dihydro-1H-furo[2,3-g]indazole-7-carboxylate (1.0 eq., 250 mg, 968 μmol) from Intermediate 36 step 4 was reacted with [(2S)-1,4-dioxan-2-yl]methanol (CAS No [406913-93-7], 1.5 eq., 172 mg, 1.45 mmol), tri-n-butylphosphine (CAS No. [998-40-3]; 1.6 eq., 380 μL, 1.5 mmol) and TMAD (CAS No. [10465-78-8]; 1.6 eq., 267 mg, 1.55 mmol) in toluene (5.5 ml) at rt overnight. The reaction mixture was filtered and extracted with water. The combined water phase was re-extracted with DCM. The combined organic layers were dried with $Na_2SO_4$, filtered and evaporated. The crude material was purified by column chromatography ($SiO_2$, hexane/DCM) to give the title compound (350 mg).

LC-MS (Method 1): $R_t$=1.19 min; MS (ESIpos): m/z=359 $[M+H]^+$

Step 2

8-cyclopropyl-2-{[(2S)-1,4-dioxan-2-yl]methyl}-4,5-dihydro-2H-furo[2,3-g]indazole-7-carboxylic acid

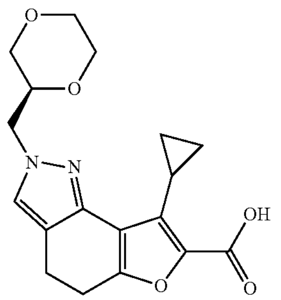 [SMILES: O=C(O)c1oc2c(c1C1CC1)-c1nn(C[C@H]3COCCO3)cc1CC2]

According to GP D methyl 8-cyclopropyl-2-{[(2S)-1,4-dioxan-2-yl]methyl}-4,5-dihydro-2H-furo[2,3-g]indazole-7-carboxylate (1.0 eq, 350 mg, 977 μmol) from step 1 was reacted with aqueous lithium hydroxide (2 M; 5 eq, 2.4 mL, 4.9 mmol) in a 1:1 mixture of ethanol and THF (5.0 mL) at 70° C. overnight. Upon acidification (pH 2) with 6 N aqueous hydrochloric acid and the resulting mixture was evaporated under reduced pressure. To the residue was added DCM (40 ml) and i-PrOH (1 ml) and stirred 30 min at rt. The organic phase was separated and evaporated under reduced pressure to give the title compound (400 mg), which was used in the following step without further purification.

LC-MS (Method 1): $R_t$=0.51 min; MS (ESIpos): m/z=345 $[M+H]^+$

Intermediate 59

Step 1 ethyl 8'-methyl-2'-[(pyridin-4-yl)methyl]-2',5'-dihydrospiro[cyclobutane-1,4'-furo[2,3-g]indazole]-7'-carboxylate

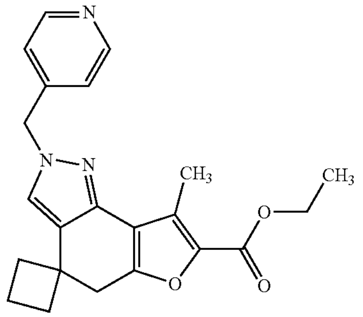 [SMILES: CCOC(=O)c1oc2c(c1C)-c1nn(Cc3ccncc3)cc1C1(CCC1)C2]

According to GP C (conditions A) ethyl 8'-methyl-2',5'-dihydrospiro[cyclobutane-1,4'-furo[2,3-g]indazole]-7'-carboxylate (190 mg, 664 μmol, intermediate 42 (step 3)) and pyridin-4-yl)methanol (109 mg, 995 μmol, CAS-RN:[586-95-8]) were suspended in toluene with (3.8 mL) together TMAD (183 mg, 1.06 mmol; CAS No. [10465-78-8]). Carefully tri-n-butylphosphine (260 μl, 1.1 mmol, CAS No. [998-40-3]) was added and the reaction mixture stirred for 18 h at rt. Water was added to the reaction mixture and then concentrated in vacuo. The residue was diluted with 3 ml acetonitrile and purified by preparative HPLC (Method A, gradient D). The product fractions were pooled and concentrated in vacuo to afford 18.0 mg (6% yield, 79% purity) of the title compound.

$^1H$ NMR (400 MHz, DMSO-d6) δ[ppm]: 1.29 (t, 3H), 2.01-2.15 (m, 6H), 2.46 (s, 3H), 3.01-3.15 (m, 2H), 4.26 (q, 2H), 5.39 (s, 2H), 7.13-7.16 (m, 2H), 7.97 (s, 1H), 8.52-8.55 (m, 2H)

LC-MS (Method 1): $R_t$=1.27 min; MS (ESIpos): m/z=378 $[M+H]^+$

Step 2

8'-methyl-2'-[(pyridin-4-yl)methyl]-2',5'-dihydrospiro[cyclobutane-1,4'-furo[2,3-g]indazole]-7'-carboxylic acid

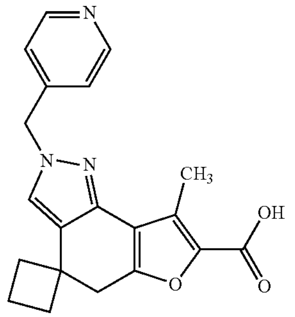 [SMILES: Cc1c(C(=O)O)oc2c1-c1nn(Cc3ccncc3)cc1C1(CCC1)C2]

According to GP D ethyl 8'-methyl-2'-[(pyridin-4-yl)methyl]-2',5'-dihydrospiro[cyclobutane-1,4'-furo[2,3-g]indazole]-7'-carboxylate (18.0 mg, 79% purity, 37.7 μmol) from step 1 was reacted with aqueous lithium hydroxide (2190 μl, 2.0 M, 380 μmol) in THF (430 μl) at rt overnight. After stirring for further 2 h at 30° C., the reaction mixture was acidified with aqueous 2 N HCl (pH 2) and concentrated in vacuo and used in the next step without further purification (12 mg, 91% yield).

LC-MS (Method 2): $R_t$=0.77 min; MS (ESIpos): m/z=350 $[M+H]^+$.

Intermediate 60

Step 1 ethyl 8'-methyl-2'-[(5-methylpyridin-2-yl)methyl]-2',5'-dihydrospiro[cyclobutane-1,4'-furo[2,3-g]indazole]-7'-carboxylate

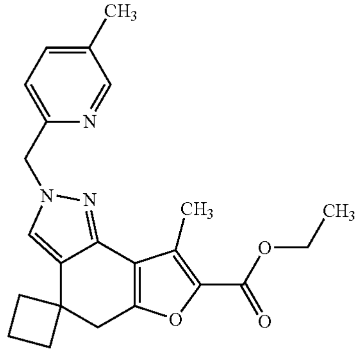 [SMILES: CCOC(=O)c1oc2c(c1C)-c1nn(Cc3ccc(C)cn3)cc1C1(CCC1)C2]

According to GP C (conditions A) ethyl 8'-methyl-2',5'-dihydrospiro[cyclobutane-1,4'-furo[2,3-g]indazole]-7'-carboxylate (190 mg, 664 μmol, intermediate 42 (step 3)) and (5-methylpyridin-2-yl)methanol (123 mg, 995 μmol, CAS-RN:[22940-71-2]) were suspended in toluene with (3.8 mL) together TMAD (183 mg, 1.06 mmol; CAS No. [10465-78-8]). Carefully tri-n-butylphosphine (260 μl, 1.1 mmol, CAS No. [998-40-3]) was added and the reaction mixture stirred for 18 h at rt. Water was added to the reaction mixture and then concentrated in vacuo. The residue was diluted with 3 ml acetonitrile and purified by preparative HPLC (Method A, gradient E). The product fractions were pooled and concentrated in vacuo to afford 49.5 mg (16% yield, 85% purity) of the title compound.

$^1H$ NMR (400 MHz, DMSO-d6) δ[ppm]: 1.29 (t, 3H), 1.99-2.14 (m, 6H), 2.27 (s, 3H), 2.45 (s, 3H), 3.07 (s, 2H), 4.26 (q, 2H), 5.36 (s, 2H), 7.01 (d, 1H), 7.56-7.62 (m, 1H), 7.91 (s, 1H), 8.36-8.40 (m, 1H).

LC-MS (Method 1): $R_t$=1.37 min; MS (ESIpos): m/z=392 $[M+H]^+$

Step 2

8'-methyl-2'-[(5-methylpyridin-2-yl)methyl]-2',5'-dihydrospiro[cyclobutane-1,4'-furo[2,3-g]indazole]-7'-carboxylic acid

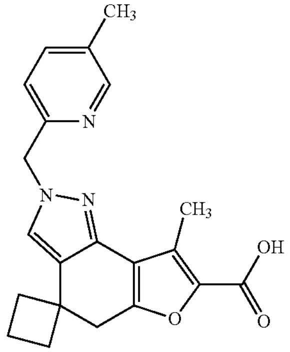 [SMILES: Cc1ccc(Cn2cc3c(n2)-c2c(oc(C(=O)O)c2C)CC32CCC2)nc1]

According to GP D ethyl 8'-methyl-2'-[(5-methylpyridin-2-yl)methyl]-2',5'-dihydrospiro[cyclobutane-1,4'-furo[2,3-g]indazole]-7'-carboxylate (49.5 mg, 85% purity, 107 μmol) from step 1 was reacted with aqueous lithium hydroxide (540 μl, 2.0 M, 1.1 mmol) in THF (1.2 ml) at rt overnight. After stirring for further 2 h at 30° C., the reaction mixture was acidified with aqueous 2 N HCl (pH 2) and concentrated in vacuo and used in the next step without further purification (35 mg, 90% yield).

LC-MS (Method 2): $R_t$=1.03 min; MS (ESIpos): m/z=364 $[M+H]^+$

Intermediate 61

Step 1 ethyl 8-methyl-2-[2-(pyridin-2-yl)ethyl]-4,5-dihydro-2H-furo[2,3-g]indazole-7-carboxylate

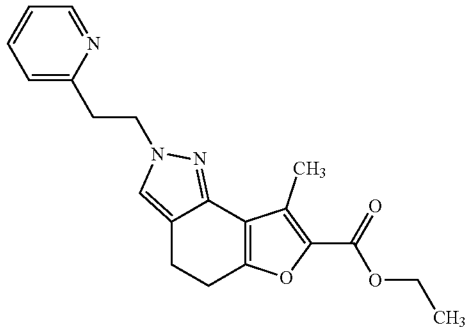 [SMILES: CCOC(=O)c1oc2c(c1C)-c1nn(CCc3ccccn3)cc1CC2]

According to GP C (conditions B), to a mixture of cesium carbonate (1.59 g, 4.87 mmol; CAS-RN:[534-17-8]) in N,N-dimethylformamide (6.0 mL) were added ethyl 8-methyl-4,5-dihydro-2H-furo[2,3-g]indazole-7-carboxylate (commercially available; 400 mg, 1.62 mmol) and 2-(pyridin-2-yl)ethyl methanesulfonate (981 mg, 4.87 mmol) at 25° C. The mixture was stirred at 60° C. for 12 h. Further 2-(pyridin-2-yl)ethyl methanesulfonate (981 mg, 4.87 mmol) was added to the mixture and then stirred at 60° C. for another 8 h. Water was added to the mixture and then extracted with ethyl acetate. The combined organic layer was concentrated under reduced pressure to give a residue. The residue was purified by pre-HPLC [Instrument: ACSWH-GX-C; Column: Phenomenex Gemini-NX C18 75*30 mm*3 um; eluent A: water (0.225% formic acid in water), eluent B: acetonitrile; gradient: 0-10 min 10-40% B; flow 25 ml/min; temperature: RT; Detector: UV 220/254 nm.] followed by lyophilization to afford 250 mg (41% yield, 94% purity) of the title compound as a light yellow solid.

$^1$H NMR (400 MHz, DMSO-d6) δ[ppm]: 1.30 (t, 3H), 2.78-2.84 (m, 2H), 2.86-2.91 (m, 2H), 3.25 (t, 2H), 4.26 (q, 2H), 4.45 (t, 2H), 7.21-7.28 (m, 2H), 7.45 (s, 1H), 7.69 (td, 1H), 8.52 (d, 1H)(methyl signal below DMSO).

LC-MS (Method B): $R_t$=0.68 min; MS (ESIpos): m/z=352 [M+H]$^+$

Step 2

8-methyl-2-[2-(pyridin-2-yl)ethyl]-4,5-dihydro-2H-furo[2,3-g]indazole-7-carboxylic acid

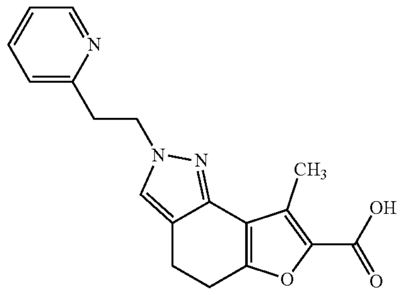 [SMILES: Cc1c(C(=O)O)oc2c1-c1nn(CCc3ccccn3)cc1CC2]

According to GP D ethyl 8-methyl-2-[2-(pyridin-2-yl)ethyl]-4,5-dihydro-2H-furo[2,3-g]indazole-7-carboxylate (150 mg, 427 μmol) from step 1 was reacted with aqueous lithium hydroxide (4.3 ml, 1.0 M, 4.3 mmol) in THF (750 μL) at rt overnight. After stirring for further 2 h at 30° C., the reaction mixture was acidified with aqueous 2 N HCl (pH 2) and concentrated in vacuo and resulting precipitate was filtered off to afford 123 mg (88% yield, 99% purity) of the title compound.

$^1$H NMR (400 MHz, DMSO-d6) δ[ppm]: 2.33 (s, 3H), 2.75-2.93 (m, 4H), 3.50 (brt, 2H), 4.57 (t, 2H), 7.51 (s, 1H), 7.81 (br d, 2H), 8.36 (br t, 1H), 8.78 (dd, 1H), 12.76 (br s, 1H).

LC-MS (Method 1): $R_t$=0.55 min; MS (ESIpos): m/z=324 [M+H]$^+$

Intermediate 62

Step 1

2,2-difluoro-2-(pyridin-2-yl)ethyl trifluoromethanesulfonate

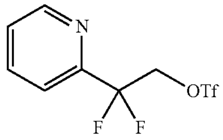 [SMILES: O=S(=O)(OCC(F)(F)c1ccccn1)C(F)(F)F]

To a solution of 2,2-difluoro-2-(pyridin-2-yl)ethan-1-ol (300 mg, 1.89 mmol; CAS-RN:[267875-65-0]) in acetonitrile (5.0 mL) were added trifluoromethanesulfonic anhydride (380 μl, 2.3 mmol; CAS-RN:[358-23-6]) and pyridine (240 μl, 3.0 mmol) at 0° C. The mixture was stirred at 25° C. for 1 h. Water was added to the mixture and extracted with ethyl acetate. The combined organic layers were dried over anhydrous sodium sulfate, filtered and concentrated under reduced pressure to afford 540 mg (crude) of the title compound.

LC-MS (Method C): $R_t$=0.85 min; MS (ESIpos): m/z=292 [M+H]$^+$

Step 2 ethyl 2-[2,2-difluoro-2-(pyridin-2-yl)ethyl]-8-methyl-4,5-dihydro-2H-furo[2,3-g]indazole-7-carboxylate

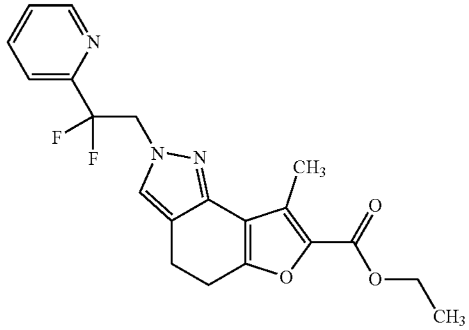 [SMILES: CCOC(=O)c1oc2c(c1C)-c1nn(CC(F)(F)c3ccccn3)cc1CC2]

According to GP C (conditions B), to a stirred solution of ethyl 8-methyl-4,5-dihydro-2H-furo[2,3-g]indazole-7-carboxylate (commercially available; 300 mg, 1.22 mmol) and 2,2-difluoro-2-(pyridin-2-yl)ethyl trifluoromethanesulfonate (532 mg, 1.83 mmol, intermediate 62 (step 1)) in acetonitrile (5.0 mL) was added potassium carbonate (337 mg, 2.44 mmol) at 25° C. The mixture was stirred at 50° C. for 12 h. Water was added to the mixture and then aqueous layer was extracted with ethyl acetate. The organic phase was washed with brine, dried over anhydrous sodium sulfate, filtered and concentrated to give a residue. The residue was purified by flash chromatography (silica gel, eluting with petroleum ether-ethyl acetate, 1:0 to 2:1) to afford 255 mg (50% yield, 93% purity) of the title compound as a yellow oil.

$^1$H NMR (400 MHz, DMSO-d6) δ[ppm]: 1.29 (t, 3H), 2.39 (s, 3H), 2.80-2.94 (m, 4H), 4.26 (q, 2H), 5.02 (t, 2H), 7.52 (s, 1H), 7.59 (dd, 1H), 7.66 (d, 1H), 7.98 (td, 1H), 8.74 (d, 1H).

LC-MS (Method B): $R_t$=0.85 min; MS (ESIpos): m/z=388 $[M+H]^+$.

Step 3

2-[2,2-difluoro-2-(pyridin-2-yl)ethyl]-8-methyl-4,5-dihydro-2H-furo[2,3-g]indazole-7-carboxylic acid

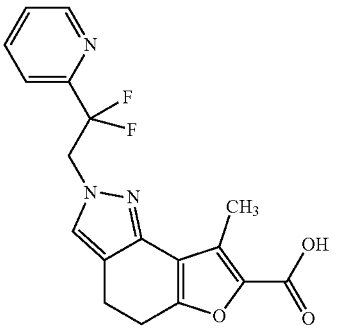 [SMILES: Cc1c(C(=O)O)oc2c1-c1nn(CC(F)(F)c3ccccn3)cc1CC2]

According to GP D ethyl 2-[2,2-difluoro-2-(pyridin-2-yl)ethyl]-8-methyl-4,5-dihydro-2H-furo[2,3-g]indazole-7-carboxylate (150 mg, 387 μmol) from step 2 was reacted with aqueous lithium hydroxide (3.9 ml, 1.0 M, 3.9 mmol) in THF (680 μL) at rt overnight. After stirring for further 4 h at 50° C., the reaction mixture was acidified with aqueous 2 N HCl (pH 2) and resulting precipitate was filtered off to afford 116 mg (80% yield, 96% purity) of the title compound.

$^1$H NMR (400 MHz, DMSO-d6) δ[ppm]: 2.37 (s, 3H), 2.79-2.92 (m, 4H), 5.01 (t, 2H), 7.51 (s, 1H), 7.59 (dd, 1H), 7.63-7.71 (m, 1H), 7.98 (td, 1H), 8.74 (d, 1H), 12.21-13.27 (m, 1H).

LC-MS (Method 1): $R_t$=0.59 min; MS (ESIpos): m/z=360 $[M+H]^+$

Intermediate 63

Step 1 ethyl 8'-methyl-2'-[(6-methylpyridin-3-yl)methyl]-2',5'-dihydrospiro[cyclopropane-1,4'-furo[2,3-g]indazole]-7'-carboxylate

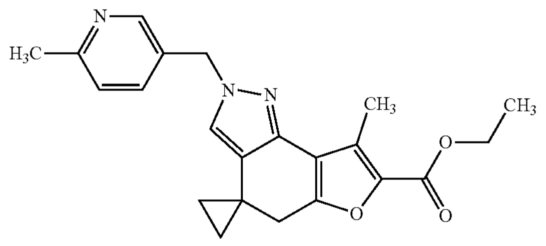 [SMILES: CCOC(=O)c1oc2c(c1C)-c1nn(Cc3ccc(C)nc3)cc1C1(CC1)C2]

According to GP C (conditions A) ethyl 8'-methyl-1',5'-dihydrospiro[cyclopropane-1,4'-furo[2,3-g]indazole]-7'-carboxylate (1.00 eq., 150 mg, 551 μmol) from Intermediate 41 step 3 was reacted with (6-methylpyridin-3-yl)methanol (CAS No [34107-46-5], 1.5 eq., 102 mg, 826 μmol), tri-n-butylphosphine (CAS No. [998-40-3]; 1.6 eq., 220 μL, 880 μmol) and TMAD (CAS No. [10465-78-8]; 1.6 eq., 152 mg, 530 μmol) in toluene (3.1 ml) at rt overnight. The reaction mixture was filtered and extracted with water. The water phase was extracted with DCM. The combined organic layers were dried with $Na_2SO_4$, filtered and evaporated under reduced pressure. The crude material was purified by column chromatography ($SiO_2$, hexane/EtOAc) to give the title compound (309 mg).

LC-MS (Method 1): $R_t$=1.24 min; MS (ESIpos): m/z=378 $[M+H]^+$

Step 2

8'-methyl-2'-[(6-methylpyridin-3-yl)methyl]-2',5'-dihydrospiro[cyclopropane-1,4'-furo[2,3-g]indazole]-7'-carboxylic acid

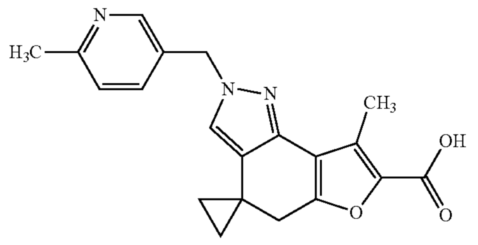 [SMILES: Cc1ccc(Cn2cc3c(n2)-c2c(oc(C(=O)O)c2C)CC32CC2)cn1]

According to GP D ethyl 8'-methyl-2'-[(6-methylpyridin-3-yl)methyl]-2',5'-dihydrospiro[cyclopropane-1,4'-furo[2,3-g]indazole]-7'-carboxylate (1.0 eq, 308 mg, 816 μmol) from step 1 was reacted with aqueous lithium hydroxide (2 M; 5 eq, 2.0 mL, 4.1 mmol) in a 1:1 mixture of ethanol and THF (11.0 mL) at 70° C. overnight. Upon acidification (pH 2) with 6 N aqueous hydrochloric acid and the resulting mixture was evaporated under reduced pressure. To the residue was added DCM (50 ml) and i-PrOH (5×1 ml) and stirred at rt. The DCM phase was decanted and evaporated to give the title compound (306 mg), which was directly used in the next step without further purification.

LC-MS (Method 1): $R_t$=0.56 min; MS (ESIpos): m/z=350 $[M+H]^+$

Intermediate 64 ethyl 2-[(azetidin-3-yl)methyl]-8-methyl-4,5-dihydro-2H-furo[2,3-g]indazole-7-carboxylate hydrogen chloride (1/1)

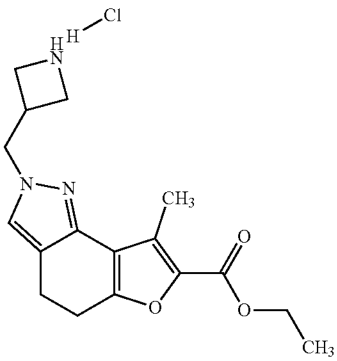

A solution of ethyl 2-{[1-(tert-butoxycarbonyl)azetidin-3-yl]methyl}-8-methyl-4,5-dihydro-2H-furo[2,3-g]indazole-7-carboxylate (4.00 g, 9.63 mmol, intermediate 32 (step 1) in 4 M HCl in dioxane (20 mL) was stirred at 25° C. for 2 h. The mixture was filtered to collect the solid. The solid was dried under reduced pressure to afford 3.40 g (100% yield) of the title compound as a light brown solid.

$^1H$ NMR (400 MHz, DMSO-d6) δ[ppm]: 1.17 (t, 3H), 1.98 (s, 3H), 2.81-2.95 (m, 4H), 3.13-3.23 (m, 1H), 3.76-3.87 (m, 2H), 3.88-3.99 (m, 2H), 4.26 (q, 2H), 4.35 (d, 2H), 7.55 (s, 1H)

Intermediate 65

Step 1 ethyl 2'-[(6-methylpyridin-3-yl)methyl]-8'-(trifluoromethyl)-2',5'-dihydrospiro[cyclopropane-1,4'-furo[2,3-g]indazole]-7'-carboxylate

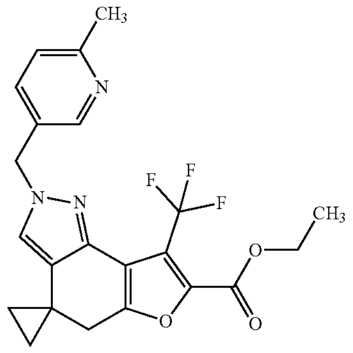 [SMILES: CCOC(=O)c1oc2c(c1C(F)(F)F)-c1nn(Cc3ccc(C)nc3)cc1C1(CC1)C2]

According to GP C (conditions A) ethyl 8'-(trifluoromethyl)-2',5'-dihydrospiro[cyclopropane-1,4'-furo[2,3-g]indazole]-7'-carboxylate (150 mg, 68% purity, 313 μmol, intermediate 50 (step 3)) and (6-methylpyridin-3-yl)methanol (46.2 mg, 375 μmol), CAS-RN:[34107-46-5]) were suspended in toluene with (2.8 mL) together TMAD (86.1 mg, 500 μmol; CAS No. [10465-78-8]). Carefully tri-n-butylphosphine (120 μl, 500 μmol, CAS No. [998-40-3]) was added and the reaction mixture stirred at rt overnight. Further TMAD (53.8 mg, 313 μmol) and tri-n-butylphosphine (75 μl, 313 μmol) were added stirring was continued for 24 h at rt. Water was added to the reaction mixture and then concentrated in vacuo. The residue was diluted with 2 ml acetonitrile and purified by preparative HPLC (Method A, gradient D). The product fractions were pooled and concentrated in vacuo to afford 97.0 mg (60% yield, 84% purity) of the title compound.

$^1H$ NMR (500 MHz, DMSO-d6) δ[ppm]: 1.30 (t, 3H), 1.55-1.66 (m, 4H), 2.43 (s, 3H), 2.96 (s, 2H), 4.34 (q, 2H), 5.25 (s, 2H), 7.22 (d, 1H), 7.51 (s, 1H), 7.54 (dd 1H), 8.38 (d, 1H).

LC-MS (Method 1): $R_t$=1.32 min; MS (ESIpos): m/z=432 $[M+H]^+$

Step 2

2'-[(6-methylpyridin-3-yl)methyl]-8'-(trifluoromethyl)-2',5'-dihydrospiro[cyclopropane-1,4'-furo[2,3-g]indazole]-7'-carboxylic acid

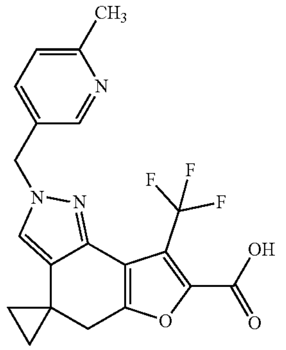 [SMILES: Cc1ccc(Cn2cc3c(n2)-c2c(oc(C(=O)O)c2C(F)(F)F)CC32CC2)cn1]

According to GP D ethyl 2'-[(6-methylpyridin-3-yl)methyl]-8'-(trifluoromethyl)-2',5'-dihydrospiro[cyclopropane-1,4'-furo[2,3-g]indazole]-7'-carboxylate (97.0 mg, 225 μmol, intermediate 65 (step 1) was dissolved in tetrahydrofuran (400 μL) and an aqueous lithium hydroxide solution (2.2 ml, 1.0 M, 2.2 mmol; CAS-RN:[1310-65-2]) was added. The reaction mixture was stirred at room temperature overnight. After neutralization with aqueous hydrogen chloride solution (4 M) stirring was continued for 30 minutes. The reaction mixture was concentrated in vacuo to afford 90.0 mg (81% yield, 82% purity) of the title compound.

$^1H$ NMR (400 MHz, DMSO-d6) δ[ppm]: 1.58-1.68 (m, 4H), 2.70 (s, 3H), 2.96 (s, 2H), 5.46 (s, 2H), 7.58 (s, 1H), 7.87 (d, 1H), 8.25 (dd, 1H), 8.72 (d, 1H).

LC-MS (Method 1): $R_t$=0.61 min; MS (ESIpos): m/z=404 $[M+H]^+$

Intermediate 66

Step 1 ethyl 2'-[(5-methylpyridin-2-yl)methyl]-8'-(trifluoromethyl)-2',5'-dihydrospiro[cyclopropane-1,4'-furo[2,3-g]indazole]-7'-carboxylate

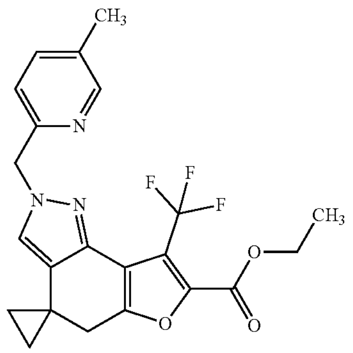 [SMILES: CCOC(=O)c1oc2c(c1C(F)(F)F)-c1nn(Cc3ccc(C)cn3)cc1C1(CC1)C2]

According to GP C (conditions A) ethyl 8'-(trifluoromethyl)-2',5'-dihydrospiro[cyclopropane-1,4'-furo[2,3-g]indazole]-7'-carboxylate (150 mg, 68% purity, 313 μmol, intermediate 50 (step 3)) and (5-methylpyridin-2-yl)methanol (46.2 mg, 375 µmol, CAS-RN:[22940-71-2]) were suspended in toluene with (2.8 mL) together TMAD (86.1 mg, 500 µmol; CAS No. [10465-78-8]). Carefully tri-n-butylphosphine (120 µl, 500 µmol, CAS No. [998-40-3]) was added and the reaction mixture stirred at rt overnight. Further TMAD (53.8 mg, 313 µmol) and tri-n-butylphosphine (75 µl, 313 µmol) were added stirring was continued for 24 h at rt. Water was added to the reaction mixture and then concentrated in vacuo. The residue was diluted with 2 ml acetonitrile and purified by preparative HPLC (Method A, gradient E). The product fractions were pooled and concentrated in vacuo to afford 63.9 mg (36% yield, 75% purity) of the title compound.

$^1$H NMR (500 MHz, DMSO-d6) δ[ppm]: 0.87-0.93 (m, 4H), 1.30 (t, 3H), 2.26 (s, 3H), 2.98 (s, 2H), 4.34 (q, 2H), 5.30 (s, 2H), 7.00 (d, 1H), 7.51 (s, 1H), 7.57-7.60 (m, 1H), 8.35-8.37 (m, 1H)

LC-MS (Method 1): $R_t$=1.38 min; MS (ESIpos): m/z=432 $[M+H]^+$

Step 2

2'-[(5-methylpyridin-2-yl)methyl]-8'-(trifluoromethyl)-2',5'-dihydrospiro[cyclopropane-1,4'-furo[2,3-g]indazole]-7'-carboxylic acid

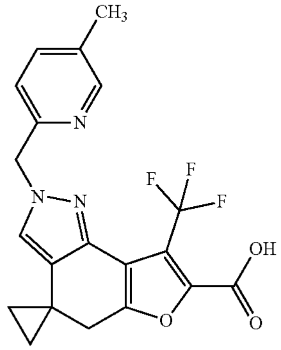 [SMILES: Cc1ccc(Cn2cc3c(n2)-c2c(oc(C(=O)O)c2C(F)(F)F)CC32CC2)nc1]

According to GP D ethyl 2'-[(5-methylpyridin-2-yl)methyl]-8'-(trifluoromethyl)-2',5'-dihydrospiro[cyclopropane-1,4'-furo[2,3-g]indazole]-7'-carboxylate (63.9 mg, 148 µmol, intermediate 66 (step 1) was dissolved in tetrahydrofuran (260 µL) and an aqueous lithium hydroxide solution (1.5 ml, 1.0 M, 1.5 mmol; CAS-RN:[1310-65-2]) was added. The reaction mixture was stirred at room temperature overnight. After neutralization with aqueous hydrogen chloride solution (4 M) stirring was continued for 30 minutes. The reaction mixture was concentrated in vacuo to afford 55.0 mg (86% yield, 93% purity) of the title compound.

$^1$H NMR (400 MHz, DMSO-d6) δ[ppm]: 0.82-0.86 (m, 2H), 0.90-0.95 (m, 2H), 2.34 (s, 3H), 2.96 (s, 2H), 5.45 (s, 2H), 7.20 (d, 1H), 7.57 (s, 1H), 7.88 (br d, 1H), 8.52 (s, 1H).

LC-MS (Method 1): $R_t$=0.66 min; MS (ESIpos): m/z=404 $[M+H]^+$

Intermediate 67

Step 1 ethyl 2'-[(pyridin-4-yl)methyl]-8'-(trifluoromethyl)-2',5'-dihydrospiro[cyclopropane-1,4'-furo[2,3-g]indazole]-7'-carboxylate

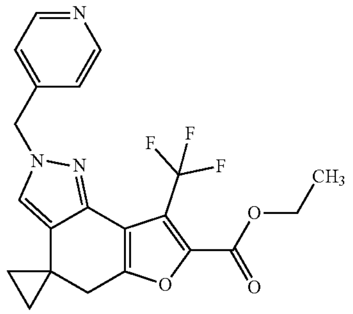 [SMILES: CCOC(=O)c1oc2c(c1C(F)(F)F)-c1nn(Cc3ccncc3)cc1C1(CC1)C2]

According to GP C (conditions A) ethyl 8'-(trifluoromethyl)-2',5'-dihydrospiro[cyclopropane-1,4'-furo[2,3-g]indazole]-7'-carboxylate (95.0 mg, 291 µmol, intermediate 50 (step 3)) and (pyridin-4-yl)methanol (41.3 mg, 379 µmol, CAS-RN:[586-95-8]) were suspended in toluene with (1.5 mL) together TMAD (80.2 mg, 466 µmol; CAS No. [10465-78-8]). Carefully tri-n-butylphosphine (120 µl, 470 µmol, CAS No. [998-40-3]) was added and the reaction mixture stirred at rt overnight. Water was added to the reaction mixture and then concentrated in vacuo. The residue was diluted with 2 ml acetonitrile and purified by preparative HPLC (Method A, gradient D). The product fractions were pooled and concentrated in vacuo to afford 40.0 mg (33% yield, 99% purity) of the title compound.

$^1$H NMR (400 MHz, DMSO-d6) δ[ppm]: 0.83-0.87 (m, 2H), 0.91-0.95 (m, 2H), 1.30 (t, 3H), 3.00 (s, 2H), 4.34 (q, 2H), 5.34 (s, 2H), 7.11-7.14 (m, 2H), 7.56 (s, 1H), 8.50-8.54 (m, 2H).

LC-MS (Method 1): $R_t$=1.26 min; MS (ESIpos): m/z=418 $[M+H]^+$

Step 2

2'-[(pyridin-4-yl)methyl]-8'-(trifluoromethyl)-2',5'-dihydrospiro[cyclopropane-1,4'-furo[2,3-g]indazole]-7'-carboxylic acid

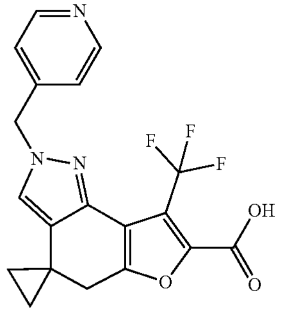 [SMILES: O=C(O)c1oc2c(c1C(F)(F)F)-c1nn(Cc3ccncc3)cc1C1(CC1)C2]

According to GP D ethyl 2'-[(pyridin-4-yl)methyl]-8'-(trifluoromethyl)-2',5'-dihydrospiro[cyclopropane-1,4'-furo[2,3-g]indazole]-7'-carboxylate (40.0 mg, 95.8 μmol, intermediate 67 (step 1) was dissolved in tetrahydrofuran (170 μL) and an aqueous lithium hydroxide solution (960 μl, 1.0 M, 960 μmol; CAS-RN:[1310-65-2]) was added. The reaction mixture was stirred at room temperature overnight. After neutralization with aqueous hydrogen chloride solution (4 M) the resulting precipitate was filtered off to afford 36.7 mg (96% yield, 98% purity) of the title compound.

$^1$H NMR (400 MHz, DMSO-d6) δ[ppm]: 0.82-0.88 (m, 2H), 0.93-0.97 (m, 2H), 2.99 (s, 2H), 5.55 (s, 2H), 7.49 (d, 2H), 7.60 (s, 1H), 8.70-8.79 (m, 2H), 14.01 (br s, 1H).

LC-MS (Method 1): $R_t$=0.56 min; MS (ESIpos): m/z=390 [M+H]$^+$

Intermediate 68

Step 1 ethyl 2'-[(pyridin-2-yl)methyl]-8'-(trifluoromethyl)-2',5'-dihydrospiro[cyclopropane-1,4'-furo[2,3-g]indazole]-7'-carboxylate

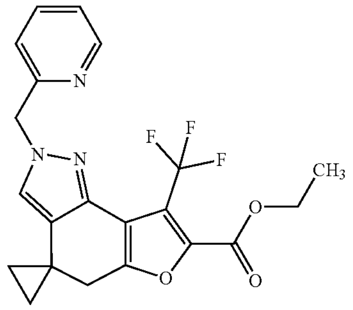 [SMILES: CCOC(=O)c1oc2c(c1C(F)(F)F)-c1nn(Cc3ccccn3)cc1C1(CC1)C2]

According to GP C (conditions A) ethyl 8'-(trifluoromethyl)-2',5'-dihydrospiro[cyclopropane-1,4'-furo[2,3-g]indazole]-7'-carboxylate (95.0 mg, 291 μmol, intermediate 50 (step 3)) and (pyridin-2-yl)methanol (41.3 mg, 379 μmol, CAS-RN:[586-98-1]) were suspended in toluene with (1.5 mL) together TMAD (80.2 mg, 466 μmol; CAS No. [10465-78-8]). Carefully tri-n-butylphosphine (120 μl, 470 μmol, CAS No. [998-40-3]) was added and the reaction mixture stirred at rt overnight. Water was added to the reaction mixture and then concentrated in vacuo. The residue was diluted with 2 ml acetonitrile and purified by preparative HPLC (Method A, gradient D). The product fractions were pooled and concentrated in vacuo to afford 47.0 mg (39% yield, 99% purity) of the title compound.

$^1$H NMR (400 MHz, DMSO-d6) δ[ppm]: 0.82-0.88 (m, 2H), 0.89-0.95 (m, 2H), 1.30 (t, 3H), 2.99 (s, 2H), 4.34 (q, 2H), 5.36 (s, 2H), 7.07 (d, 1H), 7.31 (ddd, 1H), 7.55 (s, 1H), 7.77 (td, 1H), 8.50-8.56 (m, 1H).

LC-MS (Method 1): $R_t$=1.32 min; MS (ESIpos): m/z=418 [M+H]$^+$

Step 2

2'-[(pyridin-2-yl)methyl]-8'-(trifluoromethyl)-2',5'-dihydrospiro[cyclopropane-1,4'-furo[2,3-g]indazole]-7'-carboxylic acid

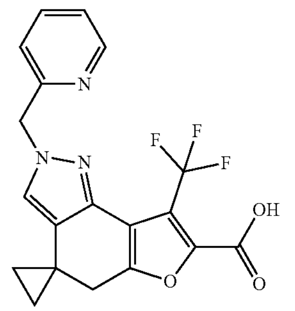 [SMILES: O=C(O)c1oc2c(c1C(F)(F)F)-c1nn(Cc3ccccn3)cc1C1(CC1)C2]

According to GP D ethyl 2'-[(pyridin-2-yl)methyl]-8'-(trifluoromethyl)-2',5'-dihydrospiro[cyclopropane-1,4'-furo[2,3-g]indazole]-7'-carboxylate (47.3 mg, 113 μmol, intermediate 68 (step 1) was dissolved in tetrahydrofuran (200 μL) and an aqueous lithium hydroxide solution (1.1 ml, 1.0 M, 1.1 mmol; CAS-RN:[1310-65-2]) was added. The reaction mixture was stirred at room temperature overnight. After neutralization with aqueous hydrogen chloride solution (4 M) the resulting precipitate was filtered off to afford 30.4 mg (67% yield, 97% purity) of the title compound.

$^1$H NMR (400 MHz, DMSO-d6) δ[ppm]: 0.81-0.88 (m, 2H), 0.89-0.94 (m, 2H), 2.96 (s, 2H), 5.36 (s, 2H), 7.08 (d, 1H), 7.30-7.37 (m, 1H), 7.54 (s, 1H), 7.80 (td1H), 8.50-8.57 (m, 1H), 13.93 (br s, 1H).

LC-MS (Method 1): $R_t$=0.59 min; MS (ESIpos): m/z=390 [M+H]$^+$

Intermediate 69

Step 1

By Mitsunobu Reaction:

ethyl 2-{[(2S)-1,4-dioxan-2-yl]methyl}-8-(trifluoromethyl)-4,5-dihydro-2H-furo[2,3-g]indazole-7-carboxylate

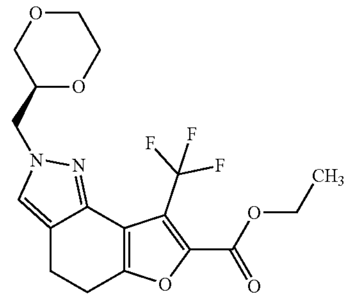 [SMILES: CCOC(=O)c1oc2c(c1C(F)(F)F)-c1nn(C[C@H]3COCCO3)cc1CC2]

Ethyl 8-(trifluoromethyl)-4,5-dihydro-1H-furo[2,3-g]indazole-7-carboxylate (Intermediate (step 4), 1.00 eq., 1.50 g, 5.00 mmol) was reacted with [(2S)-1,4-dioxan-2-yl]methanol (1.2 eq., 708 mg, 6.00 mmol), tri-n-butylphosphine (CAS No. [998-40-3]; 1.6 eq., 2.0 mL, 8.0 mmol) and TMAD (CAS No. [10465-78-8]; 1.60 eq., 1.38 g, 7.99 mmol) in toluene (15 mL) at room temperature overnight. The reaction mixture was diluted with ethyl acetate and water while stirring. After acidification with aq. 4N HCl to pH 2, the phases were separated. The aqueous phase was extracted with ethyl acetate and the combined organic phases were dried with a hydrophobic filter paper and concentrated. The obtained crude material was subjected to column chromatography ($SiO_2$, hexane/ethyl acetate) to give the title compound (1.73 g, 82%).

$^1H$ NMR (400 MHz, DMSO-d6) δ[ppm]: 1.31 (t, 3H), 2.83-2.90 (m, 2H), 2.96-3.02 (m, 2H), 3.24-3.29 (m, 1H), 3.40-3.48 (m, 1H), 3.50-3.57 (m, 1H), 3.61-3.64 (m, 1H), 3.70-3.77 (m, 2H), 3.79-3.87 (m, 1H), 4.08-4.17 (m, 2H), 4.32-4-37 (m, 2H), 7.55 (s, 1H)

LC-MS (Method 1): $R_t$=1.22 min; MS (ESIpos): m/z=401 $[M+H]^+$

By Alkylation Reaction with [(2R)-1,4-dioxan-2-yl] methyl methanesulfonate:

Ethyl 8-(trifluoromethyl)-4,5-dihydro-1H-furo[2,3-g]indazole-7-carboxylate (Intermediate (step 4), 1.00 eq., 18.3 g, 60.9 mmol) was treated with caesium carbonate (3 eq., 59.5 g, 182 mmol) in pre-degassed dioxane (730 mL) under argon at room temperature. [(2R)-1,4-dioxan-2-yl]methyl methanesulfonate (1.8 eq., 21.5 g, 110 mmol) was added and the resulting reaction mixture was degassed with argon. The mixture was heated at 100° C. for 18 h. The reaction mixture was again purged with argon and further heated at 100° C. for 24 h. The reaction was cooled to room temperature and the solids were filtered off and washed with ethyl acetate (400 mL). The filtrate was washed with water, dried over a hydrophobic filter paper and evaporated under reduced pressure to give a crude material as an oil. Purification by silica gel column chromatography (ethyl acetate/hexane) gave the title compound (11.5 g, 47%).

By Alkylation Reaction with [(2R)-1,4-dioxan-2-yl] methyl trifluoromethanesulfonate:

8-(trifluoromethyl)-4,5-dihydro-1H-furo[2,3-g]indazole-7-carboxylate (Intermediate 35 (step 4), 1.00 eq., 35.3 g, 117 mmol) was suspended in acetonitrile (400 mL) at room temperature. To the reaction mixture caesium carbonate (3 eq., 115 g, 353 mmol) was added followed by a slow addition of a solution of [(2R)-1,4-dioxan-2-yl]methyl trifluoromethanesulfonate (1.8 eq., 55.8 g, 211 mmol) in acetonitrile (100 mL). After 20 min a slight increase in the temperature was observed (20° C. to 29° C.). The reaction was cooled to room temperature with an ice bath. The reaction mixture was stirred for 18 h at room temperature. To the reaction mixture ethyl acetate (500 mL), water (200 mL), and 6N aq. HCl solution (60 mL) were added while stirring and cooling with cold water. The layers were separated. The organic layer was washed with sat. aq. $NH_4Cl$ solution, sat. aq. NaCl solution, and dried over $Na_2SO_4$ and evaporated under reduced pressure at 40° C. The crude material was dissolved in $CH_2Cl_2$ (400 mL) and washed with water (150 mL). The organic layer was dried over $Na_2SO_4$ and evaporated under reduced pressure at 40° C. To the resulting crude material ethanol/hexane (1:1, 100 mL) was added. The mixture was briefly placed under sonication, where solids formed. The solids were collected by suction and washed with ethanol/hexane (1:1, 20 mL). The collected solids were again treated with ethanol/hexane (1:1, 80 mL) and placed briefly under sonication and stirred for 30 min at room temperature. The solids were collected by suction and washed with ethanol/hexane (1:1, 20 mL) to give the title compound (21 g, 45%) as a light beige solid. The combined filtrates were evaporated under reduced pressure and the resulting oil was purified by silica gel column chromatography (ethanol/hexane) followed by trituration with ethanol/hexane (1:1, 20 mL) to give an additional amount of the title compound (10 g, 21%) as a white solid.

Step 2

2-{[(2S)-1,4-dioxan-2-yl]methyl}-8-(trifluoromethyl)-4,5-dihydro-2H-furo[2,3-g]indazole-7-carboxylic acid

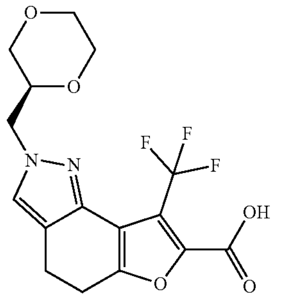 [SMILES: O=C(O)c1oc2c(c1C(F)(F)F)-c1nn(C[C@H]3COCCO3)cc1CC2]

Ethyl 2-{[(2S)-1,4-dioxan-2-yl]methyl}-8-(trifluoromethyl)-4,5-dihydro-2H-furo[2,3-g]indazole-7-carboxylate (1.00 eq., 1.96 g, 4.90 mmol; Intermediate 69 step 1) was reacted with aqueous lithium hydroxide solution (2 M; 10 eq., 24.0 mL, 49 mmol) in THF (56 mL) at 70° C. for 2 hours. The reaction mixture was acidified with aqueous 2N HCl solution. The formed precipitate was filtered off with suction and dried to give the desired carboxylic acid (1.80 g, 97%).

$^1H$ NMR (400 MHz, DMSO-d6) δ[ppm]: 2.82-2.89 (m, 2H), 2.92-3.00 (m, 2H), 3.22-3.29 (m, 1H), 3.44 (td, 1H), 3.49-3.57 (m, 1H), 3.62 (br d, 1H), 3.69-3.78 (m, 2H), 3.78-3.87 (m, 1H), 4.04-4.17 (m, 2H), 7.54 (s, 1H), 13.89 (br s, 1H)

LC-MS (Method 2): $R_t$=0.87 min; MS (ESIpos): m/z=373 $[M+H]^+$

Intermediate 70

Step 1 ethyl 2-{[(2R)-1,4-dioxan-2-yl]methyl}-8-(trifluoromethyl)-4,5-dihydro-2H-furo[2,3-g]indazole-7-carboxylate

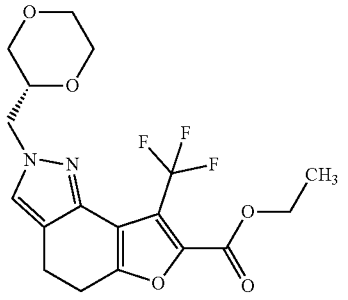 [SMILES: CCOC(=O)c1oc2c(c1C(F)(F)F)-c1nn(C[C@@H]3COCCO3)cc1CC2]

Under argon, ethyl 8-(trifluoromethyl)-4,5-dihydro-1H-furo[2,3-g]indazole-7-carboxylate (300 mg, 999 μmol, intermediate 35 (step 4)) was added to a suspension of caesium carbonate: (977 mg, 3.00 mmol; CAS-RN:[534-17-8]) in acetonitrile (2.0 ml). [(2S)-1,4-dioxan-2-yl]methyl trifluoromethanesulfonate (474 mg, 95% purity, 1.80 mmol) in acetonitrile (2.0 ml) was slowly added and the reaction mixture was stirred for 18 h at rt. To the reaction mixture, ethyl acetate (50 mL), water (10 mL) and 6 N HCl (0.5 mL) were added and the resulting phases were separated, and the organic layer was washed with aqueous saturated ammonium chloride solution and brine, dried over anhydrous sodium sulfate, filtered over an water-free filter and concentrated in vacuo. The crude material was purified by Biotage Isolera™ chromatography (SNAP KP-Sil—25 g, eluting with hexane-ethyl acetate, 1:0 to 3:2) to afford 148 mg (37% yield, 90% purity) of the title compound.

$^1$H NMR (400 MHz, DMSO-d6) δ[ppm]: 1.29-1.33 (m, 3H), 2.84-2.88 (m, 2H), 2.97-3.02 (m, 2H), 3.24-3.29 (m, 1H), 3.41-3.47 (m, 1H), 3.50-3.56 (m, 1H), 3.61-3.64 (m, 1H), 3.71-3.77 (m, 2H), 3.79-3.85 (m, 1H), 4.06-4.17 (m, 2H), 4.32-4-37 (m, 2H), 7.55 (s, 1H)

LC-MS (Method 1): $R_t$=1.22 min; MS (ESIpos): m/z=401 $[M+H]^+$

Step 2

2-{[(2R)-1,4-dioxan-2-yl]methyl}-8-(trifluoromethyl)-4,5-dihydro-2H-furo[2,3-g]indazole-7-carboxylic acid

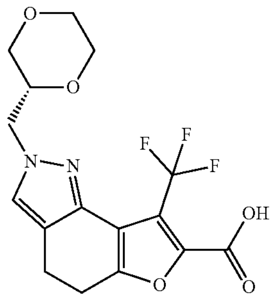 [SMILES: O=C(O)c1oc2c(c1C(F)(F)F)-c1nn(C[C@@H]3COCCO3)cc1CC2]

According to GP D ethyl 2-{[(2R)-1,4-dioxan-2-yl]methyl}-8-(trifluoromethyl)-4,5-dihydro-2H-furo[2,3-g]indazole-7-carboxylate (148 mg, 370 μmol, intermediate 70 (step 1) was dissolved in a mixture of tetrahydrofuran (590 μL) and methanol (590 μL) and an aqueous lithium hydroxide solution (370 μl, 2.0 M, 740 μmol; CAS-RN:[1310-65-2]) was added. The reaction mixture was stirred at room temperature overnight. After neutralization with aqueous hydrogen chloride solution (6 M) to pH4, the reaction mixture was evaporated under reduced pressure at 60° C. The residue was suspended in dichloromethane and brine was added and after stirring for 30 minutes, the organic layer was dried over anhydrous sodium sulphate, filtered, and concentrated in vacuo to afford the title compound (151 mg), which was used directly in the next step without further purification.

LC-MS (Method 1): $R_t$=0.54 min; MS (ESIpos): m/z=373 $[M+H]^+$

Intermediate 71

Step 1 ethyl 2-[(oxan-4-yl)methyl]-8-(trifluoromethyl)-4,5-dihydro-2H-furo[2,3-g]indazole-7-carboxylate

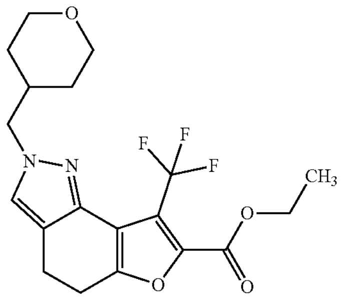 [SMILES: CCOC(=O)c1oc2c(c1C(F)(F)F)-c1nn(CC3CCOCC3)cc1CC2]

According to GP C (conditions A) ethyl 8-(trifluoromethyl)-4,5-dihydro-1H-furo[2,3-g]indazole-7-carboxylate (1.0 eq., 200 mg, 666 μmol) from Intermediate 35 step 4 was reacted with (oxan-4-yl)methanol (CAS No [14774-37-9], 1.5 eq., 116 mg, 999 μmol), tri-n-butylphosphine (CAS No. [998-40-3]; 1.6 eq., 260 μL, 1.1 mmol) and TMAD (CAS No. [10465-78-8]; 1.6 eq., 184 mg, 1.07 mmol) in toluene (15.0 ml) at rt overnight. The reaction mixture was filtered and extracted with water. The combined water phase was extracted with DCM, and the DCM and toluene phases were combined, dried with $Na_2SO_4$, filtered and evaporated under reduced pressure. The crude was purified by column chromatography ($SiO_2$, hexane/DCM) to give the title compound (270 mg, >100% yield).

LC-MS (Method 1): $R_t$=1.30 min; MS (ESIpos): m/z=399 $[M+H]^+$

Step 2

2-[(oxan-4-yl)methyl]-8-(trifluoromethyl)-4,5-dihydro-2H-furo[2,3-g]indazole-7-carboxylic acid

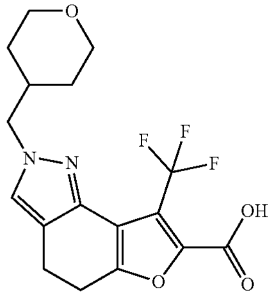 [SMILES: O=C(O)c1oc2c(c1C(F)(F)F)-c1nn(CC3CCOCC3)cc1CC2]

According to GP D ethyl 2-[(oxan-4-yl)methyl]-8-(trifluoromethyl)-4,5-dihydro-2H-furo[2,3-g]indazole-7-carboxylate (1.0 eq, 270 mg, 678 μmol) from step 1 was reacted with aqueous lithium hydroxide (2 M; 5 eq, 1.7 mL, 3.4 mmol) in a 1:1 mixture of ethanol and THF (3.5 mL) at 70° C. overnight. Upon acidification (pH 2) with 6 N aqueous hydrochloric acid, the resulting mixture was evaporated under reduced pressure. To the residue was added DCM (40 ml) and i-PrOH (1 ml) and stirred for 30 min at rt. The phases were separated, and the organic layer was evaporated under reduced pressure to give the title compound (360 mg) as a crude material, which was directly used in the next step without further purification.

LC-MS (Method 1): $R_t$=0.58 min; MS (ESIpos): m/z=371 $[M+H]^+$

Intermediate 72

Step 1 ethyl 3-(difluoromethyl)-4-oxo-4,5,6,7-tetrahydro-1-benzofuran-2-carboxylate

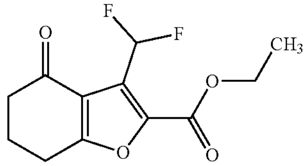 [SMILES: CCOC(=O)c1oc2c(c1C(F)F)C(=O)CCC2]

To a solution of cyclohexane-1,3-dione (1.0 eq., 14.0 g, 125 mmol) in toluene (60 ml) was added ethyl 2-chloro-4,4-difluoro-3-oxobutanoate (1.2 eq., 30.1 g, 150 mmol) at room temperature. The reaction mixture was stirred at 110° C. for 16 h. The mixture was concentrated to give a residue. It was then diluted with ethyl acetate and washed with saturated sodium bicarbonate, brine, dried over anhydrous sodium sulphate, filtered and concentrated to give a residue. The crude residue was purified by flash column chromatography (600-700 mesh, petroleum ether:ethyl acetate=1:0 to 4:1) to give the title compound as a yellow solid (5.80 g, 18% yield).

$^1$H NMR (400 MHz, DMSO-d6): δ [ppm]: 7.40 (t, 1H), 4.36 (q, 2H), 2.99 (t, 2H), 2.52-2.51 (m, 2H), 2.14-2.10 (m, 2H), 1.31 (t, 3H).

LC-MS (Method E): $R_t$=0.90 min; MS (ESIpos): m/z=259 $[M+H]^+$

Step 2 ethyl 3-(difluoromethyl)-5-(hydroxymethylidene)-4-oxo-4,5,6,7-tetrahydro-1-benzofuran-2-carboxylate

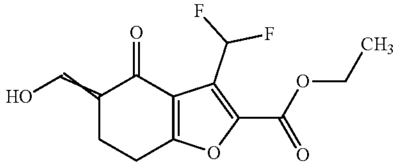 [SMILES: CCOC(=O)c1oc2c(c1C(F)F)C(=O)C(=CO)CC2]

To a solution of sodium hydride hydride (CAS No. [7646-69-7]; 2.0 eq., 1.8 g, 60% purity, 44.9 mmol) in toluene (30 ml) was added a solution of ethyl 3-(difluoromethyl)-4-oxo-4,5,6,7-tetrahydro-1-benzofuran-2-carboxylate (1.0 eq., 5.80 g, 22.5 mmol) from step 1 and ethyl formate (CAS No. [109-94-4]; 3.0 eq., 67 mmol, 5.4 mL) in toluene (30 ml) at 0° C. The mixture was stirred at 80° C. for 12 h. The mixture was diluted with ethyl acetate and then quenched with ethanol/water (80 ml, v/v=1:1) at 0° C. Then the pH of the mixture was adjusted to ~6 with aq. hydrochloride solution (2.0 M). Then the mixture was extracted with ethyl acetate and the combined organic layers were concentrated under reduced pressure to give a residue (6.60 g, 73% purity, 75% yield). The residue was used directly without further purification.

LC-MS (Method C): $R_t$=0.77 min; MS (ESIpos): m/z=287.1 $[M+H]^+$.

Step 3 ethyl 8-(difluoromethyl)-4,5-dihydro-1H-furo[2,3-g]indazole-7-carboxylate

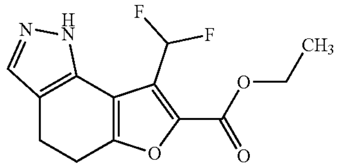 [SMILES: CCOC(=O)c1oc2c(c1C(F)F)-c1[nH]ncc1CC2]

To a mixture of ethyl 3-(difluoromethyl)-5-(hydroxymethylidene)-4-oxo-4,5,6,7-tetrahydro-1-benzofuran-2-carboxylate (1.0 eq., 200 mg, 0.70 mmol) in ethanol (2 mL) was added a solution of hydrazine dihydrochloride (CAS No [5341-61-7], 1.5 eq., 110 mg, 1.05 mmol) in water (0.2 mL) at 25° C. The mixture was stirred at 25° C. for 2 h. The reaction mixture was added to saturated sodium bicarbonate solution at 0° C. and then extracted with ethyl acetate. The combined organic layers were concentrated under reduced pressure to give a residue. The residue was purified by flash column chromatography (petroleum ether:ethyl acetate=1:0 to 3:1) to give the title compound as a yellow solid (60 mg, 30% yield).

$^1$H NMR (400 MHz, DMSO-d6) δ[ppm]: 12.56 (s, 1H), 7.46 (t, 1H), 4.34 (q, 2H), 3.00-2.96 (m, 2H), 2.91-2.87 (m, 2H), 1.32 (t, 3H).LC-MS (Method C): $R_t$=0.75 min; MS (ESIpos): m/z=283.1 $[M+H]^+$.

Step 4 ethyl 8-(difluoromethyl)-2-{[(2S)-1,4-dioxan-2-yl]methyl}-4,5-dihydro-2H-furo[2,3-g]indazole-7-carboxylate

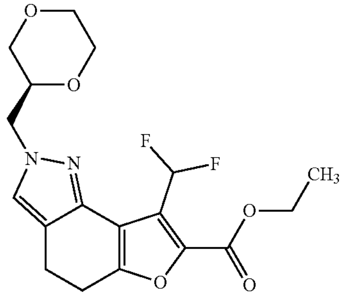 [SMILES: CCOC(=O)c1oc2c(c1C(F)F)-c1nn(C[C@H]3COCCO3)cc1CC2]

Ethyl 8-(difluoromethyl)-4,5-dihydro-1H-furo[2,3-g]indazole-7-carboxylate (1.0 eq., 500 mg, 1.77 mmol) from step 3 and caesium carbonate (CAS No [534-17-8], 3.0 eq, 1.73 g, 5.31 mmol) were added to 1,4-dioxane (20 ml). Then [(2R)-1,4-dioxan-2-yl]methyl methanesulfonate (1.8 eq., 626 mg, 3.19 mmol) was added to the mixture and stirred for 48 h at 100° C. After cooling down the mixture to rt, ethyl acetate and water were added and the phases were separated. The ethyl acetate phase was dried and evaporated under reduced pressure to yield the title compound as a brown oil (659 mg, 97% yield), which was directly used in the next step without further purification.

LC-MS (Method 1): $R_t$=1.15 min; MS (ESIpos): m/z=383 $[M+H]^+$

Step 5

8-(difluoromethyl)-2-{[(2S)-1,4-dioxan-2-yl]methyl}-4,5-dihydro-2H-furo[2,3-g]indazole-7-carboxylic acid

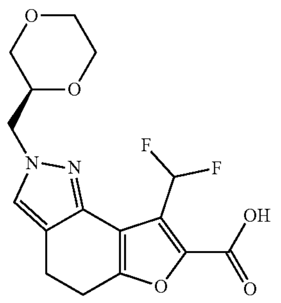 [SMILES: O=C(O)c1oc2c(c1C(F)F)-c1nn(C[C@H]3COCCO3)cc1CC2]

Ethyl 8-(difluoromethyl)-2-{[(2S)-1,4-dioxan-2-yl]methyl}-4,5-dihydro-2H-furo[2,3-g]indazole-7-carboxylate (1.00 eq., 659 mg, 1.72 mmol) from step 4 was reacted with aqueous lithium hydroxide (2 M; 5.0 eq., 4.3 mL, 8.6 mmol) in THF (13 mL) and ethanol (13 ml) at 70° C. for 18 h. The reaction mixture was diluted with DCM and acidified with aqueous 6 N HCl (pH 4) and the resulting mixture was evaporated under reduced pressure. To the residue were added DCM (100 ml) and brine (1 mL) and the resulting mixture was stirred for 1 h at rt. i-PrOH (0.2 mL) was then added and further stirred for 1 h at rt. The DCM phase was filtered, the solid was stirred with DCM (40 ml). The combined DCM phase was evaporated under reduced pressure to give the title compound (462 mg, 76% yield).

LC-MS (Method 1): $R_t$=0.51 min; MS (ESIpos): m/z=355 $[M+H]^+$

Intermediate 73

Step 1 ethyl (6±)-3,6-dimethyl-4-oxo-4,5,6,7-tetrahydro-1-benzofuran-2-carboxylate

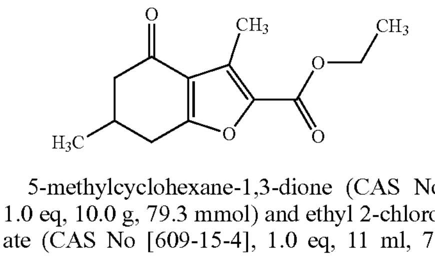

5-methylcyclohexane-1,3-dione (CAS No [4341-24-6], 1.0 eq, 10.0 g, 79.3 mmol) and ethyl 2-chloro-3-oxobutanoate (CAS No [609-15-4], 1.0 eq, 11 ml, 79 mmol) were dissolved in DCM (181 mL) and triethylamine (CAS No [121-44-8], 1.2 eq, 13 ml, 95 mmol). The reaction mixture was stirred for 18 h at 50° C. and for 48 h at rt. Additional ethyl 2-chloro-3-oxobutanoate (CAS No [609-15-4], 0.5 eq, 5.5 ml, 39.5 mmol) and triethylamine (CAS No [121-44-8], 0.6 eq, 6.5 ml, 47.5 mmol) were added and the reaction mixture was stirred at 50° C. for 18 h. 2N HCl was then added and the resulting reaction mixture was further stirred for 18 h at rt (pH 2). To the reaction mixture was added water and the resulting phases were separated. The organic layer was dried by hydrophobic filtration and evaporated under reduced pressure. The crude was purified by column chromatography ($SiO_2$, hexane/ethyl acetate) to give the title compound (9.58 g, 51% yield).

$^1H$ NMR (400 MHz, DMSO-d6) δ[ppm]: 1.06-1.11 (m, 3H) 1.27-1.31 (m, 3H) 2.28-2.42 (m, 3H) 2.45 (s, 3H) 2.60-2.68 (m, 1H) 2.94-3.06 (m, 1H) 4.28 (d, 2H)

LC-MS (Method 1): $R_t$=1.15 min; MS (ESIpos): m/z=237 $[M+H]^+$

Step 2 ethyl (6±)-5-[(dimethylamino)methylidene]-3,6-dimethyl-4-oxo-4,5,6,7-tetrahydro-1-benzofuran-2-carboxylate

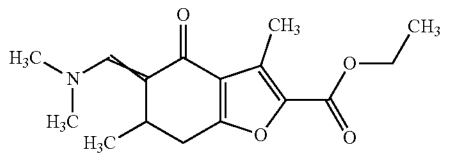 [SMILES: CCOC(=O)c1oc2c(c1C)C(=O)C(=CN(C)C)C(C)C2]

According to GP A (conditions A) ethyl (6±)-3,6-dimethyl-4-oxo-4,5,6,7-tetrahydro-1-benzofuran-2-carboxylate (1.0 eq, 9.5 g, 40.2 mmol) from step 1 was reacted with 1-tert-butoxy-N,N,N',N'-tetramethylmethanediamine (Bredereck's reagent, CAS No. [5815-08-7]; 1.20 eq., 10.0 ml, 48.0 mmol) in toluene (100 mL) at 100° C. overnight. The reaction mixture was concentrated under reduced pressure and the obtained crude title compound (11.7 g) was used in the subsequent reaction without further purification steps.

LC-MS (Method 1): $R_t$=1.12 min and 1.17 min; MS (ESIpos): m/z=292 $[M+H]^+$

Step 3 ethyl (4±)-4,8-dimethyl-4,5-dihydro-1H-furo[2,3-g]indazole-7-carboxylate

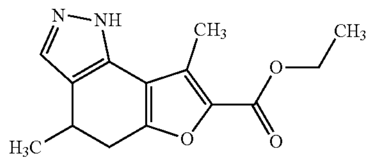 [SMILES: CCOC(=O)c1oc2c(c1C)-c1[nH]ncc1C(C)C2]

According to GP B ethyl (6±)-5-[(dimethylamino)methylidene]-3,6-dimethyl-4-oxo-4,5,6,7-tetrahydro-1-benzofuran-2-carboxylate (1.0 eq., 11.8 g, 40.4 mmol) from step 2 was reacted with hydrazine hydrate 1:1 (CAS No [7803-57-8], 5.0 eq., 9.8 mL, 200 mmol) in ethanol (200 mL) at 70° C. for 5 h. The reaction mixture was then evaporated under reduced pressure. To the residue were added water and ethyl acetate. The phases were separated, and the water phase was extracted with ethyl acetate twice. The combined organic phase was dried by hydrophobic filtration and evaporated to give upon column chromatography ($SiO_2$, hexane/ethyl acetate) the title compound (2.38 g, 23% yield) as a solid.

LC-MS (Method 1): $R_t$=1.07 min; MS (ESIpos): m/z=261 $[M+H]^+$

Step 4 ethyl (4±)-4,8-dimethyl-2-[(pyridin-2-yl)methyl]-4,5-dihydro-2H-furo[2,3-g]indazole-7-carboxylate

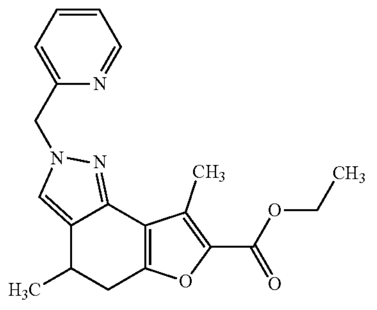 [SMILES: CCOC(=O)c1oc2c(c1C)-c1nn(Cc3ccccn3)cc1C(C)C2]

According to GP C (conditions B) ethyl (4±)-4,8-dimethyl-4,5-dihydro-1H-furo[2,3-g]indazole-7-carboxylate (1.0 eq., 500 mg, 1.92 mmol) from step 3 was reacted with 2-(bromomethyl)pyridine (1.5 eq., 496 mg, 2.88 mmol), potassium carbonate (CAS No [584-08-7], 15 eq., 3.98 g, 28.8 mmol) and DMAP (CAS No [1122-58-3], 0.05 eq, 11.7 mg, 96.0 µmol) in ethyl acetate (2.4 mL) at 75° C. overnight. Additional amounts of 2-(bromomethyl)pyridine (1.5 eq., 496 mg, 2.88 mmol), potassium carbonate (CAS No [584-08-7], 15 eq., 3.98 g, 28.8 mmol) and DMAP (CAS No [1122-58-3], 0.05 eq, 11.7 mg, 96.0 µmol) were added to the reaction mixture and stirred at 75° C. overnight. The solid was filtered and washed with ethyl acetate. The ethyl acetate phase was extracted with water, separated, dried over a hydrophobic filter paper and evaporated to give upon column chromatography ($SiO_2$, hexane/ethyl acetate) the title compound (154 mg, 23% yield).

$^1H$ NMR (400 MHz, DMSO-d6) δ[ppm]: 1.27-1.31 (m, 6H) 2.46 (s, 3H) 2.54-2.61 (m, 1H) 3.00-3.06 (m, 1H) 3.14-3.22 (m, 1H) 4.23-4.29 (m, 2H) 5.40 (s, 2H) 7.07-7.09 (m, 1H) 7.29-7.33 (m, 1H) 7.70-7.71 (m, 1H) 7.76-7.80 (m, 1H) 8.51-8.65 (m, 1H) LC-MS (Method 1): $R_t$=1.21 min; MS (ESIpos): m/z=352 $[M+H]^+$ Step 5

(4±)-4,8-dimethyl-2-[(pyridin-2-yl)methyl]-4,5-dihydro-2H-furo[2,3-g]indazole-7-carboxylic acid

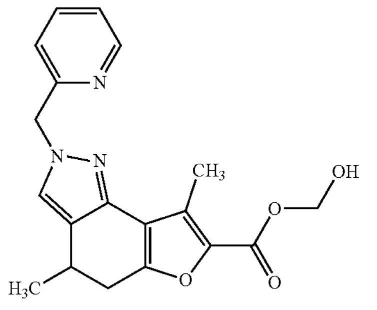 [SMILES: Cc1c(C(=O)OCO)oc2c1-c1nn(Cc3ccccn3)cc1C(C)C2]

According to GP D ethyl (4±)-4,8-dimethyl-2-[(pyridin-2-yl)methyl]-4,5-dihydro-2H-furo[2,3-g]indazole-7-carboxylate (1.0 eq, 154 mg, 438 µmol) from step 4 was reacted with aqueous lithium hydroxide (2 M; 5 eq, 1.1 mL, 2.2 mmol) in a 1:1 mixture of ethanol and THF (3.4 mL) at 70° C. overnight. Upon acidification (pH 2) with 6 N aqueous hydrochloric acid, the resulting mixture was evaporated under reduced pressure. To the residue was added DCM (50 ml) and i-PrOH (4×5 ml) and further stirred for 30 min at rt. Hexane was then added until precipitation occurred. The solid was collected by suction and washed with DCM/hexane (1:1) to give the title compound (128 mg, 90% yield) as a solid.

LC-MS (Method 1): $R_t$=0.55 min; MS (ESIpos): m/z=324 $[M+H]^+$

Intermediate 74

Step 1 ethyl (4±)-2-{[(2S)-1,4-dioxan-2-yl]methyl}-4,8-dimethyl-4,5-dihydro-2H-furo[2,3-g]indazole-7-carboxylate

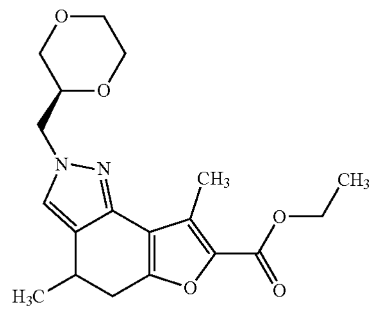 [SMILES: CCOC(=O)c1oc2c(c1C)-c1nn(C[C@H]3COCCO3)cc1C(C)C2]

According to GP C (conditions A) ethyl (4±)-4,8-dimethyl-4,5-dihydro-1H-furo[2,3-g]indazole-7-carboxylate (1.00 eq., 500 mg, 1.92 mmol) from Intermediate 73 step 3 was reacted with [(2S)-1,4-dioxan-2-yl]methanol (CAS No [34107-46-5], 1.5 eq., 340 mg, 2.88 mmol), tri-n-butylphosphine (1.6 eq., 621 mg, 3.07 mmol) and TMAD (CAS No. [10465-78-8]; 1.6 eq., 529 mg, 3.07 mmol) in toluene (17 ml) at rt overnight. The reaction mixture was filtered and extracted with water. The water phase was extracted twice with DCM. The DCM and toluene phase were dried over $Na_2SO_4$, filtered and evaporated under reduced pressure to give a crude material, which was purified by column chromatography (NH, $SiO_2$, hexane/DCM) to give the title compound (473 mg), contaminated with $n-Bu_3P{=}O$.

LC-MS (Method 1): $R_t$=1.21 min; MS (ESIpos): m/z=361 $[M+H]^+$

Step 2

(4±)-2-{[(2S)-1,4-dioxan-2-yl]methyl}-4,8-dimethyl-4,5-dihydro-2H-furo[2,3-g]indazole-7-carboxylic acid

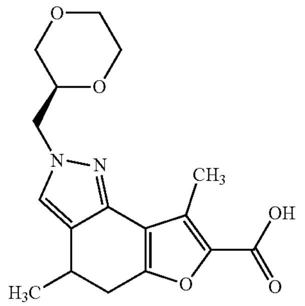 [SMILES: Cc1c(C(=O)O)oc2c1-c1nn(C[C@H]3COCCO3)cc1C(C)C2]

According to GP D ethyl (4±)-2-{[(2S)-1,4-dioxan-2-yl]methyl}-4,8-dimethyl-4,5-dihydro-2H-furo[2,3-g]indazole-7-carboxylate (1.0 eq, 473 mg, 656 μmol) from step 1 was reacted with aqueous lithium hydroxide (2 M; 5 eq, 1.6 mL, 3.3 mmol) in a 1:1 mixture of ethanol and THF (5.0 mL) at 70° C. overnight. Upon acidification (pH 2) with 6 N aqueous hydrochloric acid, the resulting mixture was evaporated under reduced pressure. To the residue was added DCM (50 ml) and i-PrOH (12 ml) and stirring was continued while hexane was added slowly until precipitation occurred. The solid was filtered off and washed with hexane/DCM (1:1). The filtrate was evaporated under reduced pressure to give the title compound (227 mg) as a crude material, which was directly used in the next step without further purification.

LC-MS (Method 1): $R_t$=0.52 min; MS (ESIpos): m/z=333 $[M+H]^+$

Intermediate 75

Step 1 ethyl (6±)-6-methyl-4-oxo-3-(trifluoromethyl)-4,5,6,7-tetrahydro-1-benzofuran-2-carboxylate (Racemate)

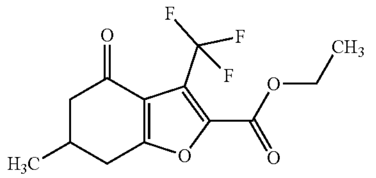 [SMILES: CCOC(=O)c1oc2c(c1C(F)(F)F)C(=O)CC(C)C2]

5-methylcyclohexane-1,3-dione (commercial available, CAS No [4341-24-6], 1.0 eq, 12.0 g, 95.3 mmol) was suspended in toluene (4.0 ml), and then ethyl 2-chloro-4,4,4-trifluoro-3-oxobutanoate (CAS No [363-58-6], 1.2 eq, 18 ml, 114 mmol) was added and the resulting mixture was stirred for 18 h at 100° C. under nitrogen until TLC and/or LCMS indicate complete consumption of the starting material. The reaction mixture was concentrated under reduced pressure and purified by column chromatography ($SiO_2$, DCM/Hexane) to give the title compound (4.3 g, 16% yield) as a solid.

$^1$H NMR (400 MHz, DMSO-d6) δ[ppm]: 1.09 (d, 3H) 1.30 (t, 3H) 2.32-2.42 (m, 2H) 2.51-2.55 (m, 1H) 2.69-2.76 (m, 1H) 3.07-3.12 (m, 1H) 4.33-4.39 (m, 2H)

LC-MS (Method 1): $R_t$=1.21 min; MS (ESIpos): m/z=291 $[M+H]^+$

Step 2 ethyl (6±)-5-(hydroxymethylidene)-6-methyl-4-oxo-3-(trifluoromethyl)-4,5,6,7-tetrahydro-1-benzofuran-2-carboxylate (Racemate)

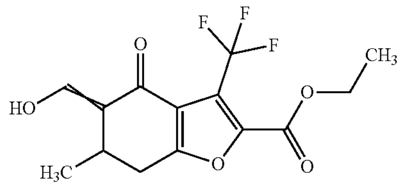 [SMILES: CCOC(=O)c1oc2c(c1C(F)(F)F)C(=O)C(=CO)C(C)C2]

According to GP A (conditions B) a solution of ethyl formate (CAS No. [109-94-4]; 6.0 eq., 21 mmol, 1.7 mL) in toluene (15 mL) was treated with sodium hydride (CAS No. [7646-69-7]; 3.00 eq., 103 mmol, 413 mg, 60% purity) at 0° C. After stirring for 0.5 h, a solution of ethyl (6±)-6-methyl-4-oxo-3-(trifluoromethyl)-4,5,6,7-tetrahydro-1-benzofuran-2-carboxylate (1.00 eq., 3.45 mmol, 1.00 g) from step 1 in toluene (5 mL) was added to the above mixture. The reaction mixture was stirred at room temperature for 18 h. The reaction mixture was diluted with ethyl acetate (50 ml) and quenched with saturated ammonium chloride solution (5×2 ml, pH-5). The phases were separated, and the organic phase washed with half saturated brine (10 ml). The combined water phases were extracted with ethyl acetate (50 ml). The combined organic phases were dried over anhydrous filter paper and concentrated. The residue was then triturated with hexane (25 ml) to give after drying the title compound (1.2 g) as an crude oil, which was directly used in the next step without further purification.

LC-MS (Method 1): $R_t$=0.65 min; MS (ESIneg): m/z=317 $[M-H]^-$

Step 3 ethyl (4±)-4-methyl-8-(trifluoromethyl)-4,5-dihydro-1H-furo[2,3-g]indazole-7-carboxylate (Racemate)

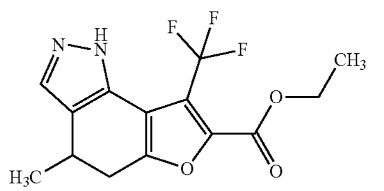 [SMILES: CCOC(=O)c1oc2c(c1C(F)(F)F)-c1[nH]ncc1C(C)C2]

According to GP B ethyl (6±)-5-(hydroxymethylidene)-6-methyl-4-oxo-3-(trifluoromethyl)-4,5,6,7-tetrahydro-1-benzofuran-2-carboxylate (1.0 eq., 1.20 g, 2.04 mmol, 54% purity) from step 2 in ethanol (8.5 ml) was reacted with hydrazine dihydrochloride (CAS No [5341-61-7], 2.0 eq., 427 mg, 4.07 mmol) in water (2.6 mL) at 60° C. for 2 h. After cooling down the reaction mixture to rt, it was diluted with DCM (150 ml) and stirred with aq. 2 N HCl (10 mL, pH 5). The phases were separated, and the DCM phase was washed with brine (25 ml). The combined water phase was extracted with DCM (50 ml). The combined DCM phase was dried with a hydrophobic filter paper and evaporated under reduced pressure. The residue was purified by column chromatography ($SiO_2$, Hexane/EtOAc) to give the title compound (250 mg, 39% yield).

$^1H$ NMR (400 MHz, DMSO-d6) δ[ppm]: 1.26-1.33 (m, 6H) 2.60-2.68 (m, 1H) 3.07-3.13 (m, 1H) 3.17-3.20 (m, 1H) 4.44 (q, 2H) 7.63 (s, 1H) 12.68 (br. s, 1H)

LC-MS (Method 1): $R_t$=1.15 min; MS (ESIpos): m/z=315 $[M+H]^+$

Step 4 ethyl (4±)-4-methyl-2-[(pyridin-2-yl)methyl]-8-(trifluoromethyl)-4,5-dihydro-2H-furo[2,3-g]indazole-7-carboxylate

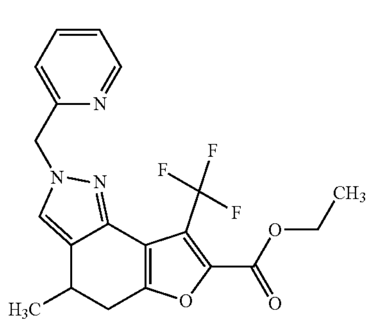 [SMILES: CCOC(=O)c1oc2c(c1C(F)(F)F)-c1nn(Cc3ccccn3)cc1C(C)C2]

According to GP C (conditions B) A solution of ethyl (4±)-4-methyl-8-(trifluoromethyl)-4,5-dihydro-1H-furo[2,3-g]indazole-7-carboxylate (1.0 eq., 250 mg, 796 μmol) from Intermediate 75 step 3 and 2-(bromomethyl)pyridine (CAS No [55401-97-3], 1.5 eq., 205 mg, 1.19 mmol) in ethyl acetate (11 ml) at rt was treated with potassium carbonate (CAS No [1122-58-7], 15 eq, 1.65 g, 11.9 mmol.) and N,N-dimethylpyridin-4-amine (DMAP, CAS No [1122-58-3]; 0.05 eq, 4.86 mg, 39.8 μmol) under nitrogen atmosphere. The reaction mixture was stirred at 70° C. overnight. The reaction mixture was cooled to rt, filtrated and concentrated under reduced pressure and the residue was subjected to column chromatography ($SiO_2$, Hexane/EtOAc) to give the title compound (179 mg, 56% yield).

LC-MS (Method 1): $R_t$=1.30 min; MS (ESIpos): m/z=406 $[M+H]^+$

Step 5

(4±)-4-methyl-2-[(pyridin-2-yl)methyl]-8-(trifluoromethyl)-4,5-dihydro-2H-furo[2,3-g]indazole-7-carboxylic acid

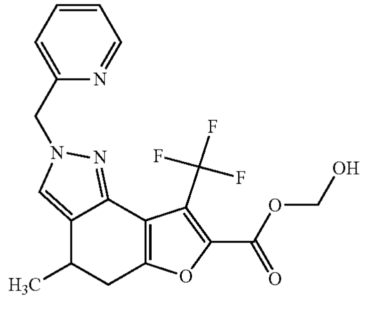 [SMILES: CC1Cc2oc(C(=O)OCO)c(C(F)(F)F)c2-c2nn(Cc3ccccn3)cc21]

According to GP D ethyl (4±)-4-methyl-2-[(pyridin-2-yl)methyl]-8-(trifluoromethyl)-4,5-dihydro-2H-furo[2,3-g]indazole-7-carboxylate (1.0 eq, 179 mg, 442 μmol) from step 4 was reacted with aqueous lithium hydroxide (2 M; 5 eq, 1.1 mL, 2.2 mmol) in a 1:1 mixture of ethanol and THF (5.2 mL) at 70° C. overnight. Upon acidification (pH 2) with 4 N aqueous hydrochloric acid, the resulting mixture was evaporated under reduced pressure. To the residue was added DCM (30 ml), water (20 ml) and i-PrOH (2 ml). During the separation of layers, solids were formed. Solids were collected by suction to give the title compound (54.0 mg, 32% yield) as a beige solid.

$^1H$ NMR (400 MHz, DMSO-d6) δ[ppm]: 1.29 (d, 3H) 2.60-2.67 (m, 1H) 3.05-3.11 (m, 1H) 3.17-3.23 (m, 1H) 5.40 (s, 2H) 7.08-7.10 (m, 1H) 7.29-7.33 (m, 1H) 7.74 (s, 1H) 7.76-7.80 (m, 1H) 8.53-8.55 (m, 1H) 13.73-14.10 (br. s, 1H) LC-MS (Method 1): $R_t$=0.56 min; MS (ESIpos): m/z=378 $[M+H]^+$ Intermediate 76

Step 1 ethyl (4±)-4-methyl-2-[(5-methylpyridin-2-yl)methyl]-8-(trifluoromethyl)-4,5-dihydro-2H-furo[2,3-g]indazole-7-carboxylate

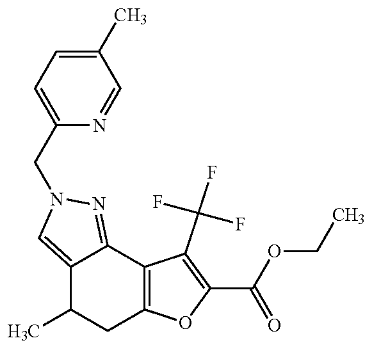 [SMILES: CCOC(=O)c1oc2c(c1C(F)(F)F)-c1nn(Cc3ccc(C)cn3)cc1C(C)C2]

According to GP C (conditions A) ethyl (4±)-4-methyl-8-(trifluoromethyl)-4,5-dihydro-1H-furo[2,3-g]indazole-7-carboxylate (150 mg, 477 μmol) from Intermediate 75 step 3, (5-methylpyridin-2-yl)methanol (88.2 mg, 716 μmol) and TMAD (131 mg, 764 μmol; CAS-RN:[10465-78-8]) were added to toluene (2.7 mL) under nitrogen. To the stirred reaction mixture was added carefully tributylphosphine (190 μl, 760 μmol; CAS-RN:[998-40-3]) and stirred for 17 h at rt. The reaction mixture was filtered and extracted with water. The water layer was extracted with dichloromethane and the combined organic layers (toluene and DCM phases) were filtered over a water-free filter and concentrated in vacuo. The crude material was purified by Biotage Isolera™ chromatography (SNAP KP-Sil—10 g, eluting with hexane-ethyl acetate, 1:0 to 2:1) to afford the title compound (236 mg). The material was used in the next step without further purification.

LC-MS (Method 1): $R_t$=1.37 min; MS (ESIpos): m/z=420 $[M+H]^+$

Step 2

(4±)-4-methyl-2-[(5-methylpyridin-2-yl)methyl]-8-(trifluoromethyl)-4,5-dihydro-2H-furo[2,3-g]indazole-7-carboxylic acid

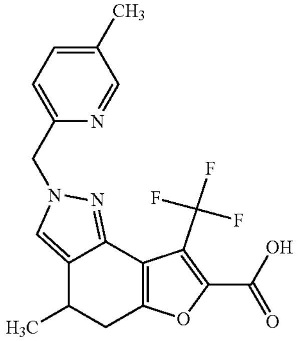 [SMILES: Cc1ccc(Cn2cc3c(n2)-c2c(oc(C(=O)O)c2C(F)(F)F)CC3C)nc1]

According to GP D ethyl (4±)-4-methyl-2-[(5-methylpyridin-2-yl)methyl]-8-(trifluoromethyl)-4,5-dihydro-2H-furo[2,3-g]indazole-7-carboxylate (200 mg, 477 μmol, intermediate 76 (step 1) was dissolved in a mixture of tetrahydrofuran (5.6 mL) and ethanol (5.6 mL) and an aqueous lithium hydroxide solution (1.2 ml, 2.0 M, 2.4 mmol; CAS-RN:[1310-65-2]) was added. The reaction mixture was stirred at 70° C. overnight. After neutralization with aqueous hydrogen chloride solution (4 M) to pH3, the resulting mixture was concentrated in vacuo. To the residue were added ethyl acetate and water. The water layer was extracted with ethyl acetate. The combined organic layers were dried by hydrophobic filtration and evaporated to give the title compound (233 mg) as a crude material, which was used in the next step without further purification.

LC-MS (Method 1): $R_t$=0.61 min; MS (ESIpos): m/z=392 $[M+H]^+$

Intermediate 77

Step 1 ethyl (4±)-4-methyl-2-[(6-methylpyridin-3-yl)methyl]-8-(trifluoromethyl)-4,5-dihydro-2H-furo[2,3-g]indazole-7-carboxylate

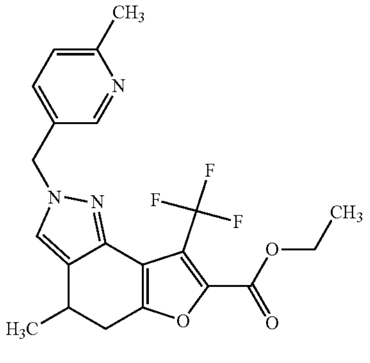

According to GP C (conditions A) ethyl (4±)-4-methyl-8-(trifluoromethyl)-4,5-dihydro-1H-furo[2,3-g]indazole-7-carboxylate (1.00 eq., 150 mg, 477 μmol) from Intermediate 75 step 3 was reacted with (6-methylpyridin-3-yl)methanol (1.5 eq., 88.2 mg, 716 μmol), tri-n-butylphosphine (CAS No. [998-40-3]; 1.6 eq., 190 μL, 760 μmol) and TMAD (CAS No. [10465-78-8]; 1.60 eq., 131 mg, 764 μmol) in toluene (2.7 mL) at rt overnight to give upon column chromatography ($SiO_2$, hexane/EtOAc) the title compound (145 mg, 71%).

LC-MS (Method 1): $R_t$=1.30 min; MS (ESIpos): m/z=420 $[M+H]^+$

Step 2

(4±)-4-methyl-2-[(6-methylpyridin-3-yl)methyl]-8-(trifluoromethyl)-4,5-dihydro-2H-furo[2,3-g]indazole-7-carboxylic acid

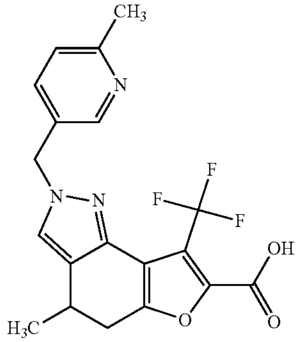 [SMILES: Cc1ccc(Cn2cc3c(n2)-c2c(oc(C(=O)O)c2C(F)(F)F)CC3C)cn1]

According to GP D ethyl (4±)-4-methyl-2-[(6-methylpyridin-3-yl)methyl]-8-(trifluoromethyl)-4,5-dihydro-2H-furo[2,3-g]indazole-7-carboxylate (1.0 eq, 145 mg, 346 μmol) from step 1 was reacted with aqueous lithium hydroxide (2 M; 5 eq., 860 μL, 1.7 mmol) in a 1:1 mixture of ethanol and THF (4.1 mL) at 70° C. overnight. Upon acidification (pH 3) with 4 N aqueous hydrochloric acid, the resulting mixture was evaporated under reduced pressure. To the residue was added DCM/i-PrOH 9:1 and water. The water phase was extracted twice with DCM/i-PrOH 9:1 and the combined organic phase was dried by hydrophobic filtration and evaporated to give the title compound (117 mg, 86% yield) as a beige solid. The crude material was used in the next step without further purification.

LC-MS (Method 1): $R_t$=0.58 min; MS (ESIpos): m/z=392 $[M+H]^+$

Intermediate 78

Step 1 ethyl (4±)-2-{[(2S)-1,4-dioxan-2-yl]methyl}-4-methyl-8-(trifluoromethyl)-4,5-dihydro-2H-furo[2,3-g]indazole-7-carboxylate

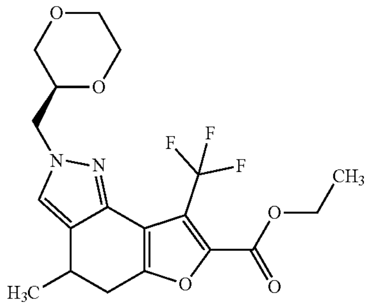 [SMILES: CCOC(=O)c1oc2c(c1C(F)(F)F)-c1nn(C[C@H]3COCCO3)cc1C(C)C2]

According to GP C (conditions A) ethyl (4±)-4-methyl-8-(trifluoromethyl)-4,5-dihydro-1H-furo[2,3-g]indazole-7-carboxylate (1.00 eq., 750 mg, 2.39 mmol) from Intermediate 75 step 3 was reacted with [(2S)-1,4-dioxan-2-yl]methanol (1.5 eq., 423 mg, 3.58 mmol), tri-n-butylphosphine (CAS No. [998-40-3]; 1.6 eq., 950 μL, 3.8 mmol) and TMAD (CAS No. [10465-78-8]; 1.60 eq., 657 mg, 3.82 mmol) in toluene (14.0 ml) at rt overnight. The reaction mixture was filtered and extracted with water. The water phase was extracted with DCM twice. The DCM and toluene phase were dried over $Na_2SO_4$, filtered and evaporated to give upon repetitive column chromatography ($SiO_2$, hexane/DCM and then with hexane/EtOAc) the title compound (528 mg, 54% yield).

$^1$H NMR (400 MHz, DMSO-d6) δ[ppm]: 1.26-1.28 (m, 3H) 1.29-1.33 (m, 3H) 2.61-2.65 (m, 1H) 3.06-3.12 (m, 1H) 3.15-3.21 (m, 1H) 3.24-3.30 (m, 1H) 3.40-3.57 (m, 2H) 3.62-3.64 (m, 1H) 3.72-3.78 (m, 2H) 3.79-3.88 (m, 1H) 4.07-4.15 (m, 2H) 4.32-4.37 (m, 2H) 7.55 (s, 1H).

LC-MS (Method 1): $R_t$=1.27 min; MS (ESIpos): m/z=415 $[M+H]^+$

Step 2

(4±)-2-{[(2S)-1,4-dioxan-2-yl]methyl}-4-methyl-8-(trifluoromethyl)-4,5-dihydro-2H-furo[2,3-g]indazole-7-carboxylic acid

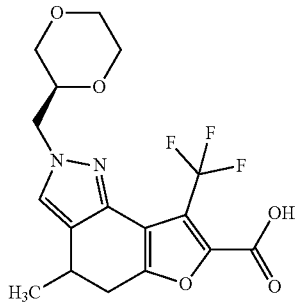 [SMILES: CC1Cc2oc(C(=O)O)c(C(F)(F)F)c2-c2nn(C[C@H]3COCCO3)cc21]

Ethyl (4±)-2-{[(2S)-1,4-dioxan-2-yl]methyl}-4-methyl-8-(trifluoromethyl)-4,5-dihydro-2H-furo[2,3-g]indazole-7-carboxylate (527 mg, 1.27 mmol, intermediate 78 (step 1) was dissolved in a mixture of tetrahydrofuran (9.8 mL) and ethanol (9.8 mL), and an aqueous lithium hydroxide solution (3.2 ml, 2.0 M, 6.36 mmol; CAS-RN:[1310-65-2]) was added. The reaction mixture was stirred at 70° C. overnight. The reaction mixture was diluted with DCM and neutralized with aqueous hydrogen chloride solution (6 M) to pH2, and the resulting mixture was concentrated in vacuo. To the residue were added DCM (50 mL) and i-PrOH (1 mL) and the resulting mixture was stirred at rt overnight. The solids were filtered off, washed with additional DCM and the combined filtrate was evaporated under reduced pressure to give the title compound (445 mg) as a crude foam, which was used in the next step without further purification.

LC-MS (Method 1): $R_t$=0.55 min; MS (ESIpos): m/z=387 $[M+H]^+$

Intermediate 79

Step 1-a ethyl (4R or 4S)-4-methyl-8-(trifluoromethyl)-4,5-dihydro-1H-furo[2,3-g]indazole-7-carboxylate (Enantiomer 1, stereochemistry not defined)

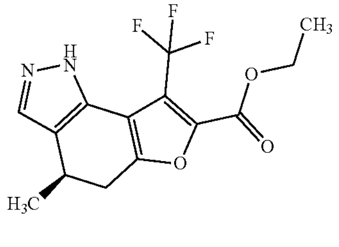 [SMILES: CCOC(=O)c1oc2c(c1C(F)(F)F)-c1[nH]ncc1[C@H](C)C2]

The enantiomers of Intermediate 75 step 3 (2.5 g, 7.96 mmol) were separated by preparative SFC method (Instrument: Sepiatec: Prep SFC100; Column: Chiralpak IC 5p 250×30 mm; eluent A: CO2; eluent B: 2-propanol+0.4 vol % diethylamin; isocratic: 10% B; flow: 100 ml/min; temperature: 40° C.; BPR: 150 bar; UV: 280 nm) and analytically characterized by SFC method (Instrument: Agilent: 1260, Aurora SFC-Modul; Column: Chiralpak IC 5μ 100×4.6 mm; eluent A: CO2; eluent B: 2-propanol+0.4 vol % diethylamin; isocratic: 15% B; flow: 4 ml/min; temperature: 37.5° C.; BPR: 100 bar; UV: 280 nm). The injection solution was prepared using dichloromethane/methanol/DMSO 1:1:0.2 (15 mL in total)

Enantiomer 1:

$R_t$=1.05 min, 912 mg, 36% yield $[\alpha]_D^{20}$=−29.2° (c=1, DMSO)

$^1$H NMR identical to Intermediate 75 step 3.

Step 1-b ethyl (4S or 4R)-4-methyl-8-(trifluoromethyl)-4,5-dihydro-1H-furo[2,3-g]indazole-7-carboxylate (Enantiomer 2, stereochemistry not defined)

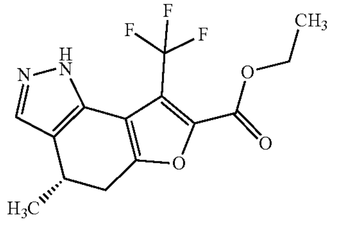 [SMILES: CCOC(=O)c1oc2c(c1C(F)(F)F)-c1[nH]ncc1[C@@H](C)C2]

The enantiomers of Intermediate 75 step 3 (2.5 g, 7.96 mmol) were separated by preparative SFC method (Instrument: Sepiatec: Prep SFC100; Column: Chiralpak IC 5p 250×30 mm; eluent A: CO2; eluent B: 2-propanol+0.4 vol % diethylamin; isocratic: 10% B; flow: 100 ml/min; temperature: 40° C.; BPR: 150 bar; UV: 280 nm) and analytically characterized by SFC method (Instrument: Agilent: 1260, Aurora SFC-Modul; Column: Chiralpak IC 5μ 100×4.6 mm; eluent A: CO2; eluent B: 2-propanol+0.4 vol % diethylamin; isocratic: 15% B; flow: 4 ml/min; temperature: 37.5° C.;

BPR: 100 bar; UV: 280 nm). The injection solution was prepared using dichloromethane/methanol/DMSO 1:1:0.2 (15 mL in total)

Enantiomer 2:

$R_t$=1.32 min, 880 mg, 35% yield $[\alpha]_D^{20}$=+51.9° (c=1, DMSO)

$^1$H NMR identical to Intermediate 75 step 3.

Step 2 ethyl (4R or 4S)-2-{[(2S)-1,4-dioxan-2-yl]methyl}-4-methyl-8-(trifluoromethyl)-4,5-dihydro-2H-furo[2,3-g]indazole-7-carboxylate

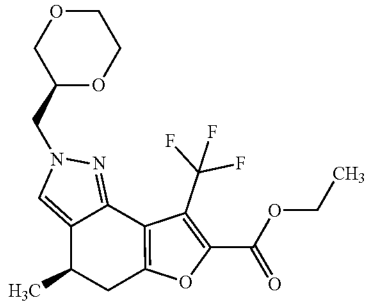 [SMILES: CCOC(=O)c1oc2c(c1C(F)(F)F)-c1nn(C[C@H]3COCCO3)cc1[C@H](C)C2]

Ethyl (4R or 4S)-4-methyl-8-(trifluoromethyl)-4,5-dihydro-1H-furo[2,3-g]indazole-7-carboxylate (200 mg, 636 μmol) from step 1-a (enantiomer 1) and caesium carbonate (622 mg, 1.91 mmol; CAS-RN:[534-17-8]) were added to 1,4-dioxane (8 ml). Then [(2R)-1,4-dioxan-2-yl]methyl methanesulfonate (225 mg, 1.15 mmol) was added to the mixture and stirred for 18 h at 100° C. After cooling the mixture to rt, the solids were filtered off and washed with EtOAc. The filtrate was evaporated under reduced pressure. The residue was diluted with DCM and water. The organic phase was evaporated to yield the title compound (251 mg) as an oil. The crude material was directly used in the next step without further purification.

LC-MS (Method 1): $R_t$=1.29 min; MS (ESIpos): m/z=415 $[M+H]^+$

Step 3

(4R or 4S)-2-{[(2S)-1,4-dioxan-2-yl]methyl}-4-methyl-8-(trifluoromethyl)-4,5-dihydro-2H-furo[2,3-g]indazole-7-carboxylic acid

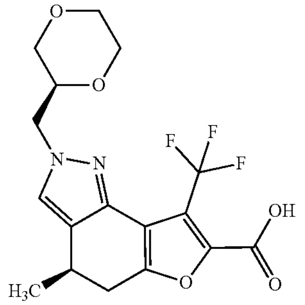 [SMILES: C[C@@H]1Cc2oc(C(=O)O)c(C(F)(F)F)c2-c2nn(C[C@H]3COCCO3)cc21]

According to GP D ethyl (4R or 4S)-2-{[(2S)-1,4-dioxan-2-yl]methyl}-4-methyl-8-(trifluoromethyl)-4,5-dihydro-2H-furo[2,3-g]indazole-7-carboxylate (251 mg, 606 μmol, intermediate 79 (step 2) was dissolved in a mixture of tetrahydrofuran (4.7 mL) and ethanol (4.7 mL) and an aqueous lithium hydroxide solution (1.5 ml, 2.0 M, 3.0 mmol; CAS-RN:[1310-65-2]) was added. The reaction mixture was stirred at 70° C. overnight. After neutralization with aqueous hydrogen chloride solution (6 M) to pH4, the reaction mixture was concentrated in vacuo. The residue was treated with dichloromethane (50 mL) and brine (0.2 mL) and the resulting mixture was stirred for 30 min at rt. The solids were filtered off and the filtrate was evaporated under reduced pressure to give the title compound (200 mg, 85% yield) as a foam. The crude material was used in the next step without further purification.

LC-MS (Method 1): $R_t$=0.6 min; MS (ESIpos): m/z=387 $[M+H]^+$

Intermediate 80

Step 1 ethyl (4R or 4S)-4-methyl-2-[(oxan-4-yl)methyl]-8-(trifluoromethyl)-4,5-dihydro-2H-furo[2,3-g]indazole-7-carboxylate

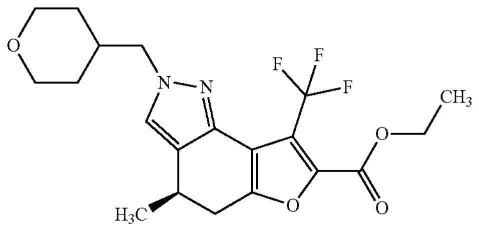 [SMILES: CCOC(=O)c1oc2c(c1C(F)(F)F)-c1nn(CC3CCOCC3)cc1[C@H](C)C2]

Ethyl (4R or 4S)-4-methyl-8-(trifluoromethyl)-4,5-dihydro-1H-furo[2,3-g]indazole-7-carboxylate (410 mg, 1.3 mmol) from Intermediate 79 step 1-a (enantiomer 1) was suspended in acetonitrile (2.9 mL) at rt. To the reaction mixture, caesium carbonate (3 eq., 1.27 g, 3.9 mol) was added followed by the addition of tetrahydropyran-4-ylmethyl trifluoromethanesulfonate (1.8 eq., 0.58 g, 2.35 mmol) in acetonitrile (1 mL) and the resulting reaction mixture was stirred for 1 h at rt. To the reaction mixture, EtOAc and $H_2O$ were added and briefly stirred. The layers were separated, and the organic layer was dried with a hydrophobic filter paper and evaporated under reduced pressure. The crude residue was treated with EtOAc:Hexane (1:3, 2 mL) and placed briefly under sonication. After stirring for 30 mins at rt, the white solids were filtered off and the filtrate was evaporated under reduced pressure to give the title compound (479 mg, 89% yield) as a brown oil, which was used in the next step without further purification.

LC-MS (Method 1): $R_t$=1.27 min; MS (ESIpos): m/z=413 $[M+H]^+$

Step 2

(4R or 4S)-4-methyl-2-[(oxan-4-yl)methyl]-8-(trifluoromethyl)-4,5-dihydro-2H-furo[2,3-g]indazole-7-carboxylic acid

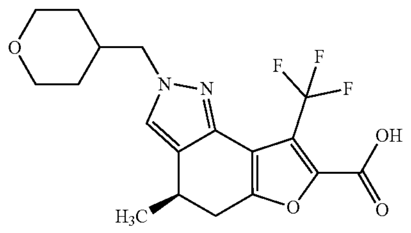 [SMILES: C[C@@H]1Cc2oc(C(=O)O)c(C(F)(F)F)c2-c2nn(CC3CCOCC3)cc21]

Ethyl (4R or 4S)-4-methyl-2-[(oxan-4-yl)methyl]-8-(trifluoromethyl)-4,5-dihydro-2H-furo[2,3-g]indazole-7-carboxylate (1.00 eq., 479 mg, 1.16 mmol) from step 1 was reacted with aqueous lithium hydroxide (2 M; 2.0 eq., 1.2 mL, 2.3 mmol) in THF (1.2 mL) and methanol (1.2 ml) at rt for 18 h. The reaction mixture was acidified with aqueous 6 N HCl to pH2 and the resulting mixture was evaporated under reduced pressure. After co-distillation with THF, the title compound (800 mg) was obtained, which was used as a crude in the next step.

LC-MS (Method 2): $R_t$=0.68 min; MS (ESIpos): m/z=385 $[M+H]^+$

Intermediate 81

Step 1 ethyl (6±)-3-methyl-4-oxo-6-(trifluoromethyl)-4,5,6,7-tetrahydro-1-benzofuran-2-carboxylate

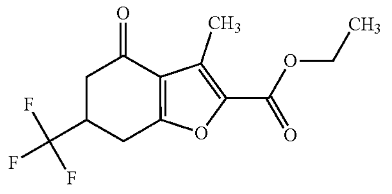 [SMILES: CCOC(=O)c1oc2c(c1C)C(=O)CC(C(F)(F)F)C2]

5-(trifluoromethyl)cyclohexane-1,3-dione (CAS No [124612-15-3], 1.0 eq, 10.0 g, 55.5 mmol), ethyl 2-chloro-3-oxobutanoate (CAS No [609-15-4], 1.0 eq, 7.7 ml, 56 mmol) and triethylamine (CAS No [121-44-8], 1.2 eq, 9.3 ml, 67 mmol) were added to 1,2-dichloroethane (127 ml) and stirred at 50° C. for 18 h. To the mixture was added aq. 6 N HCl (16 ml) and the resulting mixture was stirred for 2 h at rt (pH 5 to pH 2). The phases were separated and the organic phase was washed with water, dried over a hydrophobic filter paper and evaporated. The crude material was purified by column chromatography ($SiO_2$, hexane/ethyl acetate) to give a mixture of title compound and the intermediate product (structure not shown). This mixture was dissolved in 1,2-dichloroethane and treated with aq. 6 N HCl and stirred for 18 h at rt. The phases were separated, and the organic phase was dried by hydrophobic filtration and evaporated. The crude material was purified by column chromatography ($SiO_2$, hexane/ethyl acetate) to yield the title compound (5.6 g, 35%).

$^1H$ NMR (400 MHz, DMSO-d6) δ[ppm]: 1.30 (t, 3H) 2.46 (s, 3H) 2.59-2.74 (m, 2H) 3.07-3.14 (m, 1H) 3.22-3.29 (m, 1H) 3.44-3.53 (m, 1H) 4.30 (q, 2H)

LC-MS (Method 1): $R_t$=1.21 min; MS (ESIpos): m/z=291 $[M+H]^+$

Step 2 ethyl (6±)-5-[(dimethylamino)methylidene]-3-methyl-4-oxo-6-(trifluoromethyl)-4,5,6,7-tetrahydro-1-benzofuran-2-carboxylate

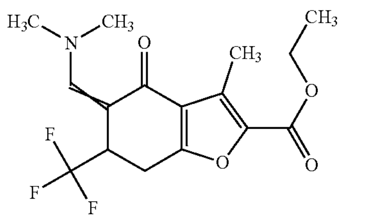 [SMILES: CCOC(=O)c1oc2c(c1C)C(=O)C(=CN(C)C)C(C(F)(F)F)C2]

According to GP A (conditions A) ethyl (6±)-3-methyl-4-oxo-6-(trifluoromethyl)-4,5,6,7-tetrahydro-1-benzofuran-2-carboxylate (1.0 eq, 5.38 g, 18.5 mmol) from step 1 was reacted with 1-tert-butoxy-N,N,N',N'-tetramethylmethanediamine (Bredereck's reagent, CAS No. [5815-08-7]; 1.20 eq., 4.6 ml, 22.0 mmol) in toluene (48 mL) for 9 h at 100° C. The reaction mixture was concentrated under reduced pressure to give the title compound (6.50 g) as a crude material, which was used in the subsequent reaction without further purification steps.

LC-MS (Method 1): $R_t$=1.18 min; MS (ESIpos): m/z=346 $[M+H]^+$

Step 3 ethyl (4±)-8-methyl-4-(trifluoromethyl)-4,5-dihydro-1H-furo[2,3-g]indazole-7-carboxylate

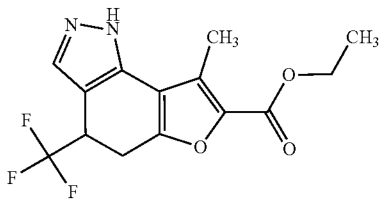 [SMILES: CCOC(=O)c1oc2c(c1C)-c1[nH]ncc1C(C(F)(F)F)C2]

According to GP B ethyl (6±)-5-[(dimethylamino)methylidene]-3-methyl-4-oxo-6-(trifluoromethyl)-4,5,6,7-tetrahydro-1-benzofuran-2-carboxylate (1.0 eq., 6.50 g, 18.8 mmol) from step 2 was reacted with hydrazine hydrate 1:1 (5.0 eq., 4.6 mL, 94 mmol) in ethanol (100 mL) at 70° C. for 5 h. The mixture was evaporated under reduced pressure. To the residue was added ethyl acetate and washed with water. The organic phase was then evaporated, and the residue was purified by column chromatography ($SiO_2$, hexane/ethyl acetate) to give the title compound (840 mg, 14% yield).

$^1H$ NMR (400 MHz, DMSO-d6) δ[ppm]: 1.30 (t, 3H) 2.52 (s, 3H) 3.08-3.14 (m, 1H) 3.30-3.37 (m, 1H) 4.20-4.30 (m, 3H) 7.76 (s, 1H) 12.89 (br.s, 1H)

LC-MS (Method 1): $R_t$=1.11 min; MS (ESIpos): m/z=315 $[M+H]^+$

Step 4 ethyl (4±)-2-{[(2S)-1,4-dioxan-2-yl]methyl}-8-methyl-4-(trifluoromethyl)-4,5-dihydro-2H-furo[2,3-g]indazole-7-carboxylate

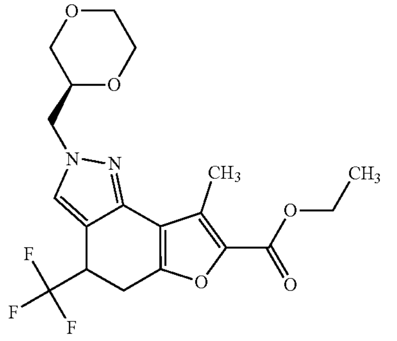 [SMILES: CCOC(=O)c1oc2c(c1C)-c1nn(C[C@H]3COCCO3)cc1C(C(F)(F)F)C2]

According to GP C (conditions A) ethyl (4±)-8-methyl-4-(trifluoromethyl)-4,5-dihydro-1H-furo[2,3-g]indazole-7-carboxylate (1.00 eq., 500 mg, 1.59 mmol) from step 3 was reacted with [(2S)-1,4-dioxan-2-yl]methanol (CAS No [406913-93-7], 1.5 eq., 282 mg, 2.39 mmol), tri-n-butylphosphine (CAS No. [998-40-3]; 1.6 eq., 630 μL, 2.55 mmol) and TMAD (CAS No. [10465-78-8]; 1.6 eq., 438 mg, 2.55 mmol) in toluene (50 ml) at rt overnight. The reaction mixture was filtered and extracted with water. The combined water phase was extracted twice with DCM. The DCM and toluene phase were combined, dried over $Na_2SO_4$, filtered and evaporated to give a crude material which was then purified by column chromatography (Si—NH, hexane/DCM) to give the title compound (559 mg, 85% yield). The material was used in the next step without further purification.

LC-MS (Method 1): $R_t$=1.25 min; MS (ESIpos): m/z=415 $[M+H]^+$

Step 5

(4±)-2-{[(2S)-1,4-dioxan-2-yl]methyl}-8-methyl-4-(trifluoromethyl)-4,5-dihydro-2H-furo[2,3-g]indazole-7-carboxylic acid

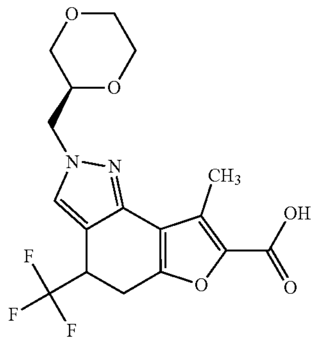 [SMILES: Cc1c(C(=O)O)oc2c1-c1nn(C[C@H]3COCCO3)cc1C(C(F)(F)F)C2]

According to GP D ethyl (4±)-2-{[(2S)-1,4-dioxan-2-yl]methyl}-8-methyl-4-(trifluoromethyl)-4,5-dihydro-2H-furo[2,3-g]indazole-7-carboxylate (1.0 eq, 559 mg, 1.35 mmol) from step 4 was reacted with aqueous lithium hydroxide (2 M; 5 eq, 3.4 mL, 6.7 mmol) in a 1:1 mixture of ethanol (5 mL) and THF (5.0 mL) at 70° C. overnight. Upon acidification (pH 2) with 6 N aqueous hydrochloric acid, the resulting mixture was evaporated. The resulting crude material was dissolved in ethyl acetate (20 ml) and brine (0.5 ml) was added and the mixture was briefly stirred. The phases were separated, and the organic phase was stirred again with brine. The organic phase was evaporated to yield the title compound (430 mg) as a crude yellow solid, which was directly used in the next step without further purification.

LC-MS (Method 1): $R_t$=0.56 min; MS (ESIpos): m/z=387 $[M+H]^+$

Intermediate 82

Step 1 ethyl 6,6-dimethyl-4-oxo-3-(trifluoromethyl)-4,5,6,7-tetrahydro-1-benzofuran-2-carboxylate

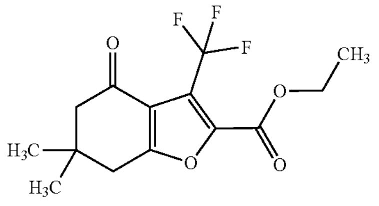 [SMILES: CCOC(=O)c1oc2c(c1C(F)(F)F)C(=O)CC(C)(C)C2]

To a mixture of 5,5-dimethylcyclohexane-1,3-dione (20.0 g, 143 mmol) in toluene (20 ml) was added ethyl 2-chloro-4,4,4-trifluoro-3-oxobutanoate (37.4 g, 171 mmol) at room temperature. The mixture was stirred at 100° C. for 12 h under nitrogen protection. Water was added to the mixture then extracted with ethyl acetate. The organic phase was washed with saturated sodium bicarbonate solution, brine, dried over anhydrous sodium sulphate, filtered and concentrated to give a residue. The residue was purified by column chromatography (1000 mesh, petroleum ether:ethyl acetate=1:0, then 50:1) to give crude ethyl 6,6-dimethyl-4-oxo-3-(trifluoromethyl)-4,5,6,7-tetrahydro-1-benzofuran-2-carboxylate as yellow oil. The crude product was further purified by reversed phase column chromatography (Instrument: Agela-OCTOPUS; Column: Welch Ultimate XB_C18 150*400 mm 20/40 μm; eluent A: water, eluent B: acetonitrile; gradient: 0-105 min 10-58% B; flow 150 ml/min; temperature: room temperature; Detector: UV 220/254 nm) to give ethyl 6,6-dimethyl-4-oxo-3-(trifluoromethyl)-4,5,6,7-tetrahydro-1-benzofuran-2-carboxylate (11.6 g, 27% yield) as yellow oil.

$^1H$ NMR (400 MHz, DMSO-d6) δ[ppm]: 4.36 (q, 2H), 2.94 (s, 2H), 2.49 (s, 2H), 1.30 (t, 3H), 1.07 (s, 6H).

Step 2 ethyl 5-(hydroxymethylidene)-6,6-dimethyl-4-oxo-3-(trifluoromethyl)-4,5,6,7-tetrahydro-1-benzofuran-2-carboxylate

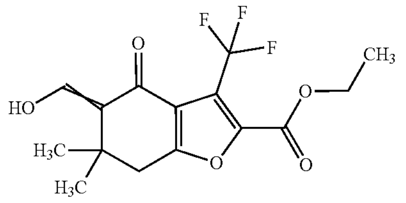 [SMILES: CCOC(=O)c1oc2c(c1C(F)(F)F)C(=O)C(=CO)C(C)(C)C2]

To a solution of sodium hydride (341 mg, 60% purity, 8.55 mmol) in toluene (10 ml) was added a solution of ethyl 6,6-dimethyl-4-oxo-3-(trifluoromethyl)-4,5,6,7-tetrahydro-1-benzofuran-2-carboxylate (1 g, 3.29 mmol) from step 1 and ethyl formate (0.82 ml, 10.2 mmol) in toluene (5 ml) at room temperature. Ethanol (0.19 ml) was added into above mixture and the mixture was stirred at 30° C. for 2 h. The reaction mixture was quenched by 2 N hydrochloric acid (pH-3) and extracted with ethyl acetate. The organic phase was washed with brine, dried over anhydrous sodium sulphate, filtered and concentrated to give crude ethyl 5-(hydroxymethylene)-6,6-dimethyl-4-oxo-3-(trifluoromethyl)-4,5,6,7-tetrahydro-1-benzofuran-2-carboxylate (1.09 g, crude) as brown oil, which was directly used in the next following step without further purification.

Step 3 ethyl 4,4-dimethyl-8-(trifluoromethyl)-4,5-dihydro-2H-furo[2,3-g]indazole-7-carboxylate

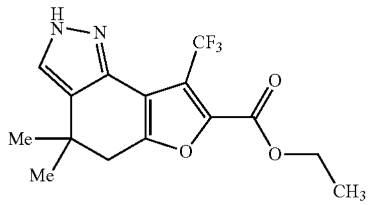 [SMILES: CCOC(=O)c1oc2c(c1C(F)(F)F)-c1n[nH]cc1C(C)(C)C2]

To a mixture of ethyl 5-(hydroxymethylidene)-6,6-dimethyl-4-oxo-3-(trifluoromethyl)-4,5,6,7-tetrahydro-1-benzofuran-2-carboxylate (8.50 g, 25.6 mmol) from step 2 in ethanol (80 ml) was added a solution of hydrazine dihydrochloride (4.03 g, 38.4 mmol) in water (15 ml) at 25° C. The mixture was stirred at 40° C. for 2 h. The mixture was concentrated to give a residue. The residue was adjusted to pH ~9 with saturated sodium carbonate and extracted with ethyl acetate. The organic phase was washed with brine, dried over anhydrous sodium sulphate, filtered and concentrated to give a residue. The residue was purified by column chromatography (100-200 mesh, petroleum ether:ethyl acetate=20:1 then 1:1) to give ethyl 4,4-dimethyl-8-(trifluoromethyl)-4,5-dihydro-2H-furo[2,3-g]indazole-7-carboxylate (540 mg, 92% purity, 6% yield) as a white solid.

$^1$H NMR (400 MHz, DMSO-d6) δ[ppm]: 12.69 (s, 1H), 7.63 (s, 1H), 4.36 (q, 2H), 2.84 (s, 2H), 1.30 (t, 3H), 1.22 (s, 6H).

LC-MS (Method B): $R_t$=0.802 min; MS (ESIpos): m/z=329.0 $[M+H]^+$.

Step 4 ethyl 2-{[(2S)-1,4-dioxan-2-yl]methyl}-4,4-dimethyl-8-(trifluoromethyl)-4,5-dihydro-2H-furo[2,3-g]indazole-7-carboxylate

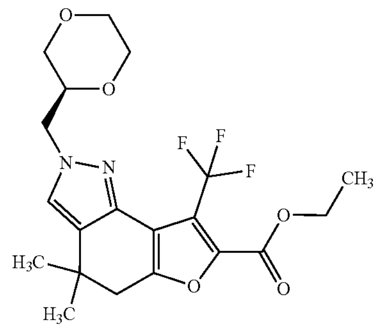 [SMILES: CCOC(=O)c1oc2c(c1C(F)(F)F)-c1nn(C[C@H]3COCCO3)cc1C(C)(C)C2]

Ethyl 4,4-dimethyl-8-(trifluoromethyl)-4,5-dihydro-1H-furo[2,3-g]indazole-7-carboxylate (250 mg, 762 μmol) from step 3 and caesium carbonate (744 mg, 2.29 mmol; CAS-RN:[534-17-8]) were added to 1,4-dioxane (10 ml). Then [(2R)-1,4-dioxan-2-yl]methyl methanesulfonate (269 mg, 1.37 mmol) was added to the mixture and stirred for 48 h at 100° C. After cooling the mixture to rt, the reaction mixture was diluted with ethyl acetate and water. The ethyl acetate phase was dried and evaporated to yield the title compound (356 mg) as a crude brown oil.

LC-MS (Method 1): $R_t$=1.33 min; MS (ESIpos): m/z=429 $[M+H]^+$

Step 5

2-{[(2S)-1,4-dioxan-2-yl]methyl}-4,4-dimethyl-8-(trifluoromethyl)-4,5-dihydro-2H-furo[2,3-g]indazole-7-carboxylic acid

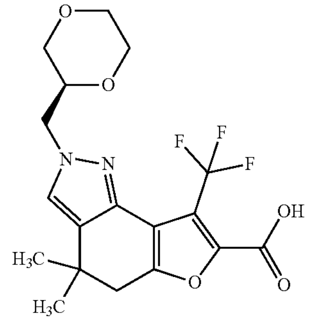 [SMILES: CC1(C)Cc2oc(C(=O)O)c(C(F)(F)F)c2-c2nn(C[C@H]3COCCO3)cc21]

According to GP D ethyl 2-{[(2S)-1,4-dioxan-2-yl]methyl}-4,4-dimethyl-8-(trifluoromethyl)-4,5-dihydro-2H-furo[2,3-g]indazole-7-carboxylate (350 mg, 817 μmol, intermediate 82 (step 4) was dissolved in a mixture of tetrahydrofuran (6.3 mL) and ethanol (6.3 mL) and an aqueous lithium hydroxide solution (2.0 ml, 2.0 M, 4.1 mmol; CAS-RN:[1310-65-2]) was added. The reaction mixture was stirred at 70° C. overnight. The reaction mixture was cooled down to rt and diluted with dichloromethane. After neutralization with aqueous hydrogen chloride solution (6 M) to pH 4, the reaction mixture was concentrated in vacuo. The residue was treated with dichloromethane (50 mL) and brine (0.5 mL) and stirred for 1 h at rt. 2-propanol (0.5 mL) was then added to the stirring mixture and further stirred for 1 h at rt. The phases were separated, and the organic phase was filtered, and the filtrate was evaporated under reduced pressure to give the title compound (287 mg) as a crude light yellowish foam, which was used in the following step without further purification.

LC-MS (Method 1): $R_t$=0.59 min; MS (ESIpos): m/z=401 $[M+H]^+$

Intermediate 83

Step 1 ethyl 4-oxo-3-(trifluoromethyl)-4,7-dihydro-5H-spiro[[1]benzofuran-6,1'-cyclobutane]-2-carboxylate

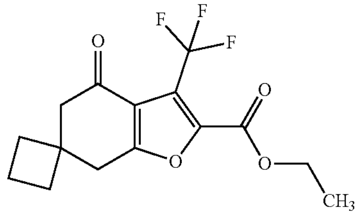 [SMILES: CCOC(=O)c1oc2c(c1C(F)(F)F)C(=O)CC1(CCC1)C2]

Spiro[3.5]nonane-6,8-dione (1.00 g, 6.57 mmol; CAS-RN:[221342-48-9]), ethyl 2-chloro-4,4,4-trifluoro-3-oxobutanoate (1.0 ml, 6.6 mmol; CAS-RN:[363-58-6]) and triethylamine (1.4 ml, 9.9 mmol; CAS-RN:[121-44-8]) were dissolved in dioxane (2.0 mL) and stirred at 100° C. overnight. The reaction mixture was concentrated in vacuo and the crude material was purified by Biotage Isolera™ chromatography (SNAP KP-Sil—10 g, eluting with hexane-ethyl acetate, 1:0 to 4:1) to afford 270 mg (12% yield, 93% purity) of the title compound.

$^1$H NMR (400 MHz, DMSO-d6) δ[ppm]: 1.30 (t, 3H), 1.80-1.96 (m, 6H), 2.71 (s, 2H), 3.18 (s, 2H), 4.36 (q, 2H).

LC-MS (Method 1): $R_t$=1.32 min; MS (ESIpos): m/z=317 $[M+H]^+$

Step 2 ethyl 5-(hydroxymethylidene)-4-oxo-3-(trifluoromethyl)-4,7-dihydro-5H-spiro[[1]benzofuran-6,1'-cyclobutane]-2-carboxylate

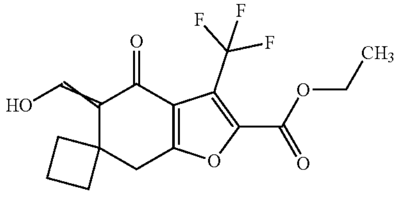 [SMILES: CCOC(=O)c1oc2c(c1C(F)(F)F)C(=O)C(=CO)C1(CCC1)C2]

According to GP A (conditions B), to a suspension of sodium hydride (439 mg, 60% purity, 11.0 mmol; CAS-RN: [7646-69-7]) in toluene (7.3 mL) was added ethyl 4-oxo-3-(trifluoromethyl)-4,7-dihydro-5H-spiro[[1]benzofuran-6,1'-cyclobutane]-2-carboxylate (1.16 g, 3.65 mmol, intermediate 83 (step 1)) at 0° C. After stirring for 30 minutes at rt, the mixture was recooled to 0° C. and ethyl formate (1.5 ml, 18 mmol; CAS-RN:[109-94-4]) was added. The reaction mixture was stirred overnight at room temperature before ethyl acetate (150 mL) and 4 N HCl (40 mL, portionwise) were added. After phase separation the organic layer was washed with brine, filtered over a water-free filter and concentrated in vacuo to afford 1.43 g (crude) of the title compound.

LC-MS (Method 2): $R_t$=1.45 min; MS (ESIpos): m/z=345 $[M+H]^+$

Step 3 ethyl 8'-(trifluoromethyl)-2',5'-dihydrospiro[cyclobutane-1,4'-furo[2,3-g]indazole]-7'-carboxylate

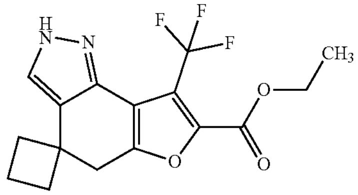 [SMILES: CCOC(=O)c1oc2c(c1C(F)(F)F)-c1n[nH]cc1C1(CCC1)C2]

To a mixture of ethyl 5-(hydroxymethylidene)-4-oxo-3-(trifluoromethyl)-4,7-dihydro-5H-spiro[[1]benzofuran-6,1'-cyclobutane]-2-carboxylate (1.40 g, 4.07 mmol, intermediate 83 (step 2)) in ethanol (12 mL) was added a solution of hydrazine monohydrochloride (362 mg, 5.29 mmol; CAS No [2644-70-4]) in water (5.0 ml) at 25° C. The mixture was stirred at 70° C. for 1 h. The mixture was added to saturated sodium bicarbonate solution at 0° C. and then extracted with dichloromethane. The combined organic layers were washed with brine, filtered and concentrated under reduced pressure to afford 1.11 g (71% yield, 89% purity) of the title compound.

$^1$H NMR (400 MHz, DMSO-d6) δ[ppm]: 1.31 (t, 3H), 1.92-2.06 (m, 2H), 2.08-2.16 (m, 4H), 3.14 (s, 2H), 4.34 (q, 2H), 7.86 (d, 1H), 12.71 (s, 1H).

LC-MS (Method 1): $R_t$=1.27 min; MS (ESIpos): m/z=341 $[M+H]^+$.

Step 4 ethyl 2'-{[(2S)-1,4-dioxan-2-yl]methyl}-8'-(trifluoromethyl)-2',5'-dihydrospiro[cyclobutane-1,4'-furo[2,3-g]indazole]-7'-carboxylate

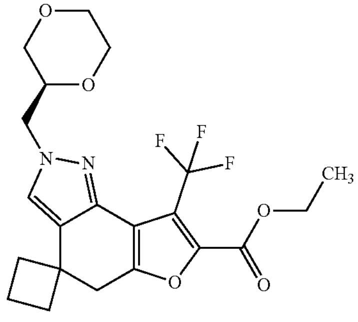 [SMILES: CCOC(=O)c1oc2c(c1C(F)(F)F)-c1nn(C[C@H]3COCCO3)cc1C1(CCC1)C2]

According to GP C (conditions A) ethyl 8'-(trifluoromethyl)-1',5'-dihydrospiro[cyclobutane-1,4'-furo[2,3-g]indazole]-7'-carboxylate (250 mg, 735 μmol, intermediate 83 (step 3)) and [(2S)-1,4-dioxan-2-yl]methanol (130 mg, 1.10 mmol, CAS-RN:[406913-93-7]) were suspended in toluene with (4.2 mL) together TMAD (202 mg, 1.18 mmol; CAS No. [10465-78-8]). Carefully tri-n-butylphosphine (290 μl, 1.2 mmol, CAS No. [998-40-3]) was added and the reaction mixture stirred at rt overnight. Water was added to the reaction mixture and then concentrated in vacuo. The residue was diluted with 1 ml acetonitrile and purified by preparative HPLC (Method A, gradient E). The product fractions were pooled and concentrated in vacuo to afford 60.0 mg (17% yield, 90% purity) of the title compound.

$^1$H NMR (400 MHz, DMSO-d6) δ[ppm]: 1.31 (t, 3H), 2.00-2.17 (m, 6H), 3.15 (s, 2H), 3.28 (dd, 1H), 3.41-3.49 (m, 1H), 3.51-3.59 (m, 1H), 3.63 (br d, 1H), 3.75 (dt, 2H), 3.82-3.91 (m, 1H), 4.09-4.15 (m, 2H), 4.34 (q, 2H), 7.82 (s, 1H).

LC-MS (Method 1): $R_t$=1.38 min; MS (ESIpos): m/z=441 $[M+H]^+$

Step 5

2'-{[(2S)-1,4-dioxan-2-yl]methyl}-8'-(trifluoromethyl)-2',5'-dihydrospiro[cyclobutane-1,4'-furo[2,3-g]indazole]-7'-carboxylic acid

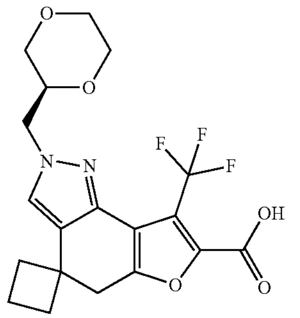 [SMILES: O=C(O)c1oc2c(c1C(F)(F)F)-c1nn(C[C@H]3COCCO3)cc1C1(CCC1)C2]

According to GP D ethyl 2'-{[(2S)-1,4-dioxan-2-yl]methyl}-8'-(trifluoromethyl)-2',5'-dihydrospiro[cyclobutane-1,4'-furo[2,3-g]indazole]-7'-carboxylate (60.0 mg, 136 μmol, intermediate 83 (step 4)) was reacted with aqueous lithium hydroxide (680 μl, 2.0 M, 1.4 mmol) in THF (1.6 ml) at rt overnight. After stirring for further 1 h at 30° C., the reaction mixture was acidified with aqueous 2 N HCl (pH 2) and stirred for 30 minutes. The precipitate was collected by filtration and used in the next step without further purification 57.2 mg (91% purity, 93% yield).

$^1$H NMR (500 MHz, DMSO-d6) δ[ppm]: 2.01-2.17 (m, 6H), 3.12 (s, 2H), 3.28 (dd, 1H), 3.45 (td, 1H), 3.55 (td, 1H), 3.58-3.61 (m, 1H), 3.63 (br d, 1H), 3.75 (dt, 2H), 3.83-3.90 (m, 1H), 4.08-4.16 (m, 2H), 7.81 (s, 1H), 13.58-14.28 (m, 1H).

LC-MS (Method 2): $R_t$=1.04 min; MS (ESIpos): m/z=413 $[M+H]^+$

Intermediate 84

Step 1 ethyl 2'-[(pyridin-2-yl)methyl]-8'-(trifluoromethyl)-2',5'-dihydrospiro[cyclobutane-1,4'-furo[2,3-g]indazole]-7'-carboxylate

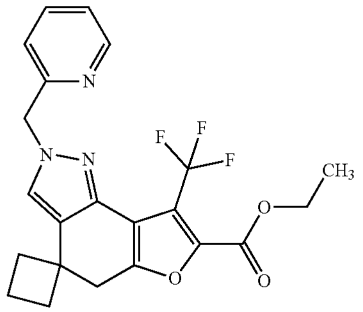 [SMILES: CCOC(=O)c1oc2c(c1C(F)(F)F)-c1nn(Cc3ccccn3)cc1C1(CCC1)C2]

According to GP C (conditions A) ethyl 8'-(trifluoromethyl)-1',5'-dihydrospiro[cyclobutane-1,4'-furo[2,3-g]indazole]-7'-carboxylate (70.0 mg, 206 μmol, intermediate 83 (step 3)) and (pyridin-2-yl)methanol (33.7 mg, 309 μmol; CAS-RN:[586-98-1]) were suspended in toluene with (1.2 mL) together TMAD (56.7 mg, 329 μmol; CAS No. [10465-78-8]). Carefully tri-n-butylphosphine (82 μl, 330 μmol, CAS No. [998-40-3]) was added and the reaction mixture stirred at rt overnight. Water was added to the reaction mixture and then concentrated in vacuo. The crude material was purified by Biotage Isolera™ chromatography (SNAP KP-Sil—10 g, eluting with hexane-ethyl acetate, 1:0 to 1:1) to afford 52.6 mg (59% yield, 99% purity) of the title compound.

$^1$H NMR (400 MHz, DMSO-d6) δ[ppm]: 1.31 (t, 3H), 1.87-1.98 (m, 1H), 2.03-2.18 (m, 5H), 3.17 (s, 2H), 4.34 (q, 2H), 5.42 (s, 2H), 7.09 (d, 1H), 7.32 (ddd, 1H), 7.79 (td, 1H), 7.99 (s, 1H), 8.49-8.58 (m, 1H).

LC-MS (Method 1): $R_t$=1.39 min; MS (ESIpos): m/z=432 $[M+H]^+$

Step 2

2'-[(pyridin-2-yl)methyl]-8'-(trifluoromethyl)-2',5'-dihydrospiro[cyclobutane-1,4'-furo[2,3-g]indazole]-7'-carboxylic acid

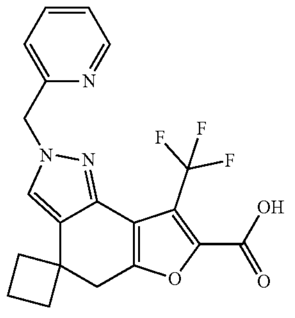 [SMILES: O=C(O)c1oc2c(c1C(F)(F)F)-c1nn(Cc3ccccn3)cc1C1(CCC1)C2]

According to GP D ethyl 2'-[(pyridin-2-yl)methyl]-8'-(trifluoromethyl)-2',5'-dihydrospiro[cyclobutane-1,4'-furo

[2,3-g]indazole]-7'-carboxylate (58.0 mg, 134 μmol, intermediate 84 (step 1)) was reacted with aqueous lithium hydroxide 670 μl, 2.0 M, 1.3 mmol; CAS-RN:[1310-65-2]) in THF (1.5 ml) for 1 h at 50° C. The reaction mixture was acidified with aqueous 4 N HCl (pH 2) and stirred for 30 minutes. The precipitate was collected by filtration and used in the next step without further purification (50.2 mg, 92% purity, 99% yield).

$^{1}H$ NMR (500 MHz, DMSO-d6) δ[ppm]: 1.89-1.98 (m, 1H), 2.01-2.18 (m, 5H), 3.14 (s, 2H), 5.47 (s, 2H), 7.16 (d, 1H), 7.42 (dd, 1H), 7.86-7.93 (m, 1H), 8.00 (s, 1H), 8.61 (d, 1H), 13.97 (br s, 1H).

LC-MS (Method 1): $R_t$=0.66 min; MS (ESIpos): m/z=404 $[M+H]^+$

Intermediate 85

Step 1 ethyl 2'-[(5-methylpyridin-2-yl)methyl]-8'-(trifluoromethyl)-2',5'-dihydrospiro[cyclobutane-1,4'-furo[2,3-g]indazole]-7'-carboxylate

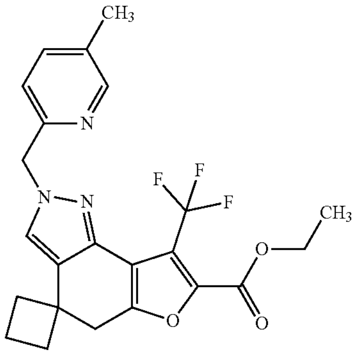 [SMILES: CCOC(=O)c1oc2c(c1C(F)(F)F)-c1nn(Cc3ccc(C)cn3)cc1C1(CCC1)C2]

According to GP C (conditions A) ethyl 8'-(trifluoromethyl)-2',5'-dihydrospiro[cyclobutane-1,4'-furo[2,3-g]indazole]-7'-carboxylate (250 mg, 735 μmol, intermediate 83 (step 3)) and (5-methylpyridin-2-yl)methanol (136 mg, 1.10 mmol, CAS-RN:[22940-71-2]) were suspended in toluene with (4.2 mL) together TMAD (202 mg, 1.18 mmol; CAS No. [10465-78-8]). Carefully tri-n-butylphosphine (290 μl, 1.2 mmol, CAS No. [998-40-3]) was added and the reaction mixture stirred at rt overnight. Water was added to the reaction mixture and then concentrated in vacuo. The residue was diluted with 1 ml acetonitrile and purified by preparative HPLC (Method A, gradient E). The product fractions were pooled and concentrated in vacuo to afford 102.0 mg (20% yield, 65% purity) of the title compound.

LC-MS (Method 1): $R_t$=1.41 min; MS (ESIpos): m/z=446 $[M+H]^+$

Step 2

2'-[(5-methylpyridin-2-yl)methyl]-8'-(trifluoromethyl)-2',5'-dihydrospiro[cyclobutane-1,4'-furo[2,3-g]indazole]-7'-carboxylic acid

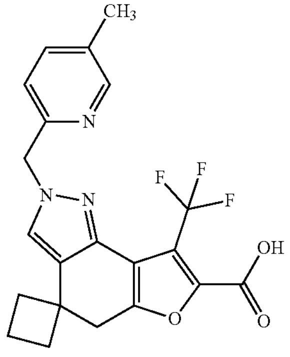 [SMILES: Cc1ccc(Cn2cc3c(n2)-c2c(oc(C(=O)O)c2C(F)(F)F)CC32CCC2)nc1]

According to GP D ethyl 2'-[(5-methylpyridin-2-yl)methyl]-8'-(trifluoromethyl)-2',5'-dihydrospiro[cyclobutane-1,4'-furo[2,3-g]indazole]-7'-carboxylate (102 mg, 229 μmol, intermediate 85 (step 1)) was reacted with aqueous lithium hydroxide (1.1 ml, 2.0 M, 2.3 mmol; CAS-RN: [1310-65-2]) in THF (2.6 ml) overnight at rt. The reaction mixture was acidified with aqueous 4 N HCl (pH 2) and stirred for 30 minutes. After concentration in vacuo the product was used in the next step without further purification (90.0 mg, 75% purity, 80% yield).

LC-MS (Method 2): $R_t$=1.06 min; MS (ESIpos): m/z=418 $[M+H]^+$

Intermediate 86

Step 1 ethyl 2'-[(pyridin-4-yl)methyl]-8'-(trifluoromethyl)-2',5'-dihydrospiro[cyclobutane-1,4'-furo[2,3-g]indazole]-7'-carboxylate

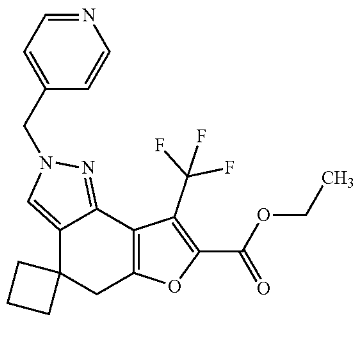 [SMILES: CCOC(=O)c1oc2c(c1C(F)(F)F)-c1nn(Cc3ccncc3)cc1C1(CCC1)C2]

According to GP C (conditions A) ethyl 8'-(trifluoromethyl)-2',5'-dihydrospiro[cyclobutane-1,4'-furo[2,3-g]indazole]-7'-carboxylate (300 mg, 564 μmol, intermediate 83 (step 3)) and (pyridin-4-yl)methanol (92.4 mg, 846 μmol, CAS-RN:[586-95-8]) were suspended in toluene with (3.2 mL) together TMAD (155 mg, 903 μmol; CAS No. [10465-78-8]). Carefully tri-n-butylphosphine (220 μl, 900 μmol; CAS No. [998-40-3]) was added and the reaction mixture stirred at rt overnight. Water was added to the reaction mixture and then concentrated in vacuo. The residue was diluted with 1 ml acetonitrile and purified by preparative HPLC (Method A, gradient E). The product fractions were pooled and concentrated in vacuo to afford 189.0 mg (78% yield) of the title compound.

LC-MS (Method 1): $R_t$=1.33 min; MS (ESIpos): m/z=432 $[M+H]^+$

Step 2

2'-[(pyridin-4-yl)methyl]-8'-(trifluoromethyl)-2',5'-dihydrospiro[cyclobutane-1,4'-furo[2,3-g]indazole]-7'-carboxylic acid

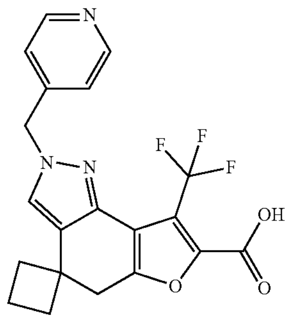 [SMILES: O=C(O)c1oc2c(c1C(F)(F)F)-c1nn(Cc3ccncc3)cc1C1(CCC1)C2]

According to GP D ethyl 2'-[(pyridin-4-yl)methyl]-8'-(trifluoromethyl)-2',5'-dihydrospiro[cyclobutane-1,4'-furo [2,3-g]indazole]-7'-carboxylate (189 mg, 438 μmol, intermediate 86 (step 1)) was reacted with aqueous lithium hydroxide (2.2 ml, 2.0 M, 4.4 mmol; CAS-RN:[1310-65-2]) in THF (5.0 ml) overnight at rt. The reaction mixture was acidified with aqueous 4 N HCl (pH 2) and stirred for 30 minutes. After concentration in vacuo to half the volume, the residue was lyophilized. The residue was diluted with 1 ml acetonitrile and purified by preparative HPLC (Method B, gradient B). The product fractions were pooled and concentrated in vacuo to afford 43.3 mg (17% yield, 63% purity) of the title compound.

$^1$H NMR (400 MHz, DMSO-d6) δ[ppm]: 1.90-2.18 (m, 6H), 3.14 (s, 2H), 5.39 (s, 2H), 7.14-7.17 (m, 2H), 8.00 (s, 1H), 8.52-8.56 (m, 2H), 13.95 (br s, 1H) LC-MS (Method 2): $R_t$=0.88 min; MS (ESIpos): m/z=404 $[M+H]^+$ Intermediate 87

Step 1 ethyl 2-(cyclopropylmethyl)-8-(trifluoromethyl)-4,5-dihydro-2H-furo[2,3-g]indazole-7-carboxylate

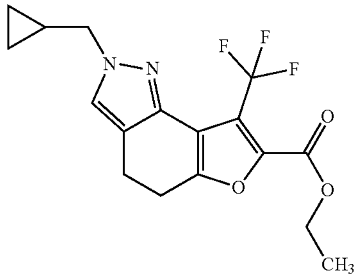 [SMILES: CCOC(=O)c1oc2c(c1C(F)(F)F)-c1nn(CC3CC3)cc1CC2]

According to GP C (conditions A) ethyl 8-(trifluoromethyl)-4,5-dihydro-1H-furo[2,3-g]indazole-7-carboxylate (1.00 eq., 100 mg, 333 μmol) from Intermediate 35 step 4 was reacted with cyclopropylmethanol (CAS No [2516-33-8], 1.5 eq., 36.0 mg, 500 μmol), tri-n-butylphosphine (CAS No. [998-40-3]; 1.6 eq., 130 μL, 530 μmol) and TMAD (CAS No. [10465-78-8]; 1.6 eq., 150 μg, 530 μmol) in toluene (8.0 ml) at rt overnight. The reaction mixture was extracted with water twice. The combined water phase was extracted three times with DCM. The DCM and toluene phase were combined, dried with NaCl, filtered and evaporated. The crude material was purified by column chromatography ($SiO_2$, hexane/EtOAc) to give the title compound (78 mg, 66% yield).

LC-MS (Method 1): $R_t$=1.38 min; MS (ESIpos): m/z=355 $[M+H]^+$

Step 2

2-(cyclopropylmethyl)-8-(trifluoromethyl)-4,5-dihydro-2H-furo[2,3-g]indazole-7-carboxylic acid

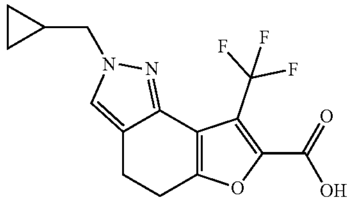 [SMILES: O=C(O)c1oc2c(c1C(F)(F)F)-c1nn(CC3CC3)cc1CC2]

According to GP D ethyl 2-(cyclopropylmethyl)-8-(trifluoromethyl)-4,5-dihydro-2H-furo[2,3-g]indazole-7-carboxylat (1.0 eq, 78.0 mg, 220 μmol) from step 1 was reacted with aqueous lithium hydroxide (2 M; 5 eq, 550 μL, 1.1 mmol) in a 1:1 mixture of ethanol and THF (5.0 mL) at 70° C. overnight. Upon acidification (pH 2) with 6 N aqueous hydrochloric acid, the resulting mixture was evaporated under reduced pressure. To the residue was added DCM (30 ml), water (20 ml) and i-PrOH (4×2 ml) and stirred for 1 h at rt. The phases were separated and the water phase was extracted with three times with DCM. The combined DCM phase was washed with brine, dried over a hydrophobic filter paper and evaporated to give the title compound (62.0 mg, 86% yield).

$^1$H NMR (400 MHz, DMSO-d6) δ[ppm]: 0.33-0.37 (m, 2H) 0.48-0.54 (m, 2H) 1.15-1.20 (m, 1H) 2.84-2.88 (m, 2H) 2.94-2.98 (m, 2H) 3.92 (d, 2H) 7.61 (s, 1H) 13.73-14.07 (br. s, 1H) LC-MS (Method 1): $R_t$=0.60 min; MS (ESIpos): m/z=327 $[M+H]^+$ Intermediate 88

Step 1 ethyl 2-{[1-(tert-butoxycarbonyl)piperidin-4-yl] methyl}-8-(trifluoromethyl)-4,5-dihydro-2H-furo[2,3-g]indazole-7-carboxylate

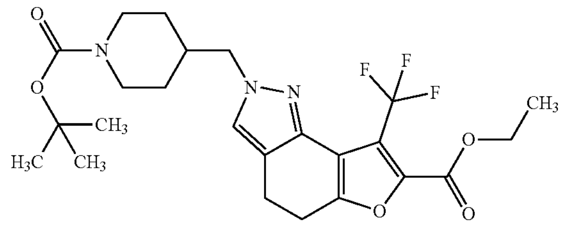 [SMILES: CCOC(=O)c1oc2c(c1C(F)(F)F)-c1nn(CC3CCN(C(=O)OC(C)(C)C)CC3)cc1CC2]

Ethyl 8-(trifluoromethyl)-4,5-dihydro-1H-furo[2,3-g]indazole-7-carboxylate (1.0 eq., 1.71 g, 5.70 mmol) from Intermediate 35 step 4 was reacted with tert-butyl 4-{[(trifluoromethanesulfonyl)oxy]methyl}piperidine-1-carboxylate (1.8 eq., 3.75 g, 95% purity, 10.3 mmol), caesium carbonate (3 eq., 5.57 g, 17.1 mmol) in acetonitrile (41 mL) for 18 h at rt. The mixture was poured into ethyl acetate (50 ml) and water (20 ml). The phases were separated and the ethyl acetate phase was washed with brine (20 ml) and dried over a hydrophobic filter paper. The filtrate was evaporated to give upon column chromatography ($SiO_2$, hexane/ethyl acetate) the title compound (1.26 g, 44% yield).

LC-MS (Method 1): $R_t$=1.51 min; MS (ESIpos): m/z=440 $[M-tBu]^+$

Step 2 ethyl 2-[(piperidin-4-yl)methyl]-8-(trifluoromethyl)-4,5-dihydro-2H-furo[2,3-g]indazole-7-carboxylate (HCl salt)

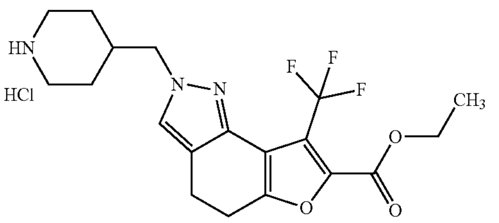 [SMILES: Cl ; CCOC(=O)c1oc2c(c1C(F)(F)F)-c1nn(CC3CCNCC3)cc1CC2]

To ethyl 2-{[1-(tert-butoxycarbonyl)piperidin-4-yl] methyl}-8-(trifluoromethyl)-4,5-dihydro-2H-furo[2,3-g]indazole-7-carboxylate (1.0 eq, 1.26 g, 2.53 mmol) from step 1 in 1,4-dioxane (14 ml) was added HCl in 1,4-dioxane (10.0 eq, 6.3 ml, 4.0 M, 25.0 mml) and stirred for 18 h at rt. The reaction mixture was evaporated under reduced pressure. To the residue was added DCM (20 ml) and further evaporated under reduced pressure to give the title compound (900 mg) as a crude material, which was used in the next step without further purification.

LC-MS (Method 1): $R_t$=1.19 min; MS (ESIpos): m/z=398 $[M+H]^+$

Step 3 ethyl 2-{[1-(methoxyacetyl)piperidin-4-yl]methyl}-8-(trifluoromethyl)-4,5-dihydro-2H-furo[2,3-g]indazole-7-carboxylate

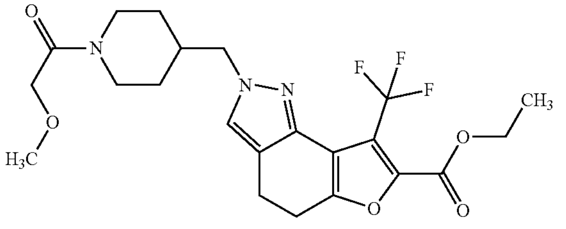 [SMILES: CCOC(=O)c1oc2c(c1C(F)(F)F)-c1nn(CC3CCN(C(=O)COC)CC3)cc1CC2]

A solution of ethyl 2-[(piperidin-4-yl)methyl]-8-(trifluoromethyl)-4,5-dihydro-2H-furo[2,3-g]indazole-7-carboxylate (1.0 eq., 250 mg, 629 µmol, as HCl salt) from Intermediate 88 step 2 was suspended in DCM (3.0 ml). To the reaction, triethylamine (CAS No [121-44-8], 2.5 eq., 220 µl, 1.6 mmol) followed by methoxyacetyl chloride (CAS No [38870-89-2], 1.1 eq., 63 µl, 690 µmol) were added and the resulting mixture was stirred for 5 h at rt. The reaction mixture was evaporated and to the residue were added hexane/ethyl acetate (95:5, 10 ml) and DCM (300 µl) while stirring. The solid was collected by suction and washed with hexane/ethyl acetate (95:5, 2× 1 ml) to yield the title compound (362 mg) as a crude solid, which was used in the following step without further purification.

LC-MS (Method 1): $R_t$=1.18 min; MS (ESIpos): m/z=470 $[M+H]^+$

Step 4

2-{[1-(methoxyacetyl)piperidin-4-yl]methyl}-8-(trifluoromethyl)-4,5-dihydro-2H-furo[2,3-g]indazole-7-carboxylic acid

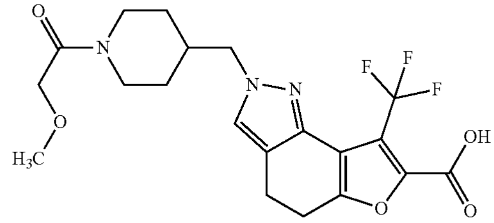 [SMILES: COCC(=O)N1CCC(Cn2cc3c(n2)-c2c(oc(C(=O)O)c2C(F)(F)F)CC3)CC1]

Ethyl 2-{[1-(methoxyacetyl)piperidin-4-yl]methyl}-8-(trifluoromethyl)-4,5-dihydro-2H-furo[2,3-g]indazole-7-carboxylate (1.00 eq., 360 mg, 767 µmol) from step 3 was reacted with aqueous lithium hydroxide (2 M; 2.0 eq., 770 µL, 1.5 mmol) in THF (3.00 mL) and methanol (3.0 ml) at rt for 18 h, and then at 55° C. for 5 h. To the reaction mixture, additional aqueous lithium hydroxide (2 M; 2.0 eq., 770 µL, 1.5 mmol) was added and further stirred for 18 h at 60° C. The reaction mixture was cooled down to rt, acidified with aqueous 6 N HCl to pH2 and the resulting mixture was evaporated under reduced pressure. Following co-distillation of the residue with THF (2×25 ml), the title compound (626 mg) was obtained as a crude material, which was directly used in the next step without further purification.

LC-MS (Method 1): $R_t$=0.56 min; MS (ESIpos): m/z=442 $[M+H]^+$

Intermediate 89

Step 1 ethyl 2-{[1-(cyclopropanecarbonyl)piperidin-4-yl]methyl}-8-(trifluoromethyl)-4,5-dihydro-2H-furo[2,3-g]indazole-7-carboxylate

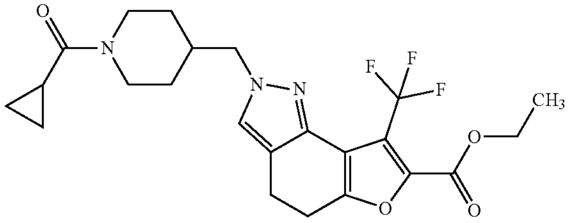 [SMILES: CCOC(=O)c1oc2c(c1C(F)(F)F)-c1nn(CC3CCN(C(=O)C4CC4)CC3)cc1CC2]

A solution of ethyl 2-[(piperidin-4-yl)methyl]-8-(trifluoromethyl)-4,5-dihydro-2H-furo[2,3-g]indazole-7-carboxylate (1.0 eq., 250 mg, 629 μmol, as a HCl salt) from Intermediate 88 step 2 was suspended in DCM (3.0 ml). To the reaction, triethylamine (CAS No [121-44-8], 2.5 eq., 220 μl, 1.6 mmol) followed by cyclopropanecarbonyl chloride (CAS No [4023-34-1], 1.1 eq., 63 μl, 690 μmol) were added and the resulting mixture was stirred for 5 h at rt. The reaction mixture was evaporated and to the residue were added hexane/ethyl acetate (95:5, 10 ml) and DCM (300 μl) while stirring. The solid was collected by suction and washed with hexane/ethyl acetate (95:5, 2× 1 ml) to yield the title compound (370 mg) as a crude solid, which was used in the following step without further purification.

LC-MS (Method 1): $R_t$=1.28 min; MS (ESIpos): m/z=466 $[M+H]^+$

Step 2

2-{[1-(cyclopropanecarbonyl)piperidin-4-yl]methyl}-8-(trifluoromethyl)-4,5-dihydro-2H-furo[2,3-g]indazole-7-carboxylic acid

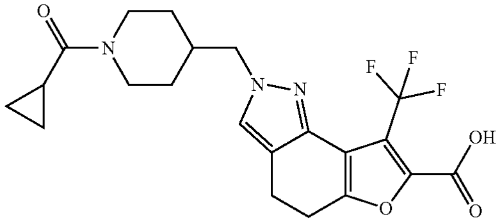 [SMILES: O=C(O)c1oc2c(c1C(F)(F)F)-c1nn(CC3CCN(C(=O)C4CC4)CC3)cc1CC2]

Ethyl 2-{[1-(cyclopropanecarbonyl)piperidin-4-yl]methyl}-8-(trifluoromethyl)-4,5-dihydro-2H-furo[2,3-g]indazole-7-carboxylate (1.00 eq., 370 mg, 795 μmol) from step 1 was reacted with aqueous lithium hydroxide (2 M; 2.0 eq., 795 μL, 1.6 mmol) in THF (820 μL) and methanol (820 μl) at rt for 18 h and then at 55° C. for 5 h. To the reaction mixture, additional aqueous lithium hydroxide (2 M; 2.0 eq., 795 μL, 1.6 mmol) was added and further stirred for 18 h at 60° C. The reaction mixture was cooled down to rt, acidified with aqueous 6 N HCl to pH2 and the resulting mixture was evaporated under reduced pressure. Following co-distillation of the residue with THF (2×25 ml), the title compound (447 mg) was obtained as a crude material, which was directly used in the next step without further purification.

LC-MS (Method 1): $R_t$=0.61 min; MS (ESIpos): m/z=438 $[M+H]^+$

Intermediate 90

Step 1 ethyl 2-[(1-benzoylpiperidin-4-yl)methyl]-8-(trifluoromethyl)-4,5-dihydro-2H-furo[2,3-g]indazole-7-carboxylate

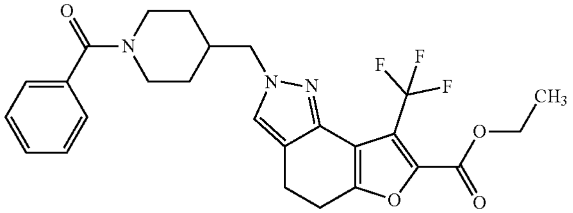 [SMILES: CCOC(=O)c1oc2c(c1C(F)(F)F)-c1nn(CC3CCN(C(=O)c4ccccc4)CC3)cc1CC2]

A solution of ethyl 2-[(piperidin-4-yl)methyl]-8-(trifluoromethyl)-4,5-dihydro-2H-furo[2,3-g]indazole-7-carboxylate (1.0 eq., 250 mg, 629 μmol, as a HCl salt) from Intermediate 88 step 2 was suspended in DCM (3.0 ml). To the reaction, triethylamine (CAS No [121-44-8], 2.5 eq., 220 μl, 1.57 mmol) followed by benzoyl chloride (CAS No [98-88-4], 1.1 eq., 80 μl, 690 μmol) were added and the resulting mixture was stirred for 5 h at rt. The reaction mixture was evaporated and to the residue were added hexane/ethyl acetate (95:5, 10 ml) and DCM (300 μl) while stirring. The solid was collected by suction and washed with hexane/ethyl acetate (95:5, 2× 1 ml) to yield the title compound (340 mg) as a crude solid, which was used in the following step without further purification.

LC-MS (Method 1): $R_t$=1.35 min; MS (ESIpos): m/z=502 $[M+H]^+$

Step 2

2-[(1-benzoylpiperidin-4-yl)methyl]-8-(trifluoromethyl)-4,5-dihydro-2H-furo[2,3-g]indazole-7-carboxylic acid

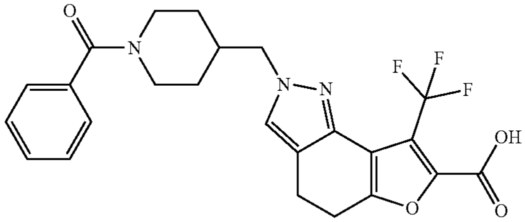 [SMILES: O=C(O)c1oc2c(c1C(F)(F)F)-c1nn(CC3CCN(C(=O)c4ccccc4)CC3)cc1CC2]

Ethyl 2-[(1-benzoylpiperidin-4-yl)methyl]-8-(trifluoromethyl)-4,5-dihydro-2H-furo[2,3-g]indazole-7-carboxylate (1.00 eq., 340 mg, 678 μmol) from step 1 was reacted with aqueous lithium hydroxide (2 M; 2.0 eq., 680 μL, 1.36 mmol) in THF (700 μL) and methanol (700 μl) at rt for 18 h, and then at 55° C. for 5 h. To the reaction mixture, additional aqueous lithium hydroxide (2 M; 2.0 eq., 680 μL, 1.36 mmol) was added and further stirred for 18 h at 60° C. The reaction mixture was cooled down to rt, acidified with aqueous 6 N HCl to pH2 and the resulting mixture was evaporated under reduced pressure. Following co-distillation of the residue with THF (2×25 ml), the title compound (460 mg) was obtained as a crude brown oil, which was directly used in the next step without further purification.

LC-MS (Method 1): $R_t$=0.67 min; MS (ESIpos): m/z=474 $[M+H]^+$

Intermediate 91

Step 1 ethyl 8-methyl-2-[2-(pyridin-3-yl)propan-2-yl]-4,5-dihydro-2H-furo[2,3-g]indazole-7-carboxylate

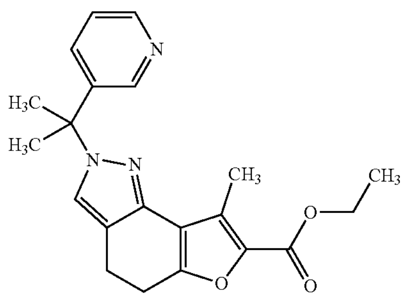 [SMILES: CCOC(=O)c1oc2c(c1C)-c1nn(C(C)(C)c3cccnc3)cc1CC2]

According to GP C (conditions A), ethyl 8-methyl-4,5-dihydro-2H-furo[2,3-g]indazole-7-carboxylate (commercially available; 100 mg, 406 μmol) and 2-(pyridin-3-yl) propan-2-ol (66.8 mg, 487 μmol; CAS-RN:[15031-77-3]) were dissolved in toluene (3.7 mL) under nitrogen atmosphere. Tri-n-butylphosphine (160 μl, 650 μmol; CAS-RN: [998-40-3]) and TMAD (112 mg, 650 μmol; CAS-RN: [10465-78-8]) were added and the reaction mixture was stirred over night at room temperature. After quenching with water, the reaction mixture was concentrated in vacuo and the residue was diluted with 2 ml acetonitrile and purified by preparative HPLC (Method A, gradient C). The product fractions were pooled and concentrated in vacuo to afford 23.5 mg (16% yield, 98% purity) of the title compound.

$^1H$ NMR (400 MHz, DMSO-d6) δ[ppm]: 1.29 (t, 3H), 1.95 (s, 6H), 2.46 (s, 3H), 2.86-2.97 (m, 4H), 4.26 (q, 2H), 7.28-7.36 (m, 1H), 7.38-7.45 (m, 1H), 7.76 (s, 1H), 8.23 (d, 1H), 8.43 (dd, 1H).

LC-MS (Method 1): $R_t$=1.29 min; MS (ESIpos): m/z=366 $[M+H]^+$

Step 2

8-methyl-2-[2-(pyridin-3-yl)propan-2-yl]-4,5-dihydro-2H-furo[2,3-g]indazole-7-carboxylic acid

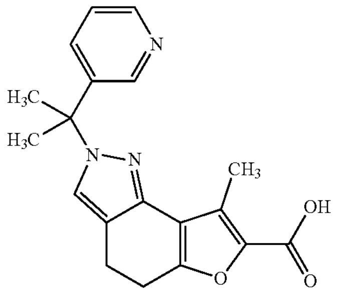 [SMILES: Cc1c(C(=O)O)oc2c1-c1nn(C(C)(C)c3cccnc3)cc1CC2]

According to GP D ethyl 8-methyl-2-[2-(pyridin-3-yl) propan-2-yl]-4,5-dihydro-2H-furo[2,3-g]indazole-7-carboxylate (20.0 mg, 54.7 μmol), intermediate 91 (step 1)) was reacted with aqueous lithium hydroxide (550 μl, 1.0 M, 550 μmol; CAS-RN:[1310-65-2]) in THF (68 μL) overnight at rt. The reaction mixture was acidified with aqueous 4 N HCl (pH 2) and concentrated in vacuo to afford 18.0 mg (96% yield, 98% purity) of the title compound.

$^1H$ NMR (400 MHz, DMSO-d6) δ[ppm]: 1.96 (s, 6H), 2.43 (s, 3H), 2.84-3.00 (m, 4H), 7.46-7.55 (m, 1H), 7.60 (br s, 1H), 7.78 (s, 1H), 8.33 (s, 1H), 8.54 (br d, 1H), 12.35-13.12 (m, 1H)

LC-MS (Method 1): $R_t$=0.57 min; MS (ESIpos): m/z=338 $[M+H]^+$

Intermediate 92

Step 1

8-methyl-4,5-dihydro-2H-furo[2,3-g]indazole-7-carboxylic acid

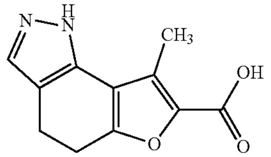 [SMILES: Cc1c(C(=O)O)oc2c1-c1[nH]ncc1CC2]

According to GP D ethyl 8-methyl-4,5-dihydro-2H-furo [2,3-g]indazole-7-carboxylate (commercially available; 380 mg, 1.54 mmol) was reacted with aqueous lithium hydroxide (7.7 ml, 1.0 M, 7.7 mmol; CAS-RN:[1310-65-2]) in THF (1.9 mL) overnight at rt. The reaction mixture was acidified with aqueous 4 N HCl (pH 2) and stirred for 30 minutes. The precipitate was collected by filtration and used in the next step without further purification (337 mg, 97% yield, 97% purity).

$^1H$ NMR (400 MHz, DMSO-d6) δ[ppm]: 2.74-3.01 (m, 4H), 7.54 (s, 1H)(methyl signal below DMSO)

LC-MS (Method 2): $R_t$=0.69 min; MS (ESIpos): m/z=219 $[M+H]^+$

Step 2

8-methyl-N-[(3R)-oxolan-3-yl]-4,5-dihydro-2H-furo[2,3-g]indazole-7-carboxamide

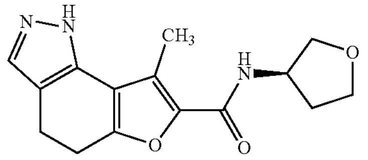 [SMILES: Cc1c(C(=O)N[C@@H]2CCOC2)oc2c1-c1[nH]ncc1CC2]

According to GP G (conditions A) 8-methyl-4,5-dihydro-2H-furo[2,3-g]indazole-7-carboxylic acid (286 mg, 1.31 mmol, intermediate 92 (step 1)) was reacted with (3R)-oxolan-3-amine (148 mg, 1.70 mmol, CAS-RN:[111769-26-7]), HATU (797 mg, 2.10 mmol; CAS-RN:[148893-10-1]) and N,N-diisopropylethylamine (910 µl, 5.2 mmol; CAS-RN:[7087-68-5]) in DMF (3.6 mL) at rt overnight to give upon preparative HPLC the title compound (215 mg, 53% yield, 93% purity).

$^1$H NMR (400 MHz, DMSO-d6) δ[ppm]: 1.87-1.98 (m, 1H), 2.04-2.15 (m, 1H), 2.49 (br s, 3H), 2.82-2.94 (m, 4H), 3.53 (dd, 1H), 3.70 (td, 1H), 3.79-3.87 (m, 2H), 4.34-4.47 (m, 1H), 7.50 (s, 1H), 8.17 (d, 1H), 12.42 (br s, 1H).

LC-MS (Method 1): $R_t$=0.77 min; MS (ESIpos): m/z=288 $[M+H]^+$

Intermediate 93

Step 1 ethyl (4R or 4S)-2-{[1-(tert-butoxycarbonyl)piperidin-4-yl]methyl}-4-methyl-8-(trifluoromethyl)-4,5-dihydro-2H-furo[2,3-g]indazole-7-carboxylate

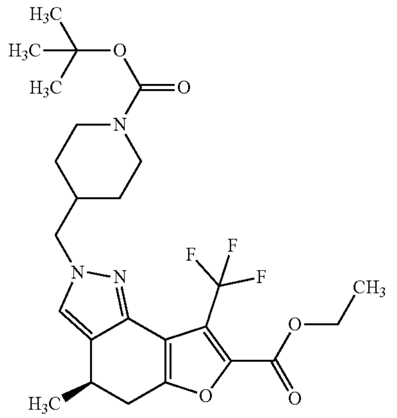 [SMILES: CCOC(=O)c1oc2c(c1C(F)(F)F)-c1nn(CC3CCN(C(=O)OC(C)(C)C)CC3)cc1[C@H](C)C2]

Ethyl (4R or 4S)-4-methyl-8-(trifluoromethyl)-4,5-dihydro-1H-furo[2,3-g]indazole-7-carboxylate (1.03 g, 3.3 mmol) from Intermediate 79 step 1-a (enantiomer 1) was suspended in acetonitrile (35 mL) at rt. To the reaction mixture, caesium carbonate (3 eq., 3.19 g, 9.8 mol) was added followed by the addition of tert-butyl 4-{[(trifluoromethanesulfonyl)oxy]methyl}piperidine-1-carboxylate (1.8 eq., 2.27 g, 90% purity, 5.88 mmol) in acetonitrile (6 mL) and the resulting reaction mixture was stirred for 1 h at rt. To the reaction mixture, EtOAc, $H_2O$ and aq. 6 N HCl solution were added and briefly stirred while cooling (use of water bath). Additional water was added, and the resulting layers were separated, and the organic layer was washed with sat. aq. $NH_4Cl$, brine, dried with $MgSO_4$ and evaporated under reduced pressure. The crude material was purified by column column chromatography ($SiO_2$, hexane/ethyl acetate) to yield the title compound (1.2 g, 58% purity) as a yellow oil, which was used in the next step without further purification.

LC-MS (Method 1): $R_t$=1.62 min; MS (ESIpos): m/z=456 $[M-tBu]^+$

Step 2 ethyl (4R or 4S)-4-methyl-2-[(piperidin-4-yl)methyl]-8-(trifluoromethyl)-4,5-dihydro-2H-furo[2,3-g]indazole-7-carboxylate (HCl salt)

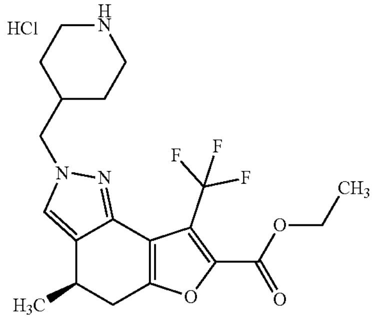 [SMILES: Cl ; CCOC(=O)c1oc2c(c1C(F)(F)F)-c1nn(CC3CCNCC3)cc1[C@H](C)C2]

To ethyl (4R or 4S)-2-{[1-(tert-butoxycarbonyl)piperidin-4-yl]methyl}-4-methyl-8-(trifluoromethyl)-4,5-dihydro-2H-furo[2,3-g]indazole-7-carboxylate (1.0 eq, 1.2 g, 2.35 mmol) from step 1 in 1,4-dioxane (12 ml) was added HCl in 1,4-dioxane (10.0 eq, 5.9 ml, 4.0 M, 23.5 mml) and stirred for 18 h at rt. The reaction mixture was evaporated under reduced pressure. To the residue was added DCM and further evaporated under reduced pressure to give the title compound (1.2 g) as a crude yellow foam, which was used in the next step without further purification.

LC-MS (Method 1): $R_t$=1.44 min; MS (ESIpos): m/z=412 $[M+H]^+$

Step 3 ethyl (4R or 4S)-2-{[1-(cyclopropanecarbonyl)piperidin-4-yl]methyl}-4-methyl-8-(trifluoromethyl)-4,5-dihydro-2H-furo[2,3-g]indazole-7-carboxylate

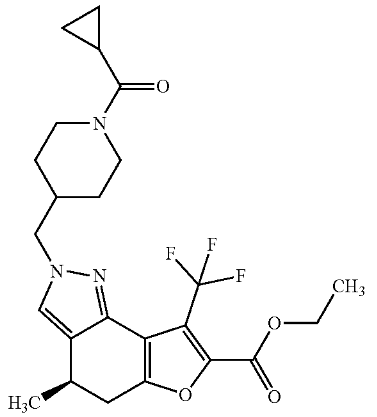 [SMILES: CCOC(=O)c1oc2c(c1C(F)(F)F)-c1nn(CC3CCN(C(=O)C4CC4)CC3)cc1[C@H](C)C2]

Ethyl (4R or 4S)-4-methyl-2-[(piperidin-4-yl)methyl]-8-(trifluoromethyl)-4,5-dihydro-2H-furo[2,3-g]indazole-7-carboxylate (1.0 eq., 250 mg, 607 μmol, as a HCl salt) from Intermediate 93 step 2 was suspended in DCM (2.9 ml). To the reaction, triethylamine (CAS No [121-44-8], 3.0 eq., 254 μl, 1.8 mmol) followed by cyclopropanecarbonyl chloride (CAS No [4023-34-1], 1.5 eq., 83 μl, 911 μmol) were added and the resulting mixture was stirred for 72 h at rt. The reaction mixture was evaporated and to the residue were added hexane/ethyl acetate (4:1, 10 ml) while stirring. The solid was collected by suction and washed with hexane/ethyl acetate (9:1, 2× 1 ml) to yield the title compound (360 mg) as a crude solid, which was used in the following step without further purification.

LC-MS (Method 1): $R_t$=1.78 min; MS (ESIpos): m/z=480 $[M+H]^+$

Step 4

(4R or 4S)-2-{[1-(cyclopropanecarbonyl)piperidin-4-yl]methyl}-4-methyl-8-(trifluoromethyl)-4,5-dihydro-2H-furo[2,3-g]indazole-7-carboxylic acid

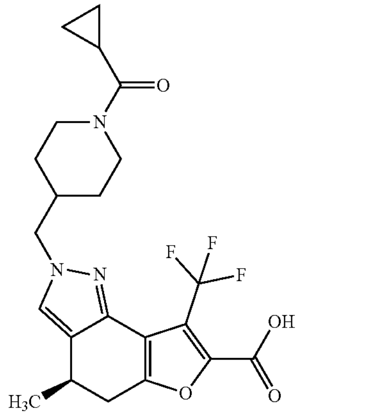 [SMILES: C[C@@H]1Cc2oc(C(=O)O)c(C(F)(F)F)c2-c2nn(CC3CCN(C(=O)C4CC4)CC3)cc21]

Ethyl (4R or 4S)-2-{[1-(cyclopropanecarbonyl)piperidin-4-yl]methyl}-4-methyl-8-(trifluoromethyl)-4,5-dihydro-2H-furo[2,3-g]indazole-7-carboxylate (1.00 eq., 360 mg, 75 μmol) from step 3 was reacted with aqueous lithium hydroxide (2 M; 2.0 eq., 752 μL, 1.5 mmol) in THF (6 mL) and methanol (6 mL) at rt for 18 h. The reaction mixture was cooled down to rt, acidified with aqueous 6 N HCl to pH4 and the resulting suspension was stirred for 5 min at rt. The resulting mixture was evaporated under reduced pressure. To the residue was added DCM (50 mL) and brine (0.2 mL) and stirred for 30 min at rt. The solids were filtered off and washed with DCM. The filtrate was evaporated under reduced pressure to give the title compound (240 mg) as a crude yellow foam, which was used in the next step without further purification.

LC-MS (Method 1): $R_t$=0.67 min; MS (ESIpos): m/z=452 $[M+H]^+$

Intermediate 94

Step 1 ethyl (4R or 4S)-2-[(1-acetylpiperidin-4-yl)methyl]-4-methyl-8-(trifluoromethyl)-4,5-dihydro-2H-furo[2,3-g]indazole-7-carboxylate

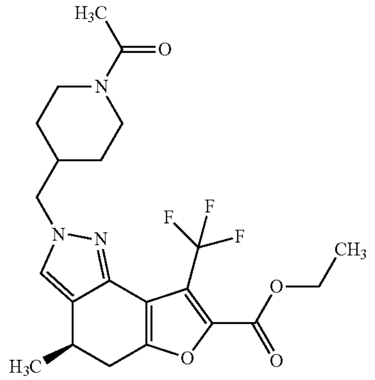 [SMILES: CCOC(=O)c1oc2c(c1C(F)(F)F)-c1nn(CC3CCN(C(C)=O)CC3)cc1[C@H](C)C2]

Ethyl (4R or 4S)-4-methyl-2-[(piperidin-4-yl)methyl]-8-(trifluoromethyl)-4,5-dihydro-2H-furo[2,3-g]indazole-7-carboxylate (1.0 eq., 250 mg, 607 μmol, as a HCl salt) from Intermediate 93 step 2 was suspended in DCM (15 ml). To the reaction, triethylamine (CAS No [121-44-8], 3 eq., 254 μl, 1.8 mmol) followed by acetyl chloride (2 eq., 86.7 μl, 1.22 mmol) were added and the resulting mixture was stirred for 72 h at rt. The reaction mixture was evaporated and to the residue were added hexane/ethyl acetate (4:1, 10 ml) while stirring. The solid was filtered off and washed with hexane/ethyl acetate (9:1, 2× 1 ml). The combined filtrate was evaporated to give a crude material, which was then purified by preparative HPLC (Method A, gradient D) to yield the title compound (100 mg, 36% yield).

$^1H$ NMR (400 MHz, DMSO-d6) δ[ppm]: 0.94-1.06 (m, 1H) 1.08-1.20 (m, 1H) 1.26-1.32 (m, 6H) 1.49-1.56 (m, 2H) 1.96 (s, 3H) 1.98-2.05 (m, 1H) 2.44-2.48 (m, 1H) 2.60-2.64 (m, 1H) 2.93-3.00 (m, 1H) 3.06-3.12 (m, 1H) 3.14-3.20 (m, 1H) 3.77-3.80 (m, 1H) 3.98 (d, 2H) 4.31-4.37 (m, 3H) 7.60 (s, 1H)

LC-MS (Method 1): $R_t$=1.24 min; MS (ESIpos): m/z=454 $[M+H]^+$

Step 2

(4R or 4S)-2-[(1-acetylpiperidin-4-yl)methyl]-4-methyl-8-(trifluoromethyl)-4,5-dihydro-2H-furo[2,3-g]indazole-7-carboxylic acid

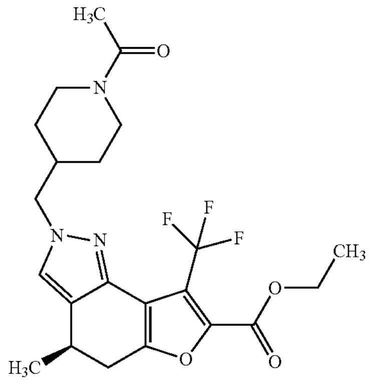

Ethyl (4R or 4S)-2-[(1-acetylpiperidin-4-yl)methyl]-4-methyl-8-(trifluoromethyl)-4,5-dihydro-2H-furo[2,3-g]indazole-7-carboxylate (1.00 eq., 100 mg, 221 μmol) from step 1 was reacted with aqueous lithium hydroxide (2 M; 2.0 eq., 221 μL, 0.44 mmol) in THF (2 mL) and methanol (2 mL) at rt for 18 h. The reaction mixture was acidified with aqueous 6 N HCl to pH4 and the resulting suspension was stirred at rt for 5 min. The mixture was evaporated under reduced pressure. Following co-distillation of the residue with toluene, the title compound (150 mg) was obtained as a crude material, which was directly used in the next step without further purification.

LC-MS (Method 1): $R_t$=0.59 min; MS (ESIpos): m/z=426 $[M+H]^+$

Intermediate 95

Step 1 ethyl (4R or 4S)-2-{[1-(1-hydroxycyclopropane-1-carbonyl)piperidin-4-yl]methyl}-4-methyl-8-(trifluoromethyl)-4,5-dihydro-2H-furo[2,3-g]indazole-7-carboxylate

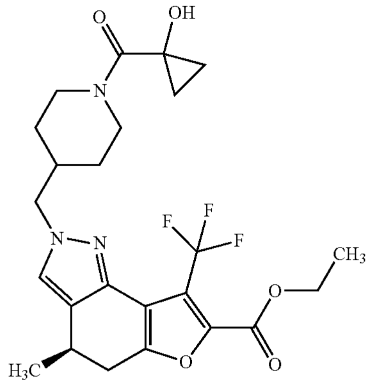 [SMILES: CCOC(=O)c1oc2c(c1C(F)(F)F)-c1nn(CC3CCN(C(=O)C4(O)CC4)CC3)cc1[C@H](C)C2]

1-Hydroxy-1-cyclopropanecarboxylic acid (2.00 eq, 124 mg, 1.22 mmol) was dissolved in tetrahydrofuran (5 mL) under Argon, and HATU (1.15 eq., 265 mg, 0.70 mmol) and DIPEA (3.0 eq., 0.32 mL, 1.82 mmol) were added and the resulting mixture was stirred for few minutes at room temperature. To this mixture, (4R or 4S)-4-methyl-2-[(piperidin-4-yl)methyl]-8-(trifluoromethyl)-4,5-dihydro-2H-furo[2,3-g]indazole-7-carboxylate (1.0 eq., 250 mg, 607 μmol, as a HCl salt) from Intermediate 93 step 2 and DMF (1 mL) were added and stirred further for 72 h at room temperature. The reaction mixture was diluted with ethyl acetate, sat. aq. sodiumbicarbonate solution, and water and the resulting mixture was stirred for 30 mins. The corresponding layers were separated, and the organic layer was washed with water, filtered through a hydrophobic filterpaper and concentrated under reduced pressure. The crude residue was purified by preparative HPLC (Method A, gradient D) to yield the title compound (100 mg, 33% yield).

$^1$H-NMR (400 MHz, DMSO-d6) δ[ppm]: 0.712 (1.00), 0.724 (3.26), 0.731 (3.89), 0.740 (1.59), 0.850 (1.69), 0.859 (3.39), 0.866 (2.54), 0.878 (1.19), 0.932 (0.48), 0.948 (0.47), 1.124 (0.56), 1.147 (0.54), 1.267 (8.35), 1.284 (8.92), 1.289 (8.22), 1.307 (16.00), 1.325 (7.21), 1.531 (1.51), 1.559 (1.29), 2.009 (0.41), 2.028 (0.55), 2.037 (0.64), 2.045 (0.52), 2.323 (0.83), 2.327 (1.15), 2.331 (0.82), 2.518 (4.49), 2.523 (2.95), 2.597 (1.35), 2.623 (1.58), 2.639 (1.67), 2.665 (2.57), 2.669 (1.55), 2.673 (1.03), 3.061 (1.52), 3.079 (2.27), 3.102 (1.17), 3.120 (2.08), 3.147 (0.67), 3.164 (0.88), 3.172 (0.72), 3.179 (0.61), 3.188 (0.82), 3.205 (0.47), 3.966 (3.65), 3.983 (3.55), 4.315 (2.14), 4.333 (6.54), 4.351 (6.44), 4.368 (2.10), 6.267 (4.12), 7.612 (5.42).

LC-MS (Method 1): $R_t$=1.24 min; MS (ESIpos): m/z=496 $[M+H]^+$

Step 2

(4R or 4S)-2-{[1-(1-hydroxycyclopropane-1-carbonyl)piperidin-4-yl]methyl}-4-methyl-8-(trifluoromethyl)-4,5-dihydro-2H-furo[2,3-g]indazole-7-carboxylic acid and (4R or 4S)-4-methyl-2-[[1-(2-oxobutanoyl)-4-piperidyl]methyl]-8-(trifluoromethyl)-4,5-dihydrofuro[2,3-g]indazole-7-carboxylic acid (As 1:1 mixture)

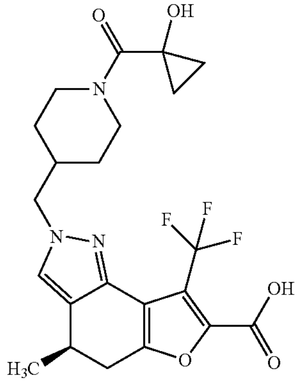

and

-continued

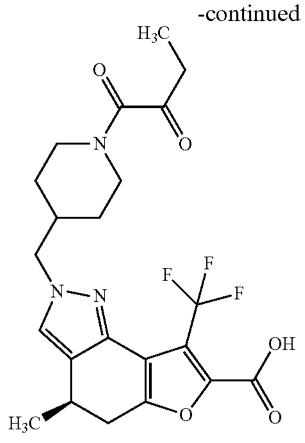

Ethyl (4R or 4S)-2-{[1-(1-hydroxycyclopropane-1-carbonyl)piperidin-4-yl]methyl}-4-methyl-8-(trifluoromethyl)-4,5-dihydro-2H-furo[2,3-g]indazole-7-carboxylate (1.00 eq., 100 mg, 202 μmol) from step 1 was reacted with aqueous lithium hydroxide (2 M; 2.0 eq., 202 μL, 0.4 mmol) in THF (2 mL) and methanol (2 mL) at rt for 18 h. The reaction mixture was acidified with aqueous 6 N HCl to pH4 and the resulting suspension was stirred at rt for 5 min. The mixture was evaporated under reduced pressure. Following co-distillation of the residue with toluene, the title compound (160 mg) was obtained as a crude material, which was directly used in the next step without further purification.

LC-MS (Method 1):

$R_t$=0.61 min; MS (ESIpos): m/z=468 $[M+H]^+$ $R_t$=0.67 min; MS (ESIpos): m/z=468 $[M+H]^+$ Intermediate 96

Step 1 ethyl (4R or 4S)-4-methyl-2-{[1-(1-methylcyclopropane-1-carbonyl)piperidin-4-yl]methyl}-8-(trifluoromethyl)-4,5-dihydro-2H-furo[2,3-g]indazole-7-carboxylate

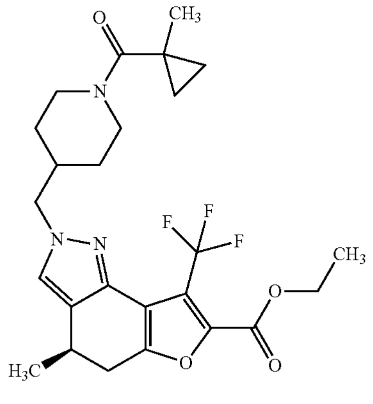 [SMILES: CCOC(=O)c1oc2c(c1C(F)(F)F)-c1nn(CC3CCN(C(=O)C4(C)CC4)CC3)cc1[C@H](C)C2]

1-Methylcyclopropane-1-carboxylic acid (2.00 eq, 122 mg, 1.22 mmol) was dissolved in tetrahydrofuran (5 mL) under Argon, and HATU (1.15 eq., 265 mg, 0.70 mmol) and DIPEA (3.0 eq., 0.32 mL, 1.82 mmol) were added and the resulting mixture was stirred for few minutes at room temperature. To this mixture, (4R or 4S)-4-methyl-2-[(piperidin-4-yl)methyl]-8-(trifluoromethyl)-4,5-dihydro-2H-furo[2,3-g]indazole-7-carboxylate (1.0 eq., 250 mg, 607 μmol, as a HCl salt) from Intermediate 93 step 2 and DMF (1 mL) were added and stirred further for 72 h at room temperature. The reaction mixture was diluted with ethyl acetate, sat. aq. sodium bicarbonate solution, and water and the resulting mixture was stirred for 30 mins. The corresponding layers were separated and the organic layer was washed with water, filtered through a hydrophobic filter paper and concentrated under reduced pressure. The crude residue was purified by preparative HPLC (Method A, gradient E) to yield the title compound (100 mg, 33% yield).

$^1$H-NMR (400 MHz, DMSO-d6) δ[ppm]: 0.496 (1.18), 0.507 (3.90), 0.512 (3.86), 0.523 (1.54), 0.729 (1.34), 0.739 (3.81), 0.743 (3.66), 0.755 (1.15), 1.090 (0.69), 1.147 (0.59), 1.192 (16.00), 1.265 (7.38), 1.281 (7.77), 1.289 (6.52), 1.307 (13.44), 1.325 (6.28), 1.534 (1.36), 1.564 (1.12), 1.998 (0.37), 2.010 (0.42), 2.017 (0.49), 2.027 (0.58), 2.036 (0.48), 2.046 (0.41), 2.323 (1.25), 2.327 (1.80), 2.331 (1.28), 2.518 (7.54), 2.523 (4.71), 2.596 (1.24), 2.622 (1.42), 2.638 (1.50), 2.664 (2.75), 2.669 (2.17), 2.673 (1.54), 2.715 (0.30), 2.723 (0.32), 2.732 (0.35), 2.737 (0.35), 2.746 (0.37), 2.752 (0.37), 2.758 (0.37), 2.767 (0.36), 2.774 (0.36), 2.782 (0.34), 2.786 (0.34), 2.795 (0.31), 2.803 (0.29), 2.806 (0.27), 3.060 (1.35), 3.078 (1.95), 3.102 (0.99), 3.120 (1.82), 3.146 (0.63), 3.163 (0.79), 3.188 (0.75), 3.205 (0.46), 3.971 (3.37), 3.989 (3.30), 4.208 (1.48), 4.241 (1.40), 4.315 (1.66), 4.332 (5.40), 4.350 (5.26), 4.368 (1.55), 7.603 (4.83).

LC-MS (Method 1): $R_t$=1.37 min; MS (ESIpos): m/z=494 $[M+H]^+$

Step 2

(4R or 4S)-4-methyl-2-{[1-(1-methylcyclopropane-1-carbonyl)piperidin-4-yl]methyl}-8-(trifluoromethyl)-4,5-dihydro-2H-furo[2,3-g]indazole-7-carboxylic acid

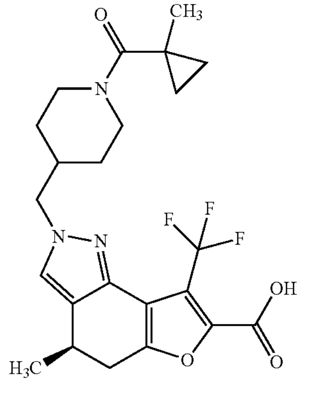 [SMILES: C[C@@H]1Cc2oc(C(=O)O)c(C(F)(F)F)c2-c2nn(CC3CCN(C(=O)C4(C)CC4)CC3)cc21]

Ethyl (4R or 4S)-4-methyl-2-{[1-(1-methylcyclopropane-1-carbonyl)piperidin-4-yl]methyl}-8-(trifluoromethyl)-4,5-dihydro-2H-furo[2,3-g]indazole-7-carboxylate (1.00 eq., 100 mg, 203 μmol) from step 1 was reacted with aqueous lithium hydroxide (2 M; 2.0 eq., 221 μL, 0.44 mmol) in THF (2 mL) and methanol (2 mL) at rt for 18 h. The reaction mixture was acidified with aqueous 6 N HCl to pH4 and the resulting suspension was stirred at rt for 5 min. The mixture was evaporated under reduced pressure. Following co-distillation of the residue with toluene, the title compound (140 mg) was obtained as a crude material, which was directly used in the next step without further purification.

LC-MS (Method 1): $R_t$=0.68 min; MS (ESIpos): m/z=466 $[M+H]^+$

Intermediate 97

Step 1 ethyl 2-[(1-acetylpiperidin-4-yl)methyl]-8-(trifluoromethyl)-4,5-dihydro-2H-furo[2,3-g]indazole-7-carboxylate

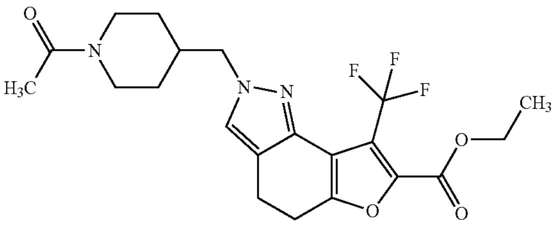 [SMILES: CCOC(=O)c1oc2c(c1C(F)(F)F)-c1nn(CC3CCN(C(C)=O)CC3)cc1CC2]

Ethyl 2-[(piperidin-4-yl)methyl]-8-(trifluoromethyl)-4,5-dihydro-2H-furo[2,3-g]indazole-7-carboxylate (1.0 eq., 225 mg, 566 μmol, as a HCl salt) from Intermediate 88 step 2 was suspended in DCM (2.7 ml). To the reaction, triethylamine (CAS No [121-44-8], 2.5 eq., 197 μl, 1.42 mmol) followed by acetyl chloride (1.5 eq., 60 μl, 0.85 mmol) were added and the resulting mixture was stirred for 5 h at rt. The reaction mixture was evaporated and to the residue were added hexane/ethyl acetate (7:3, 10 ml) while stirring. The solid was filtered off and washed with hexane/ethyl acetate (9:1, 2× 1 ml). The combined filtrate was evaporated to give a crude material, which was then purified by preparative HPLC (Method A, gradient C) to yield the title compound (92 mg, 35% yield).

$^1$H-NMR (400 MHz, DMSO-d6) δ[ppm]: 0.959 (0.20), 0.979 (0.45), 0.989 (0.47), 1.010 (0.51), 1.020 (0.48), 1.040 (0.23), 1.097 (0.20), 1.118 (0.44), 1.127 (0.49), 1.147 (0.52), 1.157 (0.48), 1.178 (0.24), 1.288 (4.70), 1.306 (10.35), 1.324 (4.90), 1.481 (0.60), 1.516 (1.00), 1.555 (0.52), 1.921 (0.24), 1.961 (16.00), 1.992 (0.45), 2.001 (0.52), 2.011 (0.42), 2.019 (0.36), 2.029 (0.29), 2.075 (0.79), 2.444 (0.46), 2.518 (3.25), 2.523 (2.08), 2.841 (0.87), 2.861 (2.87), 2.879 (2.10), 2.931 (0.48), 2.962 (2.95), 2.980 (3.38), 2.999 (1.15), 3.763 (0.61), 3.796 (0.57), 3.965 (3.15), 3.983 (3.11), 4.315 (1.84), 4.333 (4.88), 4.350 (4.74), 4.368 (1.35), 7.558 (4.29).

LC-MS (Method 1): $R_t$=1.15 min; MS (ESIpos): m/z=440 $[M+H]^+$

Step 2

2-[(1-acetylpiperidin-4-yl)methyl]-8-(trifluoromethyl)-4,5-dihydro-2H-furo[2,3-g]indazole-7-carboxylic acid

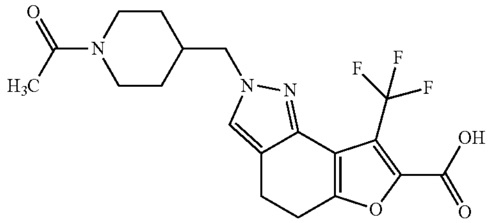 [SMILES: CC(=O)N1CCC(Cn2cc3c(n2)-c2c(oc(C(=O)O)c2C(F)(F)F)CC3)CC1]

Ethyl 2-[(1-acetylpiperidin-4-yl)methyl]-8-(trifluoromethyl)-4,5-dihydro-2H-furo[2,3-g]indazole-7-carboxylate (1.00 eq., 90 mg, 204 μmol) from step 1 was reacted with aqueous lithium hydroxide (2 M; 2.0 eq., 205 μL, 0.41 mmol) in THF (0.33 mL) and methanol (0.33 mL) at rt for 18 h. Additional aqueous lithium hydroxide (2 M; 2.0 eq., 205 μL, 0.41 mmol) was added to the reaction mixture and heated at 60° C. for 5 h. The reaction mixture was acidified with aqueous 6 N HCl to pH4 and the resulting suspension was evaporated under reduced pressure. The residue was treated with DCM (50 mL) and sat. brine solution (300 μL) was added dropwise while stirring and the resulting mixture was further stirred for 30 min at rt. Phases were separated and the organic layer was dried over $Na_2SO_4$, filtered and evaporated under reduced pressure to give the title compound (117 mg) as a crude material, which was used in the next step without further purification.

LC-MS (Method 1): $R_t$=0.51 min; MS (ESIpos): m/z=412 $[M+H]^+$

Intermediate 98

Step 1 ethyl 2-{[1-(cyclopropylmethyl)piperidin-4-yl]methyl}-8-(trifluoromethyl)-4,5-dihydro-2H-furo[2,3-g]indazole-7-carboxylate

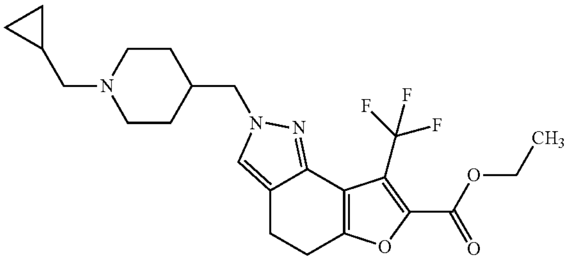 [SMILES: CCOC(=O)c1oc2c(c1C(F)(F)F)-c1nn(CC3CCN(CC4CC4)CC3)cc1CC2]

Ethyl 2-[(piperidin-4-yl)methyl]-8-(trifluoromethyl)-4,5-dihydro-2H-furo[2,3-g]indazole-7-carboxylate (1.0 eq., 225 mg, 566 μmol, as a HCl salt) from Intermediate 88 step 2 was dissolved in DMF (5 ml). To the solution, potassium carbonate (3.0 eq., 234 mg, 1.7 mmol) was added and stirred for 5 min at rt. To the reaction mixture, (bromomethyl) cyclopropane (1.5 eq., 82 μl, 0.85 mmol) was added dropwise and the resulting mixture was stirred for 18 h at 80° C.

The reaction mixture was cooled to rt and diluted with ethyl acetate and water. The phases were separated, and the organic phase was dried, filtered and evaporated under reduced pressure. The resulting crude residue was purified by purified by preparative HPLC (Method A, gradient F) to yield the title compound (34 mg, 13% yield).

$^1$H-NMR (400 MHz, DMSO-d6) δ[ppm]: 0.007 (1.05), 0.018 (3.68), 0.030 (4.04), 0.044 (1.33), 0.399 (1.27), 0.409 (3.15), 0.413 (3.18), 0.419 (1.78), 0.424 (1.74), 0.429 (3.43), 0.433 (3.29), 0.444 (1.26), 0.773 (0.77), 0.786 (1.17), 1.155 (0.54), 1.177 (1.40), 1.184 (1.50), 1.207 (1.72), 1.214 (1.56), 1.237 (0.90), 1.288 (7.23), 1.306 (16.00), 1.316 (1.36), 1.324 (7.49), 1.345 (0.49), 1.363 (0.97), 1.382 (0.48), 1.458 (1.91), 1.488 (1.52), 1.719 (0.82), 1.737 (0.68), 1.797 (1.35), 1.822 (2.40), 1.851 (1.38), 2.074 (1.26), 2.106 (5.72), 2.123 (5.85), 2.518 (11.04), 2.523 (6.74), 2.836 (1.42), 2.857 (4.33), 2.876 (3.17), 2.897 (2.19), 2.925 (2.15), 2.959 (3.36), 2.976 (4.98), 2.999 (1.44), 3.221 (0.58), 3.370 (0.78), 3.938 (4.70), 3.955 (4.50), 4.314 (2.05), 4.332 (6.77), 4.350 (6.72), 4.368 (2.04), 4.377 (0.42), 4.419 (0.43), 4.437 (0.42), 7.461 (0.53), 7.550 (6.25), 8.549 (0.43), 8.661 (0.47).

LC-MS (Method 1): $R_t$=1.46 min; MS (ESIpos): m/z=452 $[M+H]^+$

Step 2

2-{[1-(cyclopropylmethyl)piperidin-4-yl]methyl}-8-(trifluoromethyl)-4,5-dihydro-2H-furo[2,3-g]indazole-7-carboxylic acid

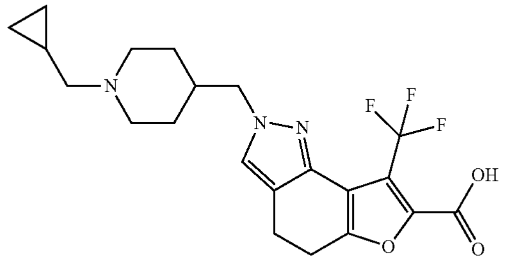 [SMILES: O=C(O)c1oc2c(c1C(F)(F)F)-c1nn(CC3CCN(CC4CC4)CC3)cc1CC2]

Ethyl 2-{[1-(cyclopropylmethyl)piperidin-4-yl]methyl}-8-(trifluoromethyl)-4,5-dihydro-2H-furo[2,3-g]indazole-7-carboxylate (1.00 eq., 33 mg, 73 μmol) from step 1 was reacted with aqueous lithium hydroxide (2 M; 2.0 eq., 73 μL, 146 μmol) in THF (0.12 mL) and methanol (0.12 mL) at rt for 18 h. Additional aqueous lithium hydroxide (2 M; 2.0 eq., 73 μL, 146 μmol) was added to the reaction mixture and heated at 60° C. for 5 h. The reaction mixture was acidified with aqueous 6 N HCl to pH4 and the resulting suspension was evaporated under reduced pressure. The residue was treated with DCM (50 mL) and sat. brine solution (300 μL) was added dropwise while stirring and the resulting mixture was further stirred for 30 min at rt. Phases were separated and the organic layer was dried over $Na_2SO_4$, filtered and evaporated under reduced pressure to give the title compound (68 mg) as a crude material, which was used in the next step without further purification.

LC-MS (Method 1): $R_t$=0.68 min; MS (ESIpos): m/z=424 $[M+H]^+$

Intermediate 99

Step 1 ethyl 2-[(1-ethylpiperidin-4-yl)methyl]-8-(trifluoromethyl)-4,5-dihydro-2H-furo[2,3-g]indazole-7-carboxylate

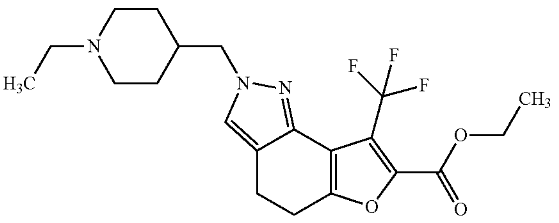 [SMILES: CCOC(=O)c1oc2c(c1C(F)(F)F)-c1nn(CC3CCN(CC)CC3)cc1CC2]

Ethyl 2-[(piperidin-4-yl)methyl]-8-(trifluoromethyl)-4,5-dihydro-2H-furo[2,3-g]indazole-7-carboxylate (1.0 eq., 225 mg, 566 μmol, as a HCl salt) from Intermediate 88 step 2 was dissolved in DMF (5 ml). To the solution, triethylamine (CAS No [121-44-8], 2.5 eq., 197 μl, 1.42 mmol) was added and stirred for 5 min at rt. To the reaction mixture, iodoethane (1.5 eq., 68 μl, 850 μmol) was added dropwise and the resulting mixture was stirred for 18 h at rt. The reaction mixture was diluted with ethyl acetate and water. The phases were separated, and the organic phase was dried, filtered and evaporated under reduced pressure. The resulting crude residue was purified by purified by preparative HPLC (Method A, gradient F) to yield the title compound (18 mg, 7% yield).

$^1$H-NMR (400 MHz, DMSO-d6) δ[ppm]: 0.911 (0.55), 0.937 (4.91), 0.955 (11.71), 0.973 (5.13), 1.125 (0.40), 1.134 (0.45), 1.155 (1.12), 1.164 (1.21), 1.186 (1.37), 1.194 (1.25), 1.216 (0.63), 1.225 (0.58), 1.288 (7.07), 1.298 (0.89), 1.306 (16.00), 1.315 (1.29), 1.323 (7.13), 1.333 (0.54), 1.457 (1.57), 1.486 (1.28), 1.693 (0.50), 1.712 (0.68), 1.734 (1.55), 1.758 (2.18), 1.787 (1.10), 2.231 (1.43), 2.249 (4.71), 2.266 (4.52), 2.285 (1.35), 2.337 (0.55), 2.518 (6.23), 2.523 (4.05), 2.678 (0.54), 2.796 (1.78), 2.825 (1.80), 2.834 (1.98), 2.855 (3.81), 2.874 (2.71), 2.958 (2.87), 2.975 (4.43), 2.994 (1.25), 2.998 (1.25), 3.933 (4.14), 3.951 (4.01), 4.314 (1.91), 4.332 (6.32), 4.349 (6.24), 4.359 (0.53), 4.367 (1.85), 7.461 (0.41), 7.550 (5.72).

LC-MS (Method 1): $R_t$=1.37 min; MS (ESIpos): m/z=426 $[M+H]^+$

Step 2

2-[(1-ethylpiperidin-4-yl)methyl]-8-(trifluoromethyl)-4,5-dihydro-2H-furo[2,3-g]indazole-7-carboxylic acid

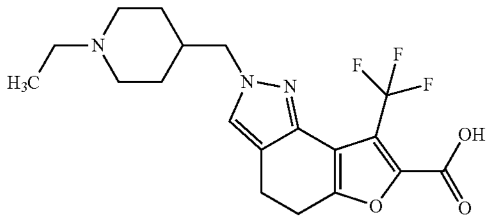 [SMILES: CCN1CCC(Cn2cc3c(n2)-c2c(oc(C(=O)O)c2C(F)(F)F)CC3)CC1]

Ethyl 2-[(1-ethylpiperidin-4-yl)methyl]-8-(trifluoromethyl)-4,5-dihydro-2H-furo[2,3-g]indazole-7-carboxylate (1.00 eq., 18 mg, 42 μmol) from step 1 was reacted with aqueous lithium hydroxide (2 M; 2.0 eq., 42 μL, 84 μmol) in THF (0.07 mL) and methanol (0.07 mL) at rt for 18 h. The reaction mixture was acidified with aqueous 6 N HCl to pH4 and the resulting suspension was evaporated under reduced pressure. The residue was treated with DCM (50 mL) and sat. brine solution (300 μL) was added dropwise while stirring and the resulting mixture was further stirred for 30 min at rt. Phases were separated and the organic layer was dried over $MgSO_4$, filtered and evaporated under reduced pressure to give the title compound (34 mg) as a crude material, which was used in the next step without further purification.

LC-MS (Method 1): $R_t$=0.63 min; MS (ESIpos): m/z=398 $[M+H]^+$

Intermediate 100

Step 1 ethyl 2-[(1-methylpiperidin-4-yl)methyl]-8-(trifluoromethyl)-4,5-dihydro-2H-furo[2,3-g]indazole-7-carboxylate

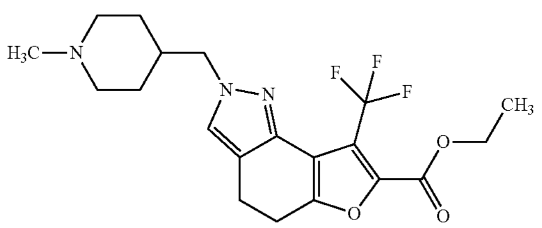 [SMILES: CCOC(=O)c1oc2c(c1C(F)(F)F)-c1nn(CC3CCN(C)CC3)cc1CC2]

Ethyl 2-[(piperidin-4-yl)methyl]-8-(trifluoromethyl)-4,5-dihydro-2H-furo[2,3-g]indazole-7-carboxylate (1.0 eq., 225 mg, 566 μmol, as a HCl salt) from Intermediate 88 step 2 was dissolved in methanol (3 ml) under nitrogen atmosphere. To the solution, acetic acid (2 eq., 65 μl, 1.13 mmol) was added and stirred for 5 min at rt. To the reaction mixture, sodium cyanoborohydride (2 eq., 71 mg, 1.13 μmol) was added portionwise and stirred for 5 min at rt. To the resulting reaction mixture, formaldehyde in water (37%-weight, 2 eq., 85 μl, 1.13 μmol) was added and the mixture was heated at 60° C. for 18 h. The reaction mixture was cooled to rt and diluted with DCM and neutralized using aq. 2 N NaOH solution to pH10. After stirring for 10 mins at rt, the phases were separated and the water phase was concentrated under reduced pressure to give the title compound (880 mg) as a crude material, which was used in the next step without further purification.

LC-MS (Method 1): $R_t$=1.27 min; MS (ESIpos): m/z=412 $[M+H]^+$

Step 2

2-[(1-methylpiperidin-4-yl)methyl]-8-(trifluoromethyl)-4,5-dihydro-2H-furo[2,3-g]indazole-7-carboxylic acid

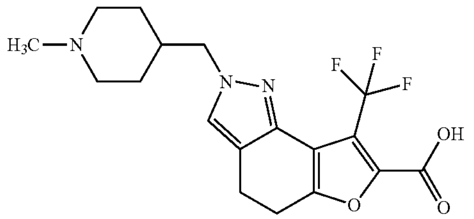 [SMILES: CN1CCC(Cn2cc3c(n2)-c2c(oc(C(=O)O)c2C(F)(F)F)CC3)CC1]

Ethyl 2-[(1-methylpiperidin-4-yl)methyl]-8-(trifluoromethyl)-4,5-dihydro-2H-furo[2,3-g]indazole-7-carboxylate (880 mg as crude, theoretically: 1.00 eq., 232 mg, 563 μmol) from step 1 was reacted with aqueous lithium hydroxide (2 M; 2.0 eq., 564 μL, 1.13 mmol) in THF (0.9 mL) and methanol (0.9 mL) at rt for 18 h. The reaction mixture was acidified with aqueous 6 N HCl to pH4 and the resulting suspension was evaporated under reduced pressure. The residue was treated with DCM (50 mL) and sat. brine solution (300 μL) was added dropwise while stirring and the resulting mixture was further stirred for 30 min at rt. Phases were separated and the organic layer was dried over $MgSO_4$, filtered and evaporated under reduced pressure to give a crude material. The crude was treated with a mixture of DCM/EtOH (9:1) and the solids were filtered off, washed with DCM and the resulting filtrate was evaporated under reduced pressure to give the title compound (465 mg) as a crude material, which was used in the next step without further purification.

LC-MS (Method 1): $R_t$=0.57 min; MS (ESIpos): m/z=384 $[M+H]^+$

EXPERIMENTAL SECTION—EXAMPLES

Example 1

2-(pyridin-2-ylmethyl)-N-[(2S)-tetrahydrofuran-2-ylmethyl]-4,5-dihydro-2H-furo[2,3-g]indazole-7-carboxamide

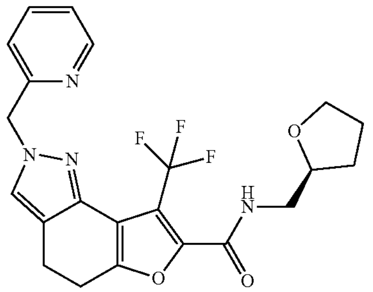 [SMILES: O=C(NC[C@@H]1CCCO1)c1oc2c(c1C(F)(F)F)-c1nn(Cc3ccccn3)cc1CC2]

According to GP G (conditions C) 2-[(pyridin-2-yl)methyl]-4,5-dihydro-2H-furo[2,3-g]indazole-7-carbaldehyde (Intermediate 1; 1.00 eq., 50.0 mg, 179 μmol) was reacted with 1-[(2S)-tetrahydrofuran-2-yl]methanamine (CAS No. [7175-81-7]; 5.0 eq., 90.5 mg, 895 μmol), sodium cyanide (1.0 eq., 8.8 mg, 180 μmol) and manganese(IV) dioxide (15.0 eq., 233 mg, 2.69 mmol) in THF (2 mL) at rt for 30 minutes. Another amount of manganese(IV) dioxide (15.0 eq., 233 mg, 2.69 mmol) was added and stirring at rt continued for 20 h. The reaction mixture was filtered over Celite, the filtrate diluted with dichloromethane and washed with water and brine. The organic phase was dried with $Na_2SO_4$, filtrated and concentrated under reduced pressure. The obtained crude product was purified by preparative HPLC to give the title compound (33 mg, 47%).

$^1H$ NMR (400 MHz, DMSO-d6) δ[ppm]: 1.52-1.60 (m, 1H), 1.74-1.91 (m, 3H), 2.87-2.97 (m, 4H), 3.20-3.29 (m, 2H), 3.58-3.64 (m, 1H), 3.73-3.78 (m, 1H), 3.90-3.97 (m, 1H), 5.37 (s, 2H), 7.07 (d, 1H), 7.21 (s, 1H), 7.31 (ddd, 1H), 7.64 (s, 1H), 7.77 (dt, 1H), 8.31 (t, 1H), 8.54 (ddd, 1H).

LC-MS (Method A): $R_t$=0.87 min; MS (ESIpos): m/z=379 $[M+H]^+$.

Example 2

8-methyl-N-[(4-methylphenyl)methyl]-2-[(pyridin-2-yl)methyl]-4,5-dihydro-2H-furo[2,3-g]indazole-7-carboxamide

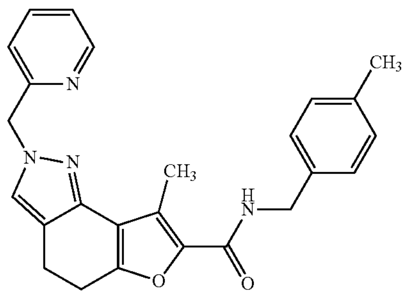 [SMILES: Cc1ccc(CNC(=O)c2oc3c(c2C)-c2nn(Cc4ccccn4)cc2CC3)cc1]

According to GP G (conditions A) 8-methyl-2-[(pyridin-2-yl)methyl]-4,5-dihydro-2H-furo[2,3-g]indazole-7-carboxylic acid (Intermediate 2; 1.00 eq., 55.0 mg, 178 μmol) was reacted with 1-(4-methylphenyl)methanamine (1.2 eq., 27 μL, 210 μmol), HATU (CAS No. [148893-10-1]; 1.5 eq., 101 mg, 267 μmol) and N,N-diisopropylethylamine (CAS No. [7087-68-5]; 3.0 eq., 93 μL, 530 μmol) in DMF (2 mL) at rt overnight to give upon preparative HPLC the title compound (30 mg, 38%).

$^1H$ NMR (400 MHz, DMSO-d6) δ[ppm]: 2.26 (s, 3H), 2.45 (s, 3H), 2.85-2.93 (m, 4H), 4.33 (d, 2H), 5.38 (s, 2H), 7.07 (d, 1H), 7.10-7.12 (m, 2H), 7.17-7.19 (m, 2H), 7.31 (ddd, 1H), 7.63 (s, 1H), 7.77 (dt, 1H), 8.54 (ddd, 1H), 8.62 (t, 1H).

LC-MS (Method A): $R_t$=1.20 min; MS (ESIpos): m/z=413 $[M+H]^+$.

Example 3

8-methyl-2-(pyridin-2-ylmethyl)-N-[(2R/S)-tetrahydrofuran-2-ylmethyl]-4,5-dihydro-2H-furo[2,3-g]indazole-7-carboxamide

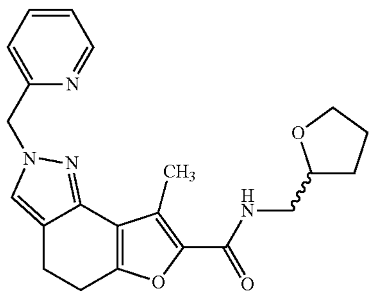 [SMILES: Cc1c(C(=O)NCC2CCCO2)oc2c1-c1nn(Cc3ccccn3)cc1CC2]

According to GP G (conditions A) 8-methyl-2-[(pyridin-2-yl)methyl]-4,5-dihydro-2H-furo[2,3-g]indazole-7-carboxylic acid (Intermediate 2; 1.00 eq., 55.0 mg, 178 μmol) was reacted with 1-[(2R/S)-tetrahydrofuran-2-yl]methanamine (CAS No. [4795-29-3]; 1.2 eq., 22 μL, 210 μmol), HATU (CAS No. [148893-10-1]; 1.5 eq., 101 mg, 267 μmol) and N,N-diisopropylethylamine (CAS No. [7087-68-5]; 3.0 eq., 93 μL, 530 μmol) in DMF (2 mL) at rt overnight to give upon preparative HPLC the title compound (40 mg, 53%).

$^1H$ NMR (400 MHz, DMSO-d6) δ[ppm]: 1.53-1.61 (m, 1H), 1.74-1.90 (m, 3H), 2.44 (s, 3H), 2.86-2.93 (m, 4H), 3.18-3.26 (m, 2H), 3.58-3.64 (m, 1H), 3.73-3.78 (m, 1H), 3.91-3.97 (m, 1H), 5.38 (s, 2H), 7.07 (d, 1H), 7.31 (ddd, 1H), 7.63 (s, 1H), 7.77 (dt, 1H), 7.98 (t, 1H), 8.53-8.54 (m, 1H).

LC-MS (Method A): $R_t$=0.97 min; MS (ESIpos): m/z=393 $[M+H]^+$.

The enantiomers of the racemic material of example 3 were separated by chiral preparative HPLC (Instrument: PrepCon Labomatic HPLC; Column: Chiralpak IE 5 μm 250×30 mm; Eluent A: tert-butyl-methylether+0.1% diethylamine; Eluent B: ethanol; Isocratic: 90% A+10% B; Flow: 40 mL/min; Temperature: 25° C.; Detection: UV 254 nm) and analytically characterized by chiral HPLC (Instrument: Agilent 1260 HPLC; Column: Chiralpak IE 3 μm 100×4.6 mm; Eluent A: tert-butyl-methylether+0.1% diethylamine; Eluent B: ethanol; Isocratic: 90% A+10% B; Flow: 1.4 mL/min; Temperature: 25° C.; Detection: UV: 254 nm):

Example 3-1: 8-methyl-2-(pyridin-2-ylmethyl)-N-[(2R)-tetrahydrofuran-2-ylmethyl]-4,5-dihydro-2H-furo[2,3-g]indazole-7-carboxamide $R_t$=3.91 min; $[\alpha]_D^{20}$=−16.3°+/−1.79° (C=10.0 mg/mL, methanol)

Example 3-2: 8-methyl-2-(pyridin-2-ylmethyl)-N-[(2S)-tetrahydrofuran-2-ylmethyl]-4,5-dihydro-2H-furo[2,3-g]indazole-7-carboxamide $R_t$=5.00 min; $[\alpha]_D^{20}$=+14.8°+/−1.89° (C=10.0 mg/mL, methanol)

TABLE 2

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| 4 | 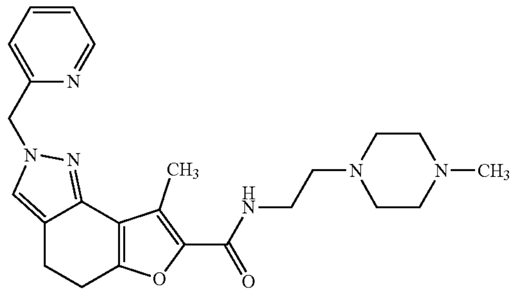 [SMILES: Cc1c(C(=O)NCCN2CCN(C)CC2)oc2c1-c1nn(Cc3ccccn3)cc1CC2] 8-methyl-N-[2-(4-methylpiperazin-1-yl)ethyl]-2-(pyridin-2-ylmethyl)-4,5-dihydro-2H-furo[2,3-g]indazole-7-carboxamide | $^1$H-NMR (400 MHz, DMSO-d6) δ [ppm]: 2.134 (13.81), 2.297 (1.26), 2.323 (2.11), 2.327 (2.46), 2.331 (2.01), 2.388 (2.65), 2.405 (4.09), 2.423 (2.65), 2.438 (16.00), 2.522 (4.49), 2.665 (1.23), 2.669 (1.63), 2.673 (1.20), 2.739 (0.45), 2.888 (10.62), 3.267 (0.91), 3.283 (2.03), 3.300 (2.19), 5.381 (6.98), 7.057 (1.85), 7.077 (1.95), 7.289 (0.94), 7.303 (1.10), 7.308 (1.12), 7.320 (1.10), 7.632 (5.03), 7.750 (1.04), 7.754 (1.04), 7.769 (1.77), 7.773 (1.74), 7.788 (0.94), 7.793 (0.91), 7.906 (0.75), 7.921 (1.61), 7.935 (0.75), 8.529 (1.47), 8.539 (1.55), 8.541 (1.53). LC-MS (Method A); $R_t$ = 0.85 min, m/z = 435 $[M + H]^+$. | Intermediate 2; GP G (conditions A with HATU) |
| 5 | 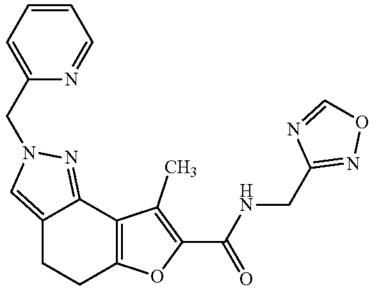 [SMILES: Cc1c(C(=O)NCc2ncon2)oc2c1-c1nn(Cc3ccccn3)cc1CC2] 8-methyl-N-[(1,2,4-oxadiazol-3-yl)ethyl]-2-(pyridin-2-yl)methyl]-4,5-dihydro-2H-furo[2,3-g]indazole-7-carboxamide | $^1$H NMR (400 MHz, DMSO-d6) δ [ppm]: 2.44 (s, 3H), 2.86-2.93 (m, 4H), 4.54 (d, 2H), 5.39 (s, 2H), 7.07 (d, 1H), 7.31 (ddd, 1H), 7.64 (s, 1H), 7.78 (dt, 1H), 8.54 (ddd, 1H), 8.75 (t, 1H), 9.54 (s, 1H). LC-MS (Method A); $R_t$ = 0.85 min, m/z = 391 $[M + H]^+$. | Intermediate 2; GPG (conditions A with HATU) |
| 6 | 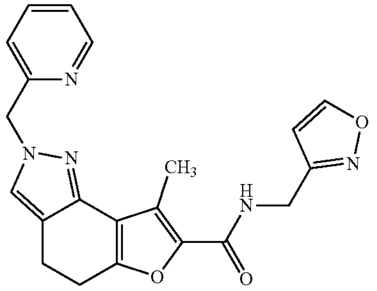 [SMILES: Cc1c(C(=O)NCc2ccon2)oc2c1-c1nn(Cc3ccccn3)cc1CC2] 8-methyl-N-(1,2-oxazol-3-ylmethyl)-2-(pyridin-2-ylmethyl)-4,5-dihydro-2H-furo[2,3-g]indazole-7-carboxamide | $^1$H-NMR (400 MHz, DMSO-d6) δ [ppm]: 2.454 (16.00), 2.518 (1.95), 2.522 (1.21), 2.755 (0.45), 2.889 (2.88), 2.897 (8.51), 2.905 (3.29), 4.452 (3.32), 4.467 (3.30), 5.385 (6.42), 6.487 (3.97), 6.492 (4.36), 7.060 (1.76), 7.079 (1.84), 7.289 (0.89), 7.291 (0.87), 7.301 (0.93), 7.304 (0.96), 7.308 (1.13), 7.310 (0.97), 7.320 (1.03), 7.322 (0.94), 7.639 (5.08), 7.750 (1.09), 7.754 (1.06), 7.769 (1.79), 7.774 (1.86), 7.788 (0.98), 7.793 (0.98), 8.527 (1.17), 8.530 (1.34), 8.532 (1.36), 8.534 (1.23), 8.539 (1.22), 8.542 (1.38), 8.544 (1.27), 8.546 (1.15), 8.703 (0.73), 8.718 (1.58), 8.733 (0.71), 8.812 (3.54), 8.815 (3.26). LC-MS (Method A); $R_t$ = 0.90 min, m/z = 390 $[M + H]^+$. | Intermediate 2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 7 | 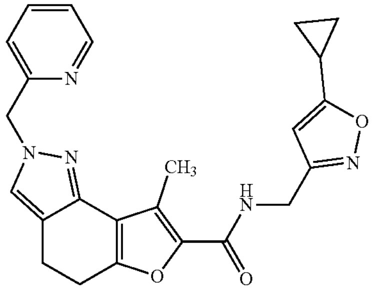 [SMILES: Cc1c(C(=O)NCc2cc(C3CC3)on2)oc2c1-c1nn(Cc3ccccn3)cc1CC2] N-[(5-cyclopropyl-1,2-oxazol-3-yl)methyl]-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: 0.821 (0.77), 0.832 (2.58), 0.838 (2.57), 0.844 (2.54), 0.847 (1.52), 0.850 (2.70), 0.860 (1.11), 0.993 (1.10), 1.003 (2.52), 1.010 (2.36), 1.014 (1.26), 1.021 (1.13), 1.024 (2.72), 1.031 (2.25), 1.042 (0.84), 1.606 (0.62), 2.081 (0.77), 2.090 (0.83), 2.094 (0.47), 2.102 (1.49), 2.111 (0.48), 2.114 (0.77), 2.123 (0.74), 2.452 (16.00), 2.518 (3.26), 2.523 (2.28), 2.893 (10.23), 2.898 (3.49), 3.566 (1.11), 4.340 (3.22), 4.355 (3.20), 5.385 (6.22), 6.089 (6.38), 7.060 (1.74), 7.080 (1.82), 7.290 (0.89), 7.293 (0.84), 7.302 (0.95), 7.305 (0.95), 7.309 (1.02), 7.311 (0.93), 7.321 (1.02), 7.323 (0.95), 7.639 (5.18), 7.751 (1.14), 7.755 (1.11), 7.770 (1.80), 7.775 (1.94), 7.789 (1.01), 7.794 (1.01), 8.528 (1.16), 8.530 (1.31), 8.532 (1.32), 8.535 (1.22), 8.540 (1.17), 8.542 (1.34), 8.544 (1.22), 8.547 (1.14), 8.634 (0.71), 8.649 (1.56), 8.664 (0.68). LC-MS (Method A); $R_t$ = 1.07 min, m/z = 430 $[M + H]^+$. | Intermediate 2; GPG (conditions A with HATU) |
| 8 | 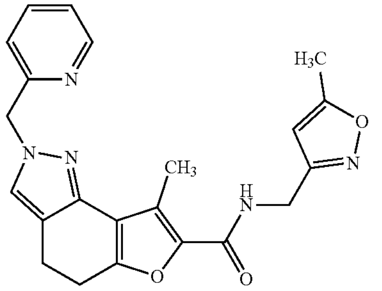 [SMILES: Cc1cc(CNC(=O)c2oc3c(c2C)-c2nn(Cc4ccccn4)cc2CC3)no1] 8-methyl-N-[(5-methyl-1,2-oxazol-3-yl)methyl]-2-(pyridin-2-ylmethyl)-4,5-dihydro-2H-furo[2,3-g]indazole-7-carboxamide | $^1$H-NMR (400 MHz, DMSO-d6) δ [ppm]: 2.336 (0.60), 2.352 (11.98), 2.354 (11.85), 2.451 (16.00), 2.518 (6.29), 2.522 (3.99), 2.678 (0.52), 2.888 (3.26), 2.894 (9.97), 2.900 (3.39), 3.566 (2.98), 4.356 (3.34), 4.372 (3.31), 5.385 (6.39), 6.134 (3.47), 6.136 (3.42), 7.061 (1.72), 7.080 (1.80), 7.289 (0.86), 7.293 (0.89), 7.302 (0.91), 7.305 (0.99), 7.308 (1.04), 7.311 (0.91), 7.320 (1.02), 7.324 (0.94), 7.638 (5.06), 7.751 (1.07), 7.755 (1.15), 7.770 (1.83), 7.774 (1.91), 7.789 (0.94), 7.794 (0.91), 8.527 (1.12), 8.530 (1.33), 8.532 (1.31), 8.534 (1.23), 8.539 (1.17), 8.542 (1.36), 8.544 (1.23), 8.546 (1.15), 8.662 (0.73), 8.677 (1.57), 8.693 (0.70). LC-MS (Method A); $R_t$ = 0.99 min, m/z = 404 $[M + H]^+$. | Intermediate 2; GP G (conditions A with HATU) |
| 9 | 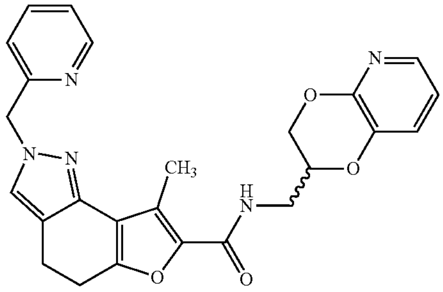 [SMILES: Cc1c(C(=O)NCC2COc3ncccc3O2)oc2c1-c1nn(Cc3ccccn3)cc1CC2] N-[(2R/S)-2,3-dihydro[1,4]dioxino[2,3-b]pyridin-2-ylmethyl]-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: 0.933 (1.22), 0.935 (0.43), 0.949 (1.24), 2.306 (0.91), 2.336 (0.51), 2.456 (16.00), 2.518 (6.12), 2.522 (3.81), 2.659 (0.51), 2.756 (0.51), 2.879 (1.02), 2.892 (2.59), 2.905 (5.54), 2.914 (3.07), 3.430 (0.63), 3.445 (0.51), 3.450 (0.69), 3.465 (1.12), 3.480 (0.58), 3.521 (0.58), 3.536 (1.14), 3.552 (0.74), 3.566 (2.39), 3.571 (0.71), 4.130 (1.07), 4.148 (1.22), 4.160 (1.19), 4.177 (1.37), 4.355 (0.79), 4.360 (0.99), 4.372 (0.79), 4.377 (0.84), 4.437 (1.50), 4.443 (1.42), 4.466 (1.30), 4.472 (1.09), 5.386 (6.40), 6.932 (2.21), 6.944 (2.03), 6.952 (2.29), 6.963 (2.26), 7.064 (1.78), 7.084 (1.85), 7.291 (0.97), 7.293 (0.99), 7.302 (3.33), 7.306 (3.35), 7.309 (1.32), 7.312 (1.12), 7.322 (3.40), 7.325 (2.59), 7.632 (0.41), 7.640 (5.03), 7.735 (2.29), 7.740 (2.59), 7.747 (2.46), 7.752 (3.25), 7.757 (1.32), 7.771 (1.90), 7.776 (1.93), 7.790 (0.99), 7.795 (0.97), 8.366 (0.69), 8.381 (1.47), 8.396 (0.69), 8.529 (1.24), 8.531 (1.40), 8.533 (1.45), 8.535 (1.27), 8.541 (1.30), 8.543 (1.42), | Intermediate 2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 8.545 (1.37), 8.547 (1.17). LC-MS (Method A); $R_t$ = 0.97 min, m/z = 458 $[M + H]^+$. | |
| 10 | 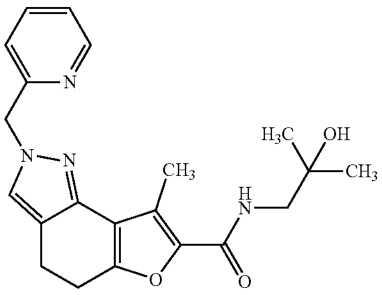 [SMILES: Cc1c(C(=O)NCC(C)(C)O)oc2c1-c1nn(Cc3ccccn3)cc1CC2] N-(2-hydroxy-2-methylpropyl)-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: 1.082 (16.00), 2.450 (9.71), 2.518 (2.68), 2.522 (1.68), 2.673 (0.49), 2.886 (1.55), 2.897 (2.45), 2.903 (2.59), 2.915 (2.00), 3.182 (2.12), 3.197 (2.12), 4.626 (4.38), 5.385 (4.13), 7.057 (1.10), 7.077 (1.16), 7.289 (0.54), 7.292 (0.54), 7.301 (0.58), 7.305 (0.59), 7.308 (0.66), 7.311 (0.59), 7.320 (0.64), 7.323 (0.59), 7.580 (0.42), 7.595 (0.90), 7.610 (0.42), 7.636 (3.12), 7.750 (0.68), 7.755 (0.70), 7.769 (1.15), 7.774 (1.16), 7.788 (0.59), 7.794 (0.59), 8.528 (0.71), 8.531 (0.79), 8.532 (0.85), 8.535 (0.72), 8.540 (0.74), 8.543 (0.82), 8.545 (0.80), 8.547 (0.69). LC-MS (Method A); $R_t$ = 0.88 min, m/z = 381 $[M + H]^+$. | Intermediate 2; GP G (conditions A with HATU) |
| 11 | 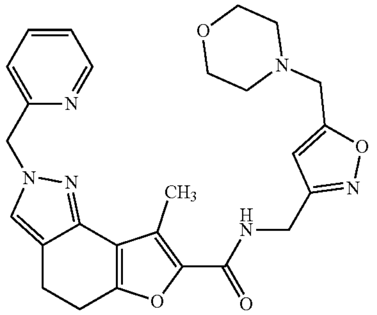 [SMILES: Cc1c(C(=O)NCc2cc(CN3CCOCC3)on2)oc2c1-c1nn(Cc3ccccn3)cc1CC2] 8-methyl-N-{[5-(morpholin-4-ylmethyl)-1,2-oxazol-3-yl]methyl}-2-(pyridin-2-ylmethyl)-4,5-dihydro-2H-furo[2,3-g]indazole-7-carboxamide | $^1$H-NMR (400 MHz, DMSO-d6) δ [ppm]: 2.331 (1.14), 2.382 (3.40), 2.394 (4.56), 2.404 (3.50), 2.456 (16.00), 2.518 (6.62), 2.522 (4.07), 2.878 (1.31), 2.896 (9.97), 2.903 (3.82), 3.542 (4.32), 3.554 (5.53), 3.565 (4.22), 3.608 (1.19), 3.637 (9.33), 4.402 (3.42), 4.417 (3.40), 5.385 (7.57), 6.312 (5.51), 7.060 (1.96), 7.079 (2.03), 7.290 (1.04), 7.305 (1.24), 7.308 (1.24), 7.321 (1.19), 7.640 (5.23), 7.750 (1.09), 7.755 (1.09), 7.770 (1.96), 7.774 (1.93), 7.789 (0.99), 7.794 (0.97), 8.530 (1.61), 8.532 (1.61), 8.542 (1.61), 8.688 (0.84), 8.703 (1.81), 8.719 (0.82). LC-MS (Method A); $R_t$ = 0.92 min, m/z = 489 $[M + H]^+$. | Intermediate 2; GPG (conditions A with HATU) |
| 12 | 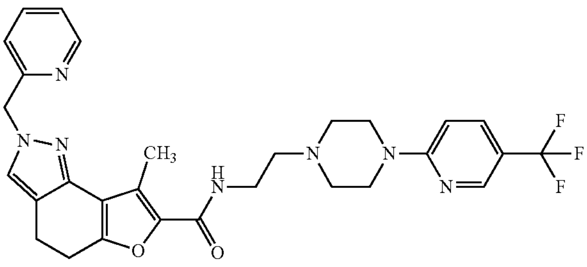 [SMILES: Cc1c(C(=O)NCCN2CCN(c3ccc(C(F)(F)F)cn3)CC2)oc2c1-c1nn(Cc3ccccn3)cc1CC2] 8-methyl-2-(pyridin-2-ylmethyl)-N-(2-{4-[5-(trifluoromethyl)pyridin-2-yl]piperazin-1-yl}ethyl)-4,5-dihydro-2H-furo[2,3-g]indazole-7-carboxamide | $^1$H-NMR (500 MHz, DMSO-d6) δ [ppm]: 2.447 (16.00), 2.472 (1.82), 2.515 (4.31), 2.518 (2.77), 2.522 (1.96), 2.881 (2.55), 2.890 (5.99), 2.898 (3.08), 3.349 (1.72), 3.362 (1.62), 3.376 (0.64), 3.606 (2.73), 3.616 (3.37), 3.625 (2.41), 5.381 (6.48), 6.945 (1.65), 6.963 (1.67), 7.061 (1.74), 7.077 (1.79), 7.291 (0.85), 7.294 (0.84), 7.301 (0.85), 7.303 (0.92), 7.306 (0.97), 7.309 (0.88), 7.317 (0.92), 7.318 (0.92), 7.632 (4.90), 7.753 (1.04), 7.757 (1.12), 7.769 (3.00), 7.772 (2.62), 7.784 (1.23), 7.788 (2.07), 7.792 (1.15), 7.992 (0.70), 8.004 (1.51), 8.015 (0.73), 8.396 (1.76), 8.401 (1.69), 8.528 (1.12), 8.530 (1.25), 8.532 (1.22), 8.533 (1.08), 8.538 (1.13), 8.540 (1.29), 8.541 (1.23), 8.543 (1.09). LC-MS (Method A); $R_t$ = 1.25 min, m/z = 564 $[M - H]^-$. | Intermediate 2; GP G (conditions A with T3P) |

TABLE 2-continued

The following examples (4 to 147) were prepared in analogy to example 3 starting from the given intermediates and commercially available amines (or their salts), applying the indicated general procedure.

| Ex-ample | Structure IUPAC-Name | Analytical Data | Preparation or Separation Methods |
|---|---|---|---|
| 13 | 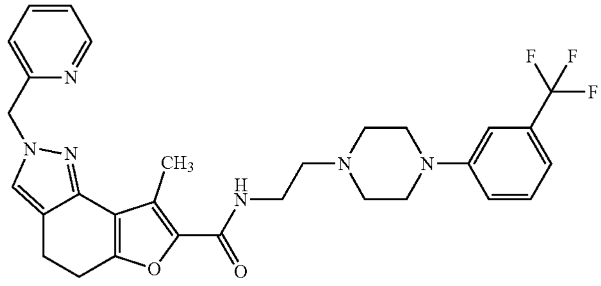 [SMILES: Cc1c(C(=O)NCCN2CCN(c3cccc(C(F)(F)F)c3)CC2)oc2c1-c1nn(Cc3ccccn3)cc1CC2] 8-methyl-2-(pyridin-2-ylmethyl)-N-(2-{4-[3-(trifluoromethyl)phenyl]piperazin-1 yl}ethyl)-4,5-dihydro-2H-furo[2,3-g]indazole-7-carboxamide | $^1$H-NMR (400 MHz, DMSO-d6) δ [ppm]: 2.448 (13.47), 2.518 (3.20), 2.522 (2.00), 2.554 (2.05), 2.567 (2.79), 2.579 (2.20), 2.673 (0.51), 2.880 (2.35), 2.888 (6.73), 2.896 (2.65), 3.208 (2.20), 3.221 (2.75), 3.232 (2.08), 3.337 (16.00), 3.350 (1.81), 3.367 (1.38), 3.383 (0.56), 5.380 (5.11), 7.045 (1.03), 7.057 (1.66), 7.060 (1.47), 7.064 (1.22), 7.077 (1.58), 7.153 (1.52), 7.207 (0.73), 7.228 (0.86), 7.233 (0.78), 7.287 (0.75), 7.290 (0.77), 7.299 (0.78), 7.302 (0.81), 7.306 (0.86), 7.309 (0.83), 7.318 (0.84), 7.321 (0.81), 7.388 (0.80), 7.408 (1.25), 7.427 (0.57), 7.631 (4.34), 7.748 (0.91), 7.753 (0.93), 7.768 (1.55), 7.772 (1.60), 7.787 (0.84), 7.791 (0.81), 7.982 (0.56), 7.997 (1.23), 8.011 (0.56), 8.526 (0.93), 8.528 (1.12), 8.531 (1.10), 8.532 (1.03), 8.538 (0.98), 8.540 (1.15), 8.543 (1.07), 8.545 (0.95). LC-MS (Method A); $R_t$ = 1.32 min, m/z = 563 $[M - H]^-$. | Intermediate 2; GPG (conditions A with T3P) |
| 14 | 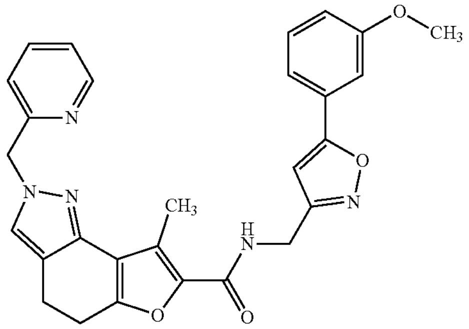 [SMILES: COc1cccc(-c2cc(CNC(=O)c3oc4c(c3C)-c3nn(Cc5ccccn5)cc3CC4)no2)c1] N-{[5-(3-methoxyphenyl)-1,2-oxazol-3-yl]methyl}-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: 2.472 (11.91), 2.518 (1.41), 2.522 (0.90), 2.893 (2.01), 2.902 (5.58), 2.910 (2.31), 3.811 (0.44), 3.821 (16.00), 3.831 (0.50), 4.475 (2.18), 4.490 (2.16), 5.387 (4.59), 6.965 (5.30), 7.037 (0.68), 7.044 (0.85), 7.051 (1.09), 7.060 (1.88), 7.063 (1.60), 7.067 (1.43), 7.083 (1.44), 7.289 (0.65), 7.293 (0.65), 7.301 (0.68), 7.305 (0.72), 7.308 (0.77), 7.311 (0.71), 7.320 (0.76), 7.323 (0.70), 7.384 (1.22), 7.388 (1.42), 7.392 (1.64), 7.401 (0.45), 7.419 (1.88), 7.425 (1.56), 7.429 (1.43), 7.434 (3.05), 7.436 (2.97), 7.641 (3.66), 7.751 (0.83), 7.755 (0.82), 7.771 (1.34), 7.775 (1.40), 7.790 (0.72), 7.794 (0.73), 8.528 (0.84), 8.531 (0.99), 8.532 (0.96), 8.535 (0.90), 8.541 (0.86), 8.543 (1.01), 8.545 (0.92), 8.547 (0.84), 8.748 (0.55), 8.763 (1.25), 8.778 (0.53). LC-MS (Method A); $R_t$ = 1.18 min, m/z = 496 $[M + H]^+$. | Intermediate 2; GP G (conditions A with T3P) |
| 15 | 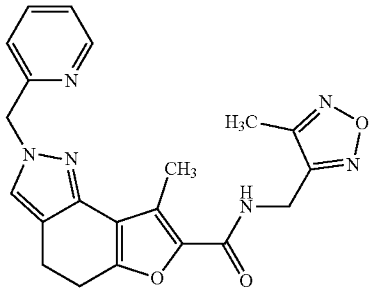 [SMILES: Cc1nonc1CNC(=O)c1oc2c(c1C)-c1nn(Cc3ccccn3)cc1CC2] 8-methyl-N-[(4-methyl-1,2,5-oxadiazol-3-yl)methyl]-2-(pyridin-2-ylmethyl)-4,5-dihydro-2H-furo[2,3-g]indazole-7-carboxamide | $^1$H-NMR (500 MHz, DMSO-d6) δ [ppm]: 2.374 (16.00), 2.445 (11.53), 2.515 (0.91), 2.518 (0.86), 2.522 (0.67), 2.890 (1.80), 2.900 (4.08), 2.907 (2.19), 4.555 (2.92), 4.566 (2.87), 5.385 (4.72), 7.058 (1.19), 7.074 (1.25), 7.291 (0.58), 7.294 (0.59), 7.301 (0.62), 7.303 (0.66), 7.306 (0.68), 7.309 (0.62), 7.317 (0.65), 7.318 (0.65), 7.640 (3.29), 7.753 (0.73), 7.757 (0.71), 7.768 (1.22), 7.772 (1.25), 7.784 (0.64), 7.787 (0.63), 8.528 (0.72), 8.530 (0.84), 8.532 (0.89), 8.534 (0.79), 8.538 (0.78), 8.540 (0.86), 8.541 (0.83), 8.543 (0.74), 8.796 (0.53), 8.807 (1.14), 8.819 (0.52). LC-MS (Method A); $R_t$ = 0.99 min, m/z = 403 $[M - H]^-$. | Intermediate 2; GPG (conditions A with T3P) |

TABLE 2-continued

| The following examples (4 to 147) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| 16 | 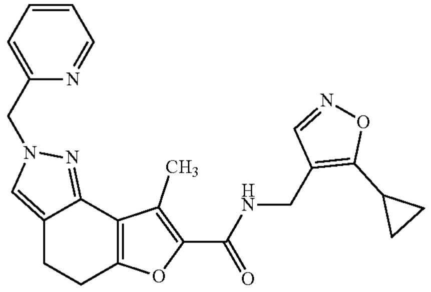 [SMILES: Cc1c(C(=O)NCc2cnoc2C2CC2)oc2c1-c1nn(Cc3ccccn3)cc1CC2] N-[(5-cyclopropyl-1,2-oxazol-4-yl)methyl]-8-methyl-2-(pyridin-2-ylmethyl)-4,5-dihydro-2H-furo[2,3-g]indazole-7-carboxamide | $^1$H-NMR (500 MHz, DMSO-d6) δ [ppm]: 0.949 (0.72), 0.958 (2.17), 0.963 (2.29), 0.968 (1.99), 0.970 (1.73), 0.973 (2.29), 0.980 (1.12), 1.038 (1.03), 1.045 (2.23), 1.050 (1.75), 1.055 (1.31), 1.060 (1.16), 1.062 (2.38), 1.067 (1.74), 1.077 (0.70), 1.298 (0.40), 2.285 (0.73), 2.291 (0.75), 2.295 (0.43), 2.301 (1.34), 2.308 (0.46), 2.312 (0.70), 2.318 (0.73), 2.365 (0.46), 2.450 (16.00), 2.515 (1.92), 2.518 (1.79), 2.522 (1.37), 2.639 (0.45), 2.881 (2.91), 2.887 (8.47), 2.893 (3.17), 4.237 (3.59), 4.249 (3.53), 5.381 (6.74), 7.059 (1.73), 7.075 (1.81), 7.291 (0.82), 7.293 (0.89), 7.301 (0.88), 7.303 (0.97), 7.306 (0.99), 7.308 (0.92), 7.316 (0.97), 7.318 (1.00), 7.632 (4.92), 7.752 (1.01), 7.756 (1.08), 7.768 (1.72), 7.771 (1.67), 7.783 (0.96), 7.787 (0.94), 8.345 (5.80), 8.528 (1.11), 8.529 (1.31), 8.531 (1.31), 8.533 (1.15), 8.537 (1.06), 8.539 (1.29), 8.541 (1.29), 8.543 (1.13), 8.582 (0.75), 8.594 (1.59), 8.605 (0.73). LC-MS (Method A); $R_t$ = 1.04 min, m/z = 430 $[M + H]^+$. | Intermediate 2; GP G (conditions A with T3P) |
| 17 | 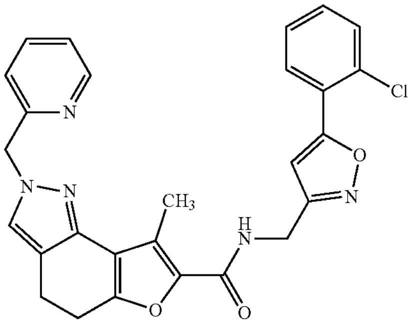 [SMILES: Cc1c(C(=O)NCc2cc(-c3ccccc3Cl)on2)oc2c1-c1nn(Cc3ccccn3)cc1CC2] N-{[5-(2-chlorophenyl)-1,2-oxazol-3-yl]methyl}-8-methyl-2-(pyridin-2-ylmethyl)-4,5-dihydro-2H-furo[2,3-g]indazole-7-carboxamide | $^1$H-NMR (500 MHz, DMSO-d6) δ [ppm]: 2.464 (16.00), 2.515 (1.40), 2.518 (1.27), 2.522 (1.00), 2.878 (0.48), 2.893 (2.70), 2.902 (4.45), 2.906 (4.56), 2.915 (3.27), 2.929 (0.51), 4.516 (3.53), 4.529 (3.46), 5.387 (7.06), 7.018 (7.13), 7.061 (1.86), 7.077 (1.90), 7.293 (0.90), 7.303 (1.02), 7.306 (1.05), 7.316 (1.00), 7.506 (0.58), 7.516 (1.66), 7.520 (2.00), 7.523 (1.87), 7.529 (3.81), 7.535 (2.05), 7.538 (1.95), 7.542 (1.93), 7.552 (0.73), 7.557 (0.41), 7.640 (5.03), 7.656 (2.05), 7.660 (1.28), 7.663 (1.03), 7.670 (1.30), 7.675 (1.50), 7.753 (1.02), 7.756 (1.03), 7.768 (1.84), 7.772 (1.82), 7.784 (0.90), 7.787 (0.94), 7.891 (1.87), 7.896 (1.40), 7.903 (1.06), 7.906 (1.10), 7.910 (1.67), 8.531 (1.34), 8.532 (1.32), 8.540 (1.37), 8.542 (1.32), 8.778 (0.83), 8.790 (1.83), 8.802 (0.81). LC-MS (Method A); $R_t$ = 1.23 min, m/z = 500 $[M + H]^+$. | Intermediate 2; GP G (conditions A with T3P) |
| 18 | 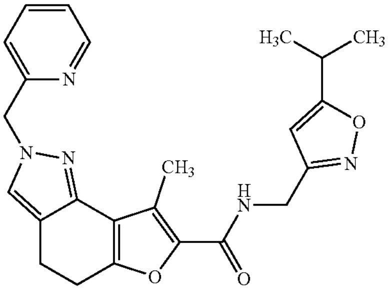 [SMILES: Cc1c(C(=O)NCc2cc(C(C)C)on2)oc2c1-c1nn(Cc3ccccn3)cc1CC2] N-[(5-isopropyl-1,2-oxazol-3-yl)methyl]-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: 1.208 (16.00), 1.225 (15.90), 2.457 (11.68), 2.518 (1.31), 2.522 (0.83), 2.889 (2.25), 2.895 (6.73), 2.902 (2.41), 3.024 (0.69), 3.039 (0.90), 3.057 (0.67), 4.375 (2.42), 4.391 (2.40), 5.385 (4.63), 6.124 (3.35), 6.126 (3.35), 7.060 (1.28), 7.079 (1.34), 7.289 (0.63), 7.292 (0.62), 7.301 (0.67), 7.304 (0.71), 7.308 (0.74), 7.310 (0.66), 7.320 (0.72), 7.323 (0.66), 7.639 (3.63), 7.750 (0.75), 7.755 (0.77), 7.769 (1.30), 7.774 (1.30), 7.788 (0.64), 7.794 (0.65), 8.528 (0.83), 8.530 (0.93), 8.532 (0.96), 8.534 (0.86), 8.540 (0.87), 8.542 (0.96), 8.545 (0.91), 8.546 (0.79), 8.661 (0.54), 8.676 (1.18), 8.691 (0.52). LC-MS (Method A); $R_t$ = 1.12 min, m/z = 432 $[M + H]^+$. | Intermediate 2; GPG (conditions A with T3P) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 19-1 | 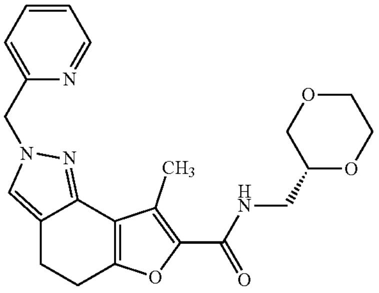 [SMILES: Cc1c(C(=O)NC[C@@H]2COCCO2)oc2c1-c1nn(Cc3ccccn3)cc1CC2] N-[(2R)-1,4-dioxan-2-ylmethyl]-8-methyl-2-(pyridin-2-ylmethyl)-4,5-dihydro-2H-furo[2,3-g]indazole-7-carboxamide | $^1$H-NMR (500 MHz, DMSO-d6) δ [ppm]: 2.441 (16.00), 2.515 (1.61), 2.518 (1.41), 2.522 (1.10), 2.883 (2.78), 2.893 (6.07), 2.900 (3.25), 3.165 (0.70), 3.180 (0.91), 3.185 (1.35), 3.192 (1.49), 3.204 (2.14), 3.208 (1.55), 3.219 (0.76), 3.227 (1.69), 3.231 (1.47), 3.244 (0.92), 3.258 (0.69), 3.420 (0.44), 3.425 (0.54), 3.442 (1.09), 3.447 (1.17), 3.464 (0.93), 3.469 (0.86), 3.515 (0.76), 3.520 (0.86), 3.538 (1.12), 3.543 (1.15), 3.560 (0.53), 3.565 (0.71), 3.609 (1.55), 3.614 (1.00), 3.621 (0.69), 3.628 (1.52), 3.633 (1.26), 3.685 (1.18), 3.689 (1.04), 3.713 (2.03), 3.737 (0.88), 5.383 (7.04), 7.062 (1.77), 7.078 (1.83), 7.293 (0.85), 7.294 (0.88), 7.302 (0.93), 7.304 (0.98), 7.307 (1.00), 7.317 (0.98), 7.319 (0.96), 7.633 (4.83), 7.754 (1.02), 7.758 (1.06), 7.770 (1.72), 7.773 (1.75), 7.785 (0.96), 7.789 (0.93), 8.047 (0.73), 8.059 (1.58), 8.071 (0.73), 8.529 (1.09), 8.531 (1.26), 8.533 (1.29), 8.535 (1.17), 8.539 (1.16), 8.541 (1.33), 8.543 (1.27). LC-MS (Method A); $R_t$ = 0.89 min, m/z = 407 $[M - H]^-$. | Intermediate 2; GP G (conditions A with T3P) |
| 19-2 | 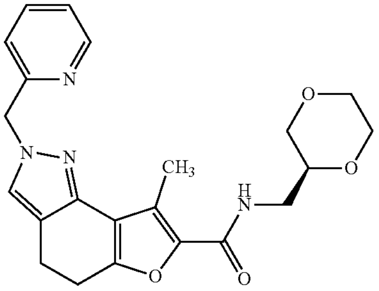 [SMILES: Cc1c(C(=O)NC[C@H]2COCCO2)oc2c1-c1nn(Cc3ccccn3)cc1CC2] N-{[(2S)-1,4-dioxan-2-yl]methyl}-8-methyl-2-[(pyridin-2-yl)methyl]-4,5-dihydro-2H-furo[2,3-g]indazole-7-carboxamide | $^1$H-NMR (500 MHz, DMSO-d6) δ [ppm]: 2.441 (16.00), 2.515 (1.58), 2.518 (1.60), 2.522 (1.25), 2.882 (2.57), 2.890 (5.32), 2.892 (5.62), 2.900 (3.23), 3.164 (0.71), 3.176 (0.53), 3.180 (0.86), 3.185 (1.32), 3.192 (1.48), 3.204 (2.11), 3.207 (1.50), 3.219 (0.74), 3.227 (1.65), 3.231 (1.42), 3.243 (0.89), 3.258 (0.66), 3.419 (0.48), 3.424 (0.59), 3.441 (1.07), 3.446 (1.17), 3.463 (0.94), 3.468 (0.86), 3.515 (0.76), 3.519 (0.84), 3.538 (1.12), 3.543 (1.12), 3.559 (0.53), 3.565 (0.71), 3.608 (1.42), 3.613 (0.94), 3.621 (0.61), 3.627 (1.40), 3.632 (1.20), 3.684 (1.14), 3.689 (0.99), 3.712 (1.88), 3.736 (0.81), 5.381 (6.77), 7.062 (1.73), 7.078 (1.81), 7.292 (0.89), 7.294 (0.84), 7.301 (0.86), 7.304 (0.94), 7.307 (0.99), 7.309 (0.89), 7.317 (0.94), 7.319 (0.92), 7.632 (4.93), 7.754 (1.02), 7.757 (1.07), 7.769 (1.91), 7.773 (1.86), 7.784 (0.97), 7.788 (1.02), 8.048 (0.71), 8.060 (1.53), 8.072 (0.69), 8.528 (1.12), 8.530 (1.25), 8.532 (1.25), 8.534 (1.09), 8.538 (1.07), 8.540 (1.22), 8.541 (1.22), 8.543 (1.09). LC-MS (Method A); $R_t$ = 0.89 min, m/z = 407 $[M - H]^-$. | Intermediate 2; GP G (conditions A with T3P) |
| 20 | 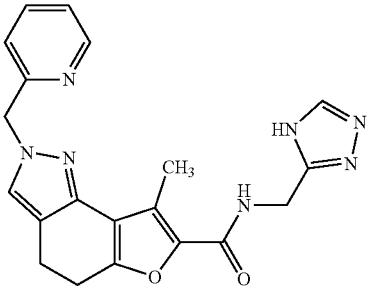 [SMILES: Cc1c(C(=O)NCc2nnc[nH]2)oc2c1-c1nn(Cc3ccccn3)cc1CC2] | $^1$H-NMR (400 MHz, DMSO-d6) δ [ppm]: 2.450 (16.00), 2.518 (2.53), 2.522 (1.57), 2.891 (3.50), 2.898 (10.01), 2.905 (3.63), 4.459 (2.72), 4.474 (2.75), 5.386 (7.11), 7.067 (1.93), 7.087 (2.01), 7.289 (0.98), 7.293 (0.96), 7.302 (1.02), 7.305 (1.11), 7.308 (1.18), 7.311 (1.08), 7.320 (1.14), 7.323 (1.05), 7.640 (5.45), 7.752 (1.18), 7.756 (1.21), 7.771 (2.01), 7.775 (2.02), 7.790 (1.01), 7.795 (1.04), 8.529 (1.60), 8.531 (1.80), 8.533 (1.78), 8.535 (1.62), 8.541 (1.53), 8.543 (1.69), 8.545 (1.58), 8.547 (1.40). | Intermediate 2; GPG (conditions A with T3P) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | 8-methyl-2-(pyridin-2-ylmethyl)-N-(4H-1,2,4-triazol-3-ylmethyl)-4,5-dihydro-2H-furo[2,3-g]indazole-7-carboxamide | LC-MS (Method A); $R_t$ = 0.63 min, m/z = 390 $[M + H]^+$. | |
| 21 | 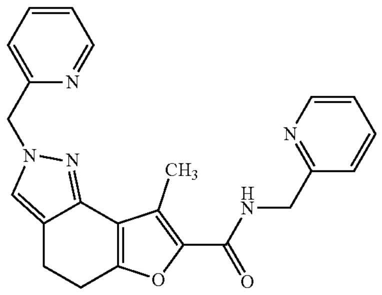 [SMILES: Cc1c(C(=O)NCc2ccccn2)oc2c1-c1nn(Cc3ccccn3)cc1CC2] 8-methyl-N,2-bis(pyridin-2-ylmethyl)-4,5-dihydro-2H-furo[2,3-g]indazole-7-carboxamide | $^1$H-NMR (500 MHz, DMSO-d6) δ [ppm]: 2.458 (16.00), 2.515 (1.95), 2.518 (1.81), 2.522 (1.41), 2.758 (0.44), 2.884 (0.57), 2.900 (2.50), 2.908 (3.86), 2.914 (4.07), 2.924 (3.19), 2.938 (0.58), 4.491 (3.16), 4.503 (3.16), 5.390 (6.89), 7.066 (1.74), 7.082 (1.83), 7.243 (0.90), 7.253 (0.98), 7.256 (0.98), 7.267 (0.98), 7.291 (1.70), 7.306 (2.70), 7.320 (1.04), 7.644 (4.62), 7.733 (0.95), 7.736 (1.01), 7.748 (1.70), 7.752 (1.69), 7.757 (1.08), 7.761 (1.23), 7.764 (1.06), 7.767 (1.00), 7.773 (1.81), 7.777 (1.76), 7.788 (0.95), 7.792 (1.01), 8.494 (1.20), 8.496 (1.26), 8.502 (1.08), 8.504 (1.22), 8.506 (1.22), 8.507 (1.09), 8.533 (1.09), 8.535 (1.23), 8.536 (1.26), 8.538 (1.18), 8.542 (1.18), 8.544 (1.32), 8.546 (1.26), 8.658 (0.74), 8.670 (1.62), 8.682 (0.76). LC-MS (Method A); $R_t$ = 0.94 min, m/z = 400 $[M + H]^+$. | Intermediate 2; GP G (conditions A with T3P) |
| 22 | 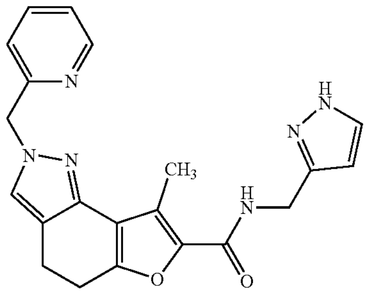 [SMILES: Cc1c(C(=O)NCc2cc[nH]n2)oc2c1-c1nn(Cc3ccccn3)cc1CC2] 8-methyl-N-(1H-pyrazol-3-ylmethyl)-2-(pyridin-2-ylmethyl)-4,5-dihydro-2H-furo[2,3-g]indazole-7-carboxamide | $^1$H-NMR (500 MHz, DMSO-d6) δ [ppm]: 1.974 (0.47), 1.978 (0.49), 2.365 (0.75), 2.453 (16.00), 2.465 (0.41), 2.515 (3.21), 2.518 (3.07), 2.522 (2.40), 2.639 (0.80), 2.885 (10.57), 2.890 (3.39), 4.378 (1.71), 4.390 (1.70), 5.383 (7.00), 6.134 (1.42), 7.060 (1.78), 7.076 (1.86), 7.293 (1.04), 7.294 (1.04), 7.302 (1.13), 7.304 (1.17), 7.307 (1.19), 7.317 (1.26), 7.319 (1.21), 7.625 (0.57), 7.632 (5.04), 7.641 (0.57), 7.703 (1.61), 7.754 (1.11), 7.757 (1.09), 7.769 (1.94), 7.773 (1.91), 7.784 (1.01), 7.788 (1.01), 7.816 (0.42), 7.820 (0.49), 8.529 (1.17), 8.531 (1.29), 8.533 (1.34), 8.535 (1.27), 8.539 (1.29), 8.541 (1.40), 8.543 (1.29), 8.544 (1.13). LC-MS (Method A); $R_t$ = 0.84 min, m/z = 389 $[M + H]^+$. | Intermediate 2; GPG (conditions A with T3P) |
| 23 | 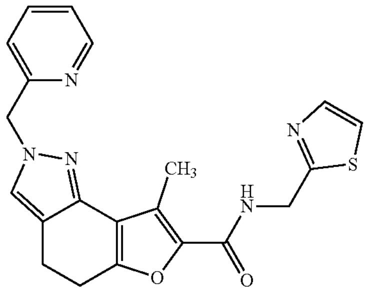 [SMILES: Cc1c(C(=O)NCc2nccs2)oc2c1-c1nn(Cc3ccccn3)cc1CC2] 8-methyl-2-(pyridin-2ylmethyl)-N-(1,3-thiazol-2-ylmethyl)-4,5-dihydro-2H-furo[2,3-g]indazole-7-carboxamide | $^1$H-NMR (500 MHz, DMSO-d6) δ [ppm]: 2.074 (0.83), 2.465 (16.00), 2.515 (1.82), 2.518 (1.76), 2.522 (1.39), 2.765 (1.16), 2.884 (0.52), 2.900 (2.46), 2.909 (3.84), 2.914 (4.05), 2.923 (3.08), 2.937 (0.51), 4.655 (3.65), 4.667 (3.70), 5.391 (6.59), 7.064 (1.67), 7.080 (1.73), 7.294 (0.83), 7.296 (0.83), 7.304 (0.87), 7.306 (0.88), 7.310 (0.92), 7.311 (0.88), 7.319 (0.93), 7.321 (0.90), 7.600 (4.43), 7.607 (4.79), 7.646 (4.62), 7.713 (4.46), 7.719 (3.52), 7.756 (1.06), 7.760 (1.07), 7.772 (1.69), 7.775 (1.76), 7.787 (0.95), 7.791 (0.93), 8.532 (1.04), 8.534 (1.17), 8.535 (1.21), 8.537 (1.12), 8.541 (1.17), 8.543 (1.27), 8.545 (1.17), 8.546 (1.02), 8.652 (0.42), 8.984 (0.74), 8.996 (1.58), 9.008 (0.74). LC-MS (Method A); $R_t$ = 0.93 min, m/z = 406 $[M + H]^+$. | Intermediate 2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 24 | 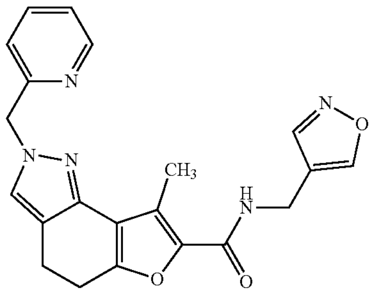 [SMILES: Cc1c(C(=O)NCc2cnoc2)oc2c1-c1nn(Cc3ccccn3)cc1CC2] 8-methyl-N-(1,2-oxazol-4-ylmethyl)-2-(pyridin-2-ylmethyl)-4,5-dihydro-2H-furo[2,3-g]indazole-7-carboxamide | $^1$H-NMR (400 MHz, DMSO-d6) δ [ppm]: 2.322 (0.59), 2.326 (0.79), 2.331 (0.59), 2.452 (16.00), 2.522 (2.85), 2.664 (0.62), 2.669 (0.81), 2.673 (0.61), 2.753 (0.59), 2.887 (11.30), 4.252 (3.34), 4.267 (3.35), 5.382 (7.01), 7.057 (1.86), 7.077 (1.96), 7.291 (0.97), 7.303 (1.12), 7.306 (1.17), 7.318 (1.21), 7.633 (5.03), 7.749 (1.06), 7.753 (1.08), 7.768 (1.84), 7.772 (1.84), 7.787 (1.00), 7.792 (0.98), 8.532 (7.66), 8.538 (1.63), 8.540 (1.71), 8.542 (1.60), 8.581 (0.86), 8.596 (1.68), 8.611 (0.78), 8.819 (4.55). LC-MS (Method A); $R_t$ = 0.90 min, m/z = 388 [M − H]$^-$. | Intermediate 2; GPG (conditions A with HATU) |
| 25 | 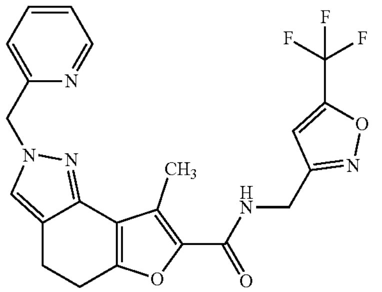 [SMILES: Cc1c(C(=O)NCc2cc(C(F)(F)F)on2)oc2c1-c1nn(Cc3ccccn3)cc1CC2] 8-methyl-2-(pyridin-2-ylmethyl)-N-{[5-(trifluoromethyl)-1,2-oxazol-3-yl]methyl}-4,5-dihydro-2H-furo[2,3-g]indazole-7-carboxamide | $^1$H-NMR (500 MHz, DMSO-d6) δ [ppm]: 2.062 (0.66), 2.365 (0.84), 2.426 (0.41), 2.457 (16.00), 2.515 (4.08), 2.518 (3.56), 2.522 (2.75), 2.758 (0.72), 2.893 (2.68), 2.903 (5.78), 2.911 (3.21), 4.526 (3.63), 4.538 (3.59), 5.387 (6.81), 7.065 (1.74), 7.081 (1.81), 7.294 (0.97), 7.306 (1.01), 7.309 (1.10), 7.318 (1.13), 7.335 (3.02), 7.337 (3.11), 7.643 (4.63), 7.755 (1.08), 7.759 (1.08), 7.771 (1.71), 7.774 (1.78), 7.786 (0.95), 7.790 (1.08), 8.530 (1.24), 8.532 (1.36), 8.534 (1.35), 8.541 (1.38), 8.782 (0.77), 8.794 (1.67), 8.806 (0.79). LC-MS (Method A); $R_t$ = 1.14 min, m/z = 458 [M + H]$^+$. | Intermediate 2; GP G (conditions A with T3P) |
| 26 | 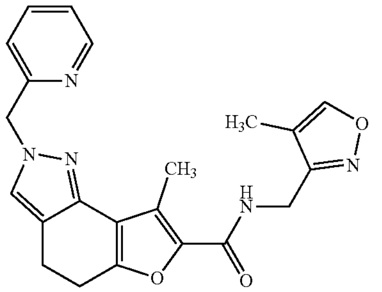 [SMILES: Cc1conc1CNC(=O)c1oc2c(c1C)-c1nn(Cc3ccccn3)cc1CC2] 8-methyl-N-[(4-methyl-1,2-oxazol-3-yl)methyl]-2-(pyridin-2-ylmethyl)-4,5-dihydro-2H-furo[2,3-g]indazole-7-carboxamide | $^1$H-NMR (500 MHz, DMSO-d6) δ [ppm]: 1.967 (12.48), 1.969 (12.22), 1.996 (0.59), 1.998 (0.61), 2.448 (16.00), 2.514 (2.01), 2.518 (1.68), 2.522 (1.28), 2.748 (0.77), 2.886 (3.31), 2.891 (10.01), 2.897 (3.54), 4.439 (3.90), 4.450 (3.84), 5.385 (7.25), 7.057 (1.82), 7.073 (1.89), 7.293 (0.94), 7.303 (1.04), 7.306 (1.18), 7.316 (1.06), 7.636 (4.99), 7.752 (1.02), 7.756 (1.06), 7.768 (1.79), 7.771 (1.79), 7.783 (0.97), 7.787 (0.98), 8.532 (1.36), 8.534 (1.25), 8.540 (1.44), 8.574 (2.79), 8.575 (2.85), 8.582 (0.97), 8.594 (1.92), 8.606 (0.88). LC-MS (Method A); $R_t$ = 0.97 min, m/z = 402 [M − H]$^-$. | Intermediate 2; GPG (conditions A with T3P) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 27 | 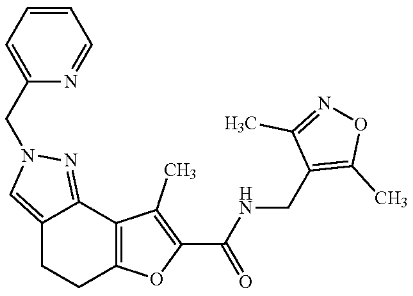 [SMILES: Cc1noc(C)c1CNC(=O)c1oc2c(c1C)-c1nn(Cc3ccccn3)cc1CC2] N-[(3,5-dimethyl-1,2-oxazol-4-yl)methyl]-8-methyl-2-(pyridin-2-ylmethyl)-4,5-dihydro-2H-furo[2,3-g]indazole-7-carboxamide | $^1$H-NMR (500 MHz, DMSO-d6) δ [ppm]: 2.205 (16.00), 2.237 (0.58), 2.384 (14.62), 2.416 (0.56), 2.441 (13.71), 2.515 (4.38), 2.518 (3.66), 2.522 (2.80), 2.741 (0.53), 2.877 (2.84), 2.883 (8.14), 2.889 (2.96), 4.117 (3.08), 4.128 (3.08), 5.378 (6.02), 7.054 (1.52), 7.070 (1.59), 7.292 (0.88), 7.302 (0.88), 7.305 (0.91), 7.315 (0.86), 7.629 (4.22), 7.751 (0.86), 7.755 (0.89), 7.767 (1.45), 7.770 (1.51), 7.782 (0.77), 7.786 (0.75), 8.519 (0.75), 8.530 (2.57), 8.540 (1.61). LC-MS (Method A); $R_t$ = 0.98 min, m/z = 418 [M + H]$^+$. | Intermediate 2; GP G (conditions A with T3P) |
| 28 | 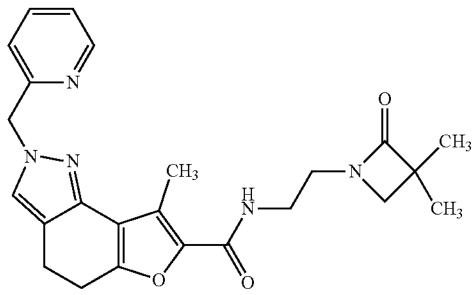 [SMILES: Cc1c(C(=O)NCCN2CC(C)(C)C2=O)oc2c1-c1nn(Cc3ccccn3)cc1CC2] N-[2-(3,3-dimethyl-2-oxoazetidin-1-yl)ethyl]-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: 1.123 (16.00), 2.306 (4.58), 2.326 (0.71), 2.438 (8.28), 2.669 (0.66), 2.879 (5.03), 2.892 (7.28), 3.022 (0.62), 3.091 (4.89), 3.216 (0.80), 3.230 (1.67), 3.244 (1.28), 3.304 (1.09), 5.383 (6.29), 7.029 (0.55), 7.043 (1.25), 7.062 (1.24), 7.289 (0.89), 7.301 (1.13), 7.305 (1.16), 7.318 (1.07), 7.634 (3.44), 7.746 (0.80), 7.750 (0.84), 7.765 (1.54), 7.769 (1.53), 7.784 (0.83), 7.789 (0.84), 8.167 (0.46), 8.182 (0.94), 8.196 (0.47), 8.530 (1.48), 8.541 (1.55). LC-MS (Method A); $R_t$ = 0.91 min, m/z = 434 [M + H]$^+$. | Intermediate 2; GPG (conditions A with T3P) |
| 29 | 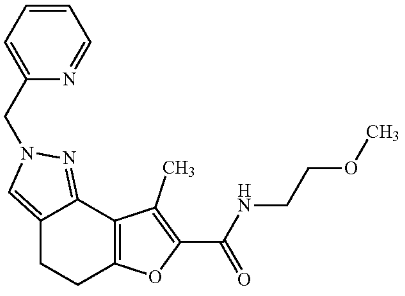 [SMILES: COCCNC(=O)c1oc2c(c1C)-c1nn(Cc3ccccn3)cc1CC2] N-(2-methoxyethyl)-8-methyl-2-(pyridin-2-ylmethyl)-4,5-dihydro-2H-furo[2,3-g]indazole-7-carboxamide | $^1$H NMR (400 MHz, DMSO-d6) δ [ppm]: 2.44 (s, 3H), 2.86-2.91 (m, 4H), 3.23-3.25 (m, 5H), 3.40-3.43 (m, 2H), 5.38 (s, 2H), 7.07 (d, 1H), 7.31 (ddd, 1H), 7.63 (s, 1H), 7.77 (dt, 1H), 8.01 (t, 1H), 8.54 (ddd, 1H). LC-MS (Method A); $R_t$ = 0.91 min, m/z = 367 [M + H]$^+$. | Intermediate 2; GPG (conditions A with T3P) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 30 | 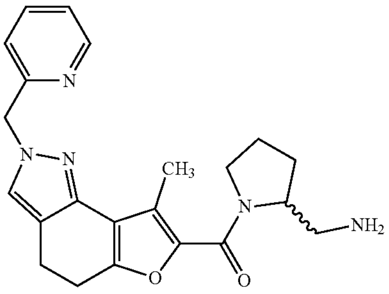 [SMILES: Cc1c(C(=O)N2CCCC2CN)oc2c1-c1nn(Cc3ccccn3)cc1CC2] [(2R/S)-2-(aminomethyl)pyrrolidin-1-yl][8-methyl-2-(pyridin-2-ylmethyl)-4,5-dihydro-2H-furo[2,3-g]indazol-7-yl]methanone | $^{1}$H NMR (400 MHz, DMSO-d6) δ [ppm]: 1.76-1.89 (m, 4H), 2.40-2.44 (m, 3H), 2.88 (br. s., 4H), 3.19-3.22 (m, 1H), 3.66-3.91 (m, 3H), 4.09-4.29 (m, 1H), 5.38 (s, 2H), 7.05 (d, 1H), 7.31 (ddd, 1H), 7.63 (s, 1H), 7.77 (dt, 1H), 8.54 (ddd, 1H). LC-MS (Method A); $R_t$ = 0.90 min, m/z = 392 $[M + H]^+$. | Intermediate 2; GP G (conditions A with T3P) |
| 31 | 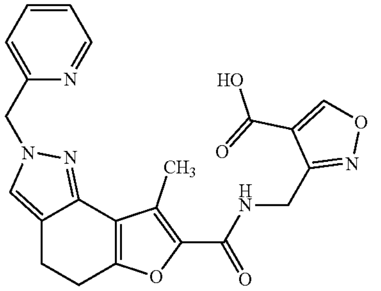 [SMILES: Cc1c(C(=O)NCc2nocc2C(=O)O)oc2c1-c1nn(Cc3ccccn3)cc1CC2] 3-[({[8-methyl-2-(pyridin-2-ylmethyl)-4,5-dihydro-2H-furo[2,3-g]indazol-7-yl]carbonyl}amino)methyl]-1,2-oxazole-4-carboxylic acid | $^{1}$H-NMR (400 MHz, DMSO-d6) δ [ppm]: 1.144 (1.60), 1.162 (3.51), 1.180 (1.68), 2.327 (0.53), 2.403 (0.40), 2.444 (16.00), 2.523 (1.73), 2.665 (0.42), 2.669 (0.58), 2.673 (0.42), 2.747 (0.51), 2.888 (11.60), 3.005 (0.40), 3.024 (1.07), 3.041 (1.07), 3.060 (0.42), 3.341 (1.54), 4.614 (3.13), 4.628 (3.14), 5.384 (6.88), 7.056 (1.96), 7.075 (2.04), 7.287 (1.09), 7.299 (1.22), 7.304 (1.32), 7.316 (1.24), 7.633 (5.21), 7.748 (1.10), 7.752 (1.14), 7.767 (1.98), 7.771 (1.96), 7.786 (1.00), 7.791 (1.08), 8.529 (1.51), 8.531 (1.56), 8.538 (1.36), 8.541 (1.55), 8.543 (1.48), 9.072 (0.45), 9.166 (1.58). LC-MS (Method A); $R_t$ = 0.57 min, m/z = 434 $[M + H]^+$. | Intermediate 2; GPG (conditions A with HATU) |
| 32 | 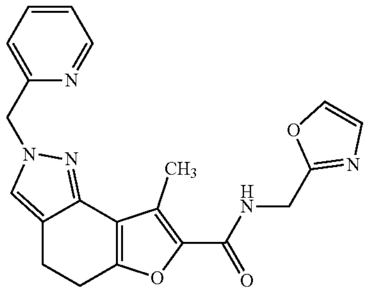 [SMILES: Cc1c(C(=O)NCc2ncco2)oc2c1-c1nn(Cc3ccccn3)cc1CC2] 8-methyl-N-(1,3-oxazol-2-ylmethyl)-2-(pyridin-2-ylmethyl)-4,5-dihydro-2H-furo[2,3-g]indazole-7-carboxamide | $^{1}$H-NMR (400 MHz, DMSO-d6) δ [ppm]: 0.899 (0.66), 0.915 (1.37), 0.932 (1.14), 1.198 (0.94), 1.471 (1.01), 1.974 (0.68), 1.978 (0.68), 2.412 (0.41), 2.435 (3.11), 2.447 (16.00), 2.518 (8.71), 2.523 (5.90), 2.708 (0.41), 2.748 (1.01), 2.816 (1.09), 2.831 (0.56), 2.838 (0.66), 2.879 (3.54), 2.886 (2.46), 2.894 (3.70), 2.902 (8.89), 2.911 (3.92), 2.928 (0.89), 2.940 (0.63), 4.479 (3.87), 4.494 (3.90), 5.387 (7.27), 5.403 (0.66), 7.055 (0.46), 7.067 (1.92), 7.086 (1.97), 7.139 (4.78), 7.141 (4.78), 7.290 (1.27), 7.305 (1.44), 7.308 (1.52), 7.321 (1.47), 7.631 (1.14), 7.642 (5.14), 7.752 (1.29), 7.756 (1.29), 7.771 (2.15), 7.776 (2.18), 7.785 (0.46), 7.790 (1.22), 7.795 (1.27), 8.030 (4.89), 8.032 (4.78), 8.531 (1.95), 8.533 (2.03), 8.543 (1.95), 8.545 (1.90), 8.719 (0.81), 8.734 (1.70), 8.748 (0.81). LC-MS (Method A); $R_t$ = 0.87 min, m/z = 390 $[M + H]^+$. | Intermediate 2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 33-1 | 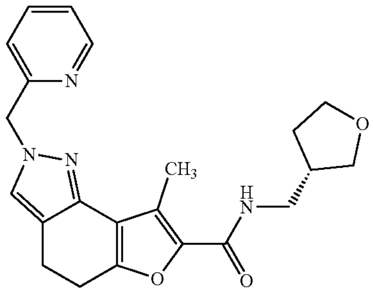 [SMILES: Cc1c(C(=O)NC[C@@H]2CCOC2)oc2c1-c1nn(Cc3ccccn3)cc1CC2] 8-methyl-2-(pyridin-2-ylmethyl)-N-[(3S)-tetrahydrofuran-3-ylmethyl]-4,5-dihydro-2H-furo[2,3-g]indazole-7-carboxamide | $^1$H-NMR (400 MHz, DMSO-d6) δ [ppm]: 1.552 (0.48), 1.566 (0.73), 1.585 (0.77), 1.600 (0.55), 1.871 (0.65), 1.886 (0.71), 1.891 (0.51), 1.896 (0.44), 1.902 (0.61), 1.916 (0.55), 2.442 (16.00), 2.456 (0.95), 2.476 (0.85), 2.518 (2.00), 2.523 (1.35), 2.883 (2.87), 2.892 (7.47), 2.902 (3.29), 3.154 (1.09), 3.162 (1.05), 3.172 (1.52), 3.176 (1.54), 3.188 (1.05), 3.195 (1.07), 3.429 (1.19), 3.442 (1.23), 3.450 (1.47), 3.464 (1.39), 3.564 (0.63), 3.583 (1.37), 3.601 (1.47), 3.620 (0.89), 3.628 (1.52), 3.645 (1.70), 3.649 (1.56), 3.667 (1.19), 3.691 (0.77), 3.705 (0.91), 3.711 (1.29), 3.725 (1.25), 3.731 (0.69), 3.745 (0.53), 5.381 (6.55), 7.060 (1.76), 7.079 (1.84), 7.289 (0.91), 7.291 (0.93), 7.301 (0.95), 7.303 (1.01), 7.308 (1.15), 7.310 (1.01), 7.320 (1.05), 7.322 (0.99), 7.630 (4.93), 7.750 (1.11), 7.754 (1.13), 7.769 (1.80), 7.773 (1.80), 7.788 (0.93), 7.793 (0.95), 8.237 (0.69), 8.252 (1.45), 8.266 (0.69), 8.527 (1.21), 8.529 (1.37), 8.531 (1.47), 8.534 (1.25), 8.539 (1.29), 8.541 (1.37), 8.543 (1.35), 8.546 (1.13). LC-MS (Method A); $R_t$ = 0.90 min, m/z = 393 $[M + H]^+$. | Intermediate 2; GP G (conditions A with HATU) |
| 33-2 | 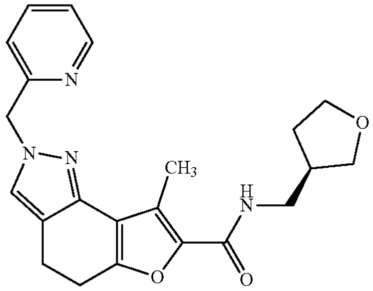 [SMILES: Cc1c(C(=O)NC[C@H]2CCOC2)oc2c1-c1nn(Cc3ccccn3)cc1CC2] 8-methyl-2-(pyridin-2-ylmethyl)-N-[(3R)-tetrahydrofuran-3-ylmethyl]-4,5-dihydro-2H-furo[2,3-g]indazole-7-carboxamide | $^1$H-NMR (400 MHz, DMSO-d6) δ [ppm]: 1.552 (0.46), 1.566 (0.72), 1.586 (0.75), 1.600 (0.55), 1.866 (0.39), 1.871 (0.65), 1.886 (0.75), 1.892 (0.55), 1.897 (0.49), 1.902 (0.65), 1.906 (0.65), 1.917 (0.59), 1.922 (0.49), 1.937 (0.39), 2.442 (16.00), 2.456 (0.98), 2.518 (3.06), 2.523 (2.12), 2.743 (3.10), 2.884 (2.80), 2.893 (6.88), 2.902 (3.10), 3.154 (1.04), 3.162 (1.01), 3.172 (1.47), 3.176 (1.47), 3.188 (1.01), 3.195 (1.08), 3.429 (1.17), 3.442 (1.21), 3.450 (1.47), 3.464 (1.37), 3.564 (0.65), 3.583 (1.40), 3.601 (1.66), 3.604 (1.37), 3.621 (1.11), 3.628 (1.53), 3.645 (1.69), 3.649 (1.56), 3.661 (0.42), 3.667 (1.24), 3.691 (0.81), 3.706 (0.95), 3.711 (1.30), 3.725 (1.27), 3.731 (0.78), 3.745 (0.59), 5.382 (6.29), 5.805 (1.08), 7.060 (1.66), 7.079 (1.76), 7.289 (0.88), 7.292 (0.88), 7.301 (0.95), 7.304 (1.01), 7.308 (1.66), 7.311 (0.98), 7.320 (1.14), 7.323 (0.98), 7.331 (0.85), 7.631 (4.92), 7.750 (1.11), 7.755 (1.21), 7.758 (0.81), 7.769 (1.86), 7.774 (1.89), 7.781 (0.75), 7.788 (1.01), 7.794 (1.04), 8.237 (0.65), 8.252 (1.37), 8.266 (0.65), 8.527 (1.14), 8.529 (1.30), 8.532 (1.37), 8.534 (1.34), 8.539 (1.34), 8.541 (1.47), 8.544 (1.34), 8.546 (1.24), 8.633 (1.21). LC-MS (Method A); $R_t$ = 0.90 min, m/z = 393 $[M + H]^+$. | Intermediate 2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 34 | 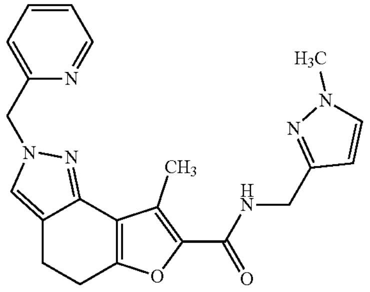 [SMILES: Cc1c(C(=O)NCc2ccn(C)n2)oc2c1-c1nn(Cc3ccccn3)cc1CC2] 8-methyl-N-[(1-methyl-1H-pyrazol-3-yl)methyl]-2-(pyridin-2-ylmethyl)-4,5-dihydro-2H-furo[2,3-g]indazole-7-carboxamide | $^1$H-NMR (400 MHz, DMSO-d6) δ [ppm]: 2.447 (12.27), 2.518 (1.68), 2.523 (1.22), 2.748 (0.45), 2.883 (9.36), 3.760 (0.50), 3.769 (16.00), 3.781 (0.70), 4.310 (2.50), 4.326 (2.48), 5.382 (4.90), 6.096 (2.69), 6.102 (2.70), 7.057 (1.34), 7.076 (1.40), 7.288 (0.71), 7.291 (0.70), 7.300 (0.72), 7.303 (0.76), 7.307 (0.82), 7.309 (0.75), 7.319 (0.85), 7.321 (0.75), 7.552 (2.31), 7.558 (2.26), 7.632 (4.03), 7.749 (0.86), 7.754 (0.92), 7.768 (1.46), 7.773 (1.51), 7.787 (0.82), 7.792 (0.80), 8.368 (0.54), 8.383 (1.17), 8.398 (0.52), 8.527 (0.90), 8.529 (1.03), 8.532 (1.08), 8.534 (1.00), 8.539 (0.98), 8.541 (1.06), 8.544 (1.01), 8.546 (0.89). LC-MS (Method A); $R_t$ = 0.89 min, m/z = 403 [M + H]$^+$. | Intermediate 2; GP G (conditions A with HATU) |
| 35 | 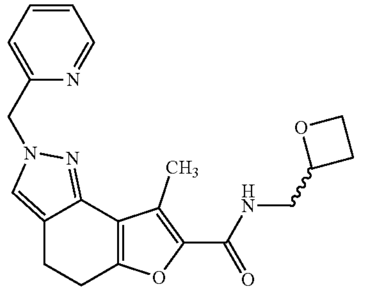 [SMILES: Cc1c(C(=O)NCC2CCO2)oc2c1-c1nn(Cc3ccccn3)cc1CC2] 8-methyl-N-[(2R/S)-oxetan-2-ylmethyl]-2-(pyridin-2-ylmethyl)-4,5-dihydro-2H-furo[2,3-g]indazole-7-carboxamide | $^1$H-NMR (400 MHz, DMSO-d6) δ [ppm]: 2.370 (0.41), 2.393 (0.48), 2.398 (0.60), 2.402 (0.43), 2.415 (0.49), 2.419 (0.54), 2.445 (16.00), 2.518 (1.30), 2.523 (0.87), 2.569 (0.41), 2.574 (0.53), 2.588 (0.53), 2.594 (0.57), 2.602 (0.45), 2.609 (0.44), 2.616 (0.42), 2.798 (0.58), 2.884 (2.59), 2.891 (8.02), 2.900 (3.13), 2.968 (0.46), 3.097 (0.49), 3.213 (0.53), 3.391 (0.65), 3.405 (0.44), 3.410 (0.78), 3.425 (1.36), 3.439 (0.69), 3.455 (0.72), 3.470 (1.30), 3.485 (0.83), 3.488 (0.48), 3.504 (0.57), 4.383 (0.57), 4.397 (1.22), 4.406 (0.68), 4.413 (0.98), 4.420 (1.20), 4.435 (0.71), 4.462 (0.73), 4.477 (0.64), 4.480 (0.92), 4.483 (1.00), 4.494 (0.70), 4.497 (0.75), 4.501 (0.83), 4.516 (0.54), 4.754 (0.75), 4.770 (0.91), 4.773 (0.94), 4.789 (0.74), 5.383 (6.29), 7.059 (1.69), 7.079 (1.76), 7.289 (0.83), 7.291 (0.86), 7.300 (0.90), 7.303 (0.94), 7.307 (0.97), 7.310 (0.99), 7.319 (0.99), 7.322 (0.94), 7.634 (4.84), 7.749 (1.08), 7.754 (1.10), 7.768 (1.74), 7.773 (1.77), 7.788 (0.96), 7.792 (0.96), 8.109 (0.64), 8.124 (1.32), 8.138 (0.63), 8.527 (1.13), 8.529 (1.22), 8.532 (1.32), 8.534 (1.11), 8.539 (1.19), 8.542 (1.26), 8.544 (1.26), 8.546 (1.05). LC-MS (Method A); $R_t$ = 0.86 min, m/z = 379 [M + H]$^+$. | Intermediate 2; GP G (conditions A with HATU) |
| 35-1 | Enantiomer 1 of Ex. 35 | $R_t$ = 3.47 min | analyt. method: Instrument: Agilent: 1260, Aurora SFC-Modul; Column: Chiralpak IA 5 μm, 100 × 4.6 mm; Eluent A: $CO_2$; Eluent B: methanol + 0.2 vol % aqueous ammonia (32%); Isocratic: 20% B; Flow: 4 mL/min; Temperature: 37.5° C.; BPR: |
| 35-2 | Enantiomer 2 of Ex. 35 | $R_t$ = 6.20 min | |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | | 100 bar; UV: 254 nm. |
| 36 | 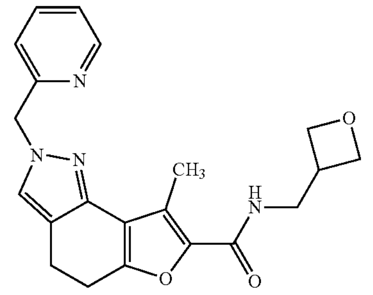 [SMILES: Cc1c(C(=O)NCC2COC2)oc2c1-c1nn(Cc3ccccn3)cc1CC2] 8-methyl-N-(oxetan-3-ylmethyl)-2-(pyridin-2-ylmethyl)-4,5-dihydro-2H-furo[2,3-g]indazole-7-carboxamide | $^{1}$H-NMR (400 MHz, DMSO-d6) δ [ppm]: 2.442 (16.00), 2.518 (1.34), 2.522 (0.93), 2.742 (0.40), 2.881 (2.67), 2.890 (7.18), 2.899 (3.07), 3.102 (0.52), 3.121 (0.79), 3.138 (0.55), 3.446 (1.76), 3.462 (2.41), 3.478 (1.57), 4.308 (2.55), 4.323 (5.35), 4.338 (2.71), 4.583 (3.23), 4.599 (3.29), 4.603 (3.45), 4.617 (2.77), 5.381 (6.29), 7.061 (1.66), 7.081 (1.73), 7.288 (0.86), 7.291 (0.86), 7.300 (0.91), 7.303 (0.98), 7.307 (1.02), 7.310 (0.93), 7.319 (0.99), 7.322 (0.91), 7.631 (4.74), 7.750 (1.06), 7.754 (1.11), 7.769 (1.85), 7.773 (1.84), 7.788 (0.95), 7.792 (0.91), 8.297 (0.65), 8.312 (1.36), 8.327 (0.62), 8.526 (1.11), 8.529 (1.29), 8.531 (1.31), 8.533 (1.21), 8.538 (1.12), 8.541 (1.31), 8.543 (1.21), 8.545 (1.12). LC-MS (Method A); $R_t$ = 0.83 min, m/z = 379 $[M + H]^+$. | Intermediate 2; GP G (conditions A with HATU) |
| 37 | 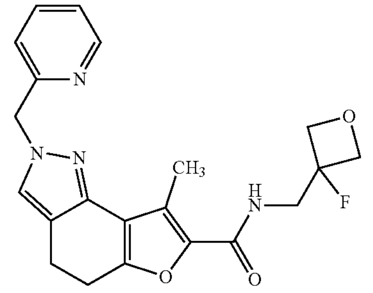 [SMILES: Cc1c(C(=O)NCC2(F)COC2)oc2c1-c1nn(Cc3ccccn3)cc1CC2] N-[(3-fluorooxetan-3-yl)methyl]-8-methyl-2-(pyridin-2-ylmethyl)-4,5-dihydro-2H-furo[2,3-g]indazole-7-carboxamide | $^{1}$H-NMR (400 MHz, DMSO-d6) δ [ppm]: 2.456 (16.00), 2.518 (0.84), 2.522 (0.58), 2.889 (2.47), 2.900 (4.13), 2.906 (4.33), 2.917 (3.09), 2.934 (0.41), 3.675 (1.43), 3.691 (1.43), 3.723 (1.42), 3.738 (1.44), 4.559 (1.15), 4.580 (1.94), 4.611 (1.23), 4.632 (2.00), 4.638 (2.20), 4.660 (1.24), 4.690 (2.03), 4.712 (1.25), 5.385 (6.41), 7.065 (1.74), 7.085 (1.83), 7.289 (0.85), 7.292 (0.88), 7.301 (0.89), 7.304 (0.96), 7.308 (0.98), 7.311 (0.92), 7.320 (0.96), 7.323 (0.95), 7.639 (4.68), 7.750 (1.01), 7.755 (1.02), 7.770 (1.76), 7.774 (1.79), 7.789 (0.92), 7.794 (0.91), 8.436 (0.67), 8.451 (1.45), 8.467 (0.66), 8.528 (1.11), 8.530 (1.27), 8.533 (1.31), 8.534 (1.17), 8.540 (1.15), 8.542 (1.27), 8.545 (1.23), 8.546 (1.08). LC-MS (Method A); $R_t$ = 0.89 min, m/z = 397 $[M + H]^+$. | Intermediate 2; GP G (conditions A with HATU) |
| 38 | 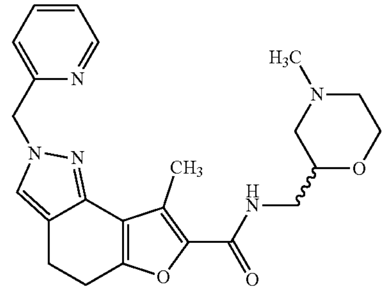 [SMILES: Cc1c(C(=O)NCC2CN(C)CCO2)oc2c1-c1nn(Cc3ccccn3)cc1CC2] 8-methyl-N-{[(2R/S)-4-methylmorpholin-2-yl]methyl}-2-(pyridin-2-ylmethyl)-4,5-dihydro-2H-furo[2,3-g]indazole-7-carboxamide | $^{1}$H-NMR (400 MHz, DMSO-d6) δ [ppm]: 1.656 (0.85), 1.682 (1.17), 1.710 (0.90), 1.917 (0.50), 1.937 (0.92), 1.945 (0.92), 1.965 (0.54), 1.973 (0.49), 2.152 (12.47), 2.440 (16.00), 2.518 (1.08), 2.522 (0.76), 2.537 (0.91), 2.567 (0.81), 2.651 (0.99), 2.669 (0.45), 2.678 (1.00), 2.882 (2.89), 2.890 (8.01), 2.898 (3.11), 3.181 (0.51), 3.200 (0.79), 3.215 (1.34), 3.230 (1.30), 3.245 (1.21), 3.261 (0.82), 3.279 (0.49), 3.427 (0.49), 3.433 (0.61), 3.455 (1.13), 3.461 (1.12), 3.483 (0.67), 3.489 (0.55), 3.536 (0.58), 3.542 (0.71), 3.551 (0.51), 3.561 (0.70), 3.566 (0.56), 3.747 (0.85), 3.751 (0.85), 3.755 (0.67), 3.771 (0.59), 3.775 (0.74), 3.778 (0.70), 5.382 (6.66), 7.058 (1.75), 7.078 (1.83), 7.288 (0.87), 7.291 (0.85), 7.300 (0.92), 7.303 (0.95), 7.307 (1.02), 7.319 (1.00), 7.633 (4.82), 7.749 (0.97), 7.754 (0.96), 7.769 (1.67), 7.773 (1.67), 7.788 (0.87), 7.792 (0.85), 8.018 (0.70), 8.032 (1.47), 8.047 (0.67), 8.527 (1.12), 8.529 (1.30), 8.531 (1.33), 8.534 (1.14), 8.539 (1.14), | Intermediate 2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 8.541 (1.32), 8.543 (1.26). LC-MS (Method A); $R_t$ = 0.87 min, m/z = 422 $[M + H]^+$. | |
| 38-1 | Enantiomer 1 of Ex. 38 | $R_t$ = 6.99 min | analyt. method: |
| 38-2 | Enantiomer 2 of Ex. 38 | $R_t$ = 8.91 min | Instrument: Waters Alliance 2695; Column: YMC Cellulose SC 3 µm, 100 × 4.6 mm; Eluent A: hexane + 0.1 vol % diethylamine; Eluent B: 2-propanol; Isocratic: 70% A + 30% B; Flow: 1.4 mL/min; Temperature: 25° C.; UV: 254 nm. |
| 39 | 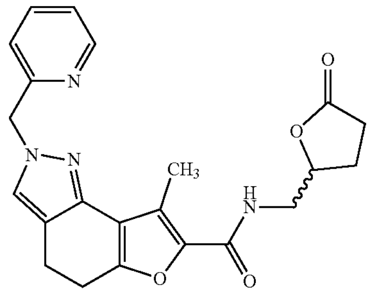 [SMILES: Cc1c(C(=O)NCC2CCC(=O)O2)oc2c1-c1nn(Cc3ccccn3)cc1CC2] 8-methyl-N-{[(2R/S)-5-oxotetrahydrofuran-2-yl]methyl}-2-(pyridin-2-ylmethyl)-4,5-dihydro-2H-furo[2,3-g]indazole-7-carboxamide | $^1$H-NMR (400 MHz, DMSO-d6) δ [ppm]: 1.154 (0.92), 1.172 (1.83), 1.190 (0.96), 1.904 (0.58), 1.922 (0.49), 1.932 (0.42), 1.936 (0.68), 1.954 (0.66), 1.959 (0.44), 1.987 (3.76), 2.189 (0.40), 2.194 (0.42), 2.204 (0.63), 2.209 (0.44), 2.212 (0.56), 2.226 (0.79), 2.240 (0.41), 2.439 (0.46), 2.451 (16.00), 2.468 (1.44), 2.483 (2.44), 2.518 (2.39), 2.523 (1.86), 2.751 (0.53), 2.889 (2.52), 2.900 (5.86), 2.910 (3.11), 3.319 (0.40), 3.406 (0.88), 3.420 (1.63), 3.431 (1.89), 3.447 (0.88), 4.017 (0.82), 4.034 (0.81), 4.628 (0.76), 4.644 (1.08), 4.658 (0.74), 5.385 (6.39), 7.060 (1.74), 7.080 (1.81), 7.289 (0.89), 7.291 (0.88), 7.301 (0.94), 7.303 (0.95), 7.308 (1.02), 7.310 (0.95), 7.320 (1.03), 7.322 (0.96), 7.637 (4.88), 7.750 (1.10), 7.754 (1.07), 7.770 (1.79), 7.774 (1.93), 7.789 (1.00), 7.793 (1.00), 8.300 (0.68), 8.315 (1.45), 8.330 (0.67), 8.528 (1.10), 8.530 (1.31), 8.532 (1.29), 8.534 (1.21), 8.540 (1.18), 8.542 (1.36), 8.544 (1.25), 8.546 (1.13). UPLC-MS (Method 1); $R_t$ = 0.84 min, m/z = 407 $[M + H]^+$. | Intermediate 2; GP G (conditions A with HATU) |
| 39-1 | Enantiomer 1 of Ex. 39 | $R_t$ = 4.18 min | analyt. method: |
| 39-2 | Enantiomer 2 of Ex. 39 | $R_t$ = 6.46 min | Instrument: Agilent: 1260, Aurora SFC-Modul; Column: Chiralpak IA 5 µm, 100 × 4.6 mm; Eluent A: $CO_2$; Eluent B: ethanol + 0.2 vol % aqueous ammonia (32%); Isocratic: 25% B; Flow: 4 mL/min; Temperature: |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | | 37.5° C.; BPR: 100 bar; UV: 254 nm. |
| 40 | 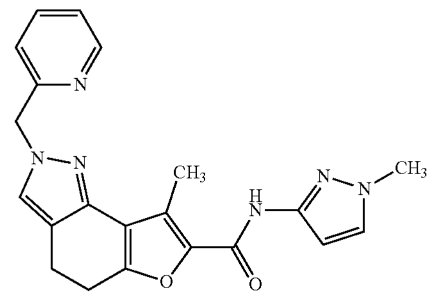 [SMILES: Cc1c(C(=O)Nc2ccn(C)n2)oc2c1-c1nn(Cc3ccccn3)cc1CC2] 8-methyl-N-(1-methyl-1H-pyrazol-3-yl)-2-(pyridin-2-ylmethyl)-4,5-dihydro-2H-furo[2,3-g]indazole-7-carboxamide | $^1$H-NMR (400 MHz, DMSO-d6) δ [ppm]: 2.485 (16.00), 2.521 (0.89), 2.525 (0.58), 2.882 (0.46), 2.900 (2.75), 2.911 (6.39), 2.921 (3.20), 3.763 (15.32), 5.395 (6.68), 6.498 (3.41), 6.504 (3.34), 7.067 (1.76), 7.087 (1.84), 7.294 (0.89), 7.296 (0.92), 7.306 (0.96), 7.308 (1.01), 7.313 (1.07), 7.325 (1.09), 7.578 (2.85), 7.584 (2.82), 7.652 (4.67), 7.756 (0.98), 7.760 (1.00), 7.775 (1.70), 7.779 (1.71), 7.795 (0.87), 7.799 (0.88), 8.536 (1.34), 8.538 (1.38), 8.540 (1.24), 8.548 (1.35), 8.550 (1.29), 10.137 (3.27). LC-MS (Method A); $R_t$ = 0.93 min, m/z = 389 $[M + H]^+$. | Intermediate 2; GP G (conditions A with HATU) |
| 41 | 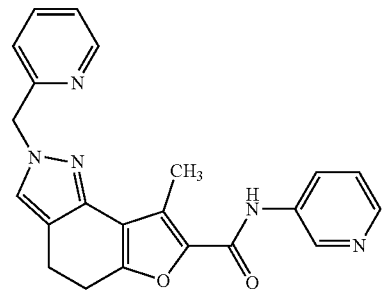 [SMILES: Cc1c(C(=O)Nc2cccnc2)oc2c1-c1nn(Cc3ccccn3)cc1CC2] 8-methyl-N-(pyridin-3-yl)-2-(pyridin-2-ylmethyl)-4,5-dihydro-2H-furo[2,3-g]indazole-7-carboxamide | $^1$H-NMR (400 MHz, DMSO-d6) δ [ppm]: 2.528 (16.00), 2.826 (0.86), 2.908 (0.55), 2.913 (0.59), 2.924 (0.93), 2.931 (2.49), 2.948 (2.21), 2.984 (2.35), 3.001 (2.81), 3.009 (0.94), 3.019 (0.69), 3.025 (0.64), 5.408 (6.78), 7.087 (1.80), 7.107 (1.88), 7.299 (0.92), 7.302 (0.91), 7.312 (0.98), 7.315 (1.05), 7.318 (1.12), 7.321 (1.01), 7.330 (1.11), 7.333 (1.03), 7.342 (1.26), 7.354 (1.25), 7.364 (1.25), 7.375 (1.27), 7.673 (4.57), 7.763 (1.09), 7.767 (1.08), 7.783 (1.81), 7.787 (1.84), 7.802 (1.00), 7.806 (1.01), 8.163 (0.98), 8.167 (1.22), 8.169 (1.12), 8.173 (1.07), 8.184 (0.96), 8.188 (1.09), 8.190 (1.11), 8.194 (0.97), 8.272 (2.08), 8.276 (1.98), 8.284 (2.02), 8.287 (1.78), 8.538 (1.22), 8.541 (1.39), 8.543 (1.46), 8.545 (1.27), 8.550 (1.30), 8.553 (1.40), 8.555 (1.36), 8.557 (1.15), 8.935 (2.42), 8.940 (2.46), 10.251 (3.28). LC-MS (Method A); $R_t$ = 0.94 min, m/z = 386 $[M + H]^+$. | Intermediate 2; GP G (conditions A with HATU) |
| 42 | 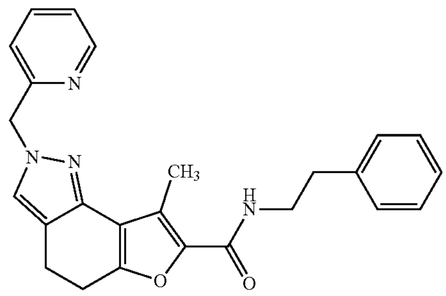 [SMILES: Cc1c(C(=O)NCCc2ccccc2)oc2c1-c1nn(Cc3ccccn3)cc1CC2] 8-methyl-N-(2-phenylethyl)-2-(pyridin-2-ylmethyl)-4,5-dihydro-2H-furo[2,3-g]indazole-7-carboxamide | $^1$H-NMR (400 MHz, DMSO-d6) δ [ppm]: 1.234 (0.52), 2.443 (16.00), 2.520 (7.38), 2.525 (4.77), 2.742 (0.49), 2.792 (1.63), 2.810 (2.30), 2.830 (1.74), 2.889 (12.79), 3.391 (1.16), 3.407 (1.77), 3.428 (1.72), 3.444 (0.88), 5.385 (7.12), 7.059 (1.89), 7.078 (1.95), 7.183 (0.68), 7.201 (1.84), 7.220 (3.33), 7.237 (4.15), 7.282 (3.30), 7.301 (3.57), 7.314 (1.49), 7.319 (1.48), 7.323 (1.63), 7.635 (5.29), 7.753 (1.04), 7.758 (1.13), 7.772 (1.84), 7.777 (1.82), 7.791 (0.93), 7.796 (0.88), 8.164 (0.79), 8.178 (1.64), 8.193 (0.77), 8.535 (1.48), 8.544 (1.45). LC-MS (Method A); $R_t$ = 1.17 min, m/z = 413 $[M + H]^+$. | Intermediate 2; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 43 | 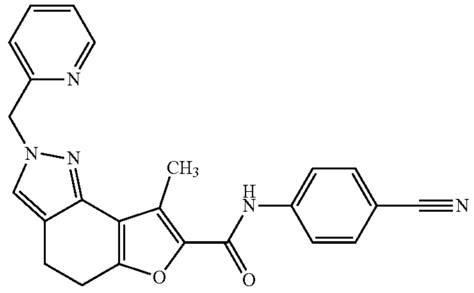 [SMILES: Cc1c(C(=O)Nc2ccc(C#N)cc2)oc2c1-c1nn(Cc3ccccn3)cc1CC2]<br>N-(4-cyanophenyl)-8-methyl-2-(pyridin-2-ylmethyl)-4,5-dihydro-2H-furo[2,3-g]indazole-7-carboxamide | $^1$H-NMR (400 MHz, DMSO-d6) δ [ppm]: −0.012 (0.44), −0.004 (11.85), 1.109 (0.45), 1.127 (1.04), 1.144 (0.48), 1.172 (1.94), 1.189 (1.96), 2.273 (1.66), 2.331 (0.56), 2.518 (3.74), 2.525 (16.00), 2.673 (0.56), 2.822 (0.81), 2.870 (2.20), 2.902 (0.60), 2.907 (0.61), 2.925 (2.47), 2.943 (2.11), 2.983 (2.27), 2.999 (2.77), 3.006 (0.97), 3.018 (0.66), 3.024 (0.64), 5.379 (0.99), 5.404 (6.56), 7.080 (1.82), 7.100 (1.91), 7.296 (0.94), 7.298 (1.04), 7.308 (1.10), 7.310 (1.06), 7.315 (1.12), 7.317 (1.12), 7.327 (1.09), 7.329 (1.00), 7.626 (0.70), 7.671 (4.58), 7.758 (1.13), 7.763 (1.35), 7.772 (4.27), 7.777 (3.11), 7.782 (2.23), 7.790 (1.72), 7.795 (5.14), 7.801 (1.52), 7.993 (5.12), 7.999 (1.56), 8.011 (1.39), 8.016 (3.91), 8.533 (1.29), 8.535 (1.43), 8.537 (1.57), 8.539 (1.45), 8.545 (1.36), 8.547 (1.43), 8.549 (1.36), 8.552 (1.19), 10.436 (2.40).<br>LC-MS (Method A); $R_t$ = 1.13 min, m/z = 410 $[M + H]^+$. | Intermediate 2; GP G (conditions A with HATU) |
| 44 | 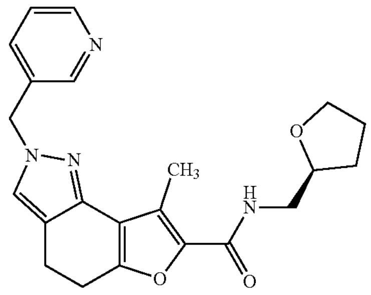 [SMILES: Cc1c(C(=O)NC[C@@H]2CCCO2)oc2c1-c1nn(Cc3cccnc3)cc1CC2]<br>8-methyl-2-(pyridin-3-ylmethyl)-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.547 (0.49), 1.564 (0.67), 1.571 (0.49), 1.579 (0.58), 1.588 (0.40), 1.593 (0.40), 1.771 (0.55), 1.778 (0.67), 1.793 (1.22), 1.810 (1.35), 1.828 (1.32), 1.839 (0.73), 1.843 (0.61), 1.848 (0.61), 1.856 (0.86), 1.871 (0.58), 1.873 (0.55), 1.878 (0.40), 2.456 (16.00), 2.518 (3.46), 2.523 (2.36), 2.859 (2.60), 2.869 (5.02), 2.872 (5.29), 2.883 (3.24), 3.209 (1.10), 3.214 (1.10), 3.224 (2.05), 3.229 (1.96), 3.239 (1.13), 3.245 (1.13), 3.580 (0.46), 3.596 (0.95), 3.599 (0.92), 3.616 (1.28), 3.634 (0.67), 3.730 (0.61), 3.744 (0.92), 3.747 (1.13), 3.761 (0.95), 3.764 (0.95), 3.782 (0.64), 3.924 (0.98), 3.940 (1.50), 3.956 (0.92), 5.335 (6.21), 7.360 (1.07), 7.362 (1.10), 7.372 (1.10), 7.374 (1.13), 7.380 (1.25), 7.382 (1.25), 7.392 (1.25), 7.394 (1.25), 7.641 (5.87), 7.650 (1.04), 7.660 (0.76), 7.666 (1.13), 7.670 (0.80), 7.967 (0.67), 7.981 (1.44), 7.997 (0.67), 8.489 (1.53), 8.493 (1.62), 8.500 (1.59), 8.505 (1.59), 8.514 (2.05), 8.519 (1.99).<br>LC-MS (Method A); $R_t$ = 0.93 min, m/z = 393 $[M + H]^+$. | Intermediate 3; GP G (conditions A with HATU) |
| 45 | 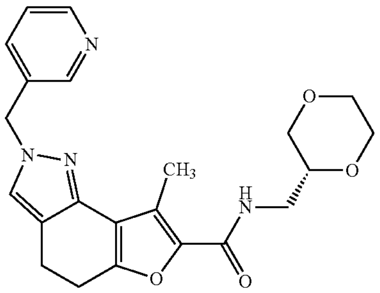 [SMILES: Cc1c(C(=O)NC[C@@H]2COCCO2)oc2c1-c1nn(Cc3cccnc3)cc1CC2]<br>N-[(2R)-1,4-dioxan-2-ylmethyl]-8-methyl-2-(pyridin-3-ylmethyl)-4,5-dihydro-2H-furo[2,3-g]indazole-7-carboxamide | $^1$H-NMR (400 MHz, DMSO-d6) δ [ppm]: 0.931 (0.80), 0.948 (0.81), 2.456 (16.00), 2.473 (0.44), 2.518 (1.31), 2.522 (0.88), 2.859 (2.51), 2.869 (4.67), 2.873 (4.96), 2.883 (3.15), 3.157 (0.57), 3.177 (1.81), 3.192 (1.43), 3.202 (1.53), 3.206 (2.06), 3.212 (0.85), 3.230 (1.90), 3.243 (0.85), 3.261 (0.56), 3.417 (0.47), 3.438 (1.01), 3.444 (1.08), 3.465 (0.90), 3.471 (0.85), 3.508 (0.78), 3.513 (0.85), 3.536 (1.03), 3.542 (1.08), 3.563 (0.43), 3.568 (0.69), 3.603 (1.62), 3.609 (1.22), 3.619 (0.59), 3.627 (1.28), 3.634 (1.28), 3.679 (1.16), 3.685 (0.95), 3.708 (2.01), 3.713 (1.72), 3.738 (0.84), 5.335 (5.97), 7.359 (1.08), 7.361 (1.06), 7.371 (1.11), 7.373 (1.13), 7.379 (1.24), 7.381 (1.21), 7.391 (1.26), 7.393 (1.23), 7.641 (5.45), | Intermediate 3; GP G (conditions A with HATU) |

TABLE 2-continued

The following examples (4 to 147) were prepared in analogy to example 3 starting from the given intermediates and commercially available amines (or their salts), applying the indicated general procedure.

| Ex-ample | Structure IUPAC-Name | Analytical Data | Preparation or Separation Methods |
|---|---|---|---|
| | | 7.650 (1.00), 7.660 (0.78), 7.665 (1.13), 7.670 (0.77), 8.043 (0.69), 8.059 (1.47), 8.073 (0.66), 8.488 (1.61), 8.492 (1.62), 8.500 (1.68), 8.504 (1.58), 8.514 (2.02), 8.518 (1.97).<br>LC-MS (Method A); $R_t$ = 0.85 min, m/z = 409 $[M + H]^+$. | |
| 46 | 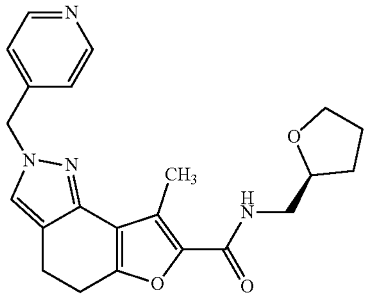 [SMILES: Cc1c(C(=O)NC[C@@H]2CCCO2)oc2c1-c1nn(Cc3ccncc3)cc1CC2]<br>8-methyl-2-(pyridin-4-ylmethyl)-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.550 (0.48), 1.565 (0.68), 1.574 (0.51), 1.582 (0.58), 1.590 (0.41), 1.595 (0.41), 1.774 (0.54), 1.779 (0.68), 1.795 (1.22), 1.813 (1.36), 1.831 (1.26), 1.842 (0.75), 1.851 (0.58), 1.859 (0.82), 1.873 (0.54), 2.446 (16.00), 2.518 (3.87), 2.523 (2.55), 2.674 (0.68), 2.886 (2.72), 2.895 (7.10), 2.905 (3.23), 3.212 (1.15), 3.217 (1.12), 3.228 (2.14), 3.232 (2.07), 3.243 (1.15), 3.247 (1.19), 3.582 (0.44), 3.598 (0.92), 3.602 (0.92), 3.619 (1.26), 3.636 (0.68), 3.732 (0.61), 3.749 (1.12), 3.764 (0.95), 3.767 (0.95), 3.785 (0.61), 3.927 (0.99), 3.943 (1.46), 3.959 (0.92), 5.363 (5.84), 7.135 (3.60), 7.139 (2.24), 7.146 (2.24), 7.150 (3.63), 7.655 (4.96), 7.974 (0.68), 7.990 (1.46), 8.005 (0.68), 8.515 (4.52), 8.520 (2.72), 8.527 (2.65), 8.531 (4.48).<br>LC-MS (Method A); $R_t$ = 0.92 min, m/z = 391 $[M - H]^-$. | Intermediate 4; GP G (conditions A with HATU) |
| 47 | 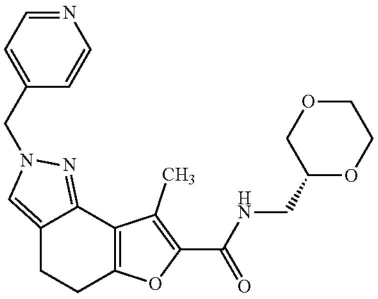 [SMILES: Cc1c(C(=O)NC[C@@H]2COCCO2)oc2c1-c1nn(Cc3ccncc3)cc1CC2]<br>N-[(2R)-1,4-dioxan-2-ylmethyl]-8-methyl-2-(pyridin-4-ylmethyl)-4,5-dihydro-2H-furo[2,3-g]indazole-7-carboxamide | $^1$H-NMR (400 MHz, DMSO-d6) δ [ppm]: 2.447 (16.00), 2.518 (0.88), 2.523 (0.58), 2.886 (2.54), 2.897 (6.53), 2.906 (3.11), 3.162 (0.57), 3.181 (1.82), 3.196 (1.43), 3.204 (1.50), 3.209 (1.82), 3.216 (0.85), 3.233 (2.23), 3.247 (0.85), 3.266 (0.57), 3.420 (0.47), 3.440 (0.99), 3.446 (1.09), 3.468 (0.88), 3.474 (0.85), 3.511 (0.75), 3.516 (0.84), 3.539 (1.04), 3.545 (1.08), 3.565 (0.43), 3.572 (0.70), 3.607 (1.48), 3.614 (0.97), 3.623 (0.61), 3.632 (1.37), 3.637 (1.18), 3.682 (1.15), 3.688 (0.96), 3.711 (2.00), 3.717 (1.70), 3.741 (0.84), 5.364 (5.55), 7.135 (3.46), 7.139 (2.21), 7.146 (2.29), 7.150 (3.64), 7.656 (5.03), 8.053 (0.69), 8.068 (1.46), 8.083 (0.67), 8.516 (4.94), 8.520 (2.98), 8.527 (2.90), 8.530 (4.70).<br>LC-MS (Method A); $R_t$ = 0.84 min, m/z = 409 $[M + H]^+$. | Intermediate 4; GPG (conditions A with HATU) |
| 48 | 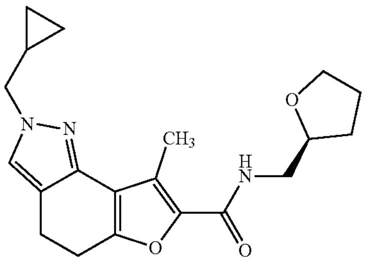 [SMILES: Cc1c(C(=O)NC[C@@H]2CCCO2)oc2c1-c1nn(CC3CC3)cc1CC2]<br>2-(cyclopropylmethyl)-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 0.330 (0.56), 0.342 (2.14), 0.346 (1.81), 0.353 (1.97), 0.357 (2.04), 0.368 (0.79), 0.491 (0.81), 0.501 (1.76), 0.506 (1.93), 0.511 (0.98), 0.516 (0.88), 0.521 (1.93), 0.526 (1.81), 0.537 (0.63), 1.201 (0.46), 1.208 (0.44), 1.220 (0.81), 1.232 (0.46), 1.240 (0.46), 1.553 (0.44), 1.570 (0.63), 1.577 (0.46), 1.586 (0.53), 1.775 (0.49), 1.782 (0.65), 1.797 (1.09), 1.815 (1.23), 1.832 (1.16), 1.844 (0.65), 1.854 (0.53), 1.858 (0.63), 1.862 (0.74), 1.876 (0.51), 1.879 (0.49), 2.476 (16.00), 2.518 (2.55), 2.522 (1.65), 2.791 (0.42), 2.853 (2.28), 2.855 (2.35), 2.865 (3.65), 2.871 (3.92), 2.883 (3.02), 2.901 (0.42), 3.214 (1.00), 3.219 (0.98), 3.229 (1.88), 3.235 | Intermediate 5; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | (1.76), 3.244 (1.02), 3.250 (1.04), 3.584 (0.39), 3.599 (0.84), 3.603 (0.84), 3.620 (1.16), 3.638 (0.65), 3.734 (0.58), 3.748 (0.84), 3.751 (1.04), 3.766 (0.88), 3.769 (0.86), 3.771 (0.70), 3.787 (0.60), 3.898 (3.76), 3.916 (3.83), 3.929 (0.98), 3.945 (1.39), 3.960 (0.84), 7.535 (4.30), 7.956 (0.58), 7.970 (1.23), 7.986 (0.58). LC-MS (Method A); $R_t$ = 1.25 min, m/z = 356 $[M + H]^+$. | |
| 49 | 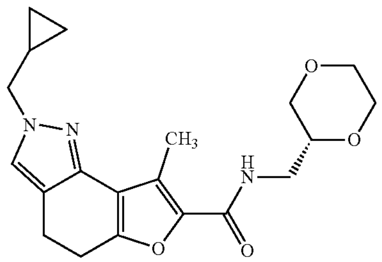 [SMILES: Cc1c(C(=O)NC[C@@H]2COCCO2)oc2c1-c1nn(CC3CC3)cc1CC2] 2-(cyclopropylmethyl)-N-[(2R)-1,4-dioxan-2-ylmethyl]-8-methyl-4,5-dihydro-2H-furo[2,3-g]indazole-7-carboxamide | $^1$H-NMR (400 MHz, DMSO-d6) δ [ppm]: 0.331 (0.55), 0.342 (2.17), 0.346 (1.83), 0.354 (2.02), 0.358 (2.08), 0.368 (0.81), 0.492 (0.83), 0.502 (1.77), 0.506 (1.94), 0.511 (1.01), 0.517 (0.94), 0.522 (1.95), 0.527 (1.84), 0.537 (0.66), 1.201 (0.46), 1.209 (0.45), 1.221 (0.80), 1.233 (0.44), 1.240 (0.45), 2.477 (16.00), 2.518 (2.12), 2.523 (1.48), 2.791 (0.54), 2.836 (0.44), 2.855 (2.24), 2.867 (3.58), 2.873 (3.80), 2.885 (2.98), 2.903 (0.44), 3.163 (0.55), 3.183 (1.63), 3.197 (1.37), 3.207 (1.49), 3.212 (1.98), 3.217 (0.86), 3.233 (1.44), 3.236 (1.65), 3.248 (0.86), 3.267 (0.54), 3.422 (0.45), 3.443 (0.96), 3.449 (1.05), 3.470 (0.89), 3.476 (0.84), 3.513 (0.77), 3.518 (0.86), 3.541 (1.02), 3.547 (1.03), 3.568 (0.44), 3.573 (0.69), 3.608 (1.45), 3.624 (0.61), 3.633 (1.28), 3.639 (1.14), 3.686 (1.09), 3.693 (0.91), 3.715 (1.82), 3.720 (1.43), 3.743 (0.79), 3.899 (3.75), 3.917 (3.72), 7.537 (4.44), 8.035 (0.60), 8.050 (1.30), 8.065 (0.59). LC-MS (Method A); $R_t$ = 1.01 min, m/z = 372 $[M + H]^+$. | Intermediate 5; GP G (conditions A with HATU) |
| 50 | 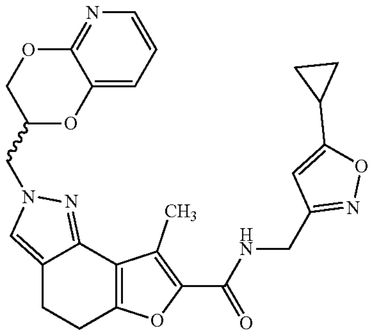 [SMILES: Cc1c(C(=O)NCc2cc(C3CC3)on2)oc2c1-c1nn(CC3COc4ncccc4O3)cc1CC2] N-[(5-cyclopropyl-1,2-oxazol-3-yl)methyl]-2-[(2R/S)-2,3-dihydro[1,4]dioxino[2,3-b]pyridin-2-ylmethyl]-8-methyl-4,5-dihydro-2H-furo[2,3-g]indazole-7-carboxamide | $^1$H-NMR (400 MHz, DMSO-d6) δ [ppm]: 0.822 (1.95), 0.834 (6.68), 0.840 (6.68), 0.846 (6.49), 0.849 (4.09), 0.852 (6.93), 0.862 (2.77), 0.932 (2.02), 0.949 (2.02), 0.995 (2.71), 1.005 (6.17), 1.012 (6.11), 1.016 (3.21), 1.023 (2.90), 1.026 (6.87), 1.033 (5.67), 1.044 (2.08), 2.071 (1.01), 2.083 (1.95), 2.092 (2.08), 2.095 (1.13), 2.104 (3.78), 2.113 (1.26), 2.117 (1.89), 2.125 (1.83), 2.138 (0.88), 2.337 (1.20), 2.518 (15.43), 2.523 (10.46), 2.678 (1.26), 2.687 (0.50), 2.801 (0.76), 2.842 (0.44), 2.857 (0.82), 2.874 (6.49), 2.886 (15.75), 2.895 (8.00), 2.913 (0.88), 2.928 (0.44), 4.177 (2.65), 4.194 (2.96), 4.207 (3.02), 4.223 (3.15), 4.345 (8.13), 4.360 (8.13), 4.372 (1.76), 4.390 (3.34), 4.408 (3.91), 4.422 (3.46), 4.433 (3.91), 4.458 (1.39), 4.470 (1.32), 4.506 (3.15), 4.511 (3.97), 4.535 (2.96), 4.541 (2.96), 4.615 (0.82), 4.620 (0.94), 4.626 (1.20), 4.632 (2.39), 4.637 (1.64), 4.643 (1.76), 4.649 (2.08), 4.665 (0.57), 6.093 (16.00), 6.943 (5.17), 6.954 (5.04), 6.962 (5.48), 6.974 (5.42), 7.294 (5.86), 7.299 (6.17), 7.314 (5.48), 7.318 (5.17), 7.544 (12.16), 7.754 (5.42), 7.759 (5.98), 7.766 (5.92), 7.771 (5.10), 8.644 (1.95), 8.659 (4.28), 8.674 (1.89). LC-MS (Method A); $R_t$ = 1.13 min, m/z = 488 $[M + H]^+$. | Intermediate 6; GP G (conditions A with HATU) |

TABLE 2-continued

| Example | Structure IUPAC-Name | Analytical Data | Preparation or Separation Methods |
|---|---|---|---|
| The following examples (4 to 147) were prepared in analogy to example 3 starting from the given intermediates and commercially available amines (or their salts), applying the indicated general procedure. | | | |
| 50-1<br>50-2 | Enantiomer 1 of Ex. 50<br>Enantiomer 2 of Ex. 50 | $R_t$ = 5.61 min<br>$R_t$ = 6.60 min | analyt. method: Instrument: Agilent HPLC 1260; Column: Amylose SA 3 μm, 100 × 4.6 mm; Eluent A: hexane + 0.1 vol % diethylamine (99%); Eluent B: ethanol; Gradient: 20-50% B in 7 min; Flow: 1.4 mL/min; Temperature: 25° C.; DAD: 220 nm. |
| 51 | 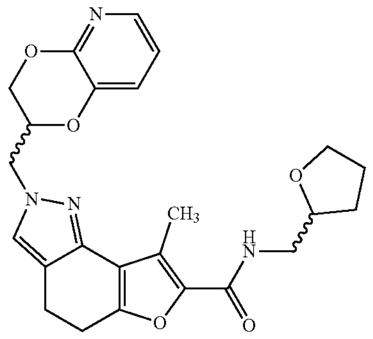 [SMILES: Cc1c(C(=O)NCC2CCCO2)oc2c1-c1nn(CC3COc4ncccc4O3)cc1CC2]<br>2-[(2R/S)-2,3-dihydro[1,4]dioxino[2,3-b]pyridin-2-ylmethyl]-8-methyl-N-[(2R/S)-tetrahydrofuran-2-ylmethyl]-4,5-dihydro-2H-furo[2,3-g]indazole-7-carboxamide | $^1$H-NMR (400 MHz, DMSO-d6) δ [ppm]: 0.932 (2.78), 0.935 (0.86), 0.948 (2.74), 0.953 (0.44), 1.553 (0.46), 1.569 (0.64), 1.577 (0.48), 1.585 (0.56), 1.775 (0.52), 1.781 (0.66), 1.796 (1.16), 1.815 (1.28), 1.832 (1.22), 1.844 (0.68), 1.853 (0.56), 1.858 (0.64), 1.861 (0.76), 1.876 (0.52), 2.318 (0.44), 2.480 (16.00), 2.518 (5.01), 2.523 (3.26), 2.869 (2.36), 2.880 (4.31), 2.885 (4.33), 2.896 (2.84), 3.215 (0.94), 3.220 (0.98), 3.230 (1.80), 3.235 (1.78), 3.245 (0.98), 3.250 (1.04), 3.584 (0.42), 3.599 (0.90), 3.603 (0.90), 3.620 (1.18), 3.638 (0.64), 3.734 (0.56), 3.751 (1.10), 3.765 (0.92), 3.769 (0.92), 3.786 (0.60), 3.929 (0.94), 3.946 (1.40), 3.961 (0.88), 4.177 (0.98), 4.194 (1.10), 4.207 (1.14), 4.223 (1.20), 4.351 (0.48), 4.368 (0.52), 4.387 (1.30), 4.405 (1.50), 4.418 (1.32), 4.430 (1.50), 4.454 (0.50), 4.466 (0.50), 4.505 (1.22), 4.511 (1.48), 4.535 (1.14), 4.541 (1.12), 4.630 (0.90), 4.636 (0.62), 4.641 (0.66), 4.647 (0.78), 6.942 (1.94), 6.953 (1.94), 6.962 (2.04), 6.973 (2.10), 7.295 (2.14), 7.299 (2.42), 7.314 (2.00), 7.318 (2.06), 7.538 (4.67), 7.754 (2.10), 7.758 (2.26), 7.766 (2.12), 7.770 (2.04), 7.977 (0.68), 7.992 (1.44), 8.007 (0.66).<br>LC-MS (Method A); $R_t$ = 1.06 min, m/z = 451 [M + H]$^+$. | Intermediate 6; GP G (conditions A with HATU) |
| 52 | 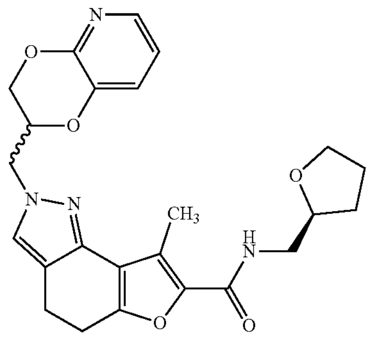 [SMILES: Cc1c(C(=O)NC[C@@H]2CCCO2)oc2c1-c1nn(CC3COc4ncccc4O3)cc1CC2] | $^1$H-NMR (400 MHz, DMSO-d6) δ [ppm]: 1.552 (0.41), 1.568 (0.53), 1.584 (0.47), 1.781 (0.65), 1.796 (1.83), 1.814 (1.18), 1.831 (1.12), 1.843 (0.77), 1.857 (0.77), 1.875 (0.47), 2.074 (6.67), 2.336 (0.83), 2.479 (16.00), 2.518 (10.10), 2.522 (6.67), 2.678 (0.89), 2.686 (5.79), 2.727 (7.14), 2.869 (3.25), 2.879 (4.66), 2.888 (10.69), 2.895 (3.07), 2.912 (0.59), 3.214 (0.89), 3.219 (0.89), 3.229 (1.54), 3.235 (1.54), 3.245 (0.89), 3.250 (0.94), 3.583 (0.41), 3.602 (0.83), 3.620 (1.06), 3.637 (0.65), 3.709 (0.47), 3.733 (0.59), 3.747 (0.89), 3.750 (0.94), 3.765 (0.77), 3.768 (0.83), 3.785 (0.53), 3.929 (0.89), | Intermediate 6; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| | 2-[(2R/S)-2,3-dihydro[1,4]dioxino[2,3-b]pyridin-2-ylmethyl]-8-methyl-N-[(2S)-tetrahydrofuran-2-ylmethyl]-4,5-dihydro-2H-furo[2,3-g]indazole-7-carboxamide | 3.945 (1.18), 3.960 (0.71), 4.176 (0.83), 4.193 (0.89), 4.206 (0.94), 4.222 (1.00), 4.350 (0.41), 4.368 (0.41), 4.386 (1.06), 4.404 (1.24), 4.417 (1.06), 4.429 (1.24), 4.454 (0.47), 4.465 (0.41), 4.504 (1.00), 4.510 (1.24), 4.534 (0.94), 4.540 (0.94), 4.629 (0.77), 4.640 (0.53), 4.646 (0.65), 6.941 (1.65), 6.953 (1.77), 6.961 (1.77), 6.973 (1.89), 7.294 (1.83), 7.298 (1.95), 7.313 (1.71), 7.318 (1.71), 7.537 (3.78), 7.754 (1.95), 7.757 (1.77), 7.766 (1.89), 7.769 (1.77), 7.950 (1.06), 7.979 (0.59), 7.994 (1.18), 8.009 (0.59), 8.546 (0.59). UPLC-MS (Method 1); $R_t$ = 1.01 min, m/z = 451 $[M + H]^+$. | |
| 52-1<br>52-2 | Diastereomer 1 of Ex. 52<br>Diastereomer 2 of Ex. 52 | $R_t$ = 4.93 min<br>$R_t$ = 9.03 min | analyt. method: Instrument: Agilent HPLC 1260; Column: Amylose SA 3 µm, 100 × 4.6 mm; Eluent A: hexane + 0.1 vol % diethylamine (99%); Eluent B: ethanol; Eluent C: MtBE; Isocratic: 60% A + 15% B + 25% C; Flow: 1.4 mL/min; Temperature: 25° C.; DAD: 280 nm. |
| 53 | 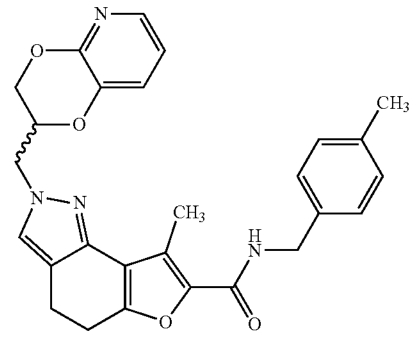 [SMILES: Cc1ccc(CNC(=O)c2oc3c(c2C)-c2nn(CC4COc5ncccc5O4)cc2CC3)cc1]<br>2-[(2R/S)-2,3-dihydro[1,4]dioxino[2,3-b][pyridin-2-ylmethyl]-8-methyl-N-(4-methylbenzyl)-4,5-dihydro-2H-furo[2,3-g]indazole-7-carboxamide | $^1$H-NMR (400 MHz, DMSO-d6) δ [ppm]: 2.264 (7.58), 2.484 (16.00), 2.518 (5.80), 2.523 (3.98), 2.869 (1.83), 2.882 (4.07), 2.891 (2.22), 4.175 (0.77), 4.192 (0.84), 4.205 (0.86), 4.221 (0.91), 4.328 (1.83), 4.343 (1.85), 4.368 (0.42), 4.387 (0.96), 4.404 (1.14), 4.418 (1.01), 4.430 (1.11), 4.504 (0.89), 4.509 (1.14), 4.533 (0.86), 4.539 (0.84), 4.630 (0.69), 4.636 (0.47), 4.641 (0.49), 4.646 (0.59), 6.941 (1.56), 6.953 (1.43), 6.961 (1.60), 6.973 (1.56), 7.104 (1.70), 7.124 (2.86), 7.177 (3.21), 7.197 (1.80), 7.294 (1.68), 7.298 (1.88), 7.313 (1.56), 7.317 (1.56), 7.537 (3.56), 7.754 (1.70), 7.758 (1.73), 7.766 (1.58), 7.770 (1.60), 8.614 (0.54), 8.630 (1.16), 8.646 (0.52). LC-MS (Method A); $R_t$ = 1.26 min, m/z = 471 $[M + H]^+$. | Intermediate 6; GP G (conditions A with HATU) |
| 53-1<br>53-2 | Enantiomer 1 of Ex. 53<br>Enantiomer 2 of Ex. 53 | $R_t$ = 2.46 min<br>$R_t$ = 4.34 min | analyt. method: Instrument: Agilent HPLC 1260; Column: Chiralpak AD-H 3 µm, 150 × 4.6 mm; Eluent A: methanol + 0.1 vol % diethylamine (99%); Eluent |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| | | | B: ethanol; Isocratic: 50% A + 50% B; Flow: 1.4 mL/min; Temperature: 25° C.; DAD: 280 nm. |
| 54 | 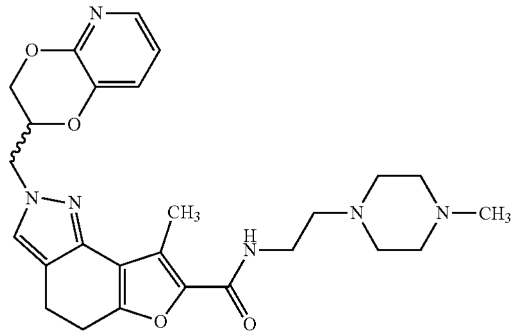 [SMILES: Cc1c(C(=O)NCCN2CCN(C)CC2)oc2c1-c1nn(CC3COc4ncccc4O3)cc1CC2]<br>2-[(2R/S)-2,3-dihydro[1,4]dioxino[2,3-b]pyridin-2-ylmethyl]-8-methyl-N-[2-(4-methylpiperazin-1-yl)ethyl]-4,5-dihydro-2H-furo[2,3-g]indazole-7-carboxamide | $^1$H-NMR (400 MHz, DMSO-d6) δ [ppm]: 2.135 (11.99), 2.298 (0.89), 2.318 (1.28), 2.322 (1.92), 2.326 (2.28), 2.331 (1.81), 2.336 (1.14), 2.392 (2.00), 2.409 (3.03), 2.426 (1.92), 2.477 (16.00), 2.518 (7.26), 2.522 (4.59), 2.659 (0.64), 2.664 (1.28), 2.669 (1.70), 2.673 (1.25), 2.678 (0.58), 2.868 (2.31), 2.878 (4.62), 2.881 (4.81), 2.891 (2.75), 3.271 (0.70), 3.288 (1.56), 3.304 (1.81), 4.175 (0.92), 4.192 (1.00), 4.205 (1.06), 4.222 (1.11), 4.349 (0.42), 4.367 (0.47), 4.386 (1.14), 4.404 (1.36), 4.417 (1.20), 4.429 (1.36), 4.453 (0.47), 4.465 (0.45), 4.504 (1.11), 4.510 (1.34), 4.534 (1.06), 4.540 (1.00), 4.629 (0.83), 4.634 (0.58), 4.639 (0.61), 4.646 (0.72), 6.941 (1.86), 6.953 (1.89), 6.961 (1.92), 6.973 (2.06), 7.293 (1.95), 7.298 (2.25), 7.313 (1.78), 7.317 (1.86), 7.536 (4.31), 7.754 (1.92), 7.758 (2.09), 7.766 (2.06), 7.770 (1.78), 7.916 (0.64), 7.931 (1.36), 7.945 (0.61). LC-MS (Method A); $R_t$ = 0.94 min, m/z = 493 $[M + H]^+$. | Intermediate 6; GP G (conditions A with HATU) |
| 55 | 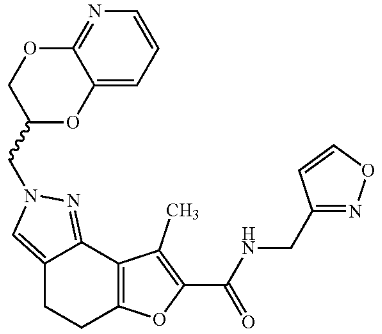 [SMILES: Cc1c(C(=O)NCc2ccon2)oc2c1-c1nn(CC3COc4ncccc4O3)cc1CC2]<br>2-[(2R/S)-2,3-dihydro[1,4]dioxino[2,3-b]pyridin-2-ylmethyl]-8-methyl-N-(1,2-oxazol-3-ylmethyl)-4,5-dihydro-2H-furo[2,3-g]indazole-7-carboxamide | $^1$H-NMR (400 MHz, DMSO-d6) δ [ppm]: 0.932 (0.98), 0.948 (0.98), 2.074 (5.60), 2.331 (2.71), 2.336 (1.23), 2.344 (0.43), 2.518 (16.00), 2.522 (9.97), 2.673 (2.71), 2.678 (1.23), 2.802 (0.74), 2.845 (0.49), 2.857 (0.92), 2.876 (6.15), 2.886 (11.32), 2.891 (11.38), 2.902 (7.20), 2.919 (0.98), 2.933 (0.49), 4.177 (2.46), 4.193 (2.71), 4.206 (2.89), 4.223 (3.02), 4.354 (1.23), 4.372 (1.29), 4.391 (3.20), 4.408 (3.75), 4.422 (3.32), 4.433 (3.82), 4.456 (8.31), 4.470 (8.74), 4.505 (3.08), 4.511 (3.69), 4.534 (3.02), 4.541 (2.83), 4.614 (0.80), 4.621 (0.92), 4.632 (2.28), 4.638 (1.60), 4.643 (1.72), 4.648 (2.03), 6.491 (9.78), 6.495 (9.23), 6.942 (4.92), 6.954 (4.62), 6.961 (5.17), 6.973 (5.05), 7.294 (5.23), 7.298 (5.97), 7.313 (4.98), 7.318 (4.98), 7.544 (11.38), 7.754 (5.42), 7.758 (5.60), 7.766 (5.17), 7.770 (5.11), 8.712 (1.85), 8.727 (4.06), 8.742 (1.85), 8.814 (8.18), 8.819 (7.94). LC-MS (Method A); $R_t$ = 1.00 min, m/z = 448 $[M + H]^+$. | Intermediate 6; GP G (conditions A with HATU) |
| 55-1 | Enantiomer 1 of Ex. 55 | $R_t$ = 5.34 min | analyt. method: Instrument: Agilent HPLC 1260; Column: Amylose SA 3 µm, 100 × 4.6 mm; Eluent A: hexane + 0.1 vol % diethylamine (99%); Eluent |
| 55-2 | Enantiomer 2 of Ex. 55 | $R_t$ = 6.88 min | |

TABLE 2-continued

| Ex-ample | Structure IUPAC-Name | Analytical Data | Preparation or Separation Methods |
|---|---|---|---|
| The following examples (4 to 147) were prepared in analogy to example 3 starting from the given intermediates and commercially available amines (or their salts), applying the indicated general procedure. | | | |
| | | | B: ethanol; Gradient: 20-50% B in 7 min; Flow: 1.4 mL/min; Temperature: 25° C.; DAD: 220 nm |
| 56 | 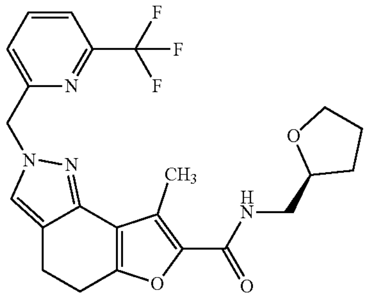 [SMILES: Cc1c(C(=O)NC[C@@H]2CCCO2)oc2c1-c1nn(Cc3cccc(C(F)(F)F)n3)cc1CC2] 8-methyl-N-[(2S)-tetrahydrofuran-2-ylmethyl]-2-{[6-(trifluoromethyl)pyridin-2-yl]methyl}-4,5-dihydro-2H-furo[2,3-g]indazole-7-carboxamide | $^1$H-NMR (400 MHz, DMSO-d6) δ [ppm]: 1.549 (0.47), 1.566 (0.68), 1.574 (0.50), 1.582 (0.58), 1.595 (0.42), 1.774 (0.53), 1.780 (0.68), 1.795 (1.18), 1.813 (1.34), 1.831 (1.26), 1.841 (0.68), 1.851 (0.55), 1.859 (0.79), 1.873 (0.55), 2.075 (4.74), 2.332 (1.11), 2.336 (0.47), 2.442 (16.00), 2.518 (6.34), 2.523 (4.16), 2.678 (0.47), 2.897 (3.03), 2.903 (9.63), 2.910 (3.34), 3.212 (1.11), 3.217 (1.08), 3.228 (2.08), 3.232 (2.00), 3.243 (1.11), 3.247 (1.16), 3.582 (0.42), 3.598 (0.92), 3.601 (0.89), 3.619 (1.26), 3.637 (0.71), 3.732 (0.63), 3.746 (0.92), 3.749 (1.13), 3.764 (0.95), 3.767 (0.95), 3.784 (0.66), 3.927 (0.97), 3.943 (1.47), 3.959 (0.92), 5.509 (6.26), 5.759 (5.95), 7.257 (1.68), 7.276 (1.74), 7.694 (5.11), 7.834 (1.74), 7.853 (2.08), 7.978 (0.71), 7.993 (1.50), 8.008 (0.71), 8.062 (1.08), 8.082 (1.87), 8.102 (0.87). LC-MS (Method A); $R_t$ = 1.16 min, m/z = 461 $[M + H]^+$. | Intermediate 7; GP G (conditions A with HATU) |
| 57 | 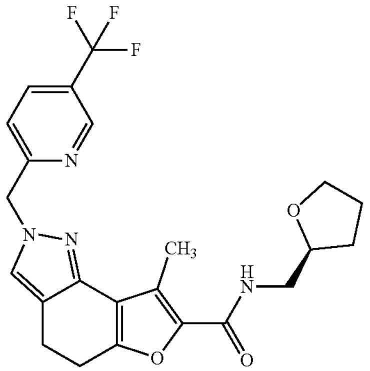 [SMILES: Cc1c(C(=O)NC[C@@H]2CCCO2)oc2c1-c1nn(Cc3ccc(C(F)(F)F)cn3)cc1CC2] 8-methyl-N-[(2S)-tetrahydrofuran-2-ylmethyl]-2-{[5-(trifluoromethyl)pyridin-2-yl]methyl}-4,5-dihydro-2H-furo[2,3-g]indazole-7-carboxamide | $^1$H-NMR (400 MHz, DMSO-d6) δ [ppm]: 0.932 (0.44), 0.948 (0.40), 1.549 (0.49), 1.565 (0.71), 1.572 (0.49), 1.580 (0.58), 1.594 (0.40), 1.773 (0.58), 1.779 (0.71), 1.794 (1.20), 1.812 (1.38), 1.830 (1.29), 1.841 (0.76), 1.851 (0.58), 1.858 (0.80), 1.872 (0.53), 2.332 (1.91), 2.336 (0.84), 2.434 (16.00), 2.518 (9.96), 2.522 (6.49), 2.673 (1.96), 2.678 (0.84), 2.902 (9.69), 2.909 (3.33), 3.211 (1.11), 3.215 (1.07), 3.226 (2.04), 3.230 (2.00), 3.242 (1.07), 3.246 (1.11), 3.582 (0.44), 3.597 (0.93), 3.601 (0.93), 3.618 (1.24), 3.636 (0.71), 3.731 (0.62), 3.748 (1.16), 3.763 (0.93), 3.766 (0.93), 3.784 (0.67), 3.925 (0.93), 3.942 (1.47), 3.958 (0.89), 5.527 (4.80), 7.241 (1.60), 7.262 (1.64), 7.684 (5.02), 7.974 (0.67), 7.989 (1.42), 8.004 (0.67), 8.198 (1.07), 8.202 (1.07), 8.218 (1.02), 8.223 (0.98), 8.547 (0.62), 8.948 (1.78), 8.954 (1.78). LC-MS (Method A); $R_t$ = 1.28 min, m/z = 461 $[M + H]^+$. | Intermediate 8; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 58 | 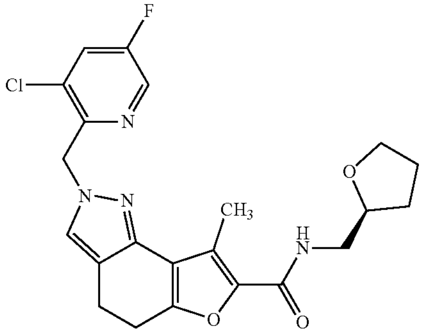 [SMILES: Cc1c(C(=O)NC[C@@H]2CCCO2)oc2c1-c1nn(Cc3ncc(F)cc3Cl)cc1CC2] 2-[(3-chloro-5-fluoropyridin-2-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.173 (0.62), 1.232 (1.05), 1.324 (0.53), 1.547 (0.53), 1.563 (0.70), 1.570 (0.53), 1.579 (0.62), 1.587 (0.44), 1.777 (0.70), 1.793 (1.23), 1.810 (1.41), 1.828 (1.32), 1.839 (0.70), 1.849 (0.62), 1.856 (0.88), 1.870 (0.53), 1.988 (0.79), 2.337 (1.05), 2.416 (16.00), 2.518 (16.00), 2.523 (11.08), 2.539 (1.14), 2.679 (1.14), 2.718 (0.97), 2.728 (9.23), 2.863 (2.55), 2.874 (6.07), 2.883 (3.34), 2.888 (10.55), 3.205 (0.97), 3.211 (1.05), 3.221 (1.93), 3.226 (1.85), 3.237 (1.05), 3.242 (1.05), 3.371 (0.79), 3.579 (0.44), 3.596 (0.88), 3.599 (0.88), 3.616 (1.32), 3.634 (0.70), 3.729 (0.62), 3.746 (1.05), 3.761 (0.88), 3.764 (0.97), 3.782 (0.70), 3.922 (0.97), 3.939 (1.41), 3.954 (0.88), 5.497 (5.80), 5.758 (10.55), 7.537 (4.84), 7.951 (1.41), 7.974 (1.41), 7.988 (0.70), 8.147 (1.85), 8.153 (2.11), 8.168 (1.85), 8.174 (2.02), 8.545 (0.62), 8.558 (0.44), 8.571 (3.96), 8.577 (3.78). UPLC-MS (Method 1); $R_t$ = 1.17 min, m/z = 445 $[M + H]^+$. | Intermediates 9-1 and 9-2 (1:1 mixture); GP G (conditions A with HATU) |
| 59 | 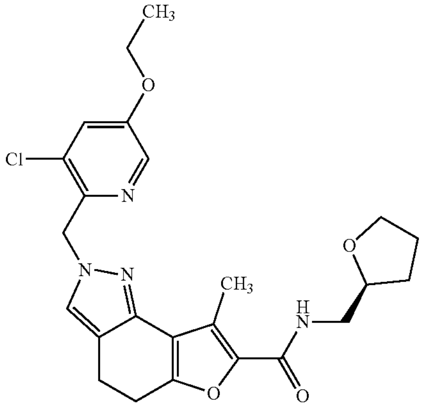 [SMILES: CCOc1cnc(Cn2cc3c(n2)-c2c(oc(C(=O)NC[C@@H]4CCCO4)c2C)CC3)c(Cl)c1] 2-[(3-chloro-5-ethoxypyridin-2-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.154 (5.07), 1.172 (10.62), 1.190 (5.28), 1.232 (0.54), 1.310 (2.76), 1.327 (6.47), 1.344 (2.79), 1.563 (0.44), 1.777 (0.44), 1.792 (0.78), 1.810 (0.89), 1.828 (0.85), 1.838 (0.48), 1.848 (0.41), 1.855 (0.54), 1.907 (1.16), 1.987 (16.00), 2.331 (1.46), 2.336 (0.65), 2.416 (0.68), 2.426 (9.43), 2.518 (8.00), 2.522 (5.00), 2.673 (1.46), 2.678 (0.68), 2.847 (1.60), 2.857 (2.79), 2.862 (3.00), 2.872 (2.08), 3.205 (0.71), 3.211 (0.68), 3.221 (1.29), 3.226 (1.23), 3.236 (0.71), 3.242 (0.75), 3.595 (0.61), 3.598 (0.61), 3.616 (0.85), 3.634 (0.48), 3.729 (0.41), 3.746 (0.75), 3.761 (0.61), 3.764 (0.61), 3.782 (0.44), 3.922 (0.65), 3.938 (0.95), 3.954 (0.58), 3.999 (1.29), 4.017 (3.74), 4.035 (3.64), 4.053 (1.16), 4.106 (0.78), 4.124 (2.79), 4.141 (2.72), 4.159 (0.78), 5.409 (4.19), 7.471 (3.00), 7.611 (2.25), 7.617 (2.31), 7.954 (0.44), 7.969 (0.92), 7.984 (0.44), 8.227 (2.62), 8.234 (2.42). UPLC-MS (Method 1); $R_t$ = 1.25 min, m/z = 471 $[M + H]^+$. | Intermediates 9-1 and 9-2 (1:1 mixture); GP G (conditions A with HATU) |
| 60 | 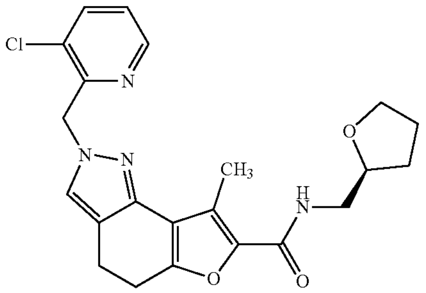 [SMILES: Cc1c(C(=O)NC[C@@H]2CCCO2)oc2c1-c1nn(Cc3ncccc3Cl)cc1CC2] 2-[(3-chloropyridin-2-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.547 (0.47), 1.563 (0.67), 1.571 (0.49), 1.579 (0.56), 1.771 (0.55), 1.777 (0.68), 1.792 (1.17), 1.810 (1.35), 1.827 (1.26), 1.839 (0.71), 1.848 (0.59), 1.856 (0.81), 1.870 (0.55), 1.873 (0.53), 1.877 (0.40), 2.332 (0.65), 2.418 (16.00), 2.518 (3.39), 2.523 (2.13), 2.673 (0.65), 2.868 (2.67), 2.877 (7.40), 2.885 (3.08), 3.206 (1.03), 3.212 (1.02), 3.221 (1.93), 3.227 (1.82), 3.237 (1.05), 3.242 (1.08), 3.579 (0.43), 3.595 (0.90), 3.599 (0.88), 3.616 (1.23), 3.634 (0.65), 3.729 (0.62), 3.744 (0.90), 3.746 (1.11), 3.762 (0.91), 3.764 (0.93), 3.782 (0.64), 3.923 (0.94), 3.939 (1.41), 3.955 (0.88), 5.514 (7.14), 7.397 (1.75), 7.408 (1.66), 7.417 (1.85), 7.428 (1.79), 7.538 (4.89), 7.957 (0.70), 7.967 | Intermediate 10; GP G (conditions A with HATU) |

TABLE 2-continued

The following examples (4 to 147) were prepared in analogy to example 3 starting from the given intermediates and commercially available amines (or their salts), applying the indicated general procedure.

| Ex-ample | Structure IUPAC-Name | Analytical Data | Preparation or Separation Methods |
| --- | --- | --- | --- |
| | | (2.55), 7.970 (3.33), 7.987 (2.77), 7.991 (2.45), 8.485 (2.07), 8.489 (2.16), 8.497 (2.02), 8.500 (1.93). LC-MS (Method A); $R_t$ = 1.09 min, m/z = 427 $[M + H]^+$. | |
| 61 | 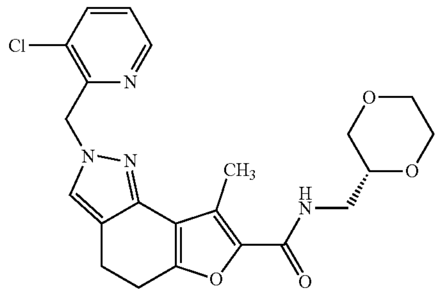 [SMILES: Cc1c(C(=O)NC[C@@H]2COCCO2)oc2c1-c1nn(Cc3ncccc3Cl)cc1CC2] 2-[(3-chloropyridin-2-yl)methyl]-N-[(2R)-1,4-dioxan-2-ylmethyl]-8-methyl-4,5-dihydro-2H-furo[2,3-g]indazole-7-carboxamide | $^1$H-NMR (400 MHz, DMSO-d6) δ [ppm]: 2.418 (16.00), 2.518 (3.03), 2.523 (2.16), 2.869 (2.58), 2.878 (6.88), 2.887 (3.05), 3.155 (0.57), 3.176 (1.48), 3.190 (1.40), 3.201 (1.61), 3.205 (2.02), 3.225 (1.39), 3.230 (1.63), 3.240 (0.86), 3.259 (0.56), 3.417 (0.46), 3.438 (1.00), 3.444 (1.10), 3.465 (0.90), 3.471 (0.87), 3.508 (0.78), 3.513 (0.86), 3.536 (1.06), 3.542 (1.08), 3.563 (0.44), 3.569 (0.70), 3.603 (1.60), 3.609 (1.31), 3.618 (0.58), 3.627 (1.22), 3.633 (1.27), 3.679 (1.14), 3.686 (0.95), 3.708 (1.94), 3.714 (1.69), 3.738 (0.82), 5.515 (6.98), 7.397 (1.68), 7.409 (1.77), 7.417 (1.76), 7.429 (1.93), 7.539 (5.02), 7.967 (2.20), 7.970 (2.27), 7.988 (2.13), 7.991 (2.04), 8.036 (0.69), 8.052 (1.44), 8.066 (0.66), 8.485 (2.13), 8.489 (2.21), 8.497 (2.06), 8.500 (1.98). LC-MS (Method A); $R_t$ = 1.00 min, m/z = 443 $[M + H]^+$. | Intermediate 10; GPG (conditions A with HATU) |
| 62 | 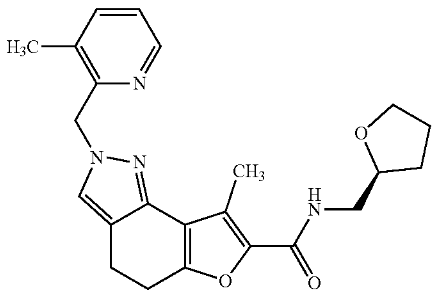 [SMILES: Cc1cccnc1Cn1cc2c(n1)-c1c(oc(C(=O)NC[C@@H]3CCCO3)c1C)CC2] 8-methyl-2-[(3-methylpyridin-2-yl)methyl]-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.547 (0.49), 1.563 (0.68), 1.571 (0.51), 1.579 (0.57), 1.592 (0.40), 1.770 (0.53), 1.776 (0.70), 1.791 (1.21), 1.810 (1.36), 1.827 (1.31), 1.838 (0.74), 1.843 (0.61), 1.848 (0.57), 1.855 (0.83), 1.869 (0.55), 1.876 (0.40), 2.074 (1.74), 2.332 (0.93), 2.336 (0.42), 2.398 (12.33), 2.437 (16.00), 2.518 (5.68), 2.522 (3.60), 2.673 (0.93), 2.678 (0.42), 2.843 (2.54), 2.853 (4.32), 2.858 (4.64), 2.869 (3.20), 2.888 (0.45), 3.205 (1.02), 3.211 (1.04), 3.221 (1.99), 3.226 (1.89), 3.236 (1.10), 3.242 (1.10), 3.578 (0.42), 3.594 (0.93), 3.598 (0.91), 3.615 (1.25), 3.633 (0.68), 3.729 (0.61), 3.746 (1.14), 3.760 (0.93), 3.764 (0.95), 3.781 (0.64), 3.922 (0.97), 3.938 (1.48), 3.953 (0.91), 5.375 (7.27), 7.231 (1.31), 7.243 (1.38), 7.250 (1.48), 7.262 (1.53), 7.447 (4.83), 7.605 (1.29), 7.608 (1.38), 7.624 (1.21), 7.627 (1.23), 7.955 (0.68), 7.969 (1.42), 7.984 (0.70), 8.337 (1.25), 8.340 (1.31), 8.349 (1.29), 8.352 (1.25). LC-MS (Method A); $R_t$ = 1.15 min, m/z = 407 $[M + H]^+$. | Intermediate 11; GP G (conditions A with HATU) |
| 63 | 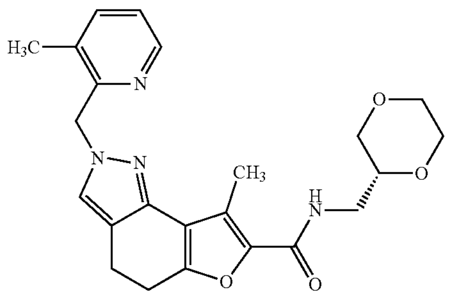 [SMILES: Cc1cccnc1Cn1cc2c(n1)-c1c(oc(C(=O)NC[C@@H]3COCCO3)c1C)CC2] | $^1$H-NMR (400 MHz, DMSO-d6) δ [ppm]: 0.932 (0.94), 0.948 (0.92), 2.075 (1.44), 2.397 (11.92), 2.438 (16.00), 2.465 (0.40), 2.518 (2.70), 2.523 (1.88), 2.843 (2.29), 2.845 (2.34), 2.855 (3.91), 2.860 (4.21), 2.871 (3.03), 2.890 (0.41), 3.155 (0.57), 3.176 (1.45), 3.189 (1.40), 3.200 (1.61), 3.205 (2.01), 3.225 (1.41), 3.229 (1.62), 3.240 (0.87), 3.259 (0.55), 3.417 (0.46), 3.437 (1.00), 3.444 (1.09), 3.464 (0.90), 3.471 (0.86), 3.507 (0.76), 3.513 (0.84), 3.535 (1.05), 3.542 (1.08), 3.562 (0.43), 3.568 (0.71), 3.603 (1.57), 3.608 (1.36), 3.617 (0.59), 3.626 (1.20), 3.632 | Intermediate 11; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | N-[(2R)-1,4-dioxan-2-ylmethyl]-8-methyl-2-[(3-methylpyridin-2-yl)methyl]-4,5-dihydro-2H-furo[2,3-g]indazole-7-carboxamide | (1.28), 3.678 (1.13), 3.684 (0.94), 3.707 (1.94), 3.713 (1.69), 3.738 (0.82), 5.376 (6.93), 7.231 (1.32), 7.243 (1.38), 7.250 (1.48), 7.262 (1.51), 7.449 (4.93), 7.604 (1.07), 7.606 (1.25), 7.608 (1.30), 7.610 (1.09), 7.623 (0.99), 7.625 (1.16), 7.627 (1.15), 7.629 (0.98), 8.034 (0.67), 8.049 (1.44), 8.064 (0.65), 8.337 (1.21), 8.340 (1.23), 8.349 (1.20), 8.352 (1.16). LC-MS (Method A); $R_t$ = 0.96 min, m/z = 423 $[M + H]^+$. | |
| 64 | 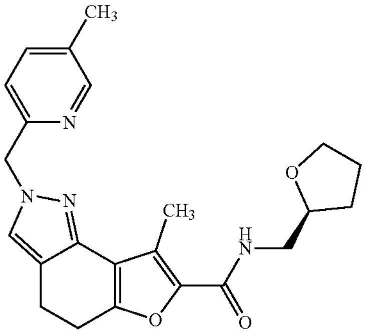 [SMILES: Cc1ccc(Cn2cc3c(n2)-c2c(oc(C(=O)NC[C@@H]4CCCO4)c2C)CC3)nc1] 8-methyl-2-[(5-methylpyridin-2-yl)methyl]-N-[(2S)-tetrahydrofuran-2-ylmethyl]-4,5-dihydro-2H-furo[2,3-g]indazole-7-carboxamide | $^1$H-NMR (500 MHz, DMSO-d6) δ [ppm]: 1.553 (0.42), 1.565 (0.42), 1.568 (0.62), 1.575 (0.57), 1.581 (0.53), 1.592 (0.52), 1.778 (0.50), 1.783 (0.47), 1.795 (0.74), 1.798 (0.67), 1.809 (0.71), 1.813 (0.82), 1.826 (0.59), 1.839 (0.54), 1.842 (0.47), 1.846 (0.59), 1.852 (0.69), 1.861 (0.61), 1.869 (0.42), 1.875 (0.47), 1.878 (0.41), 2.269 (10.04), 2.440 (16.00), 2.516 (2.22), 2.520 (2.08), 2.523 (1.69), 2.640 (0.59), 2.873 (2.40), 2.881 (4.36), 2.884 (4.61), 2.893 (3.03), 3.214 (0.99), 3.221 (1.02), 3.226 (1.87), 3.233 (1.73), 3.238 (1.03), 3.245 (1.03), 3.588 (0.45), 3.604 (0.99), 3.618 (1.16), 3.632 (0.67), 3.737 (0.58), 3.749 (0.91), 3.751 (1.05), 3.763 (1.02), 3.765 (0.87), 3.780 (0.64), 3.930 (0.97), 3.943 (1.45), 3.956 (0.91), 5.327 (5.84), 7.000 (1.84), 7.016 (1.95), 7.574 (1.03), 7.577 (1.01), 7.590 (1.04), 7.594 (1.06), 7.600 (4.73), 7.966 (0.69), 7.978 (1.40), 7.990 (0.67), 8.367 (1.77), 8.371 (1.73). LC-MS (Method A); $R_t$ = 1.03 min, m/z = 407 $[M + H]^+$. | Intermediate 12; GP G (conditions A with HATU) |
| 65 | 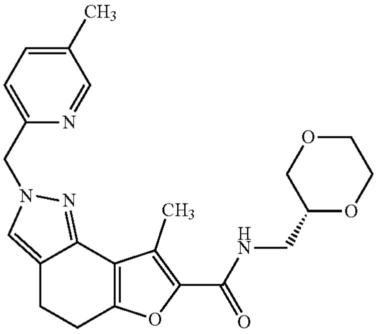 [SMILES: Cc1ccc(Cn2cc3c(n2)-c2c(oc(C(=O)NC[C@@H]4COCCO4)c2C)CC3)nc1] N-[(2R)-1,4-dioxan-2-ylmethyl]-8-methyl-2-[(5-methylpyridin-2-yl)methyl]-4,5-dihydro-2H-furo[2,3-g]indazole-7-carboxamide | $^1$H-NMR (500 MHz, DMSO-d6) δ [ppm]: 2.269 (10.58), 2.370 (0.44), 2.400 (0.46), 2.440 (16.00), 2.516 (3.88), 2.520 (3.49), 2.523 (2.77), 2.640 (0.93), 2.741 (0.49), 2.857 (0.46), 2.873 (2.62), 2.881 (4.41), 2.886 (4.72), 2.894 (3.18), 3.165 (0.70), 3.180 (0.88), 3.186 (1.35), 3.192 (1.49), 3.205 (2.05), 3.209 (1.51), 3.219 (0.71), 3.228 (1.75), 3.231 (1.48), 3.244 (0.95), 3.258 (0.66), 3.307 (0.41), 3.420 (0.44), 3.426 (0.53), 3.442 (1.10), 3.448 (1.15), 3.465 (0.93), 3.470 (0.86), 3.516 (0.77), 3.521 (0.88), 3.539 (1.10), 3.544 (1.11), 3.561 (0.56), 3.566 (0.75), 3.609 (1.64), 3.621 (0.68), 3.628 (1.45), 3.633 (1.33), 3.686 (1.18), 3.690 (1.04), 3.713 (1.97), 3.738 (0.89), 5.327 (6.11), 7.000 (1.98), 7.016 (2.07), 7.574 (1.09), 7.577 (1.09), 7.590 (1.06), 7.594 (1.12), 7.601 (4.85), 8.045 (0.73), 8.057 (1.55), 8.069 (0.72), 8.367 (1.84), 8.371 (1.84). LC-MS (Method A); $R_t$ = 0.95 min, m/z = 423 $[M + H]^+$. | Intermediate 12; GP G (conditions A with HATU) |

TABLE 2-continued

The following examples (4 to 147) were prepared in analogy to example 3 starting from the given intermediates and commercially available amines (or their salts), applying the indicated general procedure.

| Ex-ample | Structure IUPAC-Name | Analytical Data | Preparation or Separation Methods |
|---|---|---|---|
| 66 | 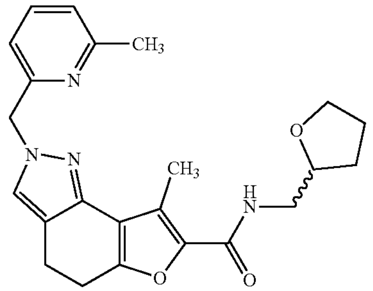 [SMILES: Cc1cccc(Cn2cc3c(n2)-c2c(oc(C(=O)NCC4CCCO4)c2C)CC3)n1] 8-methyl-2-[(6-methylpyridin-2-yl)methyl]-N-[(2R/S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.550 (0.49), 1.567 (0.68), 1.574 (0.50), 1.582 (0.58), 1.590 (0.43), 1.595 (0.42), 1.773 (0.55), 1.779 (0.70), 1.794 (1.24), 1.812 (1.38), 1.830 (1.31), 1.841 (0.74), 1.851 (0.61), 1.856 (0.72), 1.858 (0.83), 1.873 (0.58), 1.876 (0.55), 1.880 (0.41), 2.446 (16.00), 2.461 (15.04), 2.518 (1.43), 2.523 (0.98), 2.881 (2.82), 2.890 (7.60), 2.898 (3.21), 3.212 (1.13), 3.217 (1.11), 3.228 (2.13), 3.232 (2.04), 3.243 (1.14), 3.247 (1.16), 3.582 (0.44), 3.598 (0.93), 3.601 (0.94), 3.618 (1.28), 3.636 (0.68), 3.732 (0.62), 3.746 (0.94), 3.749 (1.16), 3.764 (0.96), 3.767 (0.98), 3.784 (0.64), 3.927 (0.98), 3.943 (1.49), 3.959 (0.91), 5.325 (6.48), 6.788 (1.72), 6.807 (1.79), 7.152 (1.73), 7.171 (1.88), 7.620 (5.15), 7.643 (3.07), 7.662 (1.48), 7.967 (0.72), 7.982 (1.49), 7.996 (0.70). LC-MS (Method A); $R_t$ = 1.06 min, m/z = 407 [M + H]$^+$. | Intermediate 13; GP G (conditions A with HATU) |
| 66-1 | Enantiomer 1 of Ex. 66 | $R_t$ = 2.37 min | analyt. method: Instrument: Agilent HPLC 1260; Column: Amylose SA 3 µm, 100 × 4.6 mm; Eluent A: hexane + 0.1 vol % diethylamine (99%); Eluent B: ethanol; Gradient: 20-50% B in 7 min; Flow: 1.4 mL/min; Temperature: 25° C.; DAD: 254 nm. |
| 66-2 | Enantiomer 2 of Ex. 66 | $R_t$ = 3.05 min | |
| 67 | 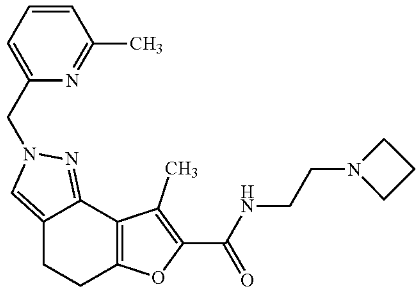 [SMILES: Cc1cccc(Cn2cc3c(n2)-c2c(oc(C(=O)NCCN4CCC4)c2C)CC3)n1] N-[2-(azetidin-1-yl)ethyl]-8-methyl-2-[(6-methylpyridin-2-yl)methyl]-4,5-dihydro-2H-furo[2,3-g]indazole-7-carboxamide | $^1$H-NMR (400 MHz, DMSO-d6) δ [ppm]: 1.905 (0.72), 1.922 (1.86), 1.940 (2.44), 1.957 (1.83), 1.974 (0.49), 2.323 (0.58), 2.327 (0.83), 2.332 (0.60), 2.425 (2.97), 2.441 (16.00), 2.461 (15.67), 2.518 (2.86), 2.523 (2.09), 2.654 (0.43), 2.665 (0.67), 2.669 (1.03), 2.673 (0.69), 2.772 (0.49), 2.851 (0.60), 2.858 (1.36), 2.880 (2.51), 2.888 (7.35), 2.896 (2.88), 3.081 (4.38), 3.088 (1.29), 3.098 (8.26), 3.104 (2.68), 3.116 (4.66), 3.136 (0.75), 4.684 (0.64), 5.324 (6.29), 6.788 (1.51), 6.807 (1.58), 7.152 (1.72), 7.171 (1.84), 7.559 (0.42), 7.618 (5.16), 7.623 (1.80), 7.643 (2.95), 7.662 (1.39), 7.859 (0.62), 7.874 (1.30), 7.888 (0.60), 8.581 (0.40), 8.794 (0.40). LC-MS (Method A); $R_t$ = 1.01 min, m/z = 406 [M + H]$^+$. | Intermediate 13; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 68 | 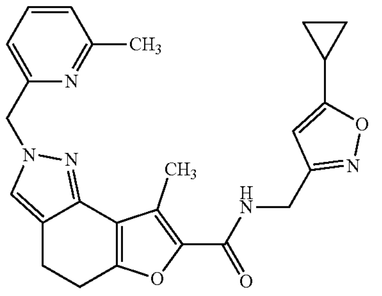 [SMILES: Cc1cccc(Cn2cc3c(n2)-c2c(oc(C(=O)NCc4cc(C5CC5)on4)c2C)CC3)n1] N-[(5-cyclopropyl-1,2-oxazol-3-yl)methyl]-8-methyl-2-[(6-methylpyridin-2-yl)methyl]-4,5-dihydro-2H-furo[2,3-g]indazole-7-carboxamide | $^1$H-NMR (400 MHz, DMSO-d6) δ [ppm]: 0.821 (0.79), 0.832 (2.61), 0.838 (2.57), 0.845 (2.43), 0.848 (1.46), 0.851 (2.60), 0.860 (1.14), 0.994 (1.01), 1.003 (2.44), 1.010 (2.39), 1.015 (1.22), 1.021 (1.14), 1.024 (2.60), 1.031 (2.19), 1.042 (0.83), 2.081 (0.75), 2.090 (0.79), 2.094 (0.46), 2.102 (1.45), 2.111 (0.47), 2.115 (0.73), 2.123 (0.70), 2.457 (16.00), 2.461 (15.48), 2.518 (2.15), 2.523 (1.48), 2.886 (2.93), 2.892 (9.21), 2.898 (3.18), 4.342 (3.08), 4.357 (3.06), 5.328 (5.84), 6.089 (6.20), 6.789 (1.58), 6.808 (1.64), 7.154 (1.61), 7.173 (1.74), 7.625 (5.95), 7.644 (2.99), 7.663 (1.47), 8.635 (0.69), 8.651 (1.55), 8.666 (0.68). LC-MS (Method A); $R_t$ = 1.14 min, m/z = 444 $[M + H]^+$. | Intermediate 13; GPG (conditions A with HATU) |
| 69 | 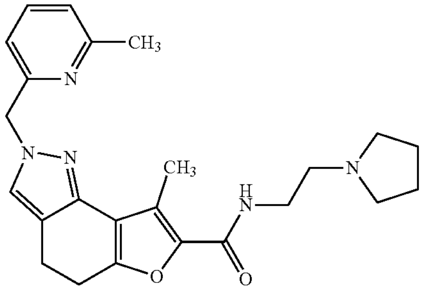 [SMILES: Cc1cccc(Cn2cc3c(n2)-c2c(oc(C(=O)NCCN4CCCC4)c2C)CC3)n1] 8-methyl-2-[(6-methylpyridin-2-yl)methyl]-N-[2-(pyrrolidin-1-yl)ethyl]-4,5-dihydro-2H-furo[2,3-g]indazole-7-carboxamide | $^1$H-NMR (400 MHz, DMSO-d6) δ [ppm]: 1.658 (2.40), 1.666 (4.40), 1.675 (2.40), 2.327 (0.44), 2.444 (16.00), 2.461 (14.79), 2.534 (1.82), 2.669 (0.42), 2.879 (2.78), 2.886 (7.65), 2.894 (2.95), 3.276 (0.85), 3.292 (1.94), 3.308 (2.16), 5.323 (5.73), 6.788 (1.55), 6.807 (1.61), 7.152 (1.57), 7.171 (1.69), 7.618 (4.22), 7.623 (1.67), 7.642 (2.56), 7.662 (1.23), 7.937 (0.65), 7.951 (1.35), 7.966 (0.63). LC-MS (Method A); $R_t$ = 1.09 min, m/z = 420 $[M + H]^+$. | Intermediate 13; GP G (conditions A with HATU) |
| 70 | 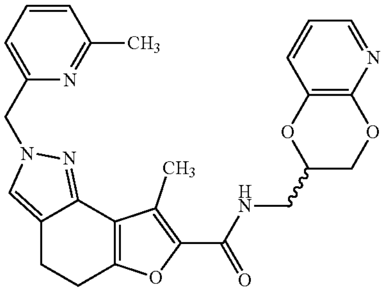 [SMILES: Cc1cccc(Cn2cc3c(n2)-c2c(oc(C(=O)NCC4COc5ncccc5O4)c2C)CC3)n1] N-[(2R/S)-2,3-dihydro[1,4]dioxino[2,3-b]pyridin-2-ylmethyl]-8-methyl-2-[(6-methylpyridin-2-yl)methyl]-4,5-dihydro-2H-furo[2,3-g]indazole-7-carboxamide | $^1$H-NMR (400 MHz, DMSO-d6) δ [ppm]: 0.932 (0.63), 0.948 (0.63), 2.461 (16.00), 2.518 (2.05), 2.523 (1.29), 2.890 (1.56), 2.900 (2.97), 2.904 (3.06), 2.914 (1.80), 3.451 (0.42), 3.466 (0.66), 3.537 (0.67), 3.553 (0.43), 4.130 (0.58), 4.148 (0.70), 4.160 (0.67), 4.177 (0.79), 4.355 (0.46), 4.361 (0.57), 4.372 (0.46), 4.377 (0.48), 4.438 (0.85), 4.443 (0.79), 4.467 (0.76), 4.472 (0.63), 5.329 (3.70), 6.792 (1.03), 6.811 (1.06), 6.932 (1.23), 6.944 (1.20), 6.952 (1.27), 6.964 (1.30), 7.154 (1.06), 7.173 (1.15), 7.302 (1.35), 7.306 (1.30), 7.322 (1.29), 7.325 (1.11), 7.627 (3.33), 7.645 (1.81), 7.664 (0.88), 7.736 (1.32), 7.740 (1.36), 7.747 (1.23), 7.752 (1.21), 8.367 (0.43), 8.382 (0.90), 8.397 (0.42). LC-MS (Method A); $R_t$ = 1.04 min, m/z = 472 $[M + H]^+$. | Intermediate 13; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 71 | 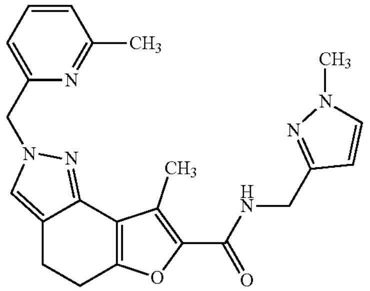 [SMILES: Cc1cccc(Cn2cc3c(n2)-c2c(oc(C(=O)NCc4ccn(C)n4)c2C)CC3)n1] 8-methyl-N-[(1-methyl-1H-pyrazol-3-yl)methyl]-2-[(6-methylpyridin-2-yl)methyl]-4,5-dihydro-2H-furo[2,3-g]indazole-7-carboxamide | $^1$H-NMR (400 MHz, DMSO-d6) δ [ppm]: 2.455 (13.22), 2.463 (12.30), 2.520 (0.63), 2.525 (0.44), 2.883 (9.07), 3.771 (16.00), 3.783 (0.51), 4.315 (2.58), 4.330 (2.58), 5.327 (4.96), 6.100 (2.71), 6.105 (2.82), 6.788 (1.34), 6.807 (1.38), 7.153 (1.36), 7.172 (1.47), 7.555 (2.34), 7.560 (2.37), 7.621 (4.20), 7.624 (1.84), 7.643 (2.46), 7.663 (1.21), 8.372 (0.59), 8.387 (1.27), 8.401 (0.57). LC-MS (Method A); $R_t$ = 0.96 min, m/z = 417 $[M + H]^+$. | Intermediate 13; GP G (conditions A with HATU) |
| 72 | 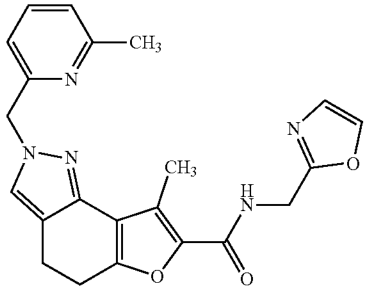 [SMILES: Cc1cccc(Cn2cc3c(n2)-c2c(oc(C(=O)NCc4ncco4)c2C)CC3)n1] 8-methyl-2-[(6-methylpyridin-2-yl)methyl]-N-(1,3-oxazol-2-ylmethyl)-4,5-dihydro-2H-furo[2,3-g]indazole-7-carboxamide | $^1$H-NMR (400 MHz, DMSO-d6) δ [ppm]: 2.454 (16.00), 2.464 (15.03), 2.520 (0.98), 2.525 (0.68), 2.757 (0.42), 2.895 (2.63), 2.904 (6.83), 2.913 (3.03), 4.483 (3.60), 4.498 (3.52), 5.332 (6.14), 6.797 (1.64), 6.817 (1.70), 7.142 (4.59), 7.144 (4.93), 7.155 (1.73), 7.174 (1.82), 7.631 (5.15), 7.647 (3.07), 7.666 (1.51), 8.032 (5.23), 8.034 (4.97), 8.721 (0.74), 8.736 (1.62), 8.751 (0.72). LC-MS (Method A); $R_t$ = 0.95 min, m/z = 404 $[M + H]^+$. | Intermediate 13; GPG (conditions A with HATU) |
| 73 | 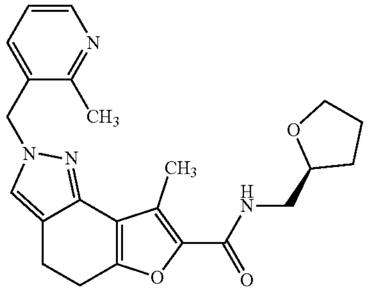 [SMILES: Cc1ncccc1Cn1cc2c(n1)-c1c(oc(C(=O)NC[C@@H]3CCCO3)c1C)CC2] 8-methyl-2-[(2-methylpyridin-3-yl)methyl]-N-[(2S)-tetrahydrofuran-2-ylmethyl]-4,5-dihydro-2H-furo[2,3-g]indazole-7-carboxamide | $^1$H-NMR (500 MHz, DMSO-d6) δ [ppm]: 1.553 (0.45), 1.565 (0.44), 1.569 (0.64), 1.575 (0.59), 1.582 (0.55), 1.592 (0.54), 1.778 (0.53), 1.783 (0.50), 1.795 (0.78), 1.799 (0.76), 1.814 (0.87), 1.829 (0.64), 1.839 (0.56), 1.846 (0.61), 1.852 (0.71), 1.861 (0.63), 1.869 (0.44), 1.872 (0.48), 1.878 (0.40), 2.447 (16.00), 2.516 (3.10), 2.520 (2.64), 2.523 (2.11), 2.545 (14.47), 2.640 (0.70), 2.855 (0.56), 2.871 (2.48), 2.880 (3.75), 2.886 (4.01), 2.895 (3.17), 2.910 (0.61), 3.216 (1.07), 3.222 (1.06), 3.228 (1.94), 3.234 (1.83), 3.240 (1.07), 3.246 (1.09), 3.589 (0.49), 3.604 (1.05), 3.618 (1.21), 3.632 (0.68), 3.738 (0.62), 3.752 (1.07), 3.764 (1.01), 3.780 (0.65), 3.931 (1.00), 3.944 (1.49), 3.956 (0.97), 5.344 (6.08), 7.179 (0.82), 7.189 (0.84), 7.195 (1.46), 7.204 (1.53), 7.232 (1.59), 7.235 (1.70), 7.247 (0.92), 7.251 (0.85), 7.569 (4.61), 7.970 (0.70), 7.982 (1.47), 7.995 (0.70), 8.350 (1.35), 8.353 (1.41), 8.359 (1.39), 8.362 (1.34). LC-MS (Method A); $R_t$ = 0.97 min, m/z = 407 $[M + H]^+$. | Intermediate 14-1; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 74 | 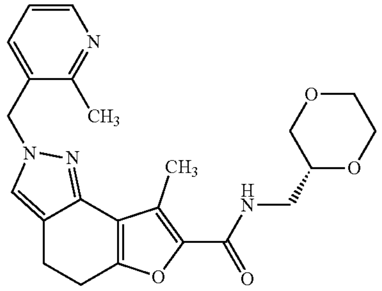 [SMILES: Cc1ncccc1Cn1cc2c(n1)-c1c(oc(C(=O)NC[C@@H]3COCCO3)c1C)CC2] N-[(2R)-1,4-dioxan-2-ylmethyl]-8-methyl-2-[(2-methylpyridin-3-yl)methyl]-4,5-dihydro-2H-furo[2,3-g]indazole-7-carboxamide | $^1$H-NMR (500 MHz, DMSO-d6) δ [ppm]: 2.448 (16.00), 2.516 (2.61), 2.520 (2.32), 2.523 (1.83), 2.545 (15.44), 2.756 (0.61), 2.856 (0.63), 2.871 (2.55), 2.881 (3.74), 2.887 (4.03), 2.897 (3.26), 2.912 (0.66), 3.166 (0.73), 3.181 (0.92), 3.187 (1.38), 3.193 (1.51), 3.205 (2.18), 3.209 (1.57), 3.221 (0.76), 3.229 (1.69), 3.233 (1.45), 3.245 (0.91), 3.260 (0.70), 3.421 (0.42), 3.426 (0.53), 3.443 (1.13), 3.448 (1.19), 3.465 (0.95), 3.470 (0.85), 3.517 (0.78), 3.522 (0.90), 3.539 (1.11), 3.545 (1.12), 3.561 (0.56), 3.567 (0.71), 3.609 (1.65), 3.622 (0.66), 3.630 (1.48), 3.634 (1.32), 3.685 (1.19), 3.690 (1.07), 3.708 (1.22), 3.713 (1.94), 3.738 (0.86), 5.344 (6.31), 7.179 (0.87), 7.189 (0.89), 7.194 (1.54), 7.204 (1.61), 7.231 (1.69), 7.235 (1.76), 7.247 (0.95), 7.250 (0.89), 7.570 (4.92), 8.050 (0.76), 8.062 (1.61), 8.074 (0.74), 8.350 (1.45), 8.353 (1.47), 8.359 (1.45), 8.362 (1.36). LC-MS (Method A); $R_t$ = 0.89 min, m/z = 423 $[M + H]^+$. | Intermediate 14-1; GP G (conditions A with HATU) |
| 75 | 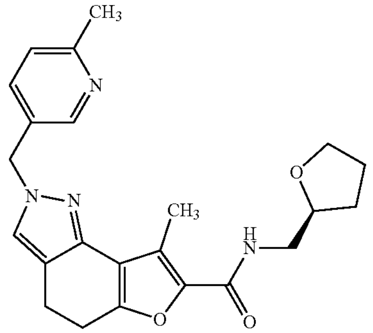 [SMILES: Cc1ccc(Cn2cc3c(n2)-c2c(oc(C(=O)NC[C@@H]4CCCO4)c2C)CC3)cn1] 8-methyl-2-[(6-methylpyridin-3-yl)methyl]-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.549 (0.49), 1.566 (0.69), 1.574 (0.51), 1.582 (0.59), 1.589 (0.43), 1.774 (0.55), 1.779 (0.70), 1.794 (1.25), 1.813 (1.39), 1.830 (1.34), 1.841 (0.76), 1.851 (0.60), 1.858 (0.85), 1.872 (0.59), 1.879 (0.42), 2.433 (13.98), 2.456 (16.00), 2.520 (3.90), 2.525 (2.46), 2.830 (0.41), 2.849 (2.59), 2.860 (4.40), 2.865 (4.69), 2.877 (3.24), 2.894 (0.46), 3.210 (1.11), 3.215 (1.10), 3.225 (2.09), 3.231 (1.99), 3.240 (1.13), 3.246 (1.14), 3.581 (0.45), 3.598 (0.95), 3.601 (0.95), 3.618 (1.29), 3.636 (0.68), 3.731 (0.63), 3.748 (1.18), 3.764 (0.96), 3.766 (0.97), 3.784 (0.64), 3.925 (1.00), 3.942 (1.52), 3.957 (0.93), 5.273 (6.06), 7.216 (2.01), 7.236 (2.24), 7.543 (1.49), 7.549 (1.49), 7.563 (1.29), 7.569 (1.32), 7.606 (4.89), 7.965 (0.73), 7.980 (1.52), 7.995 (0.70), 8.396 (2.09), 8.401 (2.08). LC-MS (Method A); $R_t$ = 1.14 min, m/z = 407 $[M + H]^+$. | Intermediates 15-1 + 15-2; GP G (conditions A with HATU) |
| 76 | 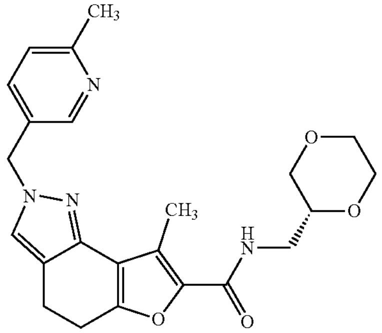 [SMILES: Cc1ccc(Cn2cc3c(n2)-c2c(oc(C(=O)NC[C@@H]4COCCO4)c2C)CC3)cn1] | $^1$H-NMR (400 MHz, DMSO-d6) δ [ppm]: 0.934 (0.41), 0.951 (0.41), 2.433 (14.10), 2.457 (16.00), 2.520 (2.84), 2.525 (1.89), 2.758 (0.65), 2.831 (0.44), 2.851 (2.62), 2.861 (4.30), 2.866 (4.57), 2.878 (3.32), 2.896 (0.51), 3.159 (0.61), 3.179 (1.76), 3.193 (1.50), 3.203 (1.69), 3.208 (2.23), 3.213 (0.98), 3.232 (1.93), 3.244 (0.92), 3.263 (0.61), 3.419 (0.50), 3.440 (1.10), 3.446 (1.18), 3.467 (0.98), 3.474 (0.94), 3.510 (0.83), 3.515 (0.90), 3.538 (1.12), 3.544 (1.17), 3.565 (0.46), 3.571 (0.73), 3.605 (1.80), 3.611 (1.50), 3.621 (0.66), 3.629 (1.35), 3.635 (1.45), 3.681 (1.26), 3.687 (1.05), 3.710 (2.19), | Intermediates 15-1 + 15-2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | N-[(2R)-1,4-dioxan-2-ylmethyl]-8-methyl-2-[(6-methylpyridin-3-yl)methyl]-4,5-dihydro-2H-furo[2,3-g]indazole-7-carboxamide | 3.716 (1.92), 3.740 (0.92), 5.273 (6.01), 7.215 (2.01), 7.236 (2.28), 7.543 (1.50), 7.549 (1.51), 7.563 (1.34), 7.569 (1.35), 7.607 (5.08), 8.042 (0.74), 8.057 (1.56), 8.072 (0.71), 8.396 (2.09), 8.401 (2.06). LC-MS (Method A); $R_t$ = 1.06 min, m/z = 423 $[M + H]^+$. | |
| 77 | 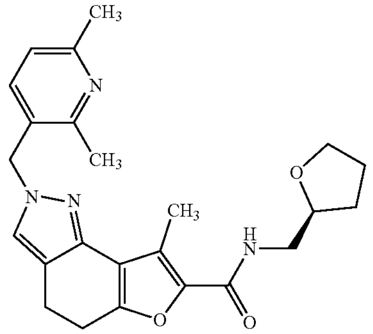 [SMILES: Cc1ccc(Cn2cc3c(n2)-c2c(oc(C(=O)NC[C@@H]4CCCO4)c2C)CC3)c(C)n1] 2-[(2,6-dimethylpyridin-3-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 0.934 (0.47), 0.951 (0.46), 1.551 (0.52), 1.567 (0.72), 1.575 (0.54), 1.583 (0.62), 1.591 (0.46), 1.778 (1.26), 1.796 (1.31), 1.813 (1.44), 1.831 (1.37), 1.841 (0.78), 1.851 (0.63), 1.858 (0.89), 1.874 (0.60), 2.334 (0.75), 2.338 (0.46), 2.390 (13.42), 2.423 (0.76), 2.447 (16.00), 2.520 (3.99), 2.525 (2.47), 2.676 (0.71), 2.837 (0.53), 2.857 (2.69), 2.868 (4.27), 2.874 (4.52), 2.886 (3.28), 2.904 (0.53), 3.212 (1.18), 3.217 (1.17), 3.227 (2.20), 3.232 (2.10), 3.242 (1.20), 3.248 (1.20), 3.583 (0.46), 3.599 (0.99), 3.602 (1.00), 3.619 (1.32), 3.637 (0.69), 3.733 (0.63), 3.750 (1.21), 3.765 (0.99), 3.767 (1.00), 3.785 (0.63), 3.927 (1.04), 3.943 (1.54), 3.959 (0.95), 5.284 (6.01), 7.032 (1.85), 7.051 (2.30), 7.199 (2.63), 7.218 (2.06), 7.526 (5.01), 7.967 (0.78), 7.982 (1.59), 7.997 (0.75). LC-MS (Method A); $R_t$ = 1.21 min, m/z = 421 $[M + H]^+$. | Intermediates 16-1 + 16-2; GP G (conditions A with HATU) |
| 78 | 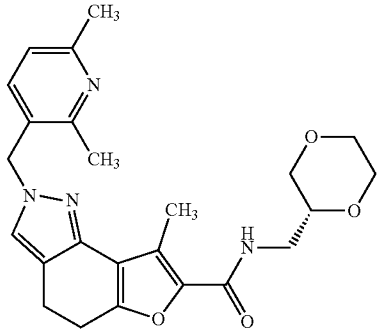 [SMILES: Cc1ccc(Cn2cc3c(n2)-c2c(oc(C(=O)NC[C@@H]4COCCO4)c2C)CC3)c(C)n1] 2-[(2,6-dimethylpyridin-3-yl)methyl]-N-[(2R)-1,4-dioxan-2-ylmethyl]-8-methyl-4,5-dihydro-2H-furo[2,3-g]indazole-7-carboxamide | $^1$H-NMR (400 MHz, DMSO-d6) δ [ppm]: 2.334 (1.11), 2.390 (14.00), 2.448 (16.00), 2.520 (6.19), 2.525 (3.81), 2.545 (0.60), 2.676 (1.08), 2.838 (0.60), 2.858 (2.77), 2.869 (4.25), 2.876 (4.53), 2.887 (3.37), 2.906 (0.59), 3.160 (0.63), 3.180 (1.85), 3.194 (1.57), 3.205 (1.77), 3.209 (2.29), 3.233 (2.13), 3.246 (0.97), 3.264 (0.65), 3.310 (0.62), 3.414 (0.42), 3.420 (0.52), 3.441 (1.14), 3.447 (1.23), 3.469 (0.99), 3.474 (0.98), 3.511 (0.84), 3.517 (0.90), 3.539 (1.18), 3.545 (1.22), 3.566 (0.47), 3.572 (0.76), 3.591 (0.40), 3.607 (1.90), 3.612 (1.64), 3.621 (0.71), 3.630 (1.46), 3.636 (1.54), 3.681 (1.33), 3.688 (1.11), 3.710 (2.33), 3.716 (2.12), 3.741 (0.97), 5.284 (6.21), 7.032 (1.93), 7.051 (2.39), 7.199 (2.70), 7.218 (2.15), 7.527 (5.15), 8.046 (0.80), 8.061 (1.70), 8.076 (0.78). LC-MS (Method A); $R_t$ = 1.12 min, m/z = 437 $[M + H]^+$. | Intermediates 16-1 + 16-2; GP G (conditions A with HATU) |
| 79 | 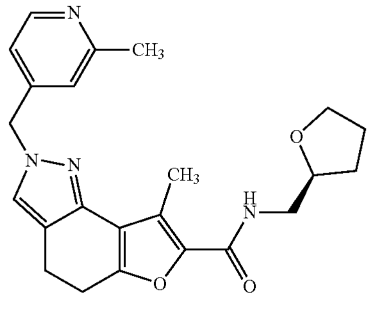 [SMILES: Cc1cc(Cn2cc3c(n2)-c2c(oc(C(=O)NC[C@@H]4CCCO4)c2C)CC3)ccn1] | $^1$H-NMR (400 MHz, DMSO-d6) δ [ppm]: 0.863 (0.42), 1.549 (0.48), 1.566 (0.67), 1.574 (0.48), 1.582 (0.57), 1.774 (0.54), 1.779 (0.70), 1.795 (1.25), 1.813 (1.34), 1.831 (1.21), 1.841 (0.70), 1.851 (0.57), 1.858 (0.80), 1.873 (0.54), 2.337 (0.42), 2.430 (14.56), 2.447 (16.00), 2.518 (5.59), 2.523 (3.77), 2.674 (0.96), 2.679 (0.42), 2.881 (2.49), 2.892 (6.10), 2.902 (3.00), 3.212 (1.09), 3.217 (1.02), 3.228 (2.01), 3.232 (1.92), 3.243 (1.05), 3.248 (1.09), 3.582 (0.48), 3.598 (0.93), 3.602 (0.93), 3.619 (1.21), 3.637 (0.64), 3.732 (0.64), 3.749 (1.09), 3.764 (0.89), 3.767 (0.93), 3.784 (0.64), 3.927 (0.93), 3.943 | Intermediate 17-2; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | 8-methyl-2-[(2-methylpyridin-4-yl)methyl]-N-[(2S)-tetrahydrofuran-2-ylmethyl]-4,5-dihydro-2H-furo[2,3-g]indazole-7-carboxamide | (1.41), 3.958 (0.86), 5.302 (5.46), 6.929 (1.21), 6.941 (1.21), 7.052 (2.33), 7.634 (4.66), 7.970 (0.64), 7.986 (1.37), 8.001 (0.64), 8.375 (2.04), 8.388 (1.98). LC-MS (Method A); $R_t$ = 0.96 min, m/z = 407 $[M + H]^+$. | |
| 80 | 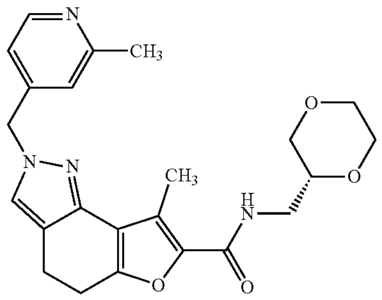 [SMILES: Cc1cc(Cn2cc3c(n2)-c2c(oc(C(=O)NC[C@@H]4COCCO4)c2C)CC3)ccn1] N-[(2R)-1,4-dioxan-2ylmethyl]-8-methyl-2-[(2-methylpyridin-4-yl)methyl]-4,5-dihydro-2H-furo[2,3-g]indazole-7-carboxamide | $^1$H-NMR (400 MHz, DMSO-d6) δ [ppm]: 0.932 (1.10), 0.948 (1.16), 2.336 (1.10), 2.430 (15.02), 2.447 (16.00), 2.518 (14.21), 2.523 (9.82), 2.678 (1.10), 2.882 (2.43), 2.893 (5.78), 2.903 (3.06), 3.161 (0.58), 3.180 (1.85), 3.194 (1.39), 3.204 (1.56), 3.209 (1.91), 3.215 (0.87), 3.232 (2.14), 3.245 (0.87), 3.264 (0.58), 3.280 (0.40), 3.419 (0.52), 3.440 (1.04), 3.446 (1.10), 3.467 (0.92), 3.473 (0.87), 3.510 (0.75), 3.516 (0.87), 3.538 (1.04), 3.544 (1.10), 3.565 (0.40), 3.571 (0.69), 3.606 (1.62), 3.621 (0.58), 3.630 (1.27), 3.636 (1.33), 3.680 (1.10), 3.687 (0.92), 3.710 (1.96), 3.715 (1.79), 3.741 (0.87), 5.302 (5.49), 6.928 (1.21), 6.941 (1.21), 7.051 (2.37), 7.635 (4.91), 8.050 (0.69), 8.066 (1.44), 8.081 (0.64), 8.375 (2.14), 8.388 (2.08), 8.550 (0.52). LC-MS (Method A); $R_t$ = 0.87 min, m/z = 423 $[M + H]^+$. | Intermediate 17-2; GP G (conditions A with HATU) |
| 81 | 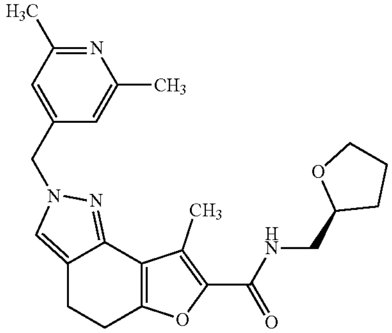 [SMILES: Cc1cc(Cn2cc3c(n2)-c2c(oc(C(=O)NC[C@@H]4CCCO4)c2C)CC3)cc(C)n1] 2-[(2,6-dimethylpyridin-4-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.552 (0.55), 1.569 (0.78), 1.576 (0.58), 1.585 (0.65), 1.598 (0.48), 1.776 (0.57), 1.781 (0.77), 1.797 (1.32), 1.814 (1.48), 1.832 (1.42), 1.843 (0.82), 1.853 (0.65), 1.861 (0.90), 1.875 (0.61), 1.882 (0.46), 2.168 (0.42), 2.221 (13.16), 2.389 (0.54), 2.414 (15.51), 2.453 (16.00), 2.520 (3.79), 2.524 (2.35), 2.880 (3.01), 2.890 (7.62), 2.899 (3.44), 3.215 (1.26), 3.220 (1.20), 3.230 (2.24), 3.235 (2.16), 3.245 (1.20), 3.250 (1.24), 3.584 (0.47), 3.600 (1.01), 3.603 (1.02), 3.621 (1.33), 3.638 (0.69), 3.734 (0.67), 3.751 (1.23), 3.766 (1.02), 3.769 (1.02), 3.787 (0.63), 3.929 (1.05), 3.945 (1.56), 3.961 (0.97), 5.274 (6.86), 6.704 (2.85), 7.002 (2.87), 7.595 (5.09), 7.968 (0.77), 7.983 (1.59), 7.997 (0.74). LC-MS (Method A); $R_t$ = 1.28 min, m/z = 421 $[M + H]^+$. | Intermediates 18-1 + 18-2; GPG (conditions A with HATU) |
| 82 | 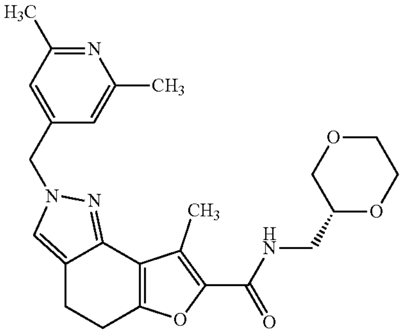 [SMILES: Cc1cc(Cn2cc3c(n2)-c2c(oc(C(=O)NC[C@@H]4COCCO4)c2C)CC3)cc(C)n1] | $^1$H-NMR (400 MHz, DMSO-d6) δ [ppm]: 2.221 (13.56), 2.414 (15.49), 2.453 (16.00), 2.520 (4.13), 2.524 (2.58), 2.881 (3.06), 2.891 (7.44), 2.901 (3.45), 3.163 (0.61), 3.182 (1.98), 3.198 (1.57), 3.206 (1.72), 3.211 (2.13), 3.234 (2.35), 3.248 (0.99), 3.267 (0.62), 3.416 (0.42), 3.421 (0.52), 3.442 (1.14), 3.448 (1.21), 3.469 (0.99), 3.475 (0.96), 3.512 (0.84), 3.518 (0.91), 3.541 (1.16), 3.546 (1.23), 3.567 (0.48), 3.573 (0.76), 3.593 (0.44), 3.608 (1.87), 3.624 (0.75), 3.633 (1.61), 3.638 (1.47), 3.684 (1.34), 3.690 (1.12), 3.712 (2.37), 3.718 (2.08), 3.742 (1.00), 5.275 (6.96), 6.703 (2.98), 7.003 (3.00), | Intermediates 18-1 + 18-2; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | 2-[(2,6-dimethylpyridin-4-yl)methyl]-N-[(2R)-1,4-dioxan-2-ylmethyl]-8-methyl-4,5-dihydro-2H-furo[2,3-g]indazole-7-carboxamide | 7.596 (5.07), 8.048 (0.79), 8.063 (1.68), 8.078 (0.79). LC-MS (Method A); $R_t$ = 1.22 min, m/z = 437 $[M + H]^+$. | |
| 83 | 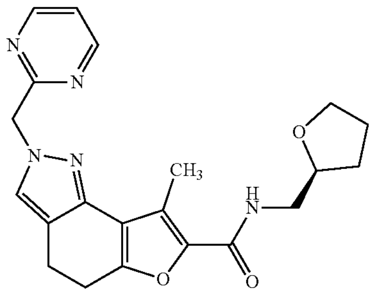 [SMILES: Cc1c(C(=O)NC[C@@H]2CCCO2)oc2c1-c1nn(Cc3ncccn3)cc1CC2] 8-methyl-2-(pyrimidin-2-ylmethyl)-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.548 (0.47), 1.564 (0.68), 1.572 (0.51), 1.580 (0.58), 1.588 (0.41), 1.772 (0.54), 1.778 (0.72), 1.793 (1.24), 1.811 (1.38), 1.829 (1.34), 1.840 (0.74), 1.850 (0.60), 1.857 (0.82), 1.872 (0.56), 1.879 (0.41), 2.414 (16.00), 2.467 (1.30), 2.518 (4.59), 2.523 (3.09), 2.895 (11.10), 3.208 (1.11), 3.213 (1.11), 3.223 (2.08), 3.228 (2.00), 3.238 (1.15), 3.243 (1.15), 3.580 (0.45), 3.597 (0.93), 3.600 (0.95), 3.617 (1.28), 3.635 (0.68), 3.730 (0.64), 3.747 (1.15), 3.763 (0.97), 3.765 (0.97), 3.783 (0.64), 3.924 (0.99), 3.941 (1.50), 3.956 (0.93), 5.496 (7.08), 7.433 (1.67), 7.445 (3.32), 7.458 (1.71), 7.610 (5.07), 7.961 (0.72), 7.976 (1.46), 7.992 (0.70), 8.786 (8.57), 8.798 (8.36). LC-MS (Method A); $R_t$ = 0.88 min, m/z = 394 $[M + H]^+$. | Intermediate 19; GPG (conditions A with HATU) |
| 84 | 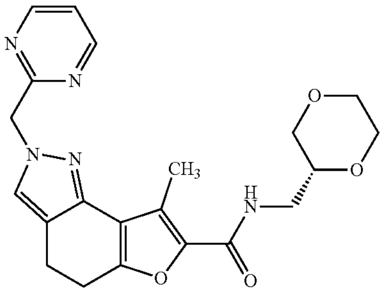 [SMILES: Cc1c(C(=O)NC[C@@H]2COCCO2)oc2c1-c1nn(Cc3ncccn3)cc1CC2] N-[(2R)-1,4-dioxan-2-ylmethyl]-8-methyl-2-(pyrimidin-2-ylmethyl)-4,5-dihydro-2H-furo[2,3-g]indazole-7-carboxamide | $^1$H-NMR (400 MHz, DMSO-d6) δ [ppm]: 2.336 (0.49), 2.414 (16.00), 2.518 (5.91), 2.523 (4.08), 2.679 (0.51), 2.716 (0.54), 2.897 (10.22), 2.902 (3.47), 3.157 (0.57), 3.178 (1.62), 3.191 (1.44), 3.202 (1.59), 3.206 (2.13), 3.226 (1.44), 3.231 (1.64), 3.242 (0.92), 3.260 (0.57), 3.412 (0.44), 3.418 (0.51), 3.439 (1.05), 3.445 (1.13), 3.466 (0.92), 3.472 (0.87), 3.509 (0.80), 3.514 (0.90), 3.537 (1.08), 3.543 (1.10), 3.564 (0.49), 3.570 (0.72), 3.604 (1.67), 3.610 (1.31), 3.619 (0.67), 3.628 (1.31), 3.634 (1.34), 3.680 (1.18), 3.687 (1.00), 3.710 (2.03), 3.715 (1.75), 3.739 (0.87), 5.496 (6.73), 7.433 (1.62), 7.445 (3.31), 7.458 (1.62), 7.611 (5.09), 8.040 (0.67), 8.055 (1.44), 8.070 (0.67), 8.786 (8.68), 8.798 (7.76). LC-MS (Method A); $R_t$ = 0.79 min, m/z = 410 $[M + H]^+$. | Intermediate 19; GP G (conditions A with HATU) |
| 85 | 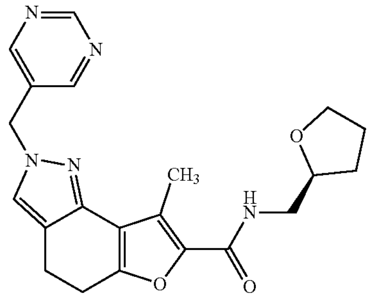 [SMILES: Cc1c(C(=O)NC[C@@H]2CCCO2)oc2c1-c1nn(Cc3cncnc3)cc1CC2] 8-methyl-2-(pyrimidin-5-ylmethyl)-N-[(2S)-tetrahydrofuran-2-ylmethyl]-4,5-dihydro-2H-furo[2,3-g]indazole-7-carboxamide | $^1$H-NMR (500 MHz, DMSO-d6) δ [ppm]: 0.934 (0.59), 0.946 (0.59), 1.548 (0.47), 1.560 (0.68), 1.565 (0.80), 1.571 (0.74), 1.577 (0.65), 1.583 (0.59), 1.587 (0.56), 1.762 (0.44), 1.774 (0.77), 1.779 (0.71), 1.791 (1.09), 1.794 (0.98), 1.805 (1.04), 1.809 (1.15), 1.826 (0.86), 1.834 (0.77), 1.839 (0.71), 1.842 (0.95), 1.848 (1.06), 1.857 (0.95), 1.865 (0.59), 1.870 (0.71), 1.874 (0.62), 1.882 (0.50), 1.887 (0.47), 2.074 (0.44), 2.368 (0.56), 2.452 (16.00), 2.514 (4.82), 2.518 (4.91), 2.522 (4.14), 2.529 (7.04), 2.627 (0.59), 2.785 (1.09), 2.801 (0.77), 2.847 (0.47), 2.862 (2.78), 2.871 (3.90), 2.876 (4.67), 2.885 (3.52), 2.899 (0.71), 3.210 (1.04), 3.217 (1.33), 3.222 (2.22), 3.229 (2.34), 3.234 (1.72), 3.241 (1.33), 3.585 (0.65), 3.600 (1.42), 3.614 (1.66), 3.628 (1.01), 3.734 (0.86), 3.747 (1.39), 3.759 (1.36), 3.761 (1.21), 3.776 (0.89), 3.926 (1.06), | Intermediate 20; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 3.939 (1.51), 3.951 (0.98), 5.377 (6.12), 5.606 (2.54), 7.439 (2.78), 7.680 (4.55), 7.972 (0.71), 7.984 (1.36), 7.996 (0.62), 8.139 (0.56), 8.543 (4.50), 8.741 (9.97), 9.104 (1.95), 9.128 (4.26). LC-MS (Method A); $R_t$ = 0.85 min, m/z = 394 $[M + H]^+$. | |
| 86 | 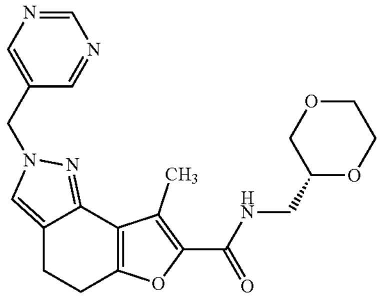 [SMILES: Cc1c(C(=O)NC[C@@H]2COCCO2)oc2c1-c1nn(Cc3cncnc3)cc1CC2] N-[(2R)-1,4-dioxan-2-ylmethyl]-8-methyl-2-(pyrimidin-5-ylmethyl)-4,5-dihydro-2H-furo[2,3-g]indazole-7-carboxamide | $^1$H-NMR (500 MHz, DMSO-d6) δ [ppm]: 0.934 (1.40), 0.947 (1.27), 2.368 (0.80), 2.452 (16.00), 2.514 (7.15), 2.518 (7.24), 2.522 (5.97), 2.530 (3.22), 2.642 (0.85), 2.786 (0.47), 2.847 (0.51), 2.863 (2.50), 2.872 (3.68), 2.878 (4.11), 2.886 (3.22), 2.902 (0.59), 3.161 (0.72), 3.176 (0.80), 3.182 (1.65), 3.188 (1.48), 3.201 (2.16), 3.205 (1.74), 3.216 (0.76), 3.224 (1.82), 3.229 (1.40), 3.241 (0.89), 3.256 (0.72), 3.417 (0.55), 3.422 (0.63), 3.439 (1.23), 3.444 (1.35), 3.461 (1.06), 3.466 (1.02), 3.512 (0.80), 3.517 (0.93), 3.536 (1.19), 3.541 (1.14), 3.557 (0.59), 3.562 (0.72), 3.605 (1.82), 3.618 (0.72), 3.625 (1.44), 3.630 (1.48), 3.680 (1.27), 3.686 (1.10), 3.704 (1.23), 3.709 (1.99), 3.734 (0.93), 5.378 (6.18), 5.605 (1.10), 7.440 (1.19), 7.680 (4.40), 8.051 (0.72), 8.063 (1.44), 8.075 (0.63), 8.542 (1.86), 8.741 (9.99), 9.105 (0.85), 9.128 (4.36). LC-MS (Method A); $R_t$ = 0.77 min, m/z = 410 $[M + H]^+$. | Intermediate 20; GP G (conditions A with HATU) |
| 87 | 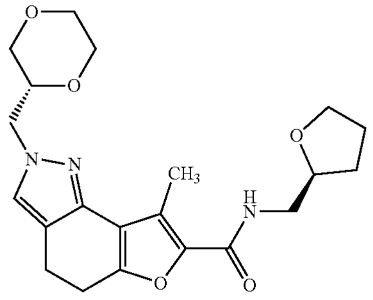 [SMILES: Cc1c(C(=O)NC[C@@H]2CCCO2)oc2c1-c1nn(C[C@@H]3COCCO3)cc1CC2] 2-[(2R)-1,4-dioxan-2-ylmethyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 0.845 (1.29), 0.863 (3.16), 0.881 (1.88), 1.312 (0.59), 1.331 (0.70), 1.352 (0.82), 1.375 (0.53), 1.395 (0.47), 1.481 (0.47), 1.513 (0.53), 1.534 (0.53), 1.553 (0.82), 1.562 (0.53), 1.570 (0.88), 1.577 (0.64), 1.585 (0.70), 1.599 (0.59), 1.615 (0.47), 1.761 (0.47), 1.782 (0.94), 1.797 (1.35), 1.815 (1.41), 1.833 (1.29), 1.844 (0.76), 1.858 (0.70), 1.862 (0.76), 1.876 (0.53), 2.318 (0.76), 2.470 (16.00), 2.518 (9.67), 2.523 (6.86), 2.633 (1.00), 2.660 (0.76), 2.740 (0.47), 2.758 (0.53), 2.762 (0.47), 2.829 (0.70), 2.848 (2.29), 2.860 (2.93), 2.869 (3.05), 2.882 (2.81), 2.900 (0.64), 3.214 (1.00), 3.219 (1.00), 3.230 (1.99), 3.234 (2.81), 3.245 (1.17), 3.250 (1.17), 3.259 (1.35), 3.263 (1.41), 3.287 (1.58), 3.419 (0.47), 3.440 (0.94), 3.446 (1.00), 3.467 (0.88), 3.473 (0.76), 3.510 (0.70), 3.516 (0.82), 3.539 (0.94), 3.545 (0.94), 3.565 (0.59), 3.572 (0.59), 3.584 (0.70), 3.603 (1.35), 3.620 (2.17), 3.639 (1.11), 3.719 (2.05), 3.734 (0.88), 3.748 (2.23), 3.751 (2.11), 3.766 (1.00), 3.769 (1.05), 3.772 (0.88), 3.787 (0.64), 3.817 (0.41), 3.824 (0.53), 3.829 (0.53), 3.835 (0.47), 3.841 (0.64), 3.929 (0.94), 3.945 (1.41), 3.961 (0.82), 4.036 (0.47), 4.072 (1.70), 4.084 (1.88), 4.088 (1.82), 4.097 (1.58), 7.348 (0.47), 7.461 (4.51), 7.966 (0.64), 7.981 (1.35), 7.996 (0.64), 8.548 (0.59). LC-MS (Method A); $R_t$ = 0.93 min, m/z = 402 $[M + H]^+$. | Intermediate 21; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 88 | 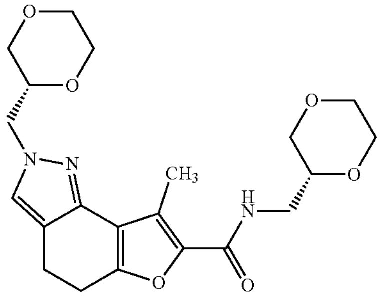 [SMILES: Cc1c(C(=O)NC[C@@H]2COCCO2)oc2c1-c1nn(C[C@@H]3COCCO3)cc1CC2]<br>N,2-bis[(2R)-1,4-dioxan-2-ylmethyl]-8-methyl-4,5-dihydro-2H-furo[2,3-g]indazole-7-carboxamide | $^1$H-NMR (400 MHz, DMSO-d6) δ [ppm]: 0.932 (0.74), 0.948 (0.72), 2.470 (16.00), 2.518 (4.16), 2.523 (2.85), 2.831 (0.61), 2.849 (2.29), 2.862 (3.03), 2.871 (3.22), 2.884 (3.03), 2.902 (0.67), 3.164 (0.57), 3.183 (1.87), 3.197 (1.44), 3.207 (1.57), 3.211 (2.00), 3.235 (2.76), 3.247 (0.94), 3.259 (1.42), 3.263 (1.50), 3.282 (0.43), 3.287 (1.39), 3.415 (0.59), 3.422 (0.65), 3.442 (1.63), 3.448 (1.59), 3.469 (1.41), 3.474 (1.31), 3.512 (1.24), 3.516 (1.24), 3.540 (1.78), 3.545 (1.96), 3.566 (0.76), 3.573 (1.11), 3.610 (1.91), 3.615 (2.05), 3.633 (1.46), 3.639 (1.78), 3.654 (0.43), 3.685 (1.22), 3.691 (1.04), 3.714 (3.11), 3.719 (3.61), 3.747 (2.18), 3.753 (1.18), 3.818 (0.44), 3.824 (0.55), 3.829 (0.57), 3.834 (0.52), 3.841 (0.67), 3.848 (0.48), 4.072 (1.79), 4.085 (2.05), 4.089 (2.02), 4.097 (1.72), 7.462 (4.83), 8.045 (0.70), 8.059 (1.50), 8.074 (0.68). LC-MS (Method A); $R_t$ = 0.85 min, m/z = 418 [M + H]$^+$. | Intermediate 21; GP G (conditions A with HATU) |
| 89 | 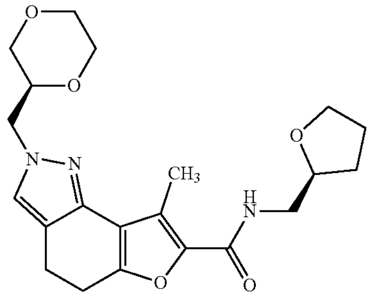 [SMILES: Cc1c(C(=O)NC[C@@H]2CCCO2)oc2c1-c1nn(C[C@H]3COCCO3)cc1CC2]<br>2-[(2S)-1,4-dioxan-2-ylmethyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.553 (0.46), 1.569 (0.67), 1.577 (0.48), 1.585 (0.56), 1.598 (0.41), 1.775 (0.51), 1.782 (0.67), 1.797 (1.16), 1.815 (1.30), 1.832 (1.24), 1.844 (0.68), 1.853 (0.55), 1.858 (0.66), 1.862 (0.78), 1.876 (0.52), 1.879 (0.51), 2.075 (2.92), 2.470 (16.00), 2.518 (3.51), 2.523 (2.43), 2.633 (0.48), 2.829 (0.63), 2.846 (2.29), 2.860 (3.13), 2.869 (3.30), 2.882 (3.02), 2.900 (0.68), 3.214 (1.01), 3.220 (1.01), 3.230 (2.02), 3.235 (2.83), 3.245 (1.15), 3.250 (1.15), 3.259 (1.45), 3.263 (1.37), 3.288 (1.38), 3.419 (0.44), 3.440 (0.93), 3.446 (1.04), 3.468 (0.87), 3.473 (0.81), 3.510 (0.72), 3.516 (0.85), 3.539 (1.00), 3.545 (1.00), 3.565 (0.44), 3.572 (0.61), 3.584 (0.45), 3.600 (0.91), 3.603 (0.96), 3.620 (2.01), 3.639 (1.13), 3.644 (0.83), 3.719 (1.88), 3.725 (1.28), 3.734 (0.74), 3.748 (2.29), 3.751 (2.10), 3.754 (1.77), 3.766 (0.97), 3.769 (0.97), 3.771 (0.78), 3.787 (0.63), 3.817 (0.42), 3.824 (0.53), 3.829 (0.55), 3.834 (0.49), 3.841 (0.67), 3.848 (0.46), 3.929 (0.96), 3.946 (1.43), 3.961 (0.89), 4.072 (1.77), 4.084 (2.02), 4.088 (1.98), 4.097 (1.68), 7.461 (4.72), 7.964 (0.66), 7.979 (1.39), 7.995 (0.64). LC-MS (Method A); $R_t$ = 0.95 min, m/z = 402 [M + H]$^+$. | Intermediate 22; GP G (conditions A with HATU) |
| 90 | 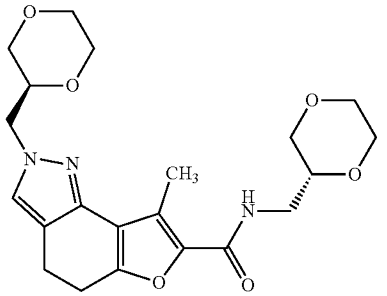 [SMILES: Cc1c(C(=O)NC[C@@H]2COCCO2)oc2c1-c1nn(C[C@H]3COCCO3)cc1CC2] | $^1$H-NMR (400 MHz, DMSO-d6) δ [ppm]: 2.318 (0.63), 2.470 (16.00), 2.518 (7.91), 2.523 (5.63), 2.679 (0.67), 2.831 (0.56), 2.849 (2.25), 2.861 (2.99), 2.871 (3.16), 2.884 (2.92), 2.902 (0.63), 3.162 (0.56), 3.182 (1.65), 3.197 (1.34), 3.207 (1.51), 3.211 (2.04), 3.218 (0.81), 3.235 (2.99), 3.249 (0.88), 3.259 (1.41), 3.263 (1.37), 3.287 (1.37), 3.415 (0.56), 3.421 (0.60), 3.442 (1.58), 3.448 (1.55), 3.469 (1.37), 3.475 (1.27), 3.512 (1.13), 3.516 (1.13), 3.518 (1.09), 3.540 (1.65), 3.545 (1.83), 3.567 (0.70), 3.573 (0.98), 3.610 | Intermediate 22; GP G (conditions A with HATU) |

TABLE 2-continued

| The following examples (4 to 147) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| | N-[(2R)-1,4-dioxan-2-ylmethyl]-2-[(2S)-1,4-dioxan-2-ylmethyl]-8-methyl-4,5-dihydro-2H-furo[2,3-g]indazole-7-carboxamide | (1.83), 3.616 (1.90), 3.633 (1.41), 3.639 (1.69), 3.685 (1.16), 3.691 (0.95), 3.714 (2.92), 3.719 (3.45), 3.747 (2.04), 3.817 (0.42), 3.824 (0.53), 3.829 (0.56), 3.835 (0.49), 3.841 (0.67), 4.072 (1.76), 4.085 (2.00), 4.089 (1.90), 4.097 (1.65), 7.462 (4.64), 8.044 (0.67), 8.059 (1.41), 8.074 (0.67). LC-MS (Method A); $R_t$ = 0.85 min, m/z = 418 $[M + H]^+$. | |
| 91 | 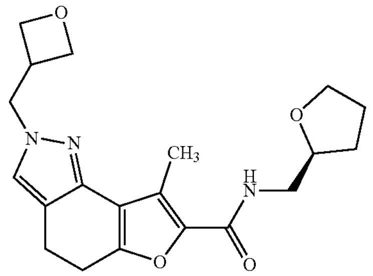 [SMILES: Cc1c(C(=O)NC[C@@H]2CCCO2)oc2c1-c1nn(CC3COC3)cc1CC2] 8-methyl-2-(oxetan-3-ylmethyl)-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.550 (0.48), 1.567 (0.65), 1.574 (0.48), 1.583 (0.58), 1.595 (0.41), 1.780 (0.69), 1.795 (1.16), 1.814 (1.34), 1.831 (1.27), 1.842 (0.72), 1.852 (0.62), 1.859 (0.79), 1.874 (0.55), 2.074 (4.15), 2.459 (16.00), 2.518 (7.40), 2.523 (4.97), 2.586 (0.51), 2.821 (0.69), 2.839 (2.50), 2.852 (3.32), 2.861 (3.53), 2.874 (3.12), 2.892 (0.72), 3.210 (1.10), 3.216 (1.06), 3.226 (2.09), 3.231 (1.95), 3.241 (1.16), 3.246 (1.16), 3.357 (0.79), 3.376 (0.96), 3.395 (0.65), 3.582 (0.45), 3.598 (0.93), 3.601 (0.93), 3.619 (1.23), 3.636 (0.69), 3.732 (0.62), 3.749 (1.10), 3.764 (0.93), 3.766 (0.93), 3.785 (0.58), 3.926 (0.93), 3.943 (1.44), 3.958 (0.86), 4.342 (3.84), 4.360 (3.73), 4.402 (2.57), 4.418 (5.31), 4.433 (2.78), 4.620 (3.19), 4.635 (3.29), 4.639 (3.56), 4.655 (2.67), 7.530 (4.45), 7.960 (0.65), 7.974 (1.37), 7.990 (0.65). LC-MS (Method A); $R_t$ = 0.90 min, m/z = 372 $[M + H]^+$. | Intermediate 23; GP G (conditions A with HATU) |
| 92 | 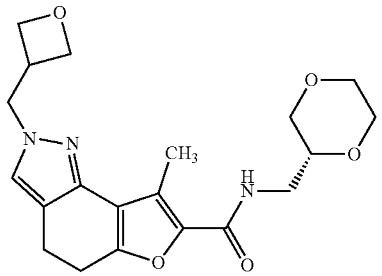 [SMILES: Cc1c(C(=O)NC[C@@H]2COCCO2)oc2c1-c1nn(CC3COC3)cc1CC2] N-[(2R)-1,4-dioxan-2-ylmethyl]-8-methyl-2-(oxetan-3-ylmethyl)-4,5-dihydro-2H-furo[2,3-g]indazole-7-carboxamide | $^1$H-NMR (400 MHz, DMSO-d6) δ [ppm]: 0.932 (0.46), 0.949 (0.46), 2.459 (16.00), 2.518 (4.36), 2.523 (3.04), 2.771 (0.42), 2.822 (0.61), 2.839 (2.33), 2.841 (2.34), 2.853 (3.10), 2.862 (3.38), 2.876 (3.08), 2.893 (0.72), 3.159 (0.59), 3.180 (1.55), 3.193 (1.44), 3.204 (1.64), 3.209 (2.10), 3.213 (0.92), 3.229 (1.51), 3.233 (1.75), 3.245 (0.92), 3.263 (0.61), 3.357 (0.74), 3.361 (0.63), 3.376 (0.98), 3.391 (0.59), 3.395 (0.65), 3.413 (0.61), 3.420 (0.52), 3.440 (1.07), 3.447 (1.16), 3.468 (0.96), 3.474 (0.90), 3.510 (0.81), 3.516 (0.89), 3.538 (1.11), 3.544 (1.13), 3.565 (0.48), 3.571 (0.76), 3.606 (1.66), 3.611 (1.40), 3.621 (0.65), 3.630 (1.27), 3.636 (1.33), 3.682 (1.18), 3.688 (1.00), 3.711 (2.03), 3.717 (1.73), 3.741 (0.87), 4.343 (3.82), 4.361 (3.75), 4.402 (2.71), 4.418 (5.63), 4.433 (2.95), 4.620 (3.41), 4.635 (3.43), 4.639 (3.86), 4.655 (2.95), 7.530 (4.80), 8.038 (0.66), 8.053 (1.42), 8.068 (0.66). LC-MS (Method A); $R_t$ = 0.81 min, m/z = 388 $[M + H]^+$. | Intermediate 23; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 93 | 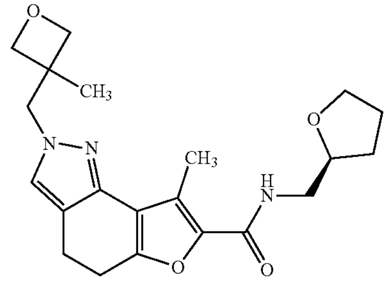 [SMILES: Cc1c(C(=O)NC[C@@H]2CCCO2)oc2c1-c1nn(CC3(C)COC3)cc1CC2] 8-methyl-2-[(3-methyloxetan-3-yl)methyl]-N-[(2S)-tetrahydrofuran-2-ylmethyl]-4,5-dihydro-2H-furo[2,3-g]indazole-7-carboxamide | $^1$H-NMR (500 MHz, DMSO-d6) δ [ppm]: 1.165 (12.32), 1.554 (0.41), 1.569 (0.61), 1.576 (0.55), 1.582 (0.49), 1.592 (0.51), 1.778 (0.47), 1.783 (0.47), 1.795 (0.73), 1.798 (0.67), 1.810 (0.69), 1.813 (0.77), 1.826 (0.57), 1.838 (0.51), 1.842 (0.45), 1.846 (0.57), 1.852 (0.65), 1.861 (0.61), 1.874 (0.45), 1.878 (0.41), 2.074 (0.77), 2.368 (0.41), 2.457 (16.00), 2.514 (3.16), 2.518 (3.26), 2.522 (2.65), 2.843 (0.59), 2.858 (2.28), 2.867 (3.18), 2.874 (3.40), 2.884 (3.01), 2.899 (0.65), 3.216 (1.02), 3.221 (1.00), 3.228 (1.87), 3.233 (1.73), 3.240 (1.00), 3.246 (1.04), 3.588 (0.45), 3.604 (0.98), 3.618 (1.12), 3.632 (0.65), 3.737 (0.59), 3.749 (0.88), 3.751 (1.02), 3.763 (1.00), 3.766 (0.83), 3.768 (0.71), 3.780 (0.65), 3.931 (0.96), 3.944 (1.38), 3.956 (0.92), 4.214 (5.05), 4.225 (5.37), 4.259 (6.92), 4.595 (4.36), 4.606 (3.91), 7.527 (4.25), 7.961 (0.63), 7.973 (1.30), 7.985 (0.65). LC-MS (Method A); $R_t$ = 0.97 min, m/z = 386 $[M + H]^+$. | Intermediate 24; GP G (conditions A with HATU) |
| 94 | 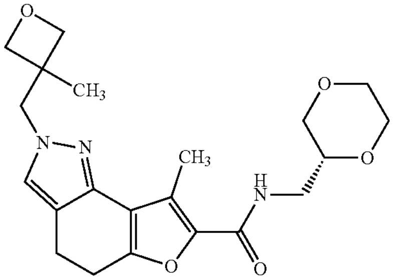 [SMILES: Cc1c(C(=O)NC[C@@H]2COCCO2)oc2c1-c1nn(CC3(C)COC3)cc1CC2] N-[(2R)-1,4-dioxan-2-ylmethyl]-8-methyl-2-[(3-methyloxetan-3-yl)methyl]-4,5-dihydro-2H-furo[2,3-g]indazole-7-carboxamide | $^1$H-NMR (500 MHz, DMSO-d6) δ [ppm]: 1.165 (12.23), 2.368 (0.41), 2.457 (16.00), 2.514 (3.62), 2.518 (3.68), 2.522 (2.98), 2.627 (0.43), 2.844 (0.58), 2.857 (2.16), 2.859 (2.23), 2.869 (3.02), 2.876 (3.28), 2.886 (2.87), 2.900 (0.66), 3.166 (0.66), 3.181 (0.79), 3.186 (1.24), 3.193 (1.35), 3.205 (1.97), 3.209 (1.41), 3.221 (0.66), 3.229 (1.50), 3.233 (1.33), 3.245 (0.84), 3.260 (0.62), 3.425 (0.47), 3.442 (0.99), 3.447 (1.05), 3.464 (0.84), 3.469 (0.77), 3.517 (0.69), 3.521 (0.77), 3.539 (1.01), 3.544 (1.03), 3.561 (0.49), 3.567 (0.64), 3.609 (1.35), 3.622 (0.56), 3.629 (1.29), 3.634 (1.14), 3.684 (1.03), 3.690 (0.90), 3.708 (1.03), 3.713 (1.67), 3.738 (0.75), 4.213 (5.16), 4.225 (5.33), 4.259 (6.77), 4.594 (4.31), 4.606 (4.09), 7.527 (4.16), 8.041 (0.64), 8.053 (1.37), 8.065 (0.62). LC-MS (Method A); $R_t$ = 0.89 min, m/z = 402 $[M + H]^+$. | Intermediate 24; GP G (conditions A with HATU) |
| 95 | 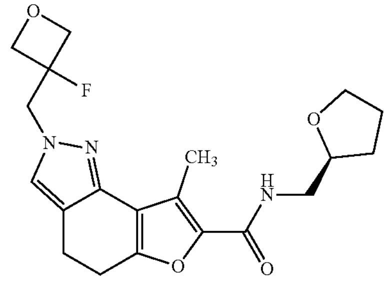 [SMILES: Cc1c(C(=O)NC[C@@H]2CCCO2)oc2c1-c1nn(CC3(F)COC3)cc1CC2] 2-[(3-fluorooxetan-3-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.552 (0.46), 1.569 (0.66), 1.576 (0.48), 1.584 (0.55), 1.776 (0.52), 1.781 (0.66), 1.797 (1.17), 1.815 (1.31), 1.832 (1.23), 1.843 (0.69), 1.853 (0.55), 1.858 (0.66), 1.861 (0.77), 1.875 (0.52), 2.074 (5.27), 2.468 (16.00), 2.518 (3.51), 2.523 (2.37), 2.839 (0.52), 2.857 (2.39), 2.858 (2.51), 2.869 (3.77), 2.876 (3.91), 2.888 (3.08), 2.906 (0.52), 3.214 (1.06), 3.219 (1.06), 3.230 (1.99), 3.234 (1.89), 3.245 (1.08), 3.250 (1.11), 3.583 (0.43), 3.599 (0.91), 3.603 (0.88), 3.620 (1.20), 3.638 (0.65), 3.733 (0.60), 3.748 (0.88), 3.751 (1.11), 3.765 (0.91), 3.768 (0.92), 3.786 (0.62), 3.929 (0.94), 3.945 (1.42), 3.961 (0.86), 4.591 (1.31), 4.614 (4.08), 4.642 (1.37), 4.669 (3.22), 4.766 (1.80), 4.788 (1.42), 4.819 (1.77), 4.842 (1.42), 7.525 (3.83), 7.976 (0.66), 7.992 (1.37), 8.006 (0.65). | Intermediate 25; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| | | LC-MS (Method A); $R_t$ = 0.96 min, m/z = 390 $[M + H]^+$. | |
| 96 | 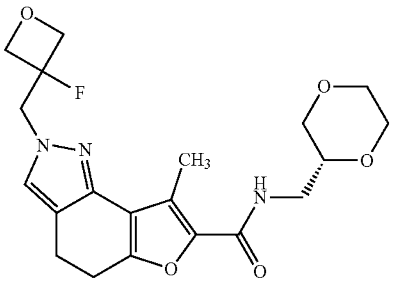 [SMILES: Cc1c(C(=O)NC[C@@H]2COCCO2)oc2c1-c1nn(CC3(F)COC3)cc1CC2] N-[(2R)-1,4-dioxan-2-ylmethyl]-2-[(3-fluorooxetan-3-yl)methyl]-8-methyl-4,5-dihydro-2H-furo[2,3-g]indazole-7-carboxamide | $^1$H-NMR (400 MHz, DMSO-d6) δ [ppm]: 2.075 (2.02), 2.468 (16.00), 2.518 (5.30), 2.523 (3.70), 2.839 (0.51), 2.859 (2.32), 2.871 (3.49), 2.878 (3.74), 2.890 (3.01), 2.908 (0.55), 3.162 (0.55), 3.181 (1.81), 3.197 (1.40), 3.206 (1.52), 3.211 (1.97), 3.216 (0.83), 3.234 (1.95), 3.248 (0.85), 3.266 (0.55), 3.421 (0.46), 3.442 (1.01), 3.448 (1.08), 3.469 (0.87), 3.475 (0.85), 3.511 (0.76), 3.517 (0.83), 3.540 (1.03), 3.546 (1.06), 3.566 (0.44), 3.573 (0.69), 3.608 (1.54), 3.624 (0.62), 3.632 (1.33), 3.639 (1.19), 3.684 (1.15), 3.690 (0.94), 3.712 (2.00), 3.719 (1.65), 3.742 (0.83), 4.591 (1.31), 4.615 (3.40), 4.642 (1.38), 4.664 (2.04), 4.669 (3.08), 4.766 (1.77), 4.788 (1.40), 4.818 (1.77), 4.841 (1.45), 7.527 (3.88), 8.055 (0.67), 8.070 (1.40), 8.085 (0.62). LC-MS (Method A); $R_t$ = 0.87 min, m/z = 406 $[M + H]^+$. | Intermediate 25; GPG (conditions A with HATU) |
| 97 | 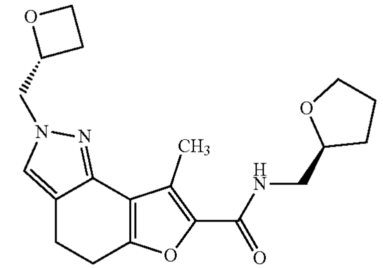 [SMILES: Cc1c(C(=O)NC[C@@H]2CCCO2)oc2c1-c1nn(C[C@H]3CCO3)cc1CC2] 8-methyl-2-[(2R)-oxetan-2-ylmethyl]-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.554 (0.44), 1.570 (0.62), 1.578 (0.46), 1.586 (0.52), 1.777 (0.49), 1.783 (0.65), 1.798 (1.12), 1.817 (1.24), 1.834 (1.18), 1.846 (0.67), 1.855 (0.55), 1.863 (0.75), 1.877 (0.51), 2.324 (0.73), 2.329 (0.99), 2.334 (0.73), 2.397 (0.43), 2.419 (0.54), 2.425 (0.66), 2.430 (0.49), 2.437 (0.45), 2.442 (0.59), 2.447 (0.73), 2.473 (16.00), 2.520 (3.45), 2.525 (2.20), 2.620 (0.51), 2.634 (0.56), 2.640 (0.55), 2.647 (0.46), 2.655 (0.42), 2.662 (0.77), 2.667 (1.01), 2.671 (1.08), 2.676 (0.78), 2.680 (0.42), 2.859 (2.24), 2.870 (4.52), 2.875 (4.03), 2.885 (2.86), 3.216 (1.06), 3.220 (1.04), 3.231 (1.97), 3.236 (1.90), 3.246 (1.06), 3.251 (1.12), 3.585 (0.42), 3.601 (0.85), 3.605 (0.85), 3.622 (1.15), 3.639 (0.63), 3.735 (0.59), 3.750 (0.84), 3.752 (1.02), 3.767 (0.86), 3.770 (0.86), 3.788 (0.57), 3.930 (0.90), 3.947 (1.37), 3.962 (0.83), 4.241 (0.55), 4.252 (0.60), 4.277 (1.53), 4.288 (1.54), 4.307 (2.04), 4.323 (2.45), 4.330 (0.82), 4.337 (0.88), 4.344 (1.57), 4.359 (1.24), 4.460 (0.64), 4.474 (0.67), 4.478 (0.83), 4.481 (0.89), 4.492 (0.73), 4.495 (0.76), 4.499 (0.72), 4.513 (0.52), 4.955 (0.63), 4.966 (0.61), 4.970 (0.73), 4.974 (0.66), 4.985 (0.58), 7.498 (4.43), 7.967 (0.61), 7.983 (1.26), 7.997 (0.59). LC-MS (Method A); $R_t$ = 0.91 min, m/z = 372 $[M + H]^+$. | Intermediate 26; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 98 | 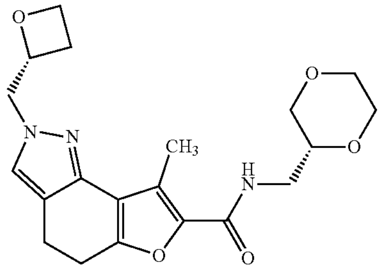 [SMILES: Cc1c(C(=O)NC[C@@H]2COCCO2)oc2c1-c1nn(C[C@H]3CCO3)cc1CC2] N-[(2R)-1,4-dioxan-2-ylmethyl]-8-methyl-2-[(2R)-oxetan-2-ylmethyl]-4,5-dihydro-2H-furo[2,3-g]indazole-7-carboxamide | $^{1}$H-NMR (400 MHz, DMSO-d6) δ [ppm]: 2.320 (0.43), 2.324 (0.96), 2.329 (1.33), 2.334 (0.99), 2.338 (0.48), 2.397 (0.47), 2.402 (0.40), 2.407 (0.45), 2.414 (0.40), 2.419 (0.56), 2.425 (0.72), 2.430 (0.52), 2.436 (0.49), 2.442 (0.63), 2.447 (0.78), 2.473 (16.00), 2.520 (7.23), 2.525 (4.50), 2.620 (0.60), 2.634 (0.63), 2.640 (0.61), 2.647 (0.51), 2.655 (0.48), 2.662 (0.91), 2.666 (1.29), 2.671 (1.42), 2.676 (1.05), 2.680 (0.57), 2.841 (0.43), 2.860 (2.36), 2.872 (4.67), 2.876 (3.98), 2.887 (2.95), 2.905 (0.46), 3.165 (0.55), 3.184 (1.80), 3.199 (1.43), 3.208 (1.54), 3.212 (1.86), 3.233 (1.50), 3.236 (1.74), 3.248 (0.91), 3.266 (0.57), 3.416 (0.42), 3.422 (0.50), 3.443 (1.03), 3.450 (1.14), 3.471 (0.92), 3.477 (0.89), 3.514 (0.79), 3.519 (0.87), 3.542 (1.05), 3.548 (1.09), 3.569 (0.45), 3.574 (0.70), 3.610 (1.59), 3.625 (0.66), 3.634 (1.37), 3.639 (1.28), 3.686 (1.15), 3.692 (0.99), 3.715 (1.98), 3.720 (1.67), 3.743 (0.86), 4.241 (0.59), 4.253 (0.65), 4.277 (1.56), 4.288 (1.65), 4.308 (1.83), 4.323 (2.05), 4.328 (1.02), 4.336 (0.96), 4.344 (1.63), 4.359 (1.17), 4.460 (0.67), 4.474 (0.71), 4.477 (0.91), 4.480 (0.95), 4.492 (0.77), 4.495 (0.83), 4.499 (0.80), 4.513 (0.56), 4.955 (0.66), 4.966 (0.66), 4.970 (0.79), 4.974 (0.74), 4.985 (0.64), 4.989 (0.40), 7.499 (4.71), 8.047 (0.64), 8.062 (1.40), 8.077 (0.65). LC-MS (Method A); $R_t$ = 0.83 min, m/z = 388 $[M + H]^+$. | Intermediate 26; GP G (conditions A with HATU) |
| 99 | 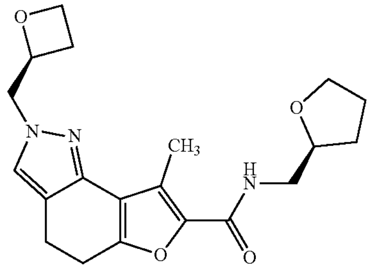 [SMILES: Cc1c(C(=O)NC[C@@H]2CCCO2)oc2c1-c1nn(C[C@@H]3CCO3)cc1CC2] 8-methyl-2-[(2S)-oxetan-2-ylmethyl]-N-[(2S)-tetrahydrofuran-2-ylmethyl]-4,5-dihydro-2H-furo[2,3-g]indazole-7-carboxamide | $^{1}$H-NMR (400 MHz, DMSO-d6) δ [ppm]: 1.555 (0.43), 1.571 (0.61), 1.579 (0.45), 1.587 (0.55), 1.777 (0.50), 1.783 (0.67), 1.798 (1.12), 1.816 (1.25), 1.834 (1.19), 1.845 (0.66), 1.855 (0.55), 1.863 (0.75), 1.877 (0.51), 2.320 (0.54), 2.398 (0.40), 2.420 (0.53), 2.426 (0.64), 2.431 (0.45), 2.437 (0.40), 2.442 (0.54), 2.447 (0.68), 2.472 (16.00), 2.520 (6.06), 2.525 (3.97), 2.619 (0.49), 2.634 (0.54), 2.640 (0.54), 2.647 (0.42), 2.655 (0.42), 2.662 (0.98), 2.859 (2.22), 2.870 (4.53), 2.875 (4.12), 2.885 (2.91), 3.215 (0.94), 3.222 (0.97), 3.230 (1.76), 3.237 (1.69), 3.245 (0.98), 3.253 (0.99), 3.585 (0.41), 3.601 (0.84), 3.605 (0.83), 3.622 (1.15), 3.640 (0.62), 3.735 (0.58), 3.752 (1.02), 3.768 (0.87), 3.770 (0.87), 3.788 (0.57), 3.930 (0.90), 3.946 (1.33), 3.962 (0.84), 4.241 (0.56), 4.252 (0.60), 4.276 (1.53), 4.288 (1.61), 4.308 (1.92), 4.322 (2.27), 4.329 (0.83), 4.336 (0.90), 4.344 (1.64), 4.359 (1.30), 4.460 (0.65), 4.474 (0.68), 4.477 (0.85), 4.481 (0.90), 4.492 (0.75), 4.495 (0.78), 4.499 (0.73), 4.513 (0.52), 4.955 (0.63), 4.966 (0.61), 4.970 (0.74), 4.974 (0.68), 4.985 (0.58), 7.498 (4.56), 7.966 (0.59), 7.982 (1.27), 7.997 (0.58). LC-MS (Method A); $R_t$ = 0.91 min, m/z = 372 $[M + H]^+$. | Intermediate 27; GP G (conditions A with HATU) |

TABLE 2-continued

| The following examples (4 to 147) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| 100 | 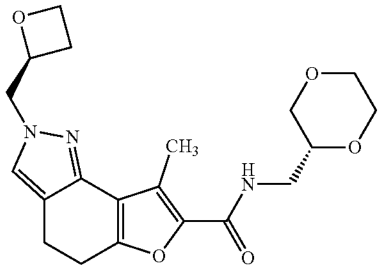 [SMILES: Cc1c(C(=O)NC[C@@H]2COCCO2)oc2c1-c1nn(C[C@@H]3CCO3)cc1CC2] N-[(2R)-1,4-dioxan-2-ylmethyl]-8-methyl-2-[(2S)-oxetan-2-ylmethyl]-4,5-dihydro-2H-furo[2,3-g]indazole-7-carboxamide | $^1$H-NMR (400 MHz, DMSO-d6) δ [ppm]: 2.324 (0.84), 2.329 (1.19), 2.334 (0.85), 2.397 (0.42), 2.419 (0.52), 2.425 (0.65), 2.430 (0.48), 2.436 (0.42), 2.442 (0.56), 2.447 (0.70), 2.473 (16.00), 2.520 (4.46), 2.525 (2.91), 2.619 (0.53), 2.634 (0.56), 2.640 (0.56), 2.647 (0.45), 2.655 (0.43), 2.662 (0.82), 2.667 (1.16), 2.671 (1.28), 2.676 (0.91), 2.681 (0.47), 2.859 (2.33), 2.871 (4.57), 2.877 (3.93), 2.887 (2.96), 2.905 (0.42), 3.163 (0.57), 3.184 (1.49), 3.197 (1.36), 3.208 (1.54), 3.213 (1.95), 3.220 (0.76), 3.236 (2.21), 3.251 (0.83), 3.269 (0.58), 3.423 (0.47), 3.444 (0.99), 3.450 (1.08), 3.471 (0.89), 3.477 (0.85), 3.513 (0.75), 3.519 (0.81), 3.541 (1.03), 3.548 (1.07), 3.568 (0.44), 3.574 (0.69), 3.609 (1.57), 3.625 (0.60), 3.633 (1.29), 3.640 (1.24), 3.686 (1.12), 3.692 (0.94), 3.715 (1.95), 3.721 (1.62), 3.744 (0.82), 4.241 (0.58), 4.253 (0.62), 4.277 (1.55), 4.288 (1.63), 4.308 (1.87), 4.323 (2.12), 4.329 (0.93), 4.336 (0.92), 4.344 (1.65), 4.360 (1.24), 4.460 (0.66), 4.474 (0.69), 4.477 (0.87), 4.481 (0.90), 4.492 (0.76), 4.495 (0.79), 4.499 (0.75), 4.513 (0.53), 4.955 (0.65), 4.966 (0.64), 4.970 (0.76), 4.974 (0.69), 4.985 (0.61), 7.499 (4.64), 8.046 (0.64), 8.061 (1.38), 8.075 (0.63). LC-MS (Method A); $R_t$ = 0.83 min, m/z = 388 $[M + H]^+$. | Intermediate 27; GP G (conditions A with HATU) |
| 101 | 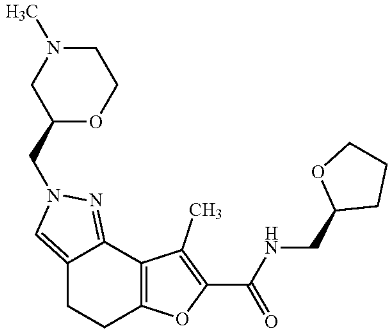 [SMILES: Cc1c(C(=O)NC[C@@H]2CCCO2)oc2c1-c1nn(C[C@H]3CN(C)CCO3)cc1CC2] 8-methyl-2-{[(2R)-4-methylmorpholin-2-yl]methyl}-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.504 (0.51), 1.553 (0.44), 1.569 (0.57), 1.577 (0.44), 1.585 (0.51), 1.722 (0.76), 1.749 (1.14), 1.775 (1.14), 1.781 (0.83), 1.797 (1.14), 1.815 (1.27), 1.832 (1.21), 1.844 (0.70), 1.853 (0.57), 1.862 (0.83), 1.876 (0.51), 1.936 (0.44), 1.957 (0.83), 1.964 (0.83), 1.985 (0.57), 1.992 (0.57), 2.156 (11.37), 2.170 (1.02), 2.318 (1.14), 2.469 (16.00), 2.518 (14.79), 2.523 (10.03), 2.547 (1.21), 2.575 (0.76), 2.635 (0.76), 2.782 (1.08), 2.828 (0.57), 2.846 (2.22), 2.858 (2.79), 2.867 (2.98), 2.881 (2.73), 2.898 (0.63), 3.214 (0.89), 3.220 (0.89), 3.229 (1.65), 3.235 (1.59), 3.244 (0.89), 3.250 (0.95), 3.422 (0.44), 3.428 (0.57), 3.449 (1.02), 3.456 (1.02), 3.478 (0.57), 3.483 (0.44), 3.600 (0.89), 3.620 (1.21), 3.638 (0.63), 3.734 (0.63), 3.754 (1.90), 3.766 (1.33), 3.769 (1.40), 3.777 (1.14), 3.786 (1.33), 3.929 (0.89), 3.945 (1.33), 3.961 (0.83), 4.083 (2.86), 4.098 (2.79), 7.457 (4.32), 7.962 (0.63), 7.977 (1.33), 7.991 (0.63), 8.463 (0.44), 8.552 (0.76). LC-MS (Method A); $R_t$ = 0.92 min, m/z = 415 $[M + H]^+$. | Intermediate 28; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 102 | 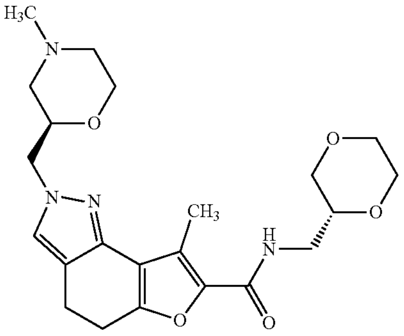 [SMILES: Cc1c(C(=O)NC[C@@H]2COCCO2)oc2c1-c1nn(C[C@H]3CN(C)CCO3)cc1CC2]<br>N[(2R)-1,4-dioxan-2-ylmethyl]-8-methyl-2-{[(2R)-4-methylmorpholin-2-yl]methyl}-4,5-dihydro-2H-furo[2,3-g]indazole-7-carboxamide | $^1$H-NMR (400 MHz, DMSO-d6) δ [ppm]: 0.932 (2.38), 0.935 (0.71), 0.948 (2.38), 0.953 (0.40), 1.352 (0.48), 1.721 (0.71), 1.748 (1.03), 1.774 (0.79), 1.936 (0.40), 1.957 (0.79), 1.964 (0.79), 1.985 (0.55), 2.155 (11.33), 2.170 (1.19), 2.318 (1.43), 2.469 (16.00), 2.518 (15.37), 2.523 (11.25), 2.543 (1.98), 2.573 (0.63), 2.635 (0.71), 2.754 (1.19), 2.782 (1.35), 2.829 (0.48), 2.847 (1.98), 2.859 (2.61), 2.869 (2.85), 2.883 (2.61), 2.900 (0.55), 3.162 (0.48), 3.182 (1.50), 3.196 (1.19), 3.207 (1.35), 3.211 (1.74), 3.218 (0.71), 3.235 (1.90), 3.249 (0.79), 3.268 (0.63), 3.283 (0.40), 3.422 (0.87), 3.428 (0.63), 3.442 (1.03), 3.449 (1.82), 3.456 (1.11), 3.469 (0.95), 3.476 (1.19), 3.512 (0.71), 3.518 (0.79), 3.540 (1.03), 3.547 (0.95), 3.567 (0.48), 3.573 (0.71), 3.608 (1.35), 3.633 (1.19), 3.638 (1.11), 3.684 (1.03), 3.691 (0.87), 3.713 (1.74), 3.748 (1.03), 3.753 (1.27), 3.784 (1.11), 4.085 (2.77), 4.099 (2.69), 7.459 (4.20), 8.041 (0.63), 8.056 (1.35), 8.071 (0.63), 8.464 (0.55), 8.551 (0.71).<br>LC-MS (Method A); $R_t$ = 0.85 min, m/z = 431 [M + H]$^+$. | Intermediate 28; GP G (conditions A with HATU) |
| 103 | 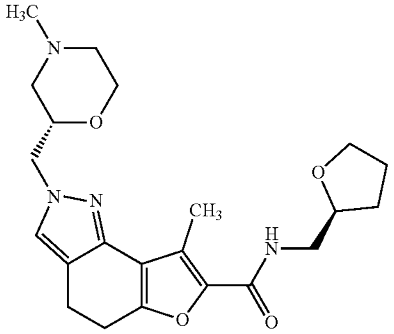 [SMILES: Cc1c(C(=O)NC[C@@H]2CCCO2)oc2c1-c1nn(C[C@@H]3CN(C)CCO3)cc1CC2]<br>8-methyl-2-{[(2S)-4-methylmorpholin-2-yl]methyl}-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.553 (0.47), 1.569 (0.68), 1.577 (0.50), 1.586 (0.57), 1.593 (0.42), 1.721 (0.81), 1.749 (1.17), 1.775 (1.15), 1.782 (0.73), 1.797 (1.15), 1.815 (1.28), 1.832 (1.25), 1.844 (0.68), 1.853 (0.55), 1.858 (0.65), 1.862 (0.76), 1.876 (0.52), 1.936 (0.47), 1.956 (0.86), 1.964 (0.86), 1.985 (0.52), 1.992 (0.44), 2.155 (12.45), 2.318 (0.50), 2.323 (1.10), 2.327 (1.57), 2.332 (1.10), 2.336 (0.47), 2.469 (16.00), 2.518 (5.22), 2.523 (3.78), 2.546 (0.76), 2.574 (0.70), 2.635 (0.84), 2.665 (1.75), 2.669 (1.88), 2.673 (1.17), 2.678 (0.50), 2.827 (0.63), 2.846 (2.27), 2.858 (2.98), 2.867 (3.21), 2.881 (2.95), 2.898 (0.65), 3.214 (1.04), 3.219 (1.02), 3.230 (1.98), 3.234 (1.91), 3.245 (1.04), 3.249 (1.12), 3.422 (0.44), 3.428 (0.57), 3.450 (1.02), 3.456 (1.02), 3.478 (0.60), 3.483 (0.47), 3.584 (0.42), 3.600 (0.86), 3.603 (0.89), 3.620 (1.20), 3.638 (0.65), 3.734 (0.65), 3.751 (1.91), 3.754 (1.93), 3.760 (1.33), 3.766 (1.38), 3.769 (1.44), 3.778 (1.20), 3.786 (1.38), 3.929 (0.94), 3.945 (1.44), 3.960 (0.89), 4.083 (3.11), 4.098 (3.00), 7.457 (4.49), 7.962 (0.65), 7.977 (1.41), 7.993 (0.65).<br>LC-MS (Method A); $R_t$ = 0.92 min, m/z = 415 [M + H]$^+$. | Intermediate 29; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| 104 | 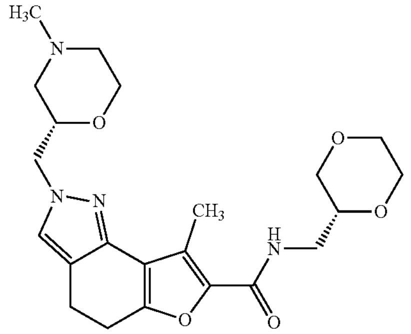 [SMILES: Cc1c(C(=O)NC[C@@H]2COCCO2)oc2c1-c1nn(C[C@@H]3CN(C)CCO3)cc1CC2] N[(2R)-1,4-dioxan-2-ylmethyl]-8-methyl-2-{[(2S)-4-methylmorpholin-2-yl]methyl}-4,5-dihydro-2H-furo[2,3-g]indazole-7-carboxamide | $^1$H-NMR (400 MHz, DMSO-d6) δ [ppm]: 0.932 (1.04), 0.948 (1.04), 1.721 (0.75), 1.748 (1.04), 1.774 (0.81), 1.936 (0.43), 1.956 (0.81), 1.964 (0.84), 1.984 (0.52), 1.992 (0.43), 2.155 (12.28), 2.169 (0.46), 2.318 (0.55), 2.322 (1.18), 2.327 (1.70), 2.332 (1.24), 2.336 (0.55), 2.469 (16.00), 2.518 (7.24), 2.523 (5.02), 2.543 (1.27), 2.575 (0.66), 2.635 (0.84), 2.665 (1.87), 2.669 (2.08), 2.673 (1.30), 2.678 (0.58), 2.829 (0.55), 2.846 (2.08), 2.860 (2.65), 2.869 (3.08), 2.882 (2.80), 2.900 (0.63), 3.164 (0.52), 3.182 (1.79), 3.198 (1.35), 3.206 (1.50), 3.211 (1.85), 3.231 (1.38), 3.235 (1.64), 3.247 (0.86), 3.265 (0.55), 3.415 (0.40), 3.422 (0.86), 3.428 (0.61), 3.442 (1.07), 3.449 (1.96), 3.456 (1.10), 3.469 (0.95), 3.476 (1.24), 3.483 (0.52), 3.512 (0.75), 3.518 (0.84), 3.540 (1.01), 3.547 (1.04), 3.567 (0.43), 3.573 (0.69), 3.608 (1.47), 3.623 (0.58), 3.632 (1.27), 3.639 (1.18), 3.685 (1.10), 3.691 (0.92), 3.713 (1.90), 3.719 (1.59), 3.748 (1.12), 3.753 (1.33), 3.760 (1.24), 3.769 (0.58), 3.778 (1.07), 3.784 (1.15), 4.084 (3.03), 4.099 (2.91), 7.459 (4.47), 8.042 (0.66), 8.057 (1.44), 8.072 (0.66). LC-MS (Method A); $R_t$ = 0.85 min, m/z = 431 $[M + H]^+$. | Intermediate 29; GP G (conditions A with HATU) |
| 105 | 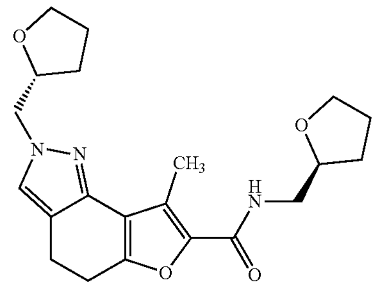 [SMILES: Cc1c(C(=O)NC[C@@H]2CCCO2)oc2c1-c1nn(C[C@H]3CCCO3)cc1CC2] 8-methyl-2-{[(2R)-tetrahydrofuran-2-yl]methyl]-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.553 (0.60), 1.570 (0.87), 1.573 (0.78), 1.585 (0.89), 1.591 (0.83), 1.600 (0.74), 1.615 (0.49), 1.622 (0.60), 1.753 (0.69), 1.770 (2.25), 1.775 (0.87), 1.782 (0.96), 1.787 (2.86), 1.796 (1.34), 1.806 (1.92), 1.815 (1.36), 1.823 (0.89), 1.832 (1.23), 1.843 (0.67), 1.853 (0.54), 1.861 (0.78), 1.876 (0.51), 1.878 (0.51), 1.886 (0.51), 1.903 (0.65), 1.917 (0.58), 1.934 (0.78), 1.950 (0.62), 2.318 (0.42), 2.470 (16.00), 2.518 (5.13), 2.523 (3.62), 2.828 (0.49), 2.848 (2.34), 2.858 (3.46), 2.866 (3.75), 2.878 (3.03), 2.897 (0.51), 3.214 (1.03), 3.219 (1.03), 3.229 (1.94), 3.234 (1.87), 3.244 (1.03), 3.249 (1.07), 3.584 (0.42), 3.596 (0.76), 3.599 (0.96), 3.603 (0.91), 3.613 (1.41), 3.616 (1.52), 3.620 (1.32), 3.633 (1.70), 3.638 (0.78), 3.650 (0.71), 3.724 (0.78), 3.734 (0.67), 3.741 (1.70), 3.744 (0.87), 3.748 (0.98), 3.751 (1.16), 3.757 (1.14), 3.761 (1.36), 3.766 (0.98), 3.769 (0.96), 3.777 (0.65), 3.786 (0.65), 3.929 (0.91), 3.944 (1.41), 3.960 (0.87), 4.038 (0.69), 4.054 (1.12), 4.074 (1.72), 4.088 (1.27), 4.098 (2.16), 4.104 (0.58), 4.111 (0.67), 4.121 (1.14), 4.124 (1.14), 4.130 (1.12), 4.140 (0.47), 7.463 (4.66), 7.959 (0.62), 7.974 (1.34), 7.989 (0.62). LC-MS (Method A); $R_t$ = 1.00 min, m/z = 386 $[M + H]^+$. | Intermediate 30; GP G (conditions A with HATU) |

TABLE 2-continued

The following examples (4 to 147) were prepared in analogy to example 3 starting from the given intermediates and commercially available amines (or their salts), applying the indicated general procedure.

| Ex-ample | Structure IUPAC-Name | Analytical Data | Preparation or Separation Methods |
|---|---|---|---|
| 106 | 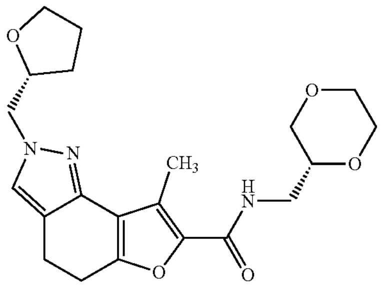 [SMILES: Cc1c(C(=O)NC[C@@H]2COCCO2)oc2c1-c1nn(C[C@H]3CCCO3)cc1CC2] N[(2R)-1,4-dioxan-2-ylmethyl]-8-methyl-2-[(2R)-tetrahydrofuran-2-ylmethyl]-4,5-dihydro-2H-furo[2,3-g]indazole-7-carboxamide | $^{1}$H-NMR (400 MHz, DMSO-d6) δ [ppm]: 0.932 (0.41), 0.948 (0.41), 1.573 (0.49), 1.589 (0.56), 1.601 (0.51), 1.605 (0.48), 1.622 (0.58), 1.752 (0.59), 1.769 (2.11), 1.786 (2.63), 1.805 (1.69), 1.822 (0.66), 1.903 (0.60), 1.917 (0.54), 1.933 (0.78), 1.950 (0.65), 2.470 (16.00), 2.518 (2.48), 2.523 (1.67), 2.829 (0.53), 2.847 (2.30), 2.860 (3.47), 2.867 (3.73), 2.879 (3.09), 2.898 (0.57), 3.163 (0.56), 3.182 (1.85), 3.197 (1.42), 3.206 (1.54), 3.211 (1.99), 3.231 (1.50), 3.235 (1.77), 3.247 (0.86), 3.266 (0.54), 3.421 (0.47), 3.442 (1.00), 3.448 (1.11), 3.469 (0.90), 3.475 (0.86), 3.512 (0.78), 3.518 (0.87), 3.540 (1.04), 3.547 (1.07), 3.567 (0.43), 3.573 (0.70), 3.596 (0.85), 3.608 (1.61), 3.613 (2.31), 3.623 (0.70), 3.633 (2.99), 3.638 (1.34), 3.650 (0.91), 3.685 (1.14), 3.691 (0.95), 3.713 (1.95), 3.719 (1.65), 3.740 (2.35), 3.757 (0.95), 3.760 (1.29), 3.777 (0.57), 4.038 (0.72), 4.055 (1.11), 4.074 (1.71), 4.088 (1.26), 4.098 (2.17), 4.104 (0.63), 4.111 (0.69), 4.121 (1.09), 4.124 (1.08), 4.130 (1.11), 4.140 (0.47), 7.464 (4.73), 8.038 (0.66), 8.053 (1.41), 8.068 (0.65). LC-MS (Method A); $R_t$ = 0.93 min, m/z = 402 $[M + H]^+$. | Intermediate 30; GP G (conditions A with HATU) |
| 107 | 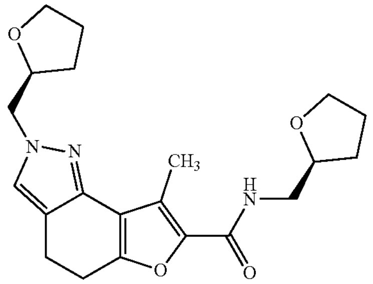 [SMILES: Cc1c(C(=O)NC[C@@H]2CCCO2)oc2c1-c1nn(C[C@@H]3CCCO3)cc1CC2] 8-methyl-N,2-bis[(2S)-tetrahydrofuran-2-ylmethyl]-4,5-dihydro-2H-furo[2,3-g]indazole-7-carboxamide | $^{1}$H-NMR (400 MHz, DMSO-d6) δ [ppm]: 1.553 (0.61), 1.562 (0.40), 1.570 (0.92), 1.577 (0.61), 1.585 (0.83), 1.592 (0.77), 1.600 (0.78), 1.605 (0.60), 1.608 (0.43), 1.615 (0.53), 1.622 (0.62), 1.752 (0.68), 1.769 (2.23), 1.775 (0.83), 1.782 (0.99), 1.786 (2.83), 1.796 (1.32), 1.799 (1.21), 1.806 (1.93), 1.815 (1.37), 1.822 (0.92), 1.832 (1.24), 1.844 (0.67), 1.853 (0.54), 1.858 (0.63), 1.861 (0.77), 1.876 (0.53), 1.878 (0.51), 1.886 (0.55), 1.903 (0.67), 1.917 (0.58), 1.933 (0.77), 1.950 (0.64), 2.470 (16.00), 2.518 (2.86), 2.523 (1.94), 2.828 (0.49), 2.848 (2.39), 2.858 (3.44), 2.865 (3.66), 2.878 (2.99), 2.896 (0.52), 3.213 (1.00), 3.219 (1.00), 3.228 (1.87), 3.235 (1.77), 3.244 (1.02), 3.250 (1.06), 3.584 (0.43), 3.596 (0.76), 3.599 (0.97), 3.603 (0.91), 3.613 (1.41), 3.616 (1.50), 3.620 (1.32), 3.633 (1.75), 3.638 (0.78), 3.650 (0.74), 3.724 (0.77), 3.734 (0.68), 3.740 (1.75), 3.744 (0.85), 3.748 (0.97), 3.751 (1.17), 3.757 (1.18), 3.760 (1.39), 3.766 (0.98), 3.769 (0.97), 3.771 (0.76), 3.777 (0.66), 3.786 (0.64), 3.928 (0.92), 3.944 (1.43), 3.960 (0.86), 4.038 (0.69), 4.054 (1.10), 4.074 (1.73), 4.088 (1.27), 4.098 (2.20), 4.104 (0.56), 4.111 (0.67), 4.123 (1.17), 4.130 (1.12), 4.140 (0.47), 7.463 (4.55), 7.959 (0.63), 7.974 (1.33), 7.989 (0.62). LC-MS (Method A); $R_t$ = 1.00 min, m/z = 386 $[M + H]^+$. | Intermediate 31; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 108 | 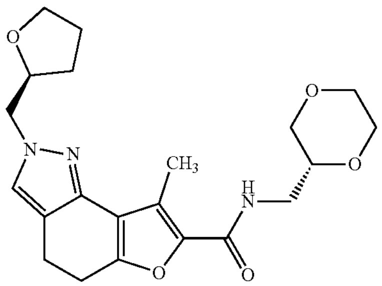 [SMILES: Cc1c(C(=O)NC[C@@H]2COCCO2)oc2c1-c1nn(C[C@@H]3CCCO3)cc1CC2] N[(2R)-1,4-dioxan-2-ylmethyl]-8-methyl-2-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 1.573 (0.46), 1.589 (0.54), 1.601 (0.48), 1.605 (0.45), 1.622 (0.55), 1.753 (0.57), 1.769 (2.00), 1.786 (2.48), 1.806 (1.61), 1.822 (0.63), 1.903 (0.57), 1.917 (0.52), 1.934 (0.75), 1.950 (0.61), 2.470 (16.00), 2.518 (4.39), 2.523 (3.12), 2.829 (0.50), 2.849 (2.30), 2.860 (3.16), 2.867 (3.50), 2.879 (2.88), 2.898 (0.52), 3.162 (0.55), 3.182 (1.59), 3.196 (1.36), 3.206 (1.46), 3.211 (1.98), 3.217 (0.79), 3.235 (1.77), 3.248 (0.82), 3.266 (0.55), 3.422 (0.45), 3.442 (0.95), 3.448 (1.04), 3.469 (0.84), 3.475 (0.80), 3.511 (0.75), 3.517 (0.84), 3.540 (1.00), 3.546 (1.04), 3.566 (0.41), 3.573 (0.68), 3.596 (0.80), 3.608 (1.55), 3.613 (2.29), 3.623 (0.64), 3.633 (2.75), 3.638 (1.32), 3.650 (0.86), 3.685 (1.07), 3.691 (0.89), 3.713 (1.86), 3.719 (1.59), 3.723 (1.11), 3.740 (2.27), 3.757 (0.91), 3.760 (1.25), 3.777 (0.54), 4.038 (0.70), 4.055 (1.07), 4.074 (1.63), 4.088 (1.21), 4.098 (2.07), 4.104 (0.59), 4.111 (0.66), 4.121 (1.04), 4.124 (1.05), 4.130 (1.05), 4.140 (0.45), 7.464 (4.64), 8.038 (0.63), 8.053 (1.36), 8.069 (0.61). LC-MS (Method A); $R_t$ = 0.92 min, m/z = 402 $[M + H]^+$. | Intermediate 31; GP G (conditions A with HATU) |
| 109 | 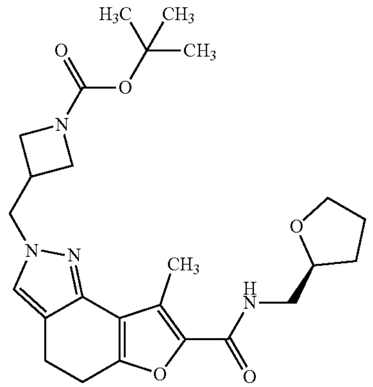 [SMILES: Cc1c(C(=O)NC[C@@H]2CCCO2)oc2c1-c1nn(CC3CN(C(=O)OC(C)(C)C)C3)cc1CC2] tert-butyl 3-[(8-methyl-7-{[(2S)-tetrahydrofuran-2-ylmethyl]carbamoyl}-4,5-dihydro-2H-furo[2,3-g]indazol-2-yl)methyl]azetidine-1-carboxylate | $^1$H-NMR (400 MHz, DMSO-d6) δ [ppm]: 1.352 (16.00), 1.362 (1.66), 1.384 (0.80), 1.814 (0.44), 1.831 (0.40), 2.468 (5.19), 2.518 (3.21), 2.523 (2.18), 2.841 (0.76), 2.853 (1.03), 2.862 (1.12), 2.874 (0.95), 3.227 (0.63), 3.231 (0.60), 3.619 (0.41), 3.943 (0.48), 4.249 (0.93), 4.267 (0.90), 7.554 (1.43), 7.976 (0.48). LC-MS (Method A); $R_t$ = 1.15 min, m/z = 471 $[M + H]^+$. | Intermediate 32; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 110 | 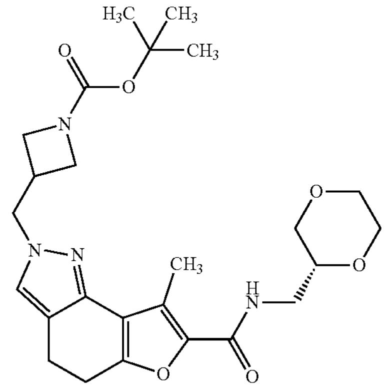 [SMILES: Cc1c(C(=O)NC[C@@H]2COCCO2)oc2c1-c1nn(CC3CN(C(=O)OC(C)(C)C)C3)cc1CC2] tert-butyl 3-[(7-{[(2R)-1,4-dioxan-2 ylmethyl]carbamoyl}-8-methyl-4,5-dihydro-2H-furo[2,3-g]indazol-2-yl)methyl]azetidine-1-carboxylate | $^1$H-NMR (400 MHz, DMSO-d6) δ [ppm]: 0.932 (0.48), 0.948 (0.49), 1.339 (0.44), 1.352 (16.00), 1.362 (1.21), 2.468 (5.30), 2.518 (4.27), 2.523 (2.99), 2.843 (0.75), 2.855 (1.01), 2.864 (1.10), 2.876 (0.95), 3.180 (0.51), 3.194 (0.46), 3.205 (0.51), 3.209 (0.70), 3.233 (0.59), 3.606 (0.53), 3.630 (0.44), 3.637 (0.46), 3.682 (0.70), 3.689 (0.57), 3.712 (0.70), 3.717 (0.60), 4.249 (0.93), 4.268 (0.92), 7.556 (1.45), 8.055 (0.49). LC-MS (Method A); $R_t$ = 1.08 min, m/z = 485 $[M - H]^-$. | Intermediate 32; GP G (conditions A with HATU) |
| 111 | 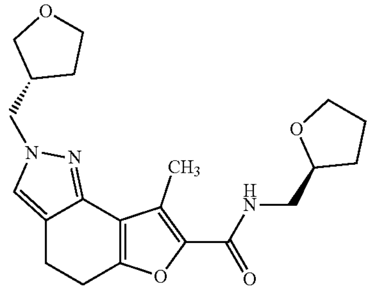 [SMILES: Cc1c(C(=O)NC[C@@H]2CCCO2)oc2c1-c1nn(C[C@H]3CCOC3)cc1CC2] 8-methyl-N-[(2S)-tetrahydrofuran-2-ylmethyl]-2-[(3R)-tetrahydrofuran-3-ylmethyl]-4,5-dihydro-2H-furo[2,3-g]indazole-7-carboxamide | $^1$H-NMR (400 MHz, DMSO-d6) δ [ppm]: 1.555 (0.52), 1.567 (0.76), 1.570 (0.80), 1.586 (1.06), 1.598 (1.15), 1.615 (1.05), 1.632 (0.62), 1.777 (0.55), 1.783 (0.74), 1.799 (1.28), 1.817 (1.48), 1.834 (1.34), 1.846 (0.77), 1.855 (0.63), 1.862 (0.86), 1.869 (0.40), 1.880 (0.87), 1.895 (0.75), 1.900 (1.00), 1.907 (0.40), 1.915 (0.92), 1.921 (0.58), 1.925 (0.50), 1.931 (0.65), 1.945 (0.56), 2.324 (0.60), 2.329 (0.84), 2.333 (0.61), 2.474 (16.00), 2.520 (3.69), 2.525 (2.32), 2.597 (0.77), 2.666 (1.11), 2.671 (1.32), 2.675 (0.87), 2.686 (0.76), 2.704 (0.57), 2.832 (0.73), 2.850 (2.69), 2.863 (3.64), 2.871 (3.91), 2.884 (3.17), 2.901 (0.71), 3.215 (1.12), 3.220 (1.14), 3.231 (2.17), 3.235 (2.12), 3.246 (1.24), 3.250 (1.26), 3.467 (1.17), 3.481 (1.18), 3.489 (1.48), 3.502 (1.40), 3.585 (0.60), 3.596 (0.74), 3.605 (1.16), 3.616 (1.66), 3.622 (1.52), 3.634 (1.52), 3.639 (1.03), 3.645 (1.63), 3.653 (0.91), 3.663 (1.72), 3.667 (1.49), 3.684 (1.18), 3.734 (1.08), 3.753 (2.48), 3.767 (2.16), 3.773 (1.47), 3.788 (1.14), 3.931 (1.01), 3.947 (1.53), 3.962 (0.93), 4.030 (2.50), 4.047 (2.64), 7.537 (4.72), 7.962 (0.73), 7.977 (1.49), 7.992 (0.69). LC-MS (Method A); $R_t$ = 1.11 min, m/z = 386 $[M + H]^+$. | Intermediate 33; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| 112 | 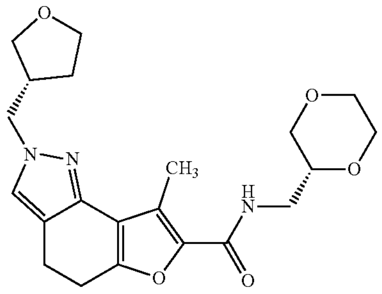 [SMILES: Cc1c(C(=O)NC[C@@H]2COCCO2)oc2c1-c1nn(C[C@H]3CCOC3)cc1CC2] N-[(2R)-1,4-dioxan-2-ylmethyl]-8-methyl-2-[(3R)-tetrahydrofuran-3-ylmethyl]-4,5-dihydro-2H-furo[2,3-g]indazole-7-carboxamide | $^1$H-NMR (400 MHz, DMSO-d6) δ [ppm]: 1.584 (0.44), 1.598 (0.66), 1.617 (0.70), 1.632 (0.55), 1.900 (0.61), 1.914 (0.68), 1.920 (0.47), 1.931 (0.58), 1.945 (0.52), 2.324 (0.59), 2.329 (0.79), 2.334 (0.57), 2.475 (16.00), 2.520 (2.94), 2.525 (1.90), 2.545 (0.44), 2.667 (1.05), 2.671 (1.21), 2.676 (0.79), 2.681 (0.62), 2.686 (0.68), 2.704 (0.51), 2.756 (0.46), 2.833 (0.65), 2.851 (2.44), 2.864 (3.31), 2.872 (3.55), 2.885 (3.01), 2.903 (0.67), 3.164 (0.57), 3.184 (1.72), 3.198 (1.45), 3.208 (1.56), 3.213 (2.13), 3.218 (0.93), 3.236 (1.85), 3.249 (0.88), 3.268 (0.57), 3.423 (0.47), 3.444 (1.04), 3.450 (1.12), 3.467 (1.34), 3.471 (1.11), 3.477 (1.13), 3.481 (1.38), 3.489 (1.47), 3.503 (1.37), 3.514 (0.82), 3.519 (0.88), 3.542 (1.08), 3.548 (1.12), 3.569 (0.46), 3.575 (0.72), 3.596 (0.91), 3.616 (2.44), 3.625 (0.74), 3.634 (2.72), 3.640 (1.56), 3.645 (1.80), 3.653 (1.03), 3.663 (1.72), 3.667 (1.46), 3.684 (2.13), 3.692 (1.03), 3.714 (2.06), 3.721 (1.78), 3.733 (0.82), 3.747 (1.48), 3.753 (1.38), 3.767 (1.19), 3.773 (0.63), 3.787 (0.51), 4.028 (2.30), 4.031 (2.33), 4.047 (2.47), 7.538 (4.60), 8.042 (0.68), 8.057 (1.45), 8.072 (0.67). LC-MS (Method A); $R_t$ = 1.03 min, m/z = 402 $[M + H]^+$. | Intermediate 33; GP G (conditions A with HATU) |
| 113 | 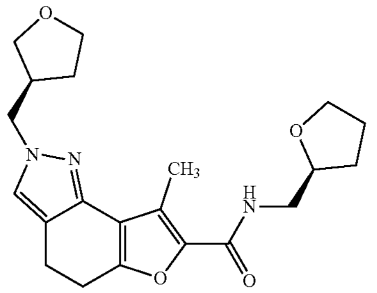 [SMILES: Cc1c(C(=O)NC[C@@H]2CCCO2)oc2c1-c1nn(C[C@@H]3CCOC3)cc1CC2] 8-methyl-N-[(2S)-tetrahydrofuran-2-ylmethyl]-2-[(3S)-tetrahydrofuran-3-ylmethyl]-4,5-dihydro-2H-furo[2,3-g]indazole-7-carboxamide | $^1$H-NMR (500 MHz, DMSO-d6) δ [ppm]: 1.556 (0.45), 1.572 (0.67), 1.578 (0.63), 1.591 (0.80), 1.595 (0.64), 1.600 (0.73), 1.609 (0.50), 1.616 (0.72), 1.628 (0.55), 1.781 (0.52), 1.786 (0.50), 1.798 (0.76), 1.800 (0.72), 1.812 (0.73), 1.816 (0.85), 1.833 (0.63), 1.842 (0.57), 1.845 (0.51), 1.849 (0.60), 1.855 (0.70), 1.864 (0.64), 1.872 (0.43), 1.878 (0.50), 1.881 (0.41), 1.889 (0.63), 1.900 (0.40), 1.905 (0.69), 1.916 (0.71), 1.921 (0.45), 1.924 (0.40), 1.929 (0.60), 1.940 (0.56), 2.370 (0.41), 2.474 (16.00), 2.516 (3.32), 2.520 (3.05), 2.523 (2.45), 2.671 (0.50), 2.686 (0.67), 2.700 (0.51), 2.837 (0.64), 2.849 (2.48), 2.861 (2.84), 2.871 (2.97), 2.883 (3.02), 2.897 (0.64), 3.218 (1.05), 3.224 (1.07), 3.230 (1.98), 3.236 (1.83), 3.242 (1.08), 3.248 (1.09), 3.471 (1.18), 3.482 (1.20), 3.488 (1.46), 3.499 (1.38), 3.591 (0.48), 3.604 (1.16), 3.606 (1.11), 3.618 (2.14), 3.634 (1.72), 3.649 (1.68), 3.664 (1.63), 3.667 (1.45), 3.681 (1.22), 3.738 (0.91), 3.749 (1.02), 3.754 (2.31), 3.766 (2.11), 3.770 (1.39), 3.782 (1.08), 3.933 (1.01), 3.947 (1.48), 3.959 (0.95), 4.029 (2.12), 4.032 (2.12), 4.044 (2.23), 4.047 (2.06), 7.537 (4.47), 7.962 (0.71), 7.974 (1.42), 7.986 (0.67). LC-MS (Method A); $R_t$ = 0.95 min, m/z = 386 $[M + H]^+$. | Intermediate 34; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 114 | 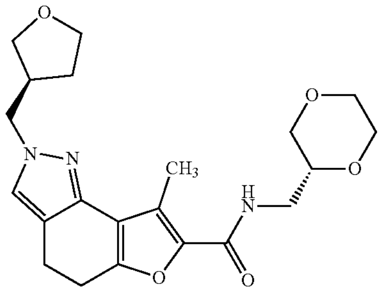 [SMILES: Cc1c(C(=O)NC[C@@H]2COCCO2)oc2c1-c1nn(C[C@@H]3CCOC3)cc1CC2] N-[(2R)-1,4-dioxan-2-ylmethyl]-8-methyl-2-[(3S)-tetrahydrofuran-3-ylmethyl]-4,5-dihydro-2H-furo[2,3-g]indazole-7-carboxamide | $^1$H-NMR (500 MHz, DMSO-d6) δ [ppm]: 1.589 (0.42), 1.601 (0.65), 1.616 (0.68), 1.628 (0.52), 1.904 (0.59), 1.916 (0.67), 1.920 (0.45), 1.929 (0.57), 1.940 (0.54), 2.474 (16.00), 2.516 (2.23), 2.520 (2.03), 2.523 (1.64), 2.671 (0.50), 2.686 (0.64), 2.701 (0.49), 2.757 (0.48), 2.787 (0.51), 2.838 (0.59), 2.850 (2.36), 2.862 (2.62), 2.873 (2.73), 2.884 (2.78), 2.896 (0.59), 3.169 (0.67), 3.184 (0.82), 3.189 (1.26), 3.196 (1.41), 3.209 (1.93), 3.212 (1.42), 3.223 (0.70), 3.232 (1.59), 3.236 (1.36), 3.248 (0.88), 3.263 (0.66), 3.423 (0.41), 3.428 (0.50), 3.445 (1.05), 3.451 (1.12), 3.468 (1.02), 3.471 (1.59), 3.481 (1.22), 3.488 (1.46), 3.498 (1.33), 3.519 (0.72), 3.524 (0.84), 3.542 (1.06), 3.547 (1.11), 3.563 (0.57), 3.568 (0.73), 3.602 (0.92), 3.618 (2.18), 3.625 (0.72), 3.632 (2.69), 3.649 (1.97), 3.663 (1.68), 3.666 (1.44), 3.680 (1.22), 3.689 (1.16), 3.694 (1.00), 3.717 (1.85), 3.738 (1.36), 3.749 (0.86), 3.754 (1.26), 3.765 (1.23), 3.770 (0.63), 3.781 (0.54), 4.029 (2.01), 4.033 (2.03), 4.044 (2.13), 4.048 (1.95), 7.537 (4.37), 8.041 (0.67), 8.053 (1.41), 8.065 (0.65). LC-MS (Method A); $R_t$ = 0.87 min, m/z = 402 $[M + H]^+$. | Intermediate 34; GP G (conditions A with HATU) |
| 115 | 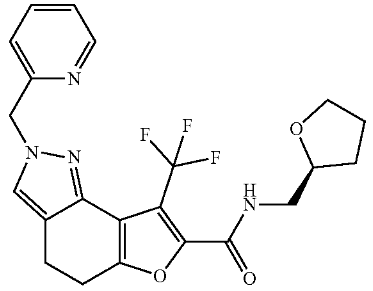 [SMILES: O=C(NC[C@@H]1CCCO1)c1oc2c(c1C(F)(F)F)-c1nn(Cc3ccccn3)cc1CC2] 2-(pyridin-2-ylmethyl)-N-[(2S)-tetrahydrofuran-2-ylmethyl]-8-(trifluoromethyl)-4,5-dihydro-2H-furo[2,3-g]indazole-7-carboxamide | $^1$H-NMR (400 MHz, DMSO-d6) δ [ppm]: 0.933 (3.11), 0.937 (0.93), 0.950 (3.17), 0.954 (0.48), 1.540 (1.10), 1.543 (1.05), 1.553 (0.88), 1.556 (0.98), 1.560 (1.57), 1.568 (1.46), 1.576 (1.20), 1.584 (0.96), 1.589 (1.38), 1.606 (0.88), 1.773 (0.73), 1.779 (0.54), 1.788 (1.31), 1.794 (1.67), 1.809 (3.02), 1.827 (2.97), 1.841 (1.47), 1.845 (1.94), 1.861 (1.65), 1.866 (0.90), 1.870 (1.12), 1.878 (1.26), 1.883 (1.12), 1.889 (1.49), 1.900 (0.96), 1.904 (1.11), 1.907 (1.12), 1.911 (1.03), 1.921 (0.84), 1.925 (0.72), 1.928 (0.77), 1.942 (0.50), 2.521 (1.53), 2.525 (0.99), 2.872 (1.16), 2.878 (1.27), 2.889 (1.90), 2.896 (5.95), 2.913 (5.18), 2.932 (0.60), 2.944 (5.64), 2.947 (5.37), 2.962 (7.25), 2.971 (2.05), 2.980 (1.63), 2.987 (1.48), 3.255 (4.67), 3.271 (9.18), 3.285 (4.82), 3.598 (1.06), 3.614 (2.18), 3.617 (2.45), 3.634 (2.94), 3.652 (1.73), 3.741 (1.44), 3.757 (2.61), 3.762 (1.75), 3.774 (2.52), 3.777 (2.23), 3.779 (1.92), 3.795 (1.51), 3.920 (0.70), 3.936 (2.17), 3.952 (3.64), 3.967 (2.29), 3.983 (0.53), 5.395 (16.00), 7.073 (4.20), 7.093 (4.39), 7.294 (2.04), 7.297 (2.10), 7.306 (2.14), 7.309 (2.29), 7.313 (2.45), 7.316 (2.17), 7.325 (2.35), 7.328 (2.21), 7.683 (10.56), 7.755 (2.55), 7.759 (2.67), 7.774 (4.44), 7.778 (4.46), 7.793 (2.25), 7.798 (2.19), 8.531 (2.64), 8.534 (3.06), 8.536 (3.05), 8.538 (2.75), 8.543 (2.71), 8.546 (3.14), 8.548 (2.90), 8.550 (2.60), 8.701 (1.55), 8.716 (3.28), 8.730 (1.54). LC-MS (Method A); $R_t$ = 1.03 min, m/z = 445 $[M - H]^-$. | Intermediate 35; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 116 | 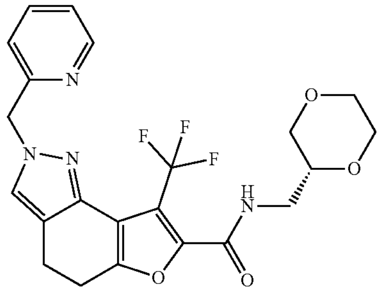 [SMILES: O=C(NC[C@@H]1COCCO1)c1oc2c(c1C(F)(F)F)-c1nn(Cc3ccccn3)cc1CC2] N-[(2R)-1,4-dioxan-2-ylmethyl]-2-(pyridin-2-ylmethyl)-8-(trifluoromethyl)-4,5-dihydro-2H-furo[2,3-g]indazole-7-carboxamide | $^1$H-NMR (400 MHz, DMSO-d6) δ [ppm]: 0.933 (1.04), 0.950 (1.03), 2.077 (2.72), 2.521 (1.33), 2.525 (0.86), 2.873 (1.27), 2.878 (1.36), 2.890 (2.09), 2.897 (5.95), 2.914 (5.08), 2.948 (5.43), 2.950 (5.29), 2.965 (7.34), 2.974 (2.20), 2.984 (1.65), 2.990 (1.54), 3.189 (0.74), 3.198 (2.95), 3.204 (1.47), 3.222 (4.51), 3.226 (4.28), 3.238 (3.86), 3.250 (5.98), 3.265 (3.52), 3.281 (2.24), 3.299 (1.28), 3.315 (0.83), 3.424 (0.97), 3.430 (1.17), 3.451 (2.54), 3.457 (2.74), 3.478 (2.27), 3.484 (2.11), 3.526 (1.94), 3.531 (2.15), 3.554 (2.65), 3.561 (2.72), 3.581 (1.09), 3.587 (1.89), 3.614 (3.08), 3.621 (3.08), 3.629 (2.03), 3.645 (3.40), 3.661 (0.62), 3.667 (0.76), 3.696 (2.91), 3.703 (2.40), 3.725 (4.83), 3.731 (3.83), 3.754 (2.05), 5.396 (16.00), 7.076 (4.28), 7.096 (4.49), 7.294 (2.13), 7.297 (2.19), 7.306 (2.23), 7.309 (2.33), 7.313 (2.44), 7.316 (2.29), 7.325 (2.40), 7.328 (2.30), 7.684 (10.66), 7.755 (2.73), 7.759 (2.71), 7.774 (4.31), 7.779 (4.51), 7.793 (2.37), 7.798 (2.39), 8.531 (2.76), 8.534 (3.11), 8.536 (3.19), 8.538 (2.82), 8.543 (2.80), 8.546 (3.18), 8.548 (2.99), 8.550 (2.65), 8.737 (1.65), 8.753 (3.49), 8.767 (1.63). LC-MS (Method A); $R_t$ = 0.95 min, m/z = 461 $[M - H]^-$. | Intermediate 35; GP G (conditions A with HATU) |
| 117 | 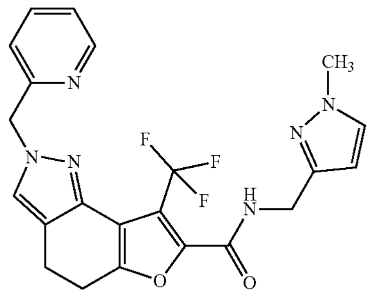 [SMILES: Cn1ccc(CNC(=O)c2oc3c(c2C(F)(F)F)-c2nn(Cc4ccccn4)cc2CC3)n1] N-[(1-methyl-1H-pyrazol-3-yl)methyl]-2-(pyridin-2-ylmethyl)-8-(trifluoromethyl)-4,5-dihydro-2H-furo[2,3-g]indazole-7-carboxamide | $^1$H-NMR (400 MHz, DMSO-d6) δ [ppm]: 0.933 (0.62), 0.950 (0.63), 2.520 (0.93), 2.525 (0.60), 2.873 (0.44), 2.882 (0.59), 2.891 (2.02), 2.908 (1.88), 2.932 (2.04), 2.934 (1.93), 2.949 (2.41), 2.959 (0.67), 2.967 (0.51), 2.975 (0.46), 3.783 (16.00), 4.346 (2.83), 4.361 (2.80), 5.393 (5.38), 6.116 (2.74), 6.122 (2.67), 7.071 (1.43), 7.091 (1.49), 7.292 (0.70), 7.296 (0.71), 7.305 (0.74), 7.308 (0.78), 7.311 (0.84), 7.314 (0.76), 7.323 (0.79), 7.326 (0.74), 7.584 (2.36), 7.590 (2.35), 7.681 (3.53), 7.753 (0.84), 7.757 (0.83), 7.772 (1.41), 7.777 (1.44), 7.791 (0.75), 7.796 (0.74), 8.530 (0.92), 8.532 (1.03), 8.534 (1.07), 8.536 (0.94), 8.542 (0.94), 8.544 (1.03), 8.546 (1.01), 8.548 (0.86), 9.067 (0.59), 9.082 (1.22), 9.097 (0.57). LC-MS (Method A); $R_t$ = 0.92 min, m/z = 457 $[M + H]^+$. | Intermediate 35; GP G (conditions A with HATU) |
| 118 | 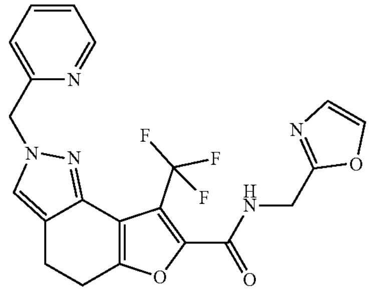 [SMILES: O=C(NCc1ncco1)c1oc2c(c1C(F)(F)F)-c1nn(Cc3ccccn3)cc1CC2] N-(1,3-oxazol-2-ylmethyl)-2-(pyridin-2-ylmethyl)-8-(trifluoromethyl)-4,5-dihydro-2H-furo[2,3-g]indazole-7-carboxamide | $^1$H-NMR (400 MHz, DMSO-d6) δ [ppm]: −0.009 (1.60), 0.008 (1.47), 2.334 (0.93), 2.520 (4.59), 2.525 (2.92), 2.676 (0.96), 2.882 (1.28), 2.887 (1.40), 2.899 (2.16), 2.905 (5.94), 2.923 (4.98), 2.959 (5.37), 2.962 (5.23), 2.977 (7.19), 2.985 (2.23), 2.996 (1.64), 3.001 (1.52), 4.538 (8.49), 4.552 (8.52), 5.399 (16.00), 5.761 (0.88), 7.082 (4.12), 7.102 (4.37), 7.170 (11.02), 7.172 (10.94), 7.295 (2.09), 7.297 (2.09), 7.307 (2.21), 7.309 (2.31), 7.314 (2.48), 7.316 (2.28), 7.326 (2.38), 7.328 (2.26), 7.693 (10.48), 7.757 (2.48), 7.761 (2.60), 7.776 (4.34), 7.780 (4.39), 7.795 (2.16), 7.800 (2.11), 8.069 (11.85), 8.071 (11.53), 8.531 (2.63), 8.534 (3.09), 8.536 (3.12), 8.538 (2.80), | Intermediate 35; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 8.543 (2.72), 8.546 (3.17), 8.548 (2.97), 8.550 (2.65), 9.348 (1.62), 9.363 (3.51), 9.378 (1.60). LC-MS (Method A); $R_t$ = 0.90 min, m/z = 444 $[M + H]^+$. | |
| 119 | 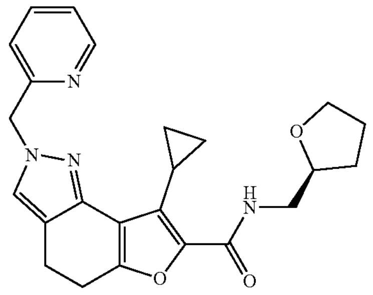 [SMILES: O=C(NC[C@@H]1CCCO1)c1oc2c(c1C1CC1)-c1nn(Cc3ccccn3)cc1CC2] 8-cyclopropyl-2-(pyridin-2-ylmethyl)-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: 0.742 (1.46), 0.751 (4.78), 0.757 (4.41), 0.765 (2.92), 0.773 (4.55), 0.779 (4.85), 0.788 (1.54), 0.919 (0.54), 0.933 (4.71), 0.937 (1.40), 0.950 (4.80), 0.954 (0.72), 1.354 (1.58), 1.362 (4.70), 1.368 (6.05), 1.376 (6.27), 1.382 (4.32), 1.391 (1.60), 1.559 (1.17), 1.569 (0.93), 1.572 (1.06), 1.576 (1.65), 1.583 (1.21), 1.592 (1.39), 1.599 (0.93), 1.604 (1.07), 1.621 (0.83), 1.766 (0.69), 1.772 (0.51), 1.780 (1.29), 1.786 (1.66), 1.802 (2.88), 1.819 (3.23), 1.837 (2.76), 1.851 (1.75), 1.857 (1.26), 1.859 (1.33), 1.864 (1.57), 1.868 (1.89), 1.883 (1.28), 1.885 (1.20), 1.890 (0.95), 1.900 (0.82), 1.906 (0.74), 1.921 (0.47), 2.406 (0.51), 2.424 (0.49), 2.521 (1.67), 2.526 (1.18), 2.785 (0.75), 2.796 (1.52), 2.811 (5.92), 2.826 (6.97), 2.838 (7.69), 2.852 (8.56), 2.870 (1.59), 2.880 (0.95), 2.897 (0.76), 2.911 (1.60), 2.920 (1.62), 2.926 (1.09), 2.934 (3.09), 2.942 (1.18), 2.947 (1.46), 2.956 (1.50), 2.970 (0.61), 3.232 (4.29), 3.248 (8.46), 3.263 (4.60), 3.589 (1.07), 3.605 (2.25), 3.609 (2.29), 3.626 (3.04), 3.643 (1.65), 3.740 (1.48), 3.754 (2.14), 3.757 (2.75), 3.771 (2.34), 3.775 (2.39), 3.792 (1.58), 3.923 (0.67), 3.939 (2.32), 3.955 (3.64), 3.971 (2.28), 3.986 (0.50), 5.351 (16.00), 7.035 (4.22), 7.054 (4.42), 7.291 (2.18), 7.294 (2.14), 7.303 (2.25), 7.306 (2.30), 7.310 (2.54), 7.313 (2.32), 7.322 (2.48), 7.325 (2.32), 7.621 (11.82), 7.757 (2.77), 7.761 (2.84), 7.776 (4.50), 7.780 (4.43), 7.795 (2.31), 7.800 (2.40), 7.947 (1.69), 7.961 (3.60), 7.976 (1.67), 8.531 (2.88), 8.533 (3.13), 8.535 (3.32), 8.538 (2.85), 8.543 (2.92), 8.545 (3.24), 8.547 (3.13), 8.550 (2.70). LC-MS (Method A); $R_t$ = 1.20 min, m/z = 419 $[M + H]^+$. | Intermediate 36; GP G (conditions A with HATU) |
| 120 | 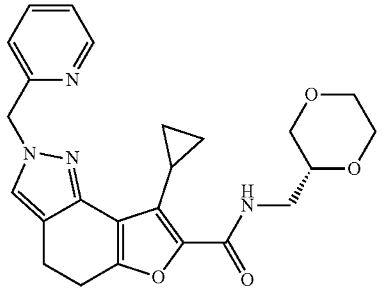 [SMILES: O=C(NC[C@@H]1COCCO1)c1oc2c(c1C1CC1)-c1nn(Cc3ccccn3)cc1CC2] 8-cyclopropyl-N-[(2R)-1,4-dioxan-2-ylmethyl]-2-(pyridin-2-ylmethyl)-4,5-dihydro-2H-furo[2,3-g]indazole-7-carboxamide | $^1$H-NMR (400 MHz, DMSO-d6) δ [ppm]: 0.745 (1.34), 0.754 (4.47), 0.760 (4.12), 0.768 (2.85), 0.776 (4.36), 0.782 (4.47), 0.791 (1.46), 0.919 (1.07), 0.933 (9.18), 0.937 (2.96), 0.950 (9.25), 0.954 (1.54), 1.356 (1.59), 1.364 (4.49), 1.370 (5.68), 1.378 (5.96), 1.385 (4.22), 1.393 (1.60), 2.406 (1.01), 2.424 (0.96), 2.521 (1.86), 2.525 (1.19), 2.785 (0.78), 2.797 (1.51), 2.813 (6.08), 2.827 (7.05), 2.839 (7.68), 2.854 (7.94), 2.871 (1.60), 2.882 (0.93), 2.894 (0.76), 2.908 (1.52), 2.916 (1.55), 2.922 (0.99), 2.930 (2.89), 2.938 (1.02), 2.943 (1.79), 2.952 (1.42), 2.959 (0.99), 2.966 (0.61), 2.975 (0.64), 3.166 (0.60), 3.181 (1.27), 3.191 (2.84), 3.200 (2.05), 3.215 (6.73), 3.219 (4.09), 3.229 (3.02), 3.243 (6.41), 3.258 (2.12), 3.277 (1.23), 3.292 (0.69), 3.420 (0.90), 3.426 (1.11), 3.446 (2.48), 3.453 (2.66), 3.474 (2.15), 3.480 (2.08), 3.519 (1.82), 3.524 (1.98), | Intermediate 36; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 3.547 (2.54), 3.553 (2.65), 3.568 (0.61), 3.574 (1.00), 3.580 (1.72), 3.611 (3.49), 3.626 (2.14), 3.635 (2.91), 3.642 (3.30), 3.650 (1.68), 3.658 (0.59), 3.665 (0.74), 3.691 (2.95), 3.698 (2.40), 3.720 (5.07), 3.747 (2.15), 5.352 (16.00), 7.034 (4.23), 7.054 (4.43), 7.292 (2.10), 7.294 (2.05), 7.304 (2.23), 7.306 (2.29), 7.311 (2.45), 7.323 (2.38), 7.622 (11.28), 7.757 (2.29), 7.762 (2.29), 7.776 (4.04), 7.781 (4.08), 7.795 (2.06), 7.800 (2.02), 8.031 (1.76), 8.047 (3.74), 8.061 (1.72), 8.533 (3.11), 8.535 (3.11), 8.543 (2.78), 8.545 (3.12), 8.547 (2.96). LC-MS (Method A); $R_t$ = 1.12 min, m/z = 435 $[M + H]^+$. | |
| 121 | 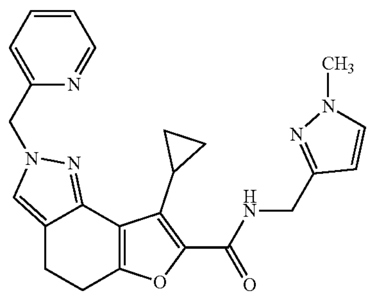 [SMILES: Cn1ccc(CNC(=O)c2oc3c(c2C2CC2)-c2nn(Cc4ccccn4)cc2CC3)n1] 8-cyclopropyl-N-[(1-methyl-1H-pyrazol-3-yl)methyl]-2-(pyridin-2-ylmethyl)-4,5-dihydro-2H-furo[2,3-g]indazole-7-carboxamide | $^1$H-NMR (400 MHz, DMSO-d6) δ [ppm]: 0.000 (6.25), 0.742 (0.51), 0.751 (1.57), 0.757 (1.47), 0.765 (1.00), 0.773 (1.51), 0.779 (1.59), 0.788 (0.52), 0.933 (0.41), 0.949 (0.42), 1.356 (0.56), 1.364 (1.57), 1.370 (2.01), 1.379 (2.06), 1.384 (1.47), 1.393 (0.54), 2.520 (0.75), 2.525 (0.49), 2.789 (0.56), 2.809 (2.16), 2.819 (3.21), 2.826 (3.43), 2.838 (2.94), 2.856 (0.47), 2.920 (0.51), 2.928 (0.53), 2.942 (1.02), 2.956 (0.50), 2.965 (0.48), 3.775 (16.00), 4.325 (2.72), 4.341 (2.75), 5.351 (5.32), 5.760 (5.02), 6.106 (2.67), 6.112 (2.81), 7.031 (1.44), 7.051 (1.51), 7.290 (0.71), 7.292 (0.73), 7.302 (0.76), 7.304 (0.81), 7.308 (0.83), 7.311 (0.78), 7.321 (0.80), 7.323 (0.79), 7.559 (2.39), 7.565 (2.41), 7.619 (3.92), 7.755 (0.80), 7.760 (0.85), 7.774 (1.44), 7.779 (1.47), 7.793 (0.75), 7.798 (0.73), 8.353 (0.61), 8.368 (1.33), 8.383 (0.60), 8.529 (0.93), 8.532 (1.06), 8.534 (1.12), 8.536 (0.95), 8.541 (0.96), 8.544 (1.08), 8.546 (1.06), 8.548 (0.89). LC-MS (Method A); $R_t$ = 0.98 min, m/z = 429 $[M + H]^+$. | Intermediate 36; GP G (conditions A with HATU) |
| 122 | 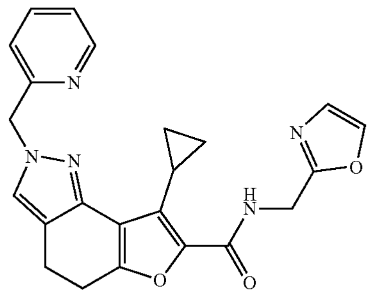 [SMILES: O=C(NCc1ncco1)c1oc2c(c1C1CC1)-c1nn(Cc3ccccn3)cc1CC2] 8-cyclopropyl-N-(1,3-oxazol-2-ylmethyl)-2-(pyridin-2-ylmethyl)-4,5-dihydro-2H-furo[2,3-g]indazole-7-carboxamide | $^1$H NMR (400 MHz, DMSO-d6) δ [ppm]: 0.75-0.79 (m, 2H), 1.37-1.40 (m, 2H), 2.79-2.95 (m, 5H), 4.50 (d, 2H), 5.35 (s, 2H), 7.05 (d, 1H), 7.14 (d, 1H), 7.31 (ddd, 1H), 7.63 (s, 1H), 7.78 (dt, 1H), 8.03 (d, 1H), 8.53-8.55 (m, 1H), 8.72 (t, 1H). LC-MS (Method A); $R_t$ = 0.97 min, m/z = 416 $[M + H]^+$. | Intermediate 36; GPG (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 123 | 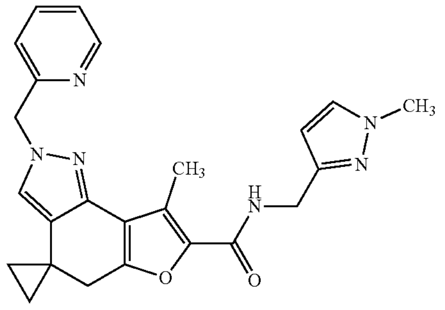 [SMILES: Cc1c(C(=O)NCc2ccn(C)n2)oc2c1-c1nn(Cc3ccccn3)cc1C1(CC1)C2] 8'-methyl-N-[(1-methyl-1H-pyrazol-3-yl)methyl]-2'-(pyridin-2-ylmethyl)-2',5'-dihydrospiro[cyclopropane-1,4'-furo[2,3-g]indazole]-7'-carboxamide | LC-MS (Method A); $R_t$ = 0.96 min, m/z = 429 $[M + H]^+$. | Intermediate 38; GP G (conditions A with HATU) |
| 124 | 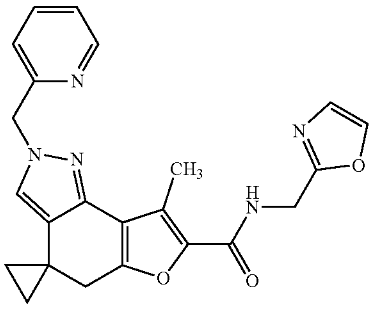 [SMILES: Cc1c(C(=O)NCc2ncco2)oc2c1-c1nn(Cc3ccccn3)cc1C1(CC1)C2] 8'-methyl-N-(1,3-oxazol-2-ylmethyl)-2'-(pyridin-2-ylmethyl)-2',5'-dihydrospiro[cyclopropane-1,4'-furo[2,3-g]indazole]-7'-carboxamide | $^1$H NMR (400 MHz, DMSO-d6) δ [ppm]: 0.80-0.92 (m, 2H), 1.03-1.14 (m, 2H), 2.47 (s, 3H), 2.72 (s, 2H), 4.56 (d, 2H), 5.45 (s, 2H), 7.11-7.20 (m, 2H), 7.29-7.34 (m, 1H), 7.62 (s, 1H), 7.75-7.82 (m, 1H), 8.04 (d, 1H), 8.53-8.55 (m, 1H), 8.72 (t, 1H). LC-MS (Method A); $R_t$ = 0.96 min, m/z = 416 $[M + H]^+$. | Intermediate 38; GPG (conditions A with HATU) |
| 125 | 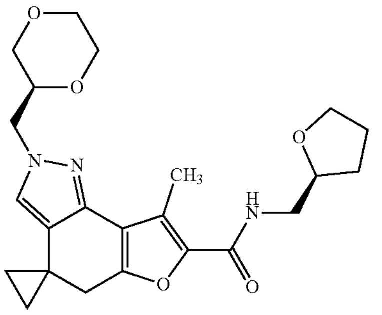 [SMILES: Cc1c(C(=O)NC[C@@H]2CCCO2)oc2c1-c1nn(C[C@H]3COCCO3)cc1C1(CC1)C2] 2'-[(2S)-1,4-dioxan-2-ylmethyl]-8'-methyl-N-[(2S)-tetrahydrofuran-2-ylmethyl]-2',5'-dihydrospiro[cyclopropane-1,4'-furo[2,3-g]indazole]-7'-carboxamide | $^1$H-NMR (400 MHz, DMSO-d6) δ [ppm]: 0.787 (4.84), 0.806 (7.12), 0.826 (2.28), 0.852 (2.57), 0.871 (10.06), 0.919 (1.91), 0.934 (13.80), 0.951 (13.28), 1.331 (0.88), 1.532 (0.59), 1.552 (1.61), 1.569 (2.20), 1.577 (1.76), 1.585 (1.98), 1.598 (1.69), 1.613 (1.25), 1.783 (2.50), 1.799 (4.40), 1.817 (4.92), 1.834 (4.33), 1.847 (2.79), 1.864 (2.64), 1.879 (2.13), 1.896 (1.47), 1.917 (0.88), 1.960 (1.61), 2.024 (1.10), 2.329 (4.48), 2.357 (4.77), 2.389 (0.73), 2.407 (1.83), 2.424 (1.83), 2.449 (1.61), 2.667 (4.92), 2.671 (4.92), 2.764 (1.25), 2.788 (2.64), 2.832 (11.52), 2.844 (11.60), 2.887 (2.13), 2.927 (0.66), 2.943 (1.17), 2.960 (1.47), 2.976 (1.17), 2.992 (0.88), 3.031 (1.03), 3.076 (0.81), 3.220 (7.56), 3.236 (9.54), 3.249 (7.85), 3.273 (4.11), 3.412 (1.54), 3.433 (3.60), 3.439 (3.60), 3.461 (3.16), 3.466 (2.94), 3.506 (2.57), 3.512 (2.57), 3.535 (3.60), 3.540 (3.60), 3.568 (2.06), 3.585 (1.54), 3.604 (3.96), 3.619 (6.97), 3.639 (5.14), 3.711 (7.93), 3.735 (7.71), 3.750 (4.33), 3.769 (3.52), 3.786 (1.98), 3.818 (2.28), 3.823 (2.28), 3.836 (2.57), 3.913 (1.17), 3.930 (3.08), 3.946 (4.40), 3.961 (2.79), 3.977 (0.88), 3.988 (1.76), 4.005 (1.39), 4.023 (5.28), 4.042 (7.71), 4.056 (4.84), 4.080 (1.54), 4.092 (1.17), | Intermediate 40-1; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 7.180 (0.73), 7.272 (3.01), 7.279 (16.00), 7.953 (2.28), 7.969 (4.48), 7.983 (2.13), 8.553 (0.81). LC-MS (Method A); $R_t$ = 1.05 min, m/z = 428 $[M + H]^+$. | |
| 126 | 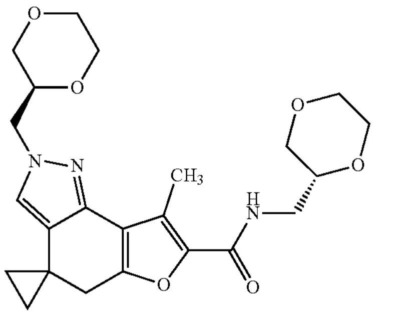 [SMILES: Cc1c(C(=O)NC[C@@H]2COCCO2)oc2c1-c1nn(C[C@H]3COCCO3)cc1C1(CC1)C2] N-[(2R)-1,4-dioxan-2-ylmethyl]-2'-[(2S)-1,4-dioxan-2-ylmethyl]-8'-methyl-2',5'-dihydrospiro[cyclopropane-1,4'-furo[2,3-g]indazole-7'-carboxamide | $^1$H-NMR (400 MHz, DMSO-d6) δ [ppm]: −0.149 (0.44), 0.146 (0.45), 0.767 (0.69), 0.775 (0.52), 0.788 (2.74), 0.797 (2.52), 0.802 (2.88), 0.808 (4.49), 0.827 (1.32), 0.853 (1.40), 0.862 (1.48), 0.873 (6.54), 0.935 (1.70), 0.938 (0.58), 0.951 (1.72), 1.960 (1.28), 2.320 (0.84), 2.325 (1.96), 2.329 (2.76), 2.334 (1.99), 2.339 (0.88), 2.521 (10.84), 2.525 (6.87), 2.542 (1.04), 2.662 (1.04), 2.667 (3.37), 2.671 (2.93), 2.676 (2.08), 2.681 (0.93), 2.764 (1.01), 2.790 (1.21), 2.833 (7.63), 2.845 (7.47), 2.889 (1.10), 3.154 (0.60), 3.170 (1.21), 3.184 (3.46), 3.203 (3.42), 3.208 (3.76), 3.213 (3.92), 3.219 (5.43), 3.237 (4.54), 3.244 (3.61), 3.249 (4.64), 3.273 (3.37), 3.284 (1.20), 3.381 (0.45), 3.406 (0.90), 3.412 (1.13), 3.416 (1.07), 3.423 (1.24), 3.433 (2.27), 3.439 (2.71), 3.443 (2.80), 3.449 (2.70), 3.460 (2.19), 3.467 (2.28), 3.470 (2.69), 3.477 (2.10), 3.507 (1.73), 3.512 (3.28), 3.519 (2.27), 3.534 (2.41), 3.541 (4.61), 3.548 (2.84), 3.562 (1.17), 3.568 (2.37), 3.574 (1.81), 3.595 (1.00), 3.610 (5.15), 3.615 (4.89), 3.625 (1.85), 3.640 (4.53), 3.655 (0.98), 3.688 (2.73), 3.695 (2.62), 3.712 (6.99), 3.741 (5.19), 3.800 (0.58), 3.806 (0.58), 3.813 (0.87), 3.818 (1.23), 3.824 (1.28), 3.830 (1.13), 3.837 (1.55), 3.842 (1.17), 3.854 (0.77), 3.860 (0.66), 3.988 (1.15), 4.006 (0.72), 4.025 (3.57), 4.044 (4.58), 4.057 (3.28), 4.080 (1.10), 4.092 (0.84), 7.181 (1.00), 7.281 (16.00), 8.032 (1.52), 8.047 (3.27), 8.062 (1.47). LC-MS (Method A); $R_t$ = 1.07 min, m/z = 444 $[M + H]^+$. | Intermediate 40-1; GP G (conditions A with HATU) |
| 127 | 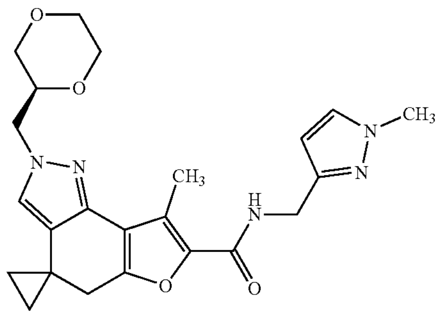 [SMILES: Cc1c(C(=O)NCc2ccn(C)n2)oc2c1-c1nn(C[C@H]3COCCO3)cc1C1(CC1)C2] 2'-[(2S)-1,4-dioxan-2-ylmethyl]-8'-methyl-N-[(1-methyl-1H-pyrazol-3-yl)methyl]-2',5'-dihydrospiro[cyclopropane-1,4'-furo[2,3-g]indazole]-7'-carboxamide | $^1$H NMR (400 MHz, DMSO-d6) δ [ppm]: 0.76-0.89 (m, 4H), 2.82-2.83 (m, 2H), 3.24 (dd, 1H), 3.43 (dt, 1H), 3.54 (dt, 1H), 3.61-3.64 (m, 1H), 3.70-3.74 (m, 2H), 3.77 (s, 3H), 3.82-3.86 (m, 1H), 3.99-4.09 (m, 2H), 4.32 (d, 2H), 6.10 (d, 1H), 7.27 (s, 1H), 7.56 (d, 1H), 8.37 (t, 1H). LC-MS (Method A); $R_t$ = 0.93 min, m/z = 438 $[M + H]^+$. | Intermediate 40-1; GP G (conditions A with HATU) |

TABLE 2-continued

The following examples (4 to 147) were prepared in analogy to example 3 starting from the given intermediates and commercially available amines (or their salts), applying the indicated general procedure.

| Ex-ample | Structure IUPAC-Name | Analytical Data | Preparation or Separation Methods |
|---|---|---|---|
| 128 | 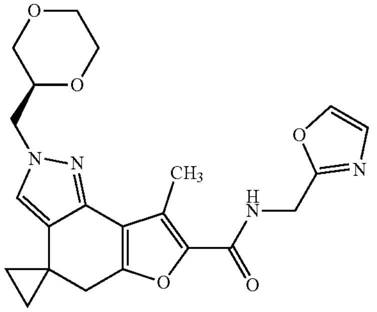 [SMILES: Cc1c(C(=O)NCc2ncco2)oc2c1-c1nn(C[C@H]3COCCO3)cc1C1(CC1)C2] 2'-[(2S)-1,4-dioxan-2-ylmethyl]-8'-methyl-N-(1,3-oxazol-2-ylmethyl)-2',5'-dihydrospiro[cyclopropane-1,4'-furo[2,3-g]indazole]-7'-carboxamide | $^{1}$H-NMR (400 MHz, DMSO-d6) δ [ppm]: −0.008 (3.17), 0.008 (3.27), 0.772 (0.78), 0.779 (0.61), 0.793 (2.96), 0.803 (2.76), 0.807 (3.10), 0.813 (4.60), 0.835 (1.23), 0.861 (1.23), 0.873 (1.60), 0.884 (6.94), 0.889 (4.83), 0.902 (0.89), 0.936 (2.04), 0.952 (2.01), 1.302 (1.53), 1.320 (3.57), 1.335 (1.06), 1.339 (1.63), 1.354 (0.44), 1.753 (0.51), 2.329 (1.91), 2.334 (1.43), 2.338 (0.75), 2.520 (6.77), 2.525 (4.36), 2.671 (2.01), 2.676 (1.60), 2.754 (0.78), 2.766 (6.23), 2.794 (1.46), 2.801 (1.29), 2.844 (7.66), 2.857 (7.52), 2.887 (1.43), 2.901 (1.36), 2.911 (0.44), 2.931 (0.99), 2.948 (0.99), 3.222 (2.38), 3.246 (2.89), 3.250 (2.86), 3.275 (2.89), 3.369 (0.71), 3.397 (0.61), 3.407 (0.85), 3.413 (0.99), 3.434 (2.21), 3.440 (2.45), 3.462 (1.97), 3.468 (2.14), 3.508 (1.67), 3.514 (1.84), 3.524 (0.61), 3.536 (2.31), 3.543 (2.31), 3.564 (1.06), 3.569 (1.40), 3.615 (2.49), 3.642 (1.97), 3.662 (0.48), 3.709 (4.63), 3.715 (4.29), 3.738 (4.02), 3.744 (3.40), 3.803 (0.61), 3.811 (0.65), 3.816 (0.95), 3.822 (1.33), 3.828 (1.50), 3.833 (1.53), 3.840 (1.84), 3.846 (1.23), 3.857 (0.99), 3.992 (1.23), 4.009 (0.82), 4.028 (3.68), 4.045 (4.05), 4.049 (4.29), 4.062 (3.44), 4.085 (1.29), 4.097 (0.99), 4.476 (0.92), 4.487 (8.07), 4.503 (8.10), 4.517 (0.78), 4.557 (1.63), 4.572 (1.63), 5.761 (0.51), 7.090 (1.67), 7.144 (10.72), 7.146 (10.55), 7.162 (2.28), 7.164 (2.25), 7.289 (16.00), 8.036 (10.49), 8.038 (10.76), 8.055 (2.35), 8.057 (2.35), 8.560 (2.31), 8.710 (1.70), 8.724 (3.68), 8.739 (1.60), 9.003 (0.61). LC-MS (Method A); $R_t$ = 0.91 min, m/z = 425 $[M + H]^+$. | Intermediate 40-1; GP G (conditions A with HATU) |
| 129 | 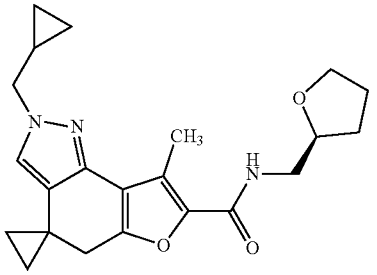 [SMILES: Cc1c(C(=O)NC[C@@H]2CCCO2)oc2c1-c1nn(CC3CC3)cc1C1(CC1)C2] 2'-(cyclopropylmethyl)-8'-methyl-N-[(2S)-tetrahydrofuran-2-ylmethyl]-2',5'-dihydrospiro[cyclopropane-1,4'-furo[2,3-g]indazole]-7'-carboxamide | $^{1}$H-NMR (400 MHz, DMSO-d6) δ [ppm]: 0.311 (1.22), 0.322 (4.85), 0.326 (4.06), 0.334 (4.44), 0.337 (4.62), 0.348 (1.74), 0.466 (0.60), 0.470 (0.46), 0.483 (2.15), 0.493 (4.10), 0.497 (4.21), 0.503 (2.19), 0.509 (2.08), 0.513 (4.36), 0.518 (4.02), 0.528 (1.39), 0.590 (0.43), 0.791 (1.87), 0.804 (4.62), 0.809 (5.94), 0.817 (3.40), 0.826 (1.17), 0.852 (1.23), 0.860 (3.05), 0.868 (5.91), 0.873 (4.21), 0.886 (1.77), 0.931 (0.63), 0.948 (0.64), 1.149 (0.46), 1.161 (0.83), 1.167 (0.91), 1.179 (1.23), 1.187 (1.13), 1.191 (0.90), 1.199 (1.82), 1.207 (0.89), 1.211 (1.05), 1.219 (1.13), 1.231 (0.97), 1.237 (0.64), 1.304 (0.93), 1.323 (2.17), 1.342 (0.92), 1.551 (0.98), 1.560 (0.76), 1.563 (0.87), 1.567 (1.36), 1.575 (1.00), 1.584 (1.15), 1.591 (0.86), 1.596 (0.88), 1.613 (0.76), 1.761 (0.60), 1.767 (0.46), 1.775 (1.08), 1.782 (1.39), 1.797 (2.44), 1.815 (2.77), 1.832 (2.48), 1.846 (1.45), 1.854 (1.26), 1.858 (1.35), 1.863 (1.58), 1.877 (1.16), 1.884 (0.88), 1.895 (0.78), 1.898 (0.68), 1.901 (0.68), 1.915 (0.46), 2.518 (3.56), 2.523 (2.41), 2.763 (3.55), 2.835 (15.26), 2.933 (0.49), 2.950 (0.48), 3.219 (3.05), 3.234 (6.16), 3.249 (3.31), 3.301 (0.72), 3.582 (0.86), 3.598 (1.86), 3.601 (1.85), 3.618 | Intermediate 41; GP G (conditions A with HATU) |

TABLE 2-continued

| The following examples (4 to 147) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| | | (2.48), 3.637 (1.39), 3.732 (1.21), 3.746 (1.79), 3.750 (2.24), 3.764 (1.95), 3.767 (1.94), 3.785 (1.29), 3.861 (7.98), 3.879 (7.87), 3.911 (0.59), 3.927 (1.92), 3.943 (2.97), 3.959 (1.85), 3.974 (0.47), 4.294 (0.77), 4.312 (0.76), 7.083 (0.96), 7.344 (16.00), 7.940 (1.36), 7.955 (2.84), 7.970 (1.31), 8.594 (1.39). LC-MS (Method A); $R_t$ = 1.19 min, m/z = 382 $[M + H]^+$. | |
| 130 | 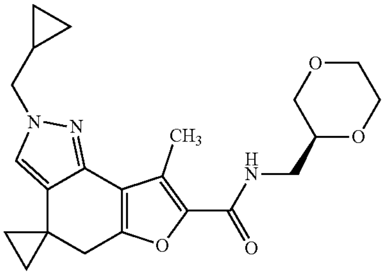 [SMILES: Cc1c(C(=O)NC[C@H]2COCCO2)oc2c1-c1nn(CC3CC3)cc1C1(CC1)C2] 2'-(cyclopropylmethyl)-N-[(2S)-1,4-dioxan-2-ylmethyl]-8'-methyl-2',5'-dihydrospiro[cyclopropane-1,4'-furo[2,3-g]indazole]-7'-carboxamide | $^1$H-NMR (400 MHz, DMSO-d6) δ [ppm]: 0.311 (1.27), 0.322 (4.94), 0.326 (4.05), 0.334 (4.49), 0.338 (4.45), 0.348 (1.71), 0.467 (0.58), 0.483 (2.14), 0.494 (4.10), 0.498 (4.18), 0.503 (2.17), 0.509 (2.05), 0.514 (4.24), 0.518 (3.90), 0.529 (1.41), 0.792 (1.89), 0.805 (4.69), 0.810 (5.82), 0.818 (3.36), 0.827 (1.05), 0.852 (1.19), 0.862 (3.02), 0.870 (5.83), 0.874 (4.09), 0.888 (1.71), 1.162 (0.58), 1.168 (0.74), 1.173 (0.84), 1.180 (1.15), 1.187 (1.09), 1.190 (0.97), 1.199 (1.80), 1.208 (0.82), 1.211 (1.01), 1.219 (1.06), 1.231 (0.84), 1.305 (0.81), 1.323 (1.94), 1.342 (0.85), 1.903 (0.69), 1.988 (0.71), 2.075 (4.47), 2.332 (1.06), 2.518 (4.50), 2.523 (3.36), 2.678 (0.44), 2.763 (3.27), 2.836 (14.91), 2.935 (0.45), 2.952 (0.44), 3.154 (0.51), 3.168 (1.05), 3.183 (3.10), 3.187 (1.82), 3.202 (3.22), 3.207 (3.47), 3.212 (3.39), 3.230 (2.96), 3.236 (3.38), 3.246 (2.02), 3.264 (1.10), 3.275 (0.46), 3.280 (0.64), 3.415 (0.76), 3.421 (0.97), 3.442 (2.13), 3.448 (2.28), 3.469 (2.04), 3.475 (1.80), 3.511 (1.66), 3.516 (1.83), 3.539 (2.25), 3.546 (2.21), 3.566 (0.98), 3.572 (1.50), 3.592 (0.75), 3.607 (3.25), 3.623 (1.39), 3.632 (2.69), 3.637 (2.51), 3.647 (0.71), 3.653 (0.74), 3.687 (2.45), 3.693 (2.04), 3.715 (3.96), 3.741 (1.85), 3.861 (7.90), 3.879 (7.81), 4.295 (0.70), 4.312 (0.70), 7.079 (0.81), 7.346 (16.00), 8.021 (1.36), 8.036 (2.92), 8.051 (1.36), 8.597 (1.30). LC-MS (Method A); $R_t$ = 1.11 min, m/z = 398 $[M + H]^+$. | Intermediate 41; GP G (conditions A with HATU) |
| 131 | 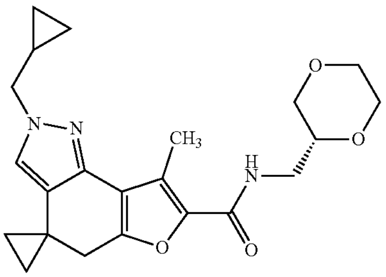 [SMILES: Cc1c(C(=O)NC[C@@H]2COCCO2)oc2c1-c1nn(CC3CC3)cc1C1(CC1)C2] 2'-(cyclopropylmethyl)-N-[(2R)-1,4-dioxan-2-ylmethyl]-8'-methyl-2',5'-dihydrospiro[cyclopropane-1,4'-furo[2,3-g]indazole]-7'-carboxamide | $^1$H-NMR (400 MHz, DMSO-d6) δ [ppm]: 0.311 (1.20), 0.322 (4.83), 0.325 (4.02), 0.334 (4.42), 0.337 (4.60), 0.347 (1.71), 0.483 (1.77), 0.493 (3.93), 0.497 (4.25), 0.502 (2.14), 0.509 (2.01), 0.513 (4.30), 0.518 (4.02), 0.528 (1.38), 0.791 (1.80), 0.804 (4.58), 0.809 (5.93), 0.817 (3.43), 0.827 (1.05), 0.852 (1.08), 0.861 (2.95), 0.869 (5.80), 0.874 (4.22), 0.887 (1.74), 0.931 (1.09), 0.948 (1.08), 1.167 (0.54), 1.179 (1.03), 1.187 (1.00), 1.199 (1.73), 1.207 (0.76), 1.211 (0.94), 1.218 (0.99), 1.230 (0.57), 1.236 (0.44), 2.074 (0.50), 2.332 (1.56), 2.336 (0.73), 2.518 (7.23), 2.522 (4.63), 2.673 (1.55), 2.678 (0.67), 2.836 (15.20), 3.153 (0.53), 3.167 (1.09), 3.182 (3.12), 3.186 (1.90), 3.202 (3.21), 3.206 (3.48), 3.211 (3.46), 3.214 (2.67), 3.230 (2.99), 3.235 (3.44), 3.245 (1.83), 3.264 (1.14), 3.279 (0.74), 3.292 (0.46), 3.415 (0.81), 3.420 (0.98), 3.441 | Intermediate 41; GP G (conditions A with HATU) |

TABLE 2-continued

| The following examples (4 to 147) were prepared in analogy to example 3 starting from the given intermediates and commercially available amines (or their salts), applying the indicated general procedure. | | | |
|---|---|---|---|
| Ex-ample | Structure IUPAC-Name | Analytical Data | Preparation or Separation Methods |
| | | (2.04), 3.447 (2.28), 3.468 (1.88), 3.475 (1.79), 3.510 (1.64), 3.516 (1.82), 3.539 (2.17), 3.545 (2.23), 3.565 (0.88), 3.572 (1.44), 3.592 (0.67), 3.607 (3.26), 3.622 (1.20), 3.631 (2.64), 3.637 (2.56), 3.646 (0.51), 3.653 (0.60), 3.686 (2.36), 3.693 (2.00), 3.715 (3.97), 3.740 (1.70), 3.861 (7.98), 3.879 (7.89), 7.345 (16.00), 8.021 (1.40), 8.036 (2.94), 8.052 (1.32). LC-MS (Method A); $R_t$ = 1.11 min, m/z = 398 $[M + H]^+$. | |
| 132 | 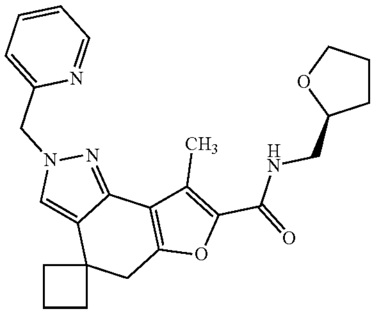 [SMILES: Cc1c(C(=O)NC[C@@H]2CCCO2)oc2c1-c1nn(Cc3ccccn3)cc1C1(CCC1)C2] 8'-methyl-2'-(pyridin-2-ylmethyl)-N-[(2S)-tetrahydrofuran-2-ylmethyl]-2',5'-dihydrospiro[cyclopropane-1,4'-furo[2,3-g]indazole]-7'-carboxamide | $^1$H-NMR (400 MHz, DMSO-d6) δ [ppm]: 1.552 (0.51), 1.569 (0.70), 1.576 (0.53), 1.585 (0.59), 1.597 (0.48), 1.779 (0.56), 1.785 (0.73), 1.800 (1.27), 1.818 (1.40), 1.836 (1.14), 1.851 (0.81), 1.859 (0.60), 1.863 (0.66), 1.868 (0.81), 1.883 (0.56), 1.890 (0.43), 1.948 (0.41), 1.954 (0.47), 1.967 (0.60), 1.977 (0.50), 1.990 (0.59), 2.013 (0.82), 2.032 (0.67), 2.051 (0.43), 2.075 (0.66), 2.089 (0.52), 2.103 (2.79), 2.118 (2.66), 2.125 (2.11), 2.143 (0.75), 2.434 (16.00), 2.520 (1.60), 2.525 (1.11), 3.037 (7.64), 3.219 (1.83), 3.234 (3.56), 3.249 (1.92), 3.586 (0.45), 3.602 (0.98), 3.605 (1.00), 3.623 (1.30), 3.641 (0.71), 3.737 (0.65), 3.751 (0.92), 3.754 (1.20), 3.769 (1.03), 3.772 (1.03), 3.790 (0.67), 3.931 (1.01), 3.947 (1.55), 3.963 (0.96), 5.405 (6.33), 7.054 (1.84), 7.073 (1.92), 7.297 (0.90), 7.299 (0.95), 7.309 (0.96), 7.311 (1.04), 7.315 (1.07), 7.318 (1.00), 7.328 (1.03), 7.330 (1.02), 7.760 (1.13), 7.765 (1.20), 7.779 (1.94), 7.784 (1.95), 7.798 (0.99), 7.803 (0.99), 7.923 (7.80), 7.960 (0.73), 7.975 (1.55), 7.990 (0.72), 8.541 (1.25), 8.543 (1.40), 8.545 (1.46), 8.548 (1.28), 8.553 (1.30), 8.555 (1.48), 8.557 (1.37), 8.560 (1.20). LC-MS (Method A); $R_t$ = 1.14 min, m/z = 433 $[M + H]^+$. | Intermediate 42; GP G (conditions A with HATU) |
| 133 | 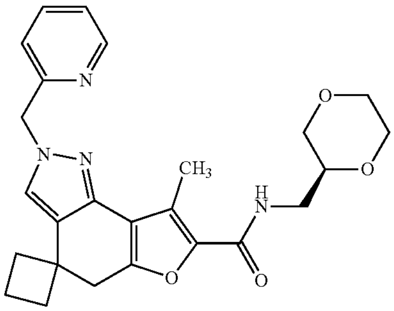 [SMILES: Cc1c(C(=O)NC[C@H]2COCCO2)oc2c1-c1nn(Cc3ccccn3)cc1C1(CCC1)C2] N-[(2S)-1,4-dioxan-2-ylmethyl]-8'-methyl-2'-(pyridin-2-ylmethyl)-2',5'-dihydrospiro[cyclobutane-1,4'-furo[2,3-g]indazole-7'-carboxamide | $^1$H-NMR (400 MHz, DMSO-d6) δ [ppm]: 0.919 (0.41), 0.933 (3.38), 0.937 (1.08), 0.950 (3.45), 0.954 (0.54), 1.955 (0.42), 1.969 (0.58), 1.978 (0.49), 1.992 (0.63), 2.014 (0.80), 2.034 (0.56), 2.051 (0.43), 2.075 (0.61), 2.104 (3.09), 2.119 (2.64), 2.144 (0.84), 2.407 (0.41), 2.424 (0.80), 2.434 (16.00), 2.520 (2.37), 2.525 (1.61), 3.037 (7.40), 3.169 (0.53), 3.185 (1.61), 3.203 (1.56), 3.210 (1.77), 3.214 (2.22), 3.229 (1.40), 3.239 (1.61), 3.245 (0.95), 3.264 (0.49), 3.419 (0.40), 3.425 (0.50), 3.446 (1.04), 3.452 (1.15), 3.473 (0.96), 3.479 (0.90), 3.514 (0.81), 3.520 (0.91), 3.543 (1.12), 3.549 (1.14), 3.569 (0.44), 3.576 (0.75), 3.597 (0.40), 3.612 (1.51), 3.619 (0.96), 3.628 (0.67), 3.636 (1.44), 3.642 (1.14), 3.691 (1.19), 3.697 (1.02), 3.719 (2.04), 3.745 (0.88), 5.406 (6.12), 7.054 (1.81), 7.073 (1.88), 7.297 (0.89), 7.300 (0.92), 7.309 (0.91), 7.312 (1.01), 7.316 (1.08), 7.318 (0.96), 7.328 (1.03), 7.331 (0.96), 7.760 (1.16), 7.765 (1.17), 7.779 (1.85), 7.784 (1.87), 7.799 (1.00), 7.803 (1.02), 7.925 (7.76), 8.040 (0.71), 8.055 (1.54), 8.070 (0.70), 8.541 (1.16), 8.543 (1.37), 8.545 (1.36), 8.548 | Intermediate 42; GP G (conditions A with HATU) |

TABLE 2-continued

| The following examples (4 to 147) were prepared in analogy to example 3 starting from the given intermediates and commercially available amines (or their salts), applying the indicated general procedure. | | | |
|---|---|---|---|
| Ex-ample | Structure IUPAC-Name | Analytical Data | Preparation or Separation Methods |
| | | (1.26), 8.553 (1.23), 8.555 (1.43), 8.557 (1.28), 8.560 (1.19). LC-MS (Method A); $R_t$ = 1.06 min, m/z = 449 $[M + H]^+$. | |
| 134 | 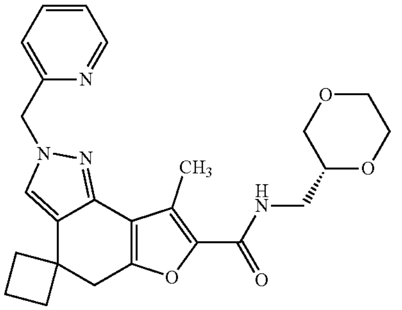 [SMILES: Cc1c(C(=O)NC[C@@H]2COCCO2)oc2c1-c1nn(Cc3ccccn3)cc1C1(CCC1)C2] N-[(2R)-1,4-dioxan-2-ylmethyl]-8'-methyl-2'-(pyridin-2-ylmethyl)-2',5'-dihydrospiro[cyclobutane-1,4'-furo[2,3-g]indazole-7'-carboxamide | $^1$H-NMR (400 MHz, DMSO-d6) δ [ppm]: 0.929 (1.25), 0.946 (1.29), 1.945 (0.40), 1.951 (0.44), 1.964 (0.61), 1.974 (0.51), 1.987 (0.65), 2.009 (0.82), 2.029 (0.60), 2.047 (0.46), 2.071 (0.66), 2.099 (3.19), 2.114 (2.75), 2.139 (0.89), 2.331 (0.43), 2.430 (16.00), 2.518 (2.15), 2.522 (1.33), 2.673 (0.41), 3.033 (7.60), 3.166 (0.56), 3.182 (1.65), 3.200 (1.60), 3.206 (1.82), 3.210 (2.28), 3.226 (1.48), 3.235 (1.62), 3.242 (1.02), 3.261 (0.55), 3.321 (0.53), 3.397 (0.90), 3.414 (0.76), 3.421 (0.77), 3.442 (1.10), 3.448 (1.35), 3.469 (1.06), 3.475 (1.01), 3.510 (0.88), 3.516 (0.97), 3.538 (1.17), 3.545 (1.19), 3.565 (0.47), 3.571 (0.79), 3.593 (0.43), 3.608 (1.60), 3.615 (1.01), 3.632 (1.51), 3.687 (1.23), 3.693 (1.05), 3.715 (2.16), 3.741 (0.94), 5.401 (6.37), 7.051 (1.81), 7.071 (1.91), 7.294 (0.88), 7.297 (0.92), 7.306 (0.94), 7.309 (1.03), 7.313 (1.11), 7.315 (1.00), 7.325 (1.06), 7.327 (0.99), 7.757 (1.09), 7.762 (1.10), 7.776 (1.87), 7.781 (1.92), 7.795 (1.00), 7.800 (0.99), 7.919 (8.03), 8.044 (0.73), 8.059 (1.60), 8.074 (0.75), 8.536 (1.21), 8.539 (1.32), 8.541 (1.44), 8.543 (1.22), 8.548 (1.25), 8.551 (1.39), 8.553 (1.38), 8.555 (1.16). LC-MS (Method A); $R_t$ = 1.04 min, m/z = 449 $[M + H]^+$. | Intermediate 42; GP G (conditions A with HATU) |
| 135 | 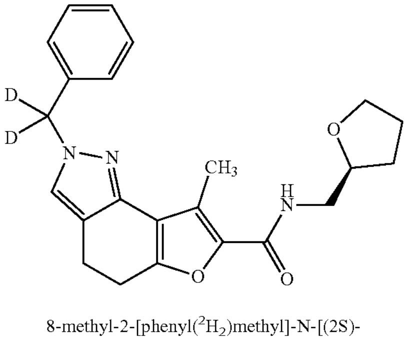 8-methyl-2-[phenyl($^2H_2$)methyl]-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: −0.008 (1.48), 0.008 (1.41), 1.551 (0.47), 1.567 (0.67), 1.575 (0.51), 1.583 (0.56), 1.591 (0.39), 1.596 (0.41), 1.774 (0.51), 1.780 (0.66), 1.795 (1.14), 1.814 (1.31), 1.831 (1.24), 1.842 (0.69), 1.852 (0.54), 1.859 (0.79), 1.874 (0.52), 2.461 (16.00), 2.520 (3.60), 2.524 (2.32), 2.857 (2.40), 2.859 (2.49), 2.868 (4.57), 2.873 (4.85), 2.883 (3.13), 3.212 (1.05), 3.217 (1.05), 3.227 (2.00), 3.232 (1.91), 3.243 (1.09), 3.248 (1.12), 3.583 (0.41), 3.598 (0.90), 3.602 (0.88), 3.619 (1.22), 3.637 (0.66), 3.733 (0.62), 3.750 (1.11), 3.765 (0.90), 3.768 (0.94), 3.785 (0.64), 3.927 (0.96), 3.943 (1.44), 3.959 (0.90), 7.243 (1.99), 7.246 (2.72), 7.250 (1.37), 7.257 (0.90), 7.263 (5.04), 7.267 (3.88), 7.275 (0.56), 7.282 (2.04), 7.288 (0.51), 7.296 (1.37), 7.300 (1.69), 7.304 (0.73), 7.325 (0.69), 7.328 (2.38), 7.330 (3.41), 7.334 (1.35), 7.345 (2.14), 7.349 (3.63), 7.353 (0.88), 7.361 (0.54), 7.365 (1.31), 7.369 (0.75), 7.586 (5.49), 7.960 (0.67), 7.975 (1.41), 7.990 (0.64), 8.553 (0.51). LC-MS (Method A); $R_t$ = 1.20 min, m/z = 394 $[M + H]^+$. | Intermediate 44; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 136 | 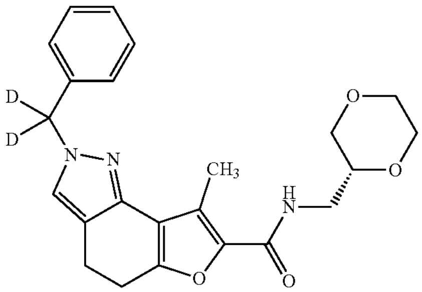 [SMILES: [2H]C([2H])(c1ccccc1)n1cc2c(n1)-c1c(oc(C(=O)NC[C@@H]3COCCO3)c1C)CC2] N-[(2R)-1,4-dioxan-2-ylmethyl]-8-methyl-2-[phenyl($^2H_2$)methyl]-4,5-dihydro-2H-furo[2,3-g]indazole-7-carboxamide | $^1$H-NMR (400 MHz, DMSO-d6) δ [ppm]: −0.008 (2.18), 0.008 (2.03), 0.934 (0.52), 0.951 (0.52), 2.338 (0.47), 2.461 (16.00), 2.520 (5.04), 2.524 (3.29), 2.662 (0.47), 2.859 (2.50), 2.870 (4.40), 2.874 (4.65), 2.885 (3.09), 3.161 (0.57), 3.180 (1.71), 3.194 (1.43), 3.204 (1.56), 3.209 (2.05), 3.214 (0.91), 3.233 (1.81), 3.246 (0.87), 3.264 (0.57), 3.308 (0.54), 3.421 (0.45), 3.441 (0.99), 3.447 (1.09), 3.468 (0.89), 3.474 (0.87), 3.511 (0.77), 3.517 (0.84), 3.539 (1.04), 3.545 (1.06), 3.566 (0.42), 3.572 (0.69), 3.607 (1.66), 3.612 (1.26), 3.622 (0.59), 3.631 (1.29), 3.637 (1.31), 3.682 (1.14), 3.688 (0.96), 3.711 (2.00), 3.717 (1.73), 3.741 (0.84), 7.243 (1.90), 7.246 (2.62), 7.250 (1.34), 7.257 (0.91), 7.263 (4.72), 7.267 (3.81), 7.275 (0.57), 7.282 (1.93), 7.288 (0.47), 7.296 (1.24), 7.300 (1.63), 7.304 (0.69), 7.328 (2.28), 7.330 (3.29), 7.334 (1.31), 7.345 (2.13), 7.349 (3.56), 7.353 (0.87), 7.361 (0.52), 7.366 (1.29), 7.369 (0.72), 7.587 (5.27), 8.040 (0.69), 8.054 (1.46), 8.070 (0.67). LC-MS (Method A); $R_t$ = 1.13 min, m/z = 410 $[M + H]^+$. | Intermediate 44; GP G (conditions A with HATU) |
| 137 | 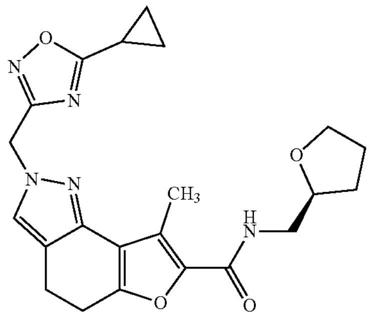 [SMILES: Cc1c(C(=O)NC[C@@H]2CCCO2)oc2c1-c1nn(Cc3noc(C4CC4)n3)cc1CC2] 2-[(5-cyclopropyl-1,2,4-oxadiazol-3-yl)methyl]-8-methyl-N-[(2S)-tetrahydrofuran-2-ylmethyl]-4,5-dihydro-2H-furo[2,3-g]indazole-7-carboxamide | $^1$H-NMR (400 MHz, DMSO-d6) δ [ppm]: −0.008 (2.11), 0.008 (1.94), 1.061 (0.62), 1.072 (2.54), 1.079 (2.63), 1.083 (2.23), 1.091 (2.63), 1.100 (0.92), 1.208 (0.88), 1.217 (2.42), 1.225 (2.01), 1.238 (2.80), 1.245 (1.94), 1.257 (0.62), 1.551 (0.50), 1.568 (0.69), 1.575 (0.52), 1.584 (0.57), 1.596 (0.43), 1.775 (0.55), 1.781 (0.71), 1.796 (1.23), 1.814 (1.37), 1.832 (1.33), 1.843 (0.73), 1.853 (0.59), 1.860 (0.81), 1.875 (0.55), 2.296 (0.45), 2.308 (0.88), 2.317 (1.02), 2.320 (1.00), 2.324 (1.21), 2.329 (3.08), 2.334 (1.16), 2.338 (1.02), 2.341 (1.00), 2.350 (0.85), 2.438 (16.00), 2.520 (4.91), 2.525 (3.13), 2.542 (0.47), 2.662 (0.45), 2.666 (1.00), 2.671 (1.40), 2.676 (1.00), 2.680 (0.45), 2.870 (2.70), 2.882 (5.71), 2.892 (3.27), 3.212 (1.09), 3.218 (1.09), 3.227 (2.01), 3.233 (1.94), 3.243 (1.11), 3.248 (1.11), 3.310 (0.55), 3.583 (0.45), 3.599 (0.95), 3.602 (0.92), 3.620 (1.28), 3.638 (0.69), 3.733 (0.64), 3.750 (1.16), 3.766 (0.95), 3.768 (0.97), 3.786 (0.64), 3.928 (1.00), 3.944 (1.49), 3.959 (0.92), 5.403 (8.01), 7.598 (4.98), 7.982 (0.71), 7.997 (1.52), 8.012 (0.71). LC-MS (Method A); $R_t$ = 1.08 min, m/z = 424 $[M + H]^+$. | Intermediate 45; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 138 | 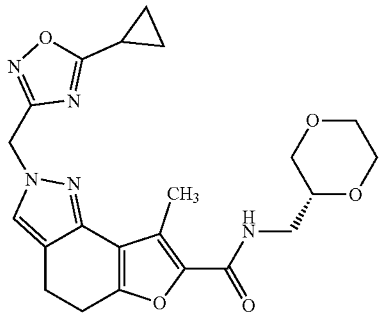 [SMILES: Cc1c(C(=O)NC[C@@H]2COCCO2)oc2c1-c1nn(Cc3noc(C4CC4)n3)cc1CC2] 2-[(5-cyclopropyl-1,2,4-oxadiazol-3-yl)methyl]-N-[(2R)-1,4-dioxan-2-ylmethyl]-8-methyl]-4,5-dihydro-2H-furo[2,3-g]indazole-7-carboxamide | $^1$H-NMR (400 MHz, DMSO-d6) δ [ppm]: −0.008 (1.49), 0.008 (1.41), 1.061 (0.65), 1.071 (2.66), 1.079 (2.75), 1.083 (2.38), 1.090 (2.84), 1.100 (1.17), 1.208 (0.93), 1.217 (2.51), 1.225 (2.19), 1.238 (2.92), 1.245 (2.12), 1.257 (0.71), 2.296 (0.45), 2.308 (0.95), 2.317 (1.08), 2.320 (1.06), 2.324 (1.15), 2.329 (3.10), 2.334 (1.13), 2.338 (1.04), 2.341 (1.13), 2.350 (0.89), 2.361 (0.45), 2.439 (16.00), 2.520 (4.72), 2.525 (3.07), 2.542 (0.56), 2.667 (0.91), 2.671 (1.26), 2.676 (0.93), 2.680 (0.43), 2.871 (2.77), 2.884 (5.76), 2.894 (3.33), 2.912 (0.41), 3.161 (0.61), 3.181 (1.93), 3.195 (1.56), 3.205 (1.71), 3.210 (2.25), 3.234 (2.08), 3.246 (0.97), 3.265 (0.63), 3.415 (0.41), 3.421 (0.50), 3.441 (1.10), 3.448 (1.19), 3.469 (0.95), 3.475 (0.93), 3.512 (0.82), 3.517 (0.89), 3.540 (1.15), 3.546 (1.19), 3.566 (0.48), 3.573 (0.76), 3.607 (1.80), 3.623 (0.69), 3.631 (1.47), 3.638 (1.43), 3.683 (1.28), 3.690 (1.08), 3.712 (2.27), 3.718 (1.91), 3.741 (0.93), 4.646 (1.02), 5.404 (8.25), 7.599 (5.15), 8.060 (0.78), 8.074 (1.65), 8.090 (0.76). LC-MS (Method A); $R_t$ = 1.00 min, m/z = 440 $[M + H]^+$. | Intermediate 45; GP G (conditions A with HATU) |
| 139 | 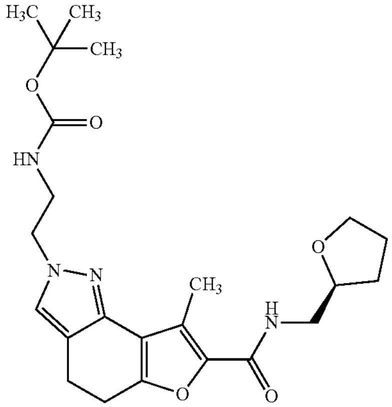 [SMILES: Cc1c(C(=O)NC[C@@H]2CCCO2)oc2c1-c1nn(CCNC(=O)OC(C)(C)C)cc1CC2] tert-butyl [2-(8-methyl-7-{[(2S)-tetrahydrofuran-2-ylmethyl]carbamoyl}-4,5-dihydro-2H-furo[2,3-g]indazol-2-yl)ethyl]carbamate | $^1$H-NMR (400 MHz, DMSO-d6) δ [ppm]: −0.008 (1.50), 0.008 (1.39), 1.157 (0.59), 1.174 (0.51), 1.234 (0.84), 1.301 (0.88), 1.365 (16.00), 1.569 (0.51), 1.577 (0.40), 1.585 (0.48), 1.783 (0.55), 1.798 (1.06), 1.816 (1.03), 1.834 (0.95), 1.846 (0.59), 1.863 (0.59), 1.878 (0.44), 2.076 (0.48), 2.324 (1.35), 2.329 (1.83), 2.333 (1.32), 2.477 (11.17), 2.524 (6.00), 2.666 (1.35), 2.671 (1.83), 2.676 (1.35), 2.824 (0.40), 2.842 (1.76), 2.854 (2.64), 2.862 (2.89), 2.874 (2.16), 2.892 (0.48), 3.215 (0.81), 3.219 (0.84), 3.230 (1.57), 3.234 (1.54), 3.250 (1.06), 3.272 (1.65), 3.286 (1.90), 3.371 (0.40), 3.603 (0.70), 3.622 (0.88), 3.640 (0.48), 3.735 (0.40), 3.752 (0.81), 3.769 (0.70), 3.930 (0.70), 3.946 (1.03), 3.962 (0.62), 4.061 (0.92), 4.077 (1.65), 4.093 (0.77), 6.942 (0.73), 7.445 (1.79), 7.963 (0.51), 7.978 (1.10), 7.994 (0.51). UPLC-MS (Method 1); $R_t$ = 1.12 min, m/z = 443 $[M - H]^-$. | Intermediate 46; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 140 | 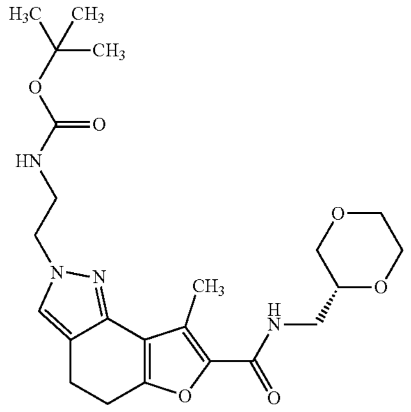 [SMILES: Cc1c(C(=O)NC[C@@H]2COCCO2)oc2c1-c1nn(CCNC(=O)OC(C)(C)C)cc1CC2] tert-butyl [2-(7-{[(2R)-1,4-dioxan-2-ylmethyl]carbamoyl}-8-methyl-4,5-dihydro-2H-furo[2,3-g]indazol-2-yl)ethyl]carbamate | $^1$H-NMR (400 MHz, DMSO-d6) δ [ppm]: 0.700 (0.41), 0.768 (0.50), 1.157 (1.52), 1.234 (1.24), 1.300 (1.05), 1.365 (16.00), 2.324 (1.24), 2.329 (1.66), 2.333 (1.24), 2.478 (11.48), 2.667 (1.27), 2.671 (1.63), 2.675 (1.21), 2.825 (0.44), 2.844 (1.74), 2.856 (2.65), 2.863 (2.84), 2.876 (2.10), 2.894 (0.44), 3.183 (1.16), 3.197 (1.02), 3.212 (1.54), 3.236 (1.41), 3.249 (0.88), 3.272 (1.79), 3.287 (1.93), 3.444 (0.80), 3.449 (0.83), 3.471 (0.69), 3.477 (0.66), 3.513 (0.55), 3.519 (0.58), 3.541 (0.77), 3.546 (0.83), 3.574 (0.47), 3.609 (1.32), 3.634 (1.10), 3.686 (0.88), 3.692 (0.77), 3.715 (1.63), 3.744 (0.72), 4.061 (0.94), 4.077 (1.71), 4.093 (0.80), 6.942 (0.74), 6.957 (0.41), 7.447 (1.82), 8.042 (0.58), 8.058 (1.10), 8.072 (0.55). UPLC-MS (Method 1); $R_t$ = 1.05 min, m/z = 461 [M + H]$^+$. | Intermediate 46; GPG (conditions A with HATU) |
| 141 | 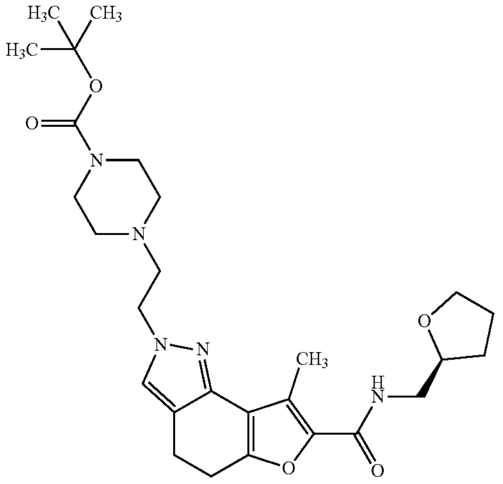 [SMILES: Cc1c(C(=O)NC[C@@H]2CCCO2)oc2c1-c1nn(CCN3CCN(C(=O)OC(C)(C)C)CC3)cc1CC2] tert-butyl 4-[2-(8-methyl-7-{[(2S)-tetrahydrofuran-2-ylmethyl]carbamoyl}-4,5-dihydro-2H-furo[2,3-g]indazol-2-yl)ethyl]piperazine-1-carboxylate | $^1$H-NMR (400 MHz, DMSO-d6) δ [ppm]: 1.157 (0.64), 1.175 (1.25), 1.192 (0.64), 1.372 (1.34), 1.389 (16.00), 1.799 (2.29), 1.816 (0.60), 1.833 (0.52), 1.989 (2.21), 2.077 (6.46), 2.367 (0.85), 2.380 (1.23), 2.392 (0.89), 2.470 (4.93), 2.520 (1.02), 2.525 (0.64), 2.680 (0.56), 2.689 (0.75), 2.697 (1.00), 2.713 (0.54), 2.730 (0.63), 2.844 (0.85), 2.857 (1.23), 2.865 (1.31), 2.877 (1.04), 2.891 (0.72), 3.214 (0.43), 3.220 (0.41), 3.230 (0.73), 3.234 (0.70), 3.245 (0.46), 3.250 (0.47), 3.289 (1.13), 3.604 (0.45), 3.622 (0.49), 3.752 (0.49), 3.767 (0.40), 3.946 (0.50), 4.019 (0.53), 4.037 (0.52), 4.154 (0.46), 4.170 (0.93), 4.187 (0.44), 7.515 (1.53), 7.974 (0.54). UPLC-MS (Method 1); $R_t$ = 1.23 min, m/z = 514 [M + H]$^+$. | Intermediate 47; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 142 | 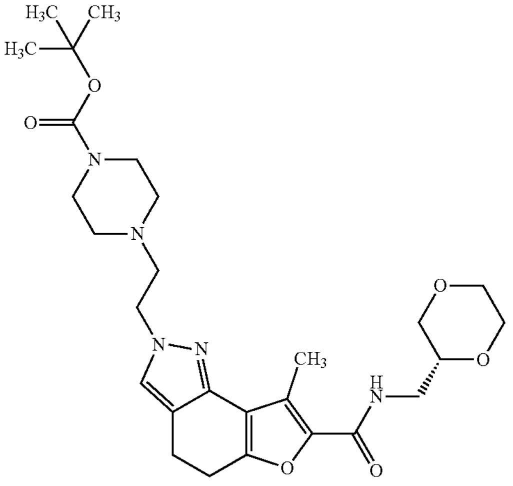 [SMILES: Cc1c(C(=O)NC[C@@H]2COCCO2)oc2c1-c1nn(CCN3CCN(C(=O)OC(C)(C)C)CC3)cc1CC2]<br>tert-butyl 4-[2-(7-{[(2R)-1,4-dioxan-2-ylmethyl]carbamoyl}-8-methyl-4,5-dihydro-2H-furo[2,3-g]indazol-2-yl)ethyl]piperazine-1-carboxylate | $^1$H-NMR (400 MHz, DMSO-d6) δ [ppm]: −0.008 (0.88), 0.008 (0.86), 0.747 (0.64), 0.767 (0.68), 1.157 (2.55), 1.175 (1.98), 1.192 (1.10), 1.235 (0.97), 1.373 (0.53), 1.389 (16.00), 1.990 (1.91), 2.077 (8.25), 2.367 (0.85), 2.380 (1.23), 2.391 (0.90), 2.470 (5.29), 2.520 (4.61), 2.525 (2.87), 2.689 (0.40), 2.697 (0.96), 2.713 (0.50), 2.846 (0.83), 2.858 (1.16), 2.867 (1.25), 2.879 (0.99), 3.183 (0.57), 3.197 (0.50), 3.208 (0.57), 3.212 (0.73), 3.236 (0.64), 3.289 (1.16), 3.609 (0.59), 3.638 (0.46), 3.685 (0.40), 3.714 (0.72), 4.019 (0.44), 4.037 (0.46), 4.154 (0.44), 4.171 (0.90), 4.187 (0.42), 7.517 (1.47), 8.054 (0.53).<br>UPLC-MS (Method 1); $R_t$ = 1.16 min, m/z = 530 [M + H]$^+$. | Intermediate 47; GPG (conditions A with HATU) |
| 143 | 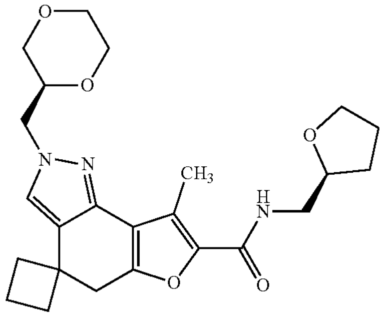 [SMILES: Cc1c(C(=O)NC[C@@H]2CCCO2)oc2c1-c1nn(C[C@H]3COCCO3)cc1C1(CCC1)C2]<br>2'-[(2S)-1,4-dioxan-2-ylmethyl]-8'-methyl-N-[(2S)-tetrahydrofuran-2-ylmethyl]-2',5'-dihydrospiro[cyclobutane-1,4'-furo[2,3-g]indazole]-7'-carboxamide | $^1$H-NMR (400 MHz, DMSO-d6) δ [ppm]: 1.554 (0.51), 1.563 (0.41), 1.567 (0.46), 1.570 (0.72), 1.578 (0.54), 1.586 (0.61), 1.594 (0.41), 1.599 (0.50), 1.780 (0.57), 1.786 (0.74), 1.801 (1.28), 1.819 (1.38), 1.837 (1.11), 1.852 (0.81), 1.860 (0.60), 1.864 (0.65), 1.869 (0.82), 1.884 (0.58), 1.886 (0.57), 1.891 (0.46), 1.901 (0.44), 1.907 (0.49), 1.922 (0.48), 1.929 (0.41), 1.947 (0.56), 1.965 (0.42), 1.971 (0.50), 1.982 (0.54), 2.002 (0.62), 2.020 (0.77), 2.038 (0.49), 2.069 (1.55), 2.086 (2.79), 2.105 (1.43), 2.131 (0.48), 2.462 (16.00), 2.518 (1.39), 2.523 (0.98), 2.627 (0.60), 3.016 (7.40), 3.221 (1.61), 3.236 (3.22), 3.250 (2.33), 3.273 (1.36), 3.278 (1.43), 3.302 (1.36), 3.423 (0.40), 3.429 (0.49), 3.450 (1.00), 3.456 (1.10), 3.477 (0.88), 3.483 (0.83), 3.525 (0.70), 3.531 (0.80), 3.554 (1.00), 3.560 (0.99), 3.581 (0.51), 3.587 (1.14), 3.603 (0.99), 3.606 (1.06), 3.623 (2.29), 3.641 (0.81), 3.652 (0.90), 3.721 (1.09), 3.728 (1.99), 3.737 (1.39), 3.751 (1.75), 3.755 (2.56), 3.769 (1.15), 3.772 (1.12), 3.790 (0.68), 3.861 (0.55), 3.867 (0.64), 3.877 (0.54), 3.885 (0.71), 3.891 (0.52), 3.932 (1.02), 3.948 (1.56), 3.963 (0.95), 4.092 (2.08), 4.097 (2.15), 4.109 (2.33), 7.735 (7.25), 7.955 (0.70), 7.970 (1.52), 7.985 (0.70).<br>LC-MS (Method A); $R_t$ = 1.12 min, m/z = 442 [M + H]$^+$. | Intermediate 48; GP G (conditions A with HATU) |

TABLE 2-continued

| The following examples (4 to 147) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| 144 | 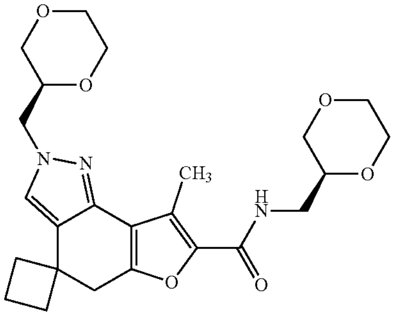 [SMILES: Cc1c(C(=O)NC[C@H]2COCCO2)oc2c1-c1nn(C[C@H]3COCCO3)cc1C1(CCC1)C2] N,2'-bis[(2S)-1,4-dioxan-2-ylmethyl]-8'-methyl-2',5'-dihydrospiro[cyclobutane-1,4'-furo[2,3-g]indazole]-7'-carboxamide | $^1$H-NMR (400 MHz, DMSO-d6) δ [ppm]: −0.003 (0.75), 0.931 (0.46), 0.948 (0.46), 1.929 (0.42), 1.934 (0.41), 1.948 (0.60), 1.959 (0.42), 1.962 (0.43), 1.971 (0.54), 1.983 (0.55), 1.987 (0.44), 2.002 (0.62), 2.019 (0.73), 2.038 (0.50), 2.068 (1.70), 2.084 (2.67), 2.099 (1.55), 2.113 (1.27), 2.133 (0.51), 2.462 (16.00), 2.518 (2.14), 2.523 (1.44), 2.627 (0.67), 3.016 (7.24), 3.172 (0.50), 3.187 (1.57), 3.191 (0.99), 3.206 (1.69), 3.211 (2.03), 3.215 (2.14), 3.221 (1.15), 3.229 (1.51), 3.240 (1.77), 3.249 (1.68), 3.264 (0.58), 3.273 (1.43), 3.278 (1.62), 3.302 (1.53), 3.425 (0.73), 3.429 (0.64), 3.452 (1.79), 3.473 (1.21), 3.477 (1.40), 3.480 (1.39), 3.514 (0.92), 3.520 (1.08), 3.525 (0.81), 3.531 (0.87), 3.543 (1.23), 3.549 (1.41), 3.553 (1.19), 3.559 (1.07), 3.569 (0.53), 3.575 (0.85), 3.580 (0.59), 3.587 (0.74), 3.597 (0.43), 3.613 (1.72), 3.620 (1.75), 3.628 (1.58), 3.637 (1.65), 3.642 (1.29), 3.652 (1.22), 3.693 (1.24), 3.699 (1.10), 3.720 (3.10), 3.727 (3.08), 3.749 (1.66), 3.755 (1.72), 3.861 (0.56), 3.867 (0.64), 3.877 (0.55), 3.884 (0.72), 3.891 (0.53), 4.093 (2.11), 4.097 (2.17), 4.109 (2.39), 7.589 (0.41), 7.737 (7.76), 8.036 (0.75), 8.052 (1.58), 8.066 (0.70). LC-MS (Method A); $R_t$ = 1.03 min, m/z = 458 $[M + H]^+$. | Intermediate 48; GP G (conditions A with HATU) |
| 145 | 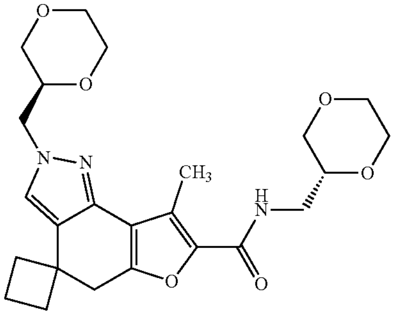 [SMILES: Cc1c(C(=O)NC[C@@H]2COCCO2)oc2c1-c1nn(C[C@H]3COCCO3)cc1C1(CCC1)C2] N-[(2R)-1,4-dioxan-2-ylmethyl]-2'-[(2S)-1,4-dioxan-2-ylmethyl]-8'-methyl-2',5'-dihydrospiro[cyclobutane-1,4'-furo[2,3-g]indazole-7'-carboxamide | $^1$H-NMR (400 MHz, DMSO-d6) δ [ppm]: 0.931 (1.65), 0.934 (0.53), 0.947 (1.63), 1.929 (0.44), 1.934 (0.44), 1.947 (0.63), 1.957 (0.45), 1.961 (0.45), 1.970 (0.56), 1.982 (0.56), 2.000 (0.65), 2.018 (0.77), 2.037 (0.54), 2.059 (1.06), 2.068 (1.74), 2.084 (2.67), 2.101 (1.49), 2.111 (1.33), 2.132 (0.55), 2.461 (16.00), 2.518 (2.08), 2.523 (1.34), 2.626 (0.79), 2.991 (0.40), 3.015 (7.27), 3.169 (0.56), 3.186 (1.79), 3.203 (1.56), 3.211 (1.80), 3.216 (2.36), 3.233 (1.50), 3.239 (1.83), 3.248 (2.20), 3.267 (0.75), 3.272 (1.60), 3.276 (1.61), 3.301 (1.61), 3.311 (0.46), 3.316 (0.51), 3.385 (0.46), 3.425 (0.80), 3.428 (0.70), 3.451 (1.91), 3.473 (1.26), 3.476 (1.46), 3.478 (1.47), 3.514 (0.96), 3.520 (1.15), 3.523 (0.89), 3.529 (0.91), 3.542 (1.28), 3.549 (1.58), 3.558 (1.14), 3.569 (0.56), 3.575 (0.92), 3.585 (0.78), 3.597 (0.47), 3.612 (1.78), 3.620 (1.85), 3.627 (1.65), 3.636 (1.74), 3.642 (1.32), 3.651 (1.27), 3.692 (1.29), 3.698 (1.19), 3.720 (3.17), 3.726 (3.20), 3.748 (1.76), 3.754 (1.81), 3.860 (0.58), 3.867 (0.67), 3.876 (0.56), 3.884 (0.74), 3.891 (0.55), 4.092 (2.20), 4.097 (2.26), 4.109 (2.52), 7.589 (0.50), 7.735 (7.87), 8.038 (0.77), 8.053 (1.61), 8.067 (0.73). LC-MS (Method A); $R_t$ = 1.03 min, m/z = 458 $[M + H]^+$. | Intermediate 48; GP G (conditions A with HATU) |

TABLE 2-continued

The following examples (4 to 147) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 146 | 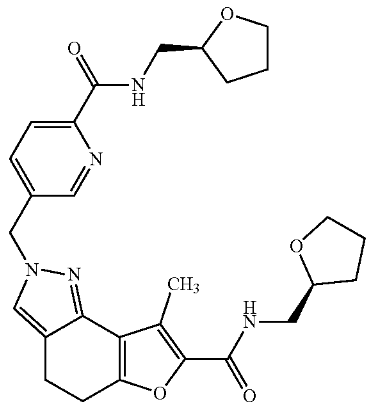 [SMILES: Cc1c(C(=O)NC[C@@H]2CCCO2)oc2c1-c1nn(Cc3ccc(C(=O)NC[C@@H]4CCCO4)nc3)cc1CC2] 8-methyl-N-[(2S)-tetrahydrofuran-2-ylmethyl]-2-[(6-{[(2S)-tetrahydrofuran-2-ylmethyl]carbamoyl}pyridin-3-yl)methyl]-4,5-dihydro-2H-furo[2,3-g]indazole-7-carboxamide | $^1$H-NMR (400 MHz, DMSO-d6) δ [ppm]: −0.149 (0.50), −0.008 (4.09), 0.008 (4.34), 0.146 (0.50), 1.537 (0.62), 1.555 (0.99), 1.564 (0.99), 1.569 (0.99), 1.585 (1.24), 1.600 (0.62), 1.776 (1.12), 1.794 (1.98), 1.812 (1.98), 1.832 (1.98), 1.843 (1.49), 1.850 (1.36), 1.860 (1.74), 1.875 (1.12), 1.892 (0.74), 1.914 (0.50), 2.334 (2.98), 2.338 (1.36), 2.443 (15.01), 2.520 (16.00), 2.524 (10.42), 2.676 (3.10), 2.680 (1.36), 2.907 (8.06), 2.915 (3.22), 3.213 (1.12), 3.220 (1.12), 3.229 (1.98), 3.234 (2.11), 3.244 (1.12), 3.249 (1.24), 3.279 (0.74), 3.295 (0.99), 3.312 (3.97), 3.361 (2.23), 3.379 (0.74), 3.584 (0.99), 3.603 (1.98), 3.621 (2.60), 3.638 (1.49), 3.735 (1.24), 3.752 (2.23), 3.767 (1.98), 3.787 (1.12), 3.929 (1.12), 3.945 (1.61), 3.959 (1.49), 3.973 (1.24), 3.988 (0.87), 5.467 (4.84), 7.375 (1.36), 7.379 (1.36), 7.387 (1.36), 7.392 (1.36), 7.692 (4.71), 7.823 (2.36), 7.980 (0.74), 7.995 (1.61), 8.011 (0.74), 8.550 (2.23), 8.596 (2.23), 8.610 (2.23), 8.648 (0.62), 8.663 (1.24), 8.679 (0.62). LC-MS (Method A); $R_t$ = 1.07 min, m/z = 520 [M + H]$^+$. | Intermediate 49; GP G (conditions A with HATU) |
| 147 | 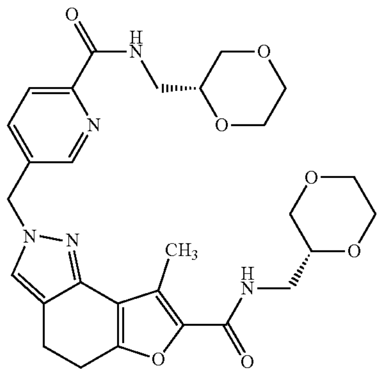 [SMILES: Cc1c(C(=O)NC[C@@H]2COCCO2)oc2c1-c1nn(Cc3ccc(C(=O)NC[C@@H]4COCCO4)nc3)cc1CC2] N-[(2R)-1,4-dioxan-2-ylmethyl]-2-[(6-{[(2R)-1,4-dioxan-2-ylmethyl]carbamoyl}pyridin-3-yl)methyl]-8-methyl-4,5-dihydro-2H-furo[2,3-g]indazole-7-carboxamide | $^1$H-NMR (400 MHz, DMSO-d6) δ [ppm]: −0.149 (0.76), −0.008 (7.51), 0.008 (6.75), 0.146 (0.76), 2.324 (4.79), 2.329 (6.31), 2.333 (4.57), 2.445 (8.93), 2.524 (16.00), 2.666 (4.79), 2.671 (6.31), 2.675 (4.57), 2.908 (4.90), 3.181 (1.20), 3.197 (1.20), 3.211 (1.41), 3.218 (1.52), 3.234 (1.63), 3.248 (1.20), 3.440 (1.09), 3.467 (0.87), 3.515 (0.87), 3.544 (1.41), 3.571 (0.87), 3.605 (1.52), 3.632 (1.52), 3.656 (0.87), 3.676 (1.96), 3.712 (2.18), 3.744 (1.20), 5.467 (3.16), 7.379 (0.87), 7.391 (0.87), 7.693 (2.83), 7.822 (1.74), 8.059 (0.54), 8.073 (0.98), 8.549 (1.52), 8.601 (1.52), 8.613 (1.41), 8.738 (0.87). LC-MS (Method A); $R_t$ = 0.93 min, m/z = 552 [M + H]$^+$. | Intermediate 49; GPG (conditions A with HATU) |

Example 148

4,4,8-trimethyl-2-(pyridin-2-ylmethyl)-N-[(2S)-tetrahydrofuran-2-ylmethyl]-4,5-dihydro-2H-furo[2,3-g] indazole-7-carboxamide

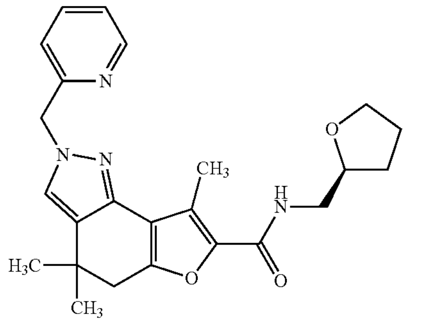 [SMILES: Cc1c(C(=O)NC[C@@H]2CCCO2)oc2c1-c1nn(Cc3ccccn3)cc1C(C)(C)C2]

According to GP G (conditions B) 7-bromo-4,4,8-trimethyl-2-[(pyridin-2-yl)methyl]-4,5-dihydro-2H-furo[2,3-g] indazole (Intermediate 37; 1.00 eq., 100 mg, 269 μmol) was reacted with 1-[(2S)-tetrahydrofuran-2-yl]methanamine (CAS No. [7175-81-7]; 5.0 eq., 140 μL, 1.30 mmol), molybdenum hexacarbonyl (CAS No. [13939-06-5]; 2.0 eq., 142 mg, 537 μmol), sodium carbonate (CAS No. [497-19-8]; 3.0 eq., 85 mg, 810 μmol), tri-tert-butylphosphonium tetrafluoroborate (CAS No. [131274-22-1]; 0.10 eq., 7.8 mg, 27 μmol) and palladium(II) acetate (CAS No. [3375-31-3]; 0.20 eq., 12 mg, 54 μmol) at 140° C. for 6 hours and at rt overnight. Another amount of molybdenum hexacarbonyl (2.0 eq., 142 mg, 537 μmol), sodium carbonate (3.0 eq., 85 mg, 810 μmol), tri-tert-butylphosphonium tetrafluoroborate (0.10 eq., 7.8 mg, 27 μmol) and palladium(II) acetate (0.20 eq., 12 mg, 54 μmol) was added and the mixture stirred at 140° C. for another 4.5 hours. The reaction mixture was cooled to rt, the solids filtered off over Celite and rinsed with ethyl acetate. The filtrate was concentrated under reduced pressure and the obtained crude product purified by preparative HPLC to give the title compound (5.3 mg, 4%).

$^1$H NMR (400 MHz, DMSO-d6) δ[ppm]: 1.26 (s, 6H), 1.55-1.61 (m, 1H), 1.76-1.91 (m, 3H), 2.45 (s, 3H), 2.75 (s, 2H), 3.21-3.24 (m, 2H), 3.58-3.64 (m, 1H), 3.72-3.82 (m, 1H), 3.91-3.98 (m, 1H), 5.38 (s, 2H), 7.07 (d, 1H), 7.31 (ddd, 1H), 7.71 (s, 1H), 7.78 (dt, 1H), 7.99 (t, 1H), 8.54 (ddd, 1H).

LC-MS (Method A): $R_t$=1.09 min; MS (ESIpos): m/z=421 [M+H]$^+$.

TABLE 3

The following examples (149 to 154) were prepared in analogy to example 148 starting from the given bromo-intermediates and commercially available amines.

| Example | Structure IUPAC-Name | Analytical Data | Intermediate |
|---|---|---|---|
| 149 | 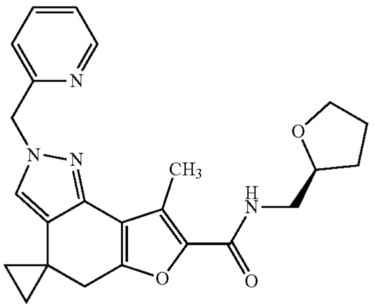 8′-methyl-2′(pyridin-2-ylmethyl)-N-[(2S)-tetrahydrofuran-2-ylmethyl]-2′,5′-dihydrospiro[cyclopropane-1,4′-furo-[2,3-g]indazole]-7′-carboxamide | $^1$H-NMR (400 MHz, DMSO-d6) δ [ppm]: 0.806 (1.08), 0.819 (2.86), 0.824 (3.50), 0.832 (1.98), 0.840 (0.76), 0.851 (0.46), 0.857 (0.70), 0.875 (2.92), 0.884 (3.64), 0.901 (1.04), 0.939 (0.72), 0.957 (0.40), 0.979 (0.40), 1.541 (0.72), 1.557 (0.96), 1.565 (0.80), 1.574 (0.88), 1.586 (0.70), 1.602 (0.52), 1.753 (0.42), 1.772 (0.92), 1.788 (1.58), 1.806 (1.72), 1.824 (1.52), 1.837 (0.98), 1.843 (0.82), 1.850 (0.86), 1.854 (0.96), 1.869 (0.72), 1.876 (0.54), 1.886 (0.44), 1.892 (0.42), 2.458 (16.00), 2.518 (1.36), 2.850 (8.32), 3.210 (1.92), 3.226 (3.72), 3.241 (2.02), 3.574 (0.54), 3.594 (1.20), 3.611 (1.52), 3.628 (0.80), 3.724 (0.72), 3.741 (1.36), 3.756 (1.16), 3.759 (1.20), 3.776 (0.70), 3.919 (1.12), 3.936 (1.68), 3.951 (1.04), 5.333 (7.30), 7.027 (2.00), 7.047 (2.10), 7.284 (1.04), 7.296 (1.20), 7.300 (1.26), 7.312 (1.24), 7.448 (6.90), 7.743 (1.12), 7.747 (1.14), 7.762 (1.90), 7.766 (1.92), 7.781 (0.98), 7.786 (1.02), 7.949 (0.82), 7.964 (1.72), 7.979 (0.82), 8.517 (1.60), 8.519 (1.66), 8.529 (1.70), 8.531 (1.68). LC-MS (Method A); $R_t$ = 1.03 min, m/z = 419 [M + H]$^+$. | Intermediate 38, step 5 |

TABLE 3-continued

| The following examples (149 to 154) were prepared in analogy to example 148 starting from the given bromo-intermediates and commercially available amines. | | | |
|---|---|---|---|
| Example | Structure IUPAC-Name | Analytical Data | Intermediate |
| 150 | 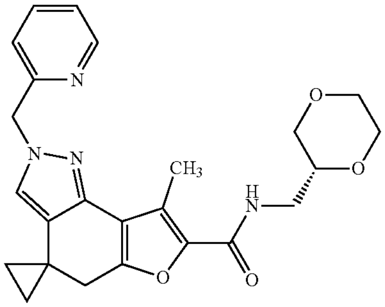 N-[(2R)-1,4-dioxan-2-ylmethyl]-8′-methyl-2′-(pyridin-2-ylmethyl)-2′,5′-dihydrospiro-[cyclopropane-1,4′-furo[2,3-g]indazole]-7′-carboxamide | $^1$H-NMR (400 MHz, DMSO-d6) δ [ppm]: 0.811 (0.94), 0.824 (2.41), 0.829 (3.04), 0.837 (1.78), 0.846 (0.58), 0.872 (0.58), 0.880 (1.52), 0.888 (2.99), 0.907 (0.94), 2.463 (16.00), 2.518 (2.05), 2.523 (2.41), 2.855 (7.61), 2.902 (0.52), 3.150 (0.47), 3.164 (0.63), 3.178 (1.57), 3.183 (1.05), 3.199 (1.78), 3.202 (1.99), 3.207 (1.84), 3.212 (1.47), 3.227 (1.68), 3.231 (1.89), 3.242 (1.05), 3.261 (0.58), 3.411 (0.52), 3.417 (0.63), 3.438 (1.15), 3.444 (1.26), 3.465 (1.00), 3.471 (0.94), 3.507 (0.89), 3.513 (1.00), 3.535 (1.21), 3.542 (1.26), 3.562 (0.52), 3.568 (0.79), 3.589 (0.42), 3.604 (1.84), 3.619 (0.73), 3.629 (1.47), 3.634 (1.47), 3.681 (1.26), 3.687 (1.15), 3.710 (2.20), 3.738 (1.00), 5.337 (6.40), 7.033 (1.84), 7.052 (1.94), 7.286 (0.94), 7.289 (0.94), 7.298 (1.00), 7.301 (1.05), 7.305 (1.10), 7.307 (1.00), 7.317 (1.10), 7.319 (1.00), 7.452 (8.45), 7.747 (1.15), 7.752 (1.21), 7.766 (1.94), 7.771 (1.99), 7.785 (1.05), 7.790 (1.00), 7.824 (0.68), 8.034 (0.73), 8.049 (1.57), 8.064 (0.73), 8.519 (1.21), 8.521 (1.42), 8.523 (1.42), 8.525 (1.26), 8.531 (1.26), 8.533 (1.42), 8.535 (1.36), 8.537 (1.21). LC-MS (Method A); $R_t$ = 0.96 min, m/z = 435 $[M + H]^+$. | Intermediate 38, step 5 |
| 151 | 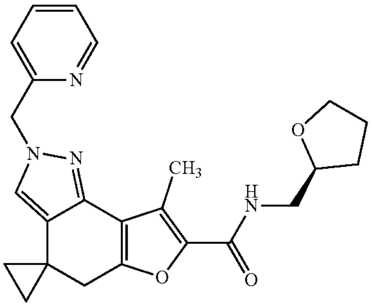 8′-methyl-2′-(pyridin-3-ylmethyl)-N-[(2S)-tetrahydrofuran-2-ylmethyl]-2′,5′-dihydro-spiro[cyclopropane-1,4′-furo[2,3-g]-indazole]-7′-carboxamide | $^1$H-NMR (500 MHz, DMSO-d6) δ [ppm]: 0.797 (0.89), 0.807 (2.43), 0.811 (2.84), 0.818 (1.54), 0.871 (1.29), 0.877 (2.84), 0.882 (2.12), 0.891 (0.89), 1.547 (0.44), 1.563 (0.62), 1.569 (0.57), 1.576 (0.50), 1.587 (0.52), 1.775 (0.52), 1.780 (0.49), 1.784 (0.42), 1.792 (0.76), 1.795 (0.69), 1.806 (0.71), 1.810 (0.81), 1.822 (0.57), 1.826 (0.59), 1.836 (0.52), 1.839 (0.49), 1.843 (0.52), 1.850 (0.62), 1.855 (0.49), 1.859 (0.59), 1.867 (0.42), 1.870 (0.47), 1.876 (0.42), 1.905 (0.49), 2.477 (16.00), 2.514 (2.84), 2.518 (2.90), 2.522 (2.38), 2.840 (7.25), 3.216 (1.29), 3.228 (2.57), 3.242 (1.34), 3.584 (0.45), 3.599 (0.99), 3.613 (1.14), 3.627 (0.71), 3.732 (0.60), 3.744 (0.91), 3.746 (1.04), 3.749 (0.69), 3.758 (1.04), 3.760 (0.87), 3.763 (0.72), 3.775 (0.69), 3.925 (0.96), 3.938 (1.49), 3.951 (0.96), 5.294 (5.81), 7.361 (1.06), 7.363 (1.04), 7.371 (1.11), 7.372 (1.02), 7.377 (1.16), 7.378 (1.18), 7.387 (1.24), 7.388 (1.18), 7.457 (8.21), 7.617 (0.77), 7.620 (1.23), 7.625 (0.82), 7.633 (0.69), 7.636 (1.06), 7.641 (0.72), 7.952 (0.65), 7.964 (1.43), 7.976 (0.65), 8.490 (1.66), 8.493 (3.27), 8.499 (2.97), 8.502 (1.58). LC-MS (Method A); $R_t$ = 0.99 min, m/z = 419 $[M + H]^+$. | Intermediate 39 |

TABLE 3-continued

The following examples (149 to 154) were prepared in analogy to example 148 starting from the given bromo-intermediates and commercially available amines.

| Example | Structure IUPAC-Name | Analytical Data | Intermediate |
|---|---|---|---|
| 152 | 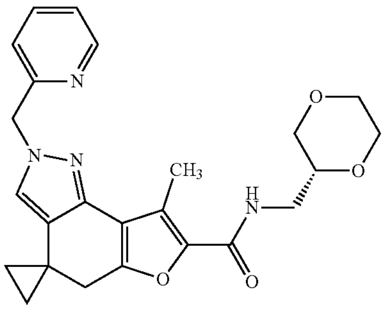 N-[(2R)-1,4-dioxan-2-ylmethyl]-8′-methyl-2′-(pyridin-3-ylmethyl)-2′,5′-dihydrospiro-[cyclopropane-1,4′-furo[2,3-g]indazole]-7′-carboxamide | $^1$H-NMR (500 MHz, DMSO-d6) δ [ppm]: 0.797 (0.91), 0.808 (2.57), 0.811 (2.96), 0.819 (1.61), 0.872 (1.39), 0.879 (3.00), 0.883 (2.26), 0.893 (0.91), 0.934 (0.43), 0.947 (0.48), 1.270 (7.87), 1.294 (8.65), 2.368 (0.70), 2.477 (16.00), 2.514 (6.43), 2.518 (6.35), 2.522 (5.17), 2.627 (0.78), 2.841 (7.61), 3.168 (0.65), 3.183 (2.04), 3.195 (1.52), 3.202 (1.52), 3.206 (1.91), 3.214 (0.78), 3.226 (2.17), 3.239 (0.91), 3.254 (0.61), 3.417 (0.43), 3.422 (0.61), 3.439 (1.09), 3.444 (1.17), 3.461 (0.96), 3.466 (0.87), 3.512 (0.83), 3.517 (0.91), 3.534 (1.13), 3.539 (1.13), 3.556 (0.52), 3.561 (0.70), 3.605 (1.61), 3.610 (1.30), 3.617 (0.65), 3.625 (1.35), 3.630 (1.35), 3.683 (1.17), 3.688 (1.00), 3.707 (1.78), 3.711 (1.91), 3.734 (0.83), 5.294 (6.13), 7.361 (1.09), 7.371 (1.13), 7.377 (1.22), 7.387 (1.26), 7.458 (8.17), 7.617 (0.87), 7.621 (1.22), 7.625 (0.83), 7.633 (0.74), 7.637 (1.13), 7.641 (0.70), 8.033 (0.74), 8.045 (1.57), 8.057 (0.70), 8.490 (1.87), 8.493 (3.48), 8.499 (3.00), 8.502 (1.61). LC-MS (Method A); $R_t$ = 0.92 min, m/z = 435 $[M + H]^+$. | Intermediate 39 |
| 153 | 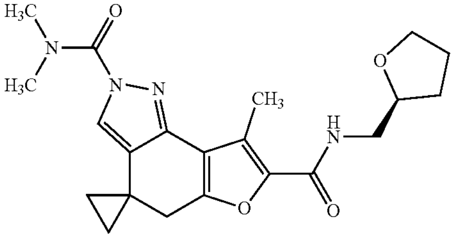 N2′,N2′,8′-trimethyl-N7′-[(2S)-tetrahydrofuran-2-ylmethyl]spiro[cyclopropane-1,4′-furo[2,3-g]-indazole]-2′,7′(5′H)-dicarboxamide | $^1$H-NMR (400 MHz, DMSO-d6) δ [ppm]: 0.918 (0.52), 0.938 (3.14), 0.944 (2.04), 0.961 (1.99), 0.967 (3.42), 0.987 (0.58), 1.555 (0.48), 1.571 (0.66), 1.579 (0.49), 1.587 (0.57), 1.600 (0.44), 1.779 (0.58), 1.785 (0.73), 1.800 (1.24), 1.819 (1.35), 1.836 (1.17), 1.850 (0.73), 1.858 (0.58), 1.862 (0.65), 1.867 (0.78), 1.881 (0.53), 1.888 (0.41), 1.898 (0.42), 2.520 (2.76), 2.525 (16.00), 2.904 (7.36), 3.146 (2.92), 3.227 (1.33), 3.229 (1.29), 3.243 (2.43), 3.260 (1.32), 3.585 (0.45), 3.602 (0.95), 3.605 (0.95), 3.622 (1.22), 3.640 (0.68), 3.735 (0.63), 3.750 (0.90), 3.752 (1.13), 3.767 (0.96), 3.770 (0.97), 3.788 (0.64), 3.935 (0.95), 3.951 (1.45), 3.966 (0.90), 7.829 (8.89), 8.061 (0.68), 8.076 (1.42), 8.090 (0.65). LC-MS (Method A); $R_t$ = 1.11 min, m/z = 399 $[M + H]^+$. | Intermediate 40-2 |
| 154 | 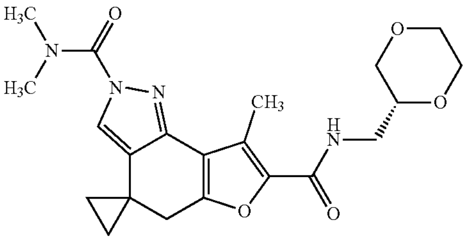 N7′-[(2R)-1,4-dioxan-2-ylmethyl]-N2′,N2′,8′-trimethyl-spiro[cyclopropane-1,4′-furo[2,3-g]indazole]-2′,7′(5′H)-dicarboxamide | $^1$H-NMR (400 MHz, DMSO-d6) δ [ppm]: 0.919 (0.54), 0.940 (3.41), 0.945 (2.22), 0.962 (2.11), 0.968 (3.71), 0.989 (0.61), 2.526 (16.00), 2.905 (7.77), 3.146 (3.20), 3.177 (1.22), 3.188 (1.67), 3.196 (1.16), 3.212 (3.01), 3.216 (1.84), 3.227 (1.51), 3.241 (2.30), 3.258 (0.96), 3.277 (0.62), 3.418 (0.42), 3.424 (0.50), 3.445 (1.10), 3.452 (1.17), 3.472 (0.98), 3.479 (0.93), 3.514 (0.84), 3.519 (0.94), 3.542 (1.15), 3.548 (1.20), 3.569 (0.48), 3.575 (0.75), 3.610 (1.36), 3.615 (1.35), 3.623 (0.95), 3.638 (1.52), 3.690 (1.29), 3.696 (1.09), 3.719 (2.16), 3.745 (0.96), 7.830 (8.99), 8.136 (0.74), 8.150 (1.56), 8.166 (0.71). LC-MS (Method A); $R_t$ = 1.01 min, m/z = 415 $[M + H]^+$. | Intermediate 40-2 |

Example 155 benzyl 3-fluoro-3-[(8-methyl-7-{[(2S)-tetrahydrofuran-2-ylmethyl]carbamoyl}-4,5-dihydro-2H-furo[2,3-g]indazol-2-yl)methyl]azetidine-1-carboxylate

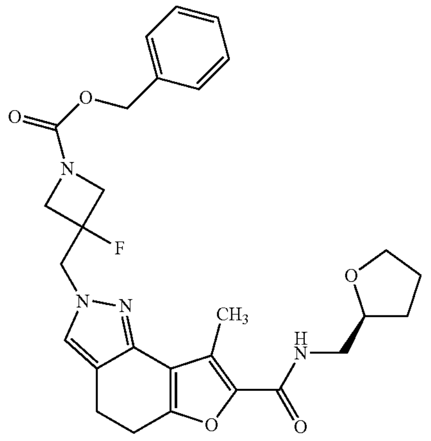 [SMILES: Cc1c(C(=O)NC[C@@H]2CCCO2)oc2c1-c1nn(CC3(F)CN(C(=O)OCc4ccccc4)C3)cc1CC2]

According to GP C (conditions A) 8-methyl-N-[(2S)-tetrahydrofuran-2-ylmethyl]-4,5-dihydro-1H-furo[2,3-g]indazole-7-carboxamide (Intermediate 43; 1.00 eq., 192 mg, 637 μmol) was reacted with benzyl 3-fluoro-3-(hydroxymethyl)azetidine-1-carboxylate (CAS No. [1374658-54-4]; 1.50 eq., 229 mg, 956 μmol), tri-n-butylphosphine (CAS No. [998-40-3]; 1.6 eq., 250 μL, 1.0 mmol) and TMAD (CAS No. [10465-78-8]; 1.60 eq., 336 mg, 1.95 mmol) in toluene (6 mL) at rt overnight to give upon column chromatography ($SiO_2$, hexane/EtOAc) the title compound (219 mg, 64%).

$^1$H NMR (400 MHz, DMSO-d6) δ[ppm]: 1.53-1.60 (m, 1H), 1.75-1.90 (m, 3H), 2.47 (s, 3H), 2.81-2.91 (m, 4H), 3.20-3.27 (m, 2H), 3.58-3.64 (m, 1H), 3.73-3.79 (m, 1H), 3.91-4.05 (m, 3H), 4.30-4.37 (m, 2H), 4.62 (d, 2H), 5.05 (s, 2H), 7.30-7.38 (m, 5H), 7.53 (s, 1H), 8.00 (t, 1H).

UPLC-MS (Method 1): $R_t$=1.20 min; MS (ESIpos): m/z=523 $[M+H]^+$.

Example 156 benzyl 3-[(8-methyl-7-{[(2S)-tetrahydrofuran-2-ylmethyl]carbamoyl}-4,5-dihydro-2H-furo[2,3-g]indazol-2-yl)methyl]azetidine-1-carboxylate

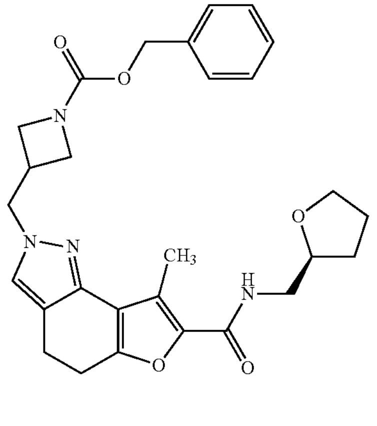 [SMILES: Cc1c(C(=O)NC[C@@H]2CCCO2)oc2c1-c1nn(CC3CN(C(=O)OCc4ccccc4)C3)cc1CC2]

According to GP C (conditions A) 8-methyl-N-[(2S)-tetrahydrofuran-2-ylmethyl]-4,5-dihydro-1H-furo[2,3-g]indazole-7-carboxamide (Intermediate 43; 1.00 eq., 233 mg, 773 μmol) from step 1 was reacted with benzyl 3-(hydroxymethyl)azetidine-1-carboxylate (CAS No. [618446-42-7]; 1.50 eq., 208 μL, 1.16 mmol), tri-n-butylphosphine (CAS No. [998-40-3]; 1.6 eq., 310 μL, 1.2 mmol) and TMAD (CAS No. [10465-78-8]; 1.60 eq., 213 mg, 1.24 mmol) in toluene (15 mL) at rt overnight to give upon column chromatography ($SiO_2$, hexane/EtOAc) the title compound (420 mg, 80% purity, 86%).

$^1$H NMR (400 MHz, DMSO-d6) δ[ppm]: 1.53-1.61 (m, 1H), 1.73-1.91 (m, 3H), 2.46 (s, 3H), 2.81-2.90 (m, 4H), 2.95-3.05 (m, 1H), 3.18-3.28 (m, 2H), 3.58-3.64 (m, 1H), 3.73-3.78 (m, 3H), 3.91-3.97 (m, 3H), 4.29 (d, 2H), 5.01 (s, 2H), 7.28-7.38 (m, 5H), 7.54 (s, 1H), 7.98 (t, 1H).

UPLC-MS (Method 1): $R_t$=1.15 min; MS (ESIpos): m/z=505 $[M+H]^+$.

Example 157

2-[(3-fluoroazetidin-3-yl)methyl]-8-methyl-N-[(2S)-tetrahydrofuran-2-ylmethyl]-4,5-dihydro-2H-furo[2,3-g]indazole-7-carboxamide

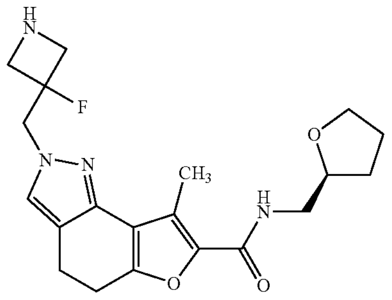 [SMILES: Cc1c(C(=O)NC[C@@H]2CCCO2)oc2c1-c1nn(CC3(F)CNC3)cc1CC2]

A stirred solution of benzyl 3-fluoro-3-[(8-methyl-7-{[(2S)-tetrahydrofuran-2-ylmethyl]carbamoyl}-4,5-dihydro-2H-furo[2,3-g]indazol-2-yl)methyl]azetidine-1-carboxylate (Example 155; 1.00 eq., 207 mg, 396 μmol) in ethanol (5 mL) was purged 3 times with argon, treated with palladium (10% on charcoal; 10 mol %, 4.2 mg, 3.9 μmol) and evacuated again. The reaction mixture was set under an atmosphere of hydrogen and stirred at room temperature overnight. As the conversion was not complete the mixture was filtered over Celite and the residue rinsed with ethanol and subsequently a mixture of ethanol and dichloromethane (1:1). The filtrate was concentrated under reduced pressure and the obtained material subjected to the hydrogenation conditions as described above and stirred overnight again. The reaction mixture was filtered over Celite and the residue rinsed with ethanol and subsequently a mixture of ethanol and dichloromethane (1:1). The filtrate was concentrated under reduced pressure to give the crude title compound (189 mg, 78% purity, 99%). A small amount of crude product (28 mg) was subjected to preparative HPLC to give an analytically pure fraction (5.8 mg).

$^1$H NMR (400 MHz, DMSO-d6) δ[ppm]: 1.53-1.61 (m, 1H), 1.75-1.91 (m, 3H), 2.48 (s, 3H), 2.83-2.91 (m, 4H), 3.18-3.28 (m, 2H), 3.49-3.64 (m, 5H), 3.73-3.79 (m, 1H), 3.91-3.98 (m, 1H), 4.50 (s, 1H), 4.56 (s, 1H), 7.47 (s, 1H), 7.99 (t, 1H).

LC-MS (Method A): $R_t$=0.89 min; MS (ESIpos): m/z=389 [M+H]$^+$.

Example 158

2-(azetidin-3-ylmethyl)-8-methyl-N-[(2S)-tetrahydrofuran-2-ylmethyl]-4,5-dihydro-2H-furo[2,3-g]indazole-7-carboxamide

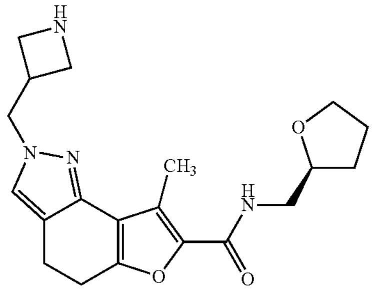 [SMILES: Cc1c(C(=O)NC[C@@H]2CCCO2)oc2c1-c1nn(CC3CNC3)cc1CC2]

In analogy to Example 157 benzyl 3-[(8-methyl-7-{[(2S)-tetrahydrofuran-2-ylmethyl]carbamoyl}-4,5-dihydro-2H-furo[2,3-g]indazol-2-yl)methyl]azetidine-1-carboxylate (Example 156; 1.00 eq., 350 mg, 694 μmol) was hydrogenated in the presence of palladium (10% on charcoal; 10 mol %, 7.4 mg, 7.0 μmol) and aqueous hydrochloric acid (1 N, 500 μL) in ethanol (6 mL) at room temperature to give upon column chromatography (Si—NH $SiO_2$, DCM/MeOH) the title compound (105 mg, 43%).

$^1$H NMR (400 MHz, DMSO-d6) δ[ppm]: 1.53-1.61 (m, 1H), 1.74-1.91 (m, 3H), 2.46 (s, 3H), 2.81-2.90 (m, 4H), 2.95-3.02 (m, 1H), 3.18-3.28 (m, 4H), 3.46-3.50 (m, 1H), 3.58-3.64 (m, 2H), 3.73-3.78 (m, 1H), 3.84 (t, 1H), 3.91-3.97 (m, 1H), 4.24 (d, 2H), 7.49 (s, 1H), 7.97 (t, 1H).

UPLC-MS (Method 1): $R_t$=0.86 min; MS (ESIpos): m/z=371 [M+H]$^+$.

Example 159

2-(azetidin-3-ylmethyl)-N-[(2R)-1,4-dioxan-2-ylmethyl]-8-methyl-4,5-dihydro-2H-furo[2,3-g]indazole-7-carboxamide

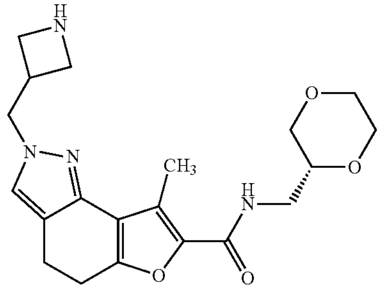 [SMILES: Cc1c(C(=O)NC[C@@H]2COCCO2)oc2c1-c1nn(CC3CNC3)cc1CC2]

A mixture of tert-butyl 3-[(7-{[(2R)-1,4-dioxan-2-ylmethyl]carbamoyl}-8-methyl-4,5-dihydro-2H-furo[2,3-g]indazol-2-yl)methyl]azetidine-1-carboxylate (Example 110; 1.0 eq., 27 mg, 56 μmol) in CPME (2 mL) was treated with hydrochloric acid (3 M in CPME; CAS No. [7647-01-0]; 10 eq., 180 μL, 550 μmol) and stirred at rt for 18 hours. The formed precipitate was filtered off and purified by preparative HPLC to give the title compound (3.7 mg, 17%).

$^1$H NMR (400 MHz, DMSO-d6) δ[ppm]: 2.46 (s, 3H), 2.81-2.89 (m, 4H), 2.94-3.01 (m, 1H), 3.14-3.29 (m, 5H), 3.41-3.57 (m, 4H), 3.59-3.65 (m, 2H), 3.68-3.74 (m, 2H), 3.82 (t, 1H), 4.24 (d, 2H), 7.49-7.53 (m, 1H), 8.05 (t, 1H).

LC-MS (Method A): $R_t$=0.81 min; MS (ESIpos): m/z=387 [M+H]$^+$.

Example 160

2-(2-aminoethyl)-8-methyl-N-[(2S)-tetrahydrofuran-2-ylmethyl]-4,5-dihydro-2H-furo[2,3-g]indazole-7-carboxamide

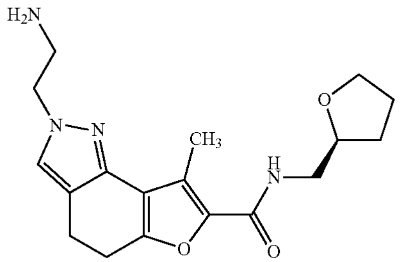 [SMILES: Cc1c(C(=O)NC[C@@H]2CCCO2)oc2c1-c1nn(CCN)cc1CC2]

A mixture of tert-butyl [2-(8-methyl-7-{[(2S)-tetrahydrofuran-2-ylmethyl]carbamoyl}-4,5-dihydro-2H-furo[2,3-g]indazol-2-yl)ethyl]carbamate (Example 139; 1.00 eq., 118 mg, 265 μmol) in dichloromethane (1.5 mL) was treated with TFA (CAS No. [76-05-1]; 10 eq., 200 μL, 2.7 mmol) and stirred at rt overnight. The reaction mixture was diluted with dichloromethane and saturated aqueous sodium hydrogencarbonate and the phases separated. The aqueous phase was extracted with ethyl acetate (twice), the combined organic phases were filtered with a hydrophobic filter and concentrated under reduced pressure. The obtained TFA salt was taken up with dichloromethane and treated with 10% aqueous ammonium hydroxide at rt under stirring. The phases were separated, and the organic phase concentrated under reduced pressure to give the crude title compound (52 mg, 51%) as free base.

$^1$H NMR (400 MHz, DMSO-d6) δ[ppm]: 1.53-1.61 (m, 1H), 1.78-1.89 (m, 3H), 2.47 (s, 3H), 2.82-2.91 (m, 6H), 3.18-3.27 (m, 2H), 3.58-3.64 (m, 1H), 3.73-3.79 (m, 1H), 3.91-3.98 (m, 1H), 3.99-4.05 (m, 2H), 7.49 (s, 1H), 7.97 (t, 1H).

UPLC-MS (Method 1): $R_t$=0.82 min; MS (ESIpos): m/z=345 [M+H]$^+$.

Example 161

2-(2-aminoethyl)-N-[(2R)-1,4-dioxan-2-ylmethyl]-8-methyl-4,5-dihydro-2H-furo[2,3-g]indazole-7-carboxamide

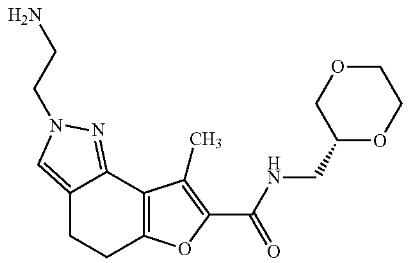 [SMILES: Cc1c(C(=O)NC[C@@H]2COCCO2)oc2c1-c1nn(CCN)cc1CC2]

In analogy to Example 160 tert-butyl [2-(7-{[(2R)-1,4-dioxan-2-ylmethyl]carbamoyl}-8-methyl-4,5-dihydro-2H-furo[2,3-g]indazol-2-yl)ethyl]carbamate (Example 140; 1.0 eq., 64 mg, 139 μmol) was reacted with TFA (CAS No. [76-05-1]; 10 eq., 110 μL, 1.4 mmol) in dichloromethane (1 mL) at rt overnight to give upon work-up the crude title compound (21 mg, 38%).

$^1$H NMR (400 MHz, DMSO-d6) δ[ppm]: 2.47 (s, 3H), 2.83-2.92 (m, 6H), 3.15-3.25 (m, 3H), 3.44 (dt, 1H), 3.54 (dt, 1H), 3.59-3.65 (m, 2H), 3.68-3.74 (m, 2H), 4.03 (t, 2H), 7.49 (s, 1H), 8.05 (t, 1H).

UPLC-MS (Method 1): $R_t$=0.75 min; MS (ESIpos): m/z=361 [M+H]$^+$.

Example 162

8-methyl-2-[2-(piperazin-1-yl)ethyl]-N-[(2S)-tetrahydrofuran-2-ylmethyl]-4,5-dihydro-2H-furo[2,3-g]indazole-7-carboxamide

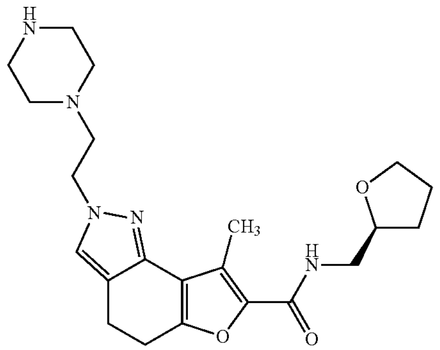 [SMILES: Cc1c(C(=O)NC[C@@H]2CCCO2)oc2c1-c1nn(CCN3CCNCC3)cc1CC2]

In analogy to Example 160 tert-butyl 4-[2-(8-methyl-7-{[(2S)-tetrahydrofuran-2-ylmethyl]carbamoyl}-4,5-dihydro-2H-furo[2,3-g]indazol-2-yl)ethyl]piperazine-1-carboxylate (Example 141; 1.00 eq., 215 mg, 419 μmol) was reacted with TFA (CAS No. [76-05-1]; 10 eq., 320 μL, 4.2 mmol) in dichloromethane (2.5 mL) at rt overnight to give upon work-up the crude title compound (82 mg, 40%).

$^1$H NMR (400 MHz, DMSO-d6) δ[ppm]: 1.53-1.61 (m, 1H), 1.76-1.90 (m, 3H), 2.35 (br. s., 4H), 2.47 (s, 3H), 2.60-2.69 (m, 6H), 2.81-2.90 (m, 4H), 3.18-3.27 (m, 2H), 3.57-3.64 (m, 1H), 3.71-3.80 (m, 1H), 3.91-3.97 (m, 1H), 4.15 (t, 2H), 7.50 (s, 1H), 7.97 (t, 1H).

UPLC-MS (Method 1): $R_t$=0.86 min; MS (ESIpos): m/z=414 [M+H]$^+$.

Example 163

N-[(2R)-1,4-dioxan-2-ylmethyl]-8-methyl-2-[2-(piperazin-1-yl)ethyl]-4,5-dihydro-2H-furo[2,3-g]indazole-7-carboxamide

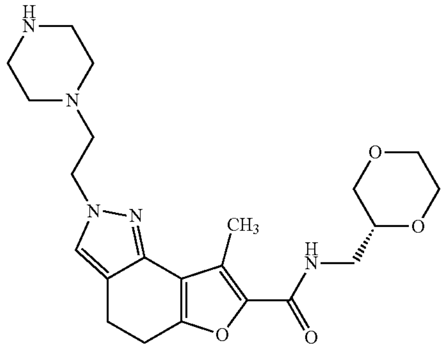 [SMILES: Cc1c(C(=O)NC[C@@H]2COCCO2)oc2c1-c1nn(CCN3CCNCC3)cc1CC2]

In analogy to Example 160 tert-butyl 4-[2-(7-{[(2R)-1,4-dioxan-2-ylmethyl]carbamoyl}-8-methyl-4,5-dihydro-2H-furo[2,3-g]indazol-2-yl)ethyl]piperazine-1-carboxylate (Example 142; 1.00 eq., 151 mg, 285 μmol) was reacted with TFA (CAS No. [76-05-1]; eq., 220 μL, 2.9 mmol) in dichloromethane (1.5 mL) at rt overnight to give upon work-up the crude title compound (30 mg, 21%).

$^1$H NMR (400 MHz, DMSO-d6) δ[ppm]: 2.35 (br. s., 4H), 2.47 (s, 3H), 2.62-2.69 (m, 6H), 2.81-2.91 (m, 4H), 3.16-3.26 (m, 3H), 3.45 (dt, 1H), 3.54 (dt, 1H), 3.59-3.65 (m, 2H), 3.68-3.74 (m, 2H), 4.15 (t, 2H), 7.51 (s, 1H), 8.05 (t, 1H).

UPLC-MS (Method 1): $R_t$=0.76 min; MS (ESIpos): m/z=430 [M+H]$^+$.

Example 164

2-[(1-acetylazetidin-3-yl)methyl]-8-methyl-N-[(2S)-tetrahydrofuran-2-ylmethyl]-4,5-dihydro-2H-furo[2,3-g]indazole-7-carboxamide

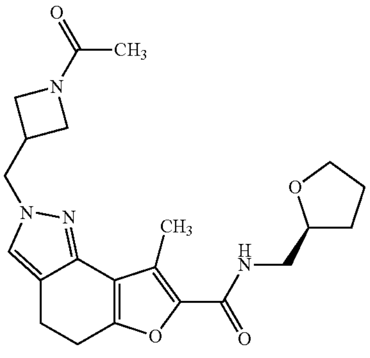 [SMILES: CC(=O)N1CC(Cn2cc3c(n2)-c2c(oc(C(=O)NC[C@@H]4CCCO4)c2C)CC3)C1]

A solution of 2-(azetidin-3-ylmethyl)-8-methyl-N-[(2S)-tetrahydrofuran-2-ylmethyl]-4,5-dihydro-2H-furo[2,3-g]indazole-7-carboxamide (Example 158; 1.00 eq., 60.0 mg, 162 μmol) in dichloromethane (2 mL) was treated with acetyl chloride (CAS no. [75-36-5]; 1.0 eq., 12 μL, 160 μmol) and triethylamine (1.5 eq., 34 μL, 240 μmol) and stirred at rt for 5 hours. The reaction mixture was quenched with water and ethyl acetate. The phases were separated, and the aqueous phase extracted with ethyl acetate. The combined organic phases were filtered with a hydrophobic filter, concentrated under reduced pressure and the obtained material subjected to preparative HPLC to give the title compound (1.6 mg, 2%).

LC-MS (Method A): $R_t$=0.88 min; MS (ESIpos): m/z=413 [M+H]$^+$.

Example 165

2-[(1-acetyl-3-fluoroazetidin-3-yl)methyl]-8-methyl-N-[(2S)-tetrahydrofuran-2-ylmethyl]-4,5-dihydro-2H-furo[2,3-g]indazole-7-carboxamide

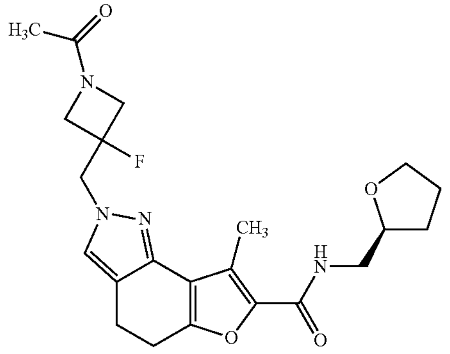 [SMILES: CC(=O)N1CC(F)(Cn2cc3c(n2)-c2c(oc(C(=O)NC[C@@H]4CCCO4)c2C)CC3)C1]

A solution of 2-[(3-fluoroazetidin-3-yl)methyl]-8-methyl-N-[(2S)-tetrahydrofuran-2-ylmethyl]-4,5-dihydro-2H-furo[2,3-g]indazole-7-carboxamide (Example 157; 1.00 eq., 53.0 mg, 136 μmol) in DMF (1.5 mL) was treated with acetyl chloride (CAS no. [75-36-5]; 1.0 eq., 10 μL, 140 μmol) and triethylamine (1.5 eq., 29 μL, 200 μmol) and stirred at rt for 3 hours. The reaction mixture was quenched with water and ethyl acetate. The phases were separated, and the aqueous phase extracted with ethyl acetate. The combined organic phases were filtered with a hydrophobic filter, concentrated under reduced pressure and the obtained material subjected to preparative HPLC to give the title compound (14 mg, 22%).

$^1$H NMR (400 MHz, DMSO-d6) δ[ppm]: 1.53-1.61 (m, 1H), 1.75-1.90 (m, 6H), 2.48 (s, 3H), 2.83-2.92 (m, 4H), 3.18-3.27 (m, 2H), 3.58-3.64 (m, 1H), 3.73-3.79 (m, 1H), 3.82-3.98 (m, 2H), 4.18-4.28 (m, 2H), 4.41-4.50 (m, 1H), 4.59 (s, 1H), 4.65 (s, 1H), 7.53 (s, 1H), 8.00 (t, 1H).

LC-MS (Method A): $R_t$=0.92 min; MS (ESIpos): m/z=431 [M+H]$^+$.

Example 166

2-{[3-fluoro-1-(methylsulfonyl)azetidin-3-yl]methyl}-8-methyl-N-[(2S)-tetrahydrofuran-2-ylmethyl]-4,5-dihydro-2H-furo[2,3-g]indazole-7-carboxamide

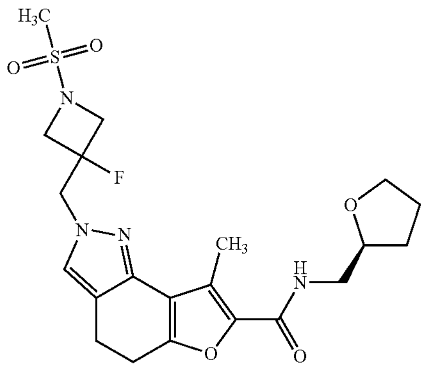 [SMILES: Cc1c(C(=O)NC[C@@H]2CCCO2)oc2c1-c1nn(CC3(F)CN(S(C)(=O)=O)C3)cc1CC2]

A solution of 2-[(3-fluoroazetidin-3-yl)methyl]-8-methyl-N-[(2S)-tetrahydrofuran-2-ylmethyl]-4,5-dihydro-2H-furo[2,3-g]indazole-7-carboxamide (Example 157; 1.00 eq., 53.0 mg, 136 μmol) in DMF (1.5 mL) was treated with methanesulfonyl chloride (CAS no. [124-63-0]; 1.0 eq., 11 μL, 140 μmol) and triethylamine (1.5 eq., 29 μL, 200 μmol) and stirred at rt for 3 hours. The reaction mixture was quenched with water and ethyl acetate. The phases were separated, and the aqueous phase extracted with ethyl acetate. The combined organic phases were filtered with a hydrophobic filter, concentrated under reduced pressure and the obtained material subjected to preparative HPLC to give the title compound (12 mg, 18%).

$^1$H NMR (400 MHz, DMSO-d6) δ[ppm]: 1.53-1.61 (m, 1H), 1.76-1.91 (m, 3H), 2.48 (s, 3H), 2.83-2.92 (m, 4H), 3.08 (s, 3H), 3.21-3.25 (m, 2H), 3.58-3.64 (m, 1H), 3.73-3.79 (m, 1H), 3.91-3.98 (m, 1H), 4.05-4.13 (m, 2H), 4.19-4.26 (m, 2H), 4.59 (s, 1H), 4.64 (s, 1H), 7.56 (s, 1H), 8.00 (t, 1H).

LC-MS (Method A): $R_t$=0.98 min; MS (ESIpos): m/z=467 [M+H]$^+$.

Example 167 methyl 3-fluoro-3-[(8-methyl-7-{[(2S)-tetrahydro-furan-2-ylmethyl]carbamoyl}-4,5-dihydro-2H-furo[2,3-g]indazol-2-yl)methyl]azetidine-1-carboxylate

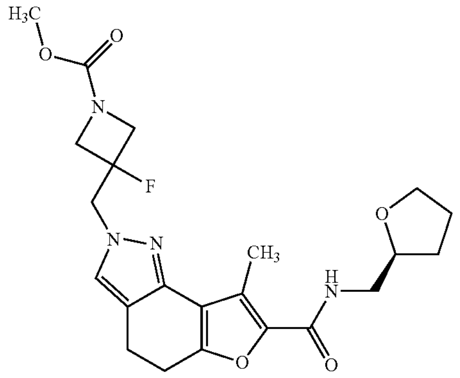 [SMILES: COC(=O)N1CC(F)(Cn2cc3c(n2)-c2c(oc(C(=O)NC[C@@H]4CCCO4)c2C)CC3)C1]

A solution of 2-[(3-fluoroazetidin-3-yl)methyl]-8-methyl-N-[(2S)-tetrahydrofuran-2-ylmethyl]-4,5-dihydro-2H-furo[2,3-g]indazole-7-carboxamide (Example 157; 1.00 eq., 53.0 mg, 136 μmol) in DMF (1.5 mL) was treated with methyl carbonochloridoate (CAS no. [79-22-1]; 1.0 eq., 11 μL, 140 μmol) and triethylamine (1.5 eq., 29 μL, 200 μmol) and stirred at rt for 3 hours. The reaction mixture was quenched with water and ethyl acetate. The phases were separated, and the aqueous phase extracted with ethyl acetate. The combined organic phases were filtered with a hydrophobic filter, concentrated under reduced pressure and the obtained material subjected to preparative HPLC to give the title compound (9.5 mg, 15%).

$^1$H NMR (400 MHz, DMSO-d6) δ[ppm]: 1.53-1.61 (m, 1H), 1.76-1.91 (m, 3H), 2.47 (s, 3H), 2.83-2.92 (m, 4H), 3.18-3.28 (m, 2H), 3.57-3.64 (m, 4H), 3.73-3.79 (m, 1H), 3.91-4.03 (m, 3H), 4.26-4.33 (m, 2H), 4.58 (s, 1H), 4.64 (s, 1H), 7.52 (s, 1H), 8.00 (t, 1H).

LC-MS (Method A): $R_t$=1.01 min; MS (ESIpos): m/z=447 [M+H]$^+$.

Example 168

2'-[(2S)-1,4-dioxan-2-ylmethyl]-N-[(2S)-tetrahydro-furan-2-ylmethyl]-8'-(trifluoromethyl)-2',5'-dihydrospiro[cyclopropane-1,4'-furo[2,3-g]indazole]-7'-carboxamide

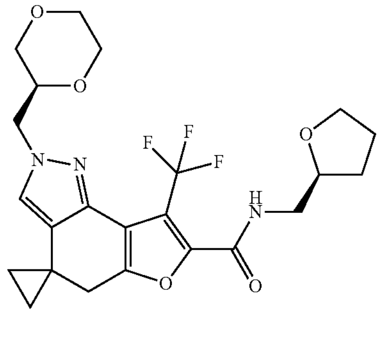 [SMILES: O=C(NC[C@@H]1CCCO1)c1oc2c(c1C(F)(F)F)-c1nn(C[C@H]3COCCO3)cc1C1(CC1)C2]

According to GP G (conditions A) 2'-{[(2S)-1,4-dioxan-2-yl]methyl}-8'-(trifluoromethyl)-2',5'-dihydrospiro[cyclopropane-1,4'-furo[2,3-g]indazole]-7'-carboxylic acid (Intermediate 50; 1.0 eq., 45 mg, 110 μmol) was reacted with 1-[(2S)-tetrahydrofuran-2-yl]methanamine (CAS No. [7175-81-7]; 1.5 eq., 17 μL, 170 μmol), HATU (CAS No. [148893-10-1]; 1.5 eq., 64 mg, 170 μmol) and N,N-diisopropylethylamine (CAS No. [7087-68-5]; 3.0 eq., 59 μL, 340 μmol) in DMF (1.5 mL) at rt for 5 days to give upon preparative HPLC the title compound (26 mg, 45%).

$^1$H NMR (400 MHz, DMSO-d6) δ[ppm]: 0.80-0.91 (m, 4H), 1.54-1.60 (m, 1H), 1.77-1.94 (m, 3H), 2.86-2.96 (m, 2H), 3.22-3.29 (m, 3H), 3.43 (dt, 1H), 3.53 (dt, 1H), 3.60-3.65 (m, 2H), 3.71-3.83 (m, 4H), 3.83-3.98 (m, 1H), 4.00-4.10 (m, 2H), 7.35 (s, 1H), 8.72 (t, 1H).

$^{19}$F NMR (377 MHz, DMSO-d6) δ[ppm]: −55.15 (s, 3F).

UPLC-MS (Method 1): $R_t$=1.09 min; MS (ESIpos): m/z=482 [M+H]$^+$.

Example 169

N-{[(2R)-1,4-dioxan-2-yl]methyl}-2'-{[(2S)-1,4-dioxan-2-yl]methyl}-8'-(trifluoromethyl)-2',5'-dihydrospiro[cyclopropane-1,4'-furo[2,3-g]indazole]-7'-carboxamide

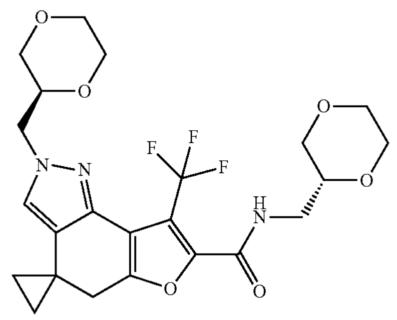 [SMILES: O=C(NC[C@@H]1COCCO1)c1oc2c(c1C(F)(F)F)-c1nn(C[C@H]3COCCO3)cc1C1(CC1)C2]

According to GP G (conditions A) 2'-{[(2S)-1,4-dioxan-2-yl]methyl}-8'-(trifluoromethyl)-2',5'-dihydrospiro[cyclopropane-1,4'-furo[2,3-g]indazole]-7'-carboxylic acid (Intermediate 50; 1.0 eq., 45 mg, 110 μmol) was reacted with 1-[(2R)-1,4-dioxan-2-yl]methanamine hydrochloride (1:1) (CAS No. [1523541-84-5]; 1.2 eq., 21 mg, 140 μmol), HATU (CAS No. [148893-10-1]; 1.5 eq., 64 mg, 170 μmol) and N,N-diisopropylethylamine (CAS No. [7087-68-5]; 3.0 eq., 59 μL, 340 μmol) in DMF (1.5 mL) at rt for 5 days to give upon preparative HPLC the title compound (29 mg, 50%).

$^1$H NMR (400 MHz, DMSO-d6) δ[ppm]: 0.80-0.92 (m, 4H), 2.86-2.96 (m, 2H), 3.19-3.30 (m, 4H), 3.40-3.48 (m, 2H), 3.50-3.58 (m, 2H), 3.58-3.66 (m, 3H), 3.70-3.75 (m, 4H), 3.80-3.84 (m, 1H), 4.00-4.10 (m, 2H), 7.35 (s, 1H), 8.76 (t, 1H).

$^{19}$F NMR (377 MHz, DMSO-d6) δ[ppm]: −54.99 (s, 3F).

UPLC-MS (Method 1): $R_t$=1.00 min; MS (ESIpos): m/z=498 [M+H]$^+$.

TABLE 4

| The following examples (170 to 211) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| 170 | 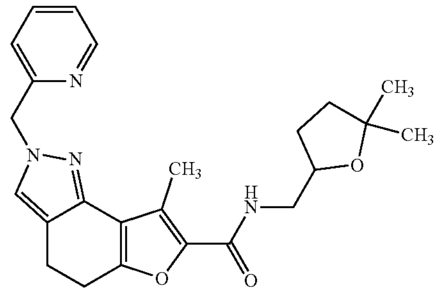 N-{[(2±)-5,5-dimethyloxolan-2-yl]methyl}-8-methyl-2-[(pyridin-2-yl)methyl]-4,5-dihydro-2H-furo[2,3-g]indazole-7-carboxamide | $^1$H-NMR (400 MHz, DMSO-d6) δ [ppm]: 0.863 (0.47), 0.881 (1.20), 0.899 (0.59), 1.139 (12.49), 1.151 (1.29), 1.200 (12.39), 1.219 (1.24), 1.234 (0.41), 1.649 (0.56), 1.657 (0.70), 1.673 (2.40), 1.679 (3.40), 1.683 (3.55), 1.702 (0.89), 1.718 (0.43), 1.723 (0.43), 1.937 (0.42), 1.951 (0.74), 1.961 (0.46), 1.973 (0.63), 2.338 (0.85), 2.442 (16.00), 2.520 (8.44), 2.525 (5.93), 2.680 (0.80), 2.743 (1.44), 2.885 (2.85), 2.892 (8.97), 2.899 (3.06), 3.205 (0.93), 3.215 (1.01), 3.221 (1.75), 3.229 (1.73), 3.236 (1.04), 3.244 (0.99), 4.009 (0.74), 4.024 (0.98), 4.039 (0.59), 5.384 (6.36), 5.807 (0.54), 7.060 (1.75), 7.080 (1.82), 7.291 (0.87), 7.294 (0.91), 7.303 (0.91), 7.306 (0.98), 7.312 (1.24), 7.322 (1.05), 7.325 (0.96), 7.335 (0.46), 7.635 (5.02), 7.752 (1.05), 7.757 (1.10), 7.761 (0.45), 7.771 (1.83), 7.776 (1.88), 7.790 (1.00), 7.795 (0.98), 7.903 (0.67), 7.918 (1.40), 7.933 (0.66), 8.529 (1.11), 8.531 (1.31), 8.534 (1.31), 8.536 (1.27), 8.541 (1.25), 8.543 (1.41), 8.546 (1.28), 8.548 (1.22), 8.637 (0.60). LC-MS (Method 1): $R_t$ = 1.15 min; MS (ESIpos): m/z = 421 $[M + H]^+$ | Intermediate 2 GP H Conditions B 2 mg, 1% yield, 95% purity Racemate |
| 171 | 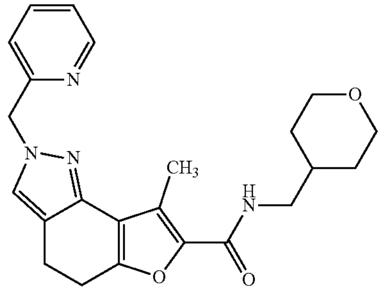 8-methyl-N-[(oxan-4-yl)methyl]-2-[(pyridin-2-yl)methyl]-4,5-dihydro-2H-furo[2,3-g]-indazole-7-carboxamide | $^1$H-NMR (400 MHz, DMSO-d6) δ [ppm]: −0.003 (8.00), 1.111 (0.46), 1.130 (0.97), 1.141 (1.10), 1.162 (1.17), 1.173 (1.06), 1.192 (0.53), 1.203 (0.47), 1.531 (1.51), 1.564 (1.25), 1.729 (0.40), 1.739 (0.44), 1.749 (0.51), 1.758 (0.61), 1.767 (0.46), 2.306 (0.69), 2.404 (0.71), 2.438 (16.00), 2.522 (2.75), 2.673 (0.72), 2.880 (4.00), 2.888 (9.86), 2.895 (3.71), 3.063 (1.85), 3.079 (2.92), 3.096 (1.69), 3.207 (1.10), 3.211 (1.25), 3.236 (2.26), 3.240 (2.27), 3.265 (1.38), 3.808 (1.45), 3.815 (1.43), 3.837 (1.34), 3.843 (1.25), 5.380 (7.22), 7.056 (1.87), 7.076 (1.96), 7.289 (0.99), 7.291 (1.00), 7.303 (1.12), 7.308 (1.16), 7.320 (1.09), 7.629 (5.18), 7.749 (1.12), 7.754 (1.09), 7.769 (1.84), 7.773 (1.82), 7.788 (0.95), 7.792 (0.91), 8.116 (0.75), 8.132 (1.55), 8.146 (0.72), 8.529 (1.52), 8.531 (1.54), 8.541 (1.48), 8.543 (1.44). LC-MS (Method 1): $R_t$ = 0.98 min; MS (ESIneg): m/z = 405 $[M - H]^-$ | Intermediate 2 GP H Conditions B 30 mg, 22% yield, 95% purity |
| 172 | 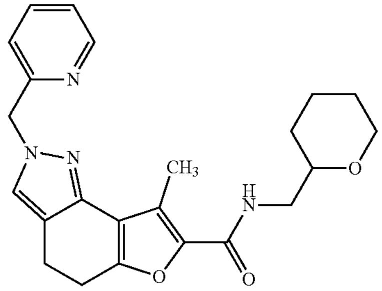 8-methyl-N-{[(2±)-oxan-2-yl]methyl}-2-[(pyridin-2-yl)methyl]-4,5-dihydro-2H-furo[2,3-g]indazole-7-carboxamide | $^1$H-NMR (400 MHz, DMSO-d6) δ [ppm]: 0.932 (1.90), 0.948 (1.85), 1.103 (0.28), 1.108 (0.28), 1.132 (0.49), 1.144 (0.36), 1.149 (0.33), 1.408 (0.86), 1.410 (0.86), 1.415 (0.89), 1.425 (1.27), 1.536 (0.48), 1.539 (0.43), 1.565 (0.39), 1.568 (0.41), 1.741 (0.48), 1.745 (0.45), 1.747 (0.47), 1.750 (0.51), 1.754 (0.51), 1.765 (0.37), 2.331 (4.37), 2.404 (8.20), 2.522 (16.00), 2.669 (5.89), 2.673 (4.34), 2.788 (0.39), 2.798 (0.51), 2.807 (1.40), 2.824 (1.28), 2.852 (1.35), 2.870 (1.47), 2.877 (0.46), 2.879 (0.52), 3.155 (0.63), 3.165 (0.72), 3.171 (1.07), 3.179 (1.09), 3.187 (0.81), 3.193 (0.74), 3.828 (0.46), 3.834 (0.54), 3.855 (0.45), 3.864 (0.44), 5.619 (3.04), 6.806 (0.98), 6.825 (0.97), 7.261 (0.53), 7.275 (0.60), 7.280 (0.57), 7.293 (0.58), 7.422 (3.27), 7.710 (0.57), 7.715 (0.55), 7.730 (0.95), 7.735 (0.91), 7.749 (0.47), 7.754 (0.50), 8.035 (0.83), 8.520 (0.80), | Intermediate 2 GP H Conditions B 1.3 mg, 1% yield, 95% purity Racemate |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| | | 8.522 (0.82), 8.524 (0.78), 8.532 (0.87), 8.534 (0.82), 8.545 (0.87). LC-MS (Method 1): $R_t$ = 1.09 min; MS (ESIpos): m/z = 407 $[M + H]^+$ | |
| 173 | 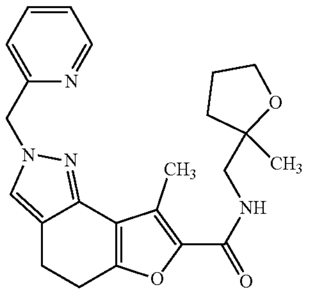 8-methyl-N-{[(2±)-2-methyloxolan-2-yl]methyl}-2-[(pyridin-2-yl)methyl]-4,5-dihydro-2H-furo[2,3-g]indazole-7-carboxamide | $^1$H-NMR (400 MHz, DMSO-d6) δ [ppm]: 0.934 (0.66), 0.951 (0.67), 1.100 (0.73), 1.119 (13.39), 1.518 (0.61), 1.529 (0.76), 1.536 (0.81), 1.549 (0.63), 1.829 (0.41), 1.845 (1.15), 1.855 (2.27), 1.862 (2.14), 1.868 (2.50), 1.875 (1.78), 1.884 (1.17), 2.334 (1.63), 2.338 (0.73), 2.412 (0.72), 2.448 (16.00), 2.520 (7.88), 2.525 (5.08), 2.676 (1.67), 2.680 (0.74), 2.866 (0.46), 2.885 (2.62), 2.895 (4.63), 2.899 (4.89), 2.910 (3.13), 3.233 (1.92), 3.240 (1.80), 3.248 (1.77), 3.256 (1.85), 3.722 (1.55), 3.738 (2.82), 3.754 (1.43), 5.385 (6.60), 7.057 (1.74), 7.077 (1.81), 7.294 (0.91), 7.306 (0.99), 7.310 (1.02), 7.322 (0.95), 7.325 (0.92), 7.636 (4.92), 7.689 (0.67), 7.705 (1.40), 7.721 (0.68), 7.752 (1.04), 7.757 (1.08), 7.771 (1.79), 7.776 (1.80), 7.790 (0.92), 7.795 (0.89), 8.530 (1.14), 8.532 (1.34), 8.534 (1.36), 8.537 (1.20), 8.542 (1.12), 8.544 (1.30), 8.546 (1.23), 8.549 (1.10). LC-MS (Method 1): $R_t$ = 1.08 min; MS (ESIneg): m/z = 405 $[M - H]^-$ | Intermediate 2 GP H Conditions B 29 mg, 21% yield, 95% purity Racemate |
| 174 | 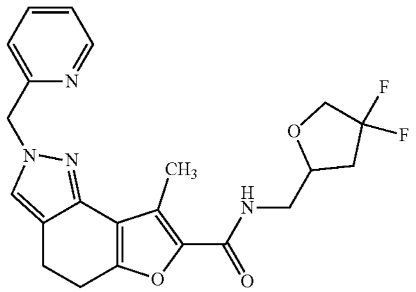 N-{[(2±)-4,4-difluorooxolan-2-yl]methyl}-8-methyl-2-[(pyridin-2-yl)methyl]-4,5-dihydro-2H-furo[2,3-g]indazole-7-carboxamide | $^1$H-NMR (400 MHz, DMSO-d6) δ [ppm]: 0.882 (0.64), 2.334 (1.13), 2.338 (0.49), 2.447 (16.00), 2.520 (5.45), 2.525 (3.48), 2.539 (0.61), 2.680 (0.50), 2.888 (2.67), 2.896 (7.77), 2.905 (3.08), 3.357 (1.39), 3.371 (0.67), 3.406 (0.52), 3.422 (0.98), 3.438 (0.73), 3.456 (0.52), 3.792 (0.46), 3.819 (0.63), 3.823 (0.60), 3.831 (0.46), 3.850 (0.62), 3.857 (0.63), 3.889 (0.52), 4.009 (0.44), 4.038 (1.15), 4.067 (1.03), 4.253 (0.64), 4.270 (0.94), 4.287 (0.58), 5.385 (6.33), 7.063 (1.70), 7.083 (1.77), 7.292 (0.89), 7.294 (0.88), 7.304 (0.92), 7.306 (0.95), 7.311 (1.01), 7.313 (0.93), 7.323 (0.99), 7.325 (0.91), 7.638 (4.94), 7.753 (1.09), 7.757 (1.10), 7.772 (1.78), 7.776 (1.72), 7.791 (0.93), 7.796 (0.92), 8.166 (0.65), 8.181 (1.39), 8.196 (0.65), 8.530 (1.14), 8.532 (1.28), 8.534 (1.32), 8.536 (1.17), 8.542 (1.21), 8.544 (1.30), 8.546 (1.25), 8.548 (1.08). LC-MS (Method 1): $R_t$ = 1.06 min; MS (ESIpos): m/z = 429 $[M + H]^+$ | Intermediate 2 GP H Conditions B 33 mg, 23% yield, 95% purity Racemate |
| 175 | 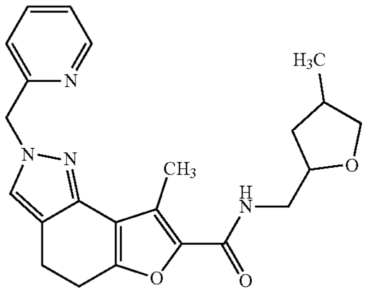 8-methyl-N-[(4-methyltetrahydrofuran-2-yl)-methyl]-2-(2-pyridylmethyl)-4,5-dihydrofuro-[2,3-g]indazole-7-carboxamide | $^1$H-NMR (400 MHz, DMSO-d6) δ [ppm]: 0.956 (1.90), 0.972 (2.18), 0.979 (6.50), 0.996 (6.72), 1.116 (0.43), 1.138 (0.80), 1.147 (0.50), 1.160 (0.48), 1.169 (0.83), 1.190 (0.47), 1.460 (0.11), 1.478 (0.18), 1.491 (0.14), 1.496 (0.13), 1.509 (0.22), 1.527 (0.14), 1.775 (0.12), 1.789 (0.12), 1.794 (0.14), 1.808 (0.16), 1.819 (0.11), 1.825 (0.12), 1.839 (0.12), 2.062 (0.35), 2.080 (0.57), 2.097 (0.55), 2.111 (0.57), 2.127 (0.45), 2.204 (0.32), 2.224 (0.48), 2.242 (0.47), 2.262 (0.33), 2.332 (0.68), 2.439 (16.00), 2.518 (3.03), 2.523 (2.10), 2.594 (0.19), 2.673 (0.68), 2.740 (0.21), 2.882 (2.93), 2.889 (8.94), 2.896 (3.14), 3.138 (0.27), 3.159 (0.35), 3.177 (0.30), 3.195 (0.35), 3.211 (0.67), 3.222 (1.25), 3.242 (2.27), 3.262 (2.15), 3.276 (1.85), | Intermediate 2 GP H Conditions B 29 mg, 21% yield, 95% purity Mixture of four isomers |

TABLE 4-continued

| Example | Structure IUPAC-Name | Analytical Data | Preparation or Separation Methods |
|---|---|---|---|
| The following examples (170 to 211) were prepared in analogy to example 3 starting from the given intermediates and commercially available amines (or their salts), applying the indicated general procedure. | | | |
| | | 3.294 (1.09), 3.750 (1.04), 3.769 (1.44), 3.788 (0.97), 3.863 (0.28), 3.880 (0.32), 3.900 (0.25), 3.934 (0.22), 3.950 (0.65), 3.965 (0.67), 3.971 (0.67), 3.981 (0.29), 3.986 (0.57), 4.002 (0.19), 4.026 (0.16), 4.041 (0.18), 4.045 (0.17), 4.059 (0.14), 5.382 (6.26), 7.058 (1.60), 7.078 (1.66), 7.289 (0.87), 7.291 (0.84), 7.300 (0.89), 7.303 (0.93), 7.307 (1.01), 7.310 (0.95), 7.319 (0.99), 7.632 (5.02), 7.749 (1.08), 7.754 (1.05), 7.769 (1.71), 7.773 (1.77), 7.788 (0.95), 7.792 (0.94), 7.957 (0.66), 7.972 (1.39), 7.986 (0.64), 8.527 (1.10), 8.529 (1.29), 8.532 (1.29), 8.534 (1.15), 8.539 (1.14), 8.541 (1.29), 8.544 (1.22), 8.546 (1.05). LC-MS (Method 1): $R_t$ = 1.07 min; MS (ESIpos): m/z = 407 $[M + H]^+$ | |
| 176 | 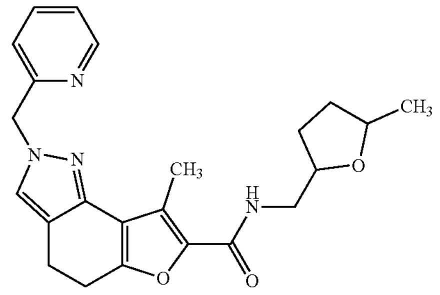 8-methyl-N-{[(2±,5±)-5-methyloxolan-2-yl]-methyl}-2-[(pyridin-2-yl)methyl]-4,5-dihydro-2H-furo[2,3-g]indazole-7-carboxamide | $^1$H-NMR (400 MHz, DMSO-d6) δ [ppm]: 1.104 (1.59), 1.120 (1.62), 1.153 (7.15), 1.168 (7.28), 1.351 (0.48), 1.370 (0.60), 1.389 (0.45), 1.399 (0.45), 1.417 (0.26), 1.565 (0.11), 1.576 (0.09), 1.582 (0.12), 1.597 (0.14), 1.606 (0.26), 1.618 (0.33), 1.621 (0.29), 1.634 (0.46), 1.640 (0.31), 1.649 (0.48), 1.652 (0.41), 1.659 (0.40), 1.663 (0.41), 1.668 (0.27), 1.675 (0.33), 1.821 (0.24), 1.840 (0.50), 1.861 (0.76), 1.873 (0.44), 1.878 (0.49), 1.890 (0.71), 1.896 (0.84), 1.904 (0.63), 1.911 (0.57), 1.913 (0.56), 1.925 (0.50), 1.928 (0.48), 1.932 (0.38), 1.933 (0.36), 1.939 (0.39), 1.946 (0.34), 1.949 (0.30), 1.961 (0.28), 1.968 (0.16), 1.974 (0.14), 1.981 (0.15), 1.986 (0.12), 1.990 (0.13), 1.996 (0.11), 2.000 (0.07), 2.004 (0.11), 2.010 (0.08), 2.014 (0.07), 2.025 (0.07), 2.443 (16.00), 2.520 (2.07), 2.525 (1.40), 2.885 (2.97), 2.892 (8.72), 2.899 (3.06), 3.206 (0.35), 3.226 (1.49), 3.241 (2.87), 3.256 (1.54), 3.847 (0.53), 3.862 (0.86), 3.877 (0.65), 3.882 (0.65), 3.897 (0.51), 3.905 (0.74), 3.920 (0.95), 3.937 (0.68), 3.952 (0.19), 4.007 (0.11), 4.023 (0.19), 4.027 (0.12), 4.038 (0.15), 4.042 (0.17), 4.056 (0.14), 4.061 (0.19), 4.077 (0.25), 4.093 (0.16), 5.384 (6.63), 7.061 (1.79), 7.080 (1.86), 7.290 (0.91), 7.293 (0.88), 7.302 (0.94), 7.306 (0.97), 7.309 (1.06), 7.321 (1.02), 7.635 (5.13), 7.752 (1.10), 7.756 (1.07), 7.771 (1.77), 7.776 (1.81), 7.790 (0.95), 7.795 (0.94), 7.944 (0.59), 7.959 (1.29), 7.974 (0.67), 8.529 (1.17), 8.531 (1.34), 8.534 (1.34), 8.536 (1.18), 8.541 (1.19), 8.543 (1.33), 8.546 (1.25), 8.548 (1.08). LC-MS (Method 1): $R_t$ = 1.07 min; MS (ESIpos): m/z = 407 $[M + H]^+$ | Intermediate 2 GP H Conditions B 39 mg, 28% yield, 95% purity mixture of trans and cis isomers |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 177 | 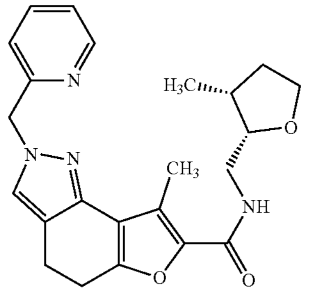 2,5-anhydro-1,3,4-trideoxy-3-methyl-1-({8-methyl-2-[(pyridin-2-yl)methyl]-4,5-dihydro-2H-furo[2,3-g]indazole-7-carbonyl}amino)-D-threo-pentitol (Racemate) | $^1$H-NMR (400 MHz, DMSO-d6) δ [ppm]: 0.928 (7.56), 0.946 (7.81), 0.957 (0.56), 1.509 (0.50), 1.513 (0.41), 1.523 (0.70), 1.527 (0.58), 1.538 (0.61), 1.543 (0.75), 1.553 (0.49), 1.557 (0.57), 2.011 (0.44), 2.016 (0.55), 2.026 (0.44), 2.029 (0.61), 2.035 (0.57), 2.041 (0.46), 2.044 (0.54), 2.050 (0.55), 2.060 (0.57), 2.065 (0.47), 2.235 (0.59), 2.253 (0.83), 2.270 (0.56), 2.334 (1.01), 2.338 (0.45), 2.441 (16.00), 2.520 (5.28), 2.525 (3.36), 2.676 (1.04), 2.680 (0.46), 2.742 (0.74), 2.883 (2.64), 2.892 (7.32), 2.901 (3.19), 3.133 (0.45), 3.140 (0.43), 3.153 (1.02), 3.166 (0.54), 3.173 (0.69), 3.187 (0.57), 3.298 (0.73), 3.313 (1.53), 3.359 (0.85), 3.583 (0.65), 3.598 (0.78), 3.603 (1.65), 3.619 (1.61), 3.624 (0.96), 3.640 (0.82), 3.792 (0.70), 3.808 (0.81), 3.813 (1.37), 3.827 (1.35), 3.832 (0.72), 3.847 (0.57), 3.862 (0.63), 3.874 (0.84), 3.883 (0.72), 3.890 (0.74), 3.897 (0.80), 3.910 (0.55), 5.384 (6.41), 7.061 (1.72), 7.081 (1.81), 7.290 (0.84), 7.294 (0.87), 7.302 (0.87), 7.306 (0.96), 7.309 (1.03), 7.312 (0.93), 7.321 (1.09), 7.325 (0.95), 7.634 (4.83), 7.752 (1.01), 7.757 (1.12), 7.771 (1.82), 7.776 (1.87), 7.790 (0.98), 7.795 (0.96), 7.822 (0.69), 7.837 (1.30), 7.851 (0.69), 8.529 (1.08), 8.531 (1.25), 8.534 (1.32), 8.536 (1.21), 8.541 (1.20), 8.543 (1.35), 8.546 (1.34), 8.548 (1.20). LC-MS (Method 1): $R_t$ = 1.08 min; MS (ESIpos): m/z = 407 $[M + H]^+$ | Intermediate 2 GP H Conditions B 15 mg, 11% yield, 92% purity Racemate |
| 178 | 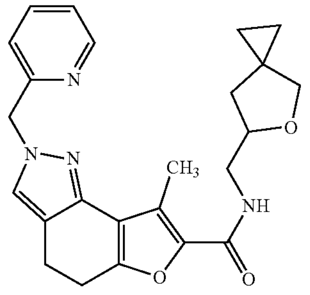 8-methyl-N-{[(6±)-5-oxaspiro[2.4]-heptan-6-yl]methyl}-2-[(pyridin-2-yl)methyl]-4,5-dihydro-2H-furo[2,3-g]indazole-7-carboxamide | $^1$H-NMR (400 MHz, DMSO-d6) δ [ppm]: 0.496 (0.58), 0.512 (1.19), 0.528 (1.19), 0.569 (0.89), 0.581 (2.01), 0.585 (1.46), 0.598 (2.72), 0.603 (2.02), 0.614 (1.35), 0.626 (1.53), 0.642 (0.91), 0.934 (0.46), 0.951 (0.47), 1.647 (0.94), 1.663 (0.97), 1.678 (1.23), 1.693 (1.23), 1.856 (1.19), 1.873 (1.35), 1.886 (1.03), 1.903 (0.95), 2.334 (0.87), 2.338 (0.41), 2.442 (16.00), 2.520 (4.59), 2.525 (2.85), 2.676 (0.87), 2.884 (3.05), 2.892 (9.13), 2.899 (3.40), 3.295 (0.45), 3.313 (1.85), 3.370 (0.54), 3.530 (1.87), 3.550 (3.24), 3.600 (3.36), 3.619 (2.00), 4.137 (1.04), 4.152 (1.52), 4.168 (1.02), 5.384 (6.73), 7.062 (1.82), 7.082 (1.89), 7.291 (0.91), 7.294 (0.92), 7.303 (0.96), 7.306 (1.01), 7.310 (1.07), 7.313 (1.01), 7.322 (1.04), 7.325 (0.99), 7.635 (5.20), 7.752 (1.09), 7.757 (1.08), 7.772 (1.77), 7.776 (1.82), 7.791 (0.96), 7.795 (0.96), 8.007 (0.72), 8.022 (1.53), 8.037 (0.72), 8.529 (1.18), 8.532 (1.33), 8.534 (1.40), 8.536 (1.20), 8.541 (1.24), 8.544 (1.39), 8.547 (1.54). LC-MS (Method 1): $R_t$ = 1.11 min; MS (ESIpos): m/z = 419 $[M + H]^+$ | Intermediate 2 GP H Conditions B 17 mg, 12% yield, 95% purity Racemate |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 179 | 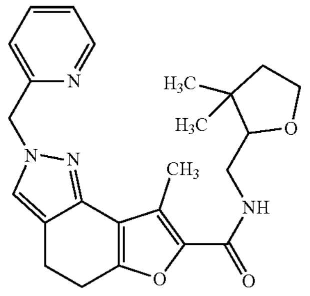 N-{[(2±)-3,3-dimethyloxolan-2-yl]-methyl}-8-methyl-2-[(pyridin-2-yl)-methyl]-4,5-dihydro-2H-furo[2,3-g]indazole-7-carboxamide | $^1$H-NMR (400 MHz, DMSO-d6) δ [ppm]: 0.938 (12.06), 1.049 (15.08), 1.685 (1.21), 1.698 (1.82), 1.704 (1.34), 1.718 (2.53), 1.737 (0.96), 2.334 (0.93), 2.338 (0.44), 2.440 (16.00), 2.520 (4.74), 2.525 (3.05), 2.676 (0.95), 2.680 (0.43), 2.883 (3.17), 2.889 (9.94), 2.896 (3.43), 3.067 (0.45), 3.080 (0.53), 3.088 (0.51), 3.101 (0.97), 3.115 (0.54), 3.122 (0.71), 3.136 (0.60), 3.365 (0.97), 3.374 (0.63), 3.383 (0.67), 3.389 (0.54), 3.398 (0.60), 3.469 (1.35), 3.479 (1.35), 3.491 (1.36), 3.500 (1.05), 3.644 (0.54), 3.657 (0.59), 3.665 (1.50), 3.677 (1.38), 3.686 (1.00), 3.698 (0.79), 3.736 (0.82), 3.755 (2.23), 3.776 (1.82), 3.795 (0.55), 5.384 (6.57), 7.058 (1.78), 7.078 (1.86), 7.290 (0.89), 7.293 (0.89), 7.302 (0.93), 7.305 (0.96), 7.309 (1.04), 7.312 (0.99), 7.322 (1.02), 7.324 (0.97), 7.634 (5.14), 7.752 (1.10), 7.756 (1.16), 7.771 (1.84), 7.775 (1.82), 7.790 (0.92), 7.795 (0.93), 7.871 (0.72), 7.885 (1.42), 7.900 (0.69), 8.529 (1.15), 8.531 (1.31), 8.534 (1.35), 8.536 (1.21), 8.541 (1.19), 8.543 (1.31), 8.546 (1.28), 8.548 (1.11). LC-MS (Method 1): $R_t$ = 1.16 min; MS (ESIpos): m/z = 421 $[M + H]^+$ | Intermediate 2 GP H Conditions B 16 mg, 11% yield, 95% purity Racemate |
| 180 | 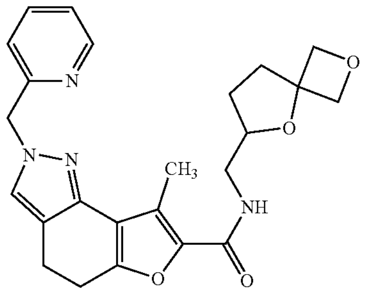 N-{[(6±)-2,5-dioxaspiro[3.4]octan-6-yl]methyl}-8-methyl-2-[(pyridin-2-yl)-methyl]-4,5-dihydro-2H-furo-[2,3-g]-indazole-7-carboxamide | $^1$H-NMR (400 MHz, DMSO-d6) δ [ppm]: 1.588 (0.60), 1.604 (0.66), 1.619 (0.76), 1.635 (0.74), 1.876 (0.45), 1.891 (0.71), 1.910 (0.76), 1.925 (0.47), 2.048 (0.48), 2.068 (0.87), 2.080 (0.83), 2.087 (0.42), 2.099 (1.51), 2.119 (0.60), 2.160 (0.66), 2.174 (0.73), 2.180 (0.75), 2.193 (0.76), 2.206 (0.46), 2.211 (0.42), 2.443 (16.00), 2.520 (4.04), 2.525 (2.63), 2.888 (2.71), 2.897 (7.12), 2.907 (3.17), 3.182 (0.85), 3.197 (1.78), 3.209 (1.77), 3.224 (0.92), 4.054 (0.92), 4.070 (1.44), 4.086 (0.90), 4.442 (1.82), 4.451 (1.78), 4.458 (2.20), 4.467 (2.25), 4.557 (2.34), 4.574 (1.87), 4.586 (2.22), 4.602 (1.73), 5.385 (6.39), 7.061 (1.75), 7.080 (1.84), 7.291 (0.94), 7.294 (0.92), 7.303 (0.98), 7.306 (1.00), 7.310 (1.08), 7.313 (1.01), 7.322 (1.07), 7.325 (1.00), 7.636 (5.14), 7.752 (1.12), 7.757 (1.16), 7.771 (1.87), 7.776 (1.84), 7.790 (0.95), 7.795 (0.96), 8.052 (0.69), 8.067 (1.48), 8.082 (0.66), 8.529 (1.17), 8.532 (1.28), 8.534 (1.38), 8.536 (1.16), 8.541 (1.24), 8.544 (1.32), 8.546 (1.32), 8.548 (1.25). LC-MS (Method 1): $R_t$ = 0.95 min; MS (ESIpos): m/z = 435 $[M + H]^+$ | Intermediate 2 GP H Conditions B 16 mg, 11% yield, 95% purity Racemate |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 181 | 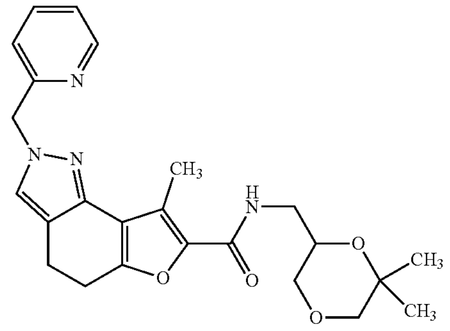 N-{[(2±)-6,6-dimethyl-1,4-dioxan-2-yl]methyl}-8-methyl-2-[(pyridin-2-yl)methyl]-4,5-dihydro-2H-furo[2,3-g]indazole-7-carboxamide | $^{1}$H-NMR (400 MHz, DMSO-d6) δ [ppm]: 0.933 (0.84), 0.950 (0.85), 1.044 (12.82), 1.060 (0.44), 1.234 (10.78), 2.441 (16.00), 2.520 (4.37), 2.524 (2.68), 2.885 (2.95), 2.892 (8.94), 2.901 (3.36), 2.989 (0.41), 3.007 (1.09), 3.035 (1.77), 3.063 (1.24), 3.096 (1.66), 3.113 (1.03), 3.126 (2.12), 3.146 (2.12), 3.161 (0.87), 3.362 (0.44), 3.426 (2.29), 3.453 (1.93), 3.709 (1.05), 3.715 (1.18), 3.737 (0.98), 3.744 (1.06), 3.875 (0.54), 3.886 (0.48), 3.895 (0.58), 5.384 (6.59), 7.058 (1.81), 7.077 (1.91), 7.290 (0.90), 7.293 (0.89), 7.302 (0.96), 7.306 (1.00), 7.309 (1.14), 7.321 (1.07), 7.324 (0.98), 7.635 (5.32), 7.752 (1.08), 7.756 (1.15), 7.771 (1.89), 7.775 (1.90), 7.790 (1.00), 7.794 (0.94), 8.032 (0.73), 8.047 (1.51), 8.063 (0.70), 8.529 (1.19), 8.531 (1.36), 8.533 (1.39), 8.536 (1.26), 8.541 (1.24), 8.543 (1.43), 8.545 (1.32), 8.548 (1.20). LC-MS (Method 1): $R_t$ = 1.07 min; MS (ESIpos): m/z = 437 $[M + H]^+$ | Intermediate 2 GP H Conditions B 18 mg, 12% yield, 95% purity Racemate |
| 182 | 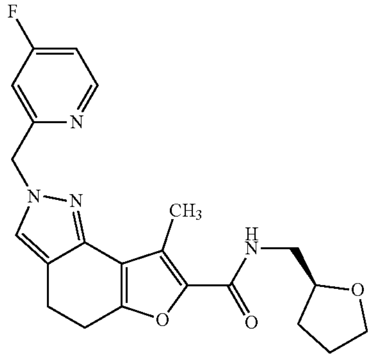 2-[(4-fluoropyridin-2-yl)methyl]-8-methyl-N-{[(2S)-oxolan-2-yl]methyl}-4,5-dihydro-2H-furo[2,3-g]indazole-7-carboxamide | $^{1}$H-NMR (400 MHz, DMSO-d6) δ [ppm]: 1.550 (0.49), 1.566 (0.70), 1.574 (0.51), 1.582 (0.59), 1.590 (0.44), 1.774 (0.54), 1.781 (0.68), 1.796 (1.22), 1.814 (1.36), 1.831 (1.29), 1.842 (0.73), 1.852 (0.60), 1.860 (0.80), 1.874 (0.57), 1.881 (0.43), 2.334 (1.11), 2.338 (0.51), 2.441 (16.00), 2.520 (5.91), 2.525 (3.73), 2.742 (0.58), 2.878 (2.66), 2.887 (7.26), 2.896 (3.16), 3.211 (1.08), 3.217 (1.09), 3.227 (2.03), 3.232 (1.97), 3.243 (1.11), 3.247 (1.15), 3.583 (0.44), 3.599 (0.93), 3.603 (0.92), 3.619 (1.26), 3.638 (0.69), 3.733 (0.60), 3.750 (1.14), 3.764 (0.94), 3.768 (0.97), 3.785 (0.63), 3.927 (0.96), 3.943 (1.43), 3.959 (0.88), 5.390 (5.71), 7.185 (1.13), 7.196 (1.17), 7.206 (1.26), 7.218 (1.23), 7.630 (4.95), 7.693 (0.96), 7.700 (0.98), 7.715 (1.72), 7.722 (1.72), 7.736 (0.86), 7.744 (0.92), 7.969 (0.68), 7.983 (1.41), 7.999 (0.65), 8.539 (2.46), 8.547 (2.47). LC-MS (Method 1): $R_t$ = 1.07 min; MS (ESIpos): m/z = 411 $[M + H]^+$ | Intermediate 51 GP H Conditions B 19 mg, 29% yield, 95% purity |
| 183 | 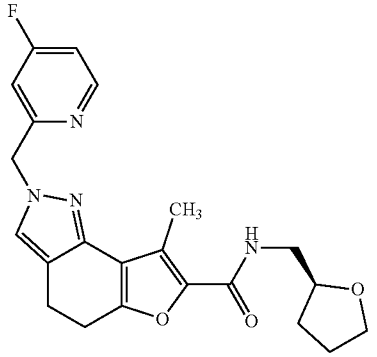 2-[(5-fluoropyridin-3-yl)methyl]-8-methyl-N-{[(2S)-oxolan-2-yl)methyl}-4,5-dihydro-2H-furo[2,3-g]indazole-7-carboxamide | $^{1}$H-NMR (400 MHz, DMSO-d6) δ [ppm]: −0.003 (4.40), 1.546 (0.68), 1.562 (0.95), 1.570 (0.77), 1.579 (0.81), 1.588 (0.69), 1.608 (0.47), 1.777 (1.04), 1.793 (1.79), 1.810 (1.98), 1.827 (1.84), 1.839 (1.22), 1.855 (1.23), 1.870 (0.89), 1.888 (0.53), 2.455 (16.00), 2.761 (0.52), 2.865 (3.87), 2.877 (8.26), 2.888 (4.21), 2.905 (0.60), 3.214 (1.70), 3.225 (2.92), 3.229 (2.92), 3.240 (1.78), 3.245 (1.72), 3.263 (0.47), 3.579 (0.58), 3.597 (1.38), 3.616 (1.68), 3.634 (0.82), 3.729 (0.73), 3.746 (1.52), 3.764 (1.35), 3.782 (0.66), 3.924 (1.23), 3.939 (1.76), 3.955 (1.13), 5.387 (7.82), 7.584 (1.39), 7.608 (1.41), 7.667 (5.14), 7.971 (0.98), 7.986 (1.90), 8.001 (0.96), 8.385 (3.27), 8.518 (2.92), 8.525 (2.92). LC-MS (Method 1): $R_t$ = 1.04 min; MS (ESIpos): m/z = 411 $[M + H]^+$ | Intermediate 51 GP H Conditions B 17 mg, 17% yield, 95% purity |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 184 | 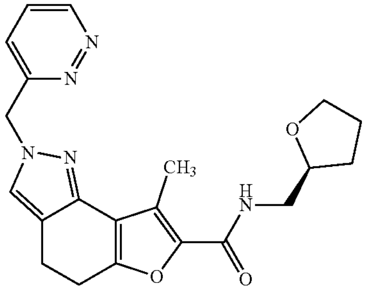 8-methyl-N-{[(2S)-oxolan-2-yl]methyl}-2-[(pyridazin-3-yl)methyl]-4,5-dihydro-2H-furo[2,3-g]indazole-7-carboxamide | $^1$H-NMR (400 MHz, DMSO-d6) δ [ppm]: 1.546 (0.48), 1.563 (0.67), 1.570 (0.51), 1.579 (0.57), 1.586 (0.42), 1.771 (0.53), 1.777 (0.69), 1.793 (1.21), 1.810 (1.35), 1.828 (1.31), 1.839 (0.74), 1.848 (0.60), 1.856 (0.81), 1.870 (0.57), 1.877 (0.42), 2.336 (0.54), 2.436 (16.00), 2.518 (6.44), 2.522 (4.06), 2.673 (1.20), 2.678 (0.52), 2.736 (0.86), 2.883 (2.85), 2.890 (8.89), 2.898 (3.23), 3.208 (1.06), 3.213 (1.04), 3.223 (2.00), 3.228 (1.92), 3.238 (1.08), 3.244 (1.12), 3.295 (0.58), 3.580 (0.42), 3.596 (0.89), 3.599 (0.90), 3.616 (1.22), 3.634 (0.68), 3.729 (0.59), 3.746 (1.11), 3.755 (0.70), 3.761 (0.93), 3.764 (0.92), 3.782 (0.62), 3.924 (0.94), 3.939 (1.45), 3.955 (0.88), 5.621 (6.71), 7.392 (1.68), 7.396 (1.67), 7.413 (1.92), 7.417 (1.91), 7.675 (2.04), 7.687 (2.25), 7.699 (5.23), 7.709 (1.88), 7.973 (0.67), 7.988 (1.41), 8.003 (0.65), 9.170 (1.63), 9.174 (1.77), 9.182 (1.73), 9.186 (1.57). LC-MS (Method 2): $R_t$ = 0.87 min; MS (ESIpos): m/z = 394 $[M + H]^+$ | Intermediate 52 GP H Conditions B 6 mg, 27% yield, 95% purity |
| 185 | 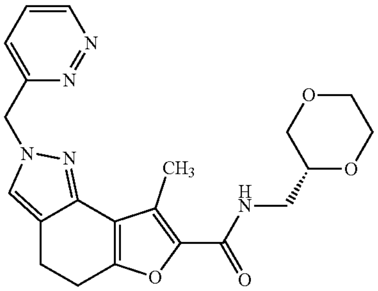 N-{[(2R)-1,4-dioxan-2-yl]methyl}-8-methyl-2-[(pyridazin-3-yl)methyl]-4,5-dihydro-2H-furo[2,3-g]indazole-7-carboxamide | $^1$H-NMR (400 MHz, DMSO-d6) δ [ppm]: 2.337 (0.61), 2.437 (16.00), 2.518 (7.61), 2.523 (5.02), 2.540 (0.46), 2.674 (1.42), 2.679 (0.65), 2.736 (1.15), 2.885 (2.78), 2.892 (8.58), 2.900 (3.23), 3.157 (0.60), 3.177 (1.73), 3.191 (1.44), 3.202 (1.56), 3.206 (2.13), 3.212 (0.89), 3.230 (1.91), 3.243 (0.95), 3.261 (0.64), 3.276 (0.42), 3.411 (0.44), 3.418 (0.52), 3.438 (1.05), 3.444 (1.12), 3.466 (0.97), 3.472 (0.89), 3.508 (0.80), 3.514 (0.90), 3.536 (1.13), 3.542 (1.12), 3.563 (0.50), 3.569 (0.74), 3.604 (1.68), 3.610 (1.42), 3.619 (0.68), 3.627 (1.28), 3.634 (1.34), 3.679 (1.20), 3.685 (0.99), 3.708 (2.00), 3.713 (1.83), 3.738 (0.87), 3.755 (1.40), 5.622 (6.81), 6.048 (0.45), 7.393 (1.75), 7.397 (1.68), 7.414 (1.96), 7.418 (1.99), 7.676 (2.22), 7.689 (2.20), 7.701 (5.40), 7.710 (2.05), 8.052 (0.72), 8.067 (1.48), 8.082 (0.68), 8.714 (0.43), 9.171 (1.62), 9.175 (1.68), 9.183 (1.65), 9.187 (1.62). LC-MS (Method 2): $R_t$ = 0.79 min; MS (ESIpos): m/z = 410 $[M + H]^+$ | Intermediate 52 GP H Conditions B 5 mg, 19% yield, 90% purity |
| 186 | 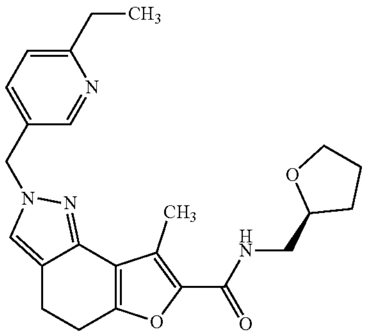 2-[(6-ethylpyridin-3-yl)methyl]-8-methyl-N-{[(2S)-oxolan-2-yl]methyl}-4,5-dihydro-2H-furo[2,3-g]indazole-7-carboxamide | $^1$H-NMR (400 MHz, DMSO-d6) δ [ppm]: 1.156 (0.99), 1.169 (5.78), 1.175 (2.48), 1.189 (13.11), 1.194 (1.49), 1.208 (5.73), 1.232 (0.45), 1.548 (0.54), 1.563 (0.72), 1.571 (0.55), 1.579 (0.65), 1.593 (0.45), 1.771 (0.64), 1.777 (0.72), 1.792 (1.28), 1.810 (1.46), 1.827 (1.36), 1.838 (0.84), 1.843 (0.72), 1.848 (0.73), 1.856 (0.86), 1.863 (0.46), 1.870 (0.62), 1.877 (0.43), 1.888 (0.41), 2.458 (16.00), 2.479 (3.24), 2.518 (4.52), 2.523 (2.85), 2.682 (1.76), 2.701 (4.16), 2.720 (3.74), 2.739 (1.14), 2.765 (0.50), 2.848 (2.59), 2.858 (4.27), 2.864 (4.56), 2.874 (3.26), 2.893 (0.48), 3.208 (1.20), 3.214 (1.11), 3.223 (2.26), 3.229 (1.94), 3.238 (1.23), 3.244 (1.11), 3.579 (0.44), 3.595 (1.04), 3.599 (0.95), 3.616 (1.29), 3.634 (0.70), 3.729 (0.63), 3.743 (0.97), 3.746 (1.16), 3.761 (1.04), 3.764 (0.96), 3.782 (0.68), 3.923 (1.00), 3.939 (1.51), 3.955 (0.90), 5.278 (5.72), 5.543 (0.75), 6.540 (0.58), 7.227 (1.92), | Intermediate 53 GP H Conditions A 5 mg, 7% yield, 90% purity |

TABLE 4-continued

| Example | Structure IUPAC-Name | Analytical Data | Preparation or Separation Methods |
|---|---|---|---|
| The following examples (170 to 211) were prepared in analogy to example 3 starting from the given intermediates and commercially available amines (or their salts), applying the indicated general procedure. | | | |
| | | 7.247 (2.18), 7.419 (0.95), 7.568 (1.49), 7.573 (1.51), 7.587 (1.28), 7.594 (1.34), 7.614 (4.69), 7.962 (0.68), 7.977 (1.43), 7.991 (0.68), 8.422 (1.95), 8.426 (1.95). LC-MS (Method 1): $R_t$ = 1.10 min; MS (ESIpos): m/z = 421 $[M + H]^+$ | |
| 187 | 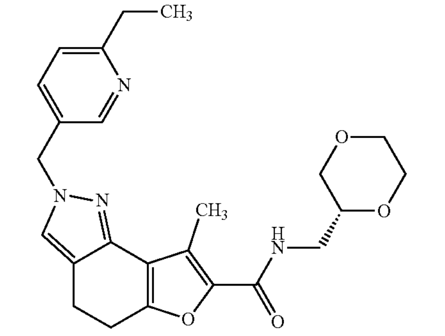 N-{[(2R)-1,4-dioxan-2-yl]methyl}-2-[(6-ethylpyridin-3-yl)methyl]-8-methyl-4,5-dihydro-2H-furo[2,3-g]indazole-7-carboxamide | $^1$H-NMR (400 MHz, DMSO-d6) δ [ppm]: 1.169 (5.44), 1.189 (12.04), 1.207 (5.70), 2.459 (16.00), 2.518 (2.66), 2.523 (1.64), 2.682 (1.33), 2.701 (3.79), 2.720 (3.63), 2.739 (1.15), 2.766 (1.23), 2.830 (0.40), 2.849 (2.51), 2.860 (4.19), 2.865 (4.46), 2.876 (3.20), 2.894 (0.44), 3.157 (0.59), 3.177 (1.77), 3.191 (1.48), 3.201 (1.63), 3.206 (2.17), 3.211 (0.95), 3.230 (1.97), 3.242 (1.01), 3.261 (0.69), 3.276 (0.48), 3.411 (0.45), 3.417 (0.54), 3.438 (1.10), 3.444 (1.17), 3.465 (1.00), 3.471 (0.92), 3.508 (0.82), 3.513 (0.90), 3.535 (1.12), 3.542 (1.14), 3.563 (0.51), 3.568 (0.73), 3.603 (1.73), 3.609 (1.42), 3.618 (0.71), 3.627 (1.33), 3.634 (1.38), 3.679 (1.22), 3.685 (1.03), 3.708 (2.10), 3.713 (1.83), 3.738 (0.90), 5.278 (5.81), 5.701 (0.41), 7.226 (1.97), 7.247 (2.32), 7.568 (1.50), 7.573 (1.53), 7.587 (1.36), 7.593 (1.37), 7.615 (4.84), 8.041 (0.71), 8.056 (1.49), 8.071 (0.69), 8.422 (2.05), 8.426 (2.05), 8.614 (0.49). LC-MS (Method 1): $R_t$ = 1.04 min; MS (ESIpos): m/z = 437 $[M + H]^+$ | Intermediate 53 GP H Conditions A 18 mg, 24% yield, 93% purity |
| 188 | 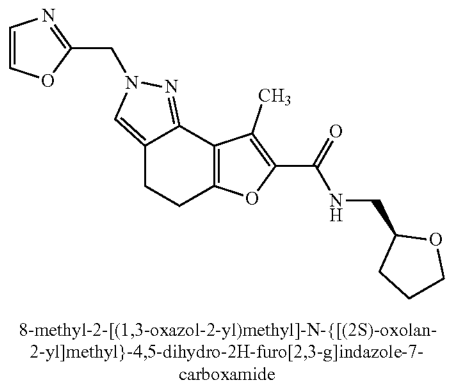 [SMILES: Cc1c(C(=O)NC[C@@H]2CCCO2)oc2c1-c1nn(Cc3ncco3)cc1CC2] 8-methyl-2-[(1,3-oxazol-2-yl)methyl]-N-{[(2S)-oxolan-2-yl]methyl}-4,5-dihydro-2H-furo[2,3-g]indazole-7-carboxamide | $^1$H-NMR (400 MHz, DMSO-d6) δ [ppm]: 1.551 (0.48), 1.567 (0.67), 1.575 (0.50), 1.583 (0.57), 1.596 (0.42), 1.774 (0.57), 1.780 (0.74), 1.796 (1.25), 1.813 (1.41), 1.831 (1.33), 1.843 (0.74), 1.852 (0.59), 1.860 (0.81), 1.874 (0.56), 1.881 (0.41), 2.334 (0.58), 2.440 (16.00), 2.520 (2.54), 2.525 (1.65), 2.676 (0.60), 2.871 (2.64), 2.882 (6.22), 2.892 (3.20), 3.211 (1.06), 3.217 (1.06), 3.226 (1.98), 3.232 (1.85), 3.241 (1.08), 3.248 (1.09), 3.583 (0.46), 3.599 (0.94), 3.602 (0.94), 3.619 (1.26), 3.637 (0.70), 3.733 (0.63), 3.750 (1.13), 3.764 (0.92), 3.767 (0.94), 3.785 (0.63), 3.927 (0.98), 3.943 (1.48), 3.959 (0.89), 5.480 (8.37), 7.213 (4.35), 7.215 (4.44), 7.619 (4.83), 7.981 (0.68), 7.996 (1.43), 8.010 (0.66), 8.101 (4.67), 8.103 (4.95). LC-MS (Method 1): $R_t$ = 0.95 min; MS (ESIpos): m/z = 383 $[M + H]^+$ | Intermediate 54 GP H Conditions B 9 mg, 9% yield, 95% purity |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 189 | 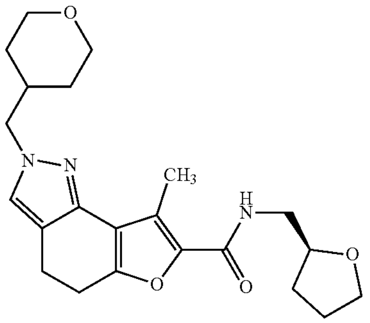<br>8-methyl-2-[(oxan-4-yl)methyl]-N-{[(2S)-oxolan-2-yl]methyl}-4,5-dihydro-2H-furo-[2,3-g]indazole-7-carboxamide | $^1$H-NMR (400 MHz, DMSO-d6) δ [ppm]: 1.209 (0.83), 1.218 (0.92), 1.239 (1.12), 1.250 (1.00), 1.269 (0.50), 1.280 (0.44), 1.404 (1.37), 1.432 (0.99), 1.553 (0.53), 1.570 (0.71), 1.577 (0.53), 1.586 (0.61), 1.593 (0.44), 1.777 (0.56), 1.783 (0.70), 1.799 (1.24), 1.816 (1.39), 1.834 (1.32), 1.845 (0.76), 1.854 (0.59), 1.862 (0.83), 1.877 (0.57), 1.884 (0.42), 2.006 (0.45), 2.015 (0.55), 2.025 (0.42), 2.471 (16.00), 2.520 (3.54), 2.525 (2.30), 2.613 (1.22), 2.827 (0.61), 2.845 (2.69), 2.857 (3.93), 2.865 (4.33), 2.877 (3.30), 2.895 (0.63), 3.220 (1.98), 3.230 (2.47), 3.234 (2.40), 3.246 (2.93), 3.250 (3.03), 3.276 (1.19), 3.585 (0.46), 3.602 (0.96), 3.605 (0.97), 3.622 (1.30), 3.639 (0.71), 3.735 (0.66), 3.752 (1.18), 3.767 (1.00), 3.770 (1.03), 3.778 (0.53), 3.788 (0.74), 3.805 (1.37), 3.811 (1.31), 3.833 (1.24), 3.840 (1.14), 3.933 (3.58), 3.951 (3.37), 3.962 (1.06), 7.481 (4.63), 7.956 (0.72), 7.971 (1.48), 7.986 (0.69). LC-MS (Method 1): $R_t$ = 1.05 min; MS (ESIpos): m/z = 400 $[M + H]^+$ | Intermediate 55<br>GP H<br>Conditions B<br>16 mg, 8% yield, 95% purity |
| 190 | 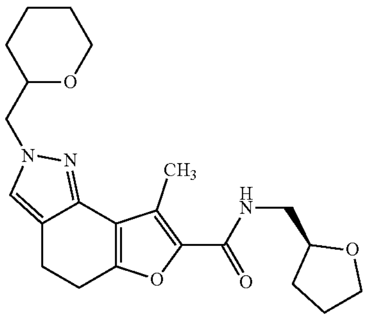<br>8-methyl-2-{[(2±)-oxan-2-yl]methyl}-N-{[(2S)-oxolan-2-yl]methyl}-4,5-dihydro-2H-furo[2,3-g]indazole-7-carboxamide | $^1$H-NMR (400 MHz, DMSO-d6) δ [ppm]: 0.861 (1.11), 0.878 (3.04), 0.896 (1.48), 1.164 (0.48), 1.194 (0.61), 1.223 (0.40), 1.340 (0.51), 1.358 (0.66), 1.373 (0.68), 1.396 (0.70), 1.448 (2.19), 1.552 (1.27), 1.569 (1.33), 1.584 (1.40), 1.613 (0.56), 1.760 (0.97), 1.781 (1.14), 1.797 (1.44), 1.814 (1.38), 1.832 (1.27), 1.845 (0.72), 1.861 (0.80), 1.876 (0.56), 1.893 (0.34), 2.467 (16.00), 2.518 (5.85), 2.522 (3.71), 2.607 (0.76), 2.824 (0.69), 2.842 (2.37), 2.855 (3.01), 2.862 (2.81), 2.877 (2.82), 2.895 (0.68), 3.212 (1.08), 3.218 (1.10), 3.228 (2.01), 3.233 (1.95), 3.243 (1.17), 3.249 (1.20), 3.267 (0.76), 3.295 (1.19), 3.603 (1.45), 3.620 (1.78), 3.637 (0.93), 3.733 (0.60), 3.751 (1.12), 3.768 (0.97), 3.786 (0.63), 3.827 (0.80), 3.854 (0.71), 3.913 (0.30), 3.929 (0.97), 3.944 (1.44), 3.960 (0.91), 4.021 (1.87), 4.029 (2.00), 4.039 (2.42), 4.064 (0.29), 7.426 (4.55), 7.595 (0.27), 7.621 (0.27), 7.960 (0.68), 7.975 (1.41), 7.990 (0.66). LC-MS (Method 1): $R_t$ = 1.16 min; MS (ESIpos): m/z = 400 $[M + H]^+$ | Intermediate 56<br>GP H<br>Conditions B<br>2 mg, 2% yield, 90% purity<br>Mixture of two isomers. |
| 191 | 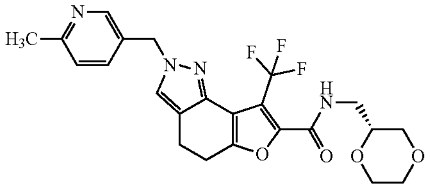<br>N-{[(2R)-1,4-dioxan-2-yl]methyl}-2-[(6-methylpyridin-3-yl)methyl]-8-trifluoromethyl)-4,5-dihydro-2H-furo-[2,3-g]indazole-7-carboxamide | $^1$H-NMR (400 MHz, DMSO-d6) δ [ppm]: 0.932 (0.51), 0.948 (0.55), 2.429 (16.00), 2.518 (7.85), 2.523 (5.44), 2.835 (0.72), 2.839 (0.72), 2.858 (3.00), 2.876 (2.45), 2.922 (2.62), 2.938 (3.60), 2.945 (1.37), 2.957 (0.96), 2.963 (0.86), 3.193 (1.44), 3.198 (0.76), 3.217 (2.65), 3.221 (1.96), 3.232 (2.00), 3.245 (3.10), 3.259 (1.75), 3.275 (1.13), 3.294 (0.66), 3.309 (0.66), 3.420 (0.50), 3.426 (0.63), 3.447 (1.29), 3.454 (1.40), 3.474 (1.11), 3.481 (1.06), 3.521 (0.93), 3.526 (1.03), 3.549 (1.31), 3.556 (1.37), 3.576 (0.58), 3.582 (0.91), 3.616 (1.82), 3.640 (1.73), 3.691 (1.48), 3.697 (1.23), 3.720 (2.55), 3.749 (1.14), 3.754 (1.06), 5.281 (7.04), 7.214 (2.30), 7.234 (2.60), 7.547 (1.70), 7.552 (1.74), 7.566 (1.52), 7.573 (1.57), 7.649 (5.25), 8.396 (2.44), 8.401 (2.43), 8.728 (0.84), 8.743 (1.76), 8.758 (0.85). LC-MS | Intermediate 57<br>GP H<br>Conditions B<br>16 mg, 7% yield, 98% purity |

TABLE 4-continued

| The following examples (170 to 211) were prepared in analogy to example 3 starting from the given intermediates and commercially available amines (or their salts), applying the indicated general procedure. | | | |
|---|---|---|---|
| Example | Structure IUPAC-Name | Analytical Data | Preparation or Separation Methods |
| | | (Method 1): $R_t$ = 0.99 min; MS (ESIpos): m/z = 477 $[M + H]^+$ | |
| 192 | 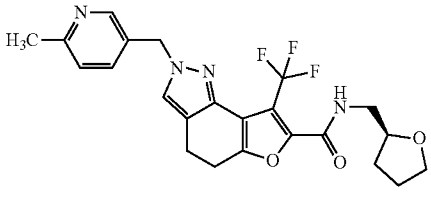<br>2-[(6-methylpyridin-3-yl)methyl]-N-{[(2S)-oxolan-2-yl]methyl}-8-(trifluoromethyl)-4,5-dihydro-2H-furo-[2,3-g]indazole-7-carboxamide | $^1$H-NMR (400 MHz, DMSO-d6) δ [ppm]: 1.535 (0.56), 1.555 (0.78), 1.564 (0.76), 1.572 (0.64), 1.584 (0.70), 1.601 (0.44), 1.790 (0.86), 1.806 (1.57), 1.824 (1.55), 1.842 (1.01), 1.857 (0.81), 1.874 (0.69), 1.885 (0.74), 1.902 (0.62), 1.918 (0.46), 2.429 (16.00), 2.518 (13.89), 2.523 (9.60), 2.839 (0.74), 2.858 (3.01), 2.876 (2.57), 2.917 (2.72), 2.934 (3.62), 2.953 (0.91), 2.959 (0.84), 3.249 (2.20), 3.264 (4.65), 3.280 (2.52), 3.594 (0.51), 3.613 (1.26), 3.630 (1.50), 3.648 (0.85), 3.737 (0.72), 3.754 (1.44), 3.770 (1.28), 3.790 (0.72), 3.930 (1.11), 3.946 (1.76), 3.961 (1.18), 5.281 (7.15), 7.214 (2.26), 7.233 (2.57), 7.545 (1.66), 7.551 (1.72), 7.565 (1.52), 7.571 (1.55), 7.647 (5.18), 8.396 (2.40), 8.400 (2.44), 8.692 (0.83), 8.707 (1.67), 8.722 (0.81). LC-MS (Method 1): $R_t$ = 1.07 min; MS (ESIpos): m/z = 461 $[M + H]^+$ | Intermediate 57<br>GP H<br>Conditions B<br>45 mg, 13% yield, 98% purity |
| 193 | 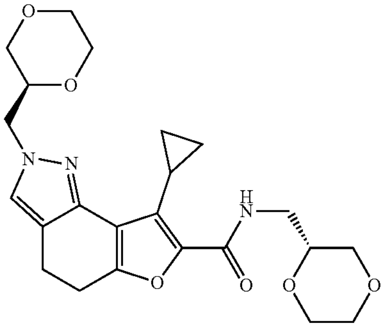<br>8-cyclopropyl-N-{[(2R)-1,4-dioxan-2-yl]-methyl}-2-{[(2S)-1,4-dioxan-2-yl]methyl}-4,5-dihydro-2H-furo[2,3-g]indazole-7-carboxamide | $^1$H-NMR (400 MHz, DMSO-d6) δ [ppm]: −0.003 (16.00), 0.806 (3.14), 0.813 (2.95), 0.828 (3.05), 0.835 (3.13), 0.851 (0.71), 0.868 (1.15), 0.886 (0.64), 0.931 (1.47), 0.948 (1.45), 1.415 (3.34), 1.418 (3.33), 2.326 (1.49), 2.331 (1.11), 2.522 (4.92), 2.669 (1.55), 2.673 (1.13), 2.753 (0.81), 2.760 (0.97), 2.768 (1.35), 2.778 (4.10), 2.794 (4.01), 2.819 (4.26), 2.836 (4.71), 2.846 (1.31), 2.853 (1.08), 2.861 (0.85), 2.927 (0.47), 2.941 (1.08), 2.949 (1.05), 2.955 (0.81), 2.963 (1.80), 2.972 (0.79), 2.977 (1.00), 2.985 (0.93), 2.999 (0.41), 3.166 (0.41), 3.181 (0.90), 3.190 (1.91), 3.199 (1.47), 3.214 (4.46), 3.228 (2.33), 3.243 (4.64), 3.259 (1.74), 3.271 (2.53), 3.276 (3.01), 3.300 (3.01), 3.409 (1.06), 3.416 (1.30), 3.424 (1.14), 3.436 (2.07), 3.445 (2.80), 3.452 (2.18), 3.464 (1.78), 3.472 (2.34), 3.479 (1.64), 3.512 (1.46), 3.518 (2.54), 3.523 (1.62), 3.546 (3.58), 3.573 (1.81), 3.578 (1.42), 3.614 (4.02), 3.625 (2.04), 3.642 (3.89), 3.664 (0.66), 3.692 (2.17), 3.697 (1.90), 3.721 (7.04), 3.750 (4.23), 3.804 (0.62), 3.818 (1.19), 3.825 (1.24), 3.832 (1.05), 3.841 (1.16), 3.856 (0.63), 4.054 (5.97), 4.068 (4.47), 7.455 (6.84), 8.030 (1.22), 8.044 (2.54), 8.059 (1.20). LC-MS (Method 1): $R_t$ = 1.01 min; MS (ESIpos): m/z = 444 $[M + H]^+$ | Intermediate 58<br>GP H<br>Conditions B<br>55 mg, 28% yield, 95% purity |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 194 | 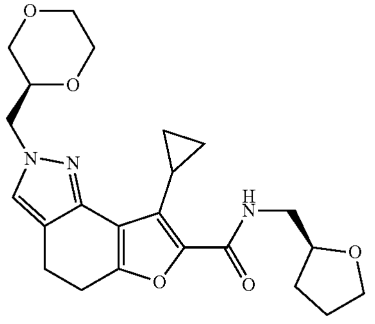 8-cyclopropyl-2-{[(2S)-1,4-dioxan-2-yl]-methyl}-N-{[(2S)-oxolan-2-yl]methyl}-4,5-dihydro-2H-furo[2,3-g]indazole-7-carboxamide | $^1$H-NMR (400 MHz, DMSO-d6) δ [ppm]: −0.002 (2.66), 0.803 (6.72), 0.810 (6.04), 0.825 (6.25), 0.831 (6.66), 1.159 (1.11), 1.232 (1.20), 1.402 (4.19), 1.413 (6.47), 1.416 (6.44), 1.427 (3.97), 1.541 (0.57), 1.560 (1.75), 1.577 (2.38), 1.584 (1.86), 1.593 (2.04), 1.605 (1.63), 1.622 (1.22), 1.754 (0.45), 1.765 (1.04), 1.780 (1.90), 1.786 (2.37), 1.801 (4.17), 1.820 (4.59), 1.838 (3.91), 1.851 (2.58), 1.860 (1.99), 1.864 (2.24), 1.869 (2.63), 1.883 (1.90), 1.900 (1.16), 1.907 (1.09), 1.922 (0.66), 2.332 (2.52), 2.336 (1.17), 2.518 (13.16), 2.522 (8.36), 2.673 (2.57), 2.752 (1.54), 2.759 (1.80), 2.768 (2.40), 2.777 (8.36), 2.794 (7.96), 2.818 (8.78), 2.834 (10.77), 2.845 (2.53), 2.853 (2.23), 2.860 (1.78), 2.931 (1.01), 2.945 (2.11), 2.954 (2.18), 2.960 (1.43), 2.967 (3.99), 2.976 (1.42), 2.981 (1.97), 2.990 (1.92), 3.003 (0.83), 3.233 (5.95), 3.248 (15.21), 3.263 (6.65), 3.272 (5.11), 3.276 (4.80), 3.301 (5.13), 3.410 (1.29), 3.417 (1.58), 3.437 (3.31), 3.443 (3.59), 3.464 (2.96), 3.471 (2.79), 3.513 (2.43), 3.518 (2.77), 3.541 (3.48), 3.547 (3.51), 3.568 (1.53), 3.574 (2.18), 3.589 (1.58), 3.609 (4.71), 3.615 (4.21), 3.625 (4.74), 3.643 (5.12), 3.722 (7.08), 3.739 (2.63), 3.753 (7.60), 3.757 (8.27), 3.771 (3.43), 3.774 (3.49), 3.792 (2.16), 3.804 (0.99), 3.810 (0.98), 3.819 (2.00), 3.826 (2.23), 3.834 (1.76), 3.843 (2.10), 3.857 (1.16), 3.863 (0.96), 3.923 (0.99), 3.939 (3.30), 3.955 (5.09), 3.970 (3.12), 3.986 (0.70), 4.054 (12.99), 4.069 (8.94), 7.454 (16.00), 7.944 (2.42), 7.958 (5.13), 7.974 (2.37). LC-MS (Method 1): $R_t$ = 1.11 min; MS (ESIpos): m/z = 428 $[M + H]^+$ | Intermediate 58 GP H Conditions B 28 mg, 14% yield, 95% purity |
| 195 | 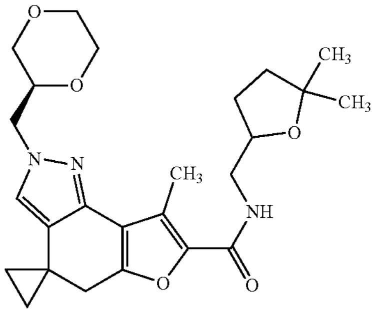 N-{[(2±)-5,5-dimethyloxolan-2-yl]methyl}-2′-{[(2S)-1,4-dioxan-2-yl]methyl}-8′-methyl-2′,5′-dihydrospiro[cyclopropane-1,4′-furo[2,3-g]indazole-7′-carboxamide | $^1$H-NMR (400 MHz, DMSO-d6) δ [ppm]: 0.784 (1.57), 0.803 (2.31), 0.824 (0.73), 0.850 (0.87), 0.860 (1.05), 0.870 (3.84), 0.932 (0.50), 0.948 (0.48), 1.137 (16.00), 1.154 (0.77), 1.198 (15.96), 1.221 (0.66), 1.230 (0.63), 1.650 (0.76), 1.658 (0.92), 1.673 (3.49), 1.679 (4.04), 1.683 (5.02), 1.697 (0.84), 1.701 (1.08), 1.716 (0.54), 1.722 (0.55), 1.939 (0.51), 1.956 (0.96), 1.975 (0.90), 1.988 (0.42), 2.336 (1.10), 2.446 (0.70), 2.518 (10.73), 2.523 (7.19), 2.678 (0.94), 2.786 (0.50), 2.829 (3.70), 2.841 (3.66), 2.885 (0.53), 3.217 (2.42), 3.227 (2.55), 3.230 (2.46), 3.242 (2.93), 3.245 (2.94), 3.270 (1.70), 3.294 (1.00), 3.307 (1.53), 3.366 (1.04), 3.370 (1.05), 3.381 (0.59), 3.403 (0.65), 3.410 (0.75), 3.430 (1.30), 3.437 (1.43), 3.457 (1.17), 3.464 (1.13), 3.504 (0.97), 3.509 (1.07), 3.532 (1.26), 3.539 (1.27), 3.559 (0.58), 3.565 (0.77), 3.612 (1.40), 3.640 (1.09), 3.703 (2.34), 3.708 (2.65), 3.731 (1.95), 3.737 (2.16), 3.815 (0.72), 3.821 (0.76), 3.827 (0.68), 3.834 (0.91), 3.840 (0.69), 3.851 (0.48), 3.857 (0.44), 3.986 (0.71), 4.003 (0.69), 4.008 (1.04), 4.022 (2.84), 4.040 (3.50), 4.053 (2.10), 4.077 (0.67), 4.089 (0.55), 7.276 (9.11), 7.882 (0.82), 7.897 (1.71), 7.912 (0.81). LC-MS (Method 1): $R_t$ = 1.22 min; MS (ESIpos): m/z = 456 $[M + H]^+$ | Intermediate 40-1 GP H Conditions B 37 mg, 17% yield, 90% purity Mixture of two isomers |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 196 | 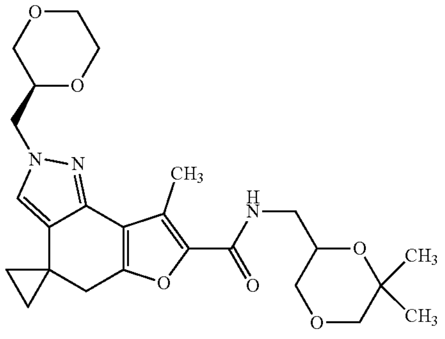 N-{[(2±)-6,6-dimethyl-1,4-dioxan-2-yl]methyl}-2'-{[(2S)-1,4-dioxan-2-yl]methyl}-8'-methyl-2',5'-dihydrospiro[cyclopropane-1,4'-furo[2,3-g]-indazole-7'-carboxamide | $^1$H-NMR (400 MHz, DMSO-d6) δ [ppm]: 0.803 (0.85), 0.861 (5.79), 0.878 (16.00), 0.896 (7.93), 0.926 (0.63), 0.944 (1.19), 0.963 (0.64), 0.985 (0.64), 1.002 (0.77), 1.023 (1.11), 1.044 (5.90), 1.063 (1.78), 1.217 (1.26), 1.234 (4.94), 1.253 (1.53), 1.323 (1.17), 1.341 (2.50), 1.359 (3.18), 1.373 (3.09), 1.386 (2.32), 1.417 (1.81), 1.437 (1.38), 1.543 (2.23), 1.572 (2.65), 1.583 (2.03), 1.597 (1.81), 1.612 (1.20), 1.997 (0.31), 2.018 (0.43), 2.755 (0.93), 2.816 (0.50), 2.830 (1.53), 2.842 (1.55), 2.987 (1.47), 3.009 (0.61), 3.037 (0.90), 3.065 (0.75), 3.097 (0.84), 3.125 (1.04), 3.147 (0.92), 3.217 (0.74), 3.245 (0.82), 3.270 (0.77), 3.426 (1.42), 3.436 (0.99), 3.454 (1.23), 3.509 (0.51), 3.532 (0.61), 3.538 (0.59), 3.565 (0.35), 3.613 (0.68), 3.638 (0.67), 3.708 (1.31), 3.737 (1.21), 3.827 (0.45), 3.834 (0.54), 3.839 (0.47), 3.857 (0.46), 3.870 (0.41), 4.022 (0.75), 4.040 (1.12), 4.054 (0.80), 4.077 (0.39), 4.089 (0.32), 4.504 (0.35), 7.278 (3.12), 7.414 (0.38), 8.012 (0.28), 8.027 (0.63), 8.043 (0.31), 8.151 (0.22). LC-MS (Method 1): $R_t$ = 1.13 min; MS (ESIpos): m/z = 472 $[M + H]^+$ | Intermediate 40-1 GP H Conditions B 37 mg, 14% yield, 80% purity Mixture of two isomers |
| 197 | 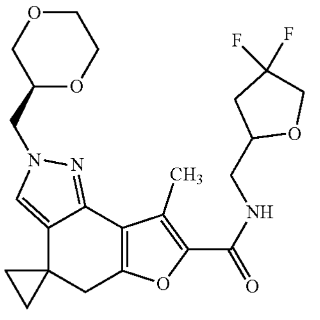 N-{[(2±)-4,4-difluorooxolan-2-yl]-methyl}-2'-{[(2S)-1,4-dioxan-2-yl]-methyl}-8'-methyl-2',5'-dihydro-spiro[cyclopropane-1,4'-furo[2,3-g]indazole]-7'-carboxamide | $^1$H-NMR (400 MHz, DMSO-d6) δ [ppm]: 0.786 (2.81), 0.806 (4.62), 0.827 (1.14), 0.852 (1.43), 0.861 (2.16), 0.872 (7.22), 0.879 (6.33), 1.231 (0.52), 2.160 (0.37), 2.181 (0.39), 2.196 (0.84), 2.205 (0.44), 2.209 (0.47), 2.216 (0.87), 2.230 (0.66), 2.243 (0.83), 2.252 (0.60), 2.262 (0.79), 2.278 (0.44), 2.297 (0.43), 2.518 (12.18), 2.523 (8.55), 2.541 (1.37), 2.789 (1.08), 2.833 (7.46), 2.845 (7.40), 2.888 (1.08), 3.218 (2.42), 3.242 (2.94), 3.247 (2.94), 3.271 (2.92), 3.364 (2.63), 3.378 (1.38), 3.410 (1.72), 3.423 (2.16), 3.430 (2.56), 3.437 (3.65), 3.458 (2.74), 3.464 (1.99), 3.504 (1.58), 3.509 (1.80), 3.532 (2.24), 3.539 (2.23), 3.565 (1.33), 3.613 (2.48), 3.640 (1.88), 3.704 (4.39), 3.710 (4.64), 3.738 (3.68), 3.791 (1.12), 3.817 (2.63), 3.822 (2.72), 3.829 (2.08), 3.850 (1.99), 3.857 (2.06), 3.888 (1.16), 3.987 (1.21), 4.009 (1.20), 4.022 (3.77), 4.040 (6.61), 4.055 (3.53), 4.066 (2.58), 4.078 (1.22), 4.091 (1.18), 4.237 (0.55), 4.254 (1.45), 4.271 (2.13), 4.286 (1.38), 7.280 (16.00), 8.148 (1.61), 8.163 (3.29), 8.177 (1.55). LC-MS (Method 1): $R_t$ = 1.13 min; MS (ESIpos): m/z = 464 $[M + H]^+$ | Intermediate 40-1 GP H Conditions B 19 mg, 9% yield, 95% purity Mixture of two isomers |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
| --- | --- | --- | --- |
| 198 | 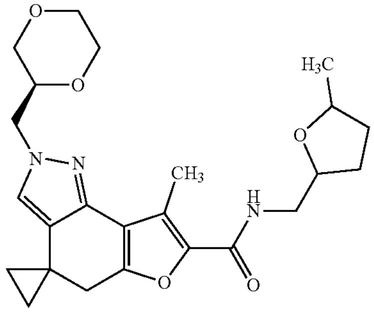 2'-{[(2S)-1,4-dioxan-2-yl]methyl}-8'-methyl-N-{[(2±,5±)-5-methyloxolan-2-yl]methyl}-2',5'-dihydrospiro[cyclopropane-1,4'-furo-[2,3-g]indazole]-7'-carboxamide | $^1$H-NMR (400 MHz, DMSO-d6) δ [ppm]: 0.783 (3.72), 0.802 (6.04), 0.823 (1.44), 0.848 (1.81), 0.869 (8.90), 1.069 (1.05), 1.101 (6.06), 1.116 (6.55), 1.134 (2.65), 1.149 (16.00), 1.164 (15.38), 1.185 (2.15), 1.193 (1.28), 1.221 (0.46), 1.293 (1.17), 1.312 (2.46), 1.331 (1.86), 1.350 (1.86), 1.369 (1.99), 1.395 (1.74), 1.417 (0.97), 1.602 (0.97), 1.614 (1.16), 1.632 (1.37), 1.644 (1.33), 1.823 (0.69), 1.841 (1.42), 1.862 (2.30), 1.879 (2.26), 1.895 (2.63), 1.913 (2.08), 1.927 (1.97), 1.958 (1.18), 1.996 (1.14), 2.008 (2.41), 2.755 (4.00), 2.784 (1.22), 2.815 (2.93), 2.828 (8.42), 2.840 (8.48), 2.883 (1.16), 2.917 (0.85), 2.935 (0.73), 3.216 (4.95), 3.229 (5.18), 3.244 (11.39), 3.259 (5.51), 3.269 (5.37), 3.313 (8.68), 3.429 (5.72), 3.435 (5.24), 3.457 (3.78), 3.463 (3.80), 3.502 (2.52), 3.508 (2.62), 3.530 (3.32), 3.536 (3.31), 3.563 (1.85), 3.611 (3.84), 3.638 (3.03), 3.706 (6.96), 3.735 (5.83), 3.832 (2.67), 3.844 (2.75), 3.859 (3.11), 3.874 (2.30), 3.879 (2.36), 3.902 (2.32), 3.919 (2.67), 3.934 (1.80), 3.950 (0.56), 3.984 (1.47), 4.002 (1.24), 4.020 (5.38), 4.038 (8.08), 4.052 (5.00), 4.075 (2.79), 4.087 (1.71), 4.145 (0.56), 4.468 (0.43), 4.496 (0.97), 4.507 (0.81), 4.617 (0.52), 7.090 (1.01), 7.273 (15.54), 7.406 (0.94), 7.926 (1.52), 7.941 (3.38), 7.954 (2.25), 8.151 (0.91), 8.539 (1.56), 8.890 (0.98), 10.144 (1.03). LC-MS (Method 1): $R_t$ = 1.16 min; MS (ESIpos): m/z = 442 $[M + H]^+$ | Intermediate 40-1 GP H Conditions B 11 mg, 3% yield, 90% purity mixture of trans and cis isomers |
| 199 | 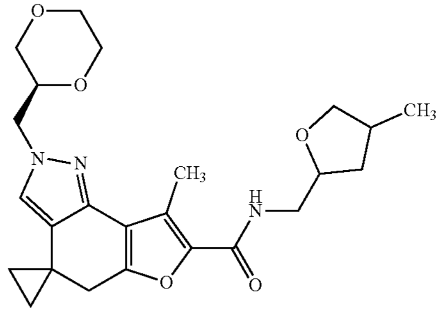 2-[[(2S)-1,4-dioxan-2-yl]methyl]-8-methyl-N-[(4-methyltetrahydrofuran-2-yl)methyl]spiro[5H-furo[2,3-g]-indazole-4,1'-cyclopropane]-7-carboxamide | $^1$H-NMR (400 MHz, DMSO-d6) δ [ppm]: 0.764 (0.61), 0.784 (2.54), 0.798 (2.74), 0.804 (4.33), 0.825 (0.95), 0.849 (1.16), 0.858 (1.32), 0.868 (6.25), 0.939 (0.40), 0.958 (3.06), 0.974 (3.78), 0.981 (15.53), 0.998 (16.00), 1.010 (0.95), 1.019 (0.84), 1.117 (1.04), 1.139 (1.85), 1.147 (1.17), 1.161 (1.14), 1.169 (2.00), 1.192 (1.21), 1.314 (0.79), 1.333 (0.44), 2.012 (0.84), 2.066 (0.85), 2.084 (1.33), 2.101 (1.31), 2.116 (1.37), 2.132 (1.11), 2.207 (0.80), 2.226 (1.23), 2.245 (1.17), 2.264 (0.82), 2.318 (1.15), 2.518 (14.14), 2.523 (8.91), 2.660 (1.13), 2.755 (1.19), 2.784 (1.03), 2.816 (1.84), 2.827 (7.22), 2.839 (7.07), 2.883 (1.03), 3.139 (0.48), 3.159 (0.60), 3.178 (0.56), 3.201 (0.73), 3.217 (3.52), 3.222 (3.18), 3.232 (0.99), 3.242 (7.67), 3.263 (3.86), 3.270 (4.48), 3.282 (6.49), 3.297 (3.80), 3.372 (0.51), 3.403 (0.84), 3.410 (0.98), 3.430 (2.04), 3.437 (2.27), 3.458 (1.88), 3.464 (1.89), 3.504 (1.55), 3.509 (1.68), 3.532 (2.15), 3.539 (2.10), 3.559 (0.95), 3.565 (1.22), 3.612 (2.36), 3.639 (1.81), 3.703 (4.04), 3.708 (4.44), 3.731 (3.46), 3.737 (3.72), 3.750 (2.63), 3.769 (3.41), 3.789 (2.30), 3.796 (0.68), 3.803 (0.73), 3.810 (0.94), 3.815 (1.20), 3.821 (1.36), 3.827 (1.15), 3.833 (1.54), 3.839 (1.22), 3.851 (0.80), 3.857 (0.78), 3.863 (0.64), 3.880 (0.57), 3.900 (0.42), 3.936 (0.54), 3.951 (1.53), 3.957 (0.75), 3.967 (1.65), 3.972 (1.60), 3.986 (1.84), 4.003 (1.16), 4.021 (3.52), 4.041 (4.77), 4.053 (3.41), 4.077 (1.26), 4.089 (0.89), 7.276 (15.10), 7.942 (1.42), 7.957 | Intermediate 40-1 GP H Conditions B 27 mg, 6% yield, 90% purity mixture of trans and cis isomers |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | (3.02), 7.972 (1.35), 8.149 (0.72), 8.542 (0.52), 8.893 (0.69), 10.146 (0.76). LC-MS (Method 1): $R_t$ = 1.15 min; MS (ESIpoa): m/z = 442 $[M + H]^+$ | |
| 200 | 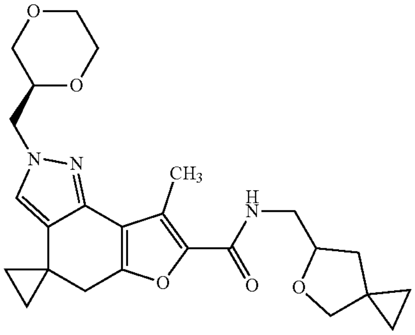 2′-{(2S)-1,4-dioxan-2-yl]methyl}-8′-methyl-N-{[(6±)-5-oxaspiro[2.4]heptan-6-yl]methyl}-2′,5′-dihydrospiro[cyclopropane-1,4′-furo[2,3-g]-indazole]-7′-carboxamide | $^1$H-NMR (400 MHz, DMSO-d6) δ [ppm]: 0.495 (1.39), 0.512 (2.89), 0.528 (3.12), 0.540 (1.29), 0.569 (2.25), 0.580 (4.92), 0.585 (3.95), 0.599 (6.80), 0.602 (5.60), 0.613 (3.96), 0.626 (4.36), 0.641 (2.67), 0.656 (1.30), 0.784 (3.01), 0.804 (5.37), 0.825 (1.41), 0.850 (1.53), 0.858 (1.83), 0.868 (7.52), 1.314 (1.34), 1.647 (2.14), 1.662 (2.22), 1.677 (2.82), 1.693 (2.94), 1.857 (2.71), 1.874 (3.07), 1.888 (2.47), 1.905 (2.23), 2.007 (1.18), 2.659 (1.17), 2.757 (2.19), 2.785 (1.27), 2.819 (1.95), 2.828 (8.21), 2.840 (8.44), 2.884 (1.27), 3.217 (2.65), 3.242 (3.32), 3.246 (3.53), 3.271 (3.41), 3.286 (0.96), 3.402 (2.27), 3.409 (2.27), 3.430 (3.07), 3.436 (3.30), 3.458 (2.52), 3.464 (2.64), 3.504 (2.01), 3.509 (2.21), 3.529 (5.30), 3.538 (3.45), 3.549 (7.98), 3.559 (1.88), 3.565 (1.96), 3.598 (7.99), 3.618 (6.48), 3.639 (2.85), 3.704 (4.93), 3.709 (5.50), 3.737 (4.52), 3.815 (1.49), 3.821 (1.57), 3.827 (1.57), 3.834 (1.98), 3.839 (1.65), 3.851 (1.16), 3.985 (1.24), 4.021 (3.89), 4.040 (5.42), 4.053 (3.97), 4.077 (1.53), 4.089 (1.22), 4.120 (0.88), 4.136 (2.56), 4.152 (3.65), 4.168 (2.51), 7.277 (16.00), 7.989 (1.73), 8.004 (3.72), 8.019 (1.83), 8.543 (0.89). LC-MS (Method 1): $R_t$ = 1.17 min; MS (ESIpos): m/z = 454 $[M + H]^+$ | Intermediate 40-1 GP H Conditions 29 mg, 13% yield, 90% purity Mixture of two isomers |
| 201 | 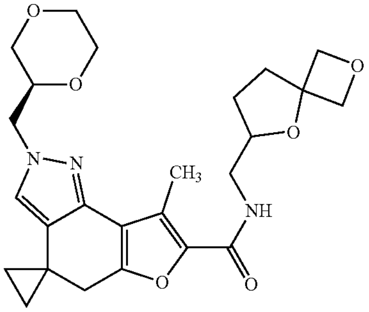 2′-{[(2S)-1,4-dioxan-2-yl]methyl}-N-{[(6±)-2,5-dioxaspiro[3.4]octan-6-yl]methyl}-8′-methyl-2′,5′-dihydrospiro[cyclopropane-1,4′-furo[2,3-g]indazole-7′-carboxamide | $^1$H-NMR (400 MHz, DMSO-d6) δ [ppm]: 0.767 (0.61), 0.786 (2.67), 0.807 (4.17), 0.829 (1.07), 0.852 (1.89), 0.873 (6.75), 0.932 (1.47), 0.948 (1.45), 1.316 (0.44), 1.350 (0.47), 1.567 (0.57), 1.586 (1.32), 1.598 (0.95), 1.603 (1.45), 1.618 (1.83), 1.634 (1.79), 1.654 (1.02), 1.862 (0.63), 1.879 (1.07), 1.893 (1.59), 1.912 (1.70), 1.927 (1.05), 1.944 (0.69), 2.049 (1.05), 2.069 (1.96), 2.081 (1.85), 2.088 (0.97), 2.100 (3.31), 2.120 (1.35), 2.160 (1.50), 2.175 (1.64), 2.181 (1.72), 2.194 (1.68), 2.206 (1.07), 2.212 (0.98), 2.226 (0.75), 2.318 (1.17), 2.518 (14.16), 2.523 (9.25), 2.758 (0.54), 2.792 (1.00), 2.836 (7.39), 2.848 (7.35), 2.891 (1.06), 3.169 (0.41), 3.187 (1.73), 3.202 (3.33), 3.211 (3.35), 3.218 (4.28), 3.226 (1.88), 3.242 (3.02), 3.246 (3.04), 3.271 (2.84), 3.289 (1.11), 3.295 (1.16), 3.303 (1.24), 3.368 (1.36), 3.375 (1.16), 3.384 (0.95), 3.404 (1.05), 3.410 (1.22), 3.431 (2.29), 3.437 (2.59), 3.458 (2.17), 3.464 (2.02), 3.504 (1.60), 3.509 (1.81), 3.532 (2.20), 3.539 (2.21), 3.559 (1.02), 3.565 (1.41), 3.613 (2.53), 3.641 (2.00), 3.704 (4.19), 3.709 (4.77), 3.732 (3.49), 3.737 (3.91), 3.798 (0.67), 3.805 (0.72), 3.816 (1.33), 3.821 (1.36), 3.828 (1.24), 3.834 (1.61), 3.840 (1.19), 3.852 (0.86), 3.858 (0.73), 3.986 (1.05), 4.003 (0.73), 4.022 (3.41), 4.041 (5.16), 4.055 (5.25), 4.070 (3.26), 4.078 (1.56), 4.086 (2.18), 4.102 (0.61), 4.442 (3.99), 4.458 (5.02), 4.469 (5.06), 4.555 (5.22), 4.572 (4.20), 4.584 (4.96), 4.600 (3.83), 7.278 (16.00), 8.032 (1.46), 8.047 (3.18), | Intermediate 40-1 GP H Conditions 46.4 mg, 20% yield, 90% purity Mixture of two isomers |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| | | 8.062 (1.50). LC-MS (Method 1): $R_t$ = 1.00 min; MS (ESIneg): m/z = 468 $[M - H]^-$ | |
| 201-1 | 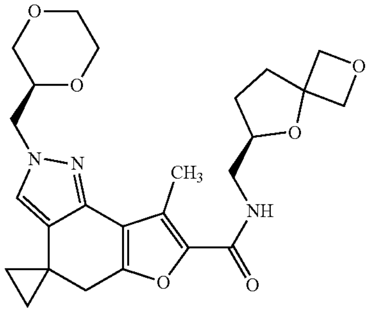 2′-{[(2S)-1,4-dioxan-2-yl]methyl}-N-{[(6R or 6S)-2,5-dioxaspiro[3.4]octan-6-yl]methyl}-8′-methyl-2′,5′-dihydro-spiro[cyclopropane-1,4′-furo[2,3-g]-indazole]-7′-carboxamide Diastereomer 1 of Ex. 201 | $R_t$ = 1.58 min $^1H$ NMR (400 MHz, DMSO-d6) δ ppm 0.77-0.81 (m, 2H), 0.86-0.89 (m, 2H), 1.56-1.67 (m, 1 H) 1.85-1.95 (m, 1 H) 2.04-2.12 (m, 1 H) 2.15-2.23 (m, 1 H) 2.49 (s, 3H, under DMSO peak), 2.83-2.89 (m, 2 H) 3.20-3.27 (m, 3 H) 3.40-3.47 (m, 1 H) 3.50-3.58 (m, 1 H) 3.60-3.65 (m, 1 H) 3.70-3.74 (m, 2 H) 3.79-3.86 (m, 1 H) 3.98-4.10 (m, 3 H) 4.44-4.47 (m, 2 H) 4.55-4.60 (m, 2 H) 7.28 (s, 1 H) 8.03-8.06 (m, 1H) | analyt. method: Instrument: Agilent: 1260, Aurora SFC-Modul; Column: Chiralpak IA 5µ 100 × 4.6 mm; eluent A: CO2; eluent B: ethanol + 0.2 vol % aqueous ammonia (32%); isocratic: 30% B; flow: 4 ml/min; temperature: 37.5° C.; BPR: 100 bar; UV: 254 nm): |
| 201-2 | 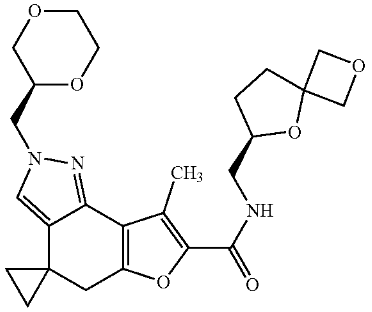 2′-{[(2S)-1,4-dioxan-2-yl]methyl}-N-{[(6S or 6R)-2,5-dioxaspiro[3.4]octan-6-yl]methyl}-8′-methyl-2′,5′-dihydrospiro[cyclopropane-1,4′-furo[2,3-g]indazole]-7′-carboxamide Diastereomer 2 of Ex. 201 | Rt = 2.73 min $^1H$ NMR (400 MHz, DMSO-d6) δ ppm 0.79-0.81 (m, 2H), 0.86-0.88 (m, 2H), 1.56-1.67(m, 1 H) 1.86-1.95 (m, 1 H) 2.04-2.12 (m, 1 H) 2.16-2.23 (m, 1 H) 2.49 (s, 3H, under DMSO peak), 2.79-2.89 (m, 2 H) 3.17-3.27 (m, 3 H) 3.40-3.47 (m, 1 H) 3.50-3.56 (m, 1 H) 3.60-3.64 (m, 1 H) 3.70-3.74 (m, 2 H) 3.80-3.86 (m, 1 H) 3.98-4.09 (m, 3 H) 4.43-4.47 (m, 2 H) 4.55-4.61 (m, 2 H) 7.28 (s, 1 H) 8.05 (t, 1H) | |
| 202 | 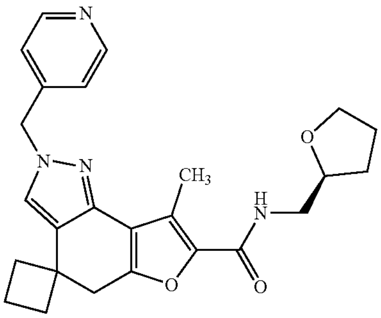 8′-Methyl-2′-(pyridin-4-ylmethyl)-N-[(2S)-tetrahydrofuran-2-ylmethyl]-2′,5′-dihydro-spiro[cyclobutan-1,4′-furo[2,3-g]indazol]-7′-carboxamide | $^1H$ NMR (400 MHz, DMSO-d6) δ 1.53-1.62 (m, 1H), 1.77-1.88 (m, 3H), 1.93-2.17 (m, 6H), 2.44 (s, 3H), 3.04 (s, 2H), 3.23 (t, 2H), 3.58-3.64 (m, 1H), 3.72-3.81 (m, 1H), 3.95 (quin, 1H), 5.38 (s, 2H), 7.13-7.17 (m, 2H), 7.95 (s, 1H), 7.98 (t, 1H), 8.50-8.55 (m, 2H) LC-MS (Method 1): $R_t$ = 1.09 min; MS (ESIpos): m/z = 433 $[M + H]^+$ | Intermediate 59 and CAS-RN: [7175-81-7] GP G Conditions A 15 mg, 89% yield, 95% purity % d. Th.) |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 203 | 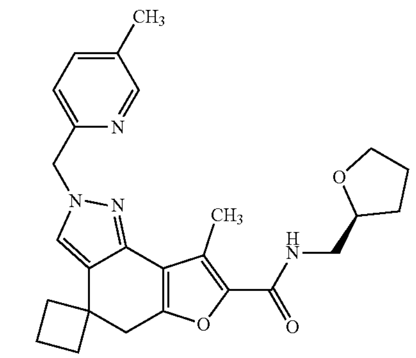 8′-Methyl-2′-[(5-methylpyridin-2-yl)methyl]-N-[(2S)-tetrahydrofuran-2-ylmethyl]-2′,5′-dihydrospiro[cyclobutan-1,4′-furo[2,3-g]-indazol]-7′-carboxamide | $^1$H NMR (400 MHz, DMSO-d6) δ 1.51-1.63 (m, 1H), 1.75-1.90 (m, 3H), 1.94-2.15 (m, 6H), 2.27 (s, 3H), 2.43 (s, 3H), 3.03 (s, 2H), 3.23 (t, 2H), 3.56-3.66 (m, 1H), 3.71-3.81 (m, 1H), 3.94 (quin, 1H), 5.35 (s, 2H), 7.01 (d, 1H), 7.57-7.62 (m, 1H), 7.88 (s, 1H), 7.97 (t, 1H), 8.36-8.39 (m, 1H) LC-MS (Method 1): $R_t$ = 1.21 min; MS (ESIpos): m/z = 447 $[M + H]^+$ | Intermediate 60 and CAS-RN: [7175-81-7] GP G Conditions A 7.6 mg, 17% yield, 94% purity % d. Th.) |
| 204 | 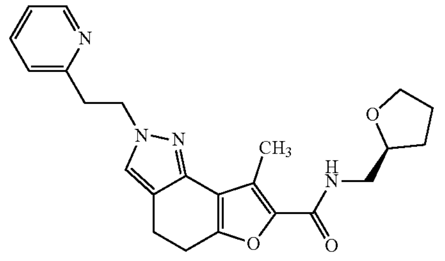 8-methyl-N-{[(2S)-oxolan-2-yl]methyl}-2-[2-(pyridin-2-yl)ethyl]-4,5-dihydro-2H-furo[2,3-g]indazole-7-carboxamide | $^1$H NMR (500 MHz, DMSO-d6) δ [ppm]: 1.54-1.61 (m, 1H), 1.74-1.91 (m, 3H), 2.47 (s, 3H), 2.78-2.83 (m, 2H), 2.84-2.89 (m, 2H), 3.20-3.28 (m, 4H), 3.57-3.64 (m, 1H), 3.76 (ddd, 1H), 3.94 (quin, 1H), 4.44 (t, 2H), 7.23 (ddd, 1H), 7.26 (d, 1H), 7.43 (s, 1H), 7.69 (td, 1H), 7.97 (t, 1H), 8.51-8.53 (m, 1H). LC-MS (Method 1): $R_t$ = 1.04 min; MS (ESIneg): m/z = 405 $[M - H]^-$ | Intermediate 61 and CAS-RN: [7175-81-7] GP G Conditions A 22.5 mg (44% yield, 99% purity) |
| 205 | 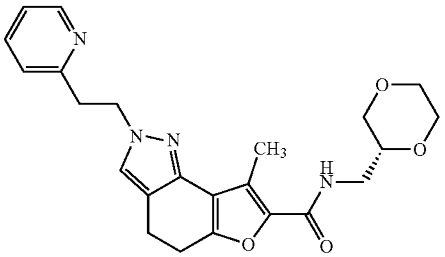 N-{[(2R)-1,4-dioxan-2-yl]methyl}-8-methyl-2-[2-(pyridin-2-yl)ethyl]-4,5-dihydro-2H-furo-[2,3-g]indazole-7-carboxamide | $^1$H NMR (500 MHz, DMSO-d6) δ [ppm]: 2.47 (s, 3H), 2.78-2.83 (m, 2H), 2.84-2.89 (m, 2H), 3.17-3.28 (m, 5H), 3.42-3.48 (m, 1H), 3.54 (td, 1H), 3.59-3.66 (m, 2H), 3.68-3.75 (m, 2H), 4.44 (t, 2H), 7.22-7.25 (m, 1H), 7.26 (d, 1H), 7.43 (s, 1H), 7.69 (td, 1H), 8.05 (t, 1H), 8.48-8.55 (m, 1H). LC-MS (Method 1): $R_t$ = 0.96 min; MS (ESIneg): m/z = 421 $[M - H]^-$ | Intermediate 61 and CAS-RN: [1523541-84-5] GPG Conditions A 30.2 mg (56% yield, 97% purity) |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 206 | 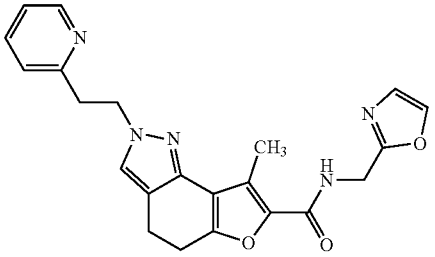 8-methyl-N-[(1,3-oxazol-2-yl)methyl]-2-[2-(pyridin-2-yl)ethyl]-4,5-dihydro-2H-furo[2,3-g]indazole-7-carboxamide | $^1$H NMR (400 MHz, DMSO-d6) δ [ppm]: 2.48 (s, 3H), 2.79-2.91 (m, 4H), 3.25 (t, 2H), 4.45 (t, 2H), 4.49 (d, 2H), 7.14 (d, 1H), 7.21-7.24 (m, 1H), 7.26 (d, 1H), 7.44 (s, 1H), 7.70 (td, 1H), 8.03 (d, 1H), 8.50-8.55 (m, 1H), 8.72 (t, 1H). LC-MS (Method 1): $R_t$ = 0.94 min; MS (ESIneg): m/z = 402 [M − H]$^-$ | Intermediate 61 and CAS-RN: [885331-17-9] GP G Conditions A 24.6 mg (48% yield, 98% purity) |
| 207 | 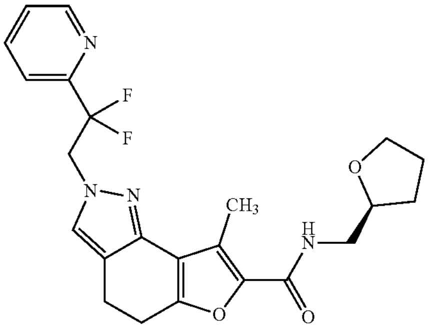 2-[2,2-difluoro-2-(pyridin-2-yl)ethyl]-8-methyl-N-{[(2S)-oxolan-2-yl]methyl}-4,5-dihydro-2H-furo[2,3-g]indazole-7-carboxamide | $^1$H NMR (400 MHz, DMSO-d6) δ [ppm]: 1.53-1.62 (m, 1H), 1.75-1.91 (m, 3H), 2.37 (s, 3H), 2.80-2.92 (m, 4H), 3.17-3.28 (m, 2H), 3.57-3.65 (m, 1H), 3.71-3.79 (m, 1H), 3.94 (quin, 1H), 5.01 (t, 2H), 7.50 (s, 1H), 7.59 (dd, 1H), 7.64-7.69 (m, 1H), 7.93-8.01 (m, 2H), 8.74 (d, 1H). LC-MS (Method 1): $R_t$ = 1.12 min; MS (ESIneg): m/z = 441 [M − H]$^-$ | Intermediate 62 and CAS-RN: [7175-81-7] GP G Conditions A 32.9 mg (69% yield, 98% purity) |
| 208 | 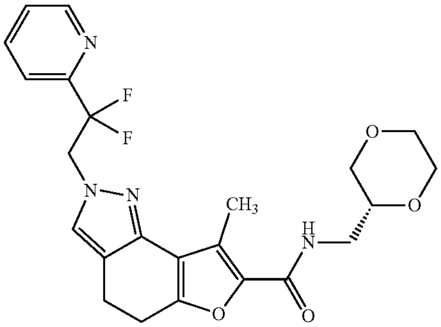 2-[2,2-difluoro-2-(pyridin-2-yl)ethyl]-N-{[(2R)-1,4-dioxan-2-yl]methyl}-8-methyl-4,5-dihydro-2H-furo-[2,3-g]indazole-7-carboxamide | $^1$H NMR (400 MHz, DMSO-d6) δ [ppm]: 2.37 (s, 3H), 2.80-2.92 (m, 4H), 3.14-3.28 (m, 3H), 3.39-3.49 (m, 1H), 3.50-3.58 (m, 1H), 3.58-3.66 (m, 2H), 3.67-3.76 (m, 2H), 5.01 (t, 2H), 7.50 (s, 1H), 7.57-7.62 (m, 1H), 7.66 (dt, 1H), 7.98 (td, 1H), 8.06 (t, 1H), 8.74 (d, 1H). LC-MS (Method 1): $R_t$ = 1.04 min; MS (ESIneg): m/z = 457 [M − H]$^-$ | Intermediate 62 and CAS-RN: [1523541-84-5] GP G Conditions A 29.8 mg (60% yield, 97% purity) |

TABLE 4-continued

The following examples (170 to 211) were prepared in analogy to example 3 starting from the given intermediates and commercially available amines (or their salts), applying the indicated general procedure.

| Example | Structure IUPAC-Name | Analytical Data | Preparation or Separation Methods |
|---|---|---|---|
| 209 | 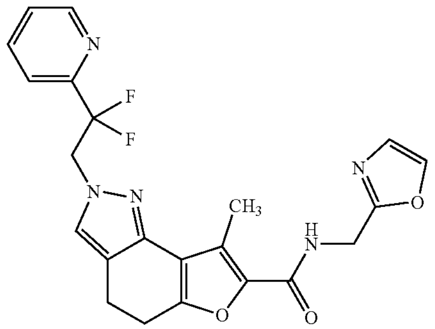 2-[2,2-difluoro-2-(pyridin-2-yl)ethyl]-8-methyl-N-[(1,3-oxazol-2-yl)methyl]-4,5-dihydro-2H-furo-[2,3-g]indazole-7-carboxamide | $^1$H NMR (400 MHz, DMSO-d6) δ [ppm]: 2.37 (s, 3H), 2.83-2.92 (m, 4H), 4.48 (d, 2H), 5.01 (t, 2H), 7.14 (d, 1H), 7.51 (s, 1H), 7.59 (dd, 1H), 7.66 (dt, 1H), 7.98 (td, 1H), 8.03 (d, 1H), 8.67-8.80 (m, 2H). LC-MS (Method 1): $R_t$ = 1.02 min; MS (ESIneg): m/z = 438 [M − H]$^-$ | Intermediate 62 and CAS-RN: [885331-17-9] GP G Conditions A 19.2 mg (39% yield, 95% purity) |
| 210 | 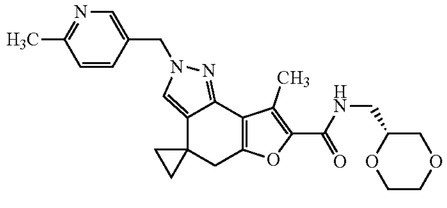 N{[(2R)-1,4-dioxan-2-yl]methyl}-8′-methyl-2′-[(6-methylpyridin-3-yl)methyl]-2′,5′-dihydrospiro-[cyclopropane-1,4′-furo[2,3-g]indazole]-7′-carboxamide | $^1$H-NMR (400 MHz, DMSO-d6) δ [ppm]: −0.011 (0.49), −0.003 (16.00), 0.005 (0.44), 0.783 (0.78), 0.795 (2.02), 0.800 (2.45), 0.809 (1.31), 0.861 (1.22), 0.870 (2.57), 0.887 (0.81), 0.931 (1.75), 0.934 (0.62), 0.948 (1.80), 2.430 (11.34), 2.477 (13.34), 2.518 (3.43), 2.522 (2.17), 2.832 (6.22), 3.161 (0.46), 3.176 (1.35), 3.195 (1.33), 3.200 (1.44), 3.205 (1.48), 3.209 (1.26), 3.224 (1.27), 3.229 (1.46), 3.240 (0.76), 3.258 (0.47), 3.305 (0.42), 3.379 (0.69), 3.409 (0.44), 3.416 (0.52), 3.436 (0.93), 3.442 (1.00), 3.464 (0.83), 3.470 (0.78), 3.505 (0.72), 3.511 (0.76), 3.533 (0.95), 3.540 (0.98), 3.566 (0.62), 3.601 (1.43), 3.607 (1.32), 3.616 (0.55), 3.625 (1.07), 3.631 (1.19), 3.679 (1.02), 3.685 (0.88), 3.707 (1.76), 3.735 (0.77), 5.229 (4.75), 7.212 (1.65), 7.231 (1.88), 7.421 (6.10), 7.516 (1.24), 7.522 (1.25), 7.536 (1.07), 7.542 (1.10), 8.030 (0.60), 8.045 (1.30), 8.060 (0.60), 8.370 (1.73), 8.375 (1.75). LC-MS (Method 1): $R_t$ = 1.02 min; MS (ESIneg): m/z = 447 [M − H]$^-$ | Intermediate 63 GP H Conditions A 15 mg, 7% yield, 95% purity |
| 211 | 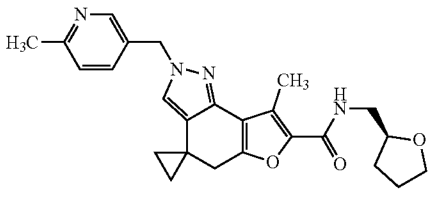 8′-methyl-2′-[(6-methylpyridin-3-yl)methyl]-N-{[(2S)-oxolan-2-yl]methyl}-2′,5′-dihydrospiro[cyclopropane-1,4′-furo[2,3-g]indazole]-7′-carboxamide | $^1$H-NMR (400 MHz, DMSO-d6) δ [ppm]: −0.011 (0.58), −0.002 (16.00), 0.005 (0.50), 0.782 (0.54), 0.795 (1.42), 0.800 (1.76), 0.809 (0.93), 0.860 (1.02), 0.869 (2.04), 0.886 (0.70), 1.560 (0.44), 1.776 (0.41), 1.792 (0.74), 1.810 (0.83), 1.828 (0.74), 1.839 (0.44), 1.857 (0.49), 2.430 (8.12), 2.476 (10.11), 2.518 (3.81), 2.522 (2.41), 2.831 (4.42), 3.212 (0.92), 3.227 (1.80), 3.243 (1.00), 3.594 (0.57), 3.597 (0.57), 3.614 (0.76), 3.631 (0.40), 3.744 (0.67), 3.759 (0.57), 3.762 (0.56), 3.921 (0.63), 3.937 (0.89), 3.953 (0.55), 5.229 (3.35), 7.212 (1.16), 7.231 (1.32), 7.420 (4.50), 7.516 (0.87), 7.522 (0.87), 7.536 (0.76), 7.542 (0.75), 7.950 (0.42), 7.964 (0.90), 7.980 (0.41), 8.371 (1.23), 8.376 (1.21). LC-MS (Method 1): $R_t$ = 1.10 min; MS (ESIpos): m/z = 433 [M + H]$^+$ | Intermediate 63 GP H Conditions A 18 mg, 9% yield, 95% purity |

TABLE 5

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 212 | 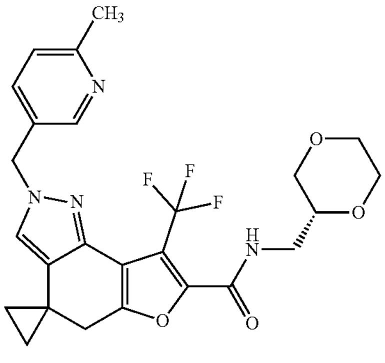 [SMILES: Cc1ccc(Cn2cc3c(n2)-c2c(oc(C(=O)NC[C@@H]4COCCO4)c2C(F)(F)F)CC32CC2)cn1] N-{[(2R)-1,4-dioxan-2-yl]methyl}-2'-[(6-methylpyridin-3-yl)methyl]-8'-(trifluoromethyl)-2',5'-dihydrospiro[cyclopropane-1,4'-furo[2,3-g]indazole]-7'-carboxamide | $^1$H NMR (400 MHz, DMSO-d6) δ [ppm]: 0.80-0.86 (m, 2H), 0.88-0.92 (m, 2H), 2.43 (s, 3H), 2.91 (s, 2H), 3.18-3.28 (m, 3H), 3.40-3.49 (m, 1H), 3.51-3.59 (m, 1H), 3.59-3.66 (m, 2H), 3.68-3.76 (m, 2H), 5.24 (s, 2H), 7.22 (d, 1H), 7.48 (s, 1H), 7.54 (dd, 1H), 8.38 (d, 1H), 8.76 (t, 1H). LC-MS (Method 1): $R_t$ = 1.06 min; MS (ESIpos): m/z = 503 [M + H]$^+$ | Intermediate 65 and CAS-RN: [1523541-84-5] GP G (conditions A with HATU) 6.7 mg (12% yield, 98% purity). |
| 213 | 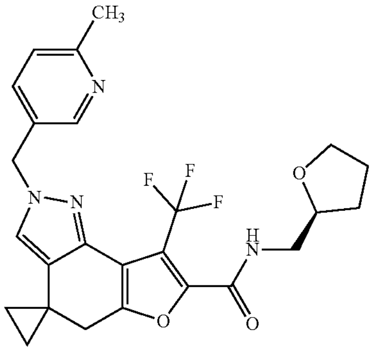 [SMILES: Cc1ccc(Cn2cc3c(n2)-c2c(oc(C(=O)NC[C@@H]4CCCO4)c2C(F)(F)F)CC32CC2)cn1] 2'-[(6-methylpyridin-3-yl)methyl]-N-{[(2S)-oxolan-2-yl]methyl}-8'-(trifluoromethyl)-2',5'-dihydrospiro[cyclopropane-1,4'-furo[2,3-g]indazole]-7'-carboxamide | $^1$H NMR (400 MHz, DMSO-d6) δ [ppm]: 0.86-0.91 (m, 4H), 1.54-1.63 (m, 1H), 1.77-1.94 (m, 3H), 2.43 (s, 3H), 2.90 (s, 2H), 3.27 (t, 2H), 3.58-3.66 (m, 1H), 3.72-3.80 (m, 1H), 3.94 (quin, 1H), 5.24 (s, 2H), 7.22 (d, 1H), 7.48 (s, 1H), 7.53 (dd, 1H), 8.33-8.40 (m, 1H), 8.72 (t, 1H). LC-MS (Method 1): $R_t$ = 1.14 min; MS (ESIpos): m/z = 487 [M + H]$^+$ | Intermediate 65 and CAS-RN: [7175-81-7] GPG (conditions A with HATU) 9.8 mg (16% yield, 90% purity). |
| 214 | 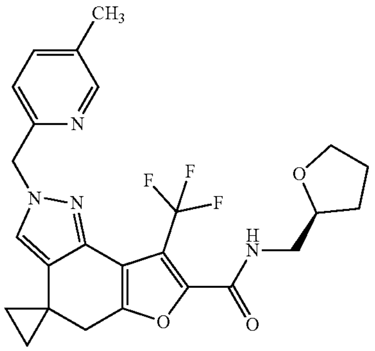 [SMILES: Cc1ccc(Cn2cc3c(n2)-c2c(oc(C(=O)NC[C@@H]4CCCO4)c2C(F)(F)F)CC32CC2)nc1] 2'-[(5-methylpyridin-2-yl)methyl]-N-{[(2S)-oxolan-2-yl]methyl}-8'-(trifluoromethyl)-2',5'-dihydrospiro[cyclopropane-1,4'-furo[2,3-g]indazole]-7'-carboxamide | $^1$H NMR (400 MHz, DMSO-d6) δ [ppm]: 0.82-0.87 (m, 2H), 0.88-0.93 (m, 2H), 1.53-1.62 (m, 1H), 1.80-1.94 (m, 3H), 2.27 (s, 3H), 2.92 (s, 2H), 3.27 (t, 2H), 3.58-3.66 (m, 1H), 3.76 (dt, 1H), 3.94 (quin, 1H), 5.29 (s, 2H), 6.99 (d, 1H), 7.48 (s, 1H), 7.54-7.61 (m, 1H), 8.33-8.40 (m, 1H), 8.72 (t, 1H). LC-MS (Method 1): $R_t$ = 1.21 min; MS (ESIpos): m/z = 487 [M + H]$^+$ | Intermediate 66 and CAS-RN: [7175-81-7] GP G (conditions A with HATU) 6.2 mg (16% yield, 83% purity). |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 215 | 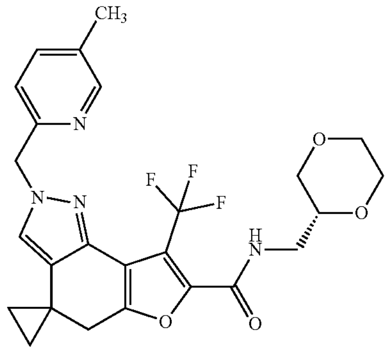 [SMILES: Cc1ccc(Cn2cc3c(n2)-c2c(oc(C(=O)NC[C@@H]4COCCO4)c2C(F)(F)F)CC32CC2)nc1] N-{[(2R)-1,4-dioxan-2-yl]methyl}-2'-[(5-methylpyridin-2-yl)methyl]-8'-(trifluoromethyl)-2',5'-dihydrospiro[cyclopropane-1,4'-furo[2,3-g]indazole]-7'-carboxamide | $^1$H NMR (400 MHz, DMSO-d6) δ [ppm]: 0.84-0.86 (m, 2H), 0.90-0.92 (m, 2H), 2.27 (s, 3H), 2.92 (s, 2H), 3.18-3.28 (m, 3H), 3.41-3.49 (m, 1H), 3.51-3.59 (m, 1H), 3.59-3.67 (m, 2H), 3.68-3.77 (m, 2H), 5.29 (s, 2H), 7.00 (d, 1H), 7.48 (s, 1H), 7.55-7.63 (m, 1H), 8.32-8.40 (m, 1H), 8.76 (t, 1H). LC-MS (Method 1): $R_t$ = 1.12 min; MS (ESIpos): m/z = 503 [M + H]$^+$ | Intermediate 66 and CAS-RN: [1523541-84-5] GPG (conditions A with HATU) 5.8 mg (17% yield, 97% purity). |
| 216 | 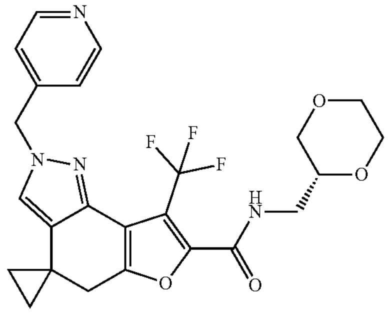 [SMILES: O=C(NC[C@@H]1COCCO1)c1oc2c(c1C(F)(F)F)-c1nn(Cc3ccncc3)cc1C1(CC1)C2] N-[(2R)-1,4-Dioxan-2-ylmethyl]-2'-(pyridin-4-ylmethyl)-8'-(trifluormethyl)-2',5'-dihydrospiro[cyclopropan-1,4'-furo[2,3-g]indazol]-7'-carboxamide | $^1$H NMR (400 MHz, DMSO-d6) δ [ppm]: 0.82-0.89 (m, 2H), 0.89-0.95 (m, 2H), 2.94 (s, 2H), 3.18-3.30 (m, 3H), 3.41-3.50 (m, 1H), 3.51-3.59 (m, 1H), 3.59-3.67 (m, 2H), 3.68-3.77 (m, 2H), 5.33 (s, 2H), 7.07-7.17 (m, 2H), 7.53 (s, 1H), 8.47-8.57 (m, 2H), 8.72-8.80 (m, 1H) LC-MS (Method 1): $R_t$ = 1.02 min; MS (ESIpos): m/z = 489 [M + H]$^+$ | Intermediate 67 and CAS-RN: [1523541-84-5] GP G (conditions A with HATU) 12.5 mg (54% yield, 98% purity) |
| 217 | 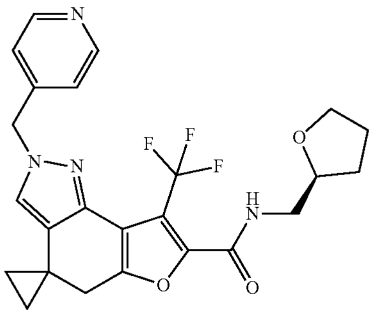 [SMILES: O=C(NC[C@@H]1CCCO1)c1oc2c(c1C(F)(F)F)-c1nn(Cc3ccncc3)cc1C1(CC1)C2] 2'-(Pyridin-4-ylmethyl)-N-[(2S)-tetrahydrofuran-2-ylmethyl]-8'-(trifluormethyl)-2',5'-dihydrospiro[cyclopropan-1,4'-furo[2,3-g]indazol]-7'-carboxamide | $^1$H NMR (400 MHz, DMSO-d6) δ [ppm]: 0.82-0.89 (m, 2H), 0.89-0.95 (m, 2H), 1.53-1.61 (m, 1H), 1.75-1.94 (m, 3H), 2.94 (s, 2H), 3.27 (t, 2H), 3.58-3.67 (m, 1H), 3.76 (td, 1H), 3.94 (quin, 1H), 5.33 (s, 2H), 7.09-7.14 (m, 2H), 7.53 (s, 1H), 8.50-8.55 (m, 2H), 8.73 (t, 1H) LC-MS (Method 1): $R_t$ = 1.10 min; MS (ESIpos): m/z = 473 [M + H]$^+$ | Intermediate 67 and CAS-RN: [7175-81-7] GP G (conditions A with HATU) 12.7 mg (58% yield, 99% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 218 | 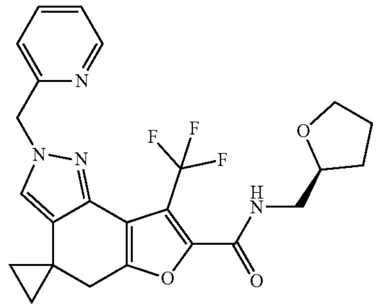 [SMILES: O=C(NC[C@@H]1CCCO1)c1oc2c(c1C(F)(F)F)-c1nn(Cc3ccccn3)cc1C1(CC1)C2] N-{[(2S)-oxolan-2-yl]methyl}-2'-[(pyridin-2-yl)methyl]-8'-(trifluoromethyl)-2',5'-dihydrospiro[cyclopropane-1,4'-furo[2,3-g]indazole]-7'-carboxamide | $^{1}$H NMR (400 MHz, DMSO-d6) δ [ppm]: 0.81-0.88 (m, 2H), 0.89-0.95 (m, 2H), 1.52-1.61 (m, 1H), 1.74-1.94 (m, 3H), 2.93 (s, 2H), 3.27 (t, 2H), 3.58-3.66 (m, 1H), 3.76 (dt, 1H), 3.94 (quin, 1H), 5.35 (s, 2H), 7.05 (d, 1H), 7.31 (ddd, 1H), 7.52 (s, 1H), 7.77 (td, 1H), 8.51-8.55 (m, 1H), 8.73 (t, 1H). LC-MS (Method 1): $R_t$ = 1.16 min; MS (ESIpos): m/z = 473 [M + H]$^+$ | Intermediate 68 and CAS-RN: [7175-81-7] GPG (conditions A with HATU) 10.9 mg (59% yield, 99% purity) |
| 219 | 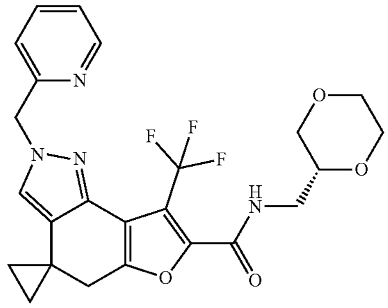 [SMILES: O=C(NC[C@@H]1COCCO1)c1oc2c(c1C(F)(F)F)-c1nn(Cc3ccccn3)cc1C1(CC1)C2] N-[(2R)-1,4-Dioxan-2-ylmethyl]-2'-(pyridin-2-ylmethyl)-8'-(trifluormethyl)-2',5'-dihydrospiro[cyclopropan-1,4'-furo[2,3-g]indazol]-7'-carboxamide | $^{1}$H NMR (400 MHz, DMSO-d6) δ 0.83-0.89 (m, 2H), 0.89-0.93 (m, 2H), 2.93 (s, 2H), 3.17-3.29 (m, 3H), 3.41-3.49 (m, 1H), 3.51-3.59 (m, 1H), 3.60-3.67 (m, 2H), 3.68-3.77 (m, 2H), 5.35 (s, 2H), 7.06 (d, 1H), 7.31 (ddd, 1H), 7.52 (s, 1H), 7.77 (td, 1.77 Hz, 1H), 8.50-8.57 (m, 1H), 8.76 (t, 1H) LC-MS (Method 1): $R_t$ = 1.06 min; MS (ESIpos): m/z = 489 [M + H]$^+$ | Intermediate 68 and CAS-RN: [1523541-84-5] GPG (conditions A with HATU) 13.4 mg (70% yield, 99% purity) |
| 220 | 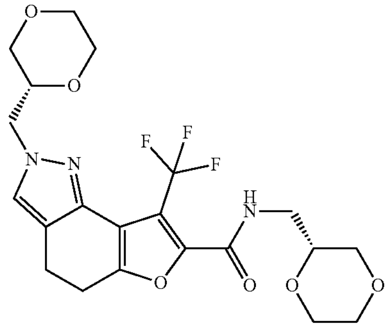 [SMILES: O=C(NC[C@@H]1COCCO1)c1oc2c(c1C(F)(F)F)-c1nn(C[C@@H]3COCCO3)cc1CC2] N,2-bis{[(2R)-1,4-dioxan-2-yl]methyl}-8-(trifluoromethyl)-4,5-dihydro-2H-furo[2,3-g]indazole-7-carboxamide | $^{1}$H-NMR (400 MHz, DMSO-d6) δ [ppm]: 2.074 (5.18), 2.331 (1.89), 2.336 (0.86), 2.518 (10.80), 2.523 (6.99), 2.673 (1.98), 2.678 (0.99), 2.842 (2.30), 2.846 (2.34), 2.865 (9.33), 2.883 (7.55), 2.930 (8.03), 2.932 (8.08), 2.948 (11.22), 2.955 (4.14), 2.967 (2.76), 2.972 (2.71), 3.188 (1.18), 3.197 (4.61), 3.203 (2.46), 3.221 (7.76), 3.226 (6.47), 3.237 (10.12), 3.250 (9.45), 3.264 (8.63), 3.280 (3.97), 3.290 (5.80), 3.298 (2.93), 3.383 (0.41), 3.406 (1.54), 3.412 (1.90), 3.424 (1.92), 3.433 (4.21), 3.439 (4.29), 3.450 (4.25), 3.457 (5.03), 3.461 (4.44), 3.467 (3.49), 3.478 (3.70), 3.485 (3.41), 3.502 (2.89), 3.508 (3.39), 3.525 (3.56), 3.531 (7.12), 3.537 (4.16), 3.553 (4.66), 3.559 (5.46), 3.564 (3.00), 3.580 (1.90), 3.586 (3.16), 3.613 (8.80), 3.628 (3.64), 3.643 (7.77), 3.660 (1.10), 3.666 (1.28), 3.696 (4.66), 3.702 (4.14), 3.725 (8.64), 3.730 (9.95), 3.737 (6.50), 3.749 (4.52), 3.759 (5.12), 3.765 (4.05), 3.789 (1.24), 3.796 (1.09), 3.802 (1.90), 3.808 (2.13), 3.813 (2.21), 3.819 (2.07), 3.826 (2.62), 3.832 (1.82), 3.842 (1.32), 3.849 (1.08), 4.052 (1.24), 4.068 (0.74), 4.088 (6.96), 4.097 (7.58), 4.104 (7.52), 4.110 (6.96), 4.133 (1.27), 4.146 (0.71), 7.467 (0.40), 7.525 (16.00), 8.734 (2.58), 8.749 | Intermediate 70 and CAS-RN: [1523541-84-5] GP G (conditions A with HATU) 29.2 mg (30% yield, 98% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | (5.30), 8.764 (2.43). LC-MS (Method 1): $R_t$ = 0.93 min; MS (ESIpos): m/z = 472 $[M + H]^+$ | |
| 221 | 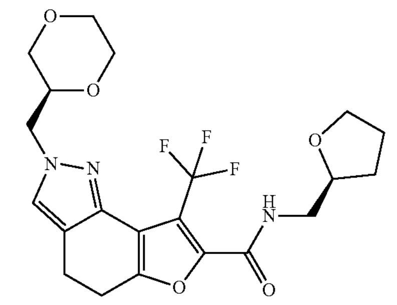 [SMILES: O=C(NC[C@@H]1CCCO1)c1oc2c(c1C(F)(F)F)-c1nn(C[C@H]3COCCO3)cc1CC2] 2-{[(2S)-1,4-dioxan-2-yl]methyl}-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.232 (0.48), 1.524 (0.53), 1.541 (1.79), 1.543 (1.70), 1.553 (1.50), 1.560 (2.55), 1.569 (2.37), 1.577 (1.98), 1.584 (1.66), 1.590 (2.26), 1.606 (1.44), 1.759 (0.51), 1.773 (1.16), 1.779 (0.92), 1.788 (2.12), 1.794 (2.79), 1.810 (5.00), 1.828 (5.03), 1.845 (3.37), 1.861 (2.76), 1.866 (1.66), 1.871 (1.94), 1.878 (2.19), 1.883 (1.91), 1.890 (2.48), 1.900 (1.68), 1.904 (1.99), 1.907 (2.00), 1.911 (1.76), 1.921 (1.47), 1.928 (1.34), 1.942 (0.85), 2.074 (1.03), 2.518 (7.06), 2.523 (5.04), 2.841 (2.23), 2.846 (2.35), 2.865 (9.77), 2.883 (8.40), 2.926 (8.76), 2.928 (8.73), 2.944 (11.58), 2.952 (4.35), 2.963 (2.98), 2.968 (2.81), 3.237 (4.39), 3.255 (7.94), 3.261 (6.89), 3.269 (15.57), 3.285 (8.59), 3.290 (6.41), 3.406 (1.43), 3.412 (1.76), 3.433 (3.82), 3.440 (4.22), 3.461 (3.59), 3.467 (3.36), 3.503 (2.84), 3.509 (3.25), 3.532 (3.97), 3.537 (4.00), 3.558 (1.92), 3.564 (2.46), 3.597 (1.92), 3.613 (7.57), 3.634 (6.63), 3.652 (3.21), 3.714 (4.15), 3.731 (4.26), 3.738 (6.56), 3.741 (6.15), 3.758 (7.46), 3.765 (4.92), 3.774 (4.55), 3.776 (4.13), 3.789 (1.64), 3.794 (3.50), 3.802 (2.16), 3.808 (2.28), 3.812 (2.41), 3.818 (2.18), 3.825 (2.74), 3.842 (1.38), 3.849 (1.17), 3.920 (1.23), 3.936 (3.55), 3.951 (5.82), 3.967 (3.70), 3.982 (0.93), 4.051 (1.24), 4.068 (0.72), 4.087 (7.26), 4.097 (7.88), 4.104 (8.01), 4.110 (7.40), 4.132 (1.33), 4.145 (0.79), 7.524 (16.00), 8.697 (2.59), 8.712 (5.41), 8.727 (2.59). LC-MS (Method 1): $R_t$ = 1.02 min; MS (ESIpos): m/z = 456 $[M + H]^+$ | Intermediate 69 GP G Conditions A 416 mg, 84% yield, 99% purity |
| 222 | 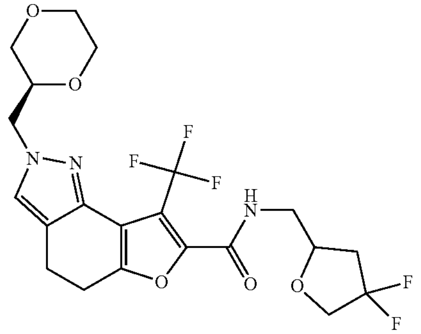 [SMILES: O=C(NCC1CC(F)(F)CO1)c1oc2c(c1C(F)(F)F)-c1nn(C[C@H]3COCCO3)cc1CC2] N-{[(2±)-4,4-difluorooxolan-2-yl]methyl}-2-{[(2S)-1,4-dioxan-2-yl]methyl}-8-(trifluoromethyl)-4,5-dihydro-2H-furo[2,3-g]indazole-7-carboxamide | $^1$H NMR (400 MHz, DMSO-d6) δ [ppm]: 2.15-2.30 (m, 1 H) 2.53-2.61 (m, 1 H) 2.84-2.89 (m, 2 H) 2.93-2.97 (m, 2 H) 3.23-3.30 (m, 1 H) 3.37-3.49 (m, 3 H) 3.49-3.57 (m, 1 H) 3.60-3.65 (m, 1 H) 3.70-3.92 (m, 4 H) 4.01-4.13 (m, 3 H) 4.24-4.32 (m, 1 H) 7.53 (s, 1 H) 8.85 (t, 1H) LC-MS (Method 1): $R_t$ = 1.09 min; MS (ESIpos): m/z = 492 [M + H]+ | Intermediate 69 GP H Conditions A 10 mg, 4% yield, 95% purity Mixture of two isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 222-1 | 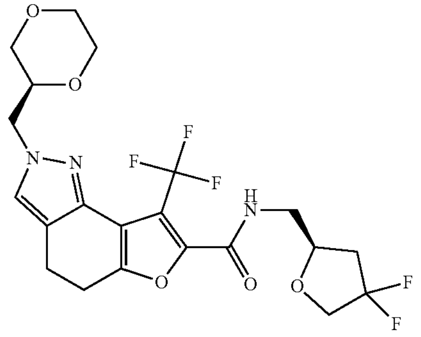 [SMILES: O=C(NC[C@H]1CC(F)(F)CO1)c1oc2c(c1C(F)(F)F)-c1nn(C[C@H]3COCCO3)cc1CC2] N-{[(2R or 2S)-4,4-difluorooxolan-2-yl]methyl}-2-{[(2S)-1,4-dioxan-2-yl]methyl}-8-(trifluoromethyl)-4,5-dihydro-2H-furo[2,3-g]indazole-7-carboxamide Diastereomer 1 of Ex. 222 | $R_t$ = 8.18 min $^1$H NMR (400 MHz, DMSO-d6) δ [ppm]: 2.15-2.30 (m, 1 H) 2.53-2.61 (m, 1 H) 2.84-2.89 (m, 2 H) 2.93-2.97 (m, 2 H) 3.23-3.30 (m, 1 H) 3.37-3.49 (m, 3 H) 3.49-3.57 (m, 1 H) 3.61-3.65 (m, 1 H) 3.71-3.91 (m, 4 H) 4.02-4.13 (m, 3 H) 4.25-4.32 (m, 1 H) 7.53 (s, 1 H) 8.85 (t, 1H) | analyt. method: Instrument: Waters Alliance 2695; Column: YMC Cellulose SB 3μ, 100 x 4.6; eluent A: hexane + 0.1 vol% diethylamine; eluent B: ethanol; isocratic: 90% A + 10% B; flow: 1.4 ml/min; temperature: 25° C.; UV: 254 nm |
| 222-2 | 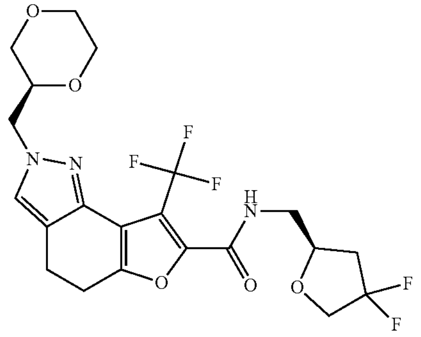 [SMILES: O=C(NC[C@H]1CC(F)(F)CO1)c1oc2c(c1C(F)(F)F)-c1nn(C[C@H]3COCCO3)cc1CC2] N-{[(2S or 2R)-4,4-difluorooxolan-2-yl]methyl}-2-{[(2S)-1,4-dioxan-2-yl]methyl}-8-(trifluoromethyl)-4,5-dihydro-2H-furo[2,3-g]indazole-7-carboxamide Diasteromer 2 of Ex. 222 | $R_t$ = 9.19 min $^1$H NMR (400 MHz, DMSO-d6) δ [ppm]: 2.15-2.30 (m, 1 H) 2.53-2.61 (m, 1 H) 2.84-2.89 (m, 2 H) 2.93-2.97 (m, 2 H) 3.23-3.30 (m, 1 H) 3.38-3.49 (m, 3 H) 3.49-3.57 (m, 1 H) 3.61-3.65 (m, 1 H) 3.71-3.91 (m, 4 H) 4.02-4.15 (m, 3 H) 4.25-4.32 (m, 1 H) 7.53 (s, 1 H) 8.85 (t, 1H) | |
| 223 | 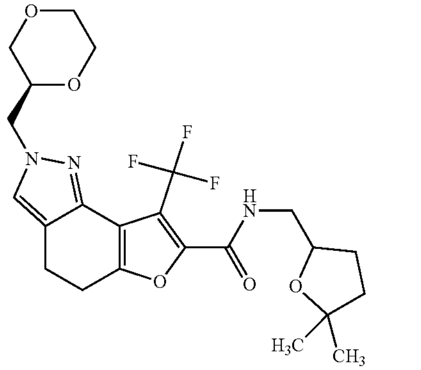 [SMILES: CC1(C)CCC(CNC(=O)c2oc3c(c2C(F)(F)F)-c2nn(C[C@H]4COCCO4)cc2CC3)O1] N-{[(2±)-5,5-dimethyloxolan-2-yl]methyl}-2-{[(2S)-1,4-dioxan-2-yl]methyl}-8-(trifluoromethyl)-4,5-dihydro-2H-furo[2,3-g]indazole-7-carboxamide | LC-MS (Method 1): $R_t$ = 1.18 min; MS (ESIpos): m/z = 484 [M + H]$^+$ $^1$H NMR (400 MHz, DMSO-d6) δ [ppm]: 1.14 (s, 3 H) 1.20 (s, 3 H) 1.66-1.73 (m, 3 H) 1.91-2.02 (m, 1 H) 2.83-2.90 (m, 2 H) 2.91-2.98 (m, 2 H) 3.22-3.30 (m, 3 H) 3.40-3.48 (m, 1 H) 3.49-3.58 (m, 1 H) 3.60-3.66 (m, 1 H) 3.70-3.78 (m, 2 H) 3.79-3.87 (m, 1 H) 3.99-4.07 (m, 1 H) 4.08-4.12 (m, 2 H) 7.52 (s, 1 H) 8.66 (t, 1H) | Intermediate 69 GP H Conditions A 54 mg, 21% yield, 99% purity Mixture of two isomers |

TABLE 5-continued

The following examples (212 to 316) were prepared in analogy to example 169 starting from the given intermediates and commercially available amines (or their salts), applying the indicated general procedure.

| Ex-ample | Structure IUPAC-Name | Analytical Data | Preparation or Separation Methods |
|---|---|---|---|
| 223-1 | 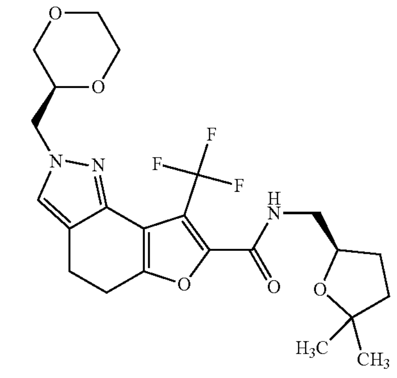 [SMILES: CC1(C)CC[C@H](CNC(=O)c2oc3c(c2C(F)(F)F)-c2nn(C[C@H]4COCCO4)cc2CC3)O1] N-{[(2R or 2S)-5,5-dimethyloxolan-2-yl]methyl}-2-{[(2S)-1,4-dioxan-2-yl]methyl}-8-(trifluoromethyl)-4,5-dihydro-2H-furo[2,3-g]indazole-7-carboxamide Diastereomer 1 of Ex. 223 | $R_t$ = 3.58 min $^{1}$H NMR (400 MHz, DMSO-d6) δ [ppm]: 1.14 (s, 3 H) 1.20 (s, 3 H) 1.66-1.73 (m, 3 H) 1.91-2.02 (m, 1 H) 2.83-2.90 (m, 2 H) 2.91-2.98 (m, 2 H) 3.22-3.30 (m, 3 H) 3.40-3.48 (m, 1 H) 3.49-3.58 (m, 1 H) 3.61-3.64 (m, 1 H) 3.70-3.78 (m, 2 H) 3.79-3.87 (m, 1 H) 3.99-4.07 (m, 1 H) 4.08-4.12 (m, 2 H) 7.52 (s, 1 H) 8.65 (t, 1H) | analyt. method: Instrument: Waters Alliance 2695; Column: Chiralpak IG 3μ, 100 × 4.6; eluent A: hexane + 0.1 vol% diethylamine; eluent B: ethanol; isocratic: 50% A + 50% B; flow: 1.4 ml/min; temperature: 25° C.; UV: 220 nm |
| 223-2 | 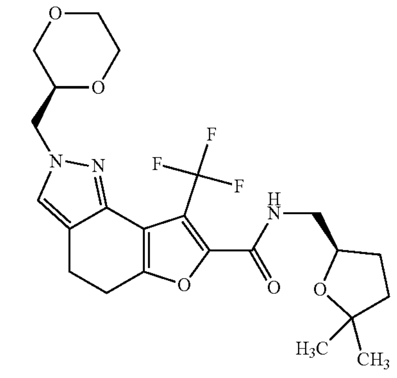 [SMILES: CC1(C)CC[C@H](CNC(=O)c2oc3c(c2C(F)(F)F)-c2nn(C[C@H]4COCCO4)cc2CC3)O1] N-{[(2S or 2R)-5,5-dimethyloxolan-2-yl]methyl}-2-{[(2S)-1,4-dioxan-2-yl]methyl}-8-(trifluoromethyl)-4,5-dihydro-2H-furo[2,3-g]indazole-7-carboxamide Diasteromer 2 of Ex. 223 | $R_t$ = 4.94 min $^{1}$H NMR (400 MHz, DMSO-d6) δ [ppm]: 1.15 (s, 3 H) 1.20 (s, 3 H) 1.66-1.73 (m, 3 H) 1.91-2.02 (m, 1 H) 2.83-2.90 (m, 2 H) 2.91-2.98 (m, 2 H) 3.22-3.30 (m, 3 H) 3.40-3.48 (m, 1 H) 3.49-3.58 (m, 1 H) 3.61-3.64 (m, 1 H) 3.70-3.78 (m, 2 H) 3.79-3.87 (m, 1 H) 3.99-4.07 (m, 1 H) 4.08-4.12 (m, 2 H) 7.52 (s, 1 H) 8.66 (t, 1H) | |
| 224 | 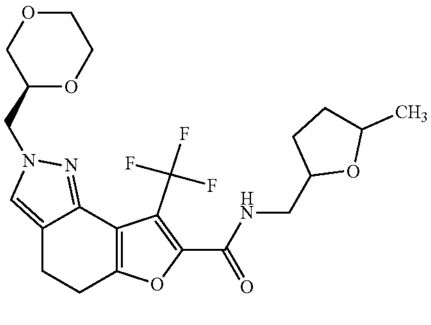 [SMILES: CC1CCC(CNC(=O)c2oc3c(c2C(F)(F)F)-c2nn(C[C@H]4COCCO4)cc2CC3)O1] 2-{[(2S)-1,4-dioxan-2-yl]methyl}-N-{[(2±,5±)-5-methyloxolan-2-yl]methyl}-8-(trifluoromethyl)-4,5-dihydro-2H-furo[2,3-g]indazole-7-carboxamide | $^{1}$H-NMR (500 MHz, DMSO-d6) δ [ppm]: 1.113 (3.94), 1.124 (4.19), 1.158 (15.40), 1.170 (16.00), 1.232 (0.49), 1.367 (0.74), 1.372 (1.10), 1.387 (1.37), 1.394 (1.00), 1.401 (0.86), 1.409 (0.92), 1.425 (0.60), 1.607 (0.73), 1.616 (0.64), 1.631 (1.07), 1.641 (0.88), 1.653 (0.86), 1.662 (0.58), 1.856 (0.48), 1.871 (0.98), 1.887 (1.59), 1.897 (0.93), 1.901 (1.11), 1.907 (1.41), 1.912 (2.04), 1.916 (1.24), 1.921 (1.31), 1.924 (1.18), 1.938 (0.91), 1.948 (0.78), 1.964 (0.59), 1.994 (0.76), 2.514 (5.34), 2.518 (4.86), 2.522 (3.96), 2.847 (1.51), 2.864 (5.78), 2.879 (4.47), 2.929 (4.77), 2.943 (5.88), 2.958 (1.57), 2.961 (1.67), 3.233 (0.69), 3.242 (2.93), 3.251 (1.01), 3.261 (4.70), 3.265 (3.65), 3.273 (3.82), 3.284 (5.71), 3.294 (2.02), 3.313 (1.15), 3.364 (0.90), 3.412 (0.99), | Intermediate 69 GP H Conditions A 20 mg, 13% yield, 99% purity Mixture of cis/trans isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | 3.417 (1.19), 3.434 (2.26), 3.439 (2.45), 3.456 (1.90), 3.461 (1.72), 3.507 (1.56), 3.512 (1.79), 3.531 (2.19), 3.536 (2.18), 3.552 (1.12), 3.557 (1.30), 3.613 (2.32), 3.637 (1.77), 3.717 (2.19), 3.732 (2.32), 3.737 (3.90), 3.755 (1.99), 3.760 (2.24), 3.794 (0.65), 3.809 (1.20), 3.813 (1.35), 3.817 (1.21), 3.823 (1.54), 3.828 (1.12), 3.837 (0.72), 3.842 (0.64), 3.865 (1.14), 3.877 (1.84), 3.882 (1.03), 3.889 (1.42), 3.893 (1.36), 3.905 (1.04), 3.912 (1.51), 3.925 (2.09), 3.938 (1.53), 3.951 (0.45), 4.034 (0.48), 4.050 (0.46), 4.058 (1.07), 4.072 (0.90), 4.087 (4.21), 4.097 (5.12), 4.101 (4.89), 4.107 (4.12), 4.126 (0.85), 4.136 (0.58), 7.522 (9.22), 8.681 (1.20), 8.693 (2.64), 8.705 (1.37). LC-MS (Method 1): $R_t$ = 1.11 min; MS (ESIpos): m/z = 470 $[M + H]^+$ | |
| 224-1 | 2-{[(2S)-1,4-dioxan-2-yl]methyl}-N-{[(2R or 2S,5R or 5S)-5-methyloxolan-2-yl]methyl}-8-(trifluoromethyl)-4,5-dihydro-2H-furo[2,3-g]indazole-7-carboxamide Diastereomer 1 of Ex. 224 | $R_t$ = 3.66 min $^1$H NMR (400 MHz, DMSO-d6) δ [ppm]: 1.17 (d, 3H) 1.35-1.43 (m, 1 H) 1.59-1.69 (m, 1 H) 1.85-1.97 (m, 2 H) 2.84-2.88 (m, 2 H) 2.93-2.97 (m, 2 H) 3.24-3.30 (m, 3 H) 3.41-3.48 (m, 1 H) 3.49-3.56 (m, 1 H) 3.61-3.64 (m, 1 H) 3.71-3.76 (m, 2 H) 3.79-3.85 (m, 1 H) 3.86-3.96 (m, 2 H) 4.04-4.15 (m, 2 H) 7.52 (s, 1 H) 8.69 (t, 1H) | analyt. method: Instrument: Thermo Fisher UltiMate 3000; Column: Chiralpak IF 3μ, 100 × 4.6; eluent A: |
| 224-2 | 2-{[(2S)-1,4-dioxan-2-yl]methyl}-N-{[(2S or 2R,5S or 5R)-5-methyloxolan-2-yl]methyl}-8-(trifluoromethyl)-4,5-dihydro-2H-furo[2,3-g]indazole-7-carboxamide Diasteromer 2 of Ex. 224 | $R_t$ = 5.84 min $^1$H NMR (400 MHz, DMSO-d6) δ [ppm]: 1.17 (d, 3H) 1.35-1.43 (m, 1 H) 1.59 - 1.69 (m, 1 H) 1.85 -2.00(m, 2H)2.84-2.88 (m, 2 H) 2.93 -2.97(m, 2H)3.24-3.30 (m, 3 H) 3.41 -3.48(m, 1H)3.49-3.56 (m, 1 H) 3.61 -3.64(m, 1H)3.71-3.76 (m, 2 H) 3.79 -3.85(m, 1H)3.86-3.96 (m, 2 H) 4.04-4.15 (m, 2 H) 7.52 (s, 1 H) 8.69 (t, 1H). | hexane + 0.1 vol% diethylamine; eluent B: 2-propanol; isocratic: 70% A + 30% B; flow: 1.4 ml/min; temperature: 25° C.; UV: 254 nm |
| 225 | 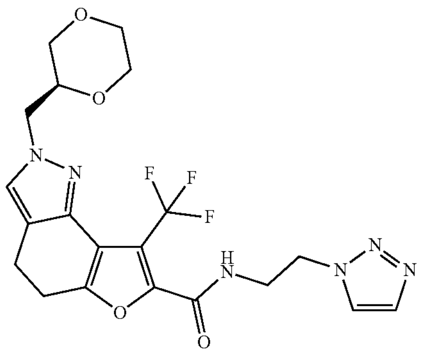 [SMILES: O=C(NCCn1ccnn1)c1oc2c(c1C(F)(F)F)-c1nn(C[C@H]3COCCO3)cc1CC2] 2-{[(2S)-1,4-dioxan-2-yl]methyl}-N-[2-(1H-1,2,3-triazol-1-yl)ethyl]-8-(trifluoromethyl)-4,5-dihydro-2H-furo[2,3-g]indazole-7-carboxamide | $^1$H NMR (400 MHz, DMSO-d6) δ [ppm]: 2.83-2.90 (m, 2H), 2.91-2.98 (m, 2H), 3.26 (dd, 1H), 3.40-3.48 (m, 1H), 3.49-3.57 (m, 1H), 3.62 (brd, 1H), 3.66-3.77 (m, 4H), 3.78-3.88 (m, 1H), 4.03-4.16 (m, 2H), 4.56 (t, 2H), 7.52 (s, 1H), 7.72 (d, 1H), 8.12 (d, 1H), 8.86 (t, 1H). LC-MS (Method 1): $R_t$ = 0.84 min; MS (ESIneg): m/z = 465 $[M - H]^-$ | Intermediate 69 and CAS-RN: [4320-94-9] GPG Conditions A 66.9 mg (76% yield, 99% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 226 | 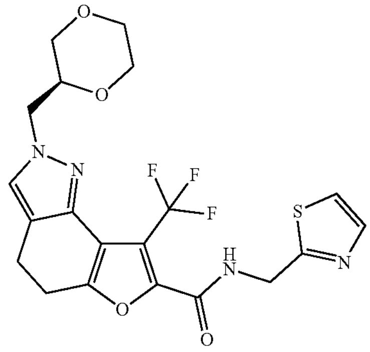 [SMILES: O=C(NCc1nccs1)c1oc2c(c1C(F)(F)F)-c1nn(C[C@H]3COCCO3)cc1CC2] 2-[(2S)-1,4-Dioxan-2-ylmethyl]-N-(1,3-thiazol-2-ylmethyl)-8-(trifluormethyl)-4,5-dihydro-2H-furo[2,3-g]indazol-7-carboxamide | $^{1}H$ NMR (400 MHz, DMSO-d6) δ [ppm]: 2.85-2.91 (m, 2H), 2.93-3.01 (m, 2H), 3.27 (dd, 1H), 3.41-3.48 (m, 1H), 3.49-3.58 (m, 1H), 3.63 (brd, 1H), 3.71-3.78 (m, 2H), 3.78-3.86 (m, 1H), 4.03-4.18 (m, 2H), 4.72 (d, 2H), 7.54 (s, 1H), 7.65 (d, 1H), 7.74 (d, 1H), 9.59 (t, 1H) LC-MS (Method 1): $R_t$ = 0.95 min; MS (ESIpos): m/z = 469 $[M + H]^+$ | Intermediate 69 and CAS-RN: [53332-78-8] GP G Conditions A 52.3 mg (58% yield, 97% purity) |
| 227 | 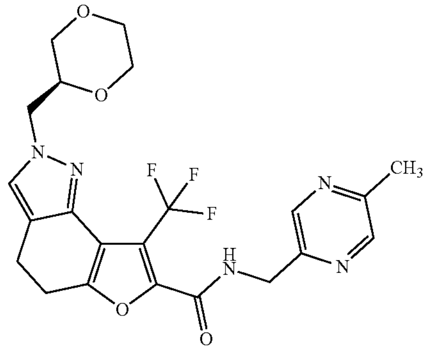 [SMILES: Cc1cnc(CNC(=O)c2oc3c(c2C(F)(F)F)-c2nn(C[C@H]4COCCO4)cc2CC3)cn1] 2-[(2S)-1,4-Dioxan-2-ylmethyl]-N-[(5-methylpyrazin-2-yl)methyl]-8-(trifluormethyl)-4,5-dihydro-2H-furo[2,3-g]indazol-7-carboxamide | $^{1}H$ NMR (400 MHz, DMSO-d6) δ [ppm]: 2.48 (s, 3H), 2.84-2.91 (m, 2H), 2.93-2.99 (m, 2H), 3.26 (dd, 1H), 3.40-3.48 (m, 1H), 3.50-3.57 (m, 1H), 3.63 (brd, 1H), 3.70-3.78 (m, 2H), 3.79-3.86 (m, 1H), 4.04-4.16 (m, 2H), 4.54 (d, 2H), 7.53 (s, 1H), 8.49 (s, 2H), 9.32 (t, 1H) LC-MS (Method 1): $R_t$ = 0.93 min; MS (ESIpos): m/z = 478 $[M + H]^+$ | Intermediate 69 and CAS-RN: [132664-85-8 GP G Conditions A 67.2 mg (70% yield, 93% purity) |
| 228 | 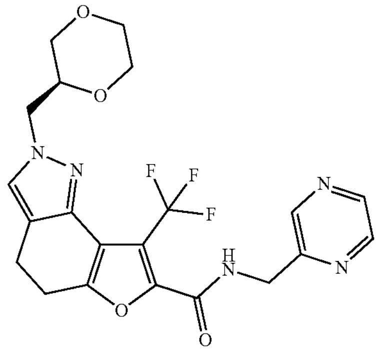 [SMILES: O=C(NCc1cnccn1)c1oc2c(c1C(F)(F)F)-c1nn(C[C@H]3COCCO3)cc1CC2] 2-[(2S)-1,4-Dioxan-2-ylmethyl]-N-(pyrazin-2-ylmethyl)-8-(trifluormethyl)-4,5-dihydro-2H-furo[2,3-g]indazol-7-carboxamide | $^{1}H$ NMR (400 MHz, DMSO-d6) δ [ppm]: 2.84-2.90 (m, 2H), 2.94-2.99 (m, 2H), 3.27 (dd, 1H), 3.40-3.48 (m, 1H), 3.49-3.57 (m, 1H), 3.63 (br d, 1H), 3.70-3.78 (m, 2H), 3.78-3.86 (m, 1H), 4.04-4.16 (m, 2H), 4.59 (d, 2H), 7.53 (s, 1H), 8.55 (d, 1H), 8.61 (dd, 1H), 8.64 (d, 1H), 9.36 (t, 1H) LC-MS (Method 1): $R_t$ = 0.89 min; MS (ESIneg): m/z = 462 $[M - H]^-$ | Intermediate 69 and CAS-RN: [20010-99-5] GP G Conditions A 65.3 mg (68% yield, 91% purity) |

TABLE 5-continued

The following examples (212 to 316) were prepared in analogy to example 169 starting from the given intermediates and commercially available amines (or their salts), applying the indicated general procedure.

| Ex-ample | Structure IUPAC-Name | Analytical Data | Preparation or Separation Methods |
| --- | --- | --- | --- |
| 229 | 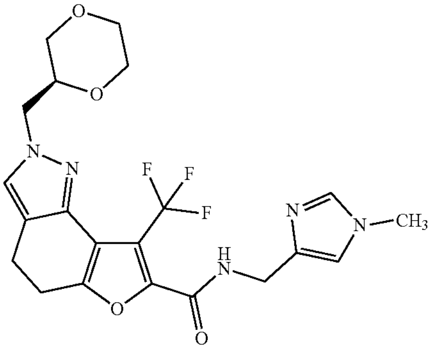 [SMILES: Cn1cnc(CNC(=O)c2oc3c(c2C(F)(F)F)-c2nn(C[C@H]4COCCO4)cc2CC3)c1] 2-[(2S)-1,4-Dioxan-2-ylmethyl]-N-[(1-methyl-1H-imidazol-4-yl)methyl]-8-(trifluormethyl)-4,5-dihydro-2H-furo[2,3-g]indazol-7-carboxamide | $^1$H NMR (400 MHz, DMSO-d6) δ [ppm]: 2.83-2.89 (m, 2H), 2.90-2.96 (m, 2H), 3.26 (dd, 1H), 3.39-3.47 (m, 1H), 3.50-3.57 (m, 1H), 3.60 (s, 3H), 3.61-3.65 (m, 1H), 3.70-3.78 (m, 2H), 3.78-3.85 (m, 1H), 4.03-4.15 (m, 2H), 4.27 (d, 2H), 6.96 (d, 1H), 7.49 (d, 1H), 7.52 (s, 1H), 8.93 (t, 1H) LC-MS (Method 1): $R_t$ = 0.87 min; MS (ESIpos): m/z = 466 $[M + H]^+$ | Intermediate 69 and CAS-RN: [486414-83-9] GP G Conditions A 40.4 mg (46% yield, 99% purity) |
| 230 | 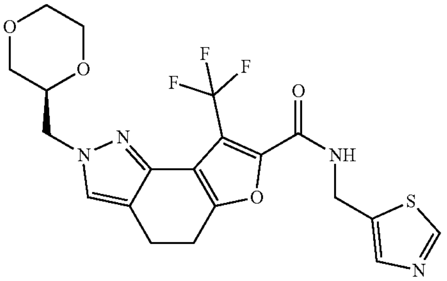 [SMILES: O=C(NCc1cncs1)c1oc2c(c1C(F)(F)F)-c1nn(C[C@H]3COCCO3)cc1CC2] 2-[(2S)-1,4-Dioxan-2-ylmethyl]-N-(1,3-thiazol-5-ylmethyl)-8-(trifluormethyl)-4,5-dihydro-2H-furo[2,3-g]indazol-7-carboxamide | $^1$H NMR (400 MHz, DMSO-d6) δ [ppm]: 2.83-2.89 (m, 2H), 2.91-2.97 (m, 2H), 3.26 (dd, 1H), 3.40-3.48 (m, 1H), 3.49-3.57 (m, 1H), 3.62 (brd, 1H), 3.69-3.77 (m, 2H), 3.78-3.87 (m, 1H), 4.01-4.15 (m, 2H), 4.64 (d, 2H), 7.52 (s, 1H), 7.81 (d, 1H), 8.99 (d, 1H), 9.40 (t, 1H) LC-MS (Method 1): $R_t$ = 0.82 min; MS (ESIneg): m/z = 467 $[M - H]^-$ | Intermediate 69 and CAS-RN: [131052-46-5] GP G Conditions A 54.8 mg (61% yield, 98% purity) |
| 231 | 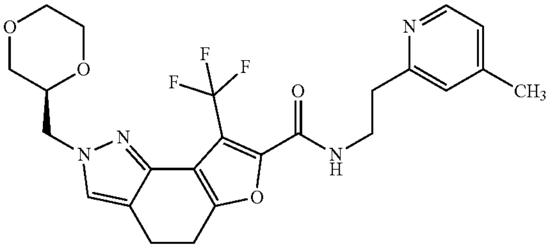 [SMILES: Cc1ccnc(CCNC(=O)c2oc3c(c2C(F)(F)F)-c2nn(C[C@H]4COCCO4)cc2CC3)c1] 2-[(2S)-1,4-Dioxan-2-ylmethyl]-N-[2-(4-methylpyridin-2-yl)ethyl]-8-(trifluormethyl)-4,5-dihydro-2H-furo[2,3-g]indazol-7-carboxamide | $^1$H NMR (400 MHz, DMSO-d6) δ [ppm]: 2.28 (s, 3H), 2.83-2.89 (m, 2H), 2.90-2.97 (m, 4H), 3.26 (dd, 1H), 3.39-3.47 (m, 1H), 3.50-3.60 (m, 3H), 3.63 (brd, 1H), 3.70-3.78 (m, 2H), 3.78-3.86 (m, 1H), 4.04-4.15 (m, 2H), 7.07 (d, 1H), 7.12 (s, 1H), 7.52 (s, 1H), 8.36 (d, 1H), 8.82 (t, 1H) LC-MS (Method 1): $R_t$ = 1.06 min; MS (ESIpos): m/z = 491 $[M + H]^+$ | Intermediate 69 and CAS-RN: [851670-49-0] GP G Conditions A 53.6 mg (50% yield, 98% purity) |
| 232 | 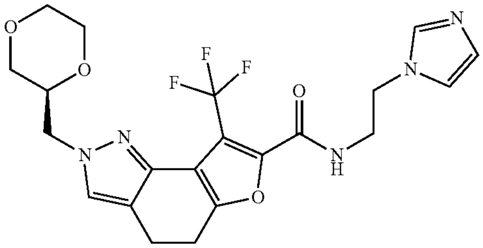 [SMILES: O=C(NCCn1ccnc1)c1oc2c(c1C(F)(F)F)-c1nn(C[C@H]3COCCO3)cc1CC2] | $^1$H NMR (400 MHz, DMSO-d6) δ [ppm]: 2.83-2.90 (m, 2H), 2.91-2.97 (m, 2H), 3.26 (dd, 1H), 3.40-3.48 (m, 1H), 3.50-3.59 (m, 3H), 3.63 (brd, 1H), 3.70-3.77 (m, 2H), 3.78-3.85 (m, 1H), 4.10 (dd, 2H), 4.15 (t, 2H), 6.88 (t, 1H), 7.16 (t, 1H), 7.52 (s, 1H), 7.59 (t, 1H), 8.84 (t, 1H). LC-MS (Method 1): $R_t$ = 0.87 min; MS (ESIneg): m/z = 464 $[M - H]^-$ | Intermediate 69 and CAS-RN: [93668-43-0] GP G Conditions A 63.5 mg (61% yield, 96% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | 2-{[(2S)-1,4-dioxan-2-yl]methyl}-N-[2-(1H-imidazol-1-yl)ethyl]-8-(trifluoromethyl)-4,5-dihydro-2H-furo[2,3-g]indazole-7-carboxamide | | |
| 233 | 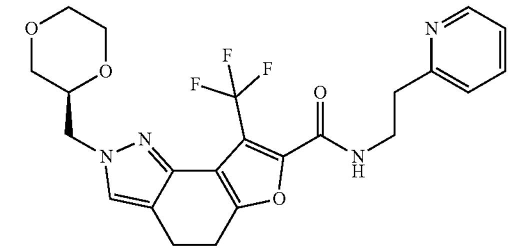 [SMILES: O=C(NCCc1ccccn1)c1oc2c(c1C(F)(F)F)-c1nn(C[C@H]3COCCO3)cc1CC2] 2-[(2S)-1,4-Dioxan-2-ylmethyl]-N-[2-(pyridin-2-yl)ethyl]-8-(trifluormethyl)-4,5-dihydro-2H-furo[2,3-g]indazol-7-carboxamide | $^{1}H$ NMR (400 MHz, DMSO-d6) δ [ppm] .2.82-2.91 (m, 2H), 2.91-3.02 (m, 4H), 3.26 (dd, 1H), 3.38-3.48 (m, 1H), 3.52 (dd, 1H), 3.55-3.65 (m, 3H), 3.70-3.77 (m, 2H), 3.78-3.86 (m, 1H), 4.03-4.15 (m, 2H), 7.23 (ddd, 1H), 7.29 (d, 1H), 7.52 (s, 1H), 7.72 (td, 1H), 8.48-8.53 (m, 1H), 8.82 (t, 1H) LC-MS (Method 1): $R_t$ = 0.87 min; MS (ESIpos): m/z = 477 $[M + H]^+$ | Intermediate 69 and CAS-RN: [2706-56-1] GP G Conditions A 62.4 mg (60% yield, 99% purity) |
| 234 | 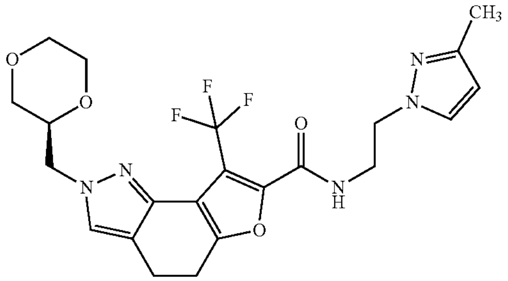 [SMILES: Cc1ccn(CCNC(=O)c2oc3c(c2C(F)(F)F)-c2nn(C[C@H]4COCCO4)cc2CC3)n1] 2-[(2S)-1,4-Dioxan-2-ylmethyl]-N-[2-(3-methyl-1H-pyrazol-1-yl)ethyl]-8-(trifluormethyl)-4,5-dihydro-2H-furo[2,3-g]indazol-7-carboxamide | $^{1}H$ NMR (400 MHz, DMSO-d6) δ [ppm]: 2.15 (s, 3H), 2.82-2.90 (m, 2H), 2.91-2.98 (m, 2H), 3.26 (dd, 1H), 3.40-3.47 (m, 1H), 3.52 (dd, 1H), 3.55-3.66 (m, 3H), 3.70-3.77 (m, 2H), 3.78-3.86 (m, 1H), 4.05-4.15 (m, 2H), 4.17 (t, 2H), 5.99 (d, 1H), 7.53 (s, 1H), 7.56 (d, 1H), 8.81 (t, 1H) LC-MS (Method 1): $R_t$ = 0.93 min; MS (ESIpos): m/z = 480 $[M + H]^+$ | Intermediate 69 and CAS-RN: [62821 -90-3] GP G Conditions A 53.2 mg (61% yield, 97% purity) |
| 235 | 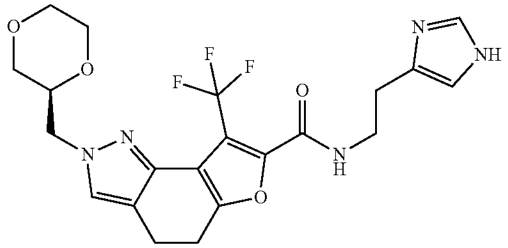 [SMILES: O=C(NCCc1c[nH]cn1)c1oc2c(c1C(F)(F)F)-c1nn(C[C@H]3COCCO3)cc1CC2] 2-[(2S)-1,4-Dioxan-2-ylmethyl]-N-[2-(1 H-imidazol-4-yl)ethyl]-8-(trifluormethyl)-4,5-dihydro-2H-furo[2,3-g]indazol-7-carboxamide | $^{1}H$ NMR (400 MHz, DMSO-d6) δ [ppm]: 2.83-2.89 (m, 4H), 2.91-2.97 (m, 2H), 3.26 (dd, 1H), 3.40-3.57 (m, 4H), 3.63 (brd, 1H), 3.70-3.77 (m, 2H), 3.78-3.87 (m, 1H), 4.03-4.15 (m, 2H), 7.32 (ddd, 1H), 7.52 (s, 1H), 7.67 (dt, 1H), 8.42 (dd, 1H), 8.45 (d, 1H), 8.83 (t, 1H) LC-MS (Method 1): $R_t$ = 0.74 min; MS (ESIneg): m/z = 464 $[M - H]^-$ | Intermediate 69 and CAS-RN: [56-92-8] GP G Conditions A 68.3 mg (66% yield, 96% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 236 | 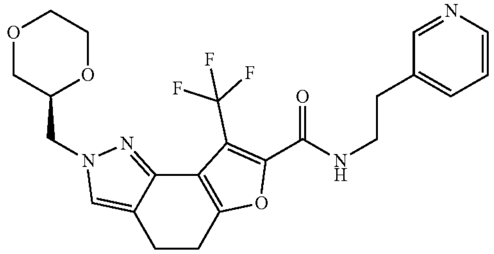 [SMILES: O=C(NCCc1cccnc1)c1oc2c(c1C(F)(F)F)-c1nn(C[C@H]3COCCO3)cc1CC2] 2-[(2S)-1,4-Dioxan-2-ylmethyl]-N-[2-(pyridin-3-yl)ethyl]-8-(trifluormethyl)-4,5-dihydro-2H-furo[2,3-g]indazol-7-carboxamide | $^1$H NMR (400 MHz, DMSO-d6) δ [ppm]: 2.83-2.89 (m, 4H), 2.91-2.97 (m, 2H), 3.26 (dd, 1H), 3.40-3.57 (m, 4H), 3.63 (brd, 1H), 3.70-3.77 (m, 2H), 3.78-3.87 (m, 1H), 4.03-4.15 (m, 2H), 7.32 (ddd, 1H), 7.52 (s, 1H), 7.67 (dt, 1H), 8.42 (dd, 1H), 8.45 (d, 1H), 8.83 (t, 1H) LC-MS (Method 1): $R_t$ = 0.92 min; MS (ESIneg): m/z = 475 $[M - H]^-$ | Intermediate 69 and CAS-RN: [20173-24-4] GP G Conditions A 64.2 mg (61% yield, 97% purity) |
| 237 | 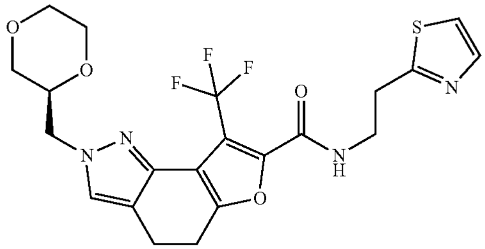 [SMILES: O=C(NCCc1nccs1)c1oc2c(c1C(F)(F)F)-c1nn(C[C@H]3COCCO3)cc1CC2] 2-[(2S)-1,4-Dioxan-2-ylmethyl]-N-[2-(1,3-thiazol-2-yl)ethyl]-8-(trifluormethyl)-4,5-dihydro-2H-furo[2,3-g]indazol-7-carboxamide | $^1$H NMR (400 MHz, DMSO-d6) δ [ppm]: 2.84-2.89 (m, 2H), 2.92-2.98 (m, 2H), 3.22-3.30 (m, 3H), 3.39-3.47 (m, 1H), 3.49-3.65 (m, 4H), 3.70-3.78 (m, 2H), 3.78-3.86 (m, 1H), 4.00-4.16 (m, 2H), 7.53 (s, 1H), 7.61 (d, 1H), 7.73 (d, 1H), 8.89 (t, 1H) LC-MS (Method 1): $R_t$ = 0.88 min; MS (ESIpos): m/z = 483 $[M + H]^+$ | Intermediate 69 and CAS-RN: [18453-07-1] GP G Conditions A 61.3 mg (59% yield, 99% purity) |
| 238 | 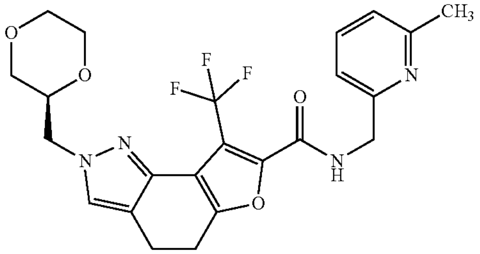 [SMILES: Cc1cccc(CNC(=O)c2oc3c(c2C(F)(F)F)-c2nn(C[C@H]4COCCO4)cc2CC3)n1] 2-[(2S)-1,4-Dioxan-2-ylmethyl]-N-[(6-methylpyridin-2-yl)methyl]-8-(trifluormethyl)-4,5-dihydro-2H-furo[2,3-g]indazol-7-carboxamide | $^1$H NMR (400 MHz, DMSO-d6) δ [ppm]: 2.46 (s, 3H), 2.84-2.91 (m, 2H), 2.93-3.00 (m, 2H), 3.27 (dd, 1H), 3.40-3.49 (m, 1H), 3.50-3.58 (m, 1H), 3.63 (brd, 1H), 3.70-3.79 (m, 2H), 3.78-3.87 (m, 1H), 4.01-4.17 (m, 2H), 4.48 (d, 2H), 7.12 (dd, 2H), 7.53 (s, 1H), 7.66 (t, 1H), 9.28 (t, 1H) LC-MS (Method 1): $R_t$ = 1.07 min; MS (ESIpos): m/z = 477 $[M + H]^+$ | Intermediate 69 and CAS-RN: [6627-60-7] GP G Conditions A 70.1 mg (64% yield, 94% purity) |
| 239 | 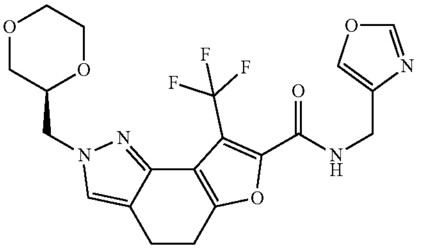 [SMILES: O=C(NCc1cocn1)c1oc2c(c1C(F)(F)F)-c1nn(C[C@H]3COCCO3)cc1CC2] 2-[(2S)-1,4-Dioxan-2-ylmethyl]-N-(1,3-oxazol-4-ylmethyl)-8-(trifluormethyl)-4,5-dihydro-2H-furo[2,3-g]indazol-7-carboxamide | $^1$H NMR (400 MHz, DMSO-d6) δ [ppm]: 2.83-2.90 (m, 2H), 2.91-2.97 (m, 2H), 3.26 (dd, 1H), 3.40-3.47 (m, 1H), 3.53 (td, 1H), 3.63 (brd, 1H), 3.70-3.78 (m, 2H), 3.78-3.86 (m, 1H), 4.04-4.15 (m, 2H), 4.33 (d, 2H), 7.53 (s, 1H), 7.97 (d, 1H), 8.33 (d, 1H), 9.13 (t, 1H). LC-MS (Method 1): $R_t$ = 0.92 min; MS (ESIpos): m/z = 453 $[M + H]^+$ | Intermediate 69 and CAS-RN: [847490-98-6] GP G Conditions A 73.6 mg (73% yield, 96% purity) |

TABLE 5-continued

| The following examples (212 to 316) were prepared in analogy to example 169 starting from the given intermediates and commercially available amines (or their salts), applying the indicated general procedure. | | | |
|---|---|---|---|
| Ex-ample | Structure IUPAC-Name | Analytical Data | Preparation or Separation Methods |
| 240 | 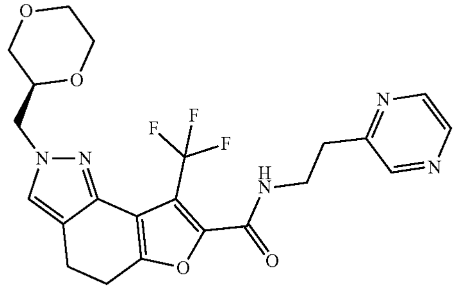 [SMILES: O=C(NCCc1cnccn1)c1oc2c(c1C(F)(F)F)-c1nn(C[C@H]3COCCO3)cc1CC2] 2-{[(2S)-1,4-dioxan-2-yl]methyl}-N-[2-(pyrazin-2-yl)ethyl]-8-(trifluoromethyl)-4,5-dihydro-2H-furo[2,3-g]indazole-7-carboxamide | $^1$H NMR (400 MHz, DMSO-d6) δ [ppm]: 2.21 (d, 3H), 2.83-2.89 (m, 2H), 2.91-2.97 (m, 2H), 3.26 (dd, 1H), 3.40-3.48 (m, 1H), 3.49-3.56 (m, 1H), 3.60-3.68 (m, 3H), 3.70-3.77 (m, 2H), 3.78-3.87 (m, 1H), 4.04-4.17 (m, 2H), 4.48 (t, 2H), 7.53 (s, 1H), 7.82 (s, 1H), 8.85 (t, 1H). LC-MS (Method 1): $R_t$ = 0.90 min; MS (ESIpos): m/z = 478 $[M + H]^+$ | Intermediate 69 and CAS-RN: [5321-59-5] GP G Conditions A 72.6 mg (69% yield, 98% purity) |
| 241 | 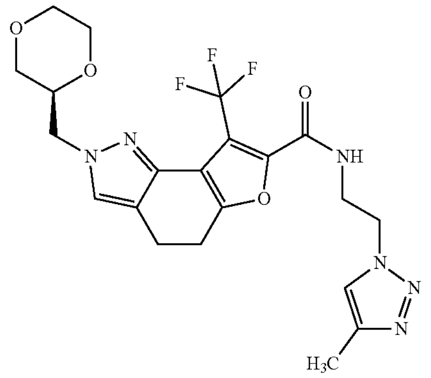 [SMILES: Cc1cn(CCNC(=O)c2oc3c(c2C(F)(F)F)-c2nn(C[C@H]4COCCO4)cc2CC3)nn1] 2-{[(2S)-1,4-dioxan-2-yl]methyl}-N-[2-(4-methyl-1H-1,2,3-triazol-1-yl)ethyl]-8-(trifluoromethyl)-4,5-dihydro-2H-furo[2,3-g]indazole-7-carboxamide | $^1$H NMR (400 MHz, DMSO-d6) δ [ppm]: 2.82-2.89 (m, 2H), 2.91-2.96 (m, 2H), 3.04 (t, 2H), 3.26 (dd, 1H), 3.39-3.47 (m, 1H), 3.49-3.57 (m, 1H), 3.59-3.65 (m, 3H), 3.70-3.77 (m, 2H), 3.78-3.85 (m, 1H), 4.02-4.15 (m, 2H), 7.52 (s, 1H), 8.50 (d, 1H), 8.56-8.59 (m, 2H), 8.84 (t, 1H) LC-MS (Method 1): $R_t$ = 0.87 min; MS (ESIpos): m/z = 481 $[M + H]^+$ | Intermediate 69 and CAS-RN: [1086601-35-5] GP G Conditions A 67.8 mg (64% yield, 98% purity) |
| 242 | 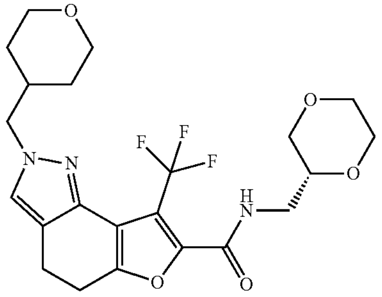 [SMILES: O=C(NC[C@@H]1COCCO1)c1oc2c(c1C(F)(F)F)-c1nn(CC3CCOCC3)cc1CC2] N-{[(2R)-1,4-dioxan-2-yl]methyl}-2-[(oxan-4-yl)methyl]-8-(trifluoromethyl)-4,5-dihydro-2H-furo[2,3-g]indazole-7-carboxamide | $^1$H-NMR (400 MHz, DMSO-d6) δ [ppm]: −0.002 (1.19), 0.931 (2.75), 0.934 (0.93), 0.948 (2.84), 0.952 (0.48), 1.173 (1.01), 1.184 (1.20), 1.203 (2.84), 1.214 (3.17), 1.235 (3.83), 1.246 (3.45), 1.265 (1.74), 1.276 (1.56), 1.343 (0.56), 1.401 (4.92), 1.428 (3.48), 1.953 (0.63), 1.963 (1.18), 1.973 (1.28), 1.981 (1.48), 1.991 (1.86), 2.000 (1.42), 2.009 (1.22), 2.019 (1.04), 2.332 (1.96), 2.336 (0.84), 2.518 (9.07), 2.523 (5.87), 2.539 (0.42), 2.678 (0.87), 2.836 (2.18), 2.841 (2.20), 2.859 (9.32), 2.877 (7.60), 2.921 (7.96), 2.924 (8.08), 2.940 (11.11), 2.946 (3.93), 2.958 (2.82), 2.964 (2.59), 3.186 (1.07), 3.195 (4.79), 3.200 (2.83), 3.207 (3.54), 3.212 (4.66), 3.220 (8.66), 3.224 (6.37), 3.235 (11.50), 3.241 (8.21), 3.249 (10.54), 3.263 (7.12), 3.278 (3.91), 3.297 (2.27), 3.313 (2.18), 3.423 (1.48), 3.429 (1.80), 3.449 (3.90), 3.456 (4.23), 3.476 (3.43), 3.483 (3.29), 3.524 (2.95), 3.530 (3.36), 3.552 (4.01), 3.558 (4.19), 3.578 (1.61), 3.585 (2.86), 3.604 (1.42), 3.611 (4.35), 3.619 (5.39), 3.626 (3.26), 3.635 (2.56), 3.643 (5.39), 3.649 (4.00), 3.658 (1.01), 3.665 (1.18), 3.694 (4.55), 3.701 (3.75), 3.723 (7.82), 3.729 (6.62), 3.752 (3.28), | Intermediate 71 GP H Conditions B 55 mg, 33% yield, 95% purity |

TABLE 5-continued

The following examples (212 to 316) were prepared in analogy to example 169 starting from the given intermediates and commercially available amines (or their salts), applying the indicated general procedure.

| Ex-ample | Structure IUPAC-Name | Analytical Data | Preparation or Separation Methods |
|---|---|---|---|
| | | 3.798 (4.37), 3.805 (4.33), 3.828 (4.00), 3.834 (3.83), 3.945 (11.67), 3.963 (11.50), 7.541 (16.00), 8.717 (2.54), 8.732 (5.33), 8.746 (2.53). LC-MS (Method 1): $R_t$ = 1.02 min; MS (ESIpos): m/z = 470 $[M + H]^+$ | |
| 243 | 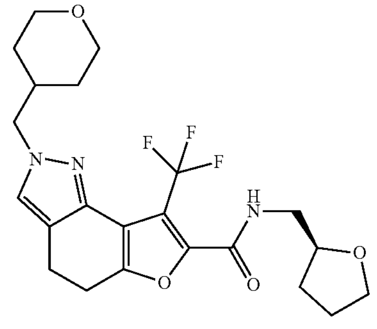 [SMILES: O=C(NC[C@@H]1CCCO1)c1oc2c(c1C(F)(F)F)-c1nn(CC3CCOCC3)cc1CC2] 2-[(oxan-4-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: −0.002 (0.42), 1.173 (1.08), 1.184 (1.20), 1.203 (2.63), 1.213 (2.94), 1.235 (3.72), 1.246 (3.18), 1.265 (1.63), 1.276 (1.43), 1.401 (4.45), 1.428 (3.17), 1.522 (0.52), 1.539 (1.66), 1.551 (1.36), 1.555 (1.49), 1.558 (2.24), 1.567 (2.08), 1.575 (1.74), 1.583 (1.40), 1.588 (1.96), 1.605 (1.23), 1.758 (0.45), 1.772 (1.01), 1.779 (0.76), 1.787 (1.85), 1.793 (2.32), 1.808 (4.31), 1.827 (4.18), 1.844 (2.73), 1.860 (2.27), 1.865 (1.30), 1.869 (1.60), 1.876 (1.78), 1.881 (1.63), 1.888 (2.08), 1.898 (1.35), 1.902 (1.59), 1.905 (1.60), 1.910 (1.44), 1.919 (1.15), 1.926 (1.09), 1.941 (0.88), 1.953 (0.60), 1.962 (1.07), 1.972 (1.20), 1.981 (1.37), 1.990 (1.71), 2.000 (1.28), 2.009 (1.09), 2.018 (0.93), 2.318 (0.93), 2.518 (9.83), 2.523 (6.49), 2.537 (0.49), 2.542 (0.50), 2.835 (1.84), 2.839 (1.93), 2.853 (3.21), 2.858 (8.35), 2.876 (6.81), 2.917 (7.33), 2.919 (7.17), 2.935 (10.19), 2.943 (3.39), 2.954 (2.40), 2.960 (2.29), 3.207 (2.87), 3.212 (3.49), 3.237 (6.28), 3.241 (6.49), 3.252 (6.92), 3.267 (16.00), 3.282 (7.26), 3.299 (1.17), 3.375 (0.89), 3.380 (0.49), 3.596 (1.49), 3.615 (3.47), 3.633 (4.18), 3.651 (2.37), 3.740 (1.99), 3.757 (3.78), 3.772 (3.63), 3.775 (3.23), 3.793 (4.98), 3.798 (4.10), 3.805 (3.96), 3.827 (3.64), 3.834 (3.49), 3.918 (1.08), 3.934 (3.60), 3.944 (11.37), 3.950 (7.36), 3.962 (11.45), 3.981 (0.91), 7.539 (14.20), 8.680 (2.22), 8.694 (4.62), 8.709 (2.19). LC-MS (Method 1): $R_t$ = 1.11 min; MS (ESIpos): m/z = 454 $[M + H]^+$ | Intermediate 71 GP H Conditions B 42 mg, 26% yield, 95% purity |
| 244 | 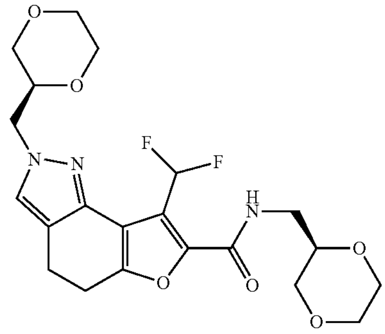 [SMILES: O=C(NC[C@@H]1COCCO1)c1oc2c(c1C(F)F)-c1nn(C[C@H]3COCCO3)cc1CC2] 8-(difluoromethyl)-N-{[(2R)-1,4-dioxan-2-yl]methyl}-2-{[(2S)-1,4-dioxan-2-yl]methyl}-4,5-dihydro-2H-furo[2,3-g]indazole-7-carboxamide | $^1$H-NMR (400 MHz, DMSO-d6) δ [ppm]: 1.172 (0.57), 1.987 (0.98), 2.074 (1.66), 2.518 (16.00), 2.522 (10.77), 2.860 (1.47), 2.879 (6.00), 2.896 (5.14), 2.939 (5.23), 2.956 (6.54), 2.975 (1.67), 2.980 (1.54), 3.179 (1.03), 3.193 (4.35), 3.217 (4.16), 3.221 (4.03), 3.227 (3.59), 3.243 (5.20), 3.268 (4.40), 3.271 (4.27), 3.285 (3.41), 3.296 (4.32), 3.301 (2.91), 3.413 (1.49), 3.421 (1.26), 3.428 (1.65), 3.434 (2.62), 3.440 (2.97), 3.449 (2.89), 3.455 (3.19), 3.462 (2.63), 3.468 (2.40), 3.476 (2.57), 3.482 (2.38), 3.504 (1.98), 3.510 (2.45), 3.516 (2.34), 3.521 (2.50), 3.533 (2.91), 3.539 (3.17), 3.544 (3.24), 3.550 (3.05), 3.559 (1.56), 3.566 (2.04), 3.570 (1.68), 3.577 (1.91), 3.612 (5.35), 3.641 (5.02), 3.658 (1.72), 3.665 (1.86), 3.673 (1.58), 3.688 (1.00), 3.702 (3.37), 3.716 (5.63), 3.730 (3.33), 3.741 (5.92), 3.746 (7.54), 3.769 (2.20), 3.775 (2.88), 3.786 (1.02), 3.805 (1.46), 3.809 (1.52), 3.823 (1.73), 3.839 (0.90), 4.049 (0.93), 4.065 (0.58), 4.084 (4.22), 4.098 (5.59), 4.110 (4.16), 4.133 (0.94), 4.146 (0.61), 7.422 (0.55), 7.473 (2.00), 7.501 (10.82), | Intermediate 72 GP H Conditions C 108 mg, 35% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | 7.610 (4.18), 7.746 (1.68), 8.696 (1.70), 8.712 (3.52), 8.726 (1.70). LC-MS (Method 1): $R_t$ = 0.92 min; MS (ESIneg): m/z = 452 $[M - H]^-$ | |
| 245 | 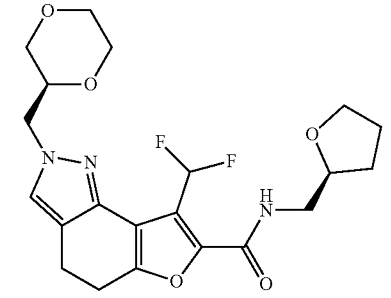 [SMILES: O=C(NC[C@@H]1CCCO1)c1oc2c(c1C(F)F)-c1nn(C[C@H]3COCCO3)cc1CC2] 8-(difluoromethyl)-2-{[(2S)-1,4-dioxan-2-yl]methyl}-N-{[(2S)-oxolan-2-yl]methyl}-4,5-dihydro-2H-furo[2,3-g]indazole-7-carboxamide | $^1$H-NMR (400 MHz, DMSO-d6) δ [ppm]: 1.232 (1.01), 1.531 (0.48), 1.549 (1.49), 1.564 (1.42), 1.568 (2.21), 1.577 (2.03), 1.585 (1.81), 1.593 (1.38), 1.598 (1.89), 1.614 (1.25), 1.754 (0.47), 1.768 (1.05), 1.774 (0.80), 1.783 (1.85), 1.789 (2.48), 1.804 (4.31), 1.822 (4.37), 1.841 (2.92), 1.854 (1.83), 1.864 (1.65), 1.871 (2.10), 1.877 (1.77), 1.883 (2.08), 1.893 (1.39), 1.897 (1.61), 1.904 (1.43), 1.914 (1.16), 1.921 (1.08), 1.936 (0.69), 2.075 (0.57), 2.327 (4.41), 2.332 (3.20), 2.336 (1.41), 2.518 (16.00), 2.523 (11.50), 2.669 (4.49), 2.673 (3.16), 2.678 (1.34), 2.855 (1.81), 2.860 (1.87), 2.879 (8.15), 2.897 (6.87), 2.938 (7.01), 2.955 (9.01), 2.962 (3.06), 2.974 (2.12), 2.980 (2.01), 3.212 (0.70), 3.227 (1.54), 3.244 (5.48), 3.261 (6.67), 3.268 (5.71), 3.272 (6.25), 3.278 (6.19), 3.296 (6.96), 3.312 (2.81), 3.408 (1.25), 3.414 (1.71), 3.435 (3.29), 3.441 (3.67), 3.462 (3.05), 3.468 (2.88), 3.504 (2.46), 3.510 (2.85), 3.533 (3.48), 3.539 (3.47), 3.560 (1.60), 3.566 (2.23), 3.591 (1.67), 3.611 (6.29), 3.627 (4.59), 3.645 (4.36), 3.716 (3.44), 3.736 (2.88), 3.741 (5.52), 3.746 (7.33), 3.750 (6.20), 3.768 (5.97), 3.774 (5.20), 3.788 (2.76), 3.799 (1.71), 3.805 (1.82), 3.810 (1.93), 3.816 (1.77), 3.822 (2.29), 3.829 (1.58), 3.840 (1.14), 3.846 (0.93), 3.941 (0.98), 3.957 (3.20), 3.974 (4.41), 3.989 (2.93), 4.005 (0.76), 4.048 (1.35), 4.065 (0.89), 4.084 (6.00), 4.097 (7.45), 4.100 (7.29), 4.109 (5.65), 4.133 (1.28), 4.145 (0.89), 7.421 (0.59), 7.480 (2.84), 7.500 (15.43), 7.617 (6.03), 7.754 (2.35), 8.553 (0.44), 8.655 (2.25), 8.670 (4.77), 8.685 (2.21). LC-MS (Method 1): $R_t$ = 1.00 min; MS (ESIneg): m/z = 436 $[M - H]^-$ | Intermediate 72 GP H Conditions C 83 mg, 28% yield, 98% purity |
| 246 | 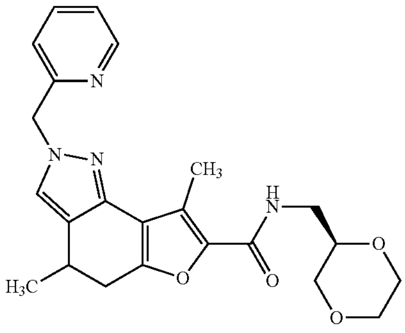 [SMILES: Cc1c(C(=O)NC[C@@H]2COCCO2)oc2c1-c1nn(Cc3ccccn3)cc1C(C)C2] (4±)-N-{[(2R)-1,4-dioxan-2-yl]methyl}-4,8-dimethyl-2-[(pyridin-2-yl)methyl]-4,5-dihydro-2H-furo[2,3-g]indazole-7-carboxamide | $^1$H-NMR (400 MHz, DMSO-d6) δ [ppm]: 1.280 (6.58), 1.297 (6.63), 2.440 (16.00), 2.522 (3.53), 2.551 (1.16), 2.567 (1.19), 2.583 (0.57), 2.592 (1.24), 2.713 (0.68), 2.960 (1.07), 2.978 (1.36), 3.001 (0.98), 3.020 (1.10), 3.159 (0.94), 3.179 (2.49), 3.194 (2.01), 3.203 (2.35), 3.208 (2.71), 3.226 (1.76), 3.232 (1.90), 3.242 (1.14), 3.261 (0.66), 3.276 (0.42), 3.413 (0.46), 3.419 (0.54), 3.440 (1.20), 3.446 (1.27), 3.467 (1.04), 3.473 (1.01), 3.509 (0.89), 3.515 (0.93), 3.537 (1.23), 3.544 (1.28), 3.564 (0.55), 3.570 (0.80), 3.606 (1.98), 3.622 (0.84), 3.630 (1.71), 3.636 (1.54), 3.652 (0.40), 3.682 (1.43), 3.689 (1.21), 3.712 (2.49), 3.740 (1.08), 5.385 (7.26), 7.067 (1.98), 7.086 (2.10), 7.294 (0.98), 7.307 (1.14), 7.310 (1.20), 7.323 (1.12), 7.682 (4.44), 7.684 (4.55), 7.755 (1.08), 7.759 (1.11), 7.774 (1.88), 7.778 (1.90), 7.794 (1.02), 7.798 (1.00), 8.043 (0.83), 8.058 (1.74), 8.073 (0.84), 8.536 (1.57), 8.546 (1.54), 8.548 (1.54). LC-MS (Method 1): $R_t$ = 1.00 min; MS (ESIneg): m/z = 421 $[M - H]^-$ | Intermediate 73 GP H Conditions B 16 mg, 18% yield, 95% purity Mixture of two isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 247 | 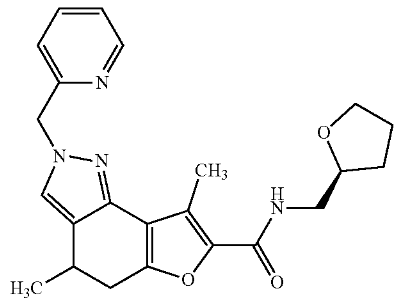 [SMILES: Cc1c(C(=O)NC[C@@H]2CCCO2)oc2c1-c1nn(Cc3ccccn3)cc1C(C)C2] (4+)-4,8-dimethyl-N-{[(2S)-oxolan-2-yl]methyl}-2-[(pyridin-2-yl)methyl]-4,5-dihydro-2H-furo[2,3-g]indazole-7-carboxamide | $^1$H-NMR (400 MHz, DMSO-d6) δ [ppm]: 1.280 (6.39), 1.296 (6.42), 1.548 (0.54), 1.565 (0.75), 1.572 (0.57), 1.580 (0.66), 1.593 (0.51), 1.774 (0.60), 1.779 (0.79), 1.794 (1.38), 1.812 (1.57), 1.830 (1.42), 1.843 (0.83), 1.856 (0.76), 1.860 (0.88), 1.874 (0.63), 1.881 (0.47), 1.891 (0.40), 2.439 (16.00), 2.517 (4.63), 2.522 (3.70), 2.548 (1.21), 2.565 (1.24), 2.582 (0.53), 2.590 (1.28), 2.673 (0.69), 2.712 (0.64), 2.959 (1.16), 2.977 (1.46), 3.000 (1.07), 3.019 (1.20), 3.157 (0.47), 3.174 (0.72), 3.181 (0.56), 3.193 (0.67), 3.199 (0.72), 3.211 (1.54), 3.214 (1.60), 3.227 (2.65), 3.245 (1.43), 3.581 (0.49), 3.600 (1.07), 3.618 (1.40), 3.636 (0.77), 3.731 (0.64), 3.748 (1.22), 3.766 (1.07), 3.784 (0.64), 3.926 (1.03), 3.943 (1.55), 3.958 (0.95), 5.385 (7.04), 7.067 (1.87), 7.086 (1.98), 7.291 (0.95), 7.294 (0.96), 7.304 (1.00), 7.307 (1.07), 7.310 (1.16), 7.313 (1.06), 7.322 (1.08), 7.325 (1.04), 7.681 (4.39), 7.683 (4.37), 7.755 (1.09), 7.759 (1.14), 7.774 (1.89), 7.778 (1.88), 7.794 (1.00), 7.798 (0.97), 7.965 (0.78), 7.980 (1.63), 7.995 (0.77), 8.532 (1.24), 8.534 (1.41), 8.536 (1.50), 8.538 (1.32), 8.544 (1.33), 8.546 (1.43), 8.548 (1.43), 8.550 (1.23).<br>LC-MS (Method 1): $R_t$ = 1.08 min; MS (ESIneg): m/z = 405 $[M - H]^-$ | Intermediate 73<br>GP H<br>Conditions B<br>16 mg, 19% yield, 95% purity<br>Mixture of two isomers |
| 248 | 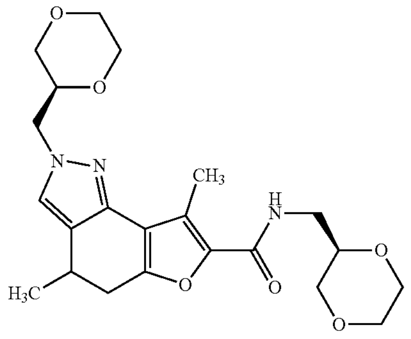 [SMILES: Cc1c(C(=O)NC[C@@H]2COCCO2)oc2c1-c1nn(C[C@H]3COCCO3)cc1C(C)C2] (4±)-N-{[(2R)-1,4-dioxan-2-yl]methyl}-2-{[(2S)-1,4-dioxan-2-yl]methyl}-4,8-dimethyl-4,5-dihydro-2H-furo[2,3-g]indazole-7-carboxamide | $^1$H-NMR (400 MHz, DMSO-d6) δ [ppm]: 1.258 (4.08), 1.265 (4.12), 1.275 (4.28), 1.281 (4.00), 2.470 (16.00), 2.522 (9.09), 2.549 (2.05), 2.574 (1.45), 2.755 (0.43), 2.938 (0.74), 2.943 (0.78), 2.957 (0.99), 2.962 (0.92), 2.980 (0.67), 2.986 (0.70), 2.998 (0.76), 3.004 (0.78), 3.124 (0.60), 3.141 (0.87), 3.148 (0.97), 3.163 (1.24), 3.183 (2.58), 3.197 (1.83), 3.207 (2.18), 3.212 (2.78), 3.231 (2.07), 3.236 (2.44), 3.247 (1.46), 3.266 (2.29), 3.281 (0.77), 3.294 (1.48), 3.416 (0.93), 3.421 (0.94), 3.443 (2.11), 3.449 (2.16), 3.470 (1.80), 3.476 (1.82), 3.512 (1.53), 3.518 (1.31), 3.540 (2.12), 3.546 (1.91), 3.568 (1.03), 3.573 (1.13), 3.616 (2.58), 3.633 (2.23), 3.639 (2.09), 3.687 (1.62), 3.692 (1.43), 3.716 (4.44), 3.745 (2.55), 3.847 (0.78), 4.071 (1.28), 4.084 (2.48), 4.096 (2.29), 7.508 (3.32), 8.043 (0.91), 8.057 (1.89), 8.073 (0.89).<br>LC-MS (Method 1): $R_t$ = 0.98 min; MS (ESIpos): m/z = 432 $[M + H]^+$ | Intermediate 74<br>GP H<br>Conditions B<br>15 mg, 10% yield, 95% purity<br>Mixture of two isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 249 | 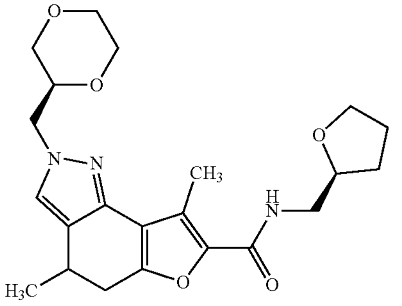 [SMILES: Cc1c(C(=O)NC[C@@H]2CCCO2)oc2c1-c1nn(C[C@H]3COCCO3)cc1C(C)C2] (4±)-2-{[(2S)-1,4-dioxan-2-yl]methyl}-4,8-dimethyl-N-{[(2S)-oxolan-2-yllmethyl}-4,5-dihydro-2H-furo[2,3-g]indazole-7-carboxamide | $^{1}$H-NMR (400 MHz, DMSO-d6) δ [ppm]: 1.257 (4.00), 1.264 (4.13), 1.274 (4.28), 1.281 (3.97), 1.551 (0.60), 1.568 (0.84), 1.576 (0.68), 1.584 (0.73), 1.596 (0.57), 1.613 (0.44), 1.781 (0.88), 1.797 (1.56), 1.815 (1.74), 1.833 (1.55), 1.846 (0.96), 1.863 (1.01), 1.877 (0.74), 1.895 (0.46), 2.469 (16.00), 2.522 (5.60), 2.545 (1.76), 2.570 (1.12), 2.937 (0.72), 2.943 (0.75), 2.955 (0.92), 2.962 (0.91), 2.979 (0.67), 2.985 (0.65), 2.997 (0.75), 3.003 (0.73), 3.122 (0.56), 3.140 (0.82), 3.157 (0.65), 3.165 (0.75), 3.182 (0.50), 3.214 (1.42), 3.218 (1.40), 3.230 (2.77), 3.233 (2.79), 3.244 (1.97), 3.249 (1.71), 3.267 (1.87), 3.292 (1.24), 3.416 (0.42), 3.427 (0.40), 3.436 (0.72), 3.443 (0.85), 3.448 (0.79), 3.454 (0.80), 3.464 (0.69), 3.475 (0.69), 3.481 (0.57), 3.507 (0.48), 3.513 (0.56), 3.521 (0.51), 3.526 (0.52), 3.535 (0.69), 3.541 (0.76), 3.549 (0.71), 3.556 (0.73), 3.568 (0.47), 3.583 (0.94), 3.602 (1.35), 3.620 (2.82), 3.638 (1.17), 3.647 (1.08), 3.723 (2.55), 3.751 (3.37), 3.768 (1.34), 3.786 (0.69), 3.847 (0.75), 3.930 (1.19), 3.946 (1.76), 3.961 (1.09), 4.070 (1.26), 4.077 (1.57), 4.084 (2.46), 4.095 (2.18), 7.507 (3.37), 7.964 (0.88), 7.980 (1.85), 7.994 (0.91). LC-MS (Method 1): $R_t$ = 1.06 min; MS (ESIpos): m/z = 416 $[M + H]^+$ | Intermediate 74 GP H Conditions B 25 mg, 17% yield, 95% purity Mixture of two isomers |
| 250 | 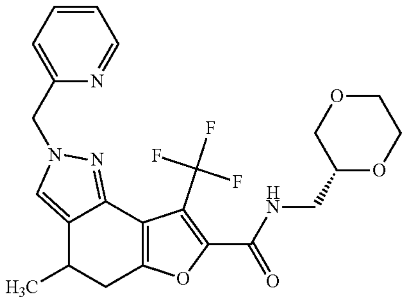 [SMILES: CC1Cc2oc(C(=O)NC[C@@H]3COCCO3)c(C(F)(F)F)c2-c2nn(Cc3ccccn3)cc21] (4±)-N-{[(2R)-1,4-dioxan-2-yl]methyl}-4-methyl-2-[(pyridin-2-yl)methyl]-8-(trifluoromethyl)-4,5-dihydro-2H-furo[2,3-g]indazole-7-carboxamide | $^{1}$H-NMR (400 MHz, DMSO-d6) δ [ppm]: 1.286 (14.45), 1.303 (15.06), 2.323 (1.51), 2.327 (2.17), 2.331 (1.66), 2.447 (0.41), 2.518 (16.00), 2.523 (11.29), 2.595 (2.75), 2.621 (2.77), 2.636 (2.93), 2.663 (3.70), 2.669 (2.37), 2.673 (1.68), 3.025 (2.61), 3.044 (3.54), 3.067 (2.40), 3.085 (2.86), 3.178 (1.21), 3.195 (4.06), 3.219 (5.91), 3.236 (3.82), 3.247 (5.44), 3.257 (2.77), 3.262 (2.58), 3.278 (2.04), 3.421 (1.32), 3.428 (1.56), 3.449 (2.73), 3.455 (2.99), 3.476 (2.43), 3.482 (2.31), 3.522 (1.95), 3.528 (2.19), 3.551 (2.73), 3.557 (2.82), 3.577 (1.08), 3.583 (1.89), 3.619 (3.47), 3.626 (2.25), 3.642 (3.70), 3.664 (0.89), 3.695 (3.03), 3.700 (2.54), 3.723 (5.17), 3.751 (2.25), 5.395 (15.85), 7.079 (4.44), 7.099 (4.68), 7.295 (2.18), 7.298 (2.30), 7.307 (2.33), 7.310 (2.48), 7.314 (2.63), 7.317 (2.51), 7.326 (2.59), 7.329 (2.49), 7.727 (9.74), 7.729 (9.75), 7.758 (2.71), 7.762 (2.82), 7.777 (4.62), 7.781 (4.67), 7.796 (2.35), 7.800 (2.29), 8.533 (2.88), 8.535 (3.27), 8.537 (3.50), 8.539 (3.02), 8.545 (3.04), 8.547 (3.46), 8.549 (3.37), 8.552 (3.16), 8.736 (1.43), 8.751 (3.01), 8.766 (1.49). LC-MS (Method 1): $R_t$ = 1.06 min; MS (ESIpos): m/z = 477 $[M + H]^+$ | Intermediate 75 GP H Conditions A 36 mg, 54% yield, 98% purity Mixture of two isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 251 | 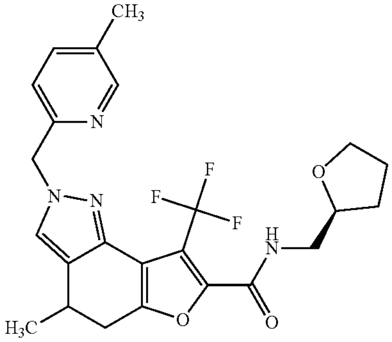 [SMILES: Cc1ccc(Cn2cc3c(n2)-c2c(oc(C(=O)NC[C@@H]4CCCO4)c2C(F)(F)F)CC3C)nc1]<br>(4±)-4-methyl-2-[(5-methyl-2-pyridyl)methyl]-N-[[(2S)-tetrahydrofuran-2-yl]methyl]-8-(trifluoromethyl)-4,5-dihydrofuro[2,3-g]indazole-7-carboxamide | $^1$H-NMR (400 MHz, DMSO-d6) δ [ppm]: 0.879 (0.46), 1.277 (8.70), 1.294 (8.74), 1.537 (0.78), 1.556 (1.06), 1.564 (1.00), 1.572 (0.90), 1.586 (0.96), 1.602 (0.58), 1.770 (0.53), 1.791 (1.24), 1.807 (2.18), 1.825 (2.16), 1.843 (1.38), 1.859 (1.10), 1.869 (0.92), 1.876 (0.96), 1.881 (0.90), 1.888 (1.06), 1.902 (0.89), 1.908 (0.77), 1.919 (0.60), 2.269 (16.00), 2.424 (0.52), 2.523 (4.02), 2.541 (2.92), 2.581 (1.49), 2.607 (1.59), 2.622 (1.71), 2.665 (1.13), 2.669 (1.46), 2.673 (1.17), 2.739 (0.74), 2.753 (2.75), 3.015 (1.62), 3.032 (2.13), 3.056 (1.48), 3.074 (1.79), 3.164 (0.70), 3.181 (1.02), 3.190 (0.83), 3.198 (0.78), 3.207 (0.96), 3.225 (0.61), 3.250 (2.77), 3.265 (5.50), 3.280 (3.17), 3.377 (1.37), 3.594 (0.80), 3.613 (1.81), 3.631 (2.05), 3.649 (1.06), 3.738 (0.91), 3.754 (1.81), 3.771 (1.57), 3.791 (0.80), 3.916 (0.41), 3.932 (1.40), 3.948 (2.03), 3.963 (1.31), 5.337 (9.13), 7.016 (2.99), 7.036 (3.17), 7.577 (1.77), 7.581 (1.79), 7.597 (1.69), 7.601 (1.69), 7.689 (5.89), 8.370 (3.12), 8.694 (1.06), 8.709 (2.10), 8.724 (1.04).<br>LC-MS (Method 1): $R_t$ = 1.16 min; MS (ESIpos): m/z = 475 [M + H]$^+$ | Intermediate 76<br>GP H<br>Conditions B<br>8 mg, 5% yield, 98% purity<br>Mixture of two isomers |
| 252 | 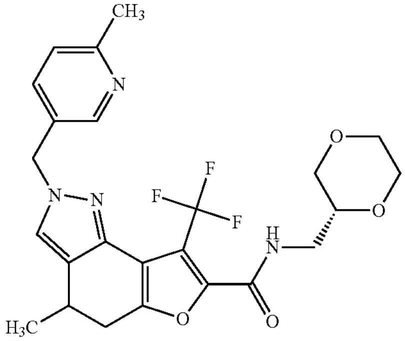 [SMILES: Cc1ccc(Cn2cc3c(n2)-c2c(oc(C(=O)NC[C@@H]4COCCO4)c2C(F)(F)F)CC3C)cn1]<br>(4±)-N-{I(2R)-1,4-dioxan-2-yl]methyl)-4-methyl-2-[(6-methylpyridin-3-yl)methyl]-8-(trifluoromethyl)-4,5-dihydro-2H-furo[2,3-g]indazole-7-carboxamide | $^1$H-NMR (400 MHz, DMSO-d6) δ [ppm]: 1.262 (7.51), 1.279 (7.71), 2.401 (2.07), 2.430 (16.00), 2.539 (1.95), 2.569 (1.49), 2.596 (1.56), 2.611 (1.50), 2.637 (1.51), 3.001 (1.33), 3.019 (1.66), 3.043 (1.11), 3.060 (1.40), 3.157 (0.91), 3.183 (1.14), 3.193 (1.71), 3.217 (2.75), 3.231 (1.84), 3.245 (3.10), 3.255 (1.74), 3.276 (1.14), 3.426 (0.83), 3.447 (1.56), 3.454 (1.64), 3.474 (1.28), 3.480 (1.27), 3.526 (1.11), 3.554 (1.58), 3.582 (0.98), 3.616 (2.30), 3.640 (2.37), 3.693 (1.78), 3.721 (3.23), 3.749 (1.40), 5.284 (7.36), 5.335 (0.42), 7.155 (0.29), 7.176 (0.39), 7.218 (2.42), 7.238 (2.75), 7.270 (0.25), 7.276 (0.25), 7.290 (0.17), 7.296 (0.18), 7.516 (0.86), 7.557 (1.76), 7.562 (1.79), 7.576 (1.61), 7.582 (1.61), 7.697 (4.88), 8.108 (0.35), 8.112 (0.34), 8.400 (2.75), 8.405 (2.75), 8.730 (0.92), 8.745 (1.85), 8.759 (0.93), 8.890 (0.19).<br>LC-MS (Method 1): $R_t$ = 1.05 min; MS (ESIpos): m/z = 491 [M + H]$^+$ | Intermediate 77<br>GP H<br>Conditions A<br>26 mg, 34% yield, 90% purity<br>Mixture of two isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 253 | 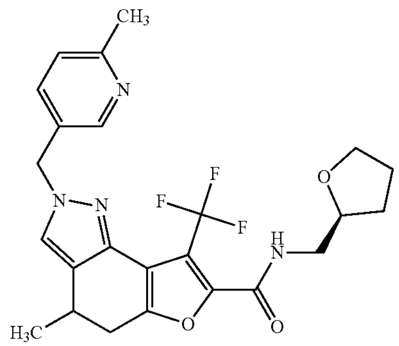 [SMILES: Cc1ccc(Cn2cc3c(n2)-c2c(oc(C(=O)NC[C@@H]4CCCO4)c2C(F)(F)F)CC3C)cn1] (4±)-4-methyl-2-[(6-methylpyridin-3-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.263 (7.06), 1.279 (7.15), 1.536 (0.55), 1.539 (0.53), 1.548 (0.47), 1.551 (0.52), 1.555 (0.79), 1.563 (0.74), 1.572 (0.64), 1.580 (0.51), 1.585 (0.72), 1.601 (0.45), 1.785 (0.66), 1.791 (0.86), 1.806 (1.54), 1.824 (1.53), 1.842 (0.99), 1.858 (0.82), 1.863 (0.48), 1.867 (0.58), 1.875 (0.64), 1.879 (0.57), 1.887 (0.75), 1.897 (0.48), 1.901 (0.57), 1.903 (0.57), 1.908 (0.53), 1.918 (0.42), 2.431 (16.00), 2.518 (2.83), 2.523 (1.88), 2.540 (0.77), 2.565 (1.15), 2.591 (1.26), 2.606 (1.32), 2.633 (1.44), 2.674 (0.47), 2.999 (1.34), 3.016 (1.75), 3.039 (1.20), 3.058 (1.49), 3.141 (0.50), 3.157 (0.72), 3.166 (0.55), 3.175 (0.51), 3.183 (0.67), 3.249 (2.12), 3.264 (4.32), 3.280 (2.35), 3.594 (0.53), 3.610 (1.11), 3.613 (1.25), 3.630 (1.48), 3.648 (0.85), 3.737 (0.67), 3.753 (1.34), 3.770 (1.16), 3.772 (1.10), 3.790 (0.67), 3.931 (1.05), 3.947 (1.56), 3.963 (1.01), 5.284 (6.79), 7.218 (2.33), 7.238 (2.60), 7.556 (1.73), 7.561 (1.73), 7.576 (1.49), 7.582 (1.54), 7.694 (4.67), 7.696 (4.66), 8.400 (2.42), 8.405 (2.42), 8.692 (0.79), 8.708 (1.63), 8.722 (0.77). LC-MS (Method 1): $R_t$ = 1.13 min; MS (ESIpos): m/z = 475 [M + H]+ | Intermediate 77 GP H Condiitons A 12 mg, 18% yield, 98% purity Mixture of two isomers |
| 254 | 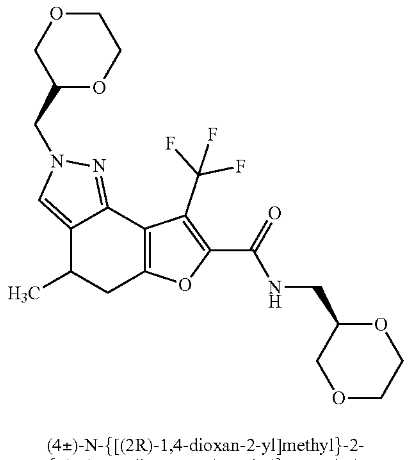 (4±)-N-{[(2R)-1,4-dioxan-2-yl]methyl}-2-{[(2S)-1,4-dioxan-2-yl]methyl}-4-methyl-8-(trifluoromethyl)-4,5-dihydro-2H-furo[2,3-g]indazole-7-carboxamide | $^1$H-NMR (400 MHz, DMSO-d6) δ [ppm]: 1.269 (7.91), 1.276 (8.23), 1.286 (8.65), 1.293 (7.98), 2.518 (16.00), 2.523 (11.32), 2.576 (1.69), 2.580 (1.60), 2.602 (1.57), 2.607 (1.54), 2.618 (1.67), 2.622 (1.55), 2.644 (1.69), 2.649 (1.60), 3.006 (1.49), 3.013 (1.48), 3.024 (1.96), 3.031 (1.94), 3.047 (1.35), 3.054 (1.42), 3.065 (1.63), 3.072 (1.65), 3.149 (1.07), 3.166 (1.57), 3.175 (1.23), 3.198 (2.91), 3.222 (4.30), 3.225 (4.27), 3.239 (3.10), 3.250 (5.34), 3.260 (2.57), 3.267 (4.05), 3.271 (3.91), 3.275 (3.49), 3.281 (1.65), 3.295 (2.81), 3.299 (3.01), 3.405 (0.82), 3.425 (2.37), 3.431 (2.01), 3.451 (4.16), 3.457 (3.39), 3.478 (3.40), 3.485 (2.30), 3.497 (1.17), 3.502 (1.26), 3.516 (1.03), 3.525 (3.36), 3.531 (3.33), 3.545 (1.54), 3.553 (3.63), 3.559 (3.26), 3.580 (1.47), 3.586 (1.84), 3.614 (5.13), 3.628 (2.41), 3.645 (5.24), 3.667 (0.88), 3.698 (3.04), 3.704 (2.56), 3.726 (7.35), 3.747 (4.43), 3.754 (4.24), 3.774 (1.45), 3.793 (0.50), 3.833 (1.30), 4.050 (0.42), 4.085 (2.45), 4.094 (4.94), 4.101 (4.25), 4.110 (3.87), 4.130 (0.51), 7.567 (9.09), 8.733 (1.66), 8.748 (3.45), 8.763 (1.65). LC-MS (Method 1): $R_t$ = 1.02 min; MS (ESIpos): m/z = 486 $[M + H]^+$ | Intermediate 78 GP H Conditions B 143 mg, 49% yield, 95% purity Mixture of two isomers |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 254-1 | 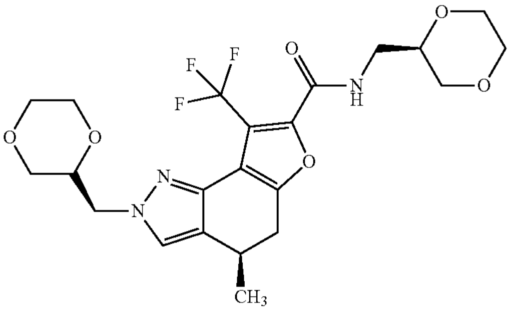 (4R or 4S)-N-{[(2R)-1,4-dioxan-2-yl]methyl}-2-{[(2S)-1,4-dioxan-2-yl]methyl}-4-methyl-8-(trifluoromethyl)-4,5-dihydro-2H-furo[2,3-g]indazole-7-carboxamide Diastereomer 1 of Ex. 254 | $R_t$ = 3.25 min $^1$H NMR (400 MHz, DMSO-d6) δ [ppm]: 1.28 (d, 3H) 2.58-2.65 (m, 1 H) 3.00-3.07 (m, 1 H) 3.15-3.30 (m, 5 H) 3.39-3.50 (m, 2 H) 3.51-3.59 (m, 2 H) 3.61-3.67 (m, 3 H) 3.70-3.77 (m, 4 H) 3.83-3.88 (m, 1 H) 4.06-4.13 (m, 2 H) 7.57 (m, 1 H) 8.75 (t, 1H). $[\alpha]_D^{20}$ = −41.4° ($_C$ = 1, DMSO) | analyt. method: Instrument: Thermo Fisher UltiMate 3000; Column: YMC Cellulose SC 3μ, 100 x 4.6; eluent A: hexane + 0.1 vol% diethylamine; eluent B: ethanol; isocratic: 70% A + 30% B; flow: 1.4 ml/min; temperature: 25° C.; UV: 254 nm |
| 254-2 | 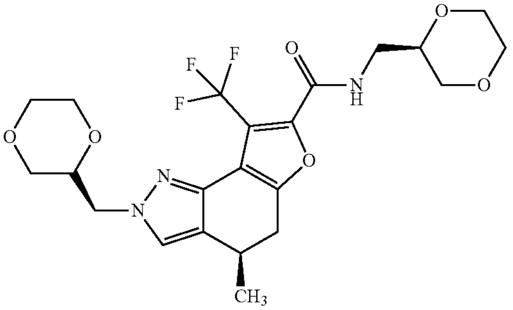 (4R or 4S)-N-{[(2R)-1,4-dioxan-2-yl]methyl}-2-{[(2S)-1,4-dioxan-2-yl]methyl}-4-methyl-8-(trifluoromethyl)-4,5-dihydro-2H-furo[2,3-g]indazole-7-carboxamide Diastereomer 2 of Ex. 254 | $R_t$ = 3.86 min $^1$H NMR (400 MHz, DMSO-d6) δ [ppm]: 1.28 (d, 3 H) 2.58-2.64 (m, 1 H) 3.01 - 3.07 (m, 1H) 3.13-3.31 (m, 5H) 3.41-3.49 (m, 2H) 3.49-3.59 (m, 2H) 3.61-3.67 (m, 3H) 3.70-3.77 (m, 4H) 3.79-3.86 (m, 1H) 4.05-4.14 (m, 2H) 7.57 (m, 1 H) 8.75 (t, 1H). $[\alpha]_D^{20}$ = +16.6° (c = 1, DMSO) | |
| 255 | 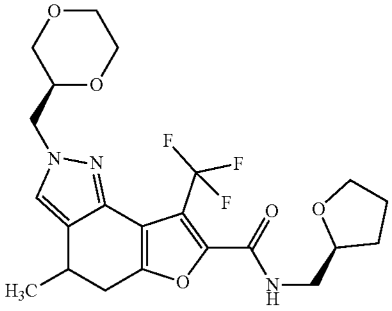 [SMILES: CC1Cc2oc(C(=O)NC[C@@H]3CCCO3)c(C(F)(F)F)c2-c2nn(C[C@H]3COCCO3)cc21] (4±)-2-{[(2S)-1,4-dioxan-2-yl]methyl}-4-methyl-N-{[(2S)-oxolan-2-yl]methyl}-8-(trifluoromethyl)-4,5-dihydro-2H-furo[2,3-g]indazole-7-carboxamide | $^1$H NMR (400 MHz, DMSO-d6) δ [ppm]: 1.25-1.30 (m, 3 H) 1.52-1.61 (m, 1 H) 1.75-1.96 (m, 3 H) 2.57-2.65 (m, 1 H) 2.99-3.08 (m, 1 H) 3.13-3.22 (m, 1 H) 3.24-3.30 (m, 3 H) 3.39-3.57 (m, 2 H) 3.60-3.67 (m, 2 H) 3.70-3.80 (m, 3 H) 3.80-3.89 (m, 1 H) 3.92-3.99 (m, 1 H) 4.08-4.11 (m, 2 H) 7.57 (s, 1 H) 8.70-8.73 (m, 1 H). LC-MS (Method 1): $R_t$ = 1.11 min; MS (ESIpos): m/z = 470 [M + H]$^+$ | Intermediate 78 GP H Conditions B 67 mg, 24% yield, 95% purity Mixture of two isomers |

TABLE 5-continued

| The following examples (212 to 316) were prepared in analogy to example 169 starting from the given intermediates and commercially available amines (or their salts), applying the indicated general procedure. | | | |
|---|---|---|---|
| Example | Structure IUPAC-Name | Analytical Data | Preparation or Separation Methods |
| 255-1 | 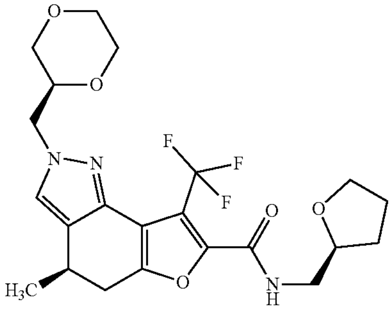 [SMILES: C[C@@H]1Cc2oc(C(=O)NC[C@@H]3CCCO3)c(C(F)(F)F)c2-c2nn(C[C@H]3COCCO3)cc21] (4R or 4S)-2-{[(2S)-1,4-dioxan-2-yl]methyl}-4-methyl-N-{[(2S)-oxolan-2-yl]methyl}-8-(trifluoromethyl)-4,5-dihydro-2H-furo[2,3-g]indazole-7-carboxamide Diastereomer 1 of Ex. 255 | $R_t$ = 3.83 min $^1$H NMR (400 MHz, DMSO-d6) δ [ppm]: 1.28 (d, 3H) 1.52-1.58 (m, 1 H) 1.75-1.96 (m, 3 H) 2.58-2.65 (m, 1 H) 3.01-3.06 (m, 1 H) 3.13-3.22 (m, 1 H) 3.24-3.30 (m, 3 H) 3.39-3.57 (m, 2 H) 3.60-3.64 (m, 2 H) 3.70-3.80 (m, 3 H) 3.80-3.89 (m, 1 H) 3.92-3.99 (m, 1 H) 4.08-4.11 (m, 2 H) 7.57 (s, 1 H) 8.71 (t, 1H). $[\alpha]_D^{20}$ = −4.6° (c = 1, DMSO) | analyt. method: Instrument: Thermo Fisher UltiMate 3000; Column: YMC Cellulose SB 3μ, 100 × 4.6; eluent A: hexane + 0.1 vol% trifluoroacetic acid; eluent B: 2-propanol; isocratic: 80% A + 20% B; flow: 1.4 ml/min; temperature: 25° C.; UV: 254 nm |
| 255-2 | 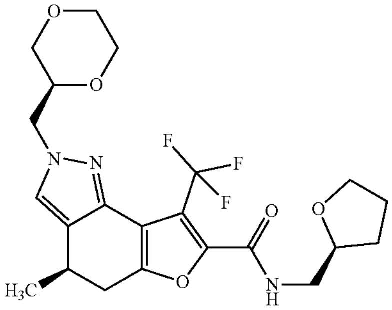 [SMILES: C[C@@H]1Cc2oc(C(=O)NC[C@@H]3CCCO3)c(C(F)(F)F)c2-c2nn(C[C@H]3COCCO3)cc21] (4R or 4S)-2-{[(2S)-1,4-dioxan-2-yl]methyl}-4-methyl-N-{[(2S)-oxolan-2-yl]methyl}-8-(trifluoromethyl)-4,5-dihydro-2H-furo[2,3-g]indazole-7-carboxamide Diastereomer 2 of Ex. 255 | $R_t$ = 4.31 min $^1$H NMR (400 MHz, DMSO-d6) δ [ppm]: 1.27 (d, 3H) 1.52-1.57 (m, 1 H) 1.75-1.94 (m, 3 H) 2.58-2.65 (m, 1 H) 3.01-3.06 (m, 1 H) 3.13-3.22 (m, 1 H) 3.25-3.30 (m, 3 H) 3.39-3.57 (m, 2 H) 3.60-3.64 (m, 2 H) 3.70-3.80 (m, 3 H) 3.80-3.89 (m, 1 H) 3.92-3.99 (m, 1 H) 4.09-4.12 (m, 2 H) 7.57 (s, 1 H) 8.71 (t, 1H). $[\alpha]_D^{20}$ = +8.3° (c = 1, DMSO) | |
| 256 | 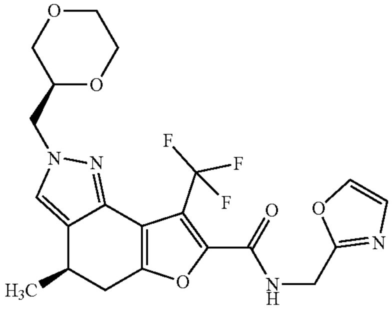 (4R or 4S)-2-{[(2S)-1,4-dioxan-2-yl]methyl}-4-methyl-N-[(1,3-oxazol-2-yl)methyl]-8-(trifluoromethyl)-4,5-dihydro-2H-furo[2,3-g]indazole-7-carboxamide | $^1$H-NMR (400 MHz, DMSO-d6) δ [ppm]: 1.280 (14.96), 1.296 (15.48), 2.318 (0.73), 2.322 (1.66), 2.326 (2.39), 2.331 (1.64), 2.518 (16.00), 2.522 (11.14), 2.596 (2.54), 2.605 (0.84), 2.623 (2.82), 2.638 (2.85), 2.664 (4.84), 2.668 (2.96), 2.673 (1.93), 3.013 (2.82), 3.031 (3.91), 3.055 (2.73), 3.073 (3.15), 3.160 (1.11), 3.177 (1.59), 3.185 (1.26), 3.193 (1.20), 3.202 (1.51), 3.219 (0.87), 3.244 (2.90), 3.269 (3.55), 3.273 (3.48), 3.297 (3.40), 3.400 (1.07), 3.406 (1.33), 3.427 (2.49), 3.433 (2.70), 3.454 (2.28), 3.461 (2.08), 3.516 (1.67), 3.523 (2.03), 3.545 (2.58), 3.552 (2.69), 3.572 (1.18), 3.578 (1.77), 3.611 (2.64), 3.639 (2.14), 3.721 (2.83), 3.728 (2.93), 3.735 (3.11), 3.747 (2.41), 3.757 (2.60), 3.764 (2.64), 3.822 (0.72), 3.828 (0.78), 3.835 (1.43), 3.842 (1.57), 3.851 (1.41), 3.860 (1.78), 3.866 (1.32), 3.875 (0.93), 3.882 (0.80), 4.062 (0.64), 4.098 (5.29), 4.104 (5.47), 4.114 (5.80), 4.117 (5.60), 4.139 (0.66), 4.536 (6.60), 4.552 (7.05), 7.170 (13.26), 7.172 (12.05), 7.574 (9.95), 7.576 (9.80), 8.069 (14.15), 8.071 (13.13), 9.345 (1.72), 9.359 (3.82), 9.373 (1.72). | Intermediate 79 GP H Conditions D 36 mg, 28% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | LC-MS (Method 1): $R_t$ = 1.00 min; MS (ESIneg): m/z = 467 [M + H]+ | |
| 257 | 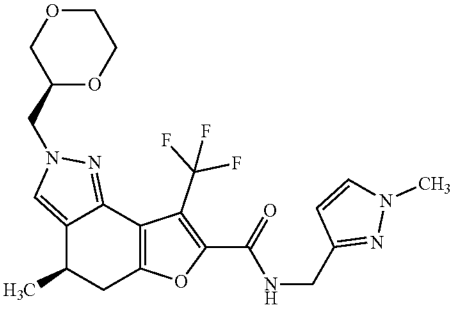 (4R or 4S)-2-{[(2S)-1,4-dioxan-2-yl]methyl}-4-methyl-N-[(1-methyl-1H-pyrazol-3-yl)methyl]-8-(trifluoromethyl)-4,5-dihydro-2H-furo[2,3-g]indazole-7-carboxamide | $^1$H-NMR (400 MHz, DMSO-d6) δ [ppm]: 1.271 (4.49), 1.288 (4.66), 2.518 (5.76), 2.522 (4.02), 2.565 (0.94), 2.592 (1.01), 2.607 (0.93), 2.634 (0.94), 2.987 (0.83), 3.006 (1.17), 3.029 (0.81), 3.047 (0.92), 3.160 (0.49), 3.186 (0.44), 3.241 (0.87), 3.266 (1.08), 3.270 (1.03), 3.294 (1.06), 3.404 (0.42), 3.425 (0.76), 3.431 (0.84), 3.452 (0.70), 3.459 (0.62), 3.514 (0.51), 3.521 (0.61), 3.544 (0.78), 3.550 (0.81), 3.577 (0.52), 3.609 (0.81), 3.638 (0.64), 3.723 (1.04), 3.732 (0.96), 3.753 (0.92), 3.760 (0.83), 3.782 (16.00), 3.796 (0.66), 3.832 (0.44), 3.838 (0.50), 3.847 (0.44), 3.855 (0.55), 3.862 (0.42), 4.092 (1.65), 4.098 (1.66), 4.108 (1.84), 4.344 (2.26), 4.360 (2.40), 6.118 (2.80), 6.124 (2.75), 7.562 (2.99), 7.564 (3.00), 7.585 (2.37), 7.590 (2.33), 9.062 (0.57), 9.078 (1.25), 9.092 (0.58). LC-MS (Method 1): $R_t$ = 1.01 min; MS (ESIpos): m/z = 480 $[M + H]^+$ | Intermediate 79 GP H Conditions A 30 mg, 23% yield, 95% purity |
| 258 | 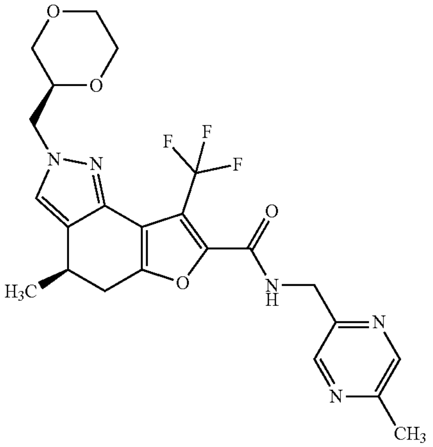 (4R or 4S)-2-{[(2S)-1,4-dioxan-2-yl]methyl}-4-methyl-N-[(5-methylpyrazin-2-yl)methyl]-8-(trifluoromethyl)-4,5-dihydro-2H-furo[2,3-g]indazole-7-carboxamide | $^1$H NMR (400 MHz, DMSO-d6) δ [ppm]: 1.21 -1.32 (m, 3 H) 2.55-2.64 (m, 1 H) 2.96-3.09 (m, 1 H) 3.10-3.23 (m, 1 H) 3.24-3.31 (m, 1 H) 3.39-3.49 (m, 1 H) 3.49-3.66 (m, 2 H) 3.69-3.78 (m, 2 H) 3.80-3.94 (m, 1 H) 4.03-4.20 (m, 2 H) 4.47-4.65 (m, 2 H) 7.41-7.68 (m, 1 H) 8.41-8.54 (m, 2 H) 9.22-9.38 (m, 1 H). LC-MS (Method 1): $R_t$ = 1.01 min; MS (ESIneg): m/z = 490 $[M - H]^-$ | Intermediate 79 GP H Conditions A 68.3 mg, 53% yield, 98% purity |
| 259 | 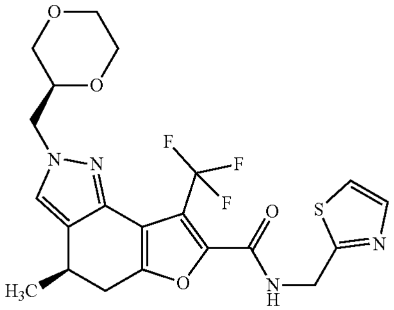 [SMILES: C[C@@H]1Cc2oc(C(=O)NCc3nccs3)c(C(F)(F)F)c2-c2nn(C[C@H]3COCCO3)cc21] | 1H NMR (400 MHz, DMSO-d6) δ [ppm]: 1.23-1.37 (m, 3 H) 2.56-2.67 (m, 1 H), 2.96-3.09 (m, 1 H) 3.13-3.22 (m, 1 H) 3.23-3.30 (m, 1 H) 3.37-3.47 (m, 1 H), 3.49-3.67 (m, 2 H) 3.69-3.78 (m, 2 H) 3.80-3.92 (m, 1 H) 4.05-4.22 (m, 2 H), 4.65-4.88 (m, 2 H) 7.53-7.63 (m, 1 H) 7.64-7.70 (m, 1 H) 7.71-7.80 (m, 1 H), 9.45-9.66 (m, 1 H). LC-MS (Method 1): $R_t$ = 1.04 min; MS (ESIpos): m/z = 483 $[M + H]^+$ | Intermediate 79 GP H Conditions A 73.6 mg, 58% yield, 98% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| | (4R or 4S)-2-{[(2S)-1,4-dioxan-2-yl]methyl}-4-methyl-N-[(1,3-thiazol-2-yl)methyl]-8-(trifluoromethyl)-4,5-dihydro-2H-furo[2,3-g]indazole-7-carboxamide | | |
| 260 | 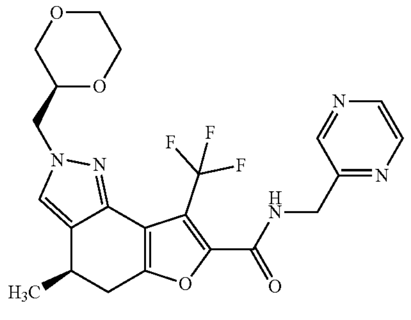 [SMILES: C[C@@H]1Cc2oc(C(=O)NCc3cnccn3)c(C(F)(F)F)c2-c2nn(C[C@H]3COCCO3)cc21] (4R or 4S)-2-{[(2S)-1,4-dioxan-2-yl]methyl}-4-methyl-N-[(pyrazin-2-yl)methyl]-8-(trifluoromethyl)-4,5-dihydro-2H-furo[2,3-g]indazole-7-carboxamide | $^1$H NMR (400 MHz, DMSO-d6) δ [ppm]: 1.29 (d, 3H), 2.63 (dd, 1H), 3.05 (dd, 1H), 3.14-3.23 (m, 1H), 3.27 (dd, 1H), 3.40-3.47 (m, 1H), 3.51-3.59 (m, 1H), 3.63 (brd, 1H), 3.74 (dt, 2H), 3.82-3.90 (m, 1H), 4.05-4.16 (m, 2H), 4.59 (d, 2H), 7.57 (d, 1H), 8.56 (d, 1H), 8.61 (dd, 1H), 8.64 (d, 1H), 9.35 (t, 1H). LC-MS (Method 1): $R_t$ = 0.99 min; MS (ESIneg): m/z = 476 [M − H]$^-$ | Intermediate 79 GP G Conditions A 37.5 mg, 59% yield, 98% purity |
| 261 | 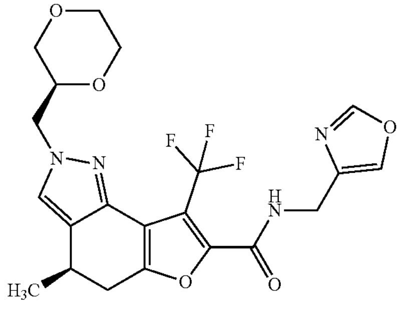 [SMILES: C[C@@H]1Cc2oc(C(=O)NCc3cocn3)c(C(F)(F)F)c2-c2nn(C[C@H]3COCCO3)cc21] (4R or 4S)-2-{[(2S)-1,4-dioxan-2-yl]methyl}-4-methyl-N-[(1,3-oxazol-4-yl)methyl]-8-(trifluoromethyl)-4,5-dihydro-2H-furo[2,3-g]indazole-7-carboxamide | $^1$H NMR (400 MHz, DMSO-d6) δ [ppm]: 1.28 (d, 3H), 2.61 (dd, 1H), 3.03 (dd, 1H), 3.14-3.21 (m, 1H), 3.27 (dd, 1H), 3.39-3.46 (m, 1H), 3.51-3.59 (m, 1H), 3.63 (brd, 1H), 3.71-3.77 (m, 2H), 3.81-3.89 (m, 1H), 4.05-4.15 (m, 2H), 4.33 (d, 2H), 7.57 (d, 1H), 7.96-7.98 (m, 1H), 8.33 (d, 1H), 9.13 (t, 1H). LC-MS (Method 1): $R_t$ = 1.00 min; MS (ESIneg): m/z = 465 [M − H]$^-$ | Intermediate 79 GP G Conditions A 34.2 mg, 55% yield, 97% purity |
| 262 | 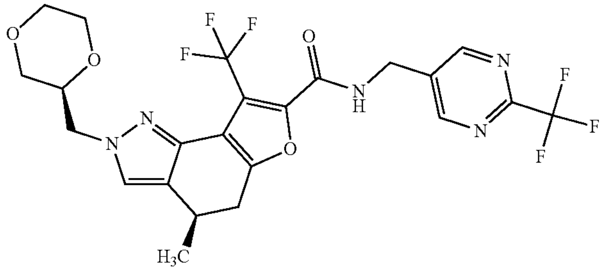 [SMILES: C[C@@H]1Cc2oc(C(=O)NCc3cnc(C(F)(F)F)nc3)c(C(F)(F)F)c2-c2nn(C[C@H]3COCCO3)cc21] (4R or 4S)-2-{[(2S)-1,4-dioxan-2-yl]methyl}-4-methyl-8-(trifluoromethyl)-N-{[2-(trifluoromethyl)pyrimidin-5-yl]methyl}-4,5-dihydro-2H-furo[2,3-g]indazole-7-carboxamide | $^1$H NMR (400 MHz, DMSO-d6) δ [ppm]: 1.23-1.33 (m, 3 H) 2.53-2.64 (m, 1 H) 2.98-3.09 (m, 1 H) 3.12-3.20 (m, 1 H) 3.20-3.29 (m, 1 H) 3.38-3.49 (m, 1 H) 3.50-3.67 (m, 2 H) 3.69-3.78 (m, 2 H) 3.81-3.91 (m, 1 H) 4.05-4.17 (m, 2 H) 4.47-4.70 (m, 2 H) 7.53-7.68 (m, 1 H) 8.91-9.13 (m, 2 H) 9.29-9.47 (m, 1 H). LC-MS (Method 1): $R_t$ = 1.17 min; MS (ESIneg): m/z = 544 [M − H]$^-$ | Intermediate 79 GP G Conditions A 36.2 mg, 41% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 263 | 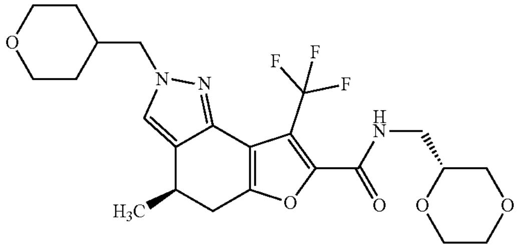 [SMILES: C[C@@H]1Cc2oc(C(=O)NC[C@@H]3COCCO3)c(C(F)(F)F)c2-c2nn(CC3CCOCC3)cc21] (4R or 4S)-N-{[(2R)-1,4-dioxan-2-yl]methyl}-4-methyl-2-[(oxan-4-yl)methyl]-8-(trifluoromethyl)-4,5-dihydro-2H-furo[2,3-g]indazole-7-carboxamide | $^1$H-NMR (400 MHz, DMSO-d6) δ [ppm]: 1.184 (0.69), 1.194 (0.60), 1.214 (2.12), 1.244 (2.52), 1.255 (1.81), 1.270 (15.98), 1.286 (16.00), 1.408 (3.17), 1.438 (2.37), 1.969 (0.83), 1.979 (0.91), 1.988 (1.10), 1.998 (1.34), 2.007 (1.00), 2.016 (0.88), 2.026 (0.72), 2.038 (0.47), 2.327 (3.36), 2.332 (2.42), 2.336 (1.11), 2.518 (15.13), 2.523 (10.05), 2.566 (2.56), 2.592 (2.76), 2.608 (2.85), 2.634 (3.15), 2.669 (3.42), 2.673 (2.43), 2.678 (1.07), 3.002 (2.86), 3.019 (3.77), 3.043 (2.57), 3.061 (3.22), 3.143 (1.13), 3.159 (1.68), 3.169 (1.32), 3.178 (1.27), 3.186 (1.98), 3.195 (3.80), 3.202 (2.63), 3.219 (6.35), 3.223 (5.95), 3.237 (6.86), 3.243 (7.33), 3.247 (7.98), 3.257 (4.64), 3.273 (4.83), 3.292 (1.64), 3.308 (2.13), 3.423 (1.07), 3.429 (1.29), 3.449 (2.77), 3.456 (3.03), 3.476 (2.43), 3.483 (2.32), 3.524 (2.09), 3.530 (2.38), 3.552 (2.91), 3.559 (2.98), 3.578 (1.30), 3.585 (2.01), 3.596 (0.47), 3.620 (3.78), 3.627 (2.37), 3.644 (3.89), 3.660 (0.76), 3.666 (0.86), 3.696 (3.51), 3.702 (2.76), 3.725 (5.56), 3.752 (2.45), 3.802 (3.05), 3.808 (3.06), 3.831 (2.81), 3.837 (2.68), 3.948 (7.59), 3.966 (7.45), 4.079 (0.44), 5.758 (0.73), 7.581 (9.73), 7.629 (0.67), 8.718 (1.80), 8.733 (3.75), 8.747 (1.76). LC-MS (Method 1): $R_t$ = 1.08 min; MS (ESIneg): m/z = 484 $[M + H]^+$ | Intermediate 80 GP H Conditions C 49.5 mg, 17% yield, 95% purity |
| 264 | 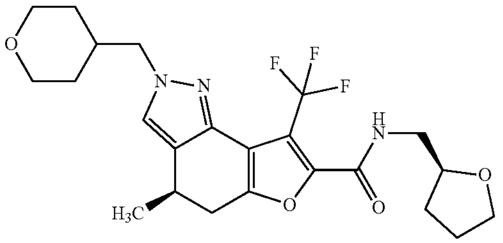 [SMILES: C[C@@H]1Cc2oc(C(=O)NC[C@@H]3CCCO3)c(C(F)(F)F)c2-c2nn(CC3CCOCC3)cc21] (4 or 4S)-4-methyl-2-[(oxan-4-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.214 (1.09), 1.244 (1.30), 1.269 (8.23), 1.286 (8.24), 1.406 (1.65), 1.437 (1.24), 1.518 (0.48), 1.538 (0.67), 1.558 (0.91), 1.566 (0.85), 1.574 (0.71), 1.587 (0.82), 1.604 (0.52), 1.772 (0.43), 1.793 (0.97), 1.809 (1.83), 1.827 (1.78), 1.844 (1.12), 1.860 (0.97), 1.870 (0.66), 1.877 (0.72), 1.889 (0.84), 1.899 (0.57), 1.903 (0.65), 1.910 (0.60), 1.921 (0.47), 1.969 (0.43), 1.987 (0.68), 1.997 (0.68), 2.332 (2.64), 2.336 (1.17), 2.518 (16.00), 2.523 (10.69), 2.562 (1.44), 2.588 (1.44), 2.603 (1.51), 2.629 (1.58), 2.673 (2.66), 2.678 (1.18), 2.999 (1.45), 3.017 (1.97), 3.040 (1.34), 3.058 (1.60), 3.142 (0.58), 3.159 (0.84), 3.168 (0.64), 3.177 (0.62), 3.185 (0.80), 3.216 (1.39), 3.245 (2.65), 3.251 (2.69), 3.267 (5.76), 3.282 (3.14), 3.373 (0.65), 3.596 (0.72), 3.615 (1.45), 3.633 (1.69), 3.651 (0.96), 3.740 (0.87), 3.757 (1.56), 3.773 (1.45), 3.776 (1.37), 3.794 (1.40), 3.802 (1.59), 3.808 (1.57), 3.830 (1.44), 3.837 (1.39), 3.918 (0.43), 3.934 (1.36), 3.948 (5.24), 3.965 (5.15), 7.579 (5.00), 8.682 (0.90), 8.697 (1.87), 8.711 (0.88). LC-MS (Method 1): $R_t$ = 1.16 min; MS (ESIneg): m/z = 468 [M + H]+ | Intermediate 80 GP H Conditions C 57 mg, 21% yield, 95% purity |

TABLE 5-continued

| The following examples (212 to 316) were prepared in analogy to example 169 starting from the given intermediates and commercially available amines (or their salts), applying the indicated general procedure. | | | |
|---|---|---|---|
| Example | Structure IUPAC-Name | Analytical Data | Preparation or Separation Methods |
| 265 | 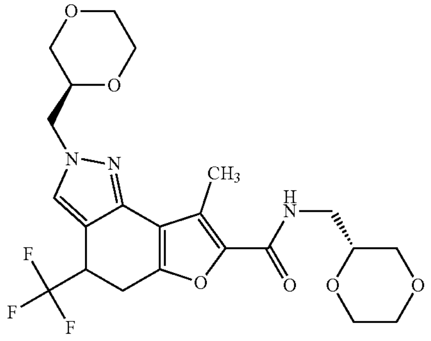 [SMILES: Cc1c(C(=O)NC[C@@H]2COCCO2)oc2c1-c1nn(C[C@H]3COCCO3)cc1C(C(F)(F)F)C2] (4±)-N-{[(2R)-1,4-dioxan-2-yl]methyl}-2-{[(2S)-1,4-dioxan-2-yl]methyl}-8-methyl-4-(trifluoromethyl)-4,5-dihydro-2H-furo[2,3-g]indazole-7-carboxamide | $^1$H-NMR (400 MHz, DMSO-d6) δ [ppm]: 1.233 (0.43), 2.481 (16.00), 2.520 (5.15), 2.525 (3.51), 2.545 (0.83), 2.756 (0.78), 3.019 (0.66), 3.032 (0.68), 3.063 (0.91), 3.076 (0.89), 3.189 (1.19), 3.218 (1.27), 3.239 (1.77), 3.254 (0.89), 3.273 (1.63), 3.289 (0.92), 3.451 (1.15), 3.479 (1.01), 3.503 (0.43), 3.515 (0.65), 3.520 (0.69), 3.532 (0.74), 3.549 (0.98), 3.560 (0.60), 3.576 (0.56), 3.615 (1.53), 3.638 (1.33), 3.692 (1.03), 3.699 (0.90), 3.721 (2.83), 3.750 (1.92), 3.779 (0.44), 3.832 (0.12), 3.839 (0.12), 3.847 (0.29), 3.854 (0.33), 3.862 (0.23), 3.871 (0.41), 3.878 (0.36), 3.886 (0.34), 3.892 (0.35), 3.902 (0.22), 3.909 (0.29), 3.916 (0.21), 3.926 (0.14), 3.931 (0.12), 4.151 (1.64), 4.165 (1.96), 4.212 (0.14), 4.238 (0.28), 4.250 (0.28), 4.251 (0.29), 4.262 (0.40), 4.274 (0.37), 4.284 (0.29), 4.298 (0.22), 7.714 (1.59), 7.728 (1.53), 8.104 (0.61), 8.118 (1.28), 8.133 (0.58). LC-MS (Method 1): $R_t$ = 1.02 min; MS (ESIpos): m/z = 486 [M + H]$^+$ | Intermediate 81 GP H Conditions B 47 mg, 25% yield, 95% purity Mixture of two isomers |
| 265-1 | 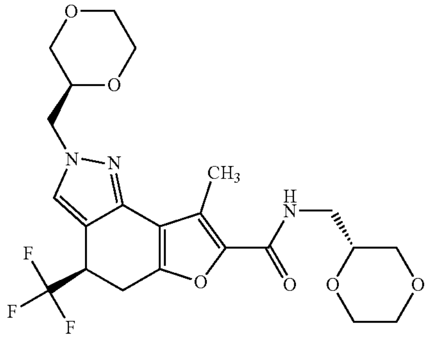 [SMILES: Cc1c(C(=O)NC[C@@H]2COCCO2)oc2c1-c1nn(C[C@H]3COCCO3)cc1[C@H](C(F)(F)F)C2] (4R or 4S)-N-{[(2R)-1,4-dioxan-2-yl]methyl}-2-{[(2S)-1,4-dioxan-2-yl]methyl}-8-methyl-4-(trifluoromethyl)-4,5-dihydro-2H-furo[2,3-g]indazole-7-carboxamide Diastereomer 1 of Ex. 265 | Rt = 3.74 min $^1$H NMR (400 MHz, DMSO-d6) δ [ppm]: 2.48-2.88 (s, 3 H) 3.04 (dd, 1H) 3.15-3.30 (m, 5 H) 3.41-3.48 (m, 2 H) 3.51-3.57 (m, 2 H) 3.58-3.66 (m, 3 H) 3.64-3.75 (m, 4 H) 3.87-3.92 (m, 1 H) 4.12-4.20 (m, 2 H) 4.22-4.30 (m, 1 H) 7.73 (s, 1 H) 8.12 (t, 1H). | analyt. method: Instrument: Waters Alliance 2695; Column: YMC Cellulose SB 3μ, 100 × 4.6; eluent A: hexane + 0.1 vol % diethylamine; eluent B: ethanol; isocratic: 80% A + 20% B; flow: 1.4 ml/min; temperature: 25° C.; UV: 254 nm |
| 265-2 | 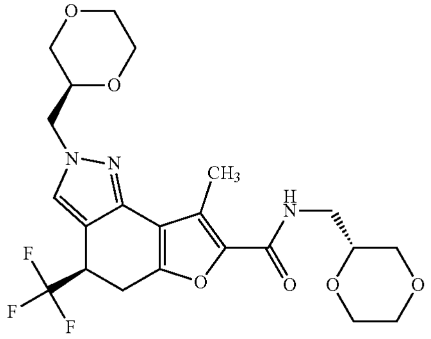 [SMILES: Cc1c(C(=O)NC[C@@H]2COCCO2)oc2c1-c1nn(C[C@H]3COCCO3)cc1[C@H](C(F)(F)F)C2] (4R or 4S)-N-{(2R)-1 ,4-dioxan-2-yl]methyl}-2-{[(2S)-1,4-dioxan-2-yl]methyl}-8-methyl-4-(trifluoromethyl)- | $R_t$ = 4.35 min $^1$H NMR (400 MHz, DMSO-d6) δ [ppm]: 2.48-2.88 (s, 3 H) 3.04 (dd, 1H) 3.15-3.30 (m, 5H) 3.41-3.48 (m, 2 H) 3.51-3.57 (m, 2H) 3.58-3.66 (m, 3 H) 3.69-3.78 (m, 4H) 3.83-3.89 (m, 1 H) 4.15-4.16 (m, 2H) 4.21-4.30 (m, 1 H) 7.71 (s, 1 H) 8.12 (t, 1H). | |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| | 4,5-dihydro-2H-furo[2,3-g]indazole-7-carboxamide Diastereomer 2 of Ex. 265 | | |
| 266 | 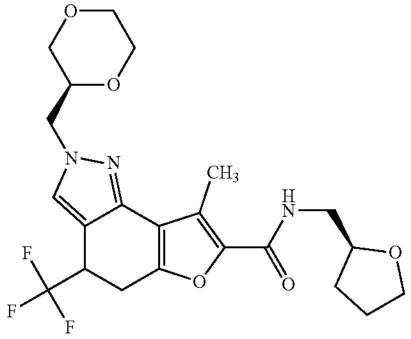 [SMILES: Cc1c(C(=O)NC[C@@H]2CCCO2)oc2c1-c1nn(C[C@H]3COCCO3)cc1C(C(F)(F)F)C2] (4±)-2-{[(2S)-1,4-dioxan-2-yl]methyl}-8-methyl-N-{[(2S)-oxolan-2-yl]methyl}-4-(trifluoromethyl)-4,5-dihydro-2H-furo[2,3-g]indazole-7-carboxamide | $^1$H-NMR (400 MHz, DMSO-d6) δ [ppm]: 1.225 (0.46), 1.234 (0.48), 1.550 (0.44), 1.568 (0.55), 1.577 (0.43), 1.584 (0.48), 1.597 (0.46), 1.786 (0.75), 1.801 (1.23), 1.820 (1.32), 1.838 (0.99), 1.853 (0.72), 1.861 (0.57), 1.871 (0.70), 1.882 (0.50), 1.910 (0.50), 2.044 (0.43), 2.320 (0.77), 2.342 (2.28), 2.481 (16.00), 2.520 (7.44), 2.525 (4.84), 2.662 (0.76), 3.020 (0.81), 3.032 (0.80), 3.064 (1.04), 3.077 (0.93), 3.224 (1.26), 3.239 (2.56), 3.255 (1.45), 3.274 (1.50), 3.279 (1.18), 3.288 (1.06), 3.298 (1.35), 3.302 (1.73), 3.311 (2.10), 3.434 (0.58), 3.440 (0.57), 3.451 (0.68), 3.457 (0.71), 3.468 (0.46), 3.478 (0.67), 3.483 (0.61), 3.499 (0.58), 3.532 (0.81), 3.559 (0.65), 3.587 (0.61), 3.607 (1.07), 3.625 (2.11), 3.642 (1.00), 3.652 (0.88), 3.726 (1.68), 3.736 (0.98), 3.752 (2.68), 3.772 (1.40), 3.790 (0.58), 3.848 (0.41), 3.854 (0.44), 3.871 (0.56), 3.878 (0.49), 3.894 (0.49), 3.909 (0.46), 3.916 (0.53), 3.933 (1.01), 3.949 (1.32), 3.964 (0.82), 4.149 (2.14), 4.164 (2.41), 4.171 (1.09), 4.260 (0.56), 4.272 (0.64), 7.713 (2.12), 7.727 (1.33), 8.031 (0.63), 8.047 (1.31), 8.061 (0.63). LC-MS (Method 1): $R_t$ = 1.08 min; MS (ESIpos): m/z = 470 [M + H]$^+$ | Intermediate 81 GP H Conditions B 4.5 mg, 2% yield, 95% purity Mixture of two isomers |
| 267 | 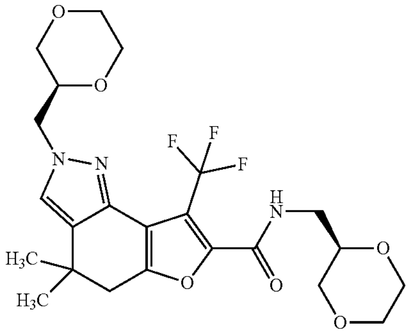 [SMILES: CC1(C)Cc2oc(C(=O)NC[C@@H]3COCCO3)c(C(F)(F)F)c2-c2nn(C[C@H]3COCCO3)cc21] N-{[(2R)-1,4-dioxan-2-yl]methyl}-2-{[(2S)-1,4-dioxan-2-yl]methyl}-4,4-dimethyl-8-(trifluoromethyl)-4,5-dihydro-2H-furo[2,3-g]indazole-7-carboxamide | $^1$H-NMR (400 MHz, DMSO-d6) δ [ppm]: 1.154 (0.55), 1.172 (1.14), 1.181 (0.66), 1.190 (0.62), 1.249 (16.00), 1.261 (15.70), 1.988 (1.97), 2.518 (13.13), 2.523 (9.04), 2.812 (10.66), 3.189 (0.48), 3.200 (2.16), 3.224 (3.77), 3.228 (2.77), 3.238 (3.28), 3.252 (4.11), 3.264 (3.86), 3.269 (2.73), 3.278 (1.93), 3.294 (2.73), 3.412 (0.79), 3.419 (1.04), 3.426 (0.91), 3.433 (1.13), 3.440 (1.79), 3.446 (2.06), 3.453 (2.02), 3.460 (2.11), 3.468 (1.70), 3.474 (1.58), 3.480 (1.78), 3.487 (1.65), 3.514 (1.30), 3.519 (1.52), 3.526 (1.56), 3.532 (1.71), 3.542 (1.82), 3.549 (1.99), 3.554 (2.29), 3.561 (2.26), 3.569 (1.01), 3.575 (1.20), 3.580 (0.99), 3.587 (1.48), 3.618 (4.23), 3.633 (1.72), 3.647 (3.68), 3.671 (0.65), 3.704 (2.14), 3.710 (1.97), 3.728 (5.11), 3.756 (3.75), 3.818 (0.52), 3.833 (1.02), 3.839 (1.14), 3.849 (0.94), 3.856 (1.24), 3.863 (0.91), 3.872 (0.61), 4.018 (0.45), 4.035 (0.41), 4.083 (4.19), 4.097 (4.84), 7.491 (0.59), 7.593 (10.60), 8.741 (1.18), 8.756 (2.43), 8.771 (1.18). LC-MS (Method 1): $R_t$ = 1.07 min; MS (ESIneg): m/z = 498 [M − H]$^-$ | Intermediate 82 GP H Conditions C 61 mg, 32% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 268 | 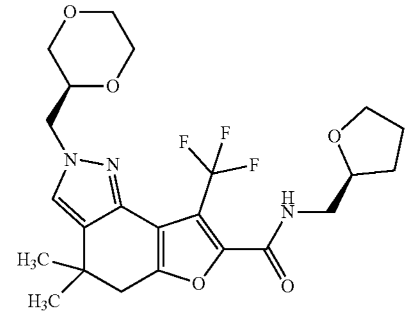 [SMILES: CC1(C)Cc2oc(C(=O)NC[C@@H]3CCCO3)c(C(F)(F)F)c2-c2nn(C[C@H]3COCCO3)cc21] 2-{[(2S)-1,4-dioxan-2-yl]methyl}-4,4-dimethyl-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.249 (5.15), 1.259 (5.05), 1.542 (0.26), 1.561 (0.35), 1.570 (0.33), 1.578 (0.26), 1.591 (0.31), 1.607 (0.19), 1.796 (0.39), 1.812 (0.68), 1.829 (0.71), 1.848 (0.42), 1.865 (0.29), 1.884 (0.32), 1.896 (0.34), 1.912 (0.26), 1.927 (0.19), 2.074 (16.00), 2.327 (0.99), 2.332 (0.72), 2.518 (4.68), 2.523 (3.12), 2.669 (1.03), 2.673 (0.74), 2.808 (3.68), 3.240 (0.61), 3.253 (1.06), 3.268 (2.62), 3.283 (1.15), 3.294 (0.85), 3.419 (0.25), 3.440 (0.53), 3.446 (0.57), 3.468 (0.48), 3.474 (0.44), 3.514 (0.38), 3.520 (0.44), 3.542 (0.55), 3.549 (0.54), 3.575 (0.34), 3.597 (0.27), 3.618 (1.12), 3.634 (0.71), 3.652 (0.62), 3.727 (0.99), 3.733 (0.68), 3.757 (1.32), 3.775 (0.57), 3.795 (0.35), 3.833 (0.32), 3.839 (0.35), 3.856 (0.39), 3.922 (0.16), 3.938 (0.49), 3.955 (0.79), 3.970 (0.52), 4.082 (1.41), 4.096 (1.58), 7.591 (3.44), 8.706 (0.37), 8.721 (0.76), 8.736 (0.37). LC-MS (Method 1): $R_t$ = 1.15 min; MS (ESIpos): m/z = 484 $[M + H]^+$ | Intermediate 82 GP H Conditions C 33 mg, 18% yield, 95% purity |
| 269 | 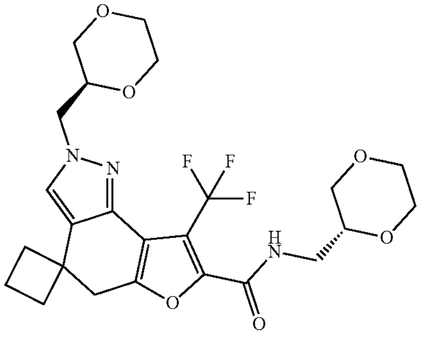 [SMILES: O=C(NC[C@@H]1COCCO1)c1oc2c(c1C(F)(F)F)-c1nn(C[C@H]3COCCO3)cc1C1(CCC1)C2] N-[(2R)-1,4-dioxan-2-ylmethyl]-2'-[(2S)-1,4-dioxan-2-ylmethyl]-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.89-2.18 (m, 6H), 3.09 (s, 2H), 3.17-3.31 (m, 4H), 3.40-3.50 (m, 2H), 3.51-3.60 (m, 2H), 3.60-3.67 (m, 3H), 3.69-3.77 (m, 4H), 3.82-3.90 (m, 1H), 4.07-4.16 (m, 2H), 7.80 (s, 1H), 8.75 (t, 1H) LC-MS (Method 1): $R_t$ = 1.08 min; MS (ESIpos): m/z = 512 $[M + H]^+$ | Intermediate 83 and CAS-RN: [1523541-84-5] GP G Conditions A 14.9 mg (44% yield, 95% purity) |
| 270 | 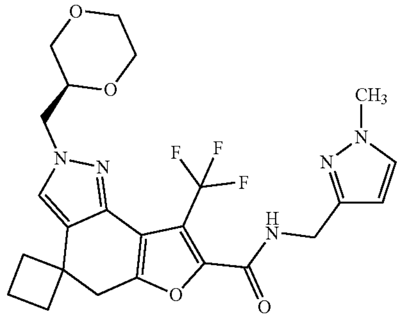 [SMILES: Cn1ccc(CNC(=O)c2oc3c(c2C(F)(F)F)-c2nn(C[C@H]4COCCO4)cc2C2(CCC2)C3)n1] 2'-[(2S)-1,4-dioxan-2-ylmethyl]-N-[(1-methyl-1H-pyrazol-3-yl)methyl]-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.88-2.18 (m, 6H), 3.08 (s, 2H), 3.28 (dd, 1H), 3.40-3.49 (m, 1H), 3.50-3.59 (m, 1H), 3.63 (brd, 1H), 3.75 (dd, 2H), 3.79 (s, 3H), 3.83-3.89 (m, 1H), 4.06-4.14 (m, 2H), 4.35 (d, 2H), 6.13 (d, 1H), 7.59 (d, 1H), 7.79 (s, 1H), 9.08 (t, 1H) LC-MS (Method 1): $R_t$ = 1.07 min; MS (ESIpos): m/z = 506 $[M + H]^+$ | Intermediate 83 and CAS-RN: [612511-81-6] GP G Conditions A 12.1 mg (36% yield, 95% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 271 | 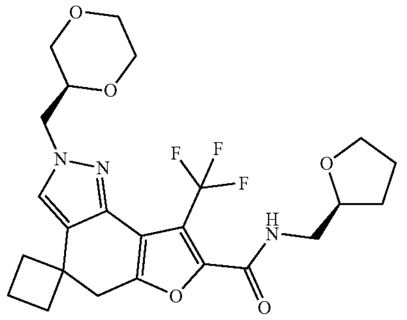 [SMILES: O=C(NC[C@@H]1CCCO1)c1oc2c(c1C(F)(F)F)-c1nn(C[C@H]3COCCO3)cc1C1(CCC1)C2] 2'-[(2S)-1,4-dioxan-2-ylmethyl]-N-[(2S)-tetrahydrofuran-2-ylmethyl]-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.53-1.62 (m, 1H), 1.75-2.00 (m, 4H), 2.01-2.15 (m, 5H), 3.09 (s, 2H), 3.24-3.31 (m, 3H), 3.40-3.49 (m, 1H), 3.51-3.61 (m, 1H), 3.61-3.67 (m, 2H), 3.72-3.79 (m, 3H), 3.82-4.01 (m, 2H), 4.06-4.16 (m, 2H), 7.79 (s, 1H), 8.72 (t, 1H). LC-MS (Method 1): $R_t$ = 1.16 min; MS (ESIpos): m/z = 496 [M + H]$^+$ | Intermediate 83 and CAS-RN: [7175-81-7] GP G Conditions A 6.9 mg (34% yield, 90% purity) |
| 272 | 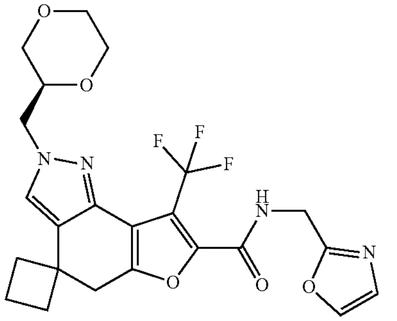 [SMILES: O=C(NCc1ncco1)c1oc2c(c1C(F)(F)F)-c1nn(C[C@H]3COCCO3)cc1C1(CCC1)C2] 2'-{[(2S)-1,4-dioxan-2-yl]methyl}-N-[(1,3-oxazol-2-yl)methyl]-8'-(trifluoromethyl)-2',51-dihydrospiro[cyclobutane-1,4'-furo[2,3-g]indazole]-7'-carboxamide | $^1$H NMR (400 MHz, DMSO-d6) δ [ppm]: 1.92-2.16 (m, 6H), 3.10 (s, 2H), 3.25-3.31 (m, 1H), 3.42-3.50 (m, 1H), 3.51-3.59 (m, 1H), 3.64 (brd, 1H), 3.72-3.79 (m, 2H), 3.82-3.91 (m, 1H), 4.06-4.18 (m, 2H), 4.55 (d, 2H), 7.17 (d, 1H), 7.80 (s, 1H), 8.07 (d, 1H), 9.37 (t, 1H). LC-MS (Method 1): $R_t$ = 1.08 min; MS (ESIpos): m/z = 493 [M + H]$^+$ | Intermediate 83 and CAS-RN: [885331-17-9] GP G Conditions A 4.20 mg (21% yield, 90% purity) |
| 273 | 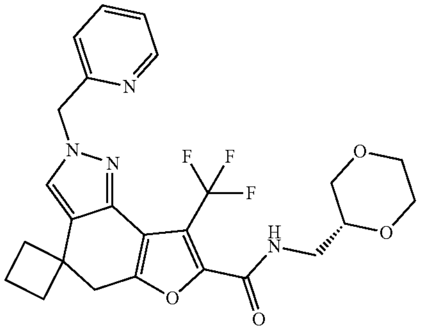 [SMILES: O=C(NC[C@@H]1COCCO1)c1oc2c(c1C(F)(F)F)-c1nn(Cc3ccccn3)cc1C1(CCC1)C2] N-[(2R)-1,4-Dioxan-2-ylmethyl]-2'-(pyridin-2-ylmethyl)-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.90-2.07 (m, 2H), 2.08-2.18 (m, 4H), 3.11 (s, 2H), 3.19-3.28 (m, 3H), 3.41-3.49 (m, 1H), 3.52-3.59 (m, 1H), 3.60-3.67 (m, 2H), 3.70-3.76 (m, 2H), 5.41 (s, 2H), 7.08 (d, 1H), 7.32 (ddd, 1H), 7.78 (td, 1H), 7.97 (s, 1H), 8.53-8.56 (m, 1H), 8.76 (t, 1H) LC-MS (Method 1): $R_t$ = 1.12 min; MS (ESIpos): m/z = 503 [M + H]$^+$ | Intermediate 84 and CAS-RN: [1523541-84-5] GP G Conditions A 14.2 mg (43% yield, 95% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 274 | 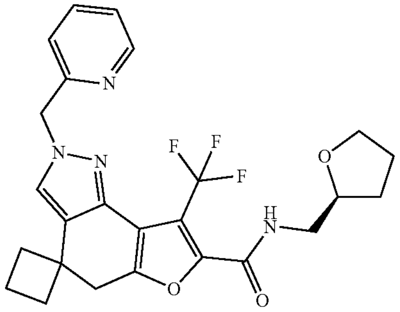 [SMILES: O=C(NC[C@@H]1CCCO1)c1oc2c(c1C(F)(F)F)-c1nn(Cc3ccccn3)cc1C1(CCC1)C2] 2'-(Pyridin-2-ylmethyl)-N-[(2S)-tetrahydrofuran-2-ylmethyl]-8'-(trifluormethyl)-2',5'-dihydrospiro[cyclobutan-1,4'-furo[2,3-g]indazol]-7'-carboxamide | $^{1}$H NMR (400 MHz, DMSO-d6) δ [ppm]: 1.53-1.64 (m, 1H), 1.74-2.01 (m, 4H), 2.02-2.17 (m, 5H), 3.11 (s, 2H), 3.27 (t, 2H), 3.59-3.66 (m, 1H), 3.74-3.81 (m, 1H), 3.95 (quin, 1H), 5.41 (s, 2H), 7.08 (d, 1H), 7.32 (ddd, 1H), 7.78 (td, 1H), 7.96 (s, 1H), 8.51-8.58 (m, 1H), 8.72 (t, 1H). LC-MS (Method 1): $R_t$ = 1.17 min; MS (ESIpos): m/z = 487 $[M + H]^+$ | Intermediate 84 and CAS-RN: [7175-81-7] GP G Conditions A 20.3 mg (65% yield, 96% purity) |
| 275 | 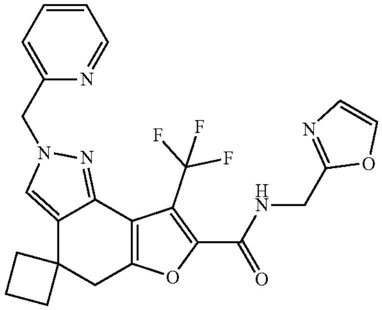 [SMILES: O=C(NCc1ncco1)c1oc2c(c1C(F)(F)F)-c1nn(Cc3ccccn3)cc1C1(CCC1)C2] N-(1,3-Oxazol-2-ylmethyl)-2'-(pyridin-2-ylmethyl)-8'-(trifluormethyl)-2',5'-dihydrospiro[cyclobutan-1,4'-furo[2,3-g]indazol]-7'-carboxamide | $^{1}$H NMR (400 MHz, DMSO-d6) δ [ppm]: 1.90-2.19 (m, 6H), 3.12 (s, 2H), 4.55 (d, 2H), 5.41 (s, 2H), 7.09 (d, 1H), 7.17 (d, 1H), 7.32 (dd, 1H), 7.79 (td, 1H), 7.97 (s, 1H), 8.07 (d, 1H), 8.53-8.57 (m, 1H), 9.37 (t, 1H) LC-MS (Method 1): $R_t$ = 1.09 min; MS (ESIpos): m/z = 484 $[M + H]^+$ | Intermediate 84 and CAS-RN: [885331-17-9] GP G Conditions A 4.1 mg (5% yield, 90% purity) |
| 276 | 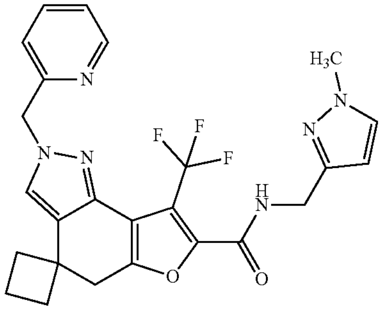 [SMILES: Cn1ccc(CNC(=O)c2oc3c(c2C(F)(F)F)-c2nn(Cc4ccccn4)cc2C2(CCC2)C3)n1] N-[(1-Methyl-1H-pyrazol-3-yl)methyl]-2'-(pyridin-2-ylmethyl)-8'-(trifluormethyl)-2',5'-dihydrospiro[cyclobutan-1,4'-furo[2,3-g]indazol]-7'-carboxamide | $^{1}$H NMR (400 MHz, DMSO-d6) δ [ppm]: 1.89-2.18 (m, 6H), 3.09 (s, 2H), 3.78 (s, 3H), 4.35 (d, 2H), 5.41 (s, 2H), 6.13 (d, 1H), 7.07 (d, 1H), 7.31 (ddd, 1H), 7.59 (d, 1H), 7.78 (td, 1H), 7.96 (s, 1H), 8.50-8.58 (m, 1H), 9.08 (t, 1H) LC-MS (Method 1): $R_t$ = 1.10 min; MS (ESIpos): m/z = 497 $[M + H]^+$ | Intermediate 84 and CAS-RN:612511-81-6] GP G Conditions A 8.6 mg (10% yield, 90% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 277 | 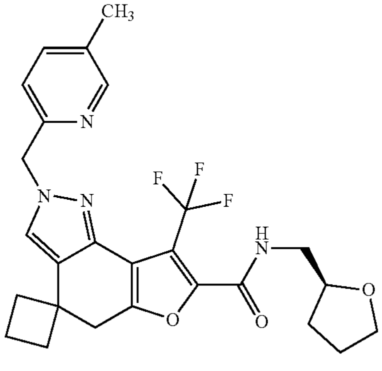 [SMILES: Cc1ccc(Cn2cc3c(n2)-c2c(oc(C(=O)NC[C@@H]4CCCO4)c2C(F)(F)F)CC32CCC2)nc1] 2'-[(5-Methylpyridin-2-yl)methyl]-N-[(2S)-tetrahydrofuran-2-ylmethyl]-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.52-1.62 (m, 1H), 1.72-1.96 (m, 3H), 1.97-2.17 (m, 6H), 2.27 (s, 3H), 3.10 (s, 2H), 3.27 (t, 2H), 3.56-3.68 (m, 1H), 3.77 (ddd, 1H), 3.95 (quin, 1H), 5.35 (s, 2H), 7.02 (d, 1H), 7.56-7.62 (m, 1H), 7.93 (s, 1H), 8.36-8.41 (m, 1H), 8.71 (t, 1H). LC-MS (Method 1): $R_t$ = 1.23 min; MS (ESIpos): m/z = 501 [M + H]$^+$ | Intermediate 85 and CAS-RN: [7175-81-7] GP G Conditions A 6.2 mg (16% yield, 95% purity) |
| 278 | 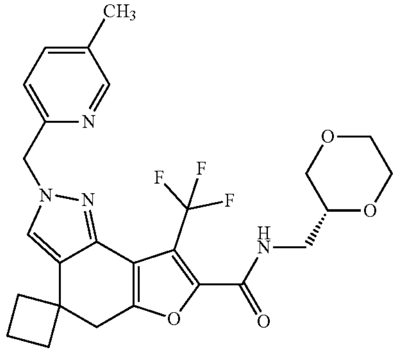 [SMILES: Cc1ccc(Cn2cc3c(n2)-c2c(oc(C(=O)NC[C@@H]4COCCO4)c2C(F)(F)F)CC32CCC2)nc1] N-[(2R)-1,4-Dioxan-2-ylmethyl]-2'-[(5-methylpyridin-2-yl)methyl]-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.95-2.17 (m, 6H), 2.27 (s, 3H), 3.10 (s, 2H), 3.18-3.29 (m, 3H), 3.42-3.49 (m, 1H), 3.51-3.59 (m, 1H), 3.60-3.67 (m, 2H), 3.69-3.78 (m, 2H), 5.35 (s, 2H), 7.02 (d, 1H), 7.56-7.63 (m, 1H), 7.93 (s, 1H), 8.36-8.41 (m, 1H), 8.75 (t, 1H) LC-MS (Method 1): $R_t$ = 1.16 min; MS (ESIpos): m/z = 517 [M + H]$^+$ | Intermediate 85 and CAS-RN: [1523541-84-5] GP G Conditions A 8.6 mg (21% yield, 91% purity) |
| 279 | 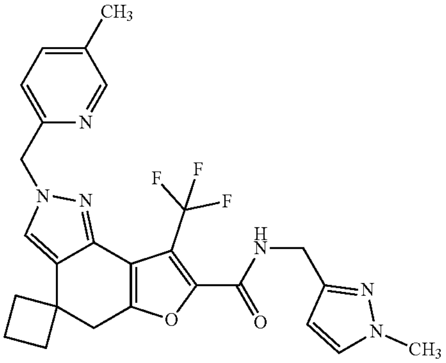 [SMILES: Cc1ccc(Cn2cc3c(n2)-c2c(oc(C(=O)NCc4ccn(C)n4)c2C(F)(F)F)CC32CCC2)nc1] N-[(1-Methyl-1H-pyrazol-3-yl)methyl]-2'-[(5-methylpyridin-2-yl)methyl]-8'-(trifluormethyl)-2',5'-dihydrospiro[cyclobutan-1,4'-furo[2,3-g]indazol]-7'-carboxamide | $^1$H NMR (400 MHz, DMSO-d6) δ [ppm]: 1.91-2.17 (m, 6H), 2.27 (s, 3H), 3.08 (s, 2H), 3.78 (s, 3H), 4.35 (d, 2H), 5.35 (s, 2H), 6.12 (d, 1H), 7.02 (d, 1H), 7.56-7.62 (m, 2H), 7.92 (s, 1H), 8.36-8.41 (m, 1H), 9.07 (t, 1H). LC-MS (Method 1): $R_t$ = 1.17 min; MS (ESIneg): m/z = 509 [M − H]$^-$ | Intermediate 85 and CAS-RN: [612511-81-6] GP G Conditions A 3.0 mg (8% yield, 95% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 280 | 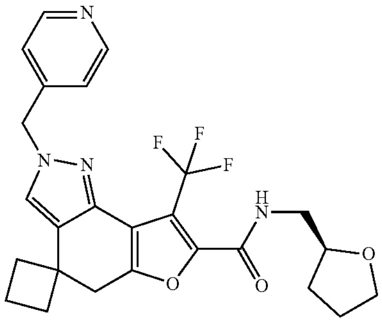 [SMILES: O=C(NC[C@@H]1CCCO1)c1oc2c(c1C(F)(F)F)-c1nn(Cc3ccncc3)cc1C1(CCC1)C2] 2'-(Pyridin-4-ylmethyl)-N-[(2S)-tetrahydrofuran-2-ylmethyl]-8'-(trifluormethyl)-2',5'-dihydrospiro[cyclobutan-1,4'-furo[2,3-g]indazol]-7'-carboxamide | $^{1}$H NMR (400 MHz, DMSO-d6) δ [ppm]: 1.53-1.62 (m, 1H), 1.78-2.07 (m, 4H), 2.08-2.16 (m, 5H), 3.11 (s, 2H), 3.27 (t, 2H), 3.58-3.67 (m, 1H), 3.73-3.82 (m, 1H), 3.91-3.99 (m, 1H), 5.39 (s, 2H), 7.13-7.18 (m, 2H), 7.99 (s, 1H), 8.51-8.56 (m, 2H), 8.73 (t, 1H) LC-MS (Method 1): $R_t$ = 1.01 min; MS (ESIneg): m/z = 501 $[M - H]^-$ | Intermediate 86 and CAS-RN: [7175-81-7] GP G Conditions A 10.8 mg (48% yield, 82% purity) |
| 281 | 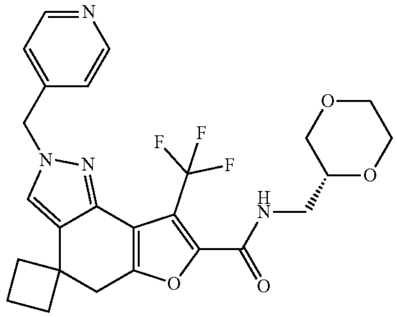 [SMILES: O=C(NC[C@@H]1COCCO1)c1oc2c(c1C(F)(F)F)-c1nn(Cc3ccncc3)cc1C1(CCC1)C2] N-[(2R)-1,4-Dioxan-2-ylmethyl]-2'-(pyridin-4-ylmethyl)-8'-(trifluormethyl)-2',5'-dihydrospiro[cyclobutan-1,4'-furo[2,3-g]indazol]-7'-carboxamide | $^{1}$H NMR (400 MHz, DMSO-d6) δ [ppm]: 1.92-2.19 (m, 6H), 3.12 (s, 2H), 3.19-3.28 (m, 3H), 3.46 (td, 1H), 3.52-3.59 (m, 1H), 3.60-3.67 (m, 2H), 3.68-3.78 (m, 2 H), 5.43 (s, 2H), 7.22 (d, 2H), 8.00 (s, 1H), 8.57 (d, 2H), 8.76 (t, 1H) LC-MS (Method 1): $R_t$ = 1.06 min; MS (ESIpos): m/z = 487 $[M + H]^+$ | Intermediate 86 and CAS-RN: [1523541-84-5] GP G Conditions A 6.9 mg (29% yield, 81% purity) |
| 282 | 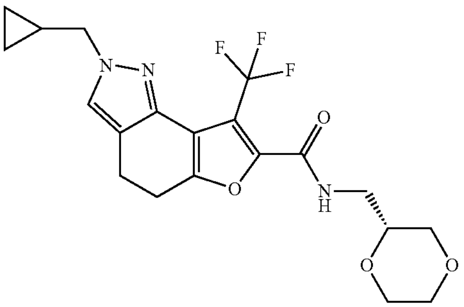 [SMILES: O=C(NC[C@@H]1COCCO1)c1oc2c(c1C(F)(F)F)-c1nn(CC3CC3)cc1CC2] 2-(cyclopropylmethyl)-N-{[(2R)-1,4-dioxan-2-yl]methyl}-8-(trifluoromethyl)-4,5-dihydro-2H-furo[2,3-g]indazole-7-carboxamide | $^{1}$H-NMR (400 MHz, DMSO-d6) δ [ppm]: 0.332 (0.48), 0.343 (2.00), 0.347 (1.74), 0.355 (1.92), 0.370 (0.72), 0.486 (0.69), 0.497 (1.62), 0.501 (1.69), 0.506 (0.90), 0.516 (1.72), 0.521 (1.57), 0.532 (0.54), 1.205 (0.72), 1.224 (0.60), 2.518 (16.00), 2.522 (11.04), 2.852 (0.64), 2.870 (2.20), 2.888 (1.88), 2.931 (2.08), 2.948 (2.51), 2.967 (0.68), 2.973 (0.62), 3.196 (0.93), 3.201 (0.69), 3.221 (1.90), 3.236 (1.37), 3.249 (2.50), 3.262 (1.39), 3.279 (1.62), 3.297 (1.08), 3.315 (2.81), 3.322 (4.01), 3.386 (3.58), 3.424 (1.11), 3.450 (1.14), 3.456 (1.30), 3.464 (0.45), 3.477 (0.98), 3.483 (0.93), 3.524 (0.70), 3.530 (0.85), 3.552 (1.12), 3.585 (0.70), 3.619 (1.22), 3.643 (1.21), 3.695 (1.01), 3.724 (1.72), 3.751 (0.81), 3.909 (3.44), 3.927 (3.42), 7.600 (3.49), 8.536 (1.12), 8.727 (0.57), 8.742 (1.14), 8.757 (0.53). LC-MS (Method 1): $R_t$ = 1.11 min; MS (ESIpos): m/z = 426 $[M + H]^+$ | Intermediate 87 GP H Conditions B 16 mg, 19% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 283 | 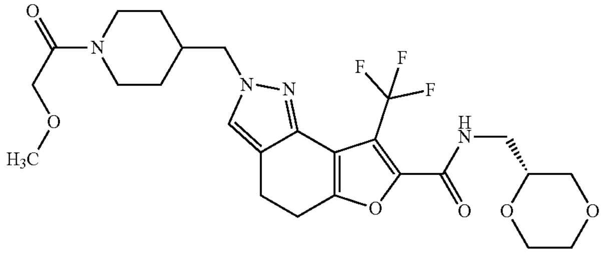 [SMILES: COCC(=O)N1CCC(Cn2cc3c(n2)-c2c(oc(C(=O)NC[C@@H]4COCCO4)c2C(F)(F)F)CC3)CC1] N-{[(2R)-1,4-dioxan-2-yl]methyl}-2-{[1-(methoxyacetyl)piperidin-4-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.007 (0.19), 1.016 (0.20), 1.038 (0.21), 1.046 (0.21), 1.120 (0.20), 1.125 (0.21), 1.128 (0.20), 1.138 (0.12), 1.151 (0.22), 1.155 (0.21), 1.513 (0.63), 1.543 (0.49), 1.993 (0.19), 2.001 (0.23), 2.009 (0.26), 2.019 (0.21), 2.331 (1.04), 2.518 (6.47), 2.523 (4.60), 2.673 (1.05), 2.844 (0.37), 2.862 (1.42), 2.880 (1.31), 2.925 (1.30), 2.943 (1.88), 2.962 (0.44), 2.967 (0.41), 3.196 (0.77), 3.220 (1.33), 3.225 (1.16), 3.235 (0.96), 3.249 (1.83), 3.257 (16.00), 3.262 (1.18), 3.278 (0.63), 3.297 (0.55), 3.429 (0.33), 3.450 (0.63), 3.456 (0.67), 3.477 (0.55), 3.484 (0.52), 3.525 (0.49), 3.530 (0.55), 3.553 (0.66), 3.559 (0.64), 3.585 (0.47), 3.620 (0.84), 3.643 (0.84), 3.695 (0.78), 3.701 (0.72), 3.723 (1.39), 3.752 (0.71), 3.956 (1.52), 3.973 (1.64), 4.011 (1.17), 4.059 (1.14), 4.093 (0.29), 4.276 (0.28), 4.309 (0.26), 7.536 (2.44), 8.722 (0.43), 8.736 (0.90), 8.751 (0.41). LC-MS (Method 1): $R_t$ = 0.89 min; MS (ESIneg): m/z = 539 $[M - H]^-$ | Intermediate 88 GP H Conditions C 24 mg, 11% yield, 95% purity |
| 284 | 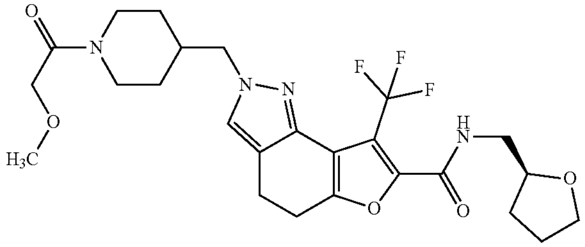 [SMILES: COCC(=O)N1CCC(Cn2cc3c(n2)-c2c(oc(C(=O)NC[C@@H]4CCCO4)c2C(F)(F)F)CC3)CC1] 2-{[1-(methoxyacetyl)piperidin-4-yl]methyl}-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.015 (0.20), 1.037 (0.21), 1.126 (0.20), 1.150 (0.20), 1.510 (0.58), 1.542 (0.75), 1.559 (0.53), 1.567 (0.41), 1.575 (0.32), 1.589 (0.36), 1.605 (0.22), 1.773 (0.22), 1.794 (0.43), 1.810 (0.78), 1.827 (0.75), 1.845 (0.49), 1.861 (0.41), 1.877 (0.33), 1.889 (0.39), 1.903 (0.29), 1.921 (0.21), 1.941 (0.13), 2.010 (0.26), 2.518 (2.76), 2.523 (2.06), 2.843 (0.32), 2.862 (1.39), 2.879 (1.32), 2.921 (1.37), 2.939 (1.88), 2.958 (0.43), 2.964 (0.40), 2.997 (0.17), 3.225 (0.17), 3.257 (16.00), 3.268 (2.28), 3.283 (1.24), 3.597 (0.27), 3.616 (0.61), 3.634 (0.75), 3.651 (0.44), 3.718 (0.30), 3.741 (0.56), 3.758 (0.80), 3.773 (0.67), 3.776 (0.58), 3.794 (0.40), 3.919 (0.19), 3.934 (0.56), 3.954 (1.70), 3.972 (1.71), 4.012 (1.14), 4.059 (1.11), 4.093 (0.28), 4.276 (0.26), 4.307 (0.25), 7.534 (2.42), 7.953 (0.13), 8.682 (0.41), 8.697 (0.88), 8.712 (0.41). LC-MS (Method 1): $R_t$ = 1.00 min; MS (ESIneg): m/z = 523 $[M - H]^-$ | Intermediate 88 GP H Conditions C 22 mg, 10% yield, 95% purity |
| 285 | 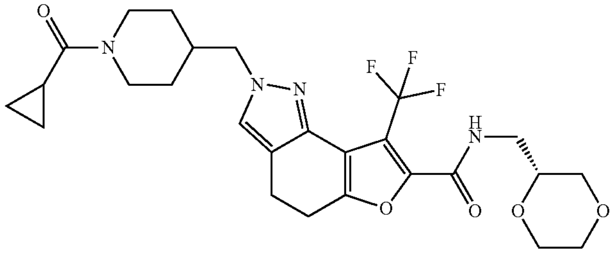 [SMILES: O=C(NC[C@@H]1COCCO1)c1oc2c(c1C(F)(F)F)-c1nn(CC3CCN(C(=O)C4CC4)CC3)cc1CC2] 2-{[1-(cyclopropanecarbonyl)piperidin-4-yl]methyl}-N-{[(2R)-1,4-dioxan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.653 (4.01), 0.674 (6.50), 0.994 (0.63), 1.024 (0.69), 1.140 (0.66), 1.169 (0.67), 1.504 (1.15), 1.567 (0.97), 1.595 (0.77), 1.914 (0.63), 1.933 (1.23), 1.938 (0.95), 1.947 (2.14), 1.964 (1.10), 1.977 (0.61), 2.007 (0.63), 2.017 (0.75), 2.026 (0.85), 2.035 (1.02), 2.045 (0.82), 2.064 (0.59), 2.075 (0.50), 2.318 (1.12), 2.323 (2.59), 2.327 (3.73), 2.332 (2.62), 2.336 (1.11), 2.518 (16.00), 2.523 (11.74), 2.660 (1.16), 2.665 (2.70), 2.669 (3.80), 2.673 (2.68), 2.679 (1.26), 2.841 (1.28), 2.846 (1.28), 2.865 (5.49), 2.883 (4.41), 2.929 (4.76), 2.945 (6.65), 2.952 (2.39), 2.964 (1.64), 2.969 (1.63), 2.999 (0.52), 3.029 (0.92), 3.062 (0.51), 3.187 (0.63), 3.197 (2.96), 3.202 (1.47), 3.221 (5.03), 3.225 (3.69), 3.236 (3.53), 3.250 (6.01), 3.264 (3.31), 3.280 (2.18), 3.298 (1.41), 3.314 | Intermediate 89 GP H Conditions C 41 mg, 18% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | (2.02), 3.423 (0.97), 3.430 (1.20), 3.450 (2.48), 3.457 (2.67), 3.478 (2.24), 3.484 (2.07), 3.525 (1.85), 3.531 (2.04), 3.553 (2.55), 3.559 (2.60), 3.580 (1.08), 3.586 (1.82), 3.606 (0.95), 3.613 (2.71), 3.621 (3.21), 3.627 (1.99), 3.644 (3.28), 3.660 (0.71), 3.667 (0.81), 3.696 (2.82), 3.701 (2.29), 3.724 (4.69), 3.730 (3.95), 3.753 (1.99), 3.967 (5.95), 3.985 (5.90), 4.205 (0.81), 4.237 (0.84), 4.308 (0.91), 4.339 (0.83), 7.540 (9.78), 8.720 (1.62), 8.735 (3.54), 8.750 (1.66). LC-MS (Method 1): $R_t$ = 0.94 min; MS (ESIneg): m/z = 535 $[M - H]^-$ | |
| 286 | 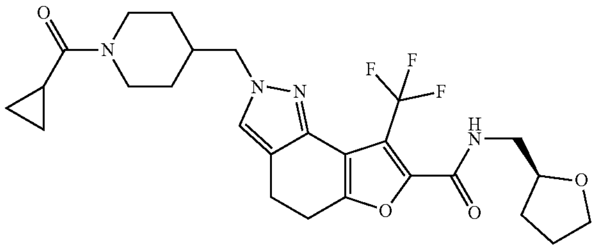 [SMILES: O=C(NC[C@@H]1CCCO1)c1oc2c(c1C(F)(F)F)-c1nn(CC3CCN(C(=O)C4CC4)CC3)cc1CC2] 2-{[1-(cyclopropanecarbonyl)piperidin-4-yl]methyl}-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.654 (6.93), 0.673 (11.20), 0.994 (1.11), 1.023 (1.22), 1.139 (1.17), 1.166 (1.20), 1.497 (1.94), 1.522 (1.96), 1.540 (2.64), 1.543 (2.59), 1.560 (4.07), 1.568 (3.92), 1.576 (3.27), 1.584 (2.69), 1.590 (3.40), 1.605 (2.35), 1.758 (0.54), 1.773 (1.27), 1.779 (0.92), 1.788 (2.17), 1.794 (2.75), 1.810 (4.87), 1.828 (4.72), 1.845 (3.09), 1.861 (2.67), 1.866 (1.48), 1.871 (1.79), 1.878 (2.13), 1.882 (1.84), 1.890 (2.41), 1.900 (1.62), 1.904 (1.93), 1.907 (1.91), 1.911 (1.98), 1.921 (1.81), 1.928 (2.97), 1.947 (3.72), 1.963 (1.94), 1.978 (1.11), 2.007 (1.13), 2.017 (1.30), 2.025 (1.52), 2.034 (1.78), 2.043 (1.42), 2.053 (1.19), 2.062 (0.99), 2.327 (4.06), 2.331 (2.87), 2.336 (1.28), 2.518 (15.60), 2.523 (10.84), 2.556 (1.16), 2.669 (4.17), 2.673 (2.88), 2.678 (1.38), 2.841 (2.14), 2.845 (2.22), 2.864 (9.11), 2.882 (7.77), 2.923 (8.53), 2.934 (4.87), 2.941 (11.65), 2.948 (3.94), 2.960 (2.82), 2.966 (2.76), 2.996 (3.71), 3.029 (1.65), 3.060 (0.92), 3.254 (7.30), 3.268 (14.11), 3.283 (7.80), 3.597 (1.79), 3.614 (3.59), 3.616 (3.90), 3.634 (4.74), 3.652 (2.78), 3.740 (2.31), 3.756 (4.17), 3.757 (4.27), 3.761 (2.86), 3.773 (4.22), 3.776 (3.61), 3.794 (2.43), 3.920 (1.16), 3.936 (3.53), 3.951 (6.28), 3.966 (13.96), 3.984 (10.67), 4.205 (1.42), 4.239 (1.49), 4.308 (1.59), 4.341 (1.44), 7.539 (16.00), 8.684 (2.67), 8.700 (5.70), 8.714 (2.69). LC-MS (Method 1): $R_t$ = 0.99 min; MS (ESIpos): m/z = 521 $[M + H]^+$ | Intermediate 89 GP H Conditions C 54 mg, 26% yield, 98% purity |
| 287 | 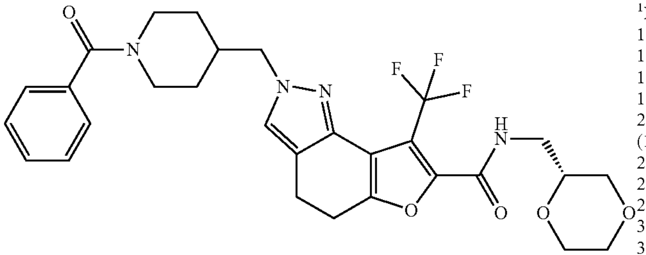 2-[(1-benzoylpiperidin-4-yl)methyl]-N-{[(2R)-1,4-dioxan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.134 (0.47), 1.144 (0.58), 1.165 (1.40), 1.175 (1.46), 1.195 (1.58), 1.206 (1.49), 1.225 (0.77), 1.237 (0.67), 1.513 (0.50), 1.598 (0.50), 2.051 (0.63), 2.059 (0.77), 2.336 (1.09), 2.518 (16.00), 2.523 (11.35), 2.679 (1.17), 2.754 (0.48), 2.836 (1.00), 2.841 (1.02), 2.860 (3.92), 2.877 (3.37), 2.922 (3.76), 2.938 (4.78), 2.957 (1.43), 2.962 (1.40), 3.185 (0.49), 3.195 (2.22), 3.199 (1.14), 3.219 (3.95), 3.223 (2.84), 3.233 (2.76), 3.247 (4.65), 3.261 (2.51), 3.276 (1.65), 3.295 (1.15), 3.311 (1.46), 3.422 (0.70), 3.428 (0.92), 3.449 (1.90), 3.455 (2.07), 3.476 (1.75), 3.482 (1.63), 3.523 (1.76), 3.528 (2.03), 3.551 (2.33), 3.558 (2.36), 3.578 (1.06), 3.584 (1.56), 3.603 (0.78), 3.618 (2.61), | Intermediate 90 GP H Conditions C 31 mg, 15% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | 3.625 (1.62), 3.634 (1.24), 3.642 (2.50), 3.648 (1.97), 3.657 (0.55), 3.663 (0.59), 3.693 (2.18), 3.700 (1.80), 3.722 (3.64), 3.727 (3.08), 3.751 (1.54), 3.981 (3.22), 3.998 (3.22), 4.448 (0.43), 7.331 (3.04), 7.334 (2.02), 7.336 (1.89), 7.340 (4.21), 7.349 (5.12), 7.355 (5.14), 7.364 (0.81), 7.418 (2.00), 7.421 (1.67), 7.426 (6.20), 7.429 (5.86), 7.431 (3.82), 7.437 (8.23), 7.443 (8.52), 7.452 (0.81), 7.544 (7.58), 8.718 (1.30), 8.732 (2.78), 8.747 (1.27). LC-MS (Method 1): $R_t$ = 1.09 min; MS (ESIneg): m/z = 571 $[M - H]^-$ | |
| 288 | 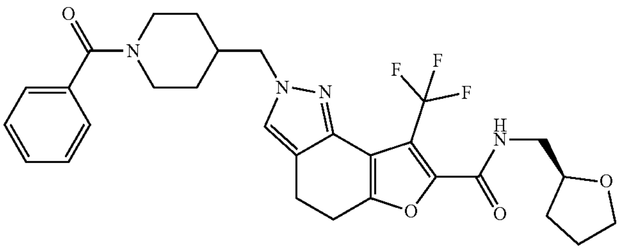 [SMILES: O=C(NC[C@@H]1CCCO1)c1oc2c(c1C(F)(F)F)-c1nn(CC3CCN(C(=O)c4ccccc4)CC3)cc1CC2] 2-[(1-benzoylpiperidin-4-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.133 (0.74), 1.144 (0.99), 1.165 (2.26), 1.173 (2.35), 1.195 (2.55), 1.206 (2.36), 1.225 (1.26), 1.235 (1.08), 1.352 (0.49), 1.496 (1.52), 1.520 (0.83), 1.537 (1.67), 1.557 (2.28), 1.565 (2.19), 1.574 (2.01), 1.582 (1.80), 1.587 (2.35), 1.603 (1.79), 1.757 (0.45), 1.771 (0.94), 1.778 (0.76), 1.787 (1.70), 1.792 (2.07), 1.808 (3.75), 1.826 (3.57), 1.844 (2.43), 1.859 (1.97), 1.864 (1.12), 1.868 (1.38), 1.876 (1.56), 1.880 (1.41), 1.887 (1.82), 1.898 (1.18), 1.902 (1.44), 1.904 (1.39), 1.908 (1.27), 1.919 (1.06), 1.940 (0.60), 2.059 (1.23), 2.337 (1.53), 2.518 (16.00), 2.523 (10.91), 2.679 (1.75), 2.736 (0.80), 2.834 (1.57), 2.840 (1.63), 2.859 (6.27), 2.876 (5.56), 2.918 (6.18), 2.935 (7.72), 2.953 (2.27), 2.959 (2.18), 2.995 (1.22), 3.251 (5.52), 3.266 (10.61), 3.281 (5.95), 3.552 (0.66), 3.596 (1.52), 3.611 (2.85), 3.615 (3.06), 3.632 (3.59), 3.650 (2.09), 3.739 (1.85), 3.756 (3.28), 3.771 (3.04), 3.774 (2.71), 3.792 (1.86), 3.917 (0.92), 3.932 (2.63), 3.949 (4.47), 3.964 (3.17), 3.980 (5.92), 3.997 (5.22), 4.430 (0.68), 7.331 (4.93), 7.334 (3.26), 7.336 (3.07), 7.340 (6.82), 7.349 (8.23), 7.355 (8.10), 7.364 (1.27), 7.402 (0.61), 7.418 (3.28), 7.421 (2.80), 7.426 (9.96), 7.429 (9.36), 7.431 (6.15), 7.437 (13.06), 7.443 (13.62), 7.452 (1.11), 7.542 (12.00), 8.680 (2.07), 8.695 (4.42), 8.709 (1.97). LC-MS (Method 1): $R_t$ = 1.06 min; MS (ESIpos): m/z = 557 $[M + H]^+$ | Intermediate 90 GP H Conditions C 35 mg, 18% yield, 98% purity |
| 289 | 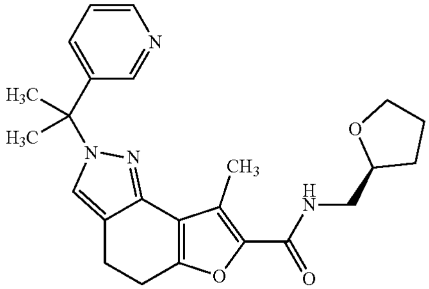 [SMILES: Cc1c(C(=O)NC[C@@H]2CCCO2)oc2c1-c1nn(C(C)(C)c3cccnc3)cc1CC2] 8-methyl-N-{[(2S)-oxolan-2-yl]methyl}-2-[2-(pyridin-3-yl) propan-2-yl]-4,5-dihydro-2H-furo[2,3-g]indazole-7-carboxamide | $^1$H NMR (400 MHz, DMSO-d6) δ [ppm]: 1.53-1.62 (m, 1H), 1.76-1.89 (m, 3H), 1.95 (s, 6H), 2.43 (s, 3H), 2.85-2.95 (m, 4H), 3.17-3.27 (m, 2H), 3.57-3.64 (m, 1H), 3.72-3.80 (m, 1H), 3.88-4.00 (m, 1H), 7.30-7.36 (m, 1H), 7.39-7.44 (m, 1H), 7.74 (s, 1H), 7.98 (t, 1H), 8.22 (dd, 1H), 8.43 (dd, 1H). LC-MS (Method 1): $R_t$ = 1.12 min; MS (ESIpos): m/z = 421 $[M + H]^+$. | Intermediate 91 and CAS-RN: [7175-81-7] GP G Conditions A 10.3 mg (43% yield, 93% purity) |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 290 | 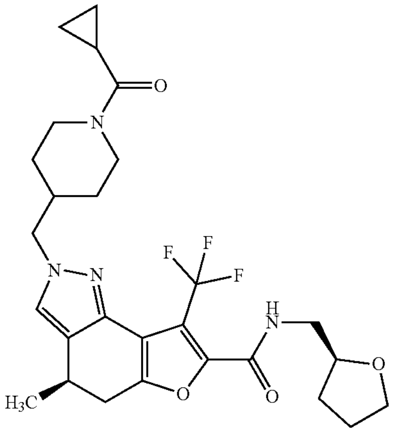 [SMILES: C[C@@H]1Cc2oc(C(=O)NC[C@@H]3CCCO3)c(C(F)(F)F)c2-c2nn(CC3CCN(C(=O)C4CC4)CC3)cc21] (4R or 4S)-2-{[1-(cyclopropanecarbonyl)piperidin-4-yl]methyl}-4-methyl-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.654 (4.29), 0.674 (6.94), 0.995 (0.63), 1.002 (0.66), 1.013 (0.71), 1.019 (0.74), 1.025 (0.72), 1.028 (0.71), 1.031 (0.68), 1.038 (0.62), 1.130 (0.60), 1.146 (0.74), 1.152 (0.70), 1.158 (0.71), 1.166 (0.71), 1.173 (0.76), 1.272 (14.64), 1.289 (15.14), 1.508 (1.99), 1.539 (2.02), 1.559 (2.58), 1.567 (2.60), 1.575 (2.36), 1.589 (2.29), 1.605 (1.78), 1.794 (1.82), 1.810 (3.32), 1.828 (3.28), 1.846 (2.15), 1.862 (1.84), 1.890 (1.60), 1.950 (2.05), 2.024 (0.81), 2.031 (0.95), 2.041 (1.20), 2.050 (0.92), 2.058 (0.78), 2.518 (16.00), 2.523 (11.88), 2.569 (2.73), 2.595 (2.80), 2.610 (2.80), 2.636 (3.01), 3.004 (3.24), 3.022 (4.37), 3.045 (3.10), 3.064 (3.57), 3.164 (1.54), 3.190 (1.42), 3.252 (4.14), 3.268 (9.11), 3.283 (5.62), 3.597 (1.16), 3.616 (2.66), 3.634 (3.18), 3.652 (1.81), 3.741 (1.53), 3.758 (2.89), 3.774 (2.68), 3.795 (1.74), 3.935 (2.34), 3.951 (3.99), 3.968 (7.76), 3.986 (6.24), 4.211 (0.92), 4.240 (0.92), 4.245 (0.95), 4.311 (0.99), 4.318 (0.95), 4.322 (0.86), 4.342 (0.87), 4.345 (0.87), 7.579 (9.73), 8.684 (1.87), 8.699 (3.99), 8.715 (1.79). LC-MS (Method 1): $R_t$ = 1.16 min; MS (ESIpos): m/z = 535 [M + H]+ | Intermediate 93 GP H Conditions C 41 mg, 32% yield, 98% purity |
| 291 | 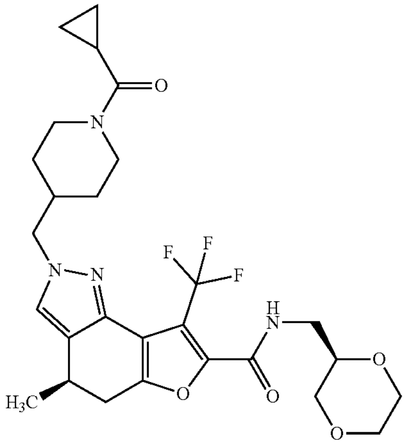 [SMILES: C[C@@H]1Cc2oc(C(=O)NC[C@@H]3COCCO3)c(C(F)(F)F)c2-c2nn(CC3CCN(C(=O)C4CC4)CC3)cc21] (4R or 4S)-2-{[1-(cyclopropanecarbonyl)piperidin-4-yl]methyl}-N-{[(2R)-1,4-dioxan-2-yl]methyl}-4-methyl-8-(trifluoromethyl)-4,5-dihydro-2H-furo[2,3-g]indazole-7-carboxamide | $^1$H-NMR (400 MHz, DMSO-d6) δ [ppm]: 0.654 (4.82), 0.674 (7.85), 1.011 (0.79), 1.019 (0.80), 1.022 (0.78), 1.026 (0.80), 1.129 (0.67), 1.131 (0.66), 1.142 (0.79), 1.148 (0.81), 1.156 (0.79), 1.158 (0.77), 1.164 (0.79), 1.169 (0.79), 1.173 (0.80), 1.175 (0.79), 1.273 (16.00), 1.289 (15.94), 1.497 (1.12), 1.527 (1.31), 1.544 (0.88), 1.553 (0.88), 1.572 (1.20), 1.575 (1.19), 1.586 (0.95), 1.588 (0.92), 1.593 (0.91), 1.596 (0.93), 1.601 (0.98), 1.935 (1.42), 1.950 (2.21), 1.966 (1.28), 2.013 (0.77), 2.023 (0.88), 2.032 (1.04), 2.041 (1.24), 2.051 (1.00), 2.061 (0.83), 2.069 (0.69), 2.518 (14.02), 2.523 (9.86), 2.572 (3.01), 2.598 (3.37), 2.613 (3.08), 2.640 (3.25), 3.007 (3.42), 3.024 (4.80), 3.048 (3.21), 3.066 (3.75), 3.148 (1.14), 3.166 (1.63), 3.196 (3.92), 3.204 (1.87), 3.220 (5.09), 3.224 (5.78), 3.238 (4.57), 3.249 (5.37), 3.259 (4.27), 3.275 (2.72), 3.294 (2.05), 3.423 (1.23), 3.430 (1.55), 3.450 (2.96), 3.457 (3.20), 3.477 (2.58), 3.484 (2.51), 3.525 (2.26), 3.530 (2.60), 3.553 (3.12), 3.559 (3.14), 3.580 (1.30), 3.586 (2.16), 3.621 (3.80), 3.629 (2.47), 3.644 (4.03), 3.697 (3.44), 3.703 (2.83), 3.725 (5.78), 3.753 (2.42), 3.969 (6.73), 3.987 (6.65), 4.209 (1.02), 4.212 (1.02), 4.221 (0.86), 4.233 (0.88), 4.239 (1.05), 4.244 (1.08), 4.247 (1.04), 4.314 (1.12), 4.332 (0.86), 4.338 (0.96), 4.343 (1.02), 7.582 (10.73), 8.722 (2.05), 8.736 (4.43), 8.751 (2.00). LC-MS (Method 1): $R_t$ = 1.08 min; MS (ESIpos): m/z = 551 [M + H]+ | Intermediate 93 GP H Conditions C 48 mg, 36% yield, 98% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 292 | 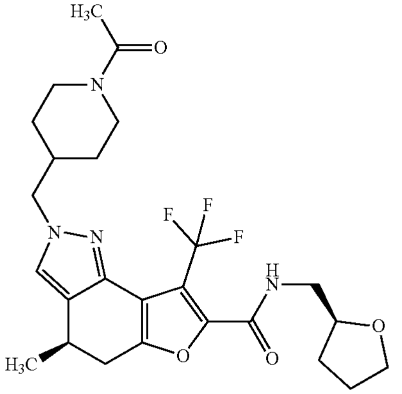 [SMILES: CC(=O)N1CCC(Cn2cc3c(n2)-c2c(oc(C(=O)NC[C@@H]4CCCO4)c2C(F)(F)F)C[C@H]3C)CC1] (4R or 4S)-2-[(1-acetylpiperidin-4-yl)methyl]-4-methyl-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.987 (0.56), 1.004 (0.47), 1.017 (0.59), 1.127 (0.62), 1.158 (0.65), 1.272 (5.97), 1.288 (6.07), 1.489 (0.82), 1.523 (1.47), 1.539 (1.32), 1.559 (1.56), 1.567 (1.44), 1.575 (1.01), 1.583 (0.69), 1.588 (0.87), 1.605 (0.53), 1.773 (0.42), 1.789 (0.80), 1.794 (1.03), 1.810 (1.87), 1.828 (1.82), 1.845 (1.17), 1.861 (1.00), 1.866 (0.58), 1.871 (0.70), 1.878 (0.80), 1.883 (0.69), 1.890 (0.91), 1.900 (0.60), 1.904 (0.72), 1.911 (0.65), 1.921 (0.54), 1.928 (0.52), 1.942 (0.45), 1.963 (16.00), 1.995 (0.58), 2.004 (0.65), 2.337 (0.50), 2.444 (0.64), 2.518 (5.93), 2.523 (3.87), 2.567 (1.31), 2.593 (1.39), 2.608 (1.50), 2.634 (1.55), 2.933 (0.58), 2.961 (1.03), 3.002 (1.27), 3.020 (1.36), 3.044 (0.88), 3.062 (1.12), 3.146 (0.53), 3.162 (0.79), 3.171 (0.65), 3.180 (0.61), 3.188 (0.73), 3.206 (0.43), 3.252 (2.29), 3.268 (4.97), 3.283 (2.85), 3.597 (0.67), 3.616 (1.49), 3.633 (1.82), 3.651 (1.01), 3.741 (0.90), 3.758 (2.12), 3.761 (1.74), 3.773 (2.13), 3.776 (1.88), 3.794 (1.47), 3.919 (0.45), 3.935 (1.36), 3.951 (2.99), 3.956 (4.19), 3.966 (2.30), 3.974 (3.91), 4.314 (0.76), 4.343 (0.73), 7.573 (5.38), 8.686 (1.03), 8.701 (2.15), 8.716 (1.00). LC-MS (Method 1): $R_t$ = 1.05 min; MS (ESIpos): m/z = 509 [M + H]+ | Intermediate 94 GP H Conditions C 23 mg, 38% yield, 98% purity |
| 293 | 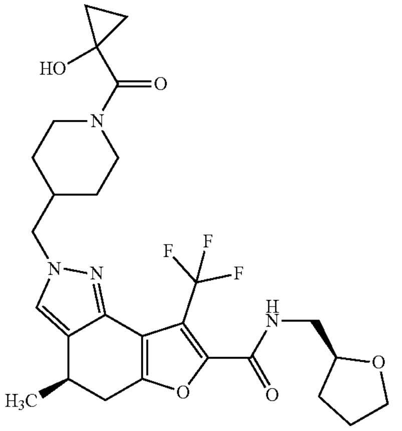 (4R or 4S)-2-{[1-(1-hydroxycyclopropane-1-carbonyl)piperidin-4-yl]methyl}-4-methyl-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.731 (8.18), 0.860 (8.04), 1.111 (1.84), 1.114 (1.78), 1.129 (2.01), 1.274 (15.79), 1.291 (15.80), 1.492 (3.89), 1.559 (5.99), 1.794 (2.73), 1.810 (4.69), 1.827 (4.65), 1.845 (3.12), 1.862 (2.48), 1.866 (1.99), 1.870 (2.19), 1.878 (2.26), 1.883 (2.20), 1.889 (2.25), 1.907 (2.05), 1.963 (2.06), 2.024 (1.70), 2.035 (1.74), 2.634 (4.01), 3.003 (3.29), 3.022 (4.10), 3.045 (2.91), 3.063 (3.36), 3.164 (3.23), 3.173 (2.99), 3.183 (3.20), 3.190 (3.46), 3.268 (16.00), 3.283 (14.67), 3.616 (3.49), 3.634 (4.05), 3.757 (3.98), 3.777 (3.48), 3.955 (10.09), 3.973 (8.61), 4.297 (0.89), 4.305 (0.99), 4.311 (1.01), 4.313 (1.03), 4.317 (1.03), 4.322 (1.06), 4.326 (1.08), 4.331 (1.15), 4.335 (1.06), 4.339 (1.14), 4.343 (1.24), 4.346 (1.12), 4.350 (1.14), 4.357 (1.21), 4.362 (1.04), 4.376 (1.01), 4.379 (1.11), 4.391 (1.05), 4.402 (0.89), 7.586 (10.27), 8.699 (4.64). LC-MS (Method 1): $R_t$ = 1.06 min; MS (ESIpos): m/z = 551 [M + H]+ | Intermediate 95 GP H Conditions C 7 mg, 12% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 294 | 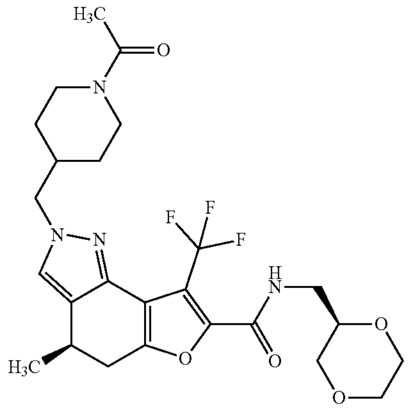 [SMILES: CC(=O)N1CCC(Cn2cc3c(n2)-c2c(oc(C(=O)NC[C@@H]4COCCO4)c2C(F)(F)F)C[C@H]3C)CC1] (4R or 4S)-2-[(1-acetylpiperidin-4-yl)methyl]-N-{[(2R)-1,4-dioxan-2-yl]methyl}-4-methyl-8-(trifluoromethyl)-4,5-dihydro-2H-furo[2,3-g]indazole-7-carboxamide | $^1$H-NMR (400 MHz, DMSO-d6) δ [ppm]: 0.987 (0.54), 1.003 (0.48), 1.016 (0.58), 1.128 (0.61), 1.159 (0.63), 1.272 (5.91), 1.289 (6.00), 1.491 (0.80), 1.526 (1.30), 1.561 (0.64), 1.963 (16.00), 2.004 (0.63), 2.336 (0.75), 2.448 (0.72), 2.518 (8.24), 2.523 (5.29), 2.571 (1.22), 2.597 (1.31), 2.612 (1.45), 2.638 (1.54), 2.678 (0.75), 2.933 (0.56), 2.961 (0.99), 3.005 (1.12), 3.024 (1.32), 3.048 (0.87), 3.065 (1.12), 3.146 (0.54), 3.163 (0.76), 3.189 (1.12), 3.195 (1.98), 3.203 (1.04), 3.220 (2.57), 3.224 (2.96), 3.237 (2.31), 3.244 (1.58), 3.249 (2.81), 3.259 (2.22), 3.275 (1.41), 3.293 (0.97), 3.423 (0.55), 3.429 (0.68), 3.450 (1.47), 3.456 (1.61), 3.477 (1.31), 3.484 (1.22), 3.524 (1.09), 3.530 (1.29), 3.552 (1.54), 3.559 (1.55), 3.579 (0.62), 3.585 (1.07), 3.621 (1.98), 3.628 (1.19), 3.644 (2.04), 3.667 (0.42), 3.696 (1.72), 3.703 (1.47), 3.725 (2.92), 3.753 (1.45), 3.801 (0.73), 3.957 (3.81), 3.975 (3.71), 4.314 (0.75), 4.345 (0.70), 7.576 (5.34), 8.721 (1.06), 8.736 (2.20), 8.751 (0.98). LC-MS (Method 1): $R_t$ = 0.98 min; MS (ESIpos): m/z = 525 [M + H]+ | Intermediate 94 GP H Conditions C 22 mg, 35% yield, 98% purity |
| 295 | 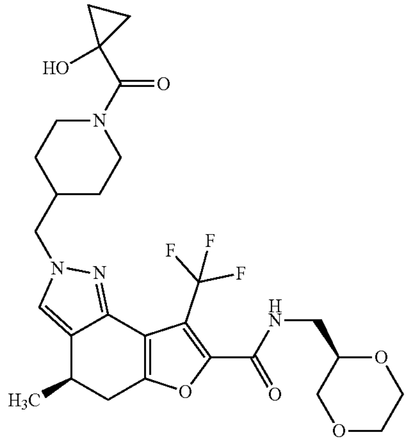 (4R or 4S)-N-{[(2R)-1,4-dioxan-2-yl]methyl}-2-{[1-(1-hydroxycyclopropane-1-carbonyl)piperidin-4-yl]methyl}-4-methyl-8-(trifluoromethyl)-4,5-dihydro-2H-furo[2,3-g]indazole-7-carboxamide | $^1$H-NMR (400 MHz, DMSO-d6) δ [ppm]: 0.724 (6.06), 0.731 (6.96), 0.741 (2.91), 0.850 (3.16), 0.860 (6.51), 0.879 (2.29), 1.003 (1.48), 1.130 (1.14), 1.275 (15.48), 1.292 (15.39), 1.500 (5.27), 1.532 (2.84), 1.561 (2.44), 2.015 (0.88), 2.024 (1.01), 2.028 (0.94), 2.033 (1.20), 2.043 (0.99), 2.052 (0.88), 2.518 (16.00), 2.523 (10.23), 2.539 (2.04), 2.571 (2.52), 2.597 (2.84), 2.612 (3.04), 2.639 (3.26), 3.007 (2.87), 3.024 (3.99), 3.048 (2.71), 3.066 (3.18), 3.148 (1.28), 3.166 (1.88), 3.196 (4.17), 3.220 (5.38), 3.225 (5.92), 3.238 (4.25), 3.249 (6.12), 3.259 (4.28), 3.275 (3.40), 3.430 (1.74), 3.450 (3.25), 3.457 (3.48), 3.478 (2.73), 3.484 (2.63), 3.525 (2.24), 3.530 (2.39), 3.553 (3.10), 3.559 (3.10), 3.586 (2.21), 3.621 (3.84), 3.629 (2.46), 3.645 (4.12), 3.697 (3.44), 3.703 (2.89), 3.726 (5.79), 3.753 (2.43), 3.957 (6.41), 3.974 (6.40), 4.352 (0.60), 4.361 (0.60), 7.587 (9.82), 8.723 (1.72), 8.737 (3.65), 8.752 (1.68). LC-MS (Method 1): $R_t$ = 0.98 min; MS (ESIpos): m/z = 567 [M + H]+ | Intermediate 95 GP H Conditions C 16 mg, 25% yield, 95% purity |

TABLE 5-continued

| The following examples (212 to 316) were prepared in analogy to example 169 starting from the given intermediates and commercially available amines (or their salts), applying the indicated general procedure. | | | |
|---|---|---|---|
| Example | Structure IUPAC-Name | Analytical Data | Preparation or Separation Methods |
| 296 | 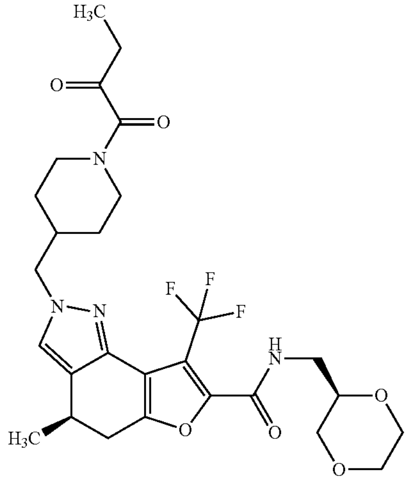 [SMILES: CCC(=O)C(=O)N1CCC(Cn2cc3c(n2)-c2c(oc(C(=O)NC[C@@H]4COCCO4)c2C(F)(F)F)C[C@H]3C)CC1] (4R or 4S)-N-{[(2R)-1,4-dioxan-2-yl]methyl}-4-methyl-2-{[1-(2-oxobutanoyl)piperidin-4-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.985 (7.07), 1.003 (16.00), 1.021 (7.28), 1.071 (0.45), 1.087 (0.52), 1.100 (0.68), 1.115 (0.67), 1.145 (0.64), 1.156 (0.70), 1.187 (0.66), 1.272 (6.56), 1.287 (6.62), 1.496 (1.65), 1.535 (0.91), 1.573 (0.81), 1.592 (0.92), 1.623 (0.76), 2.068 (0.61), 2.076 (0.72), 2.085 (0.58), 2.318 (0.57), 2.323 (1.27), 2.327 (1.82), 2.332 (1.31), 2.336 (0.56), 2.518 (5.85), 2.523 (3.95), 2.539 (0.53), 2.569 (1.34), 2.595 (1.46), 2.611 (1.57), 2.637 (1.65), 2.660 (0.70), 2.665 (1.55), 2.669 (2.41), 2.674 (2.31), 2.694 (3.37), 2.697 (3.32), 2.713 (3.99), 2.734 (1.33), 3.004 (1.69), 3.025 (1.92), 3.045 (1.19), 3.048 (1.14), 3.064 (1.87), 3.145 (0.59), 3.163 (0.87), 3.188 (1.19), 3.195 (2.26), 3.203 (1.14), 3.219 (3.06), 3.223 (3.30), 3.237 (2.41), 3.248 (3.37), 3.258 (2.32), 3.274 (1.60), 3.293 (1.43), 3.423 (0.80), 3.429 (0.95), 3.450 (2.21), 3.456 (2.71), 3.477 (1.75), 3.483 (1.92), 3.524 (1.33), 3.530 (1.49), 3.552 (1.78), 3.559 (1.80), 3.578 (0.73), 3.585 (1.23), 3.620 (2.28), 3.627 (1.42), 3.644 (2.35), 3.660 (0.44), 3.667 (0.53), 3.696 (1.97), 3.702 (1.64), 3.725 (3.33), 3.752 (1.39), 3.979 (2.82), 3.996 (2.84), 4.204 (0.87), 4.238 (0.83), 7.582 (5.97), 8.722 (1.01), 8.737 (2.22), 8.751 (1.02). LC-MS (Method 1): $R_t$ = 1.10 min; MS (ESIneg): m/z = 565 $[M - H]^-$ | Intermediate 95 GP H Conditions C 13 mg, 21% yield, 98% purity |
| 297 | 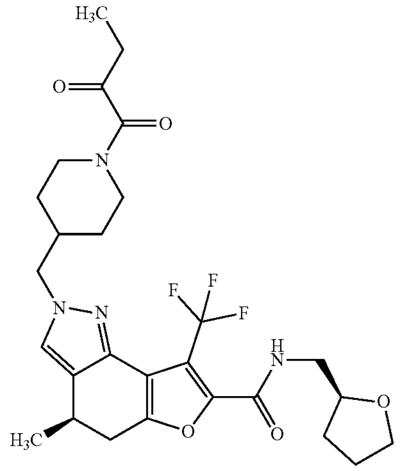 [SMILES: CCC(=O)C(=O)N1CCC(Cn2cc3c(n2)-c2c(oc(C(=O)NC[C@@H]4CCCO4)c2C(F)(F)F)C[C@H]3C)CC1] (4R or 4S)-4-methyl-2-{[1-(2-oxobutanoyl)piperidin-4-yl]methyl}-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.985 (7.18), 1.003 (16.00), 1.021 (7.50), 1.071 (0.43), 1.086 (0.56), 1.101 (0.67), 1.114 (0.69), 1.157 (0.74), 1.187 (0.71), 1.272 (6.78), 1.286 (6.82), 1.508 (0.46), 1.538 (1.64), 1.558 (1.63), 1.566 (1.81), 1.574 (1.61), 1.587 (1.87), 1.604 (1.03), 1.624 (0.81), 1.773 (0.52), 1.788 (0.93), 1.793 (1.14), 1.810 (2.11), 1.827 (2.10), 1.845 (1.33), 1.861 (1.13), 1.866 (0.67), 1.870 (0.81), 1.877 (0.89), 1.889 (1.07), 1.900 (0.67), 1.904 (0.80), 1.910 (0.73), 1.921 (0.57), 2.076 (0.72), 2.085 (0.62), 2.318 (0.89), 2.322 (2.00), 2.327 (2.92), 2.332 (2.07), 2.336 (0.90), 2.518 (10.33), 2.523 (6.76), 2.565 (1.32), 2.591 (1.43), 2.607 (1.55), 2.633 (1.69), 2.660 (0.98), 2.665 (2.26), 2.669 (3.44), 2.673 (2.97), 2.694 (3.44), 2.697 (3.40), 2.713 (4.09), 2.731 (1.33), 3.004 (1.75), 3.022 (1.76), 3.032 (1.23), 3.043 (1.35), 3.063 (1.90), 3.144 (0.59), 3.162 (0.84), 3.188 (0.82), 3.204 (0.49), 3.252 (2.62), 3.267 (5.80), 3.282 (3.35), 3.459 (0.99), 3.494 (0.87), 3.596 (0.74), 3.616 (1.69), 3.633 (2.07), 3.651 (1.18), 3.741 (0.99), 3.757 (1.84), 3.773 (1.76), 3.776 (1.57), 3.794 (1.02), 3.918 (0.51), 3.934 (1.47), 3.950 (2.45), 3.965 (1.82), 3.979 (3.07), 3.996 (2.91), 4.204 (0.90), 4.235 (0.86), 7.578 (6.14), 7.580 (6.06), 8.684 (1.20), 8.699 (2.55), 8.714 (1.17). LC-MS (Method 1): $R_t$ = 1.18 min; MS (ESIneg): m/z = 549 $[M - H]^-$ | Intermediate 95 GP H Conditions C 11 mg, 18% yield, 98% purity |

TABLE 5-continued

| The following examples (212 to 316) were prepared in analogy to example 169 starting from the given intermediates and commercially available amines (or their salts), applying the indicated general procedure. | | | |
|---|---|---|---|
| Example | Structure IUPAC-Name | Analytical Data | Preparation or Separation Methods |
| 298 | 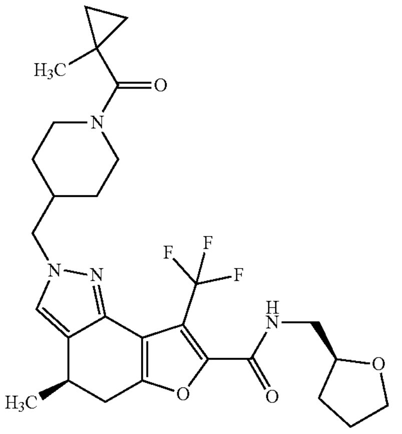 [SMILES: C[C@@H]1Cc2oc(C(=O)NC[C@@H]3CCCO3)c(C(F)(F)F)c2-c2nn(CC3CCN(C(=O)C4(C)CC4)CC3)cc21] (4R or 4S)-4-methyl-2-{[1-(1-methylcyclopropane-1-carbonyl)piperidin-4-yl]methyl}-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.496 (1.23), 0.508 (4.00), 0.512 (3.85), 0.523 (1.51), 0.730 (1.42), 0.739 (3.88), 0.743 (3.67), 0.755 (1.16), 1.085 (0.71), 1.090 (0.71), 1.106 (0.60), 1.111 (0.62), 1.192 (16.00), 1.272 (7.27), 1.289 (7.42), 1.495 (1.44), 1.539 (1.76), 1.559 (1.80), 1.567 (1.86), 1.605 (0.50), 1.794 (0.92), 1.810 (1.68), 1.828 (1.64), 1.846 (1.05), 1.862 (0.90), 1.878 (0.72), 1.890 (0.84), 1.905 (0.64), 1.922 (0.46), 2.005 (0.45), 2.014 (0.52), 2.023 (0.60), 2.031 (0.50), 2.518 (5.88), 2.523 (3.79), 2.567 (1.23), 2.593 (1.34), 2.608 (1.47), 2.634 (1.56), 2.740 (0.33), 2.746 (0.33), 2.751 (0.34), 2.755 (0.35), 2.760 (0.34), 2.763 (0.34), 2.766 (0.33), 2.772 (0.33), 3.003 (1.37), 3.022 (1.83), 3.044 (1.27), 3.063 (1.52), 3.147 (0.59), 3.164 (0.84), 3.190 (0.79), 3.207 (0.51), 3.252 (2.10), 3.268 (4.38), 3.283 (2.74), 3.597 (0.60), 3.616 (1.35), 3.634 (1.63), 3.652 (0.91), 3.741 (0.78), 3.758 (1.47), 3.774 (1.42), 3.794 (0.79), 3.919 (0.40), 3.935 (1.19), 3.951 (2.14), 3.963 (3.63), 3.980 (3.38), 4.208 (1.51), 4.241 (1.44), 7.576 (4.85), 8.688 (0.90), 8.703 (1.90), 8.717 (0.89). LC-MS (Method 1): $R_t$ = 1.18 min; MS (ESIneg): m/z = 547 $[M - H]^-$ | Intermediate 96 GP H Conditions C 20 mg, 33% yield, 98% purity |
| 299 | 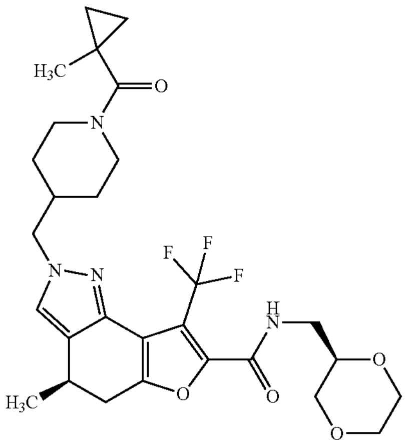 [SMILES: C[C@@H]1Cc2oc(C(=O)NC[C@@H]3COCCO3)c(C(F)(F)F)c2-c2nn(CC3CCN(C(=O)C4(C)CC4)CC3)cc21] (4R or 4S)-N-{[(2R)-1,4-dioxan-2-yl]methyl}-4-methyl-2-{[1-(1-methylcyclopropane-1-carbonyl)piperidin-4-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.497 (1.18), 0.508 (3.91), 0.512 (3.75), 0.523 (1.47), 0.729 (1.37), 0.739 (3.75), 0.743 (3.54), 0.755 (1.11), 1.060 (0.46), 1.092 (0.65), 1.102 (0.57), 1.113 (0.56), 1.123 (0.48), 1.192 (16.00), 1.272 (7.28), 1.289 (7.26), 1.502 (1.74), 1.535 (1.20), 1.564 (1.04), 2.005 (0.39), 2.014 (0.48), 2.022 (0.56), 2.031 (0.47), 2.040 (0.38), 2.518 (6.28), 2.523 (4.13), 2.570 (1.21), 2.596 (1.33), 2.612 (1.44), 2.638 (1.55), 2.734 (0.35), 2.772 (0.35), 3.006 (1.34), 3.024 (1.85), 3.047 (1.28), 3.065 (1.55), 3.148 (0.59), 3.164 (0.84), 3.196 (1.91), 3.220 (2.49), 3.224 (2.74), 3.238 (1.81), 3.249 (2.94), 3.259 (1.77), 3.274 (1.44), 3.423 (0.80), 3.429 (0.89), 3.450 (1.49), 3.457 (1.63), 3.478 (1.30), 3.484 (1.21), 3.525 (1.07), 3.530 (1.17), 3.553 (1.46), 3.559 (1.45), 3.580 (0.60), 3.586 (1.01), 3.622 (1.80), 3.628 (1.13), 3.645 (1.86), 3.697 (1.55), 3.703 (1.29), 3.726 (2.61), 3.753 (1.10), 3.963 (3.16), 3.980 (3.07), 4.208 (1.43), 4.240 (1.36), 7.578 (4.79), 8.741 (1.45). LC-MS (Method 1): $R_t$ = 1.10 min; MS (ESIpos): m/z = 565 [M + H]+ | Intermediate 96 GP H Conditions C 28 mg, 45% yield, 98% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 300 | 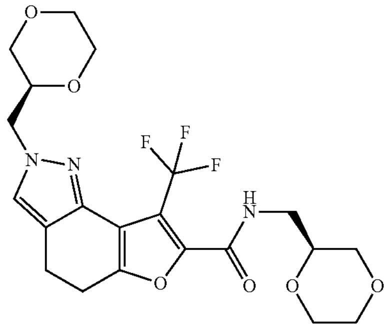 [SMILES: O=C(NC[C@H]1COCCO1)c1oc2c(c1C(F)(F)F)-c1nn(C[C@H]3COCCO3)cc1CC2] N,2-bis{[(2S)-1,4-dioxan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 2.074 (5.72), 2.331 (1.93), 2.523 (9.38), 2.673 (2.07), 2.842 (2.54), 2.846 (2.66), 2.865 (9.97), 2.883 (8.19), 2.931 (8.77), 2.948 (11.53), 2.954 (4.81), 2.967 (3.06), 2.972 (2.90), 3.188 (1.43), 3.197 (4.71), 3.202 (2.70), 3.221 (8.27), 3.225 (7.10), 3.237 (10.46), 3.250 (10.13), 3.264 (10.02), 3.280 (4.72), 3.290 (6.44), 3.298 (4.19), 3.307 (4.18), 3.383 (1.01), 3.406 (1.97), 3.412 (2.16), 3.424 (2.30), 3.433 (4.84), 3.439 (4.80), 3.450 (4.76), 3.457 (5.63), 3.460 (5.06), 3.466 (3.98), 3.478 (3.88), 3.484 (3.74), 3.502 (3.16), 3.508 (3.51), 3.525 (3.85), 3.530 (7.48), 3.537 (4.77), 3.553 (4.89), 3.559 (6.02), 3.580 (2.01), 3.586 (3.15), 3.613 (9.84), 3.627 (4.28), 3.643 (8.87), 3.659 (1.45), 3.666 (1.52), 3.696 (5.12), 3.702 (4.63), 3.725 (9.87), 3.730 (11.08), 3.737 (7.40), 3.748 (5.21), 3.758 (5.86), 3.765 (4.63), 3.789 (1.47), 3.796 (1.36), 3.808 (2.43), 3.812 (2.55), 3.818 (2.39), 3.825 (2.90), 3.842 (1.48), 3.849 (1.17), 4.051 (1.20), 4.068 (0.75), 4.087 (7.26), 4.097 (8.01), 4.104 (8.17), 4.110 (7.45), 4.132 (1.17), 4.145 (0.72), 7.525 (16.00), 8.734 (2.82), 8.749 (5.72), 8.764 (2.70). LC-MS (Method 1): $R_t$ = 0.91 min; MS (ESIpos): m/z = 472 [M + H]+ | Intermediate 69 GP H Conditions D 60 mg, 45% yield, 95% purity |
| 301 | 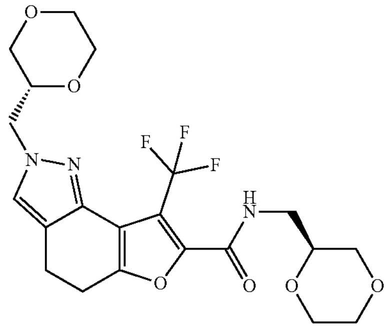 [SMILES: O=C(NC[C@H]1COCCO1)c1oc2c(c1C(F)(F)F)-c1nn(C[C@@H]3COCCO3)cc1CC2] 2-{[(2R)-1,4-dioxan-2-yl]methyl}-N-{[(2S)-1,4-dioxan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 2.073 (2.80), 2.331 (3.15), 2.522 (14.16), 2.673 (3.08), 2.846 (2.69), 2.865 (10.02), 2.883 (8.38), 2.931 (8.96), 2.948 (11.37), 2.967 (2.99), 2.972 (2.82), 3.188 (1.42), 3.197 (4.73), 3.202 (2.84), 3.221 (8.61), 3.236 (10.51), 3.249 (10.56), 3.264 (10.67), 3.280 (5.36), 3.290 (7.18), 3.298 (5.28), 3.405 (2.51), 3.412 (2.71), 3.423 (2.53), 3.433 (5.03), 3.439 (4.92), 3.450 (4.91), 3.457 (5.84), 3.466 (4.02), 3.477 (3.93), 3.484 (3.81), 3.502 (3.20), 3.507 (3.51), 3.525 (3.94), 3.530 (7.38), 3.536 (4.73), 3.553 (5.07), 3.558 (6.04), 3.580 (2.08), 3.585 (3.18), 3.613 (10.07), 3.627 (4.40), 3.642 (8.95), 3.666 (1.48), 3.695 (5.12), 3.702 (4.67), 3.725 (10.23), 3.730 (11.24), 3.737 (7.55), 3.748 (5.47), 3.758 (5.86), 3.764 (4.62), 3.789 (1.41), 3.812 (2.52), 3.818 (2.36), 3.825 (2.91), 3.842 (1.49), 4.052 (1.13), 4.068 (0.76), 4.087 (7.32), 4.096 (8.07), 4.104 (8.21), 4.109 (7.47), 4.132 (1.24), 4.145 (0.75), 7.524 (16.00), 8.734 (2.84), 8.749 (5.76), 8.764 (2.82). LC-MS (Method 1): $R_t$ = 0.89 min; MS (ESIpos): m/z = 472 [M + H]+ | Intermediate 70 GP H Conditions D 36 mg, 36% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
| --- | --- | --- | --- |
| 302 | 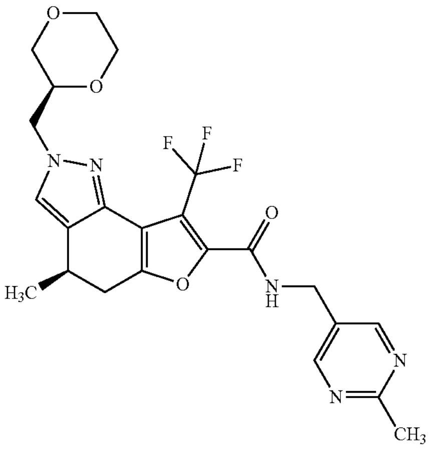 (4R or 4S)-2-{[(2S)-1,4-dioxan-2-yl]methyl}-4-methyl-N-[(2-methylpyrimidin-5-yl)methyl]-8-(trifluoromethyl)-4,5-dihydro-2H-furo[2,3-g]indazole-7-carboxamide | $^{1}$H-NMR (400 MHz, DMSO-d6) δ [ppm]: 1.270 (5.96), 1.287 (6.00), 2.518 (2.96), 2.523 (1.91), 2.579 (1.07), 2.594 (16.00), 2.605 (1.46), 2.620 (1.19), 2.646 (1.23), 2.999 (1.11), 3.018 (1.49), 3.041 (1.07), 3.059 (1.24), 3.147 (0.44), 3.164 (0.65), 3.173 (0.51), 3.181 (0.48), 3.191 (0.60), 3.240 (1.10), 3.264 (1.40), 3.268 (1.39), 3.293 (1.39), 3.396 (0.46), 3.402 (0.51), 3.423 (1.03), 3.429 (1.10), 3.450 (0.89), 3.457 (0.84), 3.513 (0.67), 3.519 (0.80), 3.542 (1.01), 3.548 (1.09), 3.568 (0.47), 3.575 (0.71), 3.609 (1.14), 3.637 (0.90), 3.721 (1.54), 3.729 (1.25), 3.744 (0.97), 3.751 (1.28), 3.757 (1.06), 3.830 (0.60), 3.837 (0.67), 3.846 (0.56), 3.854 (0.73), 3.861 (0.55), 4.093 (2.28), 4.098 (2.26), 4.109 (2.55), 4.405 (2.79), 4.419 (2.86), 7.567 (4.00), 8.643 (10.45), 8.651 (0.90), 9.295 (0.67), 9.309 (1.50), 9.324 (0.67). LC-MS (Method 1): $R_t$ = 0.92 min; MS (ESIpos): m/z = 492 [M + H]+ | Intermediate 79 GP H Conditions D 50 mg, 66% yield, 95% purity |
| 303 | 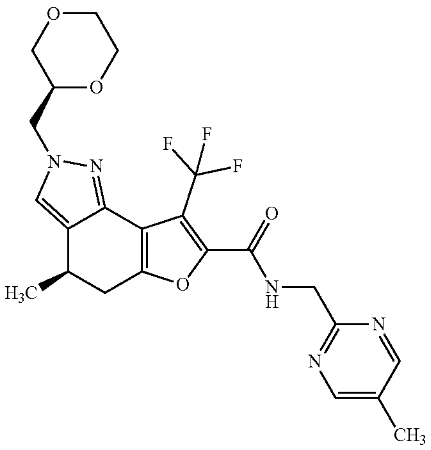 (4R or 4S)-2-{[(2S)-1,4-dioxan-2-yl]methyl}-4-methyl-N-[(5-methylpyrimidin-2-yl)methyl]-8-(trifluoromethyl)-4,5-dihydro-2H-furo[2,3-g]indazole-7-carboxamide | $^{1}$H-NMR (400 MHz, DMSO-d6) δ [ppm]: 1.289 (8.86), 1.306 (8.88), 2.259 (16.00), 2.331 (0.85), 2.518 (4.54), 2.523 (2.88), 2.612 (1.45), 2.639 (1.54), 2.665 (0.93), 2.669 (1.27), 2.674 (1.06), 2.680 (2.01), 3.031 (1.63), 3.049 (2.23), 3.072 (1.48), 3.090 (1.84), 3.170 (0.67), 3.186 (0.97), 3.196 (0.75), 3.203 (0.71), 3.212 (0.91), 3.230 (0.56), 3.248 (1.78), 3.272 (2.06), 3.276 (2.08), 3.301 (2.21), 3.402 (0.60), 3.409 (0.73), 3.429 (1.50), 3.436 (1.60), 3.457 (1.27), 3.464 (1.19), 3.520 (1.00), 3.526 (1.15), 3.549 (1.50), 3.555 (1.55), 3.575 (0.68), 3.582 (1.01), 3.613 (1.62), 3.642 (1.28), 3.724 (1.71), 3.731 (1.78), 3.737 (1.84), 3.751 (1.42), 3.760 (1.57), 3.766 (1.54), 3.825 (0.45), 3.832 (0.46), 3.839 (0.85), 3.846 (0.94), 3.855 (0.82), 3.863 (1.03), 3.870 (0.77), 3.879 (0.53), 3.885 (0.44), 4.100 (3.20), 4.106 (3.25), 4.116 (3.54), 4.575 (4.14), 4.590 (4.24), 7.578 (5.92), 8.623 (12.02), 9.124 (1.16), 9.138 (2.58), 9.153 (1.15). LC-MS (Method 1): $R_t$ = 1.04 min; MS (ESIpos): m/z = 492 [M + H]+ | Intermediate 79 GP H Conditions D 36 mg, 45% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 304 | 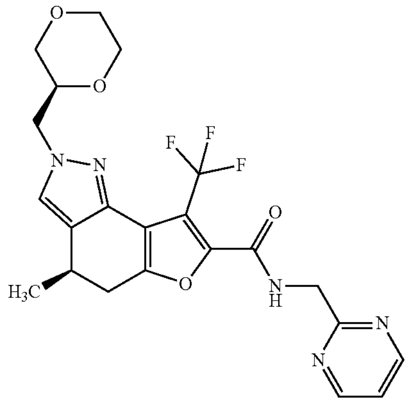 [SMILES: C[C@@H]1Cc2oc(C(=O)NCc3ncccn3)c(C(F)(F)F)c2-c2nn(C[C@H]3COCCO3)cc21] (4R or4S)-2-{[(2S)-1,4-dioxan-2-yl]methyl}-4-methyl-N-[(pyrimidin-2-yl)methyl]-8-(trifluoromethyl)-4,5-dihydro-2H-furo[2,3-g]indazole-7-carboxamide | $^1$H-NMR (400 MHz, DMSO-d6) δ [ppm]: 1.291 (11.62), 1.307 (11.61), 2.323 (1.38), 2.327 (1.92), 2.331 (1.39), 2.336 (0.64), 2.518 (7.04), 2.523 (4.45), 2.617 (1.86), 2.643 (2.06), 2.658 (2.52), 2.665 (1.64), 2.669 (2.07), 2.673 (1.49), 2.678 (0.92), 2.685 (2.39), 3.034 (2.15), 3.053 (2.92), 3.076 (1.93), 3.094 (2.42), 3.172 (0.87), 3.189 (1.26), 3.198 (0.98), 3.205 (0.92), 3.215 (1.15), 3.232 (0.72), 3.249 (2.34), 3.273 (2.75), 3.278 (2.72), 3.301 (2.99), 3.403 (0.80), 3.409 (1.00), 3.430 (1.96), 3.436 (2.11), 3.457 (1.66), 3.464 (1.55), 3.521 (1.27), 3.526 (1.53), 3.549 (1.97), 3.556 (2.05), 3.576 (0.87), 3.582 (1.34), 3.614 (2.08), 3.642 (1.63), 3.725 (2.16), 3.732 (2.26), 3.738 (2.39), 3.751 (1.82), 3.761 (1.99), 3.767 (1.98), 3.827 (0.58), 3.833 (0.58), 3.840 (1.09), 3.847 (1.23), 3.856 (1.06), 3.864 (1.34), 3.871 (1.01), 3.880 (0.69), 3.886 (0.58), 4.065 (0.45), 4.101 (4.18), 4.107 (4.26), 4.117 (4.61), 4.143 (0.45), 4.620 (5.98), 4.635 (6.24), 7.405 (2.91), 7.417 (5.93), 7.429 (2.98), 7.578 (7.70), 7.580 (7.66), 8.782 (15.68), 8.794 (16.00), 9.154 (1.54), 9.169 (3.35), 9.183 (1.51). LC-MS (Method 1): $R_t$ = 0.97 min; MS (ESIpos): m/z = 478 [M + H]+ | Intermediate 79 GP H Conditions D 46 mg, 62% yield, 95% purity |
| 305 | 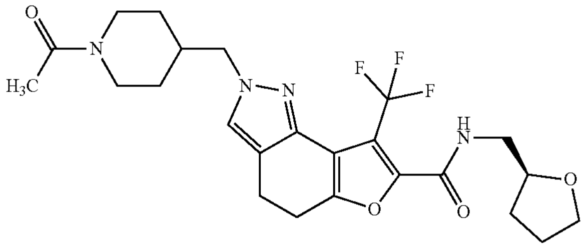 [SMILES: CC(=O)N1CCC(Cn2cc3c(n2)-c2c(oc(C(=O)NC[C@@H]4CCCO4)c2C(F)(F)F)CC3)CC1] 2-[(1-acetylpiperidin-4-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.977 (0.41), 0.986 (0.42), 1.007 (0.46), 1.017 (0.44), 1.118 (0.41), 1.126 (0.42), 1.148 (0.46), 1.157 (0.42), 1.480 (0.53), 1.518 (0.88), 1.539 (0.73), 1.559 (1.12), 1.567 (0.84), 1.576 (0.57), 1.583 (0.43), 1.589 (0.59), 1.788 (0.58), 1.793 (0.71), 1.809 (1.28), 1.828 (1.25), 1.845 (0.82), 1.861 (0.69), 1.870 (0.47), 1.877 (0.54), 1.882 (0.48), 1.889 (0.64), 1.899 (0.41), 1.903 (0.50), 1.910 (0.45), 1.924 (0.41), 1.961 (16.00), 1.987 (0.42), 1.997 (0.48), 2.331 (1.16), 2.337 (0.52), 2.445 (0.57), 2.518 (5.61), 2.523 (3.69), 2.673 (1.12), 2.678 (0.51), 2.839 (0.56), 2.844 (0.57), 2.862 (2.43), 2.880 (2.03), 2.924 (2.41), 2.940 (3.05), 2.947 (1.08), 2.959 (1.38), 2.964 (1.25), 2.990 (0.42), 3.253 (1.98), 3.268 (3.82), 3.283 (2.16), 3.597 (0.45), 3.613 (0.96), 3.616 (1.00), 3.633 (1.23), 3.651 (0.72), 3.740 (0.65), 3.757 (1.58), 3.761 (1.30), 3.773 (1.39), 3.776 (1.16), 3.794 (1.12), 3.934 (0.96), 3.954 (3.12), 3.966 (1.71), 3.972 (2.80), 4.308 (0.55), 4.340 (0.54), 7.533 (4.18), 8.684 (0.72), 8.699 (1.47), 8.713 (0.67). LC-MS (Method 1): $R_t$ = 0.92 min; MS (ESIpos): m/z = 495 [M + H]+ | Intermediate 97 GP H Conditions C 28 mg, 53% yield, 98% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 306 | 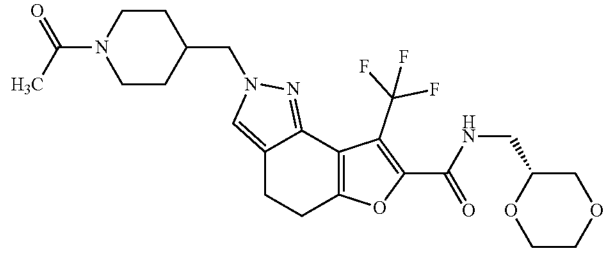 [SMILES: CC(=O)N1CCC(Cn2cc3c(n2)-c2c(oc(C(=O)NC[C@@H]4COCCO4)c2C(F)(F)F)CC3)CC1]<br>2-[(1-acetylpiperidin-4-yl)methyl]-N-{I(2R)-1,4-dioxan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.976 (0.62), 1.009 (0.68), 1.128 (0.61), 1.150 (0.69), 1.352 (0.44), 1.480 (0.82), 1.518 (1.27), 1.555 (1.04), 1.961 (16.00), 2.073 (1.13), 2.845 (0.82), 2.863 (3.01), 2.880 (2.63), 2.926 (3.19), 2.943 (3.48), 2.962 (1.85), 2.990 (0.62), 3.196 (1.46), 3.220 (2.81), 3.235 (2.24), 3.249 (3.50), 3.263 (2.66), 3.279 (2.67), 3.423 (1.58), 3.449 (1.76), 3.456 (1.76), 3.477 (1.40), 3.483 (1.35), 3.524 (1.09), 3.530 (1.11), 3.558 (1.47), 3.585 (0.99), 3.620 (2.07), 3.644 (2.00), 3.694 (1.55), 3.723 (2.79), 3.753 (1.64), 3.795 (0.84), 3.955 (3.45), 3.972 (3.37), 4.307 (0.84), 4.340 (0.80), 7.534 (4.75), 8.542 (0.64), 8.721 (0.90), 8.735 (1.88), 8.750 (0.90).<br>LC-MS (Method 1): $R_t$ = 0.88 min; MS (ESIpos): m/z = 511 [M + H]+ | Intermediate 97<br>GP H<br>Conditions C<br>30 mg, 55% yield, 95% purity |
| 307 | 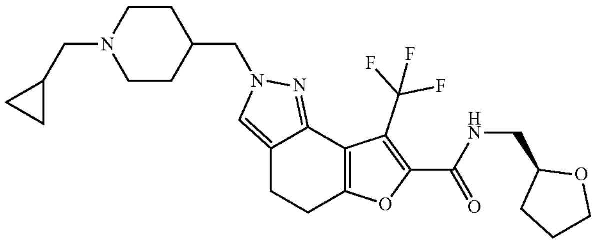 [SMILES: O=C(NC[C@@H]1CCCO1)c1oc2c(c1C(F)(F)F)-c1nn(CC3CCN(CC4CC4)CC3)cc1CC2]<br>2-{[1-(cyclopropylmethyl)piperidin-4-yl]methyl}-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.008 (2.55), 0.018 (8.58), 0.022 (8.22), 0.030 (9.00), 0.044 (2.87), 0.399 (3.12), 0.409 (7.61), 0.414 (7.81), 0.419 (4.13), 0.424 (3.93), 0.429 (8.16), 0.433 (7.76), 0.444 (2.81), 0.766 (1.66), 0.770 (1.71), 0.773 (1.68), 0.778 (1.45), 0.786 (2.67), 0.794 (1.41), 0.798 (1.52), 0.802 (1.57), 0.806 (1.37), 1.154 (1.12), 1.183 (3.20), 1.206 (3.64), 1.235 (1.71), 1.458 (4.29), 1.488 (3.44), 1.539 (2.00), 1.559 (2.61), 1.567 (2.43), 1.576 (2.03), 1.589 (2.28), 1.605 (1.45), 1.715 (1.87), 1.772 (1.57), 1.793 (5.43), 1.809 (5.93), 1.827 (10.05), 1.845 (4.63), 1.869 (2.18), 1.877 (2.28), 1.888 (2.59), 1.903 (2.00), 1.920 (1.48), 1.941 (0.96), 2.107 (13.45), 2.123 (13.18), 2.518 (13.07), 2.523 (8.65), 2.540 (1.06), 2.673 (2.63), 2.839 (2.45), 2.858 (9.34), 2.876 (7.76), 2.897 (5.04), 2.921 (11.25), 2.936 (13.18), 2.955 (2.84), 2.961 (2.63), 3.252 (7.48), 3.268 (14.65), 3.283 (7.91), 3.597 (1.74), 3.616 (4.01), 3.633 (4.86), 3.651 (2.80), 3.740 (2.34), 3.757 (4.36), 3.773 (4.32), 3.775 (3.71), 3.793 (2.43), 3.927 (10.53), 3.934 (5.97), 3.944 (11.00), 3.950 (7.99), 3.966 (3.92), 3.981 (1.01), 4.331 (0.70), 4.349 (0.68), 7.436 (1.15), 7.458 (0.75), 7.524 (16.00), 7.883 (0.70), 7.906 (0.65), 8.636 (1.06), 8.681 (2.67), 8.696 (5.62), 8.711 (2.61).<br>LC-MS (Method 1): $R_t$ = 1.27 min; MS (ESIneg): m/z = 505 [M − H]$^-$ | Intermediate 98<br>GP H<br>Conditions C<br>14 mg, 73% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 308 | 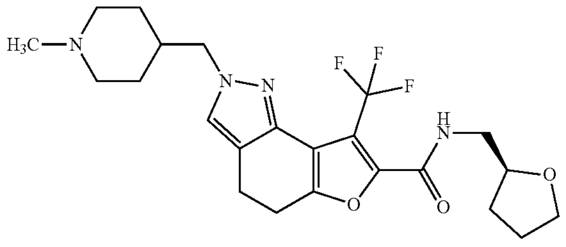 [SMILES: CN1CCC(Cn2cc3c(n2)-c2c(oc(C(=O)NC[C@@H]4CCCO4)c2C(F)(F)F)CC3)CC1] 2-[(1-methylpiperidin-4-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 1.151 (0.67), 1.171 (1.26), 1.180 (1.29), 1.203 (1.43), 1.210 (1.33), 1.232 (1.07), 1.435 (1.55), 1.462 (1.22), 1.539 (0.68), 1.542 (0.65), 1.555 (0.69), 1.559 (0.98), 1.567 (0.91), 1.575 (0.73), 1.583 (0.62), 1.588 (0.81), 1.605 (0.52), 1.659 (0.45), 1.668 (0.49), 1.677 (0.56), 1.687 (0.68), 1.696 (0.52), 1.705 (0.47), 1.726 (1.16), 1.731 (1.23), 1.760 (2.08), 1.772 (0.72), 1.788 (1.67), 1.809 (1.78), 1.827 (1.71), 1.845 (1.14), 1.860 (0.93), 1.865 (0.55), 1.869 (0.65), 1.876 (0.74), 1.881 (0.68), 1.888 (0.86), 1.899 (0.56), 1.902 (0.67), 1.905 (0.66), 1.909 (0.60), 1.920 (0.49), 1.926 (0.46), 2.107 (16.00), 2.337 (0.60), 2.518 (6.75), 2.523 (4.48), 2.673 (1.46), 2.678 (0.89), 2.693 (1.79), 2.722 (1.66), 2.832 (0.83), 2.837 (0.84), 2.856 (3.35), 2.874 (2.65), 2.917 (2.82), 2.919 (2.79), 2.934 (4.06), 2.941 (1.40), 2.953 (0.96), 2.959 (0.92), 3.252 (2.67), 3.267 (5.16), 3.282 (2.92), 3.596 (0.64), 3.613 (1.28), 3.616 (1.38), 3.633 (1.65), 3.650 (0.96), 3.740 (0.84), 3.755 (1.50), 3.757 (1.54), 3.760 (1.05), 3.773 (1.48), 3.775 (1.30), 3.778 (1.09), 3.793 (0.89), 3.922 (3.99), 3.939 (4.10), 3.950 (2.26), 3.965 (1.31), 7.528 (5.50), 8.681 (0.90), 8.696 (1.86), 8.710 (0.87). LC-MS (Method 1): $R_t$ = 1.09 min; MS (ESIneg): m/z = 465 $[M - H]^-$ | Intermediate 100 GP H Conditions C 11 mg, 8% yield, 95% purity |
| 309 | 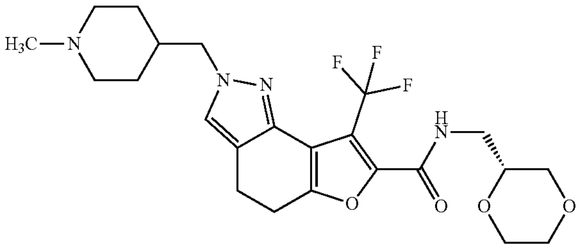 [SMILES: CN1CCC(Cn2cc3c(n2)-c2c(oc(C(=O)NC[C@@H]4COCCO4)c2C(F)(F)F)CC3)CC1] N-{[(2R)-1,4-dioxan-2-yl]methyl}-2-[(1-methylpiperidin-4-yl)methyl]-8-(trifluoromethyl)-4,5-dihydro-2H-furo[2,3-g]indazole-7-carboxamide | $^1$H-NMR (400 MHz, DMSO-d6) δ [ppm]: 1.150 (0.42), 1.172 (1.11), 1.180 (1.20), 1.203 (1.38), 1.211 (1.28), 1.232 (0.72), 1.241 (0.59), 1.436 (1.63), 1.462 (1.27), 1.659 (0.44), 1.669 (0.48), 1.677 (0.58), 1.687 (0.69), 1.696 (0.53), 1.706 (0.48), 1.726 (1.20), 1.731 (1.26), 1.755 (2.03), 1.760 (2.01), 1.784 (1.08), 2.107 (16.00), 2.518 (4.46), 2.523 (2.86), 2.693 (1.89), 2.722 (1.75), 2.833 (0.83), 2.838 (0.84), 2.857 (3.36), 2.874 (2.70), 2.922 (2.88), 2.938 (4.05), 2.945 (1.50), 2.957 (1.00), 2.963 (0.95), 3.195 (1.70), 3.200 (0.90), 3.219 (2.96), 3.224 (2.21), 3.235 (2.11), 3.249 (3.49), 3.262 (1.97), 3.278 (1.35), 3.297 (1.04), 3.423 (0.65), 3.429 (0.77), 3.449 (1.49), 3.455 (1.58), 3.476 (1.27), 3.483 (1.24), 3.524 (1.11), 3.530 (1.24), 3.552 (1.52), 3.559 (1.56), 3.579 (0.65), 3.585 (1.06), 3.620 (2.01), 3.626 (1.25), 3.643 (2.01), 3.658 (0.41), 3.665 (0.47), 3.694 (1.66), 3.700 (1.40), 3.723 (2.86), 3.728 (2.43), 3.752 (1.20), 3.922 (3.95), 3.940 (3.90), 7.530 (5.61), 8.719 (0.92), 8.734 (1.94), 8.748 (0.92). LC-MS (Method 1): $R_t$ = 0.95 min; MS (ESIneg): m/z = 481 $[M - H]^-$ | Intermediate 100 GP H Conditions C 34 mg, 26% yield, 98% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| 310 | 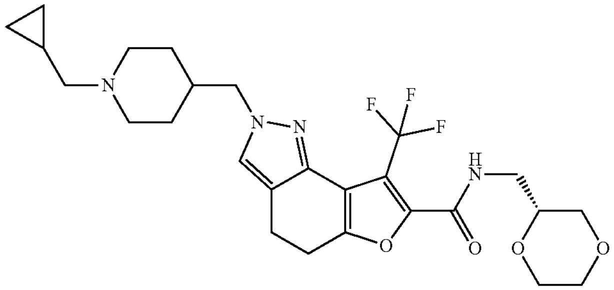 [SMILES: O=C(NC[C@@H]1COCCO1)c1oc2c(c1C(F)(F)F)-c1nn(CC3CCN(CC4CC4)CC3)cc1CC2] 2-{[1-(cyclopropylmethyl)piperidin-4-yl]methyl}-N-{[(2R)-1,4-dioxan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.008 (2.45), 0.018 (8.53), 0.022 (8.17), 0.030 (8.93), 0.034 (8.25), 0.044 (2.80), 0.399 (2.88), 0.409 (7.44), 0.414 (7.53), 0.419 (4.02), 0.424 (3.86), 0.429 (8.04), 0.433 (7.65), 0.444 (2.73), 0.754 (0.91), 0.766 (1.65), 0.769 (1.69), 0.773 (1.71), 0.786 (2.66), 0.798 (1.62), 0.802 (1.66), 1.154 (1.18), 1.176 (3.03), 1.183 (3.27), 1.206 (3.78), 1.214 (3.44), 1.236 (2.08), 1.459 (4.33), 1.487 (3.49), 1.498 (3.93), 1.688 (1.15), 1.706 (1.50), 1.715 (1.76), 1.724 (1.43), 1.743 (1.05), 1.797 (3.01), 1.822 (5.28), 1.850 (2.85), 2.107 (13.10), 2.123 (12.96), 2.337 (1.20), 2.518 (15.59), 2.523 (10.22), 2.678 (1.32), 2.836 (2.35), 2.840 (2.42), 2.859 (9.17), 2.877 (7.59), 2.897 (5.05), 2.924 (12.16), 2.940 (11.91), 2.947 (4.28), 2.959 (2.82), 2.964 (2.64), 3.186 (1.11), 3.195 (4.67), 3.200 (2.41), 3.220 (8.23), 3.224 (6.27), 3.235 (5.64), 3.249 (9.88), 3.262 (5.36), 3.278 (3.91), 3.297 (3.72), 3.423 (2.04), 3.429 (2.33), 3.450 (4.20), 3.456 (4.52), 3.477 (3.71), 3.483 (3.53), 3.524 (3.09), 3.530 (3.42), 3.552 (4.24), 3.559 (4.32), 3.579 (1.83), 3.585 (3.03), 3.605 (1.68), 3.620 (5.53), 3.627 (3.43), 3.643 (5.60), 3.659 (1.15), 3.665 (1.25), 3.694 (4.62), 3.700 (3.88), 3.723 (7.84), 3.729 (6.64), 3.752 (3.36), 3.928 (10.11), 3.945 (9.91), 7.526 (16.00), 8.546 (0.78), 8.720 (2.45), 8.734 (5.25), 8.749 (2.45). LC-MS (Method 1): $R_t$ = 1.11 min; MS (ESIneg): m/z = 521 [M − H]$^-$ | Intermediate 98 GP H Conditions C 10 mg, 52% yield, 95% purity |
| 311 | 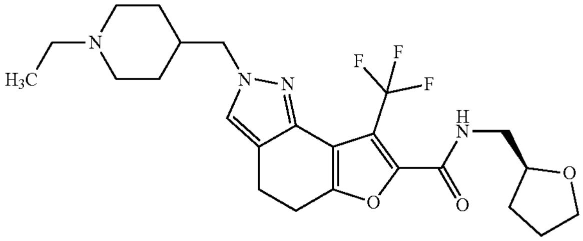 [SMILES: CCN1CCC(Cn2cc3c(n2)-c2c(oc(C(=O)NC[C@@H]4CCCO4)c2C(F)(F)F)CC3)CC1] 2-[(1-ethylpiperidin-4-yl)methyl]-N-{[(2S)-oxolan-2-yl]methyl}-8-(trifluoromethyl)-4,5-dihydro-2H-furo[2,3-g]indazole-7-carboxamide | $^1$H-NMR (400 MHz, DMSO-d6) δ [ppm]: 0.914 (0.63), 0.937 (6.72), 0.955 (16.00), 0.973 (6.90), 1.123 (0.49), 1.133 (0.58), 1.154 (1.48), 1.163 (1.59), 1.185 (1.83), 1.192 (1.66), 1.215 (0.81), 1.224 (0.72), 1.457 (2.10), 1.484 (1.70), 1.508 (0.80), 1.538 (0.89), 1.541 (0.85), 1.550 (0.74), 1.554 (0.83), 1.558 (1.28), 1.566 (1.19), 1.574 (0.99), 1.583 (0.80), 1.588 (1.11), 1.604 (0.71), 1.689 (0.69), 1.708 (0.83), 1.717 (1.09), 1.729 (1.95), 1.734 (2.09), 1.757 (3.15), 1.762 (3.03), 1.772 (1.22), 1.787 (2.54), 1.792 (2.56), 1.808 (2.49), 1.826 (2.43), 1.844 (1.60), 1.859 (1.32), 1.864 (0.77), 1.869 (0.94), 1.876 (1.05), 1.881 (0.94), 1.888 (1.25), 1.898 (0.80), 1.902 (0.92), 1.905 (0.93), 1.909 (0.87), 1.919 (0.69), 1.926 (0.65), 1.940 (0.41), 2.231 (1.89), 2.249 (6.31), 2.266 (6.22), 2.284 (1.75), 2.337 (0.67), 2.518 (7.15), 2.523 (4.76), 2.678 (0.73), 2.796 (2.41), 2.825 (2.37), 2.832 (2.28), 2.857 (4.68), 2.874 (3.71), 2.917 (3.97), 2.919 (3.94), 2.935 (5.65), 2.942 (1.93), 2.954 (1.36), 2.960 (1.29), 3.252 (3.84), 3.267 (7.41), 3.282 (4.34), 3.596 (0.90), 3.612 (1.83), 3.615 (2.01), 3.633 (2.38), 3.650 (1.37), 3.739 (1.21), 3.754 (2.12), 3.756 (2.19), 3.759 (1.53), 3.772 (2.06), 3.775 (1.85), 3.776 (1.59), 3.792 (1.25), 3.921 (5.52), 3.939 (5.69), 3.949 (3.19), 3.965 (1.88), 3.980 (0.46), 7.436 (0.48), 7.523 (7.83), 8.682 (1.24), 8.696 (2.61), 8.711 (1.22). | Intermediate 99 GP H Conditions C 1.4 mg, 14% yield, 95% purity |

TABLE 5-continued

The following examples (212 to 316) were prepared in analogy to example 169 starting from the given intermediates and commercially available amines (or their salts), applying the indicated general procedure.

| Example | Structure IUPAC-Name | Analytical Data | Preparation or Separation Methods |
|---|---|---|---|
| | | LC-MS (Method 1): $R_t$ = 1.17 min; MS (ESIneg): m/z = 479 [M − H]⁻ | |
| 312 | 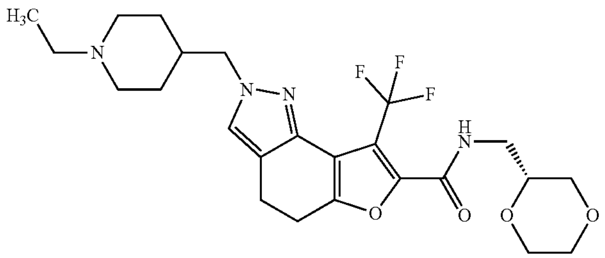 [SMILES: CCN1CCC(Cn2cc3c(n2)-c2c(oc(C(=O)NC[C@@H]4COCCO4)c2C(F)(F)F)CC3)CC1] N-{[(2R)-1,4-dioxan-2-yl]methyl}-2-[(1-ethylpiperidin-4-yl)methyl]-8-(trifluoromethyl)-4,5-dihydro-2H-furo[2,3-g]indazole-7-carboxamide | $^1$H-NMR (400 MHz, DMSO-d6) δ [ppm]: 0.914 (0.41), 0.938 (4.08), 0.956 (9.64), 0.973 (4.17), 1.163 (0.99), 1.185 (1.12), 1.224 (0.49), 1.457 (1.33), 1.495 (4.36), 1.735 (1.32), 1.758 (1.84), 1.788 (0.89), 2.232 (1.17), 2.249 (3.87), 2.267 (3.69), 2.285 (1.09), 2.327 (4.41), 2.331 (3.13), 2.336 (1.40), 2.518 (16.00), 2.523 (10.47), 2.540 (3.30), 2.673 (3.04), 2.678 (1.37), 2.797 (1.49), 2.826 (1.46), 2.834 (1.38), 2.858 (2.88), 2.876 (2.21), 2.924 (2.42), 2.940 (3.44), 2.959 (0.82), 2.964 (0.80), 3.195 (1.56), 3.219 (2.64), 3.224 (2.06), 3.234 (1.93), 3.249 (3.35), 3.262 (2.04), 3.278 (1.98), 3.423 (1.08), 3.429 (1.15), 3.450 (1.61), 3.456 (1.65), 3.477 (1.32), 3.483 (1.31), 3.524 (1.08), 3.530 (1.23), 3.552 (1.42), 3.559 (1.47), 3.579 (0.66), 3.585 (1.03), 3.620 (1.79), 3.643 (1.76), 3.693 (1.46), 3.700 (1.21), 3.723 (2.49), 3.752 (1.09), 3.923 (3.27), 3.941 (3.22), 7.526 (4.95), 8.719 (0.74), 8.734 (1.56), 8.749 (0.79). LC-MS (Method 1): $R_t$ = 1.09 min; MS (ESIneg): m/z = 495 [M − H]⁻ | Intermediate 99 GP H Conditions C 2.2 mg, 21% yield, 95% purity |
| 313 | 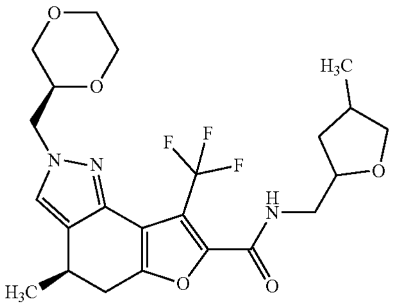 [SMILES: CC1COC(CNC(=O)c2oc3c(c2C(F)(F)F)-c2nn(C[C@H]4COCCO4)cc2[C@H](C)C3)C1] 2,5-anhydro-1,3,4-trideoxy-1-{[(4R or 4S)-2-{[(2S)-1,4-dioxan-2-yl]methyl}-4-methyl-8-(trifluoromethyl)-4,5-dihydro-2H-furo[2,3-g]indazole-7-carbonyl]amino}-4-methylpentitol (mixture of cis/trans isomers) | $^1$H NMR (400 MHz, DMSO-d6) δ [ppm]: 0.99 (d, 3H), 1.16 (dt, 1H), 1.28 (d, 3H), 2.12 (dt, 1H), 2.19-2.30 (m, 1H), 2.61 (dd, 1H), 3.03 (dd, 1H), 3.13-3.22 (m, 1H), 3.23-3.28 (m, 2H), 3.29-3.32 (m, 1H), 3.39-3.47 (m, 1H), 3.51-3.58 (m, 1H), 3.62 (brd, 1H), 3.71-3.76 (m, 2H), 3.76-3.81 (m, 1H), 3.81-3.90 (m, 1H), 3.98 (dq, 1H), 4.05-4.15 (m, 2H), 7.56 (d, 1H), 8.67-8.76 (m, 1H), 1H under DMSO. LC-MS (Method 1): $R_t$ = 1.21 min; MS (ESIpos): m/z = 484 [M + H]⁺ | Intermediate 79 GP G Conditions A 47 mg, 40% yield, 96% purity |
| 314 | 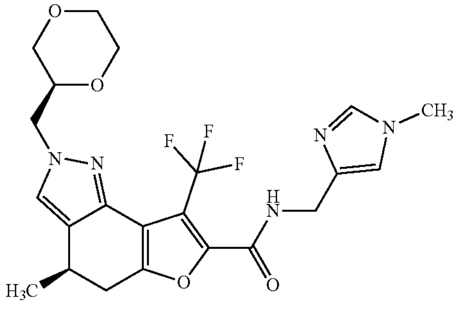 (4R or 4S)-2-{[(2S)-1,4-dioxan-2-yl]methyl}-4-methyl-N-[(1-methyl-1H-imidazol-4-yl)methyl]-8-(trifluoromethyl)- | $^1$H NMR (400 MHz, DMSO-d6) δ [ppm]: 1.28 (d, 3H), 2.59 (dd, 1H), 3.01 (dd, 1H), 3.12-3.21 (m, 1H), 3.27 (dd, 1H), 3.39-3.47 (m, 1H), 3.51-3.59 (m, 1H), 3.60 (s, 3H), 3.63 (d, 1H), 3.70-3.77 (m, 2H), 3.81-3.89 (m, 1H), 4.05-4.15 (m, 2H), 4.27 (dd, 2H), 6.96 (d, 1H), 7.49 (d, 1H), 7.56 (d, 1H), 8.93 (t, 1H). LC-MS (Method 1): $R_t$ = 0.96 min; MS (ESIpos): m/z = 480 [M + H]⁺ | Intermediate 79 GP G Conditions A 17 mg, 27% yield, 97% purity |

TABLE 5-continued

| Ex-ample | Structure IUPAC-Name | Analytical Data | Preparation or Separation Methods |
| --- | --- | --- | --- |
| | The following examples (212 to 316) were prepared in analogy to example 169 starting from the given intermediates and commercially available amines (or their salts), applying the indicated general procedure. | | |
| | 4,5-dihydro-2H-furo[2,3-g]indazole-7-carboxamide | | |
| 315 | 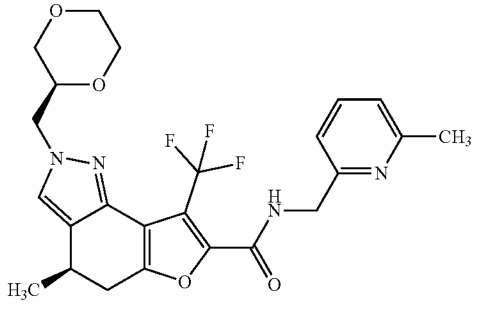 (4R or 4S)-2-{[(2S)-1,4-dioxan-2-yl]methyl}-4-methyl-N-[(6-methylpyridin-2-yl)methyl]-8-(trifluoromethyl)-4,5-dihydro-2H-furo[2,3-g]indazole-7-carboxamide | $^1$H NMR (400 MHz, DMSO-d6) δ [ppm]: 1.29 (d, 3H), 2.46 (s, 3H), 2.63 (dd, 1H), 3.05 (dd, 1H), 3.14-3.23 (m, 1H), 3.27 (dd, 1H), 3.40-3.47 (m, 1H), 3.51-3.59 (m, 1H), 3.63 (brd, 1H), 3.74 (dt, 2H), 3.82-3.89 (m, 1H), 4.04-4.17 (m, 2H), 4.48 (d, 2H), 7.09-7.12 (m, 1H), 7.14 (d, 1H), 7.57 (d, 1H), 7.66 (t, 1H), 9.28 (t, 1H). LC-MS (Method 1): $R_t$ = 1.14 min; MS (ESIpos): m/z = 491 $[M + H]^+$ | Intermediate 79 GP G Conditions A 31 mg, 47% yield, 95% purity |
| 316 | 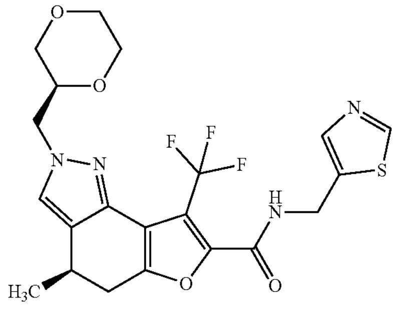 [SMILES: C[C@@H]1Cc2oc(C(=O)NCc3cncs3)c(C(F)(F)F)c2-c2nn(C[C@H]3COCCO3)cc21] (4R or 4S)-2-{[(2S)-1,4-dioxan-2-yl]methyl}-4-methyl-N-[(1,3-thiazol-5-yl)methyl]-8-(trifluoromethyl)-4,5-dihydro-2H-furo[2,3-g]indazole-7-carboxamide | 1H NMR (400 MHz, DMSO-d6) δ [ppm]: 1.28 (d, 3H), 2.61 (dd, 1H), 3.02 (dd, 1H), 3.18 (dt, 1H), 3.27 (dd, 1H), 3.39-3.47 (m, 1H), 3.50-3.58 (m, 1H), 3.62 (br d, 1H), 3.74 (dt, 2H), 3.81-3.88 (m, 1H), 4.03-4.15 (m, 2H), 4.64 (d, 2H), 7.57 (d, 1H), 7.81 (d, 1H), 8.99 (d, 1H), 9.40 (t, 1H) LC-MS (Method 1): $R_t$ = 1.03 min; MS (ESIpos): m/z = 483 $[M + H]^+$ | Intermediate 79 GP G Conditions A 40 mg, 61% yield, 97% purity |

Example 317

8-methyl-N-{[(2S)-oxolan-2-yl]methyl}-2-[(1±)-1-(pyridin-2-yl)ethyl]-4,5-dihydro-2H-furo[2,3-g]indazole-7-carboxamide

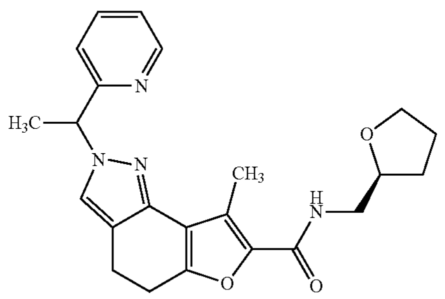 [SMILES: Cc1c(C(=O)NC[C@@H]2CCCO2)oc2c1-c1nn(C(C)c3ccccn3)cc1CC2]

According to GP C (conditions A), 8-methyl-N-{[(2S)-oxolan-2-yl]methyl}-4,5-dihydro-2H-furo[2,3-g]indazole-7-carboxamide (30.0 mg, 99.6 μmol, intermediate 43) together with (1±)-1-(pyridin-2-yl)ethan-1-ol (14.7 mg, 119 μmol; CAS-RN:[18728-61-5]) was dissolved under nitrogen atmosphere in toluene (1 mL). Tri-n-butylphosphine (40 μl, 160 μmol; CAS-RN:[998-40-3]) und TMAD (27.4 mg, 159 μmol; CAS-RN:[10465-78-8]) were added and stirring continued at room temperature overnight. The reaction was diluted with water and concentrated in vacuo. The residue was diluted with 2 ml acetonitrile and purified by preparative HPLC (Method A, gradient C). The product fractions were pooled and concentrated in vacuo to afford 20.4 mg (49% yield, 98% purity) of the title compound.

$^1$H NMR (400 MHz, DMSO-d6) δ[ppm]: 1.52-1.62 (m, 1H), 1.84-1.92 (m, 3H), 1.82 (d, 3H), 2.45 (s, 3H), 2.84-2.92 (m, 4H), 3.18-3.27 (m, 2H), 3.56-3.67 (m, 1H), 3.76 (td, 1H), 3.94 (quin, 1H), 5.61 (q, 1H), 7.09 (d, 1H), 7.29 (ddd, 1H), 7.68 (s, 1H), 7.76 (td, 1H), 7.98 (t, 1H), 8.49-8.57 (m, 1H).

LC-MS (Method 1): $R_t$=1.09 min; MS (ESIpos): m/z=407 $[M+H]^+$

In analogy to the procedure described for example 317, the following example was prepared from the corresponding intermediates.

| | | | |
|---|---|---|---|
| 318 | 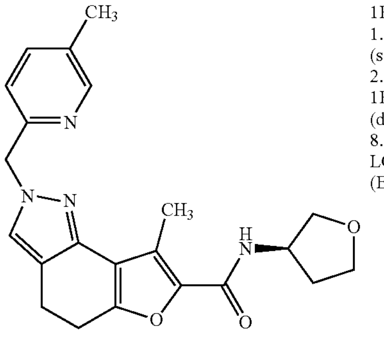 8-methyl-2-[(5-methylpyridin-2-yl)methyl]-N-[(3R)-oxolan-3-yl]-4,5-dihydro-2H-furo[2,3-g]indazole-7-carboxamide | 1H NMR (400 MHz, DMSO-d6) δ [ppm]: 1.87-1.97 (m, 1H), 2.02-2.14 (m, 1H), 2.27 (s, 3H), 2.44 (s, 3H), 2.52-2.53 (m, 1H), 2.84-2.92 (m, 4H), 3.53 (dd, 1H), 3.69 (td, 1H), 3.78-3.88 (m, 2H), 5.32 (s, 2H), 7.01 (d, 1H), 7.56-7.59 (m, 1H), 7.60 (s, 1H), 8.18 (d, 1H), 8.33-8.39 (m, 1H). LC-MS (Method 1): R = 0.99 min; MS (ESIneg): m/z = 391 $[M-H]^-$ | Intermediate 92 and CAS-RN: [22940-71-2] 19.6 mg (26% yield, 91% purity) |

Example 319

2-[(5-cyanopyridin-2-yl)methyl]-8-methyl-N-{[(2S)-oxolan-2-yl]methyl}-4,5-dihydro-2H-furo[2,3-g]indazole-7-carboxamide

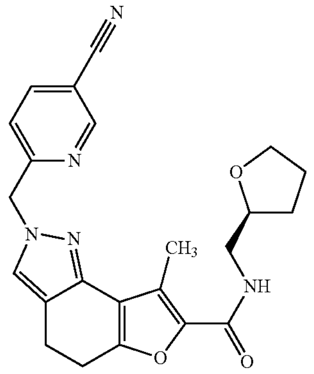 [SMILES: Cc1c(C(=O)NC[C@@H]2CCCO2)oc2c1-c1nn(Cc3ccc(C#N)cn3)cc1CC2]

8-Methyl-N-{[(2S)-oxolan-2-yl]methyl}-4,5-dihydro-1H-furo[2,3-g]indazole-7-carboxamide (Intermediate 43, 1.00 eq, 100 mg, 332 μmol), 6-bromomethyl-nicotinonitrile (CAS No [158626-15-4], 1.5 eq, 98.1 mg, 498 μmol), DMAP (CAS No [1122-58-3], 0.025 eq, 1.01 mg, 8.30 μmol) and potassium carbonate (CAS No [584-08-7], 15 eq, 688 mg, 4.98 mmol) were added to ethyl acetate (5 ml) and was stirred at 70° C. for 18 h under nitrogen. After cooling down to rt, 6-chloromethyl-nicotinonitrile (CAS No [83640-36-2], 1.5 eq, 76.0 mg, 498 μmol) was added to the reaction mixture and stirred at 70° C. for 3 h. The reaction mixture was filtered and additional potassium carbonate (CAS No [584-08-7], 15.0 eq, 688 mg, 4.98 mmol) was added and stirred at 70° C. for 18 h. After cooling down to rt, caesium carbonate (CAS No [534-17-8], 5.00 eq, 541 mg, 1.66 mmol) was added to the reaction mixture and stirred at 70° C. for 18 h. After cooling down to rt, the reaction mixture was filtered and purified by preparative HPLC (Method A, condition C) followed by column chromatography ($SiO_2$, Hexane/EtOAc) to give the title compound (21.0 mg, 13% yield).

$^1$H-NMR (400 MHz, DMSO-d6) δ[ppm]: 0.698 (0.75), 0.771 (0.65), 0.851 (0.72), 0.868 (0.94), 0.887 (0.73), 0.906 (1.21), 0.924 (0.63), 1.162 (2.03), 1.232 (2.59), 1.256 (1.73), 1.296 (1.06), 1.332 (0.88), 1.348 (0.65), 1.548 (0.58), 1.565 (0.76), 1.581 (0.66), 1.609 (0.45), 1.779 (0.70), 1.795 (1.22), 1.812 (1.38), 1.830 (1.32), 1.841 (0.82), 1.858 (0.91), 1.875 (0.60), 2.074 (1.80), 2.428 (16.00), 2.518 (15.89), 2.523 (10.87), 2.901 (8.84), 2.908 (3.38), 3.210 (1.04), 3.215 (1.09), 3.226 (1.99), 3.230 (1.95), 3.241 (1.12), 3.245 (1.21), 3.582 (0.43), 3.601 (0.89), 3.618 (1.26), 3.636 (0.68), 3.731 (0.59), 3.749 (1.11), 3.766 (0.96), 3.783 (0.64), 3.926 (0.98), 3.942 (1.47), 3.957 (0.91), 5.513 (5.98), 7.195 (1.92), 7.214 (2.05), 7.674 (5.03), 7.976 (0.67), 7.991 (1.47), 8.006 (0.70), 8.089 (1.92), 8.276 (2.08), 8.282 (2.16), 8.297 (2.00), 8.302 (1.90), 8.998 (2.16), 9.000 (2.28), 9.003 (2.23), 9.006 (1.96).

LC-MS (Method 1): $R_t$=1.03 min; MS (ESIpos): m/z=418 $[M+H]^+$

Example 320

N-{[(2R)-1,4-dioxan-2-yl]methyl}-2-{[(2S)-1,4-dioxan-2-yl]methyl}-8-(trifluoromethyl)-4,5-dihydro-2H-furo[2,3-g]indazole-7-carboxamide

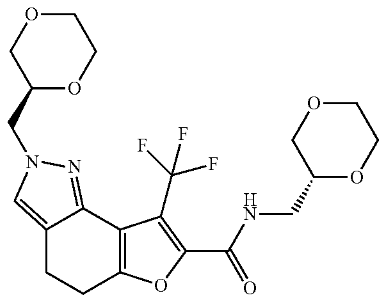 [SMILES: O=C(NC[C@@H]1COCCO1)c1oc2c(c1C(F)(F)F)-c1nn(C[C@H]3COCCO3)cc1CC2]

2-{[(2S)-1,4-dioxan-2-yl]methyl}-8-(trifluoromethyl)-4,5-dihydro-2H-furo[2,3-g]indazole-7-carboxylic acid (Intermediate 69, 1.00 eq., 10.1 g, 27.1 mmol) was dissolved in tetrahydrofuran (110 mL) under Argon, HATU (1.15 eq., 11.8 g, 31.2 mmol) and DIPEA (3.0 eq., 14.1 mL, 81 mmol) were added and the resulting mixture was stirred for few minutes at room temperature. To this mixture (R)-(1,4-dioxan-2-yl)methanamine hydrochloride (1.1 eq., 4.58 g, 29.8 mmol) was added and the mixture stirred for 16 h at room temperature. The reaction mixture was diluted with ethyl acetate and saturated aqueous sodium bicarbonate solution and the corresponding layers were separated. The organic layer was washed with saturated aqueous sodium chloride solution and the resulting organic phase was filtered through a filter paper and concentrated under reduced pressure. Precipitation occurred and the resulting white solids were collected under suction and washed with ethyl acetate to give the desired product (9.7 g, 76% yield) after drying in a rotary evaporator at 50° C. under vacuum.

$^1$H-NMR (400 MHz, DMSO-d6) δ[ppm]: 2.83-2.89 (m, 2H), 2.92-2.98 (m, 2H), 3.19-3.31 (m, 4H), 3.40-3.49 (m, 2H), 3.50-3.59 (m, 2H), 3.60-3.68 (m, 3H), 3.69-3.77 (m, 4H), 3.79-3.83 (m, 1H), 4.05-4.15 (m, 2H), 7.52 (s, 1H), 8.75 (t, 1H)

LC-MS (Method 1): $R_t$=0.92 min; MS (ESIpos): m/z=472 $[M+H]^+$ $[\alpha]_D^{20}$=−11.07° (c=1, DMSO)

Example 321

N-[(5-cyclopropylpyrazin-2-yl)methyl]-2-{[(2S)-1,4-dioxan-2-yl]methyl}-8-(trifluoromethyl)-4,5-dihydro-2H-furo[2,3-g]indazole-7-carboxamide

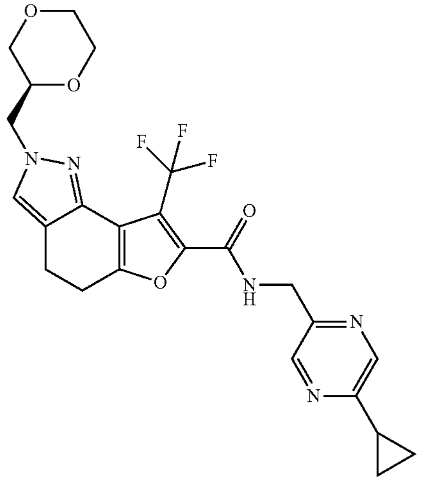 [SMILES: O=C(NCc1cnc(C2CC2)cn1)c1oc2c(c1C(F)(F)F)-c1nn(C[C@H]3COCCO3)cc1CC2]

2-{[(2S)-1,4-dioxan-2-yl]methyl}-8-(trifluoromethyl)-4,5-dihydro-2H-furo[2,3-g]indazole-7-carboxylic acid (Intermediate 69, 1.00 eq, 60 mg, 0.16 mmol) was dissolved in tetrahydrofuran (2.1 mL) under Argon, and HATU (1.5 eq., 92 mg, 0.24 mmol) and DIPEA (3.0 eq., 84 μL, 0.48 mmol) were added and the resulting mixture was stirred for few minutes at room temperature. To this mixture, (5-cyclopropylpyrazin-2-yl)methanamine (2.0 eq., 48 mg, 0.32 mmol) was added and stirred further for 18 h at room temperature. The reaction mixture was diluted with ethyl acetate and saturated aqueous sodium bicarbonate solution and the corresponding layers were separated. The organic layer was washed with saturated aqueous sodium chloride solution and the resulting organic phase was dried with $MgSO_4$, filtered and concentrated under reduced pressure. The residue was diluted with 3 ml DMSO and purified by preparative HPLC (Method A, gradient D). The product fractions were pooled and concentrated in vacuo to afford 24.7 mg (29% yield, 95% purity) of the title compound.

$^1$H NMR (400 MHz, DMSO-$d_6$) δ ppm 0.90-0.94 (m, 2H) 1.00-1.05 (m, 2H) 2.16-2.22 (m, 1H) 2.85-2.89 (m, 2H) 2.94-2.98 (m, 2H) 3.24-3.29 (m, 1H) 3.41-3.47 (m, 1H) 3.51-3.56 (m, 1H) 3.61-3.64 (m, 1H) 3.71-3.77 (m, 2H) 3.79-3.86 (m, 1H) 4.05-4.15 (m, 2H) 4.51-4.52 (m, 2H) 7.52 (s, 1H) 8.41-8.42 (m, 1H) 8.56-8.57 (m, 1H) 9.28-9.31 (m, 1H)

LC-MS (Method 1): $R_t$=1.08 min; MS (ESIpos): m/z=504 $[M+H]^+$

Example 322

(4R or 4S)—N-[(5-cyclopropylpyrazin-2-yl)methyl]-2-{[(2S)-1,4-dioxan-2-yl]methyl}-4-methyl-8-(trifluoromethyl)-4,5-dihydro-2H-furo[2,3-g]indazole-7-carboxamide

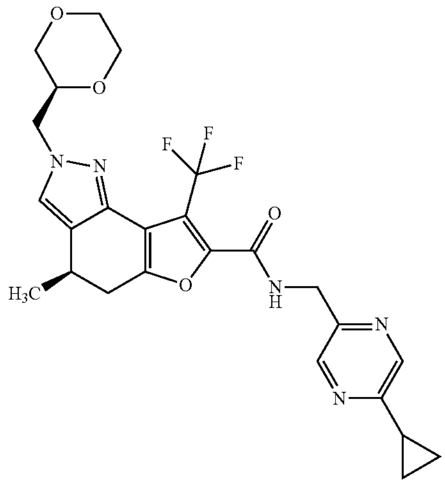 [SMILES: C[C@@H]1Cc2oc(C(=O)NCc3cnc(C4CC4)cn3)c(C(F)(F)F)c2-c2nn(C[C@H]3COCCO3)cc21]

(4R or 4S)-2-{[(2S)-1,4-dioxan-2-yl]methyl}-4-methyl-8-(trifluoromethyl)-4,5-dihydro-2H-furo[2,3-g]indazole-7-carboxylic acid (Intermediate 79, 1.00 eq, 60 mg, 0.15 mmol) was dissolved in tetrahydrofuran (2.0 mL) under Argon, and HATU (1.5 eq., 88 mg, 0.23 mmol) and DIPEA (3.0 eq., 81 μL, 0.47 mmol) were added and the resulting mixture was stirred for few minutes at room temperature. To this mixture, (5-cyclopropylpyrazin-2-yl)methanamine (2.0 eq., 46 mg, 0.31 mmol) was added and stirred further for 18 h at room temperature. The reaction mixture was diluted with ethyl acetate and saturated aqueous sodium bicarbonate solution and the corresponding layers were separated. The organic layer was washed with saturated aqueous sodium chloride solution and the resulting organic phase was dried with $MgSO_4$, filtered and concentrated under reduced pressure. The residue was diluted with 3 ml DMSO and purified by preparative HPLC (Method A, gradient D). The product fractions were pooled and concentrated in vacuo to afford 15 mg (18% yield, 95% purity) of the title compound.

$^1$H NMR (400 MHz, DMSO-$d_6$) δ ppm 0.90-0.94 (m, 2H) 1.00-1.05 (m, 2H) 1.28-1.29 (m, 3H) 2.16-2.22 (m, 1H) 2.59-2.66 (m, 1H) 3.01-3.07 (m, 1H) 3.14-3.22 (m, 1H) 3.24-3.30 (m, 1H) 3.40-3.46 (m, 1H) 3.51-3.56 (m, 1H) 3.61-3.64 (m, 1H) 3.72-3.76 (m, 2H) 3.81-3.88 (m, 1H) 4.05-4.15 (m, 2H) 4.51-4.52 (m, 2H) 7.57 (s, 1H) 8.42-8.43 (m, 1H) 8.56-8.57 (m, 1H) 9.28-9.31 (m, 1H)

LC-MS (Method 1): $R_t$=1.14 min; MS (ESIneg): m/z=516 $[M-H]^-$

Example 323

(4R or 4S)—N-[(5-chloropyrazin-2-yl)methyl]-2-{[(2S)-1,4-dioxan-2-yl]methyl}-4-methyl-8-(trifluoromethyl)-4,5-dihydro-2H-furo[2,3-g]indazole-7-carboxamide

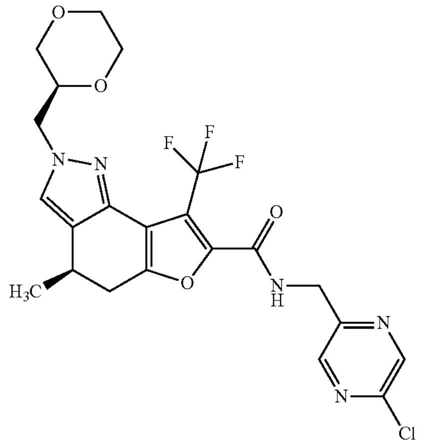 [SMILES: C[C@@H]1Cc2oc(C(=O)NCc3cnc(Cl)cn3)c(C(F)(F)F)c2-c2nn(C[C@H]3COCCO3)cc21]

(4R or 4S)-2-{[(2S)-1,4-dioxan-2-yl]methyl}-4-methyl-8-(trifluoromethyl)-4,5-dihydro-2H-furo[2,3-g]indazole-7-carboxylic acid (Intermediate 79, 1.00 eq, 60 mg, 0.15 mmol) was dissolved in tetrahydrofuran (2.0 mL) under Argon, and HATU (1.5 eq., 88 mg, 0.23 mmol) and DIPEA (3.0 eq., 81 μL, 0.47 mmol) were added and the resulting mixture was stirred for few minutes at room temperature. To this mixture, (5-chloropyrazin-2-yl)methanamine (2.0 eq., 45 mg, 0.31 mmol) was added and stirred further for 18 h at room temperature. The reaction mixture was diluted with ethyl acetate and saturated aqueous sodium bicarbonate solution and the corresponding layers were separated. The organic layer was washed with saturated aqueous sodium chloride solution and the resulting organic phase was dried with $MgSO_4$, filtered and concentrated under reduced pressure. The residue was diluted with 4 ml DMSO and purified by preparative HPLC (Method A, gradient D). The product fractions were pooled and concentrated in vacuo to afford 38.8 mg (49% yield, 95% purity) of the title compound.

$^1$H NMR (400 MHz, DMSO-$d_6$) δ ppm 1.28-1.30 (m, 3H) 2.59-2.66 (m, 1H) 3.01-3.07 (m, 1H) 3.14-3.22 (m, 1H) 3.24-3.30 (m, 1H) 3.41-3.46 (m, 1H) 3.52-3.57 (m, 1H) 3.61-3.64 (m, 1H) 3.72-3.76 (m, 2H) 3.81-3.88 (m, 1H) 4.06-4.15 (m, 2H) 4.58-4.60 (m, 2H) 7.56-7.57 (m, 1H) 8.50-8.51 (m, 1H) 8.76-8.77 (m, 1H) 9.35-9.38 (m, 1H)

LC-MS (Method 1): $R_t$=1.13 min; MS (ESIneg): m/z=510 $[M-H]^-$

EXPERIMENTAL SECTION—BIOLOGICAL ASSAYS

The in vitro activity of the compounds of the present invention can be demonstrated in the following assay:

cAMP HTRF® Assay for Identification of Cellular GPR84 Antagonists

By using a Homogenous Time-Resolved Fluorescence (HTRF®) based assay (#62AM5PEJ, Cisbio, Condolet, France) the inhibition of the Gi-coupled GPR84 receptor can be detected. CHO-K1 cells stably expressing human GPR84 receptor (purchased from DiscoveRx, now Eurofins) were used and treated with Forskolin (F6886, Sigma, Germany) to stimulate membrane adenylyl cyclases and thereby unspecific cAMP formation. Activation of the Gi-coupled GPR84 by a natural or small molecule agonist (e.g. 6-n-octyl aminouracile, inhouse) results in inhibition of cellular cAMP formation which can be released again by antagonists to this receptor. Detection and quantification of cellular cAMP levels in this HTRF assay is achieved by interaction between a fluorescent cAMP tracer (cAMP-d2) and an Eu-cryptate labelled anti-cAMP antibody. Following excitation at 337 nm this pairing allows for the generation of a fluorescence resonance energy transfer (FRET) between the partners and results in FRET induced emissions at 665 nm and 620 nm, the latter representing background signal by Eu-cryptate labelled anti-cAMP antibody. Maximal signal is obtained in the absence of any cellular cAMP (no competition for the binding of the tracer to the antibody). Given the combination of the Gi coupling properties of GPR84 and the competitive nature of the detection system agonist treatment should result in an increase in the HTRF signal due to lowered cAMP levels. Any signal decrease in the presence of Forskolin, agonist and compound is indicative of antagonist mediated abrogation of GPR84 signalling.

For the assay, frozen aliquots of CHO-K1 cells expressing hGPR84 (prepared by acCELLerate, Hamburg, Germany) were thawed and a cell suspension (1.67E+06 cells/mL) in assay media (Ham's F12 Nutrient Mix, Thermo Fisher Scientific, Waltham, USA; 5% fetal calf serum, Biomol, Hamburg, Germany) containing cAMP-d2 (dilution 1:20, supplied with the kit #62AM5PEJ, Cisbio, Condolet, France) was prepared. After recovery of cells for 20 minutes at 37° C., 3 μL/well cell suspension including cAMP-d2 were added to a pre-dispensed assay plate (Greiner Bio-One, Kremsmuenster, Austria) containing 50 nl/well test compound in 100% DMSO or 100% DMSO as control. This was followed by a 30 minutes incubation step at room temperature. The stimulation time was started by addition of 2 μL/well assay media containing 2.5×$EC_{80}$ agonist 6-OAU and 2.5×$EC_{90}$ Forskolin (negative control: 2.5×$EC_{90}$ Forskolin in assay media) and was continued for 30 minutes at room temperature. The reaction was stopped by addition of 3 μL/well lysis buffer containing cAMP Eu-Cryptate antibody (dilution 1:20) (both supplied with the kit #62AM5PEJ, Cisbio, Condolet, France). To enable complete lysis, plates were incubated for 60 minutes at room temperature before measurement in an HTRF reader, e.g. a PHERAstar (BMG Labtech, Ortenberg, Germany).

From the fluorescence emissions at 665 nm (FRET) and at 620 nm (background signal of Eu-cryptate) the ratio (emission at 665 nm divided by emission at 620 nm×10000) was calculated and the data were normalized (reaction without test compound, only 100% DMSO=0% inhibition; all other assay components except agonist=100% inhibition). For dose response testing on the same microtiter plate, compounds were tested at 11 different concentrations in the range of 20 μM to 0.07 nM (20 μM, 5.7 μM, 1.6 μM, 0.47 μM, 0.13 μM, 38 nM, 11 nM, 3.1 nM, 0.89 nM, 0.25 and 0.07 nM; dilution series prepared before the assay at the level of the 100-fold conc. stock solutions by serial 1:3.5 dilutions in 100% DMSO) in duplicate values for each concentration. $IC_{50}$ values were calculated by 4-parameter fitting using a commercial software package (Genedata Screener, Basel, Switzerland).

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

TABLE 6

Potency in GPR84 cAMP HTRF ® assay, the potency is given as $IC_{50}$ [μM].

| Example | GPR84 $IC_{50}$ [μM] |
|---|---|
| 1 | 1.00 |
| 2 | 0.078 |
| 3 | 0.24 |
| 3-1 | 1.16 |
| 3-2 | 0.11 |
| 4 | 1.62 |
| 5 | 1.41 |
| 6 | 0.80 |
| 7 | 0.15 |
| 8 | 0.21 |
| 9 | 0.19 |
| 10 | >20 |
| 11 | >20 |
| 12 | 2.76 |
| 13 | 1.65 |
| 14 | 4.79 |
| 15 | 2.00 |
| 16 | 11.2 |
| 17 | 10.1 |
| 18 | 0.097 |
| 19-1 | 0.064 |
| 19-2 | 0.83 |
| 20 | 5.07 |
| 21 | 0.30 |
| 22 | 0.34 |
| 23 | 0.16 |
| 24 | 6.56 |
| 25 | 0.16 |
| 26 | 1.19 |
| 27 | 17.5 |
| 28 | 4.57 |
| 29 | 0.29 |
| 30 | 3.57 |
| 31 | >20 |
| 32 | 0.15 |
| 33-1 | 1.89 |
| 33-2 | 2.89 |
| 34 | 0.28 |
| 35 | 0.47 |
| 35-1 | 0.18 |
| 35-2 | 0.77 |
| 36 | 1.72 |
| 37 | 9.50 |
| 38 | 0.70 |
| 38-1 | 1.42 |
| 38-2 | 3.52 |
| 39 | 0.96 |
| 39-1 | 0.67 |
| 39-2 | 7.05 |
| 40 | 0.67 |
| 41 | 5.42 |
| 42 | 1.53 |
| 43 | 11.1 |
| 44 | 0.018 |
| 45 | 0.029 |
| 46 | 0.013 |

TABLE 6-continued

| Potency in GPR84 cAMP HTRF ® assay, the potency is given as $IC_{50}$ [μM]. | |
|---|---|
| Example | GPR84 $IC_{50}$ [μM] |
| 47 | 0.019 |
| 48 | 0.097 |
| 49 | 0.11 |
| 50 | 0.035 |
| 50-1 | 0.11 |
| 50-2 | 0.017 |
| 51 | 0.056 |
| 52 | 0.042 |
| 52-1 | 0.095 |
| 52-2 | 0.016 |
| 53 | 0.032 |
| 53-1 | 0.022 |
| 53-2 | 0.072 |
| 54 | 0.55 |
| 55 | 0.049 |
| 55-1 | 0.34 |
| 55-2 | 0.043 |
| 56 | 0.092 |
| 57 | 0.19 |
| 58 | 0.24 |
| 59 | 0.070 |
| 60 | 0.027 |
| 61 | 0.020 |
| 62 | 0.11 |
| 63 | 0.060 |
| 64 | 0.028 |
| 65 | 0.026 |
| 66 | 0.16 |
| 66-1 | 0.063 |
| 66-2 | 0.66 |
| 67 | 1.81 |
| 68 | 0.17 |
| 69 | 0.75 |
| 70 | 0.077 |
| 71 | 0.36 |
| 72 | 0.24 |
| 73 | 0.14 |
| 74 | 0.16 |
| 75 | 0.060 |
| 76 | 0.065 |
| 77 | 0.17 |
| 78 | 0.19 |
| 79 | 0.058 |
| 80 | 0.057 |
| 81 | 0.38 |
| 82 | 0.44 |
| 83 | 0.18 |
| 84 | 0.18 |
| 85 | 0.26 |
| 86 | 0.18 |
| 87 | 0.20 |
| 88 | 0.11 |
| 89 | 0.040 |
| 90 | 0.047 |
| 91 | 0.064 |
| 92 | 0.13 |
| 93 | 0.017 |
| 94 | 0.021 |
| 95 | 0.031 |
| 96 | 0.047 |
| 97 | 0.62 |
| 98 | 0.47 |
| 99 | 0.21 |
| 100 | 0.31 |
| 101 | 1.54 |
| 102 | 0.76 |
| 103 | 0.17 |
| 104 | 0.18 |
| 105 | 0.072 |
| 106 | 0.077 |
| 107 | 0.035 |
| 108 | 0.058 |
| 109 | 0.011 |
| 110 | 0.010 |
| 111 | 0.14 |

TABLE 6-continued

| Potency in GPR84 cAMP HTRF ® assay, the potency is given as $IC_{50}$ [μM]. | |
|---|---|
| Example | GPR84 $IC_{50}$ [μM] |
| 112 | 0.32 |
| 113 | 0.091 |
| 114 | 0.20 |
| 115 | 0.027 |
| 116 | 0.028 |
| 117 | 0.055 |
| 118 | 0.024 |
| 119 | 0.028 |
| 120 | 0.051 |
| 121 | 0.067 |
| 122 | 0.061 |
| 123 | 0.12 |
| 124 | 0.18 |
| 125 | 0.051 |
| 126 | 0.039 |
| 127 | 0.17 |
| 128 | 0.11 |
| 129 | 0.055 |
| 130 | 1.29 |
| 131 | 0.035 |
| 132 | 0.020 |
| 133 | 0.94 |
| 134 | 0.043 |
| 135 | 0.026 |
| 136 | 0.025 |
| 137 | 0.045 |
| 138 | 0.043 |
| 139 | 0.080 |
| 140 | 0.083 |
| 141 | 0.70 |
| 142 | 0.67 |
| 143 | 0.077 |
| 144 | 7.39 |
| 145 | 0.11 |
| 146 | 0.047 |
| 147 | 0.13 |
| 148 | 0.035 |
| 149 | 0.010 |
| 150 | 0.011 |
| 151 | 0.009 |
| 152 | 0.012 |
| 153 | 0.24 |
| 154 | 0.27 |
| 155 | 0.013 |
| 156 | 0.009 |
| 157 | 0.18 |
| 158 | 1.55 |
| 159 | 1.96 |
| 160 | 2.54 |
| 161 | 6.52 |
| 162 | 6.74 |
| 163 | >20 |
| 164 | 0.98 |
| 165 | 0.11 |
| 166 | 0.11 |
| 167 | 0.060 |
| 168 | 0.010 |
| 169 | 0.013 |
| 170 | 0.030 |
| 171 | 3.69 |
| 172 | 12 |
| 173 | 7.07 |
| 174 | 0.097 |
| 175 | 0.061 |
| 176 | 0.118 |
| 177 | 2.60 |
| 178 | 0.092 |
| 179 | 6.41 |
| 180 | 0.210 |
| 181 | 0.102 |
| 182 | 0.168 |
| 183 | 0.213 |
| 184 | 0.447 |
| 185 | 0.551 |
| 186 | 0.063 |

TABLE 6-continued

| Potency in GPR84 cAMP HTRF ® assay, the potency is given as $IC_{50}$ [μM]. | |
|---|---|
| Example | GPR84 $IC_{50}$ [μM] |
| 187 | 0.040 |
| 188 | 0.223 |
| 189 | 0.109 |
| 190 | 0.238 |
| 191 | 0.008 |
| 192 | 0.006 |
| 193 | 0.032 |
| 194 | 0.030 |
| 195 | 0.029 |
| 196 | 0.182 |
| 197 | 0.098 |
| 198 | 0.094 |
| 199 | 0.079 |
| 200 | 0.111 |
| 201 | 0.080 |
| 201-1 | 0.683 |
| 201-2 | 0.112 |
| 202 | 0.077 |
| 203 | 0.022 |
| 210 | 0.016 |
| 211 | 0.017 |
| 212 | 0.004 |
| 213 | 0.007 |
| 214 | 0.005 |
| 215 | 0.003 |
| 216 | 0.006 |
| 217 | 0.006 |
| 218 | 0.009 |
| 219 | 0.007 |
| 220 | 0.018 |
| 221 | 0.008 |
| 222 | 0.020 |
| 222-1 | 0.012 |
| 222-2 | 0.054 |
| 223 | 0.023 |
| 223-1 | 0.012 |
| 223-2 | 0.051 |
| 224 | 0.018 |
| 224-1 | 0.016 |
| 224-2 | 0.154 |
| 226 | 0.016 |
| 227 | 0.024 |
| 228 | 0.038 |
| 229 | 0.089 |
| 230 | 0.881 |
| 231 | 1.39 |
| 233 | 1.12 |
| 234 | 3.47 |
| 235 | 1.60 |
| 236 | 8.76 |
| 237 | 0.496 |
| 238 | 0.500 |
| 239 | 0.136 |
| 240 | 2.81 |
| 242 | 0.029 |
| 243 | 0.026 |
| 244 | 0.053 |
| 245 | 0.061 |
| 246 | 0.075 |
| 247 | 0.066 |
| 248 | 0.145 |
| 249 | 0.122 |
| 250 | 0.017 |
| 251 | 0.009 |
| 252 | 0.009 |
| 253 | 0.005 |
| 254 | 0.006 |
| 254-1 | 0.010 |
| 254-2 | 0.046 |
| 255 | 0.005 |
| 255-1 | 0.003 |
| 255-2 | 0.016 |
| 256 | 0.014 |
| 257 | 0.025 |
| 258 | 0.005 |

TABLE 6-continued

| Potency in GPR84 cAMP HTRF ® assay, the potency is given as $IC_{50}$ [μM]. | |
|---|---|
| Example | GPR84 $IC_{50}$ [μM] |
| 259 | 0.005 |
| 260 | 0.024 |
| 261 | 0.063 |
| 262 | 0.195 |
| 263 | 0.013 |
| 264 | 0.013 |
| 265 | 0.238 |
| 265-1 | 0.185 |
| 265-2 | 1.21 |
| 266 | 0.607 |
| 267 | 0.057 |
| 268 | 0.038 |
| 269 | 0.027 |
| 270 | 0.192 |
| 271 | 0.026 |
| 272 | 0.042 |
| 273 | 0.009 |
| 274 | 0.010 |
| 275 | 0.141 |
| 276 | 0.156 |
| 277 | 0.008 |
| 278 | 0.010 |
| 279 | 0.053 |
| 280 | 0.016 |
| 281 | 0.021 |
| 282 | 0.010 |
| 283 | 0.139 |
| 284 | 0.086 |
| 285 | 0.021 |
| 286 | 0.011 |
| 287 | 0.010 |
| 288 | 0.101 |
| 289 | 0.801 |
| 290 | 0.004 |
| 291 | 0.005 |
| 292 | 0.006 |
| 293 | 0.007 |
| 294 | 0.008 |
| 295 | 0.008 |
| 296 | 0.009 |
| 297 | 0.013 |
| 298 | 0.009 |
| 299 | 0.024 |
| 300 | 0.322 |
| 301 | 0.723 |
| 302 | 1.51 |
| 303 | 0.006 |
| 304 | 0.013 |
| 305 | 0.016 |
| 306 | 0.027 |
| 307 | 0.062 |
| 308 | 0.151 |
| 309 | 0.154 |
| 310 | 0.197 |
| 311 | 0.202 |
| 312 | 0.760 |
| 313 | 0.021 |
| 314 | 0.040 |
| 315 | 0.266 |
| 316 | 0.374 |
| 317 | 0.578 |
| 318 | 8.31 |
| 319 | 1.12 |
| 320 | 0.012 |
| 321 | 0.003 |
| 322 | 0.002 |
| 323 | 0.003 |

The suitability of the compounds of the present invention for the treatment of PCOS and associated symptoms and pain disorders can be demonstrated in the following animal models:

In Vivo Assay 1: GPR84 Ligand and Antagonist Characterization in PCOS Model

The efficacy of Example 3-2 in vivo on the treatment of POCS was measured in the DHT driven rat PCOS model. At 3 weeks of age, Han-Wistar rats were randomly divided into three experimental groups [control (n=10), DHT (n=10), and DHT plus Example 3-2 (n=10)] and implanted s.c. with 60-d continuous-DHT-release pellets (80 μg/d, Bayer AG, Germany). The dose of DHT was chosen to mimic the hyperandrogenic state in women with PCOS. Controls received identical pellets lacking the bioactive DHT molecule. Animal received a standard chow, only for the last week standard show was replaced by a high fat diet. Rats were weighted bi-weekly from 21 d of age. The study was concluded after 26 days of drug administration. Example 3-2 treated animal gained less weight compared to the untreated control. Statistical analysis was performed with one-way analysis of variance, followed by Bonferroni's multiple comparison test against vehicle control groups using the GraphPad PRISM software, *p<0.05.

TABLE 7

Efficacy of GPR84 antagonist in the rat DHT-PCOS model

| Example | mg/kg p.o.: morning dose s.c.: evening dose | Relative weight vs. Vehicle control |
|---|---|---|
| Vehicle | Vehicle | 100% |
| DHT-Vehicle | Vehicle | 111% |
| DHT - Example 3-2 | p.o.: 60 mg/kg in PEG400/$H_2O$ s.c.: 60 mg/kg in benzyl benzoate/Castor oil (1:9) | 103% * (significant vs. DHT-Vehicle group) |

In Vivo Assay 2: Effects of Example 3-2 in the CFA Pain Model

The efficacy of Example 3-2 in vivo on inflammatory pain was measured in inflamed paws after administration of complete Freund's adjuvant (CFA) (24 h) in the dynamic weight-bearing (DWB) model. The effects of repeated preventive treatment with Example 3-2 on pain following repeated oral administration (3×) in the mouse CFA model of inflammation were investigated using a preventive setting. The GPR84 antagonist Example 3-2 (20 or 60 mg/kg, 3× doses) was administered 2 h before injection of CFA and 6-8 h later at day 0. At 24 h after CFA application, the third dose of Example 3-2 was given 2 h before DWB testing. Statistical analysis was performed with one-way analysis of variance, followed by Bonferroni's multiple comparison test against vehicle control groups using the GraphPad PRISM software, *p<0.05.

TABLE 8

Effects of GPR84 antagonist in the CFA pain model

| Example | mg/kg p.o. | Weight distribution (% weight on injected paw) mean +/− SD |
|---|---|---|
| Vehicle | | 43 +/− 20 |
| Example 3-2 | 3x 20 mg | 60 +/− 21 (not significant vs. vehicle group) |
| Example 3-2 | 3x 60 mg | 83 +/− 18 (significant vs. vehicle group) |

The in vivo activity of the compounds of the present invention can be demonstrated in the following assays:

In Vivo Assay 3: Effects in the Kidney Fibrosis (UUO) Model

The anti-fibrotic effect of examples is evaluated in the kidney fibrosis model. The study is performed on male Sprague Dawley rats (age: 7-8 weeks) that can be obtained from Charles River. Rats are anesthetized with continuous inhaled isoflurane, and the left ureter is exposed via a mid-abdominal incision. The mid-ureter is obstructed by two-point ligation with silk sutures. The SHAM-operated rats (n=6) undergo the same procedure except for the obstruction of the left ureter.

Rats are randomized into three groups (n=12 each group) and are dosed bidaily with vehicle and example compound starting directly after UUO. At nine days after surgery, blood samples as well as kidneys are collected under terminal anesthesia. After centrifugation of the blood samples, serum is isolated. Serum osteopontin levels are assessed via Ella Automated Immunoassay System according to the manufacturers protocol. Kidneys are divided in two parts. One part is snap-frozen in liquid nitrogen for RNA analysis. The other part is stored in Davidson's fixative for the preparation of histological sections. Total RNA is isolated from parts of the harvested kidneys. Kidney tissue is homogenized, and RNA is obtained and transcribed to cDNA. Using TaqMan real time PCR renal mRNA expression of inflammatory and fibrotic markers is analyzed in kidney tissues. For the assessment of fibrosis on the protein level paraffin tissue sections are stained with alpha-smooth muscle actin (αSMA) and Sirius Red/Fast Green Collagen Stainings using standard procedures.

Quantitative measurements of alpha-smooth muscle actin (αSMA)-positive as well as Sirius Red (collagen) positive areas within the kidneys are obtained by computer image analysis using the Axio Scan Z1 (Zeiss) microscope and the Zen software.

All data are expressed as means±S.D. Differences between groups are analyzed by one-way ANOVA with Dunnett's corrections for multiple comparisons. Statistical significance is defined as p<0.05.

In Vivo Assay 4: Effects in Silica Induced Pulmonary Fibrosis

Anti-fibrotic and anti-inflammatory effects of examples are evaluated in the silica mouse model of pulmonary fibrosis in a therapeutic treatment setting.

Adult C57BL/6JR male mice (18-20 g; 9 weeks old) are purchased from (Janvier Labs, Germany). Mice are anesthetized in a chamber with isoflurane (3% v/v) and 2.5 mg of the fine crystalline silica DQ12 dissolved in 70 μl of sterile phosphate buffered saline is applied intratracheally. Control animals receive the same volume of phosphate buffered saline. From day 10 after silica instillation, the animals receive either the GPR84 antagonist examples (p.o. bid) or the ethanesulfonate salt of nintedanib (60 mg/kg p.o bid) for the following 20 days. 30 days after silica instillation, mice are anesthetized with an intraperitoneal injection of ketamine/medetomidine (50 mg/kg and 0.33 mg/kg i.p.) combined with a subcutaneous injection of temgesic (0.06 mg/kg s.c.) and EDTA plasma samples are taken for pharmacokinetic determination of examples plasma levels and determination of biomarkers. After exsanguination, the trachea is cannulated and the lungs of the animals are lavaged (broncho-alveolar lavage fluid, BALF) three times, each time with 0.5 ml ice-cold PBS. Then the lungs of the animals are excised, weighed and snap-frozen on dry ice for biomarker analysis. Cytokines are determined with the Bio-Plex cytokine array system (BIORAD), procollagen Iα1 with an ELISA (R&D Systems) and hydroxyproline with HPLC (Waters). 13,14-dihydro-15keto-PGF2α is measured with an ELISA (Cayman).

Data are presented as means±SEM from 12 animals per group. Statistical analyses are performed using unpaired Student's t-test. P values of <0.05 are considered significant.

In Vivo Assay 5: Effects in Mouse Model of Bleomycin Induced Pulmonary Fibrosis

Example compounds are evaluated in another preclinical model of pulmonary fibrosis. The study is performed on male C57BL/6N mice (age 8 weeks at arrival) that are obtained from Charles River, Germany. At least one day prior to the start of the experiment, all animals are allocated randomly into 11 groups (n=7-12 per group). The rats are dosed bidaily (p.o.) with vehicle, Nintedanib and example compounds starting on day 7 till day (group 1-6) or starting on day 20 till day 34 (group 7-11).

Bleomycin is administered intranasally at a dose of 1 mg/kg to all animals in groups 2-11 on DO. Prior to i.n. administration, mice are anaesthetized i.p. with a combination of ketamine and xylazine.

Animals are examined clinically twice daily. Animals are weighted on D0, D1, from D4 they are weighted every day until D34. On day 21 and 34, after anesthesia, blood is sampled (except group 1) from groups 2-6 and 7-11 respectively. On day 21 and 34, lungs are sampled from groups 1-6 and 7-11, respectively. The lungs are excised by gently opening the thorax and by cutting down either side of the sternum and ribs and trimming back. The lungs are weighted individually using precise analytical balance and weights are recorded. Lungs are placed into marked bottles containing 10% buffered formalin for further histopathological valuation (Ashcroft/Matsuse score, collagen I quantification).

Data for assessment of body weight and lung weight are processed by using MS Excel. Statistical analysis and graphical presentation are performed using Graphpad Prism software (version 8.1.1). One-way ANOVA or Mann-Whitney test is employed. Mixed effects analysis for body weight changes is employed. Differences between groups are considered statistically significant when $p<0.05$.

For histopathological evaluation, whole lungs are embedded in paraffin and stained according to Crossman's Trichrome (Gray P. The Microtomist's Formulary and Guide. Published by Robert E. Krieger Publishing Co.). Pulmonary histological changes are assessed using Matsuse modification of Ashcroft score (Ashcroft H et al. J Clin Pathol (1988) 41:467-70; Matsuse T et al. Eur Respir J (1999) 13:71-77).

Immunohistochemistry for collagen are performed using the anti-collagen 1A1 (COL1A1) antibody. Antigen retrieval is performed using Bloxall pH 9 (PT Link modul, DAKO). Slides are incubated with primary rabbit polyclonal anti-COL1A1 antibody for 1 hour (1:2000) followed by ImmPRESS Detection Kit (Vector) (Autostainer Link48, DAKO). Level of de novo collagen 1A1 (COL1A1) deposition are evaluated using digital image analysis software (Calopix software, TRIBVN, France).

Statistical analysis and graphical presentation are performed using GraphPad Prism software (version 8.1.1). Mann-Whitney test is employed. Differences between groups are considered statistically significant when $p<0.05$.

In Vivo Assay 6: Effects in Kidney Injury (ZSF1) Model

Kidney protective effects of example compounds are evaluated in ZSF1 rats, a model of renal disease.

A total of 45 male obese ZSF1 rats and 30 lean littermates (Charles River) are used in the study. At 14 weeks of age, animals are assigned to one of the 5 experimental groups: lean control animals receiving no drug treatment for 12 weeks (Ln-ZSF1 group); obese control animals receiving vehicle treatment for 12 weeks (Ln-vehicle group); obese animals receiving vehicle treatment for 12 weeks (Ob-vehicle group); obese animals receiving enalapril in drinking water (per day) for 12 weeks (Ob-enalapril group); or obese animals receiving example compounds for 12 weeks (Ob-GPR84).

Metabolic cage studies are performed at 0, 4, 8, 12 weeks of treatment. Urine from the measurement period is collected and stored at −80° C. for measurement of creatinine, urinary total protein, albumin and glucose. Plasma samples are analyzed for triglycerides and cholesterol and non-esterified fatty acids.

Kidneys are divided in two parts. One part is snap-frozen in liquid nitrogen for RNA analysis. The other part is stored in Davidson's fixative for the preparation of histological sections. Total RNA is isolated from parts of harvested kidneys. Kidney tissue is homogenized, and RNA is obtained and transcribed to cDNA. Using TaqMan real time PCR renal mRNA expression of inflammatory and fibrotic markers is analyzed in kidney tissues. For the assessment of fibrosis on the protein level paraffin tissue sections are stained with alpha-smooth muscle actin (αSMA) and Sirius Red/Fast Green Collagen Stainings using standard procedures.

Quantitative measurements of alpha-smooth muscle actin (αSMA)-positive as well as Sirius Red (collagen) positive areas within the kidneys are obtained by computer image analysis using the Axio Scan Z1 (Zeiss) microscope and the Zen software.

In Vivo Assay 7: GPR84 Ligand and Antagonist Characterization in HFD-PCOS Model

The efficacy of example compounds in vivo on the treatment of POCS is measured in the DHT driven rat PCOS model with high fat diet. At 15 weeks of age, Han-Wistar rats are randomly divided into experimental groups [DHT (n=10), and DHT plus example compounds (n=10)] and 60-d continuous-DHT-release pellets are implanted (80 μg/d, Bayer AG, Germany). The dose of DHT is chosen to mimic the hyperandrogenic state in women with PCOS. Controls receive identical pellets lacking the bioactive DHT molecule. Animal receive a high fat diet (RD12492). Rats are weighted bi-weekly. The study is concluded after 28 days of drug administration. The metabolic, fibrotic and inflammatory profile is analyzed including insulin levels and adiponectin/leptin ratio compared to the untreated control. Plasma insulin, adiponectin and leptin is measured with MSD (mesoscale). Statistical analysis is performed with an unpaired t test and the Grubbs test to identify outliers using the GraphPad PRISM software, *$p<0.05$.

In Vivo Assay 8: Effects in the 48 h CFA Pain Model

The efficacy of example compounds in vivo on inflammatory pain is measured in inflamed paws after administration of complete Freunds' adjuvans (CFA, 50 μl) with von Frey measurement after 48 h. The effects of repeated preventive treatment with example compounds on pain following repeated administration in the rat (Han Wistar female, 8 weeks) CFA model of inflammation is investigated using a preventive setting. The GPR84 antagonist example compounds are administered with the first application 2 h before injection of CFA at day 0. At 48 h after CFA application, example compounds are given 2 h before von Frey testing (5 repeated measurements). Statistical analysis is performed with an unpaired t test and the Grubbs test to identify outliers using the GraphPad PRISM software, *$p<0.05$.

In Vivo Assay 9: Effects in the Oxaliplatin Induced Pain Model

The efficacy of example compounds in vivo on chemotherapy (Oxaliplatin; OPNP)) induced pain is measured in a rat Oxaliplatin-induced 6 weeks neuropathic pain model. Sprague Dawley male rats at the age of about 9 weeks are used for the experiment. Rats are randomly divided into experimental groups (e.g. n=10). Pain is induced by oxaliplatin application (2 mg/kg) once per day for 5 days. The GPR84 antagonist example compounds are administered with the first application at d1. Rats are habituated to the circumstances for 30 min before starting with behavioral test. Prior to treatment, von Frey test is conducted on all animals for baseline measurement. To assess mechanical allodynia, paw withdrawal thresholds is measured by applying the von Frey filaments (with ascending weights; 0.4, 0.6, 1.4, 2, 4, 6, 8, 15 g) on the center of the right hind paw. Von Frey tests are conducted prior to test article administration (baseline) and once per week, 1 hr, 2 hr and 4 hr post dosing until the end of the experiment. Statistical analysis is performed with one-way analysis of variance, followed by Dunnett multiple comparison test against vehicle control group using the GraphPad PRISM software, *p<0.05.

In Vivo Assay 10: Effects in the Streptozotocin (STZ)-Induced Neuropathic Pain Model The study assesses the analgesic effect of example compounds to reverse diabetic neuropathy, in the Streptozotocin (STZ)-induced neuropathic pain model. Diabetes is induced in Sprague Dawley male rats by dosing of Streptozotocin (STZ, 60 mg/kg) on study day 0. The development of diabetes is confirmed by the measurement of blood glucose levels on study day 3. On study day 10 the sensitivity of all animals to von Frey filaments is tested and diabetic animals (>300 mg/dL) that show a decrease in the withdrawal force threshold (average pain threshold of ≤15 g for both hind paws) are included in the study. Animals are treated with the example compounds or the vehicle from study day 5 (or alternatively day 10) until day 25. Mechanical pain sensitivity is tested using the von Frey test, which measures the withdrawal force threshold of the animals. Statistical analysis is performed with one-way analysis of variance, followed by Dunnett multiple comparison test against vehicle control group using the GraphPad PRISM software, *p<0.05.

In Vivo Assay 11: Effects in the CDAA-HFD NASH Rat Model

The study assesses the effect of 8 weeks treatment with example compounds on NAFLD activity score including fibrosis stage in male CDAA-HFD rats. About 14 weeks old male Sprague Dawley rats receive the CDAA-HFD diet (Gubra, A16092003) 4 weeks for liver fibrosis induction and for the duration of the study. Rats are randomly divided into experimental groups (e.g. n=12) (Vehicle and example compounds). Animals are treated with the example compounds or the vehicle alone from study day 28 until end of week 14.

After autopsy, liver samples stained with Hematoxylin and Eosin (H&E) are used to score for NAS and fibrosis stage respectively using the clinical criteria outlined by Kleiner et al. 2005. Total NAS represents the sum of scores for steatosis, inflammation, and ballooning, and ranges from 0-8.

The invention claimed is:

1. A compound of general formula (I):

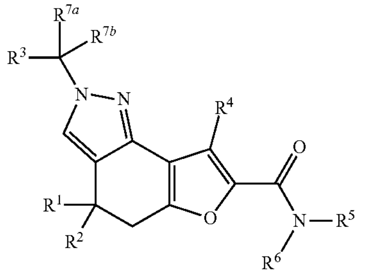

(I)

in which:

$R^1$ represents hydrogen, $C_1$-$C_4$-alkyl or $C_1$-$C_4$-haloalkyl;

$R^2$ represents hydrogen, $C_1$-$C_4$-alkyl or $C_1$-$C_4$-haloalkyl;

or $R^1$ and $R^2$ together with the carbon atom to which they are attached form a 3- to 6-membered cycloalkyl or heterocycloalkyl ring;

$R^3$ represents $C_3$-$C_6$-cycloalkyl, 3- to 6-membered heterocycloalkyl, heterocycloalkyl fused with phenyl or heteroaryl, or heteroaryl, wherein said groups are optionally substituted, one or more times, independently of each other, with $R^8$, and additionally $R^{7a}$ represents hydrogen, deuterium, or $C_1$-$C_4$-alkyl, and $R^{7b}$ represents hydrogen, deuterium, or $C_1$-$C_4$-alkyl;

or $R^3$ represents phenyl, which is optionally substituted, one or more times, independently of each other, with $R^8$, and additionally $R^{7a}$ and $R^{7b}$ represent deuterium;

$R^4$ represents hydrogen, $C_1$-$C_4$-alkyl, $C_1$-$C_4$-haloalkyl or $C_3$-$C_6$-cycloalkyl;

$R^5$, $R^6$ represent, independently of each other, hydrogen, $C_1$-$C_4$-alkyl, $C_2$-$C_4$-hydroxyalkyl, ($C_1$-$C_4$-alkoxy)-($C_2$-$C_4$-alkyl)-, $C_3$-$C_6$-cycloalkyl, $C_1$-$C_4$-haloalkyl, $C_3$-$C_6$-halocycloalkyl, 3- to 6-membered heterocycloalkyl, heterospirocycloalkyl, phenyl, heteroaryl, heterocycloalkyl fused with phenyl or heteroaryl, 3- to 6-membered heterocycloalkyl-($C_1$-$C_3$-alkyl)-, heterospirocycloalkyl-($C_1$-$C_3$-alkyl)-, (heterocycloalkyl fused with phenyl or heteroaryl)-($C_1$-$C_3$-alkyl)-, phenyl-($C_1$-$C_3$-alkyl)- or heteroaryl-($C_1$-$C_3$-alkyl)-, wherein said 3- to 6-membered heterocycloalkyl, heterospirocycloalkyl, heterocycloalkyl fused with phenyl or heteroaryl, phenyl or heteroaryl groups are optionally substituted, one or more times, independently of each other, with $R^9$, or $R^5$ and $R^6$ together with the nitrogen atom to which they are attached form a 3- to 6-membered nitrogen containing heterocyclic ring, optionally containing one additional heteroatom or heteroatom containing group selected from O, NH and S, and which may be optionally substituted, one or more times, independently of each other, with $R^9$;

$R^8$ represents halogen, cyano, $C_1$-$C_4$-alkyl, $C_1$-$C_4$-haloalkyl, $C_1$-$C_3$-alkoxy, $C_1$-$C_3$-haloalkoxy, $C_3$-$C_6$-cycloalkyl, $C_3$-$C_6$-cycloalkyl-($C_1$-$C_3$-alkyl)-, $R^{13}$—(C═O)—, $R^{10}$—O—(C═O)—, $R^{11}$—NH—(C═O)—, or $R^{12}$—($SO_2$)—;

$R^9$ represents halogen, cyano, $C_1$-$C_4$-alkyl, $C_1$-$C_4$-haloalkyl, $H_2N$—$C_1$-$C_4$-alkyl, $C_1$-$C_3$-alkoxy, $C_1$-$C_3$-haloalkoxy, $C_3$-$C_6$-cycloalkyl, $R^{10}$—O—(C═O)—, oxo, 5- to 6-membered heterocycloalkyl-, 5- to 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

$R^{10}$ represents hydrogen, $C_1$-$C_4$-alkyl, or phenyl-$CH_2$—;

$R^{11}$ represents hydrogen, $C_1$-$C_4$-alkyl, or 5- to 6-membered heterocycloalkyl-($C_1$-$C_3$-alkyl)-;

$R^{12}$ represents $C_1$-$C_4$-alkyl or phenyl;

$R^{13}$ represents $C_1$-$C_4$-alkyl, $C_1$-$C_4$-haloalkyl, ($C_1$-$C_4$-alkoxy)-($C_1$-$C_4$-alkyl)-, $C_1$-$C_4$-alkyl-(C═O)—, $C_3$-$C_6$-cycloalkyl, or phenyl, wherein said $C_3$-$C_6$-cycloalkyl group is optionally substituted with $C_1$-$C_4$-alkyl or hydroxy and said phenyl group is optionally substituted, one or more times, independently of each other, with halogen, $C_1$-$C_4$-alkyl, $C_1$-$C_4$-haloalkyl, $C_1$-$C_3$-alkoxy, or $C_1$-$C_3$-haloalkoxy;

or a stereoisomer, a tautomer, an N-oxide, a hydrate, a solvate, or a salt thereof, or a mixture of same.

2. The compound according to claim 1, wherein $R^1$ represents hydrogen, $C_1$-$C_4$-alkyl or $C_1$-$C_4$-haloalkyl;

$R^2$ represents hydrogen or $C_1$-$C_4$-alkyl; or $R^1$ and $R^2$ together with the carbon atom to which they are attached form a 3- to 4-membered cycloalkyl or heterocycloalkyl ring;

$R^3$ represents $C_3$-$C_6$-cycloalkyl, 4- to 6-membered heterocycloalkyl, heterocycloalkyl fused with heteroaryl, or heteroaryl, wherein said groups are optionally substituted, one or more times, independently of each other, with $R^8$, and additionally $R^{7a}$ represents hydrogen, deuterium, or methyl, and $R^{7b}$ represents hydrogen, deuterium, or methyl; or $R^3$ represents phenyl, which is optionally substituted, one or more times, independently of each other, with $R^8$, and additionally $R^{7a}$ and $R^{7b}$ represent deuterium;

$R^4$ represents hydrogen, $C_1$-$C_4$-alkyl, $C_1$-$C_4$-haloalkyl or $C_3$-$C_6$-cycloalkyl;

$R^5$, $R^6$ represent, independently of each other, hydrogen, $C_2$-$C_4$-hydroxyalkyl, ($C_1$-$C_4$-alkoxy)-($C_2$-$C_4$-alkyl)-, 3- to 6-membered heterocycloalkyl, heterospirocycloalkyl, phenyl, heteroaryl, 4- to 6-membered heterocycloalkyl-($C_1$-$C_3$-alkyl)-, heterospirocycloalkyl-($C_1$-$C_3$-alkyl)-, (heterocycloalkyl fused with heteroaryl)-($C_1$-$C_3$-alkyl)-, or heteroaryl-($C_1$-$C_3$-alkyl)-, wherein said 3- to 6-membered heterocycloalkyl, phenyl or heteroaryl groups are optionally substituted, one or more times, independently of each other, with $R^9$, or $R^5$ and $R^6$ together with the nitrogen atom to which they are attached form a 5-membered nitrogen containing heterocyclic ring, which may be optionally substituted, once with $R^9$;

$R^8$ represents halogen, cyano, $C_1$-$C_4$-alkyl, $C_1$-$C_4$-haloalkyl, $C_1$-$C_3$-alkoxy, $C_3$-$C_6$-cycloalkyl, $C_3$-$C_6$-cycloalkyl-($C_1$-$C_3$-alkyl)-, $R^{13}$—(C═O)—, $R^{10}$—O—(C═O)—, $R^{11}$—NH—(C═O)—, or $R^{12}$—($SO_2$)—;

$R^9$ represents halogen, cyano, $C_1$-$C_4$-alkyl, $C_1$-$C_4$-haloalkyl, $H_2N$—$C_1$-$C_4$-alkyl, $C_3$-$C_6$-cycloalkyl, $R^{10}$—O—(C═O)—, oxo, 6-membered heterocycloalkyl-($C_1$-$C_3$-alkyl)-, phenyl, or heteroaryl, wherein said phenyl or heteroaryl group is optionally substituted, one or more times, independently of each other, with halogen, $C_1$-$C_4$-haloalkyl, or $C_1$-$C_3$-alkoxy;

$R^{10}$ represents hydrogen, $C_1$-$C_4$-alkyl, or phenyl-$CH_2$—;

$R^{11}$ represents 5- to 6-membered heterocycloalkyl-($C_1$-$C_3$-alkyl)-;

$R^{12}$ represents $C_1$-$C_4$-alkyl;

$R^{13}$ represents $C_1$-$C_4$-alkyl, ($C_1$-$C_4$-alkoxy)-($C_1$-$C_4$-alkyl)-, $C_1$-$C_4$-alkyl-(C═O)—, $C_3$-$C_6$-cycloalkyl, or phenyl, wherein said $C_3$-$C_6$-cycloalkyl group is optionally substituted with methyl or hydroxy;

or a stereoisomer, a tautomer, an N-oxide, a hydrate, a solvate, or a salt thereof, or a mixture of same.

3. The compound according to claim 1, wherein:

$R^1$ represents hydrogen, methyl or trifluoromethyl;

$R^2$ represents hydrogen or methyl; or $R^1$ and $R^2$ together with the carbon atom to which they are attached form a 3- to 4-membered cycloalkyl ring;

$R^3$ represents cyclopropyl, 4- to 6-membered heterocycloalkyl, 2,3-dihydro[1,4]dioxino[2,3-b]pyridin-2-yl, or heteroaryl, wherein said groups are optionally substituted, one or more times, independently of each other, with $R^8$, and additionally $R^{7a}$ represents hydrogen, deuterium, or methyl, and $R^{7b}$ represents hydrogen, deuterium, or methyl;

or $R^3$ represents phenyl, which is optionally substituted, one or more times, independently of each other, with $R^8$, and additionally $R^{7a}$ and $R^{7b}$ represent deuterium;

$R^4$ represents hydrogen, methyl, $C_1$-haloalkyl or cyclopropyl;

$R^5$ represents hydrogen;

$R^6$ represents methoxy-ethyl, 5-membered heteroaryl, 4- to 6-membered heterocycloalkyl-($C_1$-$C_2$-alkyl)-, heterospirocycloalkyl-methyl, 2,3-dihydro [1,4]dioxino[2,3-b]pyridin-2-ylmethyl, or 5- to 6-membered heteroaryl-($C_1$-$C_2$-alkyl)-, wherein said 4- to 6-membered heterocycloalkyl or heteroaryl groups are optionally substituted, one or more times, independently of each other, with $R^9$;

$R^8$ represents fluoro, chloro, $C_1$-$C_2$-alkyl, trifluoromethyl, $C_1$-$C_3$-alkoxy, cyclopropyl, cyclopropylmethyl, $R^{13}$—(C═O)—, $R^{10}$—O—(C═O)—, $R^{11}$—NH—(C═O)—, or $R^{12}$—($SO_2$)—;

$R^9$ represents fluoro, chloro, $C_1$-$C_3$-alkyl, trifluoromethyl, cyclopropyl, or oxo;

$R^{10}$ represents $C_1$-$C_4$-alkyl, or phenyl-$CH_2$—;

$R^{11}$ represents 5- to 6-membered heterocycloalkyl-methyl;

$R^{12}$ represents methyl;

$R^{13}$ represents methyl, methoxymethyl, ethyl-(C═O)—, cyclopropyl, or phenyl, wherein said cyclopropyl group is optionally substituted with methyl or hydroxy;

or a stereoisomer, a tautomer, an N-oxide, a hydrate, a solvate, or a salt thereof, or a mixture of same.

4. The compound according to claim 1, wherein:

$R^1$ represents hydrogen or methyl;

$R^2$ represents hydrogen or methyl; or $R^1$ and $R^2$ together with the carbon atom to which they are attached form a 3- to 4-membered cycloalkyl ring;

$R^3$ represents cyclopropyl, 2,3-dihydro [1,4]dioxino[2,3-b]pyridin-2-yl, oxetan-3-yl, oxolan-3-yl, oxolan-2-yl, 3-methyloxetan-3-yl, 3-fluorooxetan-3-yl, pyridin-4-yl, pyridin-3-yl, pyridin-2-yl, oxan-4-yl, 1,4-dioxan-2-yl, 6-methylpyridin-3-yl, 5-methylpyridin-2-yl, 3-methylpyridin-2-yl, 2-methylpyridin-4-yl, 6-methylpyridin-2-yl, 3-chloropyridin-2-yl, 6-ethylpyridin-3-yl, 1-acetylpiperidin-4-yl, 3-chloro-5-ethoxypyridin-2-yl, 1-benzoylpiperidin-4-yl, or a group selected from:

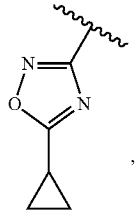 , 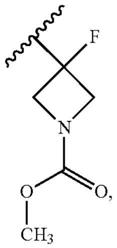 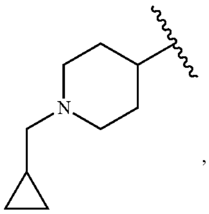 ,

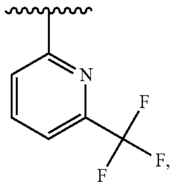 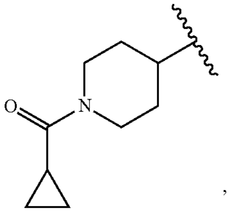 ,

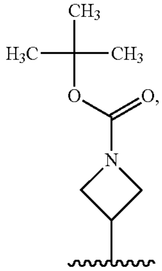 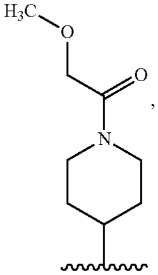 , 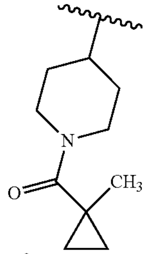 ,

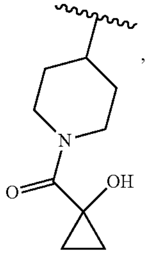 , 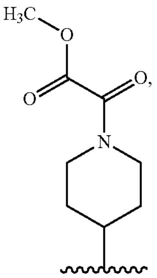 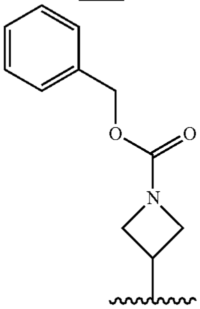 ,

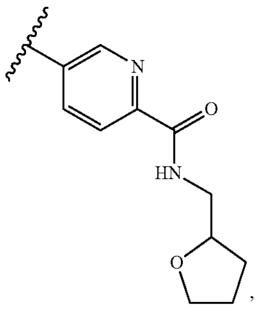 , or 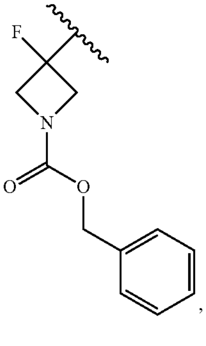 , and additionally $R^{7a}$ represents hydrogen, and $R^{7b}$ represents hydrogen or $R^3$ represents phenyl, and additionally $R^{7a}$ and $R^{7b}$ represent deuterium;

$R^4$ represents methyl, difluoromethyl, trifluoromethyl, or cyclopropyl;

$R^5$ represents hydrogen;

$R^6$ represents (oxolan-2-yl) methyl, (1,3-oxazol-4-yl) methyl, (1,2-oxazol-3-yl) methyl, (4-methyloxolan-2-yl) methyl, (pyrimidin-2-yl) methyl, (pyrazin-2-yl) methyl, (5-methyloxolan-2-yl) methyl, (5-methyloxolan-2-yl) methyl, (1,4-dioxan-2-yl) methyl, (4-methylphenyl) methyl, (5-methylpyrimidin-2-yl) methyl, (5-methylpyrazin-2-yl) methyl, (5-chloropyrazin-2-yl) methyl, (5-cyclopropyl-pyrazin-2-yl) methyl, 2,3-dihydro [1,4]dioxino[2,3-b]pyridin-2-ylmethyl, 1,3-oxazol-2-ylmethyl, 1,3-thiazol-2-ylmethyl, (1-methyl-1H-pyrazol-3-yl) methyl, (1-methyl-1H-imidazol-4-yl) methyl, (5-isopropyl-1,2-oxazol-3-yl) methyl, (5-cyclopropyl-1,2-oxazol-3-yl) methyl, (5,5-dimethyltetrahydrofuran-2-yl) methyl, (4,4-difluorotetrahydrofuran-2-yl) methyl, (6,6-dimethyl-1,4-dioxan-2-yl) methyl, 5-oxaspiro [2.4]heptan-6-ylmethyl, or 2,6-dioxaspiro [3.4]octan-7-ylmethyl;

or a stereoisomer, a tautomer, an N-oxide, a hydrate, a solvate, or a salt thereof, or a mixture of same.

5. The compound according to claim 1, which is selected from the group consisting of:

2-(pyridin-2-ylmethyl)-N-[(2S)-tetrahydrofuran-2-ylmethyl]-4,5-dihydro-2H-furo[2,3-g]indazole-7-carboxamide;

8-methyl-N-[(4-methylphenyl) methyl]-2-[(pyridin-2-yl) methyl]-4,5-dihydro-2H-furo[2,3-g]indazole-7-carboxamide;

8-methyl-2-(pyridin-2-ylmethyl)-N-[(2R/S)-tetrahydrofuran-2-ylmethyl]-4,5-dihydro-2H-furo[2,3-g]indazole-7-carboxamide;

8-methyl-2-(pyridin-2-ylmethyl)-N-[(2R)-tetrahydrofuran-2-ylmethyl]-4,5-dihydro-2H-furo[2,3-g]indazole-7-carboxamide;

8-methyl-2-(pyridin-2-ylmethyl)-N-[(2S)-tetrahydrofuran-2-ylmethyl]-4,5-dihydro-2H-furo[2,3-g]indazole-7-carboxamide;

8-methyl-N-[2-(4-methylpiperazin-1-yl) ethyl]-2-(pyridin-2-ylmethyl)-4,5-dihydro-2H-furo[2,3-g]indazole-7-carboxamide;

8-methyl-N-[(1,2,4-oxadiazol-3-yl) methyl]-2-[(pyridin-2-yl) methyl]-4,5-dihydro-2H-furo[2,3-g]indazole-7-carboxamide;

8-methyl-N-(1,2-oxazol-3-ylmethyl)-2-(pyridin-2-ylmethyl)-4,5-dihydro-2H-furo[2,3-g]indazole-7-carboxamide;

N-[(5-cyclopropyl-1,2-oxazol-3-yl) methyl]-8-methyl-2-(pyridin-2-ylmethyl)-4,5-dihydro-2H-furo[2,3-g]indazole-7-carboxamide;

8-methyl-N-[(5-methyl-1,2-oxazol-3-yl) methyl]-2-(pyridin-2-ylmethyl)-4,5-dihydro-2H-furo[2,3-g]indazole-7-carboxamide;

N-[(2R/S)-2,3-dihydro [1,4]dioxino[2,3-b]pyridin-2-ylmethyl]-8-methyl-2-(pyridin-2-ylmethyl)-4,5-dihydro-2H-furo[2,3-g]indazole-7-carboxamide;

N-[(2R)-2,3-dihydro [1,4]dioxino[2,3-b]pyridin-2-ylmethyl]-8-methyl-2-(pyridin-2-ylmethyl)-4,5-dihydro-2H-furo[2,3-g]indazole-7-carboxamide;

N-[(2S)-2,3-dihydro [1,4]dioxino[2,3-b]pyridin-2-ylmethyl]-8-methyl-2-(pyridin-2-ylmethyl)-4,5-dihydro-2H-furo[2,3-g]indazole-7-carboxamide;

N-(2-hydroxy-2-methylpropyl)-8-methyl-2-(pyridin-2-ylmethyl)-4,5-dihydro-2H-furo[2,3-g]indazole-7-carboxamide;

8-methyl-N-{[5-(morpholin-4-ylmethyl)-1,2-oxazol-3-yl]methyl}-2-(pyridin-2-ylmethyl)-4,5-dihydro-2H-furo[2,3-g]indazole-7-carboxamide;

8-methyl-2-(pyridin-2-ylmethyl)-N-(2-{4-[5-(trifluoromethyl) pyridin-2-yl]piperazin-1-yl}ethyl)-4,5-dihydro-2H-furo[2,3-g]indazole-7-carboxamide;

8-methyl-2-(pyridin-2-ylmethyl)-N-(2-{4-[3-(trifluoromethyl) phenyl]piperazin-1-yl}ethyl)-4,5-dihydro-2H-furo[2,3-g]indazole-7-carboxamide;

N-{[5-(3-methoxyphenyl)-1,2-oxazol-3-yl]methyl}-8-methyl-2-(pyridin-2-ylmethyl)-4,5-dihydro-2H-furo[2,3-g]indazole-7-carboxamide;

8-methyl-N-[(4-methyl-1,2,5-oxadiazol-3-yl) methyl]-2-(pyridin-2-ylmethyl)-4,5-dihydro-2H-furo[2,3-g]indazole-7-carboxamide;

N-[(5-cyclopropyl-1,2-oxazol-4-yl) methyl]-8-methyl-2-(pyridin-2-ylmethyl)-4,5-dihydro-2H-furo[2,3-g]indazole-7-carboxamide;

N-{[5-(2-chlorophenyl)-1,2-oxazol-3-yl]methyl}-8-methyl-2-(pyridin-2-ylmethyl)-4,5-dihydro-2H-furo[2,3-g]indazole-7-carboxamide;

N-[(5-isopropyl-1,2-oxazol-3-yl) methyl]-8-methyl-2-(pyridin-2-ylmethyl)-4,5-dihydro-2H-furo[2,3-g]indazole-7-carboxamide;

N-[(2R)-1,4-dioxan-2-ylmethyl]-8-methyl-2-(pyridin-2-ylmethyl)-4,5-dihydro-2H-furo[2,3-g]indazole-7-carboxamide;

N-{[(2S)-1,4-dioxan-2-yl]methyl}-8-methyl-2-[(pyridin-2-yl) methyl]-4,5-dihydro-2H-furo[2,3-g]indazole-7-carboxamide;

8-methyl-2-(pyridin-2-ylmethyl)-N-(4H-1,2,4-triazol-3-ylmethyl)-4,5-dihydro-2H-furo[2,3-g]indazole-7-carboxamide;

8-methyl-N,2-bis (pyridin-2-ylmethyl)-4,5-dihydro-2H-furo[2,3-g]indazole-7-carboxamide;

8-methyl-N-(1H-pyrazol-3-ylmethyl)-2-(pyridin-2-ylmethyl)-4,5-dihydro-2H-furo[2,3-g]indazole-7-carboxamide;

8-methyl-2-(pyridin-2-ylmethyl)-N-(1,3-thiazol-2-ylmethyl)-4,5-dihydro-2H-furo[2,3-g]indazole-7-carboxamide;

8-methyl-N-(1,2-oxazol-4-ylmethyl)-2-(pyridin-2-ylmethyl)-4,5-dihydro-2H-furo[2,3-g]indazole-7-carboxamide;

8-methyl-2-(pyridin-2-ylmethyl)-N-{[5-(trifluoromethyl)-1,2-oxazol-3-yl]methyl}-4,5-dihydro-2H-furo[2,3-g]indazole-7-carboxamide;

8-methyl-N-[(4-methyl-1,2-oxazol-3-yl) methyl]-2-(pyridin-2-ylmethyl)-4,5-dihydro-2H-furo[2,3-g]indazole-7-carboxamide;

N-[(3,5-dimethyl-1,2-oxazol-4-yl) methyl]-8-methyl-2-(pyridin-2-ylmethyl)-4,5-dihydro-2H-furo[2,3-g]indazole-7-carboxamide;

N-[2-(3,3-dimethyl-2-oxoazetidin-1-yl) ethyl]-8-methyl-2-(pyridin-2-ylmethyl)-4,5-dihydro-2H-furo[2,3-g]indazole-7-carboxamide;

N-(2-methoxyethyl)-8-methyl-2-(pyridin-2-ylmethyl)-4,5-dihydro-2H-furo[2,3-g]indazole-7-carboxamide;

[(2R)-2-(aminomethyl) pyrrolidin-1-yl][8-methyl-2-(pyridin-2-ylmethyl)-4,5-dihydro-2H-furo[2,3-g]indazol-7-yl]methanone;

[(2S)-2-(aminomethyl) pyrrolidin-1-yl][8-methyl-2-(pyridin-2-ylmethyl)-4,5-dihydro-2H-furo[2,3-g]indazol-7-yl]methanone;

3-[{{[8-methyl-2-(pyridin-2-ylmethyl)-4,5-dihydro-2H-furo[2,3-g]indazol-7-yl]carbonyl}amino) methyl]-1,2-oxazole-4-carboxylic acid;

8-methyl-N-(1,3-oxazol-2-ylmethyl)-2-(pyridin-2-ylmethyl)-4,5-dihydro-2H-furo[2,3-g]indazole-7-carboxamide;

8-methyl-2-(pyridin-2-ylmethyl)-N-[(3S)-tetrahydrofuran-3-ylmethyl]-4,5-dihydro-2H-furo[2,3-g]indazole-7-carboxamide;

8-methyl-2-(pyridin-2-ylmethyl)-N-[(3R)-tetrahydrofuran-3-ylmethyl]-4,5-dihydro-2H-furo[2,3-g]indazole-7-carboxamide;

8-methyl-N-[(1-methyl-1H-pyrazol-3-yl) methyl]-2-(pyridin-2-ylmethyl)-4,5-dihydro-2H-furo[2,3-g]indazole-7-carboxamide;

8-methyl-N-[(2R/S)-oxetan-2-ylmethyl]-2-(pyridin-2-ylmethyl)-4,5-dihydro-2H-furo[2,3-g]indazole-7-carboxamide;

8-methyl-N-[(2R)-oxetan-2-ylmethyl]-2-(pyridin-2-ylmethyl)-4,5-dihydro-2H-furo[2,3-g]indazole-7-carboxamide;

8-methyl-N-[(2S)-oxetan-2-ylmethyl]-2-(pyridin-2-ylmethyl)-4,5-dihydro-2H-furo[2,3-g]indazole-7-carboxamide;

8-methyl-N-(oxetan-3-ylmethyl)-2-(pyridin-2-ylmethyl)-4,5-dihydro-2H-furo[2,3-g]indazole-7-carboxamide;

N-[(3-fluorooxetan-3-yl) methyl]-8-methyl-2-(pyridin-2-ylmethyl)-4,5-dihydro-2H-furo[2,3-g]indazole-7-carboxamide;

8-methyl-N-{[(2R/S)-4-methylmorpholin-2-yl]methyl}-2-(pyridin-2-ylmethyl)-4,5-dihydro-2H-furo[2,3-g]indazole-7-carboxamide;

8-methyl-N-{[(2R)-4-methylmorpholin-2-yl]methyl}-2-(pyridin-2-ylmethyl)-4,5-dihydro-2H-furo[2,3-g]indazole-7-carboxamide;

8-methyl-N-{[(2S)-4-methylmorpholin-2-yl]methyl}-2-(pyridin-2-ylmethyl)-4,5-dihydro-2H-furo[2,3-g]indazole-7-carboxamide;

8-methyl-N-{[(2R/S)-5-oxotetrahydrofuran-2-yl] methyl}-2-(pyridin-2-ylmethyl)-4,5-dihydro-2H-furo[2,3-g]indazole-7-carboxamide;

8-methyl-N-{[(2R)-5-oxotetrahydrofuran-2-yl]methyl}-2-(pyridin-2-ylmethyl)-4,5-dihydro-2H-furo[2,3-g]indazole-7-carboxamide;

8-methyl-N-{[(2S)-5-oxotetrahydrofuran-2-yl]methyl}-2-(pyridin-2-ylmethyl)-4,5-dihydro-2H-furo[2,3-g]indazole-7-carboxamide;

8-methyl-N-(1-methyl-1H-pyrazol-3-yl)-2-(pyridin-2-ylmethyl)-4,5-dihydro-2H-furo[2,3-g]indazole-7-carboxamide;

8-methyl-N-(pyridin-3-yl)-2-(pyridin-2-ylmethyl)-4,5-dihydro-2H-furo[2,3-g]indazole-7-carboxamide;

8-methyl-N-(2-phenylethyl)-2-(pyridin-2-ylmethyl)-4,5-dihydro-2H-furo[2,3-g]indazole-7-carboxamide;

N-(4-cyanophenyl)-8-methyl-2-(pyridin-2-ylmethyl)-4,5-dihydro-2H-furo[2,3-g]indazole-7-carboxamide;

8-methyl-2-(pyridin-3-ylmethyl)-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-(pyridin-3-ylmethyl)-4,5-dihydro-2H-furo[2,3-g]indazole-7-carboxamide;

8-methyl-2-(pyridin-4-ylmethyl)-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-(pyridin-4-ylmethyl)-4,5-dihydro-2H-furo[2,3-g]indazole-7-carboxamide;

2-(cyclopropylmethyl)-8-methyl-N-[(2S)-tetrahydrofuran-2-ylmethyl]-4,5-dihydro-2H-furo[2,3-g]indazole-7-carboxamide;

2-(cyclopropylmethyl)-N-[(2R)-1,4-dioxan-2-ylmethyl]-8-methyl-4,5-dihydro-2H-furo[2,3-g]indazole-7-carboxamide;

N-[(5-cyclopropyl-1,2-oxazol-3-yl) methyl]-2-[(2R/S)-2,3-dihydro [1,4]dioxino[2,3-b]pyridin-2-ylmethyl]-8-methyl-4,5-dihydro-2H-furo[2,3-g]indazole-7-carboxamide;

N-[(5-cyclopropyl-1,2-oxazol-3-yl) methyl]-2-[(2R)-2,3-dihydro [1,4]dioxino[2,3-b]pyridin-2-ylmethyl]-8-methyl-4,5-dihydro-2H-furo[2,3-g]indazole-7-carboxamide;

N-[(5-cyclopropyl-1,2-oxazol-3-yl) methyl]-2-[(2S)-2,3-dihydro [1,4]dioxino[2,3-b]pyridin-2-ylmethyl]-8-methyl-4,5-dihydro-2H-furo[2,3-g]indazole-7-carboxamide;

2-[(2R/S)-2,3-dihydro [1,4]dioxino[2,3-b]pyridin-2-ylmethyl]-8-methyl-N-[(2R/S)-tetrahydrofuran-2-ylmethyl]-4,5-dihydro-2H-furo[2,3-g]indazole-7-carboxamide;

2-[(2R)-2,3-dihydro [1,4]dioxino[2,3-b]pyridin-2-ylmethyl]-8-methyl-N-[(2R/S)-tetrahydrofuran-2-ylmethyl]-4,5-dihydro-2H-furo[2,3-g]indazole-7-carboxamide;

2-[(2S)-2,3-dihydro [1,4]dioxino[2,3-b]pyridin-2-ylmethyl]-8-methyl-N-[(2R/S)-tetrahydrofuran-2-ylmethyl]-4,5-dihydro-2H-furo[2,3-g]indazole-7-carboxamide;

2-[(2R/S)-2,3-dihydro [1,4]dioxino[2,3-b]pyridin-2-ylmethyl]-8-methyl-N-[(2S)-tetrahydrofuran-2-ylmethyl]-4,5-dihydro-2H-furo[2,3-g]indazole-7-carboxamide;

2-[(2R)-2,3-dihydro [1,4]dioxino[2,3-b]pyridin-2-ylmethyl]-8-methyl-N-[(2S)-tetrahydrofuran-2-ylmethyl]-4,5-dihydro-2H-furo[2,3-g]indazole-7-carboxamide;

2-[(2S)-2,3-dihydro [1,4]dioxino[2,3-b]pyridin-2-ylmethyl]-8-methyl-N-[(2S)-tetrahydrofuran-2-ylmethyl]-4,5-dihydro-2H-furo[2,3-g]indazole-7-carboxamide;

2-[(2R/S)-2,3-dihydro [1,4]dioxino[2,3-b]pyridin-2-ylmethyl]-8-methyl-N-(4-methylbenzyl)-4,5-dihydro-2H-furo[2,3-g]indazole-7-carboxamide;

2-[(2R)-2,3-dihydro [1,4]dioxino[2,3-b]pyridin-2-ylmethyl]-8-methyl-N-(4-methylbenzyl)-4,5-dihydro-2H-furo[2,3-g]indazole-7-carboxamide;

2-[(2S)-2,3-dihydro [1,4]dioxino[2,3-b]pyridin-2-ylmethyl]-8-methyl-N-(4-methylbenzyl)-4,5-dihydro-2H-furo[2,3-g]indazole-7-carboxamide;

2-[(2R/S)-2,3-dihydro [1,4]dioxino[2,3-b]pyridin-2-ylmethyl]-8-methyl-N-[2-(4-methylpiperazin-1-yl) ethyl]-4,5-dihydro-2H-furo[2,3-g]indazole-7-carboxamide;

2-[(2R)-2,3-dihydro [1,4]dioxino[2,3-b]pyridin-2-ylmethyl]-8-methyl-N-[2-(4-methylpiperazin-1-yl) ethyl]-4,5-dihydro-2H-furo[2,3-g]indazole-7-carboxamide;

2-[(2S)-2,3-dihydro [1,4]dioxino[2,3-b]pyridin-2-ylmethyl]-8-methyl-N-[2-(4-methylpiperazin-1-yl) ethyl]-4,5-dihydro-2H-furo[2,3-g]indazole-7-carboxamide;

2-[(2R/S)-2,3-dihydro [1,4]dioxino[2,3-b]pyridin-2-ylmethyl]-8-methyl-N-(1,2-oxazol-3-ylmethyl)-4,5-dihydro-2H-furo[2,3-g]indazole-7-carboxamide;

2-[(2R)-2,3-dihydro [1,4]dioxino[2,3-b]pyridin-2-ylmethyl]-8-methyl-N-(1,2-oxazol-3-ylmethyl)-4,5-dihydro-2H-furo[2,3-g]indazole-7-carboxamide;

2-[(2S)-2,3-dihydro [1,4]dioxino[2,3-b]pyridin-2-ylmethyl]-8-methyl-N-(1,2-oxazol-3-ylmethyl)-4,5-dihydro-2H-furo[2,3-g]indazole-7-carboxamide;

8-methyl-N-[(2S)-tetrahydrofuran-2-ylmethyl]-2-{[6-(trifluoromethyl) pyridin-2-yl]methyl}-4,5-dihydro-2H-furo[2,3-g]indazole-7-carboxamide;

8-methyl-N-[(2S)-tetrahydrofuran-2-ylmethyl]-2-{[5-(trifluoromethyl) pyridin-2-yl]methyl}-4,5-dihydro-2H-furo[2,3-g]indazole-7-carboxamide;

2-[(3-chloro-5-fluoropyridin-2-yl) methyl]-8-methyl-N-[(2S)-tetrahydrofuran-2-ylmethyl]-4,5-dihydro-2H-furo[2,3-g]indazole-7-carboxamide;

2-[(3-chloro-5-ethoxypyridin-2-yl) methyl]-8-methyl-N-[(2S)-tetrahydrofuran-2-ylmethyl]-4,5-dihydro-2H-furo[2,3-g]indazole-7-carboxamide;

2-[(3-chloropyridin-2-yl) methyl]-8-methyl-N-[(2S)-tetrahydrofuran-2-ylmethyl]-4,5-dihydro-2H-furo[2,3-g]indazole-7-carboxamide;

2-[(3-chloropyridin-2-yl) methyl]-N-[(2R)-1,4-dioxan-2-ylmethyl]-8-methyl-4,5-dihydro-2H-furo[2,3-g]indazole-7-carboxamide;

8-methyl-2-[(3-methylpyridin-2-yl) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(3-methylpyridin-2-yl) methyl]-4,5-dihydro-2H-furo[2,3-g]indazole-7-carboxamide;

8-methyl-2-[(5-methylpyridin-2-yl) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(5-methylpyridin-2-yl) methyl]-4,5-dihydro-2H-furo[2,3-g]indazole-7-carboxamide;

8-methyl-2-[(6-methylpyridin-2-yl) methyl]-N-[(2R/S)-tetrahydrofuran-2-ylmethyl]-4,5-dihydro-2H-furo[2,3-g]indazole-7-carboxamide;

8-methyl-2-[(6-methylpyridin-2-yl) methyl]-N-[(2R)-tetrahydrofuran-2-ylmethyl]-4,5-dihydro-2H-furo[2,3-g]indazole-7-carboxamide;

8-methyl-2-[(6-methylpyridin-2-yl) methyl]-N-[(2S)-tetrahydrofuran-2-ylmethyl]-4,5-dihydro-2H-furo[2,3-g]indazole-7-carboxamide;

N-[2-(azetidin-1-yl) ethyl]-8-methyl-2-[(6-methylpyridin-2-yl) methyl]-4,5-dihydro-2H-furo[2,3-g]indazole-7-carboxamide;

N-[(5-cyclopropyl-1,2-oxazol-3-yl) methyl]-8-methyl-2-[(6-methylpyridin-2-yl) methyl]-4,5-dihydro-2H-furo[2,3-g]indazole-7-carboxamide;

8-methyl-2-[(6-methylpyridin-2-yl) methyl]-N-[2-(pyrrolidin-1-yl) ethyl]-4,5-dihydro-2H-furo[2,3-g]indazole-7-carboxamide;

N-[(2R/S)-2,3-dihydro [1,4]dioxino[2,3-b]pyridin-2-ylmethyl]-8-methyl-2-[(6-methylpyridin-2-yl) methyl]-4,5-dihydro-2H-furo[2,3-g]indazole-7-carboxamide;

N-[(2R)-2,3-dihydro [1,4]dioxino[2,3-b]pyridin-2-ylmethyl]-8-methyl-2-[(6-methylpyridin-2-yl) methyl]-4,5-dihydro-2H-furo[2,3-g]indazole-7-carboxamide;

N-[(2S)-2,3-dihydro [1,4]dioxino[2,3-b]pyridin-2-ylmethyl]-8-methyl-2-[(6-methylpyridin-2-yl) methyl]-4,5-dihydro-2H-furo[2,3-g]indazole-7-carboxamide;

8-methyl-N-[(1-methyl-1H-pyrazol-3-yl) methyl]-2-[(6-methylpyridin-2-yl) methyl]-4,5-dihydro-2H-furo[2,3-g]indazole-7-carboxamide;

8-methyl-2-[(6-methylpyridin-2-yl) methyl]-N-(1,3-oxazol-2-ylmethyl)-4,5-dihydro-2H-furo[2,3-g]indazole-7-carboxamide;

8-methyl-2-[(2-methylpyridin-3-yl) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(2-methylpyridin-3-yl) methyl]-4,5-dihydro-2H-furo[2,3-g]indazole-7-carboxamide;

8-methyl-2-[(6-methylpyridin-3-yl) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(6-methylpyridin-3-yl) methyl]-4,5-dihydro-2H-furo[2,3-g]indazole-7-carboxamide;

2-[(2,6-dimethylpyridin-3-yl) methyl]-8-methyl-N-[(2S)-tetrahydrofuran-2-ylmethyl]-4,5-dihydro-2H-furo[2,3-g]indazole-7-carboxamide;

2-[(2,6-dimethylpyridin-3-yl) methyl]-N-[(2R)-1,4-dioxan-2-ylmethyl]-8-methyl-4,5-dihydro-2H-furo[2,3-g]indazole-7-carboxamide;

8-methyl-2-[(2-methylpyridin-4-yl) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(2-methylpyridin-4-yl) methyl]-4,5-dihydro-2H-furo[2,3-g]indazole-7-carboxamide;

2-[(2,6-dimethylpyridin-4-yl) methyl]-8-methyl-N-[(2S)-tetrahydrofuran-2-ylmethyl]-4,5-dihydro-2H-furo[2,3-g]indazole-7-carboxamide;

2-[(2,6-dimethylpyridin-4-yl) methyl]-N-[(2R)-1,4-dioxan-2-ylmethyl]-8-methyl-4,5-dihydro-2H-furo[2,3-g]indazole-7-carboxamide;

8-methyl-2-(pyrimidin-2-ylmethyl)-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-(pyrimidin-2-ylmethyl)-4,5-dihydro-2H-furo[2,3-g]indazole-7-carboxamide;

8-methyl-2-(pyrimidin-5-ylmethyl)-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-(pyrimidin-5-ylmethyl)-4,5-dihydro-2H-furo[2,3-g]indazole-7-carboxamide 2-[(2R)-1,4-dioxan-2-ylmethyl]-8-methyl-N-[(2S)-tetrahydrofuran-2-ylmethyl]-4,5-dihydro-2H-furo[2,3-g]indazole-7-carboxamide;

N,2-bis [(2R)-1,4-dioxan-2-ylmethyl]-8-methyl-4,5-dihydro-2H-furo[2,3-g]indazole-7-carboxamide;

2-[(2S)-1,4-dioxan-2-ylmethyl]-8-methyl-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-2-[(2S)-1,4-dioxan-2-ylmethyl]-8-methyl-4,5-dihydro-2H-furo[2,3-g]indazole-7-carboxamide;

8-methyl-2-(oxetan-3-ylmethyl)-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-(oxetan-3-ylmethyl)-4,5-dihydro-2H-furo[2,3-g]indazole-7-carboxamide;

8-methyl-2-[(3-methyloxetan-3-yl) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(3-methyloxetan-3-yl) methyl]-4,5-dihydro-2H-furo[2,3-g]indazole-7-carboxamide;

2-[(3-fluorooxetan-3-yl) methyl]-8-methyl-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-2-[(3-fluorooxetan-3-yl) methyl]-8-methyl-4,5-dihydro-2H-furo[2,3-g]indazole-7-carboxamide;

8-methyl-2-[(2R)-oxetan-2-ylmethyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(2R)-oxetan-2-ylmethyl]-4,5-dihydro-2H-furo[2,3-g]indazole-7-carboxamide;

8-methyl-2-[(2S)-oxetan-2-ylmethyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(2S)-oxetan-2-ylmethyl]-4,5-dihydro-2H-furo[2,3-g]indazole-7-carboxamide;

8-methyl-2-{[(2R)-4-methylmorpholin-2-yl]methyl}-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-{[(2R)-4-methylmorpholin-2-yl]methyl}-4,5-dihydro-2H-furo[2,3-g]indazole-7-carboxamide;

8-methyl-2-{[(2S)-4-methylmorpholin-2-yl]methyl}-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-{[(2S)-4-methylmorpholin-2-yl]methyl}-4,5-dihydro-2H-furo[2,3-g]indazole-7-carboxamide;

8-methyl-2-[(2R)-tetrahydrofuran-2-ylmethyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(2R)-tetrahydrofuran-2-ylmethyl]-4,5-dihydro-2H-furo[2,3-g]indazole-7-carboxamide;

8-methyl-N,2-bis [(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[(2S)-tetrahydrofuran-2-ylmethyl]-4,5-dihydro-2H-furo[2,3-g]indazole-7-carboxamide;

tert-butyl 3-[(8-methyl-7-{[(2S)-tetrahydrofuran-2-ylmethyl]carbamoyl}-4,5-dihydro-2H-furo[2,3-g]indazol-2-yl) methyl]azetidine-1-carboxylate;

tert-butyl 3-[(7-{[(2R)-1,4-dioxan-2-ylmethyl]carbamoyl}-8-methyl-4,5-dihydro-2H-furo[2,3-g]indazol-2-yl) methyl]azetidine-1-carboxylate;

8-methyl-N-[(2S)-tetrahydrofuran-2-ylmethyl]-2-[(3R)-tetrahydrofuran-3-ylmethyl]-4,5-dihydro-2H-furo[2,3-g]indazole-7-carboxamide;

N-[(2R)-1,4-dioxan-2-ylmethyl]-8-methyl-2-[(3R)-tetrahydrofuran-3-ylmethyl]-4,5-dihydro-2H-furo[2,3-g]indazole-7-carboxamide;

8-methyl-N-[(2S)-tetrahydrofuran-2-ylmethyl]-2-[(3S)-tetrahydrofuran-3-ylmethyl]-4,5-dihydro-2H-furo[2,3-g]indazole-7-carboxamide;

N-[(2R)-1,4-dioxan-2-ylmethyl]-8-methyl-2-[(3S)-tetrahydrofuran-3-ylmethyl]-4,5-dihydro-2H-furo[2,3-g]indazole-7-carboxamide;

2-(pyridin-2-ylmethyl)-N-[(2S)-tetrahydrofuran-2-ylmethyl]-8-(trifluoromethyl)-4,5-dihydro-2H-furo[2,3-g]indazole-7-carboxamide;

N-[(2R)-1,4-dioxan-2-ylmethyl]-2-(pyridin-2-ylmethyl)-8-(trifluoromethyl)-4,5-dihydro-2H-furo[2,3-g]indazole-7-carboxamide;

N-[(1-methyl-1H-pyrazol-3-yl) methyl]-2-(pyridin-2-ylmethyl)-8-(trifluoromethyl)-4,5-dihydro-2H-furo[2,3-g]indazole-7-carboxamide;

N-(1,3-oxazol-2-ylmethyl)-2-(pyridin-2-ylmethyl)-8-(trifluoromethyl)-4,5-dihydro-2H-furo[2,3-g]indazole-7-carboxamide;

8-cyclopropyl-2-(pyridin-2-ylmethyl)-N-[(2S)-tetrahydrofuran-2-ylmethyl]-4,5-dihydro-2H-furo[2,3-g]indazole-7-carboxamide;

8-cyclopropyl-N-[(2R)-1,4-dioxan-2-ylmethyl]-2-(pyridin-2-ylmethyl)-4,5-dihydro-2H-furo[2,3-g]indazole-7-carboxamide;

8-cyclopropyl-N-[(1-methyl-1H-pyrazol-3-yl) methyl]-2-(pyridin-2-ylmethyl)-4,5-dihydro-2H-furo[2,3-g]indazole-7-carboxamide;

8-cyclopropyl-N-(1,3-oxazol-2-ylmethyl)-2-(pyridin-2-ylmethyl)-4,5-dihydro-2H-furo[2,3-g]indazole-7-carboxamide;

8'-methyl-N-[(1-methyl-1H-pyrazol-3-yl) methyl]-2'-(pyridin-2-ylmethyl)-2',5'-dihydrospiro [cyclopropane-1,4'-furo[2,3-g]indazole]-7'-carboxamide;

8'-methyl-N-(1,3-oxazol-2-ylmethyl)-2'-(pyridin-2-ylmethyl)-2',5'-dihydrospiro [cyclopropane-1,4'-furo[2,3-g]indazole]-7'-carboxamide;

2'-[(2S)-1,4-dioxan-2-ylmethyl]-8'-methyl-N-[(2S)-tetrahydrofuran-2-ylmethyl]-2',5'-dihydrospiro [cyclopropane-1,4'-furo[2,3-g]indazole]-7'-carboxamide;

N-[(2R)-1,4-dioxan-2-ylmethyl]-2'-[(2S)-1,4-dioxan-2-ylmethyl]-8'-methyl-2',5'-dihydrospiro [cyclopropane-1,4'-furo[2,3-g]indazole]-7'-carboxamide;

2'-[(2S)-1,4-dioxan-2-ylmethyl]-8'-methyl-N-[(1-methyl-1H-pyrazol-3-yl) methyl]-2',5'-dihydrospiro [cyclopropane-1,4'-furo[2,3-g]indazole]-7'-carboxamide;

2'-[(2S)-1,4-dioxan-2-ylmethyl]-8'-methyl-N-(1,3-oxazol-2-ylmethyl)-2',5'-dihydrospiro [cyclopropane-1,4'-furo[2,3-g]indazole]-7'-carboxamide;

2'-(cyclopropylmethyl)-8'-methyl-N-[(2S)-tetrahydrofuran-2-ylmethyl]-2',5'-dihydrospiro [cyclopropane-1,4'-furo[2,3-g]indazole]-7'-carboxamide;

2'-(cyclopropylmethyl)-N-[(2S)-1,4-dioxan-2-ylmethyl]-8'-methyl-2',5'-dihydrospiro [cyclopropane-1,4'-furo[2,3-g]indazole]-7'-carboxamide;

2'-(cyclopropylmethyl)-N-[(2R)-1,4-dioxan-2-ylmethyl]-8'-methyl-2',5'-dihydrospiro [cyclopropane-1,4'-furo[2,3-g]indazole]-7'-carboxamide;

8'-methyl-2'-(pyridin-2-ylmethyl)-N-[(2S)-tetrahydrofuran-2-ylmethyl]-2',5'-dihydrospiro [cyclobutane-1,4'-furo[2,3-g]indazole]-7'-carboxamide;

N-[(2S)-1,4-dioxan-2-ylmethyl]-8'-methyl-2'-(pyridin-2-ylmethyl)-2',5'-dihydrospiro [cyclobutane-1,4'-furo[2,3-g]indazole]-7'-carboxamide;

N-[(2R)-1,4-dioxan-2-ylmethyl]-8'-methyl-2'-(pyridin-2-ylmethyl)-2',5'-dihydrospiro [cyclobutane-1,4'-furo[2,3-g]indazole]-7'-carboxamide;

8-methyl-2-[phenyl ($2H_2$) methyl]-N-[(2S)-tetrahydrofuran-2-ylmethyl]-4,5-dihydro-2H-furo[2,3-g]indazole-7-carboxamide;

N-[(2R)-1,4-dioxan-2-ylmethyl]-8-methyl-2-[phenyl ($2H_2$) methyl]-4,5-dihydro-2H-furo[2,3-g]indazole-7-carboxamide;

2-[(5-cyclopropyl-1,2,4-oxadiazol-3-yl) methyl]-8-methyl-N-[(2S)-tetrahydrofuran-2-ylmethyl]-4,5-dihydro-2H-furo[2,3-g]indazole-7-carboxamide;

2-[(5-cyclopropyl-1,2,4-oxadiazol-3-yl) methyl]-N-[(2R)-1,4-dioxan-2-ylmethyl]-8-methyl-4,5-dihydro-2H-furo[2,3-g]indazole-7-carboxamide;

2'-[(2S)-1,4-dioxan-2-ylmethyl]-8'-methyl-N-[(2S)-tetrahydrofuran-2-ylmethyl]-2',5'-dihydrospiro [cyclobutane-1,4'-furo[2,3-g]indazole]-7'-carboxamide;

N,2'-bis [(2S)-1,4-dioxan-2-ylmethyl]-8'-methyl-2',5'-dihydrospiro [cyclobutane-1,4'-furo[2,3-g]indazole]-7'-carboxamide;

N-[(2R)-1,4-dioxan-2-ylmethyl]-2'-[(2S)-1,4-dioxan-2-ylmethyl]-8'-methyl-2',5'-dihydrospiro [cyclobutane-1,4'-furo[2,3-g]indazole]-7'-carboxamide;

8-methyl-N-[(2S)-tetrahydrofuran-2-ylmethyl]-2-[(6-{[(2S)-tetrahydrofuran-2-ylmethyl] carbamoyl}pyridin-3-yl) methyl]-4,5-dihydro-2H-furo [2,3-g]indazole-7-carboxamide;

N-[(2R)-1,4-dioxan-2-ylmethyl]-2-[(6-{[(2R)-1,4-dioxan-2-ylmethyl]carbamoyl}pyridin-3-yl) methyl]-8-methyl-4,5-dihydro-2H-furo[2,3-g]indazole-7-carboxamide;

4,4,8-trimethyl-2-(pyridin-2-ylmethyl)-N-[(2S)-tetrahydrofuran-2-ylmethyl]-4,5-dihydro-2H-furo[2,3-g]indazole-7-carboxamide;

8'-methyl-2'-(pyridin-2-ylmethyl)-N-[(2S)-tetrahydrofuran-2-ylmethyl]-2',5'-dihydrospiro [cyclopropane-1, 4'-furo[2,3-g]indazole]-7'-carboxamide;

N-[(2R)-1,4-dioxan-2-ylmethyl]-8'-methyl-2'-(pyridin-2-ylmethyl)-2',5'-dihydrospiro [cyclopropane-1,4'-furo [2,3-g]indazole]-7'-carboxamide;

8'-methyl-2'-(pyridin-3-ylmethyl)-N-[(2S)-tetrahydrofuran-2-ylmethyl]-2',5'-dihydrospiro [cyclopropane-1, 4'-furo[2,3-g]indazole]-7'-carboxamide;

N-[(2R)-1,4-dioxan-2-ylmethyl]-8'-methyl-2'-(pyridin-3-ylmethyl)-2',5'-dihydrospiro [cyclopropane-1,4'-furo [2,3-g]indazole]-7'-carboxamide;

benzyl 3-fluoro-3-[(8-methyl-7-{[(2S)-tetrahydrofuran-2-ylmethyl]carbamoyl}-4,5-dihydro-2H-furo[2,3-g]indazol-2-yl) methyl]azetidine-1-carboxylate;

benzyl 3-[(8-methyl-7-{[(2S)-tetrahydrofuran-2-ylmethyl]carbamoyl}-4,5-dihydro-2H-furo[2,3-g]indazol-2-yl) methyl]azetidine-1-carboxylate;

2-[(3-fluoroazetidin-3-yl) methyl]-8-methyl-N-[(2S)-tetrahydrofuran-2-ylmethyl]-4,5-dihydro-2H-furo[2,3-g] indazole-7-carboxamide;

2-(azetidin-3-ylmethyl)-8-methyl-N-[(2S)-tetrahydrofuran-2-ylmethyl]-4,5-dihydro-2H-furo[2,3-g]indazole-7-carboxamide;

2-(azetidin-3-ylmethyl)-N-[(2R)-1,4-dioxan-2-ylmethyl]-8-methyl-4,5-dihydro-2H-furo[2,3-g]indazole-7-carboxamide;

2-[(1-acetylazetidin-3-yl) methyl]-8-methyl-N-[(2S)-tetrahydrofuran-2-ylmethyl]-4,5-dihydro-2H-furo[2,3-g] indazole-7-carboxamide;

2-[(1-acetyl-3-fluoroazetidin-3-yl) methyl]-8-methyl-N-[(2S)-tetrahydrofuran-2-ylmethyl]-4,5-dihydro-2H-furo[2,3-g]indazole-7-carboxamide;

2-{[3-fluoro-1-(methylsulfonyl) azetidin-3-yl]methyl}-8-methyl-N-[(2S)-tetrahydrofuran-2-ylmethyl]-4,5-dihydro-2H-furo[2,3-g]indazole-7-carboxamide;

methyl 3-fluoro-3-[(8-methyl-7-{[(2S)-tetrahydrofuran-2-ylmethyl]carbamoyl}-4,5-dihydro-2H-furo[2,3-g]indazol-2-yl) methyl]azetidine-1-carboxylate;

2'-[(2S)-1,4-dioxan-2-ylmethyl]-N-[(2S)-tetrahydrofuran-2-ylmethyl]-8'-(trifluoromethyl)-2',5'-dihydrospiro [cyclopropane-1,4'-furo[2,3-g]indazole]-7'-carboxamide;

N-{[(2R)-1,4-dioxan-2-yl]methyl}-2'-{[(2S)-1,4-dioxan-2-yl]methyl}-8'-(trifluoromethyl)-2',5'-dihydrospiro [cyclopropane-1,4'-furo[2,3-g]indazole]-7'-carboxamide;

N-{[(2±)-5,5-dimethyloxolan-2-yl]methyl}-8-methyl-2-[(pyridin-2-yl) methyl]-4,5-dihydro-2H-furo[2,3-g]indazole-7-carboxamide;

8-methyl-N-[(oxan-4-yl) methyl]-2-[(pyridin-2-yl) methyl]-4,5-dihydro-2H-furo[2,3-g]indazole-7-carboxamide;

8-methyl-N-{[(2±)-oxan-2-yl]methyl}-2-[(pyridin-2-yl) methyl]-4,5-dihydro-2H-furo[2,3-g]indazole-7-carboxamide;

8-methyl-N-{[(2±)-2-methyloxolan-2-yl]methyl}-2-[(pyridin-2-yl) methyl]-4,5-dihydro-2H-furo[2,3-g]indazole-7-carboxamide;

N-{[(2±)-4,4-difluorooxolan-2-yl]methyl}-8-methyl-2-[(pyridin-2-yl) methyl]-4,5-dihydro-2H-furo[2,3-g]indazole-7-carboxamide;

8-methyl-N-[(4-methyltetrahydrofuran-2-yl) methyl]-2-(2-pyridylmethyl)-4,5-dihydrofuro[2,3-g]indazole-7-carboxamide;

8-methyl-N—{[(2±,5±)-5-methyloxolan-2-yl]methyl}-2-[(pyridin-2-yl) methyl]-4,5-dihydro-2H-furo[2,3-g]indazole-7-carboxamide;

2,5-anhydro-1,3,4-trideoxy-3-methyl-1-({8-methyl-2-[(pyridin-2-yl) methyl]-4,5-dihydro-2H-furo[2,3-g]indazole-7-carbonyl}amino)-D-threo-pentitol (Racemate);

8-methyl-N-{[(6±)-5-oxaspiro [2.4]heptan-6-yl]methyl}-2-[(pyridin-2-yl) methyl]-4,5-dihydro-2H-furo[2,3-g]indazole-7-carboxamide;

N-{[(2±)-3,3-dimethyloxolan-2-yl]methyl}-8-methyl-2-[(pyridin-2-yl) methyl]-4,5-dihydro-2H-furo[2,3-g]indazole-7-carboxamide;

N-{[(6±)-2,5-dioxaspiro [3.4]octan-6-yl]methyl}-8-methyl-2-[(pyridin-2-yl) methyl]-4,5-dihydro-2H-furo[2,3-g]indazole-7-carboxamide;

N-{[(2±)-6,6-dimethyl-1,4-dioxan-2-yl]methyl}-8-methyl-2-[(pyridin-2-yl) methyl]-4,5-dihydro-2H-furo[2,3-g]indazole-7-carboxamide;

2-[(4-fluoropyridin-2-yl) methyl]-8-methyl-N-{[(2S)-oxolan-2-yl]methyl}-4,5-dihydro-2H-furo[2,3-g]indazole-7-carboxamide;

2-[(5-fluoropyridin-3-yl) methyl]-8-methyl-N-{[(2S)-oxolan-2-yl]methyl}-4,5-dihydro-2H-furo[2,3-g]indazole-7-carboxamide;

8-methyl-N-{[(2S)-oxolan-2-yl]methyl}-2-[(pyridazin-3-yl) methyl]-4,5-dihydro-2H-furo[2,3-g]indazole-7-carboxamide;

N-{[(2R)-1,4-dioxan-2-yl]methyl}-8-methyl-2-[(pyridazin-3-yl) methyl]-4,5-dihydro-2H-furo[2,3-g]indazole-7-carboxamide;

2-[(6-ethylpyridin-3-yl) methyl]-8-methyl-N-{[(2S)-oxolan-2-yl]methyl}-4,5-dihydro-2H-furo[2,3-g]indazole-7-carboxamide;

N-{[(2R)-1,4-dioxan-2-yl]methyl}-2-[(6-ethylpyridin-3-yl) methyl]-8-methyl-4,5-dihydro-2H-furo[2,3-g]indazole-7-carboxamide;

8-methyl-2-[(1,3-oxazol-2-yl) methyl]-N-{[(2S)-oxolan-2-yl]methyl}-4,5-dihydro-2H-furo[2,3-g]indazole-7-carboxamide;

8-methyl-2-[(oxan-4-yl) methyl]-N-{[(2S)-oxolan-2-yl]methyl}-4,5-dihydro-2H-furo[2,3-g]indazole-7-carboxamide;

8-methyl-2-{[(2±)-oxan-2-yl]methyl}-N-{[(2S)-oxolan-2-yl]methyl}-4,5-dihydro-2H-furo[2,3-g]indazole-7-carboxamide;

N-{[(2R)-1,4-dioxan-2-yl]methyl}-2-[(6-methylpyridin-3-yl) methyl]-8-(trifluoromethyl)-4,5-dihydro-2H-furo[2,3-g]indazole-7-carboxamide;

2-[(6-methylpyridin-3-yl) methyl]-N-{[(2S)-oxolan-2-yl]methyl}-8-(trifluoromethyl)-4,5-dihydro-2H-furo[2,3-g]indazole-7-carboxamide;

8-cyclopropyl-N-{[(2R)-1,4-dioxan-2-yl]methyl}-2-{[(2S)-1,4-dioxan-2-yl]methyl}-4,5-dihydro-2H-furo[2,3-g]indazole-7-carboxamide;

8-cyclopropyl-2-{[(2S)-1,4-dioxan-2-yl]methyl}-N-{[(2S)-oxolan-2-yl]methyl}-4,5-dihydro-2H-furo[2,3-g]indazole-7-carboxamide;

N-{[(2±)-5,5-dimethyloxolan-2-yl]methyl}-2'-{[(2S)-1,4-dioxan-2-yl]methyl}-8'-methyl-2',5'-dihydrospiro [cyclopropane-1,4'-furo[2,3-g]indazole]-7'-carboxamide;

N-{[(2±)-6,6-dimethyl-1,4-dioxan-2-yl]methyl}-2'-{[(2S)-1,4-dioxan-2-yl]methyl}-8'-methyl-2',5'-dihydrospiro [cyclopropane-1,4'-furo[2,3-g]indazole]-7'-carboxamide;

N-{[(2±)-4,4-difluorooxolan-2-yl]methyl}-2'-{[(2S)-1,4-dioxan-2-yl]methyl}-8'-methyl-2',5'-dihydrospiro [cyclopropane-1,4'-furo[2,3-g]indazole]-7'-carboxamide;

2'-{[(2S)-1,4-dioxan-2-yl]methyl}-8'-methyl-N—{[(2±,5±)-5-methyloxolan-2-yl]methyl}-2',5'-dihydrospiro [cyclopropane-1,4'-furo[2,3-g]indazole]-7'-carboxamide;

2-[(2S)-1,4-dioxan-2-yl]methyl]-8-methyl-N-[(4-methyltetrahydrofuran-2-yl) methyl]spiro [5H-furo[2,3-g]indazole-4,1'-cyclopropane]-7-carboxamide;

2'-{[(2S)-1,4-dioxan-2-yl]methyl}-8'-methyl-N-{[(6±)-5-oxaspiro [2.4]heptan-6-yl]methyl}-2',5'-dihydrospiro [cyclopropane-1,4'-furo[2,3-g]indazole]-7'-carboxamide;

2'-{[(2S)-1,4-dioxan-2-yl]methyl}-N-{[(6±)-2,5-dioxaspiro [3.4]octan-6-yl]methyl}-8'-methyl-2',5'-dihydrospiro [cyclopropane-1,4'-furo[2,3-g]indazole]-7'-carboxamide;

2'-{[(2S)-1,4-dioxan-2-yl]methyl}-N-{[(6R)-2,5-dioxaspiro [3.4]octan-6-yl]methyl}-8'-methyl-2',5'-dihydrospiro [cyclopropane-1,4'-furo[2,3-g]indazole]-7'-carboxamide 2'-{[(2S)-1,4-dioxan-2-yl]methyl}-N-{[(6S)-2,5-dioxaspiro [3.4]octan-6-yl]methyl}-8'-methyl-2',5'-dihydrospiro [cyclopropane-1,4'-furo[2,3-g]indazole]-7'-carboxamide;

8'-Methyl-2'-(pyridin-4-ylmethyl)-N-[(2S)-tetrahydrofuran-2-ylmethyl]-2',5'-dihydrospiro [cyclobutan-1,4'-furo[2,3-g]indazol]-7'-carboxamide;

8'-Methyl-2'-[(5-methylpyridin-2-yl) methyl]-N-[(2S)-tetrahydrofuran-2-ylmethyl]-2',5'-dihydrospiro [cyclobutan-1,4'-furo[2,3-g]indazol]-7'-carboxamide;

N-{[(2R)-1,4-dioxan-2-yl]methyl}-8'-methyl-2'-[(6-methylpyridin-3-yl) methyl]-2',5'-dihydrospiro [cyclopropane-1,4'-furo[2,3-g]indazole]-7'-carboxamide;

8'-methyl-2'-[(6-methylpyridin-3-yl) methyl]-N-{[(2S)-oxolan-2-yl]methyl}-2',5'-dihydrospiro [cyclopropane-1,4'-furo[2,3-g]indazole]-7'-carboxamide;

N-{[(2R)-1,4-dioxan-2-yl]methyl}-2'-[(6-methylpyridin-3-yl) methyl]-8'-(trifluoromethyl)-2',5'-dihydrospiro [cyclopropane-1,4'-furo[2,3-g]indazole]-7'-carboxamide;

2'-[(6-methylpyridin-3-yl) methyl]-N-{[(2S)-oxolan-2-yl]methyl}-8'-(trifluoromethyl)-2',5'-dihydrospiro [cyclopropane-1,4'-furo[2,3-g]indazole]-7'-carboxamide;

2'-[(5-methylpyridin-2-yl) methyl]-N-{[(2S)-oxolan-2-yl]methyl}-8'-(trifluoromethyl)-2',5'-dihydrospiro [cyclopropane-1,4'-furo[2,3-g]indazole]-7'-carboxamide;

N-{[(2R)-1,4-dioxan-2-yl]methyl}-2'-[(5-methylpyridin-2-yl) methyl]-8'-(trifluoromethyl)-2',5'-dihydrospiro [cyclopropane-1,4'-furo[2,3-g]indazole]-7'-carboxamide;

N-[(2R)-1,4-Dioxan-2-ylmethyl]-2'-(pyridin-4-ylmethyl)-8'-(trifluormethyl)-2',5'-dihydrospiro [cyclopropan-1,4'-furo[2,3-g]indazol]-7'-carboxamide;

2'-(Pyridin-4-ylmethyl)-N-[(2S)-tetrahydrofuran-2-ylmethyl]-8'-(trifluormethyl)-2',5'-dihydrospiro [cyclopropan-1,4'-furo[2,3-g]indazol]-7'-carboxamide;

N-{[(2S)-oxolan-2-yl]methyl}-2'-[(pyridin-2-yl) methyl]-8'-(trifluoromethyl)-2',5'-dihydrospiro [cyclopropane-1,4'-furo[2,3-g]indazole]-7'-carboxamide;

N-[(2R)-1,4-Dioxan-2-ylmethyl]-2'-(pyridin-2-ylmethyl)-8'-(trifluormethyl)-2',5'-dihydrospiro [cyclopropan-1,4'-furo[2,3-g]indazol]-7'-carboxamide;

N,2-bis {[(2R)-1,4-dioxan-2-yl]methyl}-8-(trifluoromethyl)-4,5-dihydro-2H-furo[2,3-g]indazole-7-carboxamide;

2-{[(2S)-1,4-dioxan-2-yl]methyl}-N-{[(2S)-oxolan-2-yl]methyl}-8-(trifluoromethyl)-4,5-dihydro-2H-furo[2,3-g]indazole-7-carboxamide;

N-{[(2±)-4,4-difluorooxolan-2-yl]methyl}-2-{[(2S)-1,4-dioxan-2-yl]methyl}-8-(trifluoromethyl)-4,5-dihydro-2H-furo[2,3-g]indazole-7-carboxamide;

N-{[(2R)-4,4-difluorooxolan-2-yl]methyl}-2-{[(2S)-1,4-dioxan-2-yl]methyl}-8-(trifluoromethyl)-4,5-dihydro-2H-furo[2,3-g]indazole-7-carboxamide;

N-{[(2S)-4,4-difluorooxolan-2-yl]methyl}-2-{[(2S)-1,4-dioxan-2-yl]methyl}-8-(trifluoromethyl)-4,5-dihydro-2H-furo[2,3-g]indazole-7-carboxamide;

N-{[(2±)-5,5-dimethyloxolan-2-yl]methyl}-2-{[(2S)-1,4-dioxan-2-yl]methyl}-8-(trifluoromethyl)-4,5-dihydro-2H-furo[2,3-g]indazole-7-carboxamide;

N-{[(2R)-5,5-dimethyloxolan-2-yl]methyl}-2-{[(2S)-1,4-dioxan-2-yl]methyl}-8-(trifluoromethyl)-4,5-dihydro-2H-furo[2,3-g]indazole-7-carboxamide;

N-{[(2S)-5,5-dimethyloxolan-2-yl]methyl}-2-{[(2S)-1,4-dioxan-2-yl]methyl}-8-(trifluoromethyl)-4,5-dihydro-2H-furo[2,3-g]indazole-7-carboxamide;

2-{[(2S)-1,4-dioxan-2-yl]methyl}-N—{[(2±, 5±)-5-methyloxolan-2-yl]methyl}-8-(trifluoromethyl)-4,5-dihydro-2H-furo[2,3-g]indazole-7-carboxamide;

2-{[(2S)-1,4-dioxan-2-yl]methyl}-N-{[(2R,5R)-5-methyloxolan-2-yl]methyl}-8-(trifluoromethyl)-4,5-dihydro-2H-furo[2,3-g]indazole-7-carboxamide;

2-{[(2S)-1,4-dioxan-2-yl]methyl}-N-{[(2S,5R)-5-methyloxolan-2-yl]methyl}-8-(trifluoromethyl)-4,5-dihydro-2H-furo[2,3-g]indazole-7-carboxamide;

2-{[(2S)-1,4-dioxan-2-yl]methyl}-N-{[(2R,5S)-5-methyloxolan-2-yl]methyl}-8-(trifluoromethyl)-4,5-dihydro-2H-furo[2,3-g]indazole-7-carboxamide;

2-{[(2S)-1,4-dioxan-2-yl]methyl}-N-{[(2S,5S)-5-methyloxolan-2-yl]methyl}-8-(trifluoromethyl)-4,5-dihydro-2H-furo[2,3-g]indazole-7-carboxamide;

2-[(2S)-1,4-Dioxan-2-ylmethyl]-N-(1,3-thiazol-2-ylmethyl)-8-(trifluormethyl)-4,5-dihydro-2H-furo[2,3-g]indazol-7-carboxamide;

2-[(2S)-1,4-Dioxan-2-ylmethyl]-N-[(5-methylpyrazin-2-yl) methyl]-8-(trifluormethyl)-4,5-dihydro-2H-furo[2,3-g]indazol-7-carboxamide;

2-[(2S)-1,4-Dioxan-2-ylmethyl]-N-(pyrazin-2-ylmethyl)-8-(trifluormethyl)-4,5-dihydro-2H-furo[2,3-g]indazol-7-carboxamide;

2-[(2S)-1,4-Dioxan-2-ylmethyl]-N-[(1-methyl-1H-imidazol-4-yl) methyl]-8-(trifluormethyl)-4,5-dihydro-2H-furo[2,3-g]indazol-7-carboxamide;

2-[(2S)-1,4-Dioxan-2-ylmethyl]-N-(1,3-thiazol-5-ylmethyl)-8-(trifluormethyl)-4,5-dihydro-2H-furo[2,3-g]indazol-7-carboxamide;

2-[(2S)-1,4-Dioxan-2-ylmethyl]-N-[2-(4-methylpyridin-2-yl) ethyl]-8-(trifluormethyl)-4,5-dihydro-2H-furo[2,3-g]indazol-7-carboxamide;

2-[(2S)-1,4-Dioxan-2-ylmethyl]-N-[2-(pyridin-2-yl) ethyl]-8-(trifluormethyl)-4,5-dihydro-2H-furo[2,3-g]indazol-7-carboxamide;

2-[(2S)-1,4-Dioxan-2-ylmethyl]-N-[2-(3-methyl-1H-pyrazol-1-yl) ethyl]-8-(trifluormethyl)-4,5-dihydro-2H-furo[2,3-g]indazol-7-carboxamide;

2-[(2S)-1,4-Dioxan-2-ylmethyl]-N-[2-(1H-imidazol-4-yl) ethyl]-8-(trifluormethyl)-4,5-dihydro-2H-furo[2,3-g]indazol-7-carboxamide;

2-[(2S)-1,4-Dioxan-2-ylmethyl]-N-[2-(pyridin-3-yl) ethyl]-8-(trifluormethyl)-4,5-dihydro-2H-furo[2,3-g]indazol-7-carboxamide;

2-[(2S)-1,4-Dioxan-2-ylmethyl]-N-[2-(1,3-thiazol-2-yl) ethyl]-8-(trifluormethyl)-4,5-dihydro-2H-furo[2,3-g]indazol-7-carboxamide;

2-[(2S)-1,4-Dioxan-2-ylmethyl]-N-[(6-methylpyridin-2-yl) methyl]-8-(trifluormethyl)-4,5-dihydro-2H-furo[2,3-g]indazol-7-carboxamide;

2-[(2S)-1,4-Dioxan-2-ylmethyl]-N-(1,3-oxazol-4-ylmethyl)-8-(trifluormethyl)-4,5-dihydro-2H-furo[2,3-g]indazol-7-carboxamide;

2-{[(2S)-1,4-dioxan-2-yl]methyl}-N-[2-(pyrazin-2-yl) ethyl]-8-(trifluoromethyl)-4,5-dihydro-2H-furo[2,3-g]indazole-7-carboxamide;

N-{[(2R)-1,4-dioxan-2-yl]methyl}-2-[(oxan-4-yl) methyl]-8-(trifluoromethyl)-4,5-dihydro-2H-furo[2,3-g]indazole-7-carboxamide;

2-[(oxan-4-yl) methyl]-N-{[(2S)-oxolan-2-yl]methyl}-8-(trifluoromethyl)-4,5-dihydro-2H-furo[2,3-g]indazole-7-carboxamide;

8-(difluoromethyl)-N-{[(2R)-1,4-dioxan-2-yl]methyl}-2-{[(2S)-1,4-dioxan-2-yl]methyl}-4,5-dihydro-2H-furo[2,3-g]indazole-7-carboxamide;

8-(difluoromethyl)-2-{[(2S)-1,4-dioxan-2-yl]methyl}-N-{[(2S)-oxolan-2-yl]methyl}-4,5-dihydro-2H-furo[2,3-g]indazole-7-carboxamide;

(4±)-N-{[(2R)-1,4-dioxan-2-yl]methyl}-4,8-dimethyl-2-[(pyridin-2-yl) methyl]-4,5-dihydro-2H-furo[2,3-g]indazole-7-carboxamide;

(4±)-4,8-dimethyl-N-{[(2S)-oxolan-2-yl]methyl}-2-[(pyridin-2-yl) methyl]-4,5-dihydro-2H-furo[2,3-g]indazole-7-carboxamide;

(4±)-N-{[(2R)-1,4-dioxan-2-yl]methyl}-2-{[(2S)-1,4-dioxan-2-yl]methyl}-4,8-dimethyl-4,5-dihydro-2H-furo[2,3-g]indazole-7-carboxamide;

(4±)-2-{[(2S)-1,4-dioxan-2-yl]methyl}-4,8-dimethyl-N-{[(2S)-oxolan-2-yl]methyl}-4,5-dihydro-2H-furo[2,3-g]indazole-7-carboxamide;

(4±)-N-{[(2R)-1,4-dioxan-2-yl]methyl}-4-methyl-2-[(pyridin-2-yl) methyl]-8-(trifluoromethyl)-4,5-dihydro-2H-furo[2,3-g]indazole-7-carboxamide;

(4±)-4-methyl-2-[(5-methyl-2-pyridyl) methyl]-N-[(2S)-tetrahydrofuran-2-yl]methyl]-8-(trifluoromethyl)-4,5-dihydrofuro[2,3-g]indazole-7-carboxamide;

(4±)-N-{[(2R)-1,4-dioxan-2-yl]methyl}-4-methyl-2-[(6-methylpyridin-3-yl) methyl]-8-(trifluoromethyl)-4,5-dihydro-2H-furo[2,3-g]indazole-7-carboxamide;

(4±)-4-methyl-2-[(6-methylpyridin-3-yl) methyl]-N-{[(2S)-oxolan-2-yl]methyl}-8-(trifluoromethyl)-4,5-dihydro-2H-furo[2,3-g]indazole-7-carboxamide;

(4±)-N-{[(2R)-1,4-dioxan-2-yl]methyl}-2-{[(2S)-1,4-dioxan-2-yl]methyl}-4-methyl-8-(trifluoromethyl)-4,5-dihydro-2H-furo[2,3-g]indazole-7-carboxamide;

(4R)—N-{[(2R)-1,4-dioxan-2-yl]methyl}-2-{[(2S)-1,4-dioxan-2-yl]methyl}-4-methyl-8-(trifluoromethyl)-4,5-dihydro-2H-furo[2,3-g]indazole-7-carboxamide;

(4S)—N-{[(2R)-1,4-dioxan-2-yl]methyl}-2-{[(2S)-1,4-dioxan-2-yl]methyl}-4-methyl-8-(trifluoromethyl)-4,5-dihydro-2H-furo[2,3-g]indazole-7-carboxamide;

(4±)-2-{[(2S)-1,4-dioxan-2-yl]methyl}-4-methyl-N-{[(2S)-oxolan-2-yl]methyl}-8-(trifluoromethyl)-4,5-dihydro-2H-furo[2,3-g]indazole-7-carboxamide;

(4R)-2-{[(2S)-1,4-dioxan-2-yl]methyl}-4-methyl-N-{[(2S)-oxolan-2-yl]methyl}-8-(trifluoromethyl)-4,5-dihydro-2H-furo[2,3-g]indazole-7-carboxamide;

(4S)-2-{[(2S)-1,4-dioxan-2-yl]methyl}-4-methyl-N-{[(2S)-oxolan-2-yl]methyl}-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(1,3-oxazol-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(1,3-oxazol-2-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(1-methyl-1H-pyrazol-3-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(1-methyl-1H-pyrazol-3-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(5-methylpyrazin-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(5-methylpyrazin-2-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(1,3-thiazol-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(1,3-thiazol-2-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(pyrazin-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(pyrazin-2-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(1,3-oxazol-4-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(1,3-oxazol-4-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-8-(trifluoromethyl)-N-{[2-(trifluoromethyl) pyrimidin-5-yl]methyl}-4,5-dihydro-2H-furo[2,3-g]indazole-7-carboxamide;

(4S)-2-{[(2S)-1,4-dioxan-2-yl]methyl}-4-methyl-8-(trifluoromethyl)-N-{[2-(trifluoromethyl) pyrimidin-5-yl-]methyl}-4,5-dihydro-2H-furo[2,3-g]indazole-7-carboxamide;

(4R)—N-{[(2R)-1,4-dioxan-2-yl]methyl}-4-methyl-2-[(oxan-4-yl) methyl]-8-(trifluoromethyl)-4,5-dihydro-2H-furo[2,3-g]indazole-7-carboxamide;

(4S)—N-{[(2R)-1,4-dioxan-2-yl]methyl}-4-methyl-2-[(oxan-4-yl) methyl]-8-(trifluoromethyl)-4,5-dihydro-2H-furo[2,3-g]indazole-7-carboxamide;

(4R)-4-methyl-2-[(oxan-4-yl) methyl]-N-{[(2S)-oxolan-2-yl]methyl}-8-(trifluoromethyl)-4,5-dihydro-2H-furo[2,3-g]indazole-7-carboxamide;

(4S)-4-methyl-2-[(oxan-4-yl) methyl]-N-{[(2S)-oxolan-2-yl]methyl}-8-(trifluoromethyl)-4,5-dihydro-2H-furo[2,3-g]indazole-7-carboxamide;

(4±)-N-{[(2R)-1,4-dioxan-2-yl]methyl}-2-{[(2S)-1,4-dioxan-2-yl]methyl}-8-methyl-4-(trifluoromethyl)-4,5-dihydro-2H-furo[2,3-g]indazole-7-carboxamide;

(4R)—N-{[(2R)-1,4-dioxan-2-yl]methyl}-2-{[(2S)-1,4-dioxan-2-yl]methyl}-8-methyl-4-(trifluoromethyl)-4,5-dihydro-2H-furo[2,3-g]indazole-7-carboxamide;

(4S)—N-{[(2R)-1,4-dioxan-2-yl]methyl}-2-{[(2S)-1,4-dioxan-2-yl]methyl}-8-methyl-4-(trifluoromethyl)-4,5-dihydro-2H-furo[2,3-g]indazole-7-carboxamide;

(4±)-2-{[(2S)-1,4-dioxan-2-yl]methyl}-8-methyl-N-{[(2S)-oxolan-2-yl]methyl}-4-(trifluoromethyl)-4,5-dihydro-2H-furo[2,3-g]indazole-7-carboxamide;

2-{[(2S)-1,4-dioxan-2-yl]methyl}-8-methyl-N-{[(2S)-oxolan-2-yl]methyl}-(4R)-4-(trifluoromethyl)-4,5-dihydro-2H-furo[2,3-g]indazole-7-carboxamide;

2-{[(2S)-1,4-dioxan-2-yl]methyl}-8-methyl-N-{[(2S)-oxolan-2-yl]methyl}-(4S)-4-(trifluoromethyl)-4,5-dihydro-2H-furo[2,3-g]indazole-7-carboxamide;

N-{[(2R)-1,4-dioxan-2-yl]methyl}-2-{[(2S)-1,4-dioxan-2-yl]methyl}-4,4-dimethyl-8-(trifluoromethyl)-4,5-dihydro-2H-furo[2,3-g]indazole-7-carboxamide;

2-{[(2S)-1,4-dioxan-2-yl]methyl}-4,4-dimethyl-N-{[(2S)-oxolan-2-yl]methyl}-8-(trifluoromethyl)-4,5-dihydro-2H-furo[2,3-g]indazole-7-carboxamide;

N-[(2R)-1,4-dioxan-2-ylmethyl]-2'-[(2S)-1,4-dioxan-2-ylmethyl]-8'-(trifluormethyl)-2',5'-dihydrospiro [cyclobutan-1,4'-furo[2,3-g]indazol]-7'-carboxamide;

2'-[(2S)-1,4-dioxan-2-ylmethyl]-N-[(1-methyl-1H-pyrazol-3-yl) methyl]-8'-(trifluormethyl)-2',5'-dihydrospiro [cyclobutan-1,4'-furo[2,3-g]indazol]-7'-carboxamide;

2'-[(2S)-1,4-dioxan-2-ylmethyl]-N-[(2S)-tetrahydrofuran-2-ylmethyl]-8'-(trifluormethyl)-2',5'-dihydrospiro [cyclobutan-1,4'-furo[2,3-g]indazol]-7'-carboxamide;

2'-{[(2S)-1,4-dioxan-2-yl]methyl}-N-[(1,3-oxazol-2-yl) methyl]-8'-(trifluoromethyl)-2',5'-dihydrospiro [cyclobutane-1,4'-furo[2,3-g]indazole]-7'-carboxamide;

N-[(2R)-1,4-Dioxan-2-ylmethyl]-2'-(pyridin-2-ylmethyl)-8'-(trifluormethyl)-2',5'-dihydrospiro [cyclobutan-1,4'-furo[2,3-g]indazol]-7'-carboxamide;

2'-(Pyridin-2-ylmethyl)-N-[(2S)-tetrahydrofuran-2-ylmethyl]-8'-(trifluormethyl)-2',5'-dihydrospiro [cyclobutan-1,4'-furo[2,3-g]indazol]-7'-carboxamide;

N-(1,3-Oxazol-2-ylmethyl)-2'-(pyridin-2-ylmethyl)-8'-(trifluormethyl)-2',5'-dihydrospiro [cyclobutan-1,4'-furo[2,3-g]indazol]-7'-carboxamide;

N-[(1-Methyl-1H-pyrazol-3-yl) methyl]-2'-(pyridin-2-ylmethyl)-8'-(trifluormethyl)-2',5'-dihydrospiro [cyclobutan-1,4'-furo[2,3-g]indazol]-7'-carboxamide;

2'-[(5-Methylpyridin-2-yl) methyl]-N-[(2S)-tetrahydrofuran-2-ylmethyl]-8'-(trifluormethyl)-2',5'-dihydrospiro [cyclobutan-1,4'-furo[2,3-g]indazol]-7'-carboxamide;

N-[(2R)-1,4-Dioxan-2-ylmethyl]-2'-[(5-methylpyridin-2-yl) methyl]-8'-(trifluormethyl)-2',5'-dihydrospiro [cyclobutan-1,4'-furo[2,3-g]indazol]-7'-carboxamide;

N-[(1-Methyl-1H-pyrazol-3-yl) methyl]-2'-[(5-methylpyridin-2-yl) methyl]-8'-(trifluormethyl)-2',5'-dihydrospiro [cyclobutan-1,4'-furo[2,3-g]indazol]-7'-carboxamide;

2'-(Pyridin-4-ylmethyl)-N-[(2S)-tetrahydrofuran-2-ylmethyl]-8'-(trifluormethyl)-2',5'-dihydrospiro [cyclobutan-1,4'-furo[2,3-g]indazol]-7'-carboxamide;

N-[(2R)-1,4-Dioxan-2-ylmethyl]-2'-(pyridin-4-ylmethyl)-8'-(trifluormethyl)-2',5'-dihydrospiro [cyclobutan-1,4'-furo[2,3-g]indazol]-7'-carboxamide;

2-(cyclopropylmethyl)-N-{[(2R)-1,4-dioxan-2-yl]methyl}-8-(trifluoromethyl)-4,5-dihydro-2H-furo[2,3-g]indazole-7-carboxamide;

N-{[(2R)-1,4-dioxan-2-yl]methyl}-2-{[1-(methoxyacetyl) piperidin-4-yl]methyl}-8-(trifluoromethyl)-4,5-dihydro-2H-furo[2,3-g]indazole-7-carboxamide;

2-{[1-(methoxyacetyl) piperidin-4-yl]methyl}-N-{[(2S)-oxolan-2-yl]methyl}-8-(trifluoromethyl)-4,5-dihydro-2H-furo[2,3-g]indazole-7-carboxamide;

2-{[1-(cyclopropanecarbonyl) piperidin-4-yl]methyl}-N-{[(2R)-1,4-dioxan-2-yl]methyl}-8-(trifluoromethyl)-4,5-dihydro-2H-furo[2,3-g]indazole-7-carboxamide;

2-{[1-(cyclopropanecarbonyl) piperidin-4-yl]methyl}-N-{[(2S)-oxolan-2-yl]methyl}-8-(trifluoromethyl)-4,5-dihydro-2H-furo[2,3-g]indazole-7-carboxamide;

2-[(1-benzoylpiperidin-4-yl) methyl]-N-{[(2R)-1,4-dioxan-2-yl]methyl}-8-(trifluoromethyl)-4,5-dihydro-2H-furo[2,3-g]indazole-7-carboxamide;

2-[(1-benzoylpiperidin-4-yl) methyl]-N-{[(2S)-oxolan-2-yl]methyl}-8-(trifluoromethyl)-4,5-dihydro-2H-furo[2,3-g]indazole-7-carboxamide;

8-methyl-N-{[(2S)-oxolan-2-yl]methyl}-2-[2-(pyridin-3-yl) propan-2-yl]-4,5-dihydro-2H-furo[2,3-g]indazole-7-carboxamide;

(4R)-2-{[1-(cyclopropanecarbonyl) piperidin-4-yl]methyl}-4-methyl-N-{[(2S)-oxolan-2-yl]methyl}-8-(trifluoromethyl)-4,5-dihydro-2H-furo[2,3-g]indazole-7-carboxamide;

(4S)-2-{[1-(cyclopropanecarbonyl) piperidin-4-yl]methyl}-4-methyl-N-{[(2S)-oxolan-2-yl]methyl}-8-(trifluoromethyl)-4,5-dihydro-2H-furo[2,3-g]indazole-7-carboxamide;

(4R)-2-{[1-(cyclopropanecarbonyl) piperidin-4-yl]methyl}-N-{[(2R)-1,4-dioxan-2-yl]methyl}-4-methyl-8-(trifluoromethyl)-4,5-dihydro-2H-furo[2,3-g]indazole-7-carboxamide;

(4S)-2-{[1-(cyclopropanecarbonyl) piperidin-4-yl]methyl}-N-{[(2R)-1,4-dioxan-2-yl]methyl}-4-methyl-8-(trifluoromethyl)-4,5-dihydro-2H-furo[2,3-g]indazole-7-carboxamide;

(4R)-2-[(1-acetylpiperidin-4-yl) methyl]-4-methyl-N-{[(2S)-oxolan-2-yl]methyl}-8-(trifluoromethyl)-4,5-dihydro-2H-furo[2,3-g]indazole-7-carboxamide;

(4S)-2-[(1-acetylpiperidin-4-yl) methyl]-4-methyl-N-{[(2S)-oxolan-2-yl]methyl}-8-(trifluoromethyl)-4,5-dihydro-2H-furo[2,3-g]indazole-7-carboxamide;

(4R)-2-{[1-(1-hydroxycyclopropane-1-carbonyl) piperidin-4-yl]methyl}-4-methyl-N-{[(2S)-oxolan-2-yl]methyl}-8-(trifluoromethyl)-4,5-dihydro-2H-furo[2,3-g]indazole-7-carboxamide;

(4S)-2-{[1-(1-hydroxycyclopropane-1-carbonyl) piperidin-4-yl]methyl}-4-methyl-N-{[(2S)-oxolan-2-yl]methyl}-8-(trifluoromethyl)-4,5-dihydro-2H-furo[2,3-g]indazole-7-carboxamide;

(4R)-2-[(1-acetylpiperidin-4-yl) methyl]-N-{[(2R)-1,4-dioxan-2-yl]methyl}-4-methyl-8-(trifluoromethyl)-4,5-dihydro-2H-furo[2,3-g]indazole-7-carboxamide;

(4S)-2-[(1-acetylpiperidin-4-yl) methyl]-N-{[(2R)-1,4-dioxan-2-yl]methyl}-4-methyl-8-(trifluoromethyl)-4,5-dihydro-2H-furo[2,3-g]indazole-7-carboxamide;

(4R)—N-{[(2R)-1,4-dioxan-2-yl]methyl}-2-{[1-(1-hydroxycyclopropane-1-carbonyl) piperidin-4-yl]methyl}-4-methyl-8-(trifluoromethyl)-4,5-dihydro-2H-furo[2,3-g]indazole-7-carboxamide;

(4S)—N-{[(2R)-1,4-dioxan-2-yl]methyl}-2-{[1-(1-hydroxycyclopropane-1-carbonyl) piperidin-4-yl]methyl}-4-methyl-8-(trifluoromethyl)-4,5-dihydro-2H-furo[2,3-g]indazole-7-carboxamide;

(4R)—N-{[(2R)-1,4-dioxan-2-yl]methyl}-4-methyl-2-{[1-(2-oxobutanoyl) piperidin-4-yl]methyl}-8-(trifluoromethyl)-4,5-dihydro-2H-furo[2,3-g]indazole-7-carboxamide;

(4S)—N-{[(2R)-1,4-dioxan-2-yl]methyl}-4-methyl-2-{[1-(2-oxobutanoyl) piperidin-4-yl]methyl}-8-(trifluoromethyl)-4,5-dihydro-2H-furo[2,3-g]indazole-7-carboxamide;

(4R)-4-methyl-2-{[1-(2-oxobutanoyl) piperidin-4-yl]methyl}-N-{[(2S)-oxolan-2-yl]methyl}-8-(trifluoromethyl)-4,5-dihydro-2H-furo[2,3-g]indazole-7-carboxamide;

(4S)-4-methyl-2-{[1-(2-oxobutanoyl) piperidin-4-yl]methyl}-N-{[(2S)-oxolan-2-yl]methyl}-8-(trifluoromethyl)-4,5-dihydro-2H-furo[2,3-g]indazole-7-carboxamide;

(4R)-4-methyl-2-{[1-(1-methylcyclopropane-1-carbonyl) piperidin-4-yl]methyl}-N-{[(2S)-oxolan-2-yl]methyl}-8-(trifluoromethyl)-4,5-dihydro-2H-furo[2,3-g]indazole-7-carboxamide;

(4S)-4-methyl-2-{[1-(1-methylcyclopropane-1-carbonyl) piperidin-4-yl]methyl}-N-{[(2S)-oxolan-2-yl]methyl}-8-(trifluoromethyl)-4,5-dihydro-2H-furo[2,3-g]indazole-7-carboxamide;

(4R)—N-{[(2R)-1,4-dioxan-2-yl]methyl}-4-methyl-2-{[1-(1-methylcyclopropane-1-carbonyl) piperidin-4-yl]methyl}-8-(trifluoromethyl)-4,5-dihydro-2H-furo[2,3-g]indazole-7-carboxamide;

(4S)—N-{[(2R)-1,4-dioxan-2-yl]methyl}-4-methyl-2-{[1-(1-methylcyclopropane-1-carbonyl) piperidin-4-yl]methyl}-8-(trifluoromethyl)-4,5-dihydro-2H-furo[2,3-g]indazole-7-carboxamide;

N,2-bis {[(2S)-1,4-dioxan-2-yl]methyl}-8-(trifluoromethyl)-4,5-dihydro-2H-furo[2,3-g]indazole-7-carboxamide;

2-{[(2R)-1,4-dioxan-2-yl]methyl}-N-{[(2S)-1,4-dioxan-2-yl]methyl}-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(2-methylpyrimidin-5-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(2-methylpyrimidin-5-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(5-methylpyrimidin-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(5-methylpyrimidin-2-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(pyrimidin-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(pyrimidin-2-yl) methyl]-8-(trifluoromethyl)-4,5-dihydro-2H-furo[2,3-g]indazole-7-carboxamide;

2-[(1-acetylpiperidin-4-yl) methyl]-N-{[(2S)-oxolan-2-yl]methyl}-8-(trifluoromethyl)-4,5-dihydro-2H-furo[2,3-g]indazole-7-carboxamide;

2-[(1-acetylpiperidin-4-yl) methyl]-N-{[(2R)-1,4-dioxan-2-yl]methyl}-8-(trifluoromethyl)-4,5-dihydro-2H-furo[2,3-g]indazole-7-carboxamide;

2-{[1-(cyclopropylmethyl) piperidin-4-yl]methyl}-N-{[(2S)-oxolan-2-yl]methyl}-8-(trifluoromethyl)-4,5-dihydro-2H-furo[2,3-g]indazole-7-carboxamide;

2-[(1-methylpiperidin-4-yl) methyl]-N-{[(2S)-oxolan-2-yl]methyl}-8-(trifluoromethyl)-4,5-dihydro-2H-furo[2,3-g]indazole-7-carboxamide;

N-{[(2R)-1,4-dioxan-2-yl]methyl}-2-[(1-methylpiperidin-4-yl) methyl]-8-(trifluoromethyl)-4,5-dihydro-2H-furo[2,3-g]indazole-7-carboxamide;

2-{[1-(cyclopropylmethyl) piperidin-4-yl]methyl}-N-{[(2R)-1,4-dioxan-2-yl]methyl}-8-(trifluoromethyl)-4,5-dihydro-2H-furo[2,3-g]indazole-7-carboxamide;

2-[(1-ethylpiperidin-4-yl) methyl]-N-{[(2S)-oxolan-2-yl] methyl}-8-(trifluoromethyl)-4,5-dihydro-2H-furo[2,3-g]indazole-7-carboxamide;

N-{[(2R)-1,4-dioxan-2-yl]methyl}-2-[(1-ethylpiperidin-4-yl) methyl]-8-(trifluoromethyl)-4,5-dihydro-2H-furo [2,3-g]indazole-7-carboxamide;

2,5-anhydro-1,3,4-trideoxy-1-{[(4R)-2-{[(2S)-1,4-dioxan-2-yl]methyl}-4-methyl-8-(trifluoromethyl)-4,5-dihydro-2H-furo[2,3-g]indazole-7-carbonyl]amino}-4-methylpentitol;

2,5-anhydro-1,3,4-trideoxy-1-{[(4S)-2-{[(2S)-1,4-dioxan-2-yl]methyl}-4-methyl-8-(trifluoromethyl)-4,5-dihydro-2H-furo[2,3-g]indazole-7-carbonyl]amino}-4-methylpentitol;

(4R)-2-{[(2S)-1,4-dioxan-2-yl]methyl}-4-methyl-N-[(1-methyl-1H-imidazol-4-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(1-methyl-1H-imidazol-4-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(6-methylpyridin-2-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(6-methylpyridin-2-yl) methyl]-8-(trifluoromethyl)-4,5-dihydro-2H-furo[2,3-g]indazole-7-carboxamide;

(4R)-2-{[(2S)-1,4-dioxan-2-yl]methyl}-4-methyl-N-[(1,3-thiazol-5-yl) methyl]-8-(trifluoromethyl)-4,5-dihydro-2H-furo[2,3-g]indazole-7-carboxamide;

(4S)-2-{[(2S)-1,4-dioxan-2-yl]methyl}-4-methyl-N-[(1,3-thiazol-5-yl) methyl]-8-(trifluoromethyl)-4,5-dihydro-2H-furo[2,3-g]indazole-7-carboxamide;

8-methyl-N-{[(2S)-oxolan-2-yl]methyl}-2-[(1±)-1-(pyridin-2-yl) ethyl]-4,5-dihydro-2H-furo[2,3-g]indazole-7-carboxamide;

8-methyl-2-[(5-methylpyridin-2-yl) methyl]-N-[(3R)-oxolan-3-yl]-4,5-dihydro-2H-furo[2,3-g]indazole-7-carboxamide;

2-[(5-cyanopyridin-2-yl) methyl]-8-methyl-N-{[(2S)-oxolan-2-yl]methyl}-4,5-dihydro-2H-furo[2,3-g]indazole-7-carboxamide;

N-{[(2R)-1,4-dioxan-2-yl]methyl}-2-{[(2S)-1,4-dioxan-2-yl]methyl}-8-(trifluoromethyl)-4,5-dihydro-2H-furo [2,3-g]indazole-7-carboxamide;

N-[(5-cyclopropylpyrazin-2-yl) methyl]-2-{[(2S)-1,4-dioxan-2-yl]methyl}-8-(trifluoromethyl)-4,5-dihydro-2H-furo[2,3-g]indazole-7-carboxamide;

(4R)—N-[(5-cyclopropylpyrazin-2-yl) methyl]-2-{[(2S)-1,4-dioxan-2-yl]methyl}-4-methyl-8-(trifluoromethyl)-4,5-dihydro-2H-furo[2,3-g]indazole-7-carboxamide;

(4S)—N-[(5-cyclopropylpyrazin-2-yl) methyl]-2-{[(2S)-1,4-dioxan-2-yl]methyl}-4-methyl-8-(trifluoromethyl)-4,5-dihydro-2H-furo[2,3-g]indazole-7-carboxamide;

(4R)—N-[(5-chloropyrazin-2-yl) methyl]-2-{[(2S)-1,4-dioxan-2-yl]methyl}-4-methyl-8-(trifluoromethyl)-4,5-dihydro-2H-furo[2,3-g]indazole-7-carboxamide; and (4S)—N-[(5-chloropyrazin-2-yl) methyl]-2-{[(2S)-1,4-dioxan-2-yl]methyl}-4-methyl-8-(trifluoromethyl)-4,5-dihydro-2H-furo[2,3-g]indazole-7-carboxamide, or a stereoisomer, a tautomer, an N-oxide, a hydrate, a solvate, or a salt thereof, or a mixture of same.

6. A method of preparing a compound of general formula (I) according to claim 1, said method comprising the step of reacting an intermediate compound of general formula (II):

(II)

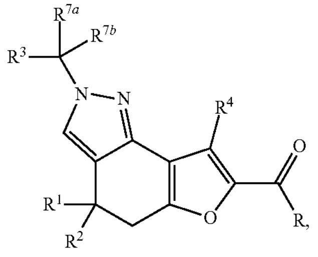

in which R is H, OH, OMe, or OEt and $R^1$, $R^2$, $R^3$, $R^4$, $R^{7a}$ and $R^{7b}$ are as defined for the compound of general formula (I) according to claim 1, with a compound of general formula (III):

(III)

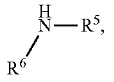

in which $R^5$ and $R^6$ are as defined for the compound of general formula (I) according to claim 1, thereby giving a compound of general formula (I):

(I)

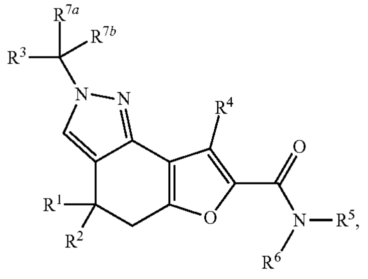

in which $R^1$, $R^2$, $R^3$, $R^5$, $R^6$, $R^{7a}$ and $R^{7b}$ are as defined for the compound of general formula (I) according to claim 1.

7. A compound of general formula (II):

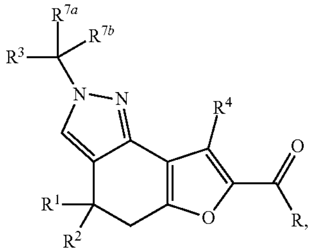

(II)

in which R is H, OH, OMe, or OEt and $R^1$, $R^2$, $R^3$, $R^4$, $R^{7a}$ and $R^{7b}$ are as defined for the compound of general formula (I) according to claim 1.

8. The compound according to claim 1, wherein the compound is N-{[(2R)-1,4-dioxan-2-yl]methyl}-2-{[(2S)-1,4-dioxan-2-yl]methyl}-8-(trifluoromethyl)-4,5-dihydro-2H-furo[2,3-g]indazole-7-carboxamide, or a stereoisomer, a tautomer, a hydrate, or a salt thereof, or a mixture of same.

9. The compound according to claim 1, wherein the compound is N-{[(2R)-1,4-dioxan-2-yl]methyl}-2-{[(2S)-1,4-dioxan-2-yl]methyl}-8-(trifluoromethyl)-4,5-dihydro-2H-furo[2,3-g]indazole-7-carboxamide:

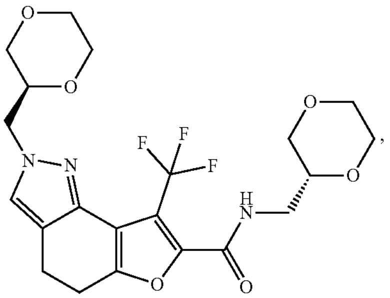 [SMILES: O=C(NC[C@@H]1COCCO1)c1oc2c(c1C(F)(F)F)-c1nn(C[C@H]3COCCO3)cc1CC2]

or a pharmaceutically acceptable salt thereof.

10. The compound according to claim 1, wherein the compound is N-{[(2R)-1,4-dioxan-2-yl]methyl}-2-{[(2S)-1,4-dioxan-2-yl]methyl}-8-(trifluoromethyl)-4,5-dihydro-2H-furo[2,3-g]indazole-7-carboxamide:

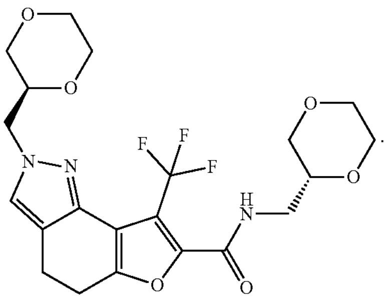 [SMILES: O=C(NC[C@@H]1COCCO1)c1oc2c(c1C(F)(F)F)-c1nn(C[C@H]3COCCO3)cc1CC2]

11. A pharmaceutical composition comprising, the compound according to claim 1, or a stereoisomer, a tautomer, an N-oxide, a hydrate, a solvate, or a salt thereof, or a mixture of same, and one or more pharmaceutically suitable excipients.

12. A pharmaceutical composition comprising, the compound according to claim 9, or a pharmaceutically acceptable salt thereof, and one or more pharmaceutically suitable excipients.

* * * * *